United States Patent [19]

Koziel et al.

[11] Patent Number: 6,018,104
[45] Date of Patent: Jan. 25, 2000

[54] NUCLEIC ACID PROMOTER FRAGMENT ISOLATED FROM A PLANT TRYPTOPHAN SYNTHASE ALPHA SUBUNIT (TRPA) GENE

[75] Inventors: Michael G. Koziel; Nalini M. Desai, both of Cary; Kelly S. Lewis; Vance C. Kramer, both of Hillsborough; Gregory W. Warren, Cary; Stephen V. Evola, Apex; Martha S. Wright, Cary; Karen L. Launis, Franklinton, all of N.C.; Steven J. Rothstein, Guelph, Canada; Cindy G. Bowman, Cary, N.C.; John L. Dawson; Erik M. Dunder, both of Chapel Hill, N.C.; Gary M. Pace, Cary, N.C.; Janet L. Suttie, Raleigh, N.C.

[73] Assignee: Novartis Finance Corporation, New York, N.Y.

[21] Appl. No.: 08/459,595

[22] Filed: Jun. 2, 1995

Related U.S. Application Data

[60] Division of application No. 07/951,715, Sep. 25, 1992, Pat. No. 5,625,136, which is a continuation-in-part of application No. 07/772,027, Oct. 4, 1991, abandoned.

[51] Int. Cl.[7] .............................. A01H 5/00; C12N 15/82; C07H 21/04
[52] U.S. Cl. ........................... 800/298; 800/278; 800/279; 800/302; 800/320.1; 435/69.1; 435/320.1; 435/419; 435/468; 536/24.1; 536/23.71
[58] Field of Search ........................... 800/205, DIG. 56, 800/298, 302, 320.1, 278, 279; 435/69.1, 172.3, 240.4, 320.1, 468, 419; 536/23.1, 24.1, 23.71

[56] References Cited

U.S. PATENT DOCUMENTS

| | | | |
|---|---|---|---|
| 5,380,831 | 1/1995 | Adang et al. | 536/32.71 |
| 5,436,391 | 7/1995 | Fujimoto et al. | 800/205 |
| 5,484,956 | 1/1996 | Lundquist | 800/205 |

FOREIGN PATENT DOCUMENTS

| | | |
|---|---|---|
| 0290395 | 11/1988 | European Pat. Off. . |
| 0431829 | 6/1989 | European Pat. Off. . |
| 0348348 | 12/1989 | European Pat. Off. . |
| 0353908 | 2/1990 | European Pat. Off. . |
| 0359472 | 3/1990 | European Pat. Off. . |
| 0374753 | 6/1990 | European Pat. Off. . |
| 0385962 | 9/1990 | European Pat. Off. . |
| 0408403 | 1/1991 | European Pat. Off. . |
| 0431829 | 6/1991 | European Pat. Off. . |
| WO/9010076 | 9/1990 | WIPO . |
| WO/9110725 | 7/1991 | WIPO . |
| WO/9116432 | 10/1991 | WIPO . |

OTHER PUBLICATIONS

Kim et al (1994) Plant Mol Biol 24:105–117.
Keller et al (1989) EMBO J. 8(5): 1309–1314.
Rhodes et al (1988) Science 240: 204–207.
Barton et al., *Plant Physiol.*, 85:1103–1109 (1987).
Fischhoff et al., "Insect Tolerant Transgenic Tomato Plants", *Bio/Technology*, 5:807–813 (1987).
Geiser et al., *Gene,* 48:109–118 (1986).
Ohta et al., *Mol. Gen. Genet.,* 225:369–378 (1991).
Murray et al., "Codon usage in plant genes", *Nucleic Acids Research,* 17(2):477–498 (1989).
Perlack et al., "Modification of the coding sequence enchances plant expression of insect control protein genes", *Proc. Natl. Acad. Sci. USA,* 88:3324–3328 (1991).
Vaeck et al., "Transgenic plants protected from insect attack", *Nature,* 328:33–37 (1987).

*Primary Examiner*—Elizabeth F. McElwain
*Attorney, Agent, or Firm*—J. Timothy Meigs; Gary M. Pace

[57] ABSTRACT

DNA sequences optimized for expression in plants are disclosed. The DNA sequences preferably encode for an insecticidal polypeptides, particularly insecticidal proteins from *Bacillus thuringiensis*. Plant promoters, particular tissue-specific and tissue-preferred promoters are also provided. Additionally disclosed are transformation vectors comprising said DNA sequences. The transformation vectors demonstrate high levels of insecticidal activity when transformed into maize.

15 Claims, 90 Drawing Sheets

Fig. 1A

```
                       10        20        30        40        50        60
                        *         *         *         *         *         *
BTHKURHD      ATGGATAACAATCCGAACATCAATGAATGCATTCCTTATAATTGTTTAAGTAACCCTGAA
flsynbt.fin   .....C.....C..C........C..G.....C..C..C..C..CC.G..C.....C..G
bssyn         .....C.....C..C........C..G.....C..C..C..C..CC.G..C.....C..G 70        80        90       100       110       120
                        *         *         *         *         *         *
BTHKURHD      GTAGAAGTATTAGGTGGAGAAAGAATAGAAACTGGTTACACCCCAATCGATATTTCCTTG
flsynbt.fin   ..G..G..GC.G..C..C..GC.C..C..G..C..C........C.....C..CAG.C..
bssyn         ..G..G..GC.G..C..C..GC.C..C..G..C..C........C.....C..CAG.C..

130       140       150       160       170       180
                        *         *         *         *         *         *
BTHKURHD      TCGCTAACGCAATTTCTTTTGAGTGAATTTGTTCCCGGTGCTGGATTTGTGTTAGGACTA
flsynbt.fin   AGC..G..C..G..C..GC....C..G..C..G.....C..C..C..C...C.G..C..G
bssyn         AGC..G..C..G..C..GC....C..G..C..G.....C..C..C..C...C.G..C..G 190       200       210       220       230       240
                        *         *         *         *         *         *
BTHKURHD      GTTGATATAATATGGGGAATTTTTGGTCCCTCTCAATGGGACGCATTTCTTGTACAAATT
flsynbt.fin   ..G..C..C..C.....C..C..C..C...AGC..G........C..C..G..G..G..C
bssyn         ..G..C..C..C.....C..C..C..C...AGC..G........C..C..G..G..G..C 250       260       270       280       290       300
                        *         *         *         *         *         *
BTHKURHD      GAACAGTTAATTAACCAAAGAATAGAAGAATTCGCTAGGAACCAAGCCATTTCTAGATTA
flsynbt.fin   ..G...C.G..C.....GC.C..C..G..G.....CC.C.....G.....CAGCC.CC.G
bssyn         ..G...C.G..C.....GC.C..C..G..G.....CC.C.....G.....CAGCC.CC.G 310       320       330       340       350       360
                        *         *         *         *         *         *
BTHKURHD      GAAGGACTAAGCAATCTTTATCAAATTTACGCAGAATCTTTTAGAGAGTGGGAAGCAGAT
flsynbt.fin   ..G..C..G.....C..G..C.....C.....C..GAGC..CC.C........G..C..C
bssyn         ..G..C..G.....C..G..C.....C.....C..GAGC..CC.C........G..C..C 370       380       390       400       410       420
                        *         *         *         *         *         *
BTHKURHD      CCTACTAATCCAGCATTAAGAGAAGAGATGCGTATTCAATTCAATGACATGAACAGTGCC
flsynbt.fin   ..C..C..C..C..CC.GC.C..G........C..C..G.....C...........C...
bssyn         ..C..C..C..C..CC.GC.C..G........C..C..G.....C...........C...

430       440       450       460       470       480
                        *         *         *         *         *         *
BTHKURHD      CTTACAACCGCTATTCCTCTTTTTGCAGTTCAAAATTATCAAGTTCCTCTTTTATCAGTA
flsynbt.fin   ..G..C.....C..C..C..G..C..C..G..G..C..C..G..G..C..GC.GAGC..G
bssyn         ..G..C.....C..C..C..G..C..C..G..G..C..C..G..G..C..GC.GAGC..G 490       500       510       520       530       540
                        *         *         *         *         *         *
BTHKURHD      TATGTTCAAGCTGCAAATTTACATTTATCAGTTTTGAGAGATGTTTCAGTGTTTGGACAA
flsynbt.fin   ..C..G..G..C..C..CC.G..CC.GAGC..GC..C.C..C..CAGC.....C..C..G
bssyn         ..C..G..G..C..C..CC.G..CC.GAGC..GC..C.C..C..CAGC.....C..C..G 550       560       570       580       590       600
                        *         *         *         *         *         *
BTHKURHD      AGGTGGGGATTTGATGCCGCGACTATCAATAGTCGTTATAATGATTTAACTAGGCTTATT
flsynbt.fin   C.C.....C..C..C.....C..C.....C..C..C..C..C..CC.G..CC.C..G..C
bssyn         C.C.....C..C..C.....C..C.....C..C..C..C..C..CC.G..CC.C..G..C
```

Fig. 1B

```
                        610        620        630        640        650        660
                         *          *          *          *          *          *
BTHKURHD     GGCAACTATACAGATCATGCTGTACGCTGGTACAATACGGGATTAGAGCGTGTATGGGGA
flsynbt.fin  ........C...C...C...C...C..G...........C...C..CC.G.....C..G.....T
bssyn        ........C...C...C...C...C..G...........C...C..CC.G.....C..G.....T 670        680        690        700        710        720
                         *          *          *          *          *          *
BTHKURHD     CCGGATTCTAGAGATTGGATAAGATATAATCAATTTAGAAGAGAATTAACACTAACTGTA
flsynbt.fin  ..C...CAGCC.C...C.....C...G...C...C...G..CC.CC.C...GC.G...C...G...C...G
bssyn        ..C...CAGCC.C...C.....C...G...C...C...G..CC.CC.C...GC.G...C...G...C...G 730        740        750        760        770        780
                         *          *          *          *          *          *
BTHKURHD     TTAGATATCGTTTCTCTATTTCCGAACTATGATAGTAGAACGTATCCAATTCGAACAGTT
flsynbt.fin  C.G...C.....GAGC..G..C...C.....C...C...CC.C...C...C...C...C...C..G
bssyn        C.G...C.....GAGC..G..C...C.....C...C...CC.C...C...C...C...C...C..G 790        800        810        820        830        840
                         *          *          *          *          *          *
BTHKURHD     TCCCAATTAACAAGAGAAATTTATACAAACCCAGTATTAGAAAATTTTGATGGTAGTTTT
flsynbt.fin  AG...GC.G...CC.C...G.....C...C.....C..GC.G...G...C...C...C...C...C
bssyn        AG...GC.G...CC.C...G.....C...C.....C..GC.G...G...C...C...C...C...C 850        860        870        880        890        900
                         *          *          *          *          *          *
BTHKURHD     CGAGGCTCGGCTCAGGGCATAGAAGGAAGTATTAGGAGTCCACATTTGATGGATATACTT
flsynbt.fin  ..C....AGC...C........C...G...C...C...CC.C...C...C...CC........C...C...G
bssyn        ..C....AGC...C........C...G...C...C...CC.C...C...C...CC........C...C...G 910        920        930        940        950        960
                         *          *          *          *          *          *
BTHKURHD     AACAGTATAACCATCTATACGGATGCTCATAGAGGAGAATATTATTGGTCAGGGCATCAA
flsynbt.fin  .....C..C........C...C...C...C..CC.C...C...G...C...C....AGC...C...C..G
bssyn        .....C..C........C...C...C...C..CC.C...C...G...C...C....AGC...C...C..G 970        980        990       1000       1010       1020
                         *          *          *          *          *          *
BTHKURHD     ATAATGGCTTCTCCTGTAGGGTTTTCGGGGCCAGAATTCACTTTTCCGCTATATGGAACT
flsynbt.fin  ..C.....CAGC..C...C...C..CAGC...C...C...G.....C...C...C...G...C...C...C
bssyn        ..C.....CAGC..C...C...C..CAGC...C...C...G.....C...C...C...G...C...C...C 1030       1040       1050       1060       1070       1080
                         *          *          *          *          *          *
BTHKURHD     ATGGGAAATGCAGCTCCACAACAACGTATTGTTGCTCAACTAGGTCAGGGCGTGTATAGA
flsynbt.fin  .....C..C...T..A...T..G..G...C..C...G..A..G..G...C.....A.....CC.C
bssyn        .....C..C...T..A...T..G..G...C..C...G..A..G..G...C.....A.....CC.C 1090       1100       1110       1120       1130       1140
                         *          *          *          *          *          *
BTHKURHD     ACATTATCGTCCACTTTATATAGAAGACCTTTTAATATAGGGATAAATAATCAACAACTA
flsynbt.fin  ..CC.GAGCAG...CC.G..CC.TC.........C...C...C...C...C...G..G..G
bssyn        ..CC.GAGCAG...CC.G..CC.TC.........C...C...C...C...C...G..G..G 1150       1160       1170       1180       1190       1200
                         *          *          *          *          *          *
BTHKURHD     TCTGTTCTTGACGGGACAGAATTTGCTTATGGAACCTCCTCAAATTTGCCATCCGCTGTA
flsynbt.fin  AGC..G..G.....C...C..G..C...C...C...C...AG.AGC..CC....CAG...C..G
bssyn        AGC..G..G.....C...C..G..C...C...C...C...AG.AGC..CC....CAG...C..G
```

Fig. 1C

```
                   1210       1220       1230       1240       1250       1260
                     *          *          *          *          *          *
BTHKURHD      TACAGAAAAAGCGGAACGGTAGATTCGCTGGATGAAATACCGCCACAGAATAACAACGTG
flsynbt.fin   ...C.C..G.....C..C..G..CAGC.....C..G..C..C...T.....C.........
bssyn         ...C.C..G.....C..C..G..CAGC.....C..G..C..C...T.....C.........

1270       1280       1290       1300       1310       1320
                     *          *          *          *          *          *
BTHKURHD      CCACCTAGGCAAGGATTTAGTCATCGATTAAGCCATGTTTCAATGTTTCGTTCAGGCTTT
flsynbt.fin   ......C.A..G..C..C..C..C...TC.G.....C..GAGC.....C...CAGT.....C
bssyn         ......C.A..G..C..C..C..C...TC.G.....C..GAGC.....C...CAGT.....C 1330       1340       1350       1360       1370       1380
                     *          *          *          *          *          *
BTHKURHD      AGTAATAGTAGTGTAAGTATAATAAGAGCTCCTATGTTCTCTTGGATACATCGTAGTGCT
flsynbt.fin   ..C...C..C..C..G..C..C..CC.T...A.........AGC.....T..C..C.....C
bssyn         ..C...C..C..C..G..C..C..CC.T...A.........AGC.....T..C..C.....C 1390       1400       1410       1420       1430
                     *          *          *          *          *
BTHKURHD      GAATTTAATAATATAATTCCTTCATCA--CAAATTACACAAATACCTTTAACAAAATCTA
flsynbt.fin   ..G..C..C..C..C..C..--..G...GC..G..C..C..G..C..CC.G..C..GAGC.
bssyn         ..G..C..C..C..C..C..--..G...GC..G..C..C..G..C..CC.G..C..GAGC.

1440       1450       1460       1470       1480       1490
                     *          *          *          *          *          *
BTHKURHD      CTAATCTTGGCTCTGGAACTTCTGTCGTTAAAGGACCAGGATTTACAGGAGGAGATATTC
flsynbt.fin   .C...C..G...AGC..C..CAGC..G..G..G..C..C..C..C..C..C..C..C
bssyn         .C...C..G...AGC..C..CAGC..G..G..G..C..C..C..C..C..C..C..C 1500       1510       1520       1530       1540       1550
                     *          *          *          *          *          *
BTHKURHD      TTCGAAGAACTTCACCTGGCCAGATTTCAACCTTAAGAGTAAATATTACTGCACCATTAT
flsynbt.fin   .G..CC.C..CAGC..C........CAGC....C.GC.C..G..C..C..C..CC.GA
bssyn         .G..CC.C..CAGC..C........CAGC....C.GC.C..G..C..C..C..CC.GA 1560       1570       1580       1590       1600       1610
                     *          *          *          *          *          *
BTHKURHD      CACAAAGATATCGGGTAAGAATTCGCTACGCTTCTACCACAAATTTACAATTCCATACAT
flsynbt.fin   GC..GC.C..C..C..CC.C..C........CAGC.....C..CC.G..G.....C..CA
bssyn         GC..GC.C..C..C..CC.C..C........CAGC.....C..CC.G..G.....C..CA 1620       1630       1640       1650       1660       1670
                     *          *          *          *          *          *
BTHKURHD      CAATTGACGGAAGACCTATTAATCAGGGGAATTTTTCAGCAACTATGAGTAGTGGGAGTA
flsynbt.fin   GC..C.....CC.C..C..C..C.....C..C..C..CAGC..C..C.....C..C..C..C.
bssyn         GC..C.....CC.C..C..C..C.....C..C..C..CAGC..C..C.....C..C..C..C.

1680       1690       1700       1710       1720       1730
                     *          *          *          *          *          *
BTHKURHD      ATTTACAGTCCGGAAGCTTTAGGACTGTAGGTTTTACTACTCCGTTTAACTTTTCAAATG
flsynbt.fin   .CC.G...AG...C.....CC.C..C..G..C..C..C..C..C.....CAGC..C.
bssyn         .CC.G...AG...C.....CC.C..C..G..C..C..C..C..C.....CAGC..C.

1740       1750       1760       1770       1780       1790
                     *          *          *          *          *          *
BTHKURHD      GATCAAGTGTATTTACGTTAAGTGCTCATGTCTTCAATTCAGGCAATGAAGTTTATATAG
flsynbt.fin   .CAGC...C..G..C..CC.G..C..C..C..G.....CAGC.....C..G..G..C..C.
bssyn         .CAGC...C..G..C..CC.G..C..C..C..G.....CAGC.....C..G..G..C..C.
```

Fig. 1D

```
                   1800       1810       1820       1830       1840       1850
                     *          *          *          *          *          *
BTHKURHD      ATCGAATTGAATTTGTTCCGGCAGAAGTAACCTTTGAGGCAGAATATGATTTAGAAAGAG
flsynbt.fin   .C...C...C...G...C...G...C...C...G...G.....C.....C..G...C..CC.G..G...G.
bssyn         .C...C...C...G...C...G...C...C...G...G.....C.....C..G...C..CC.G..G...G.

1860       1870       1880       1890       1900       1910
                     *          *          *          *          *          *
BTHKURHD      CACAAAAGGCGGTGAATGAGCTGTTTACTTCTTCCAATCAAATCGGGTTAAAAACAGATG
flsynbt.fin   .T..G.....C.....C........C...CAGCAG...C..G.....CC.G..G...C..C.
bssyn         .T..G.....C.....C........C...CAGCAG...C..G.....CC.G..G...C..C.

1920       1930       1940       1950       1960       1970
                     *          *          *          *          *          *
BTHKURHD      TGACGGATTATCATATTGATCAAGTATCCAATTTAGTTGAGTGTTTATCTGATGAATTTT
flsynbt.fin   ....C..C..C..C..C.....G..GAG...CC.G..G.....CC.GAGC..C..G..C.
bssyn         ....C..C..C..C..C....------------------------------------------

1980       1990       2000       2010       2020       2030
                     *          *          *          *          *          *
BTHKURHD      GTCTGGATGAAAAAAAAGAATTGTCCGAGAAAGTCAAACATGCGAAGCGACTTAGTGATG
flsynbt.fin   .C.....C..G..G..G..GC..AG......G..G...G..C..C.....C..G..C..C.
bssyn         ------------------------------------------------------------

2040       2050       2060       2070       2080       2090
                     *          *          *          *          *          *
BTHKURHD      AGCGGAATTTACTTCAAGATCCAAACTTTAGAGGGATCAATAGACAACTAGACCGTGGCT
flsynbt.fin   ....C..CC.G..G..G..C..C.....CC.C..C.....CC.C...G..G.....C....
bssyn         ------------------------------------------------------------

2100       2110       2120       2130       2140       2150
                     *          *          *          *          *          *
BTHKURHD      GGAGAGGAAGTACGGATATTACCATCCAAGGAGGCGATGACGTATTCAAAGAGAATTACG
flsynbt.fin   ..C.C..C..C..C..C..C.......G..C.....C.....G.....G.....C....
bssyn         ------------------------------------------------------------

2160       2170       2180       2190       2200       2210
                     *          *          *          *          *          *
BTHKURHD      TTACGCTATTGGGTACCTTTGATGAGTGCTATCCAACGTATTTATATCAAAAAATAGATG
flsynbt.fin   .G...C...GC....C.....C...C.........C...C..C..CC.G..C..G..C..C.
bssyn         ------------------------------------------------------------

2220       2230       2240       2250       2260       2270
                     *          *          *          *          *          *
BTHKURHD      AGTCGAAATTAAAAGCCTATACCCGTTACCAATTAAGAGGGTATATCGAAGATAGTCAAG
flsynbt.fin   ..AGC..GC.G...G.....C.....C.....GC.GC.C..C...C.....G..C..C..G.
bssyn         ------------------------------------------------------------

2280       2290       2300       2310       2320       2330
                     *          *          *          *          *          *
BTHKURHD      ACTTAGAAATCTATTTAATTCGCTACAATGCCAAACACGAAACAGTAAATGTGCCAGGTA
flsynbt.fin   ..C.G..G.....CC.G..C.........C.......G..G..C..G..C.....C..C.
bssyn         ------------------------------------------------------------

2340       2350       2360       2370       2380       2390
                     *          *          *          *          *          *
BTHKURHD      CGGGTTCCTTATGGCCGCTTTCAGCCCCAAGTCCAATCGGAAAATGTGCCCATCATTCCC
flsynbt.fin   .C..CAG.C.G.....C..GAGC.....C..C..C.....C..G..C.....C...CAG..
bssyn         ------------------------------------------------------------
```

Fig. 1E

```
              2400       2410       2420       2430       2440       2450
                *          *          *          *          *          *
BTHKURHD     ATCATTTCTCCTTGGACATTGATGTTGGATGTACAGACTTAAATGAGGACTTAGGTGTAT
flsynbt.fin  .C..C...AG.C.......C..C..G..C..C..C...C.G..C......C.G..C..G.
bssyn        ------------------------------------------------------------

2460       2470       2480       2490       2500       2510
                *          *          *          *          *          *
BTHKURHD     GGGTGATATTCAAGATTAAGACGCAAGATGGCCATGCAAGACTAGGAAATCTAGAATTTC
flsynbt.fin  .......C.........C.....C..G..C.....C..CC.C..G..C..C..G..G..C.
bssyn        ------------------------------------------------------------

2520       2530       2540       2550       2560       2570
                *          *          *          *          *          *
BTHKURHD     TCGAAGAGAAACCATTAGTAGGAGAAGCACTAGCTCGTGTGAAAAGAGCGGAGAAAAAAT
flsynbt.fin  .G...G.....G..CC.G..G..C..G..C..G..C..C.....GC.C..C.....G..G.
bssyn        ------------------------------------------------------------

2580       2590       2600       2610       2620       2630
                *          *          *          *          *          *
BTHKURHD     GGAGAGACAAACGTGAAAAATTGGAATGGGAAACAAATATTGTTTATAAAGAGGCAAAAG
flsynbt.fin  ..C.C.....G..C..G..GC....G.....G..C..C..C.G..C..G.....C..G.
bssyn        ------------------------------------------------------------

2640       2650       2660       2670       2680       2690
                *          *          *          *          *          *
BTHKURHD     AATCTGTAGATGCTTTATTTGTAAACTCTCAATATGATAGATTACAAGCGGATACCAACA
flsynbt.fin  .GAGC..G..C...CC.G...C..G...AGC...G..C...CC.CC.G...G..C..C.......
bssyn        ------------------------------------------------------------

2700       2710       2720       2730       2740       2750
                *          *          *          *          *          *
BTHKURHD     TCGCGATGATTCATGCGGCAGATAAACGCGTTCATAGCATTCGAGAAGCTTATCTGCCTG
flsynbt.fin  ....C.....C..C..C..C..C..G.....G..C.........C..G..C..C.....C.
bssyn        ------------------------------------------------------------

2760       2770       2780       2790       2800       2810
                *          *          *          *          *          *
BTHKURHD     AGCTGTCTGTGATTCCGGGTGTCAATGCGGCTATTTTTGAAGAATTAGAAGGGCGTATTT
flsynbt.fin  .....AGC.....C..C..C..G..C..C..C..C..C..G..GC.G..G..C..C..C.
bssyn        ------------------------------------------------------------

2820       2830       2840       2850       2860       2870
                *          *          *          *          *          *
BTHKURHD     TCACTGCATTCTCCCTATATGATGCGAGAAATGTCATTAAAAATGGTGATTTTAATAATG
flsynbt.fin  ....C..C...AG...G..C..C..CC.C..C..G..C..G...C..C..C..C..C.
bssyn        ------------------------------------------------------------

2880       2890       2900       2910       2920       2930
                *          *          *          *          *          *
BTHKURHD     GCTTATCCTGCTGGAACGTGAAAGGGCATGTAGATGTAGAAGAACAAAACAACCACCGTT
flsynbt.fin  ..C.GAG...........G..C..C..G..C..G..G..G..G............CA
bssyn        ------------------------------------------------------------

2940       2950       2960       2970       2980       2990
                *          *          *          *          *          *
BTHKURHD     CGGTCCTTGTTGTTCCGGAATGGGAAGCAGAAGTGTCACAAGAAGTTCGTGTCTGTCCGG
flsynbt.fin  GC..G..G..G..G..C..G.....G..C..G...AGC..G..G..G..C..G..C..C.
bssyn        ------------------------------------------------------------
```

Fig. 1F

```
                 3000       3010       3020       3030       3040       3050
                   *          *          *          *          *          *
BTHKURHD      GTCGTGGCTATATCCTTCGTGTCACAGCGTACAAGGAGGGATATGGAGAAGGTTGCGTAA
flsynbt.fin   .C..C.....C.....G..C..G..C..C............C..C..C..G..C.....G.
bssyn         ------------------------------------------------------------

3060       3070       3080       3090       3100       3110
                   *          *          *          *          *          *
BTHKURHD      CCATTCATGAGATCGAGAACAATACAGACGAACTGAAGTTTAGCAACTGTGTAGAAGAGG
flsynbt.fin   ....C..C.............C..C.....G..C.....C........C..G..G....
bssyn         ------------------------------------------------------------

3120       3130       3140       3150       3160       3170
                   *          *          *          *          *          *
BTHKURHD      AAGTATATCCAAACAACACGGTAACGTGTAATGATTATACTGCGACTCAAGAAGAATATG
flsynbt.fin   .G..G..C..C........C..G..C..C..C..C..C..C..C..C..G..G..G...C.
bssyn         ------------------------------------------------------------

3180       3190       3200       3210       3220       3230
                   *          *          *          *          *          *
BTHKURHD      AGGGTACGTACACTTCTCGTAATCGAGGATATGACGGAGCCTATGAAAGCAATTCTTCTG
flsynbt.fin   ....C..C....CAGC..C..C..C..C..C.....C.....C..G.....CAGCAGC.
bssyn         ------------------------------------------------------------

3240       3250       3260       3270       3280       3290
                   *          *          *          *          *          *
BTHKURHD      TACCAGCTGATTATGCATCAGCCTATGAAGAAAAAGCATATACAGATGGACGAAGAGACA
flsynbt.fin   .G..C..C..C..C..CAGC.....C..G..G..G..C..C..C..C..C..CC.C....
bssyn         ------------------------------------------------------------

3300       3310       3320       3330       3340       3350
                   *          *          *          *          *          *
BTHKURHD      ATCCTTGTGAATCTAACAGAGGATATGGGGATTACACACCACTACCAGCTGGCTATGTGA
flsynbt.fin   .C..C..C..C..GAGC...C.C..C..C..C..C.....C..C..G..C..C.....C....
bssyn         ------------------------------------------------------------

3360       3370       3380       3390       3400       3410
                   *          *          *          *          *          *
BTHKURHD      CAAAAGAATTAGAGTACTTCCCAGAAACCGATAAGGTATGGATTGAGATCGGAGAAACGG
flsynbt.fin   .C..G..GC.G..........C..G.....C.....G.....C........C..G..C.
bssyn         ------------------------------------------------------------

3420       3430       3440       3450       3460
                   *          *          *          *          *
BTHKURHD      AAGGAACATTCATCGTGGACAGCGTGGAATTACTTCTTATGGAGGAATAA
flsynbt.fin   .G..C..C............GC.G..G..G........G..G
bssyn         ---------------------------------------...TG..G
```

Fig. 2A

```
             10        20        30        40        50        60
              *         *         *         *         *         *
BTHKURHD  ATGGATAACAATCCGAACATCAATGAATGCATTCCTTATAATTGTTTAAGTAACCCTGAA
bssyn     .....C.....C...C.........C...G.....C...C...C...C...CC.G...C.....C...G 70        80        90       100       110       120
              *         *         *         *         *         *
BTHKURHD  GTAGAAGTATTAGGTGGAGAAAGAATAGAAACTGGTTACACCCCAATCGATATTTCCTTG
bssyn     ..G...G...GC.G...C...C...GC.C...C...G...C...C.........C.....C..CAG.C...

130       140       150       160       170       180
              *         *         *         *         *         *
BTHKURHD  TCGCTAACGCAATTTCTTTTGAGTGAATTTGTTCCCGGTGCTGGATTTGTGTTAGGACTA
bssyn     AGC...G...C...G...C...GC....C...G...C...G.....C...C...C...C.G..C...G 190       200       210       220       230       240
              *         *         *         *         *         *
BTHKURHD  GTTGATATAATATGGGGAATTTTTGGTCCCTCTCAATGGGACGCATTTCTTGTACAAATT
bssyn     ..G...C...C...C.....C...C...C...C...AGC...G.........C...C...G...G...G...C 250       260       270       280       290       300
              *         *         *         *         *         *
BTHKURHD  GAACAGTTAATTAACCAAAGAATAGAAGAATTCGCTAGGAACCAAGCCATTTCTAGATTA
bssyn     ..G...C.G...C.....GC.C...C...G...G.....CC.C.....G.....CAGCC.CC.G 310       320       330       340       350       360
              *         *         *         *         *         *
BTHKURHD  GAAGGACTAAGCAATCTTTATCAAATTTACGCAGAATCTTTTAGAGAGTGGGAAGCAGAT
bssyn     ..G...C...G.....C..G...C......C...C...GAGC..CC.C.........G...C...C 370       380       390       400       410       420
              *         *         *         *         *         *
BTHKURHD  CCTACTAATCCAGCATTAAGAGAAGAGATGCGTATTCAATTCAATGACATGAACAGTGCC
bssyn     ..C...C...C...C...CC.GC.C...G.........C...C...G.....C.............C...

430       440       450       460       470       480
              *         *         *         *         *         *
BTHKURHD  CTTACAACCGCTATTCCTCTTTTTGCAGTTCAAAATTATCAAGTTCCTCTTTTATCAGTA
bssyn     ..G...C.....C...C...C...G...C...C...G...G...C...C...G...G...C...GC.GAGC...G 490       500       510       520       530       540
              *         *         *         *         *         *
BTHKURHD  TATGTTCAAGCTGCAAATTTACATTTATCAGTTTTGAGAGATGTTTCAGTGTTTGGACAA
bssyn     ..C...G...G...C...C...CC.G...CC.GAGC...GC...C.C...C...CAGC.....C..C...G 550       560       570       580       590       600
              *         *         *         *         *         *
BTHKURHD  AGGTGGGGATTTGATGCCGCGACTATCAATAGTCGTTATAATGATTTAACTAGGCTTATT
bssyn     C.C.....C...C...C.....C...C.....C...C...C...C...C...CC.G...CC.C..G...C 610       620       630       640       650       660
              *         *         *         *         *         *
BTHKURHD  GGCAACTATACAGATCATGCTGTACGCTGGTACAATACGGGATTAGAGCGTGTATGGGGA
bssyn     .........C...C...C...C...C...G...........C...C...CC.G.....C...G.....T 670       680       690       700       710       720
              *         *         *         *         *         *
BTHKURHD  CCGGATTCTAGAGATTGGATAAGATATAATCAATTTAGAAGAGAATTAACACTAACTGTA
bssyn     ..C...CAGCC.C...C.....C...G...C...G.....CC.CC.C..GC.G...C...G...G
```

Fig. 2B

```
                    730        740        750        760        770        780
                     *          *          *          *          *          *
BTHKURHD    TTAGATATCGTTTCTCTATTTCCGAACTATGATAGTAGAACGTATCCAATTCGAACAGTT
bssyn       C.G..C.....GAGC..G..C..C.....C..C..CC.C..C...C..C..C..C...G 790        800        810        820        830        840
                     *          *          *          *          *          *
BTHKURHD    TCCCAATTAACAAGAGAAATTTATACAAACCCAGTATTAGAAAATTTTGATGGTAGTTTT
bssyn       AG...GC.G..CC.C..G.....C..C.....C..GC.G..G..C..C..C..C..C 850        860        870        880        890        900
                     *          *          *          *          *          *
BTHKURHD    CGAGGCTCGGCTCAGGGCATAGAAGGAAGTATTAGGAGTCCACATTTGATGGATATACTT
bssyn       ..C...AGC..C........C..G..C..C..CC.C..C..C..CC.......C..C..G 910        920        930        940        950        960
                     *          *          *          *          *          *
BTHKURHD    AACAGTATAACCATCTATACGGATGCTCATAGAGGAGAATATTATTGGTCAGGGCATCAA
bssyn       .....C..C........C..C..C..C..CC.C..C..G..C..C...AGC..C..C..G 970        980        990        1000       1010       1020
                     *          *          *          *          *          *
BTHKURHD    ATAATGGCTTCTCCTGTAGGGTTTTCGGGGCCAGAATTCACTTTTCCGCTATATGGAACT
bssyn       ..C.....CAGC..C..C..C..CAGC..C..C..G.....C..C..G..C..C..C 1030       1040       1050       1060       1070       1080
                     *          *          *          *          *          *
BTHKURHD    ATGGGAAATGCAGCTCCACAACAACGTATTGTTGCTCAACTAGGTCAGGGCGTGTATAGA
bssyn       .....C..C..T..A..T..G..G..C..C..G..A..G..G..C.....A.....CC.C 1090       1100       1110       1120       1130       1140
                     *          *          *          *          *          *
BTHKURHD    ACATTATCGTCCACTTTATATAGAAGACCTTTTAATATAGGGATAAATAATCAACAACTA
bssyn       ..CC.GAGCAG...CC.G..CC.TC.......C..C..C..C..C..C..G..G..G 1150       1160       1170       1180       1190       1200
                     *          *          *          *          *          *
BTHKURHD    TCTGTTCTTGACGGGACAGAATTTGCTTATGGAACCTCCTCAAATTTGCCATCCGCTGTA
bssyn       AGC..G..G.....C..C..G..C..C..C..C...AG.AGC..CC....CAG...C..G 1210       1220       1230       1240       1250       1260
                     *          *          *          *          *          *
BTHKURHD    TACAGAAAAAGCGGAACGGTAGATTCGCTGGATGAAATACCGCCACAGAATAACAACGTG
bssyn       ...C.C..G.....C..C..G..CAGC.....C..G..C..C..T.....C.........

1270       1280       1290       1300       1310       1320
                     *          *          *          *          *          *
BTHKURHD    CCACCTAGGCAAGGATTTAGTCATCGATTAAGCCATGTTTCAATGTTTCGTTCAGGCTTT
bssyn       ......C.A..G..C..C..C..C...TC.G.....C..GAGC.....C..CAGT.....C 1330       1340       1350       1360       1370       1380
                     *          *          *          *          *          *
BTHKURHD    AGTAATAGTAGTGTAAGTATAATAAGAGCTCCTATGTTCTCTTGGATACATCGTAGTGCT
bssyn       ..C..C..C..C..G..C..C..CC.T..A.........AGC.....T..C..C.....C 1390       1400       1410       1420       1430
                     *          *          *          *          *
BTHKURHD    GAATTTAATAATATAATTCCTTCATCA--CAAATTACACAAATACCTTTAACAAAATCTA
bssyn       ..G..C..C..C..C..C..C..--..G..GC..G..C..C..G..C..CC.G..C..GAGC.
```

Fig. 2C

```
               1440      1450      1460      1470      1480      1490
                  *         *         *         *         *         *
BTHKURHD    CTAATCTTGGCTCTGGAACTTCTGTCGTTAAAGGACCAGGATTTACAGGAGGAGATATTC
bssyn       .C..C..G...AGC..C..CAGC..G..G..G..C..C..C..C..C..C..C..C..C.

1500      1510      1520      1530      1540      1550
                  *         *         *         *         *         *
BTHKURHD    TTCGAAGAACTTCACCTGGCCAGATTTCAACCTTAAGAGTAAATATTACTGCACCATTAT
bssyn       .G..CC.C..CAGC..C........CAGC...C.GC.C..G..C..C..C..C..CC.GA 1560      1570      1580      1590      1600      1610
                  *         *         *         *         *         *
BTHKURHD    CACAAAGATATCGGGTAAGAATTCGCTACGCTTCTACCACAAATTTACAATTCCATACAT
bssyn       GC..GC.C..C..C..CC.C..C........CAGC.....C..CC.G..G.....C..CA 1620      1630      1640      1650      1660      1670
                  *         *         *         *         *         *
BTHKURHD    CAATTGACGGAAGACCTATTAATCAGGGGAATTTTTCAGCAACTATGAGTAGTGGAGTA
bssyn       GC..C.....CC.C..C..C..C.....C..C..CAGC..C..C.....C..C..C..C.

1680      1690      1700      1710      1720      1730
                  *         *         *         *         *         *
BTHKURHD    ATTTACAGTCCGGAAGCTTTAGGACTGTAGGTTTTACTACTCCGTTTAACTTTTCAAATG
bssyn       .CC.G...AG...C.....CC.C..C..G..C..C..C..C..C..C.....CAGC..C.

1740      1750      1760      1770      1780      1790
                  *         *         *         *         *         *
BTHKURHD    GATCAAGTGTATTTACGTTAAGTGCTCATGTCTTCAATTCAGGCAATGAAGTTTATATAG
bssyn       .CAGC..C..G..C..CC.G..C..C..C..G.....CAGC.....C..G..G..C..C.

1800      1810      1820      1830      1840      1850
                  *         *         *         *         *         *
BTHKURHD    ATCGAATTGAATTTGTTCCGGCAGAAGTAACCTTTGAGGCAGAATATGATTTAGAAAGAG
bssyn       .C..C..C..G..C..G..C..C..G..G.....C.....C..G..C..CC.G..G..G.

1860      1870      1880      1890      1900      1910
                  *         *         *         *         *         *
BTHKURHD    CACAAAAGGCGGTGAATGAGCTGTTTACTTCTTCCAATCAAATCGGGTTAAAAACAGATG
bssyn       .T..G.....C.....C........C..CAGCAG...C..G.....CC.G..G..C..C.

1920      1930      1940
                  *         *         *
BTHKURHD    TGACGGATTATCATATTGATCAAGTATCC
bssyn       ....C..C..C..C..C.....G..G.AG
```

Fig. 3A

```
                    10         20         30         40         50         60
                     *          *          *          *          *          *
syn1T.mze   ATGGACAACAACCCCAACATCAACGAGTGCATCCCCTACAACTGCCTGAGCAACCCCGAG
bssyn       ............................................................
synful.mod  ............................................................

70         80         90        100        110        120
                     *          *          *          *          *          *
syn1T.mze   GTGGAGGTGCTGGGCGGCGAGCGCATCGAGACCGGCTACACCCCCATCGACATCAGCCTG
bssyn       ............................................................
synful.mod  ............................................................

130        140        150        160        170        180
                     *          *          *          *          *          *
syn1T.mze   AGCCTGACCCAGTTCCTGCTGAGCGAGTTCGTGCCCGGCGCCGGCTTCGTGCTGGGCCTG
bssyn       ............................................................
synful.mod  ............................................................

190        200        210        220        230        240
                     *          *          *          *          *          *
syn1T.mze   GTGGACATCATCTGGGGCATCTTCGGCCCCAGCCAGTGGGACGCCTTCCTGGTGCAGATC
bssyn       ............................................................
synful.mod  ............................................................

250        260        270        280        290        300
                     *          *          *          *          *          *
syn1T.mze   GAGCAGCTGATCAACCAGCGCATCGAGGAGTTCGCCCGCAACCAGGCCATCAGCCGCCTG
bssyn       ............................................................
synful.mod  ............................................................

310        320        330        340        350        360
                     *          *          *          *          *          *
syn1T.mze   GAGGGCCTGAGCAACCTGTACCAGATCTACGCCGAGAGCTTCCGCGAGTGGGAGGCCGAC
bssyn       ............................A...............................
synful.mod  ............................A...............................

370        380        390        400        410        420
                     *          *          *          *          *          *
syn1T.mze   CCCACCAACCCCGCCCTGCGCGAGGAGATGCGCATCCAGTTCAACGACATGAACAGCGCC
bssyn       ............................................................
synful.mod  ............................................................

430        440        450        460        470        480
                     *          *          *          *          *          *
syn1T.mze   CTGACCACCGCCATCCCCCTGTTCGCCGTGCAGAACTACCAGGTGCCCCTGCTGAGCGTG
bssyn       ............................................................
synful.mod  ............................................................

490        500        510        520        530        540
                     *          *          *          *          *          *
syn1T.mze   TACGTGCAGGCCGCCAACCTGCACCTGAGCGTGCTGCGCGACGTGAGCGTGTTCGGCCAG
bssyn       ..................................C.........................
synful.mod  ..................................C.........................

550        560        570        580        590        600
                     *          *          *          *          *          *
syn1T.mze   CGCTGGGGCTTCGACGCCGCCACCATCAACAGCCGCTACAACGACCTGACCCGCCTGATC
bssyn       ............................................................
synful.mod  ............................................................
```

Fig. 3B

```
                       610        620        630        640        650        660
                        *          *          *          *          *          *
syn1T.mze      GGCAACTACACCGACCACGCCGTGCGCTGGTACAACACCGGCCTGGAGCGCGTGTGGGGC
bssyn          ............................................................T
synful.mod     ............................................................T 670        680        690        700        710        720
                        *          *          *          *          *          *
syn1T.mze      CCCGACAGCCGCGACTGGATCCGCTACAACCAGTTCCGCCGCGAGCTGACCCTGACCGTG
bssyn          .....................A..G..................................
synful.mod     .....................A..G..................................

730        740        750        760        770        780
                        *          *          *          *          *          *
syn1T.mze      CTGGACATCGTGAGCCTGTTCCCCAACTACGACAGCCGCACCTACCCCATCCGCACCGTG
bssyn          ............................................................
synful.mod     ............................................................

790        800        810        820        830        840
                        *          *          *          *          *          *
syn1T.mze      AGCCAGCTGACCCGCGAGATCTACACCAACCCCGTGCTGGAGAACTTCGACGGCAGCTTC
bssyn          ....................T.......................................
synful.mod     ....................T.......................................

850        860        870        880        890        900
                        *          *          *          *          *          *
syn1T.mze      CGCGGCAGCGCCCAGGGCATCGAGGGCAGCATCCGCAGCCCCCACCTGATGGACATCCTG
bssyn          ............................................................
synful.mod     ............................................................

910        920        930        940        950        960
                        *          *          *          *          *          *
syn1T.mze      AACAGCATCACCATCTACACCGACGCCCACCGCGGCGAGTACTACTGGAGCGGCCACCAG
bssyn          ............................................................
synful.mod     ............................................................

970        980        990        1000       1010       1020
                        *          *          *          *          *          *
syn1T.mze      ATCATGGCCAGCCCCGTGGGCTTCAGCGGCCCCGAGTTCACCTTCCCCCTGTACGGCACC
bssyn          ..................C.........................................
synful.mod     ..................C.........................................

1030       1040       1050       1060       1070       1080
                        *          *          *          *          *          *
syn1T.mze      ATGGGCAACGCCGCCCCCAGCAGCGCATCGTGGCCCAGCTGGGCCAGGGCGTGTACCGC
bssyn          ............T..A..T.................A...............A........
synful.mod     ............T..A..T.................A...............A........

1090       1100       1110       1120       1130       1140
                        *          *          *          *          *          *
syn1T.mze      ACCCTGAGCAGCACCCTGTACCGCCGCCCCTTCAACATCGGCATCAACAACCAGCAGCTG
bssyn          ....................T..A..T.................................
synful.mod     ....................T..A..T.................................

1150       1160       1170       1180       1190       1200
                        *          *          *          *          *          *
syn1T.mze      AGCGTGCTGGACGGCACCGAGTTCGCCTACGGCACCAGCAGCAACCTGCCCAGCGCCGTG
bssyn          ............................................................
synful.mod     ............................................................
```

Fig. 3C

```
              1210      1220      1230      1240      1250      1260
                *         *         *         *         *         *
syn1T.mze   TACCGCAAGAGCGGCACCGTGGACAGCCTGGACGAGATCCCCCCCCAGAACAACAACGTG
bssyn       ..........................................T...............
synful.mod  ..........................................T...............

1270      1280      1290      1300      1310      1320
                *         *         *         *         *         *
syn1T.mze   CCCCCCCGCCAGGGCTTCAGCCACCGCCTGAGCCACGTGAGCATGTTCCGCAGCGGCTTC
bssyn       ..A..T..A...................T..........................T......
synful.mod  ..A..T..A...................T..........................T......

1330      1340      1350      1360      1370      1380
                *         *         *         *         *         *
syn1T.mze   AGCAACAGCAGCGTGAGCATCATCCGCGCCCCCATGTTCAGCTGGATCCACCGCAGCGCC
bssyn       ..................T..A..T.............T.........T...
synful.mod  ..................T..A..T.............T.........T...

1390      1400      1410      1420      1430      1440
                *         *         *         *         *         *
syn1T.mze   GAGTTCAACAACATCATCCCCAGCAGCCAGATCACCCAGATCCCCCTGACCAAGAGCACC
bssyn       ............................................................
synful.mod  ............................................................

1450      1460      1470      1480      1490      1500
                *         *         *         *         *         *
syn1T.mze   AACCTGGGCAGCGGCACCAGCGTGGTGAAGGGCCCCGGCTTCACCGGCGGCGACATCCTG
bssyn       ............................................................
synful.mod  ............................................................

1510      1520      1530      1540      1550      1560
                *         *         *         *         *         *
syn1T.mze   CGCCGCACCAGCCCCGGCCAGATCAGCACCCTGCGCGTGAACATCACCGCCCCCCTGAGC
bssyn       ............................................................
synful.mod  ............................................................

1570      1580      1590      1600      1610      1620
                *         *         *         *         *         *
syn1T.mze   CAGCGCTACCGCGTGCGCATCCGCTACGCCAGCACCACCAACCTGCAGTTCCACACCAGC
bssyn       ..............C.............................................
synful.mod  ..............C.............................................

1630      1640      1650      1660      1670      1680
                *         *         *         *         *         *
syn1T.mze   ATCGACGGCCGCCCCATCAACCAGGGCAACTTCAGCGCCACCATGAGCAGCGGCAGCAAC
bssyn       ............................................................
synful.mod  ............................................................

1690      1700      1710      1720      1730      1740
                *         *         *         *         *         *
syn1T.mze   CTGCAGAGCGGCAGCTTCCGCACCGTGGGCTTCACCACCCCCTTCAACTTCAGCAACGGC
bssyn       ............................................................
synful.mod  ............................................................

1750      1760      1770      1780      1790      1800
                *         *         *         *         *         *
syn1T.mze   AGCAGCGTGTTCACCCTGAGCGCCCACGTGTTCAACAGCGGCAACGAGGTGTACATCGAC
bssyn       ............................................................
synful.mod  ............................................................
```

Fig. 3D

```
                    1810       1820       1830       1840       1850       1860
                     *          *          *          *          *          *
syn1T.mze   CGCATCGAGTTCGTGCCCGCCGAGGTGACCTTCGAGGCCGAGTACGACCTGGAGCGCGCC
bssyn       ................................................A.G..T
synful.mod  ................................................A.G..T 1870       1880       1890       1900       1910       1920
                     *          *          *          *          *          *
syn1T.mze   CAGAAGGCCGTGAACGAGCTGTTCACCAGCAGCAACCAGATCGGCCTGAAGACCGACGTG
bssyn       ............................................................
synful.mod  ............................................................

1930       1940       1950       1960       1970       1980
                     *          *          *          *          *          *
syn1T.mze   ACCGACTACCACATCGACCAGGTGAGCAACCTGGTGGAGTGCCTGAGCGACGAGTTCTGC
bssyn       ..................T.....------------------------------------
synful.mod  ..................T.........................................

1990       2000       2010       2020       2030       2040
                     *          *          *          *          *          *
syn1T.mze   CTGGACGAGAAGAAGGAGCTGAGCGAGAAGGTGAAGCACGCCAAGCGCCTGAGCGACGAG
bssyn       ------------------------------------------------------------
synful.mod  ............................................................

2050       2060       2070       2080       2090       2100
                     *          *          *          *          *          *
syn1T.mze   CGCAACCTGCTGCAGGACCCCAACTTCCGCGGCATCAACCGCCAGCTGGACCGCGGCTGG
bssyn       ------------------------------------------------------------
synful.mod  ............................................................

2110       2120       2130       2140       2150       2160
                     *          *          *          *          *          *
syn1T.mze   CGCGGCAGCACCGACATCACCATCCAGGGCGGCGACGACGTGTTCAAGGAGAACTACGTG
bssyn       ------------------------------------------------------------
synful.mod  ............................................................

2170       2180       2190       2200       2210       2220
                     *          *          *          *          *          *
syn1T.mze   ACCCTGCTGGGCACCTTCGACGAGTGCTACCCCACCTACCTGTACCAGAAGATCGACGAG
bssyn       ------------------------------------------------------------
synful.mod  ............................................................

2230       2240       2250       2260       2270       2280
                     *          *          *          *          *          *
syn1T.mze   AGCAAGCTGAAGGCCTACACCCGCTACCAGCTGCGCGGCTACATCGAGGACAGCCAGGAC
bssyn       ------------------------------------------------------------
synful.mod  ............................................................

2290       2300       2310       2320       2330       2340
                     *          *          *          *          *          *
syn1T.mze   CTGGAGATCTACCTGATCCGCTACAACGCCAAGCACGAGACCGTGAACGTGCCCGGCACC
bssyn       ------------------------------------------------------------
synful.mod  ............................................................

2350       2360       2370       2380       2390       2400
                     *          *          *          *          *          *
syn1T.mze   GGCAGCCTGTGGCCCCTGAGCGCCCCCAGCCCCATCGGCAAGTGCGCCCACCACAGCCAC
bssyn       ------------------------------------------------------------
synful.mod  ............................................................
```

Fig. 3E

```
                    2410      2420      2430      2440      2450      2460
                      *         *         *         *         *         *
syn1T.mze    CACTTCAGCCTGGACATCGACGTGGGCTGCACCGACCTGAACGAGGACCTGGGCGTGTGG
bssyn        ------------------------------------------------------------
synful.mod   ............................................................

2470      2480      2490      2500      2510      2520
                      *         *         *         *         *         *
syn1T.mze    GTGATCTTCAAGATCAAGACCCAGGACGGCCACGCCCGCCTGGGCAACCTGGAGTTCCTG
bssyn        ------------------------------------------------------------
synful.mod   ............................................................

2530      2540      2550      2560      2570      2580
                      *         *         *         *         *         *
syn1T.mze    GAGGAGAAGCCCCTGGTGGGCGAGGCCCTGGCCCGCGTGAAGCGCGCCGAGAAGAAGTGG
bssyn        ------------------------------------------------------------
synful.mod   ............................................................

2590      2600      2610      2620      2630      2640
                      *         *         *         *         *         *
syn1T.mze    CGCGACAAGCGCGAGAAGCTGGAGTGGGAGACCAACATCGTGTACAAGGAGGCCAAGGAG
bssyn        ------------------------------------------------------------
synful.mod   ............................................................

2650      2660      2670      2680      2690      2700
                      *         *         *         *         *         *
syn1T.mze    AGCGTGGACGCCCTGTTCGTGAACAGCCAGTACGACCGCCTGCAGGCCGACACCAACATC
bssyn        ------------------------------------------------------------
synful.mod   ............................................................

2710      2720      2730      2740      2750      2760
                      *         *         *         *         *         *
syn1T.mze    GCCATGATCCACGCCGCCGACAAGCGCGTGCACAGCATCCGCGAGGCCTACCTGCCCGAG
bssyn        ------------------------------------------------------------
synful.mod   ...............................T............................

2770      2780      2790      2800      2810      2820
                      *         *         *         *         *         *
syn1T.mze    CTGAGCGTGATCCCCGGCGTGAACGCCGCCATCTTCGAGGAGCTGGAGGGCCGCATCTTC
bssyn        ------------------------------------------------------------
synful.mod   ............................................................

2830      2840      2850      2860      2870      2880
                      *         *         *         *         *         *
syn1T.mze    ACCGCCTTCAGCCTGTACGACGCCCGCAACGTGATCAAGAACGGCGACTTCAACAACGGC
bssyn        ------------------------------------------------------------
synful.mod   ............................................................

2890      2900      2910      2920      2930      2940
                      *         *         *         *         *         *
syn1T.mze    CTGAGCTGCTGGAACGTGAAGGGCCACGTGGACGTGGAGGAGCAGAACAACCACCGCAGC
bssyn        ------------------------------------------------------------
synful.mod   ............................................................

2950      2960      2970      2980      2990      3000
                      *         *         *         *         *         *
syn1T.mze    GTGCTGGTGGTGCCCGAGTGGGAGGCCGAGGTGAGCCAGGAGGTGCGCGTGTGCCCCGGC
bssyn        ------------------------------------------------------------
synful.mod   ............................................................
```

Fig. 3F

```
                    3010       3020       3030       3040       3050       3060
                      *          *          *          *          *          *
syn1T.mze   CGCGGCTACATCCTGCGCGTGACCGCCTACAAGGAGGGCTACGGCGAGGGCTGCGTGACC
bssyn       ------------------------------------------------------------
synful.mod  ............................................................

3070       3080       3090       3100       3110       3120
                      *          *          *          *          *          *
syn1T.mze   ATCCACGAGATCGAGAACAACACCGACGAGCTGAAGTTCAGCAACTGCGTGGAGGAGGAG
bssyn       ------------------------------------------------------------
synful.mod  ..................................C.........................

3130       3140       3150       3160       3170       3180
                      *          *          *          *          *          *
syn1T.mze   GTGTACCCCAACAACACCGTGACCTGCAACGACTACACCGCCACCCAGGAGGAGTACGAG
bssyn       ------------------------------------------------------------
synful.mod  ............................................................

3190       3200       3210       3220       3230       3240
                      *          *          *          *          *          *
syn1T.mze   GGCACCTACACCAGCCGCAACCGCGGCTACGACGGCGCCTACGAGAGCAACAGCAGCGTG
bssyn       ------------------------------------------------------------
synful.mod  ............................................................

3250       3260       3270       3280       3290       3300
                      *          *          *          *          *          *
syn1T.mze   CCCGCCGACTACGCCAGCGCCTACGAGGAGAAGGCCTACACCGACGGCCGCCGCGACAAC
bssyn       ------------------------------------------------------------
synful.mod  ............................................................

3310       3320       3330       3340       3350       3360
                      *          *          *          *          *          *
syn1T.mze   CCCTGCGAGAGCAACCGCGGCTACGGCGACTACACCCCCCTGCCCGCCGGCTACGTGACC
bssyn       ------------------------------------------------------------
synful.mod  ............................................................

3370       3380       3390       3400       3410       3420
                      *          *          *          *          *          *
syn1T.mze   AAGGAGCTGGAGTACTTCCCCGAGACCGACAAGGTGTGGATCGAGATCGGCGAGACCGAG
bssyn       ------------------------------------------------------------
synful.mod  ............................................................

3430       3440       3450       3460
                      *          *          *          *
syn1T.mze   GGCACCTTCATCGTGGACAGCGTGGAGCTGCTGCTGATGGAGGAGTAG
bssyn       ------------------------------------------------....
synful.mod  ................................................
```

Fig. 4A

```
                   10        20        30        40        50        60
                    *         *         *         *         *         *
BTHKURHD   ATGGATAACAATCCGAACATCAATGAATGCATTCCTTATAATTGTTTAAGTAACCCTGAA
PMONBT     .....C.....C..A........C...........A..C..C..C..G........A...
bssyn      .....C.....C..C........C..G.....C..C..C..C..CC.G..C.....C..G 70        80        90       100       110       120
                    *         *         *         *         *         *
BTHKURHD   GTAGAAGTATTAGGTGGAGAAAGAATAGAAACTGGTTACACCCCAATCGATATTTCCTTG
PMONBT     ..T......C.T.........C.C..T.....C........T..C.....C..C......
bssyn      ..G..G..GC.G..C..C..GC.C..C..G..C..C........C.....C..CAG.C..

130       140       150       160       170       180
                    *         *         *         *         *         *
BTHKURHD   TCGCTAACGCAATTTCTTTTGAGTGAATTTGTTCCCGGTGCTGGATTTGTGTTAGGACTA
PMONBT     ..CT.G..A..G.....GC.C..C..G..C..G..A........G..C..TC.C......
bssyn      AGC..G..C..G..C..GC....C..G..C..G.....C..C..C..C...C.G..C..G 190       200       210       220       230       240
                    *         *         *         *         *         *
BTHKURHD   GTTGATATAATATGGGGAATTTTTGGTCCCTCTCAATGGGACGCATTTCTTGTACAAATT
PMONBT     .....C..C..C.....T..C........A...........T.....C..G..G......
bssyn      ..G..C..C..C.....C..C..C..C...AGC..G........C..C..G..G..G..C 250       260       270       280       290       300
                    *         *         *         *         *         *
BTHKURHD   GAACAGTTAATTAACCAAAGAATAGAAGAATTCGCTAGGAACCAAGCCATTTCTAGATTA
PMONBT     ..G.....G..C.....G..G..C.....G.....C........G.....C.....G..G
bssyn      ..G...C.G..C.....GC.C..C..G..G.....CC.C.....G.....CAGCC.CC.G 310       320       330       340       350       360
                    *         *         *         *         *         *
BTHKURHD   GAAGGACTAAGCAATCTTTATCAAATTTACGCAGAATCTTTTAGAGAGTGGGAAGCAGAT
PMONBT     ......T.G........C..C.....C..T.....GAGC..C..............C...
bssyn      ..G..C..G.....C..G..C.....C.....C..GAGC..CC.C........G..C..C 370       380       390       400       410       420
                    *         *         *         *         *         *
BTHKURHD   CCTACTAATCCAGCATTAAGAGAAGAGATGCGTATTCAATTCAATGACATGAACAGTGCC
PMONBT     ........C.....TC.CC.C..G..A.................C...........C...
bssyn      ..C..C..C..C..CC.GC.C..G........C..C..G.....C...........C...

430       440       450       460       470       480
                    *         *         *         *         *         *
BTHKURHD   CTTACAACCGCTATTCCTCTTTTTGCAGTTCAAAATTATCAAGTTCCTCTTTTATCAGTA
PMONBT     T.G..C..A.....C..AT.G..C.....C..G..C..C...........C..G..C..G
bssyn      ..G..C.....C..C..C..G..C..C..G..G..C..C..G..G..C..GC.GAGC..G 490       500       510       520       530       540
                    *         *         *         *         *         *
BTHKURHD   TATGTTCAAGCTGCAAATTTACATTTATCAGTTTTGAGAGATGTTTCAGTGTTTGGACAA
PMONBT     ..C........A..T...C.T..CC.CAGC..GC.TC....C...AGC........G...
bssyn      ..C..G..G..C..C..CC.G..CC.GAGC..GC..C.C..C..CAGC.....C..C..G 550       560       570       580       590       600
                    *         *         *         *         *         *
BTHKURHD   AGGTGGGGATTTGATGCCGCGACTATCAATAGTCGTTATAATGATTTAACTAGGCTTATT
PMONBT     ...........C.....T..A..C........C.....C..C..CC.T........G...
bssyn      C.C.....C..C..C.....C..C.....C..C..C..C..C..CC.G..CC.C..G..C
```

Fig. 4B

```
                       610       620       630       640       650       660
                         *         *         *         *         *         *
BTHKURHD      GGCAACTATACAGATCATGCTGTACGCTGGTACAATACGGGATTAGAGCGTGTATGGGGA
PMONBT        ..A.....C..C..C..C.....T..T........C..T..C..G........C.....T
bssyn         ........C..C..C..C..C..G...........C..C..CC.G.....C..G.....T 670       680       690       700       710       720
                         *         *         *         *         *         *
BTHKURHD      CCGGATTCTAGAGATTGGATAAGATATAATCAATTTAGAAGAGAATTAACACTAACTGTA
PMONBT        ..T.................T.....C..C..G..C..G........G..C..C..A..T
bssyn         ..C..CAGCC.C..C.....C..G..C..C..G..CC.CC.C..GC.G..C..G..C..G 730       740       750       760       770       780
                         *         *         *         *         *         *
BTHKURHD      TTAGATATCGTTTCTCTATTTCCGAACTATGATAGTAGAACGTATCCAATTCGAACAGTT
PMONBT        ..G..C..T..G.....C..C...........CTCC.....C..C..T..C..T.....G
bssyn         C.G..C.....GAGC..G..C..C.....C..C..CC.C..C..C..C..C..C..C..G 790       800       810       820       830       840
                         *         *         *         *         *         *
BTHKURHD      TCCCAATTAACAAGAGAAATTTATACAAACCCAGTATTAGAAAATTTTGATGGTAGTTTT
PMONBT        ......C.T..C........C.....T........TC.T..G..C..C..C.....C..C
bssyn         AG...GC.G..CC.C..G.....C..C.....C..GC.G..G..C..C..C..C..C..C 850       860       870       880       890       900
                         *         *         *         *         *         *
BTHKURHD      CGAGGCTCGGCTCAGGGCATAGAAGGAAGTATTAGGAGTCCACATTTGATGGATATACTT
PMONBT        ..T..T..T..C..A..T..C.....CTCC..C.....C.....C........C..CT.G
bssyn         ..C...AGC..C........C..G..C..C..CC.C..C..C..CC.......C..C..G 910       920       930       940       950       960
                         *         *         *         *         *         *
BTHKURHD      AACAGTATAACCATCTATACGGATGCTCATAGAGGAGAATATTATTGGTCAGGGCATCAA
PMONBT        .....C.....T.....C.GC........C........G.....C.....T..A..C..G
bssyn         .....C..C........C..C..C..C..CC.C..C..G..C..C...AGC..C..C..G 970       980       990      1000      1010      1020
                         *         *         *         *         *         *
BTHKURHD      ATAATGGCTTCTCCTGTAGGGTTTTCGGGGCCAGAATTCACTTTTCCGCTATATGGAACT
PMONBT        ..C.....C.....A..T..A..CAGC.....C..G..T..C.....T..C.........
bssyn         ..C.....CAGC..C..C..C..CAGC..C..C..G.....C..C..C..G..C..C..C 1030      1040      1050      1060      1070      1080
                         *         *         *         *         *         *
BTHKURHD      ATGGGAAATGCAGCTCCACAACAACGTATTGTTGCTCAACTAGGTCAGGGCGTGTATAGA
PMONBT        ........C..C.................C....................T..C..C...
bssyn         .....C..C..T..A..T..G..G..C..C..G..A..G..G..C.....A.....CC.C 1090      1100      1110      1120      1130      1140
                         *         *         *         *         *         *
BTHKURHD      ACATTATCGTCCACTTTATATAGAAGACCTTTTAATATAGGGATAAATAATCAACAACTA
PMONBT        ..C..G..T.....C..G..C........C..C.....C..T..C..C..C..G.....T
bssyn         ..CC.GAGCAG...CC.G..CC.TC.......C..C..C..C..C..C..C..G..G..G 1150      1160      1170      1180      1190      1200
                         *         *         *         *         *         *
BTHKURHD      TCTGTTCTTGACGGGACAGAATTTGCTTATGGAACCTCCTCAAATTTGCCATCCGCTGTA
PMONBT        ..C...........A.....G..C..C...........T..T..C..............T
bssyn         AGC..G..G.....C..C..G..C..C..C..C...AG.AGC..CC....CAG...C..G
```

Fig. 4C

```
                      1210       1220       1230       1240       1250       1260
                        *          *          *          *          *          *
BTHKURHD   TACAGAAAAAGCGGAACGGTAGATTCGCTGGATGAAATACCGCCACAGAATAACAACGTG
PMONBT     .........G.......C..T.....CT.....C.....C..A.........C.....T...
bssyn      ...C..C..G.....C..C..G..CAGC.....C..G..C..C..T.....C..........

1270       1280       1290       1300       1310       1320
                        *          *          *          *          *          *
BTHKURHD   CCACCTAGGCAAGGATTTAGTCATCGATTAAGCCATGTTTCAATGTTTCGTTCAGGCTTT
PMONBT     .....C............CTCC..CA.G..G.....C..G..C.....C.....C..A..C
bssyn     ......C..A..G..C..C..C..C..TC.G.....C..GAGC.....C..CAGT.....C 1330       1340       1350       1360       1370       1380
                        *          *          *          *          *          *
BTHKURHD   AGTAATAGTAGTGTAAGTATAATAAGAGCTCCTATGTTCTCTTGGATACATCGTAGTGCT
PMONBT     ..C..C...TCC..G..C..C..C.................A.....T..C.........
bssyn      ..C..C..C..C..G..C..C..CC.T..A.........AGC.....T..C..C.....C 1390       1400       1410       1420       1430
                        *          *          *          *          *
BTHKURHD   GAATTTAATAATATAATTCCTTCATCA  CAAATTACACAAATACCTTTAACAAAATCTA
PMONBT     ..G..C..C.....C.........C..T.....C..C.....C..A..G..C..G....
bssyn      ..G..C..C..C..C..C..   ..G...GC..G..C..C..G..C..CC.G..C..GAGC.

1440       1450       1460       1470       1480       1490
                        *          *          *          *          *          *
BTHKURHD   CTAATCTTGGCTCTGGAACTTCTGTCGTTAAAGGACCAGGATTTACAGGAGGAGATATTC
PMONBT     ....C.....A.................G...........C..C.......T.......
bssyn      .C..C..G...AGC..C..CAGC..G..G..G..C..C..C..C..C..C..C..C..C.

1500       1510       1520       1530       1540       1550
                        *          *          *          *          *          *
BTHKURHD   TTCGAAGAACTTCACCTGGCCAGATTTCAACCTTAAGAGTAAATATTACTGCACCATTAT
PMONBT     ..A........T.........AGC...C.C.....T..C..C...........C.T.
bssyn      .G..CC.C..CAGC..C.......CAGC...C.GC.C..G..C.....C..C..CC.GA 1560       1570       1580       1590       1600       1610
                        *          *          *          *          *          *
BTHKURHD   CACAAAGATATCGGGTAAGAATTCGCTACGCTTCTACCACAAATTTACAATTCCATACAT
PMONBT     .T.........T..C..G.....T......A.........T..C..G.........C..C.
bssyn      GC..GC.C..C..C..CC.C..C.........CAGC.....C..CC.G..G.....C..CA 1620       1630       1640       1650       1660       1670
                        *          *          *          *          *          *
BTHKURHD   CAATTGACGGAAGACCTATTAATCAGGGGAATTTTTCAGCAACTATGAGTAGTGGGAGTA
PMONBT     .C..C........G.....C.........T..C..C.....C....TCA...C..C..C.
bssyn      GC..C.....CC.C..C..C..C.....C..C..CAGC..C..C.....C..C..C..C.

1680       1690       1700       1710       1720       1730
                        *          *          *          *          *          *
BTHKURHD   ATTTACAGTCCGGAAGCTTTAGGACTGTAGGTTTTACTACTCCGTTTAACTTTTTCAAATG
PMONBT     .C..G..A.....C....C..A..C..C.....C.......T..C.....C..T..C.
bssyn      .CC.G...AG...C.....CC.C..C..G..C..C..C..C..C.....CAGC...C.

1740       1750       1760       1770       1780       1790
                        *          *          *          *          *          *
BTHKURHD   GATCAAGTGTATTTACGTTAAGTGCTCATGTCTTCAATTCAGGCAATGAAGTTTATATAG
PMONBT     .........C...T..C..CC.T..C.........G........T...........G..C..T.
bssyn      .CAGC..C..G..C..CC.G..C..C..C..G.....CAGC.....C..G..G..C..C.
```

Fig. 4D

```
                 1800       1810       1820       1830       1840
                   *          *          *          *          *
BTHKURHD    ATCGAATTGAATTTGTTCCGGCAGAAGTAACCTTTGAGGCAGAATA---------------
PMONBT      .C..T.....G.....G..T..C.....T......C.....T..G..---------------
bssyn       .C..C..C..G..C..G..C..C..G..G.....C.....C..G...CGACCTGGAGAGGG BTHKURHD    ----------------------------------------------------------------
PMONBT      ----------------------------------------------------------------
bssyn       CTCAGAAGGCCGTGAACGAGCTGTTCACCAGCAGCAACCAGATCGGCCTGAAGACCGACG BTHKURHD    ----------------------------T
PMONBT      ----------------------------C
bssyn       TGACCGACT

Fig. 5A

```
                   10        20        30        40        50        60
                    *         *         *         *         *         *
PMONBT     ATGGACAACAACCCAAACATCAACGAATGCATTCCATACAACTGCTTGAGTAACCCAGAA
bssyn      ..............C...........G.....C..C.........C....C.....C..G 70        80        90       100       110       120
                    *         *         *         *         *         *
PMONBT     GTTGAAGTACTTGGTGGAGAACGCATTGAAACCGGTTACACTCCCATCGACATCTCCTTG
bssyn      ..G..G..G..G..C..C..G.....C..G.....C.....C.............AG.C..

130       140       150       160       170       180
                    *         *         *         *         *         *
PMONBT     TCCTTGACACAGTTTCTGCTCAGCGAGTTCGTGCCAGGTGCTGGGTTCGTTCTCGGACTA
bssyn      AG.C....C.....C.....G..............C..C..C..C.....G..G..C..G 190       200       210       220       230       240
                    *         *         *         *         *         *
PMONBT     GTTGACATCATCTGGGGTATCTTTGGTCCATCTCAATGGGATGCATTCCTGGTGCAAATT
bssyn      ..G..............C.....C..C..CAGC..G.....C..C...........G..C 250       260       270       280       290       300
                    *         *         *         *         *         *
PMONBT     GAGCAGTTGATCAACCAGAGGATCGAAGAGTTCGCCAGGAACCAGGCCATCTCTAGGTTG
bssyn      ......C...........C.C.....G.........C.C............AGCC.CC..

310       320       330       340       350       360
                    *         *         *         *         *         *
PMONBT     GAAGGATTGAGCAATCTCTACCAAATCTATGCAGAGAGCTTCAGAGAGTGGGAAGCCGAT
bssyn      ..G..CC.......C..G...........C..C.........C.C........G.....C 370       380       390       400       410       420
                    *         *         *         *         *         *
PMONBT     CCTACTAACCCAGCTCTCCGCGAGGAAATGCGTATTCAATTCAACGACATGAACAGCGCC
bssyn      ..C..C.....C..C..G........G.....C..C..G.....................

430       440       450       460       470       480
                    *         *         *         *         *         *
PMONBT     TTGACCACAGCTATCCCATTGTTCGCAGTCCAGAACTACCAAGTTCCTCTCTTGTCCGTG
bssyn      C.......C..C.....CC.......C..G...........G..G..C..GC..AG....

490       500       510       520       530       540
                    *         *         *         *         *         *
PMONBT     TACGTTCAAGCAGCTAATCTTCACCTCAGCGTGCTTCGAGACGTTAGCGTGTTTGGGCAA
bssyn      .....G..G..C..C..C..G.....G........G..C.....C........C..C..G 550       560       570       580       590       600
                    *         *         *         *         *         *
PMONBT     AGGTGGGGATTCGATGCTGCAACCATCAATAGCCGTTACAACGACCTTACTAGGCTGATT
bssyn      C.C.....C.....C..C..C........C.....C...........G..CC.C.....C 610       620       630       640       650       660
                    *         *         *         *         *         *
PMONBT     GGAAACTACACCGACCACGCTGTTCGTTGGTACAACACTGGCTTGGAGCGTGTCTGGGGT
bssyn      ..C.................C..G..C...........C...C.......C..G......

670       680       690       700       710       720
                    *         *         *         *         *         *
PMONBT     CCTGATTCTAGAGATTGGATTAGATACAACCAGTTCAGGAGAGAATTGACCCTCACAGTT
bssyn      ..C..CAGCC.C..C.....C..G............C.CC.C..GC.......G..C..G
```

Fig. 5B

```
                   730       740       750       760       770       780
                     *         *         *         *         *         *
PMONBT     TTGGACATTGTGTCTCTCTTCCCGAACTATGACTCCAGAACCTACCCTATCCGTACAGTG
bssyn      C.......C...AGC..G.....C.....C...AG.C.C........C.....C..C...

790       800       810       820       830       840
                     *         *         *         *         *         *
PMONBT     TCCCAACTTACCAGAGAAATCTATACTAACCCAGTTCTTGAGAACTTCGACGGTAGCTTC
bssyn      AG...G..G...C.C..G..T..C..C.....C..G..G..............C......

850       860       870       880       890       900
                     *         *         *         *         *         *
PMONBT     CGTGGTTCTGCCCAAGGTATCGAAGGCTCCATCAGGAGCCCACACTTGATGGACATCTTG
bssyn      ..C..CAGC.....G..C.....G...AG....C.C.....C...C...........C..

910       920       930       940       950       960
                     *         *         *         *         *         *
PMONBT     AACAGCATAACTATCTACAGCGATGCTCACAGAGGAGAGTATTACTGGTCTGGACACCAG
bssyn      ........C..C.......C...C..C...C.C..C.....C......AGC..C......

970       980       990      1000      1010      1020
                     *         *         *         *         *         *
PMONBT     ATCATGGCCTCTCCAGTTGGATTCAGCGGGCCCGAGTTTACCTTTCCTCTCTATGGAACT
bssyn      .........AGC..C..C..C........C........C.....C..C..G..C..C..C 1030      1040      1050      1060      1070      1080
                     *         *         *         *         *         *
PMONBT     ATGGGAAACGCCGCTCCACAACAACGTATCGTTGCTCAACTAGGTCAGGGTGTCTACAGA
bssyn      .....C.....T..A..T..G..G..C.....G..A..G..G..C.....A..G...C.C 1090      1100      1110      1120      1130      1140
                     *         *         *         *         *         *
PMONBT     ACCTTGTCTTCCACCTTGTACAGAAGACCCTTCAATATCGGTATCAACAACCAGCAACTT
bssyn      ...C..AGCAG....C.....C.TC....T.....C.....C..............G..G 1150      1160      1170      1180      1190      1200
                     *         *         *         *         *         *
PMONBT     TCCGTTCTTGACGGAACAGAGTTCGCCTATGGAACCTCTTCTAACTTGCCATCCGCTGTT
bssyn      AG...G..G.....C..C...........C..C...AGCAGC...C....CAG...C..G 1210      1220      1230      1240      1250      1260
                     *         *         *         *         *         *
PMONBT     TACAGAAAGAGCGGAACCGTTGATTCCTTGGACGAAATCCCACCACAGAACAACAATGTG
bssyn      ...C.C........C.....G..CAG.C.......G.....C..T...........C...

1270      1280      1290      1300      1310      1320
                     *         *         *         *         *         *
PMONBT     CCACCCAGGCAAGGATTCTCCCACAGGTTGAGCCACGTGTCCATGTTCCGTTCCGGATTC
bssyn      .....TC.A..G..C...AG....C.TC...........AG.........CAGT..C...

1330      1340      1350      1360      1370      1380
                     *         *         *         *         *         *
PMONBT     AGCAACAGTTCCGTGAGCATCATCAGAGCTCCTATGTTCTCATGGATTCATCGTAGTGCT
bssyn      ........CAG.............C.T..A.........AGC........C..C.....C 1390      1400      1410      1420      1430      1440
                     *         *         *         *         *         *
PMONBT     GAGTTCAACAATATCATTCCTTCCTCTCAAATCACCCAAATCCCATTGACCAAGTCTACT
bssyn      ...........C.....C..CAG.AGC..G........G.....CC........AGC..C
```

Fig. 5C

```
                 1450      1460      1470      1480      1490      1500
                   *         *         *         *         *         *
PMONBT   AACCTTGGATCTGGAACTTCTGTCGTGAAAGGACCAGGCTTCACAGGAGGTGATATTCTT
bssyn    .....G..CAGC..C..CAGC..G.....G..C...C.........C..C..C..C..G 1510      1520      1530      1540      1550      1560
                   *         *         *         *         *         *
PMONBT   AGAAGAACTTCTCCTGGCCAGATTAGCACCCTCAGAGTTAACATCACTGCACCACTTTCT
bssyn    C.CC.C..CAGC..C.........C.........GC.C..G.........C...C...C..GAGC 1570      1580      1590      1600      1610      1620
                   *         *         *         *         *         *
PMONBT   CAAAGATATCGTGTCAGGATTCGTTACGCATCTACCACTAACTTGCAATTCCACACCTCC
bssyn    ..GC.C..C...C....C.C..C..C......CAGC.....C....C.....G.........AG.

1630      1640      1650      1660      1670      1680
                   *         *         *         *         *         *
PMONBT   ATCGACGGAAGGCCTATCAATCAGGGTAACTTCTCCGCAACCATGTCAAGCGGCAGCAAC
bssyn    ........CC.C..C.....C......C......AG...C.......AGC............

1690      1700      1710      1720      1730      1740
                   *         *         *         *         *         *
PMONBT   TTGCAATCCGGCAGCTTCAGAACCGTCGGTTTCACTACTCCTTTCAACTTCTCTAACGGA
bssyn    C....GAG..........C.C.....G..C......C..C..C.........AGC.....C 1750      1760      1770      1780      1790      1800
                   *         *         *         *         *         *
PMONBT   TCAAGCGTTTTCACCCTTAGCGCTCATGTGTTCAATTCTGGCAATGAAGTGTACATTGAC
bssyn    AGC.....G........G.....C..C........CAGC......C..G.........C...

1810      1820      1830      1840
                   *         *         *         *
PMONBT   CGTATTGAGTTTGTGCCTGCCGAAGTTACCTTCGAGGCTGAGTA----------------
bssyn    ..C..C.....C......C......G..G............C.....CGACCTGGAGAGGGCT PMONBT   ------------------------------------------------------------
bssyn    CAGAAGGCCGTGAACGAGCTGTTCACCAGCAGCAACCAGATCGGCCTGAAGACCGACGTG PMONBT   ---------------------------C
bssyn    ACCGACTACCACATCGATCAGGTGTAG
```

Fig. 6A

```
  64  ATGGACCTGC TGCCCGACGC CCGCATCGAG GACAGCCTGT GCATCGCCGA GGGCAACAAC
      MetAspLeu  LeuProAsp  AlaArgIleGlu DspSerLeu  CysIleAla  GluGlyAsnAsn

124  ATCGACCCCT TCGTGAGCGC CAGCACCGTG CAGACCGGCA TCAACATCGC CGGCCGCATC
      IleAspPro  PheValSer  AlaSerThrVal GlnThrGly  IleAsnIle  AlaGlyArgIle

184  CTGGGCGTGC TGGGCGTGCC CTTCGCCGGC CAGCTGGCCA GCTTCTACAG CTTCCTGGTG
      LeuGlyVal  LeuGlyVal  ProPheAlaGly GlnLeuAla  SerPheTyr  SerPheLeuVal

244  GGCGAGCTGT GGCCCCGCGG CCGCGACCAG TGGGAGATCT TCCTGGAGCA CGTGGAGCAG
      GlyGluLeu  TrpProArg  GlyArgAspGln TrpGluIle  PheLeuGlu  HisValGluGln

304  CTGATCAACC AGCAGATCAC CGAGAACGCC CGCAACACCG CCCTGGCCCG CCTGCAGGGC
      LeuIleAsn  GlnGlnIle  ThrGluAsnAla ArgAsnThr  AlaLeuAla  ArgLeuGlnGly

364  CTGGGCGACA GCTTCCGCGC CTACCAGCAG AGCCTGGAGG ACTGGCTGGA GAACCGCGAC
      LeuGlyAsp  SerPheArg  AlaTyrGlnGln SerLeuGlu  AspTrpLeu  GluAsnArgAsp

424  GACGCCCGCA CCCGCAGCGT GCTGTACACC CAGTACATCG CCCTGGAGCT GGACTTCCTG
      AspAlaArg  ThrArgSer  ValLeuTyrThr GlnTyrIle  AlaLeuGlu  LeuAspPheLeu

484  AACGCCATGC CCCTGTTCGC CATCCGCAAC CAGGAGGTGC CCCTGCTGAT GGTGTACGCC
      AsnAlaMet  ProLeuPhe  AlaIleArgAsn GlnGluVal  ProLeuLeu  MetValTyrAla

544  CAGGCCGCCA ACCTGCACCT GCTGCTGCTG CGCGACGCCA GCCTGTTCGG CAGCGAGTTC
      GlnAlaAla  AsnLeuHis  LeuLeuLeuLeu ArgAspAla  SerLeuPhe  GlySerGluPhe

604  GGCCTGACCA GCCAGGAGAT CCAGCGCTAC TACGAGCGCC AGGTGGAGCG CACCCGCGAC
      GlyLeuThr  SerGlnGlu  IleGlnArgTyr TyrGluArg  GlnValGlu  ArgThrArgAsp

664  TACAGCGACT ACTGCGTGGA GTGGTACAAC ACCGGCCTGA ACAGCCTGCG CGGCACCAAC
      TyrSerAsp  TyrCysVal  GluTrpTyrAsn ThrGlyLeu  AsnSerLeu  ArgGlyThrAsn

724  GCCGCCAGCT GGGTGCGCTA CAACCAGTTC CGCCGCGACC TGACCCTGGG CGTGCTGGAC
      AlaAlaSer  TrpValArg  TyrAsnGlnPhe ArgArgAsp  LeuThrLeu  GlyValLeuAsp

784  CTGGTGGCCC TGTTCCCCAG CTACGACACC CGCACCTACC CCATCAACAC CAGCGCCCAG
      LeuValAla  LeuPhePro  SerTyrAspThr ArgThrTyr  ProIleAsn  ThrSerAlaGln

844  CTGACCCGCG AGGTGTACAC CGACGCCATC GGCGCCACCG GCGTGAACAT GGCCAGCATG
      LeuThrArg  GluValTyr  ThrAspAlaIle GlyAlaThr  GlyValAsn  MetAlaSerMet

904  AACTGGTACA ACAACAACGC CCCCAGCTTC AGCGCCATCG AGGCCGCCGC CATCCGCAGC
      AsnTrpTyr  AsnAsnAsn  AlaProSerPhe SerAlaIle  GluAlaAla  AlaIleArgSer

964  CCCCACCTGC TGGACTTCCT GGAGCAGCTG ACCATCTTCA GCGCCAGCAG CCGCTGGAGC
      ProHisLeu  LeuAspPhe  LeuGluGlnLeu ThrIlePhe  SerAlaSer  SerArgTrpSer

1024  AACACCCGCC ACATGACCTA CTGGCGCGGC CACACCATCC AGAGCCGCCC CATCGGCGGC
      AsnThrArg  HisMetThr  TyrTrpArgGly HisThrIle  GlnSerArg  ProIleGlyGly
```

Fig. 6B

```
1084  GGCCTGAACA CCAGCACCCA CGGCGCCACC AACACCAGCA TCAACCCCGT GACCCTGCGC
      GlyLeuAsn  ThrSerThr  HisGlyAlaThr AsnThrSer  IleAsnPro  ValThrLeuArg

1144  TTCGCCAGCC GCGACGTGTA CCGCACCGAG AGCTACGCCG GCGTGCTGCT GTGGGGCATC
      PheAlaSer  ArgAspVal  TyrArgThrGlu SerTyrAla  GlyValLeu  LeuTrpGlyIle

1204  TACCTGGAGC CCATCCACGG CGTGCCCACC GTGCGCTTCA ACTTCACCAA CCCCCAGAAC
      TyrLeuGlu  ProIleHis  GlyValProThr ValArgPhe  AsnPheThr  AsnProGlnAsn

1264  ATCAGCGACC GCGGCACCGC CAACTACAGC CAGCCCTACG AGAGCCCCGG CCTGCAGCTG
      IleSerAsp  ArgGlyThr  AlaAsnTyrSer GlnProTyr  GluSerPro  GlyLeuGlnLeu

1324  AAGGACAGCG AGACCGAGCT GCCCCCCGAG ACCACCGAGC GCCCCAACTA CGAGAGCTAC
      LysAspSer  GluThrGlu  LeuProProGlu ThrThrGlu  ArgProAsn  TyrGluSerTyr

1384  AGCCACCGCC TGAGCCACAT CGGCATCATC CTGCAGAGCC GCGTGAACGT GCCCGTGTAC
      SerHisArg  LeuSerHis  IleGlyIleIle LeuGlnSer  ArgValAsn  ValProValTyr

1444  AGCTGGACCC ACCGCAGCGC CGACCGCACC AACACCATCG GCCCCAACCG CATCACCCAG
      SerTrpThr  HisArgSer  AlaAspArgThr AsnThrIle  GlyProAsn  ArgIleThrGln

1504  ATCCCCATGG TGAAGGCCAG CGAGCTGCCC CAGGGCACCA CCGTGGTGCG CGGCCCCGGC
      IleProMet  ValLysAla  SerGluLeuPro GlnGlyThr  ThrValVal  ArgGlyProGly

1564  TTCACCGGCG GCGACATCCT GCGCCGCACC AACACCGGCG GCTTCGGCCC CATCCGCGTG
      PheThrGly  GlyAspIle  LeuArgArgThr AsnThrGly  GlyPheGly  ProIleArgVal

1624  ACCGTGAACG GCCCCCTGAC CCAGCGCTAC CGCATCGGCT TCCGCTACGC CAGCACCGTG
      ThrValAsn  GlyProLeu  ThrGlnArgTyr ArgIleGly  PheArgTyr  AlaSerThrVal

1684  GACTTCGACT TCTTCGTGAG CCGCGGCGGC ACCACCGTGA ACAACTTCCG CTTCCTGCGC
      AspPheAsp  PhePheVal  SerArgGlyGly ThrThrVal  AsnAsnPhe  ArgPheLeuArg

1744  ACCATGAACA GCGGCGACGA GCTGAAGTAC GGCAACTTCG TGCGCCGCGC CTTCACCACC
      ThrMetAsn  SerGlyAsp  GluLeuLysTyr GlyAsnPhe  ValArgArg  AlaPheThrThr

1804  CCCTTCACCT TCACCCAGAT CCAGGACATC ATCCGCACCA GCATCCAGGG CCTGAGCGGC
      ProPheThr  PheThrGln  IleGlnAspIle IleArgThr  SerIleGln  GlyLeuSerGly

1864  AACGGCGAGG TGTACATCGA CAAGATCGAG ATCATCCCCG TGACCGCCAC CTTCGAGGCC
      AsnGlyGlu  ValTyrIle  AspLysIleGlu IleIlePro  ValThrAla  ThrPheGluAla

1924  GAGTACGACC TGGAGCGCGC CCAGGAGGCC GTGAACGCCC TGTTCACCAA CACCAACCCC
      GluTyrAsp  LeuGluArg  AlaGlnGluAla ValAsnAla  LeuPheThr  AsnThrAsnPro

1984  CGCCGCCTGA AGACCGACGT GACCGACTAC CACATCGACC AGGTGAGCAA CCTGGTGGCC
      ArgArgLeu  LysThrAsp  ValThrAspTyr HisIleAsp  GlnValSer  AsnLeuValAla

2044  TGCCTGAGCG ACGAGTTCTG CCTGGACGAG AAGCGCGAGC TGCTGGAGAA GGTGAAGTAC
      CysLeuSer  AspGluPhe  CysLeuAspGlu LysArgGlu  LeuLeuGlu  LysValLysTyr
```

Fig. 6C

```
2104  GCCAAGCGCC TGAGCGACGA GCGCAACCTG CTGCAGGACC CCAACTTCAC CAGCATCAAC
      AlaLysArg  LeuSerAsp  GluArgAsnLeu LeuGlnAsp  ProAsnPhe  ThrSerIleAsn
2164  AAGCAGCCCG ACTTCATCAG CACCAACGAG CAGAGCAACT TCACCAGCAT CCACGAGCAG
      LysGlnPro  AspPheIle  SerThrAsnGlu GlnSerAsn  PheThrSer  IleHisGluGln
2224  AGCGAGCACG GCTGGTGGGG CAGCGAGAAC ATCACCATCC AGGAGGGCAA CGACGTGTTC
      SerGluHis  GlyTrpTrp  GlySerGluAsn IleThrIle  GlnGluGly  AsnAspValPhe
2284  AAGGAGAACT ACGTGACCCT GCCCGGCACC TTCAACGAGT GCTACCCCAC CTACCTGTAC
      LysGluAsn  TyrValThr  LeuProGlyThr PheAsnGlu  CysTyrPro  ThrTyrLeuTyr
2344  CAGAAGATCG GCGAGAGCGA GCTGAAGGCC TACACCCGCT ACCAGCTGCG CGGCTACATC
      GlnLysIle  GlyGluSer  GluLeuLysAla TyrThrArg  TyrGlnLeu  ArgGlyTyrIle
2404  GAGGACAGCC AGGACCTGGA GATCTACCTG ATCCGCTACA ACGCCAAGCA CGAGACCCTG
      GluAspSer  GlnAspLeu  GluIleTyrLeu IleArgTyr  AsnAlaLys  HisGluThrLeu
2464  GACGTGCCCG GCACCGAGAG CCTGTGGCCC CTGAGCGTGG AGAGCCCCAT CGGCCGCTGC
      AspValPro  GlyThrGlu  SerLeuTrpPro LeuSerVal  GluSerPro  IleGlyArgCys
2524  GGCGAGCCCA ACCGCTGCGC CCCCCACTTC GAGTGGAACC CCGACCTGGA CTGCAGCTGC
      GlyGluPro  AsnArgCys  AlaProHisPhe GluTrpAsn  ProAspLeu  AspCysSerCys
2584  CGCGACGGCG AGAAGTGCGC CCACCACAGC CACCACTTCA GCCTGGACAT CGACGTGGGC
      ArgAspGly  GluLysCys  AlaHisHisSer HisHisPhe  SerLeuAsp  IleAspValGly
2644  TGCACCGACC TGCACGAGAA CCTGGGCGTG TGGGTGGTGT TCAAGATCAA GACCCAGGAG
      CysThrAsp  LeuHisGlu  AsnLeuGlyVal TrpValVal  PheLysIle  LysThrGlnGlu
2704  GGCCACGCCC GCCTGGGCAA CCTGGAGTTC ATCGAGGAGA AGCCCCTGCT GGGCGAGGCC
      GlyHisAla  ArgLeuGly  AsnLeuGluPhe IleGluGlu  LysProLeu  LeuGlyGluAla
2764  CTGAGCCGCG TGAAGCGCGC CGAGAAGAAG TGGCGCGACA AGCGCGAGAA GCTGCAGCTG
      LeuSerArg  ValLysArg  AlaGluLysLys TrpArgAsp  LysArgGlu  LysLeuGlnLeu
2824  GAGACCAAGC GCGTGTACAC CGAGGCCAAG GAGGCCGTGG ACGCCCTGTT CGTGGACAGC
      GluThrLys  ArgValTyr  ThrGluAlaLys GluAlaVal  AspAlaLeu  PheValAspSer
2884  CAGTACGACC GCCTGCAGGC CGACACCAAC ATCGGCATGA TCCACGCCGC CGACAAGCTG
      GlnTyrAsp  ArgLeuGln  AlaAspThrAsn IleGlyMet  IleHisAla  AlaAspLysLeu
2944  GTGCACCGCA TCCGCGAGGC CTACCTGAGC GAGCTGCCCG TGATCCCCGG CGTGAACGCC
      ValHisArg  IleArgGlu  AlaTyrLeuSer GluLeuPro  ValIlePro  GlyValAsnAla
3004  GAGATCTTCG AGGAGCTGGA GGGCCACATC ATCACCGCCA TCAGCCTGTA CGACGCCCGC
      GluIlePhe  GluGluLeu  GluGlyHisIle IleThrAla  IleSerLeu  TyrAspAlaArg
```

Fig. 6D

```
3064  AACGTGGTGA AGAACGGCGA CTTCAACAAC GGCCTGACCT GCTGGAACGT GAAGGGCCAC
      AsnValVal  LysAsnGly  AspPheAsnAsn GlyLeuThr  CysTrpAsn  ValLysGlyHis

3124  GTGGACGTGC AGCAGAGCCA CCACCGCAGC GACCTGGTGA TCCCCGAGTG GGAGGCCGAG
      ValAspVal  GlnGlnSer  HisHisArgSer AspLeuVal IleProGlu  TrpGluAlaGlu

3184  GTGAGCCAGG CCGTGCGCGT GTGCCCCGGC TGCGGCTACA TCCTGCGCGT GACCGCCTAC
      ValSerGln  AlaValArg  ValCysProGly CysGlyTyr IleLeuArg  ValThrAlaTyr

3244  AAGGAGGGCT ACGGCGAGGG CTGCGTGACC ATCCACGAGA TCGAGAACAA CACCGACGAG
      LysGluGly  TyrGlyGlu  GlyCysValThr IleHisGlu IleGluAsn  AsnThrAspGlu

3304  CTGAAGTTCA AGAACCGCGA GGAGGAGGAG GTGTACCCCA CCGACACCGG CACCTGCAAC
      LeuLysPhe  LysAsnArg  GluGluGluGlu ValTyrPro ThrAspThr  GlyThrCysAsn

3364  GACTACACCG CCCACCAGGG CACCGCCGGC TGCGCCGACG CCTGCAACAG CCGCAACGCC
      AspTyrThr  AlaHisGln  GlyThrAlaGly CysAlaAsp AlaCysAsn  SerArgAsnAla

3424  GGCTACGAGG ACGCCTACGA GGTGGACACC ACCGCCAGCG TGAACTACAA GCCCACCTAC
      GlyTyrGlu  AspAlaTyr  GluValAspThr ThrAlaSer ValAsnTyr  LysProThrTyr

3484  GAGGAGGAGA CCTACACCGA CGTGCGCCGC GACAACCACT GCGAGTACGA CCGCGGCTAC
      GluGluGlu  ThrTyrThr  AspValArgArg AspAsnHis CysGluTyr  AspArgGlyTyr

3544  GTGAACTACC CCCCCGTGCC CGCCGGCTAC GTGACCAAGG AGCTGGAGTA CTTCCCCGAG
      ValAsnTyr  ProProVal  ProAlaGlyTyr ValThrLys GluLeuGlu  TyrPheProGlu

3604  ACCGACACCG TGTGGATCGA GATCGGCGAG ACCGAGGGCA AGTTCATCGT GGACAGCGTG
      ThrAspThr  ValTrpIle  GluIleGlyGlu ThrGluGly LysPheIle  ValAspSerVal

3664  GAGCTGCTGC TGATGGAGGA GTAG
      GluLeuLeu  LeuMetGlu  Glu---
```

Fig. 7A

SEQUENCE OF THE FULL-LENGTH HYBRID SYNTHETIC/NATIVE CRYIA(B) CHIMERIC GENE
The fusion point between the synthetic and native coding sequences is indicated by a slash (/) in the sequence.

```
  1  ATGGACAACA ACCCCAACAT CAACGAGTGC ATCCCCTACA ACTGCCTGAG CAACCCCGAG
     MetAspAsn AsnProAsn IleAsnGluCys IleProTyr AsnCysLeu SerAsnProGlu

61  GTGGAGGTGC TGGGCGGCGA GCGCATCGAG ACCGGCTACA CCCCCATCGA CATCAGCCTG
     ValGluVal LeuGlyGly GluArgIleGlu ThrGlyTyr ThrProIle AspIleSerLeu

121  AGCCTGACCC AGTTCCTGCT GAGCGAGTTC GTGCCCGGCG CCGGCTTCGT GCTGGGCCTG
     SerLeuThr GlnPheLeu LeuSerGluPhe ValProGly AlaGlyPhe ValLeuGlyLeu

181  GTGGACATCA TCTGGGGCAT CTTCGGCCCC AGCCAGTGGG ACGCCTTCCT GGTGCAGATC
     ValAspIle IleTrpGly IlePheGlyPro SerGlnTrp AspAlaPhe LeuValGlnIle

241  GAGCAGCTGA TCAACCAGCG CATCGAGGAG TTCGCCCGCA ACCAGGCCAT CAGCCGCCTG
     GluGlnLeu IleAsnGln ArgIleGluGlu PheAlaArg AsnGlnAla IleSerArgLeu

301  GAGGGCCTGA GCAACCTGTA CCAAATCTAC GCCGAGAGCT TCCGCGAGTG GGAGGCCGAC
     GluGlyLeu SerAsnLeu TyrGlnIleTyr AlaGluSer PheArgGlu TrpGluAlaAsp

361  CCCACCAACC CCGCCCTGCG CGAGGAGATG CGCATCCAGT TCAACGACAT GAACAGCGCC
     ProThrAsn ProAlaLeu ArgGluGluMet ArgIleGln PheAsnAsp MetAsnSerAla

421  CTGACCACCG CCATCCCCCT GTTCGCCGTG CAGAACTACC AGGTGCCCCT GCTGAGCGTG
     LeuThrThr AlaIlePro LeuPheAlaVal GlnAsnTyr GlnValPro LeuLeuSerVal

481  TACGTGCAGG CCGCCAACCT GCACCTGAGC GTGCTGCGCG ACGTCAGCGT GTTCGGCCAG
     TyrValGln AlaAlaAsn LeuHisLeuSer ValLeuArg AspValSer ValPheGlyGln

541  CGCTGGGGCT TCGACGCCGC CACCATCAAC AGCCGCTACA ACGACCTGAC CCGCCTGATC
     ArgTrpGly PheAspAla AlaThrIleAsn SerArgTyr AsnAspLeu ThrArgLeuIle

601  GGCAACTACA CCGACCACGC CGTGCGCTGG TACAACACCG GCCTGGAGCG CGTGTGGGGT
     GlyAsnTyr ThrAspHis AlaValArgTrp TyrAsnThr GlyLeuGlu ArgValTrpGly

661  CCCGACAGCC GCGACTGGAT CAGGTACAAC CAGTTCCGCC GCGAGCTGAC CCTGACCGTG
     ProAspSer ArgAspTrp IleArgTyrAsn GlnPheArg ArgGluLeu ThrLeuThrVal

721  CTGGACATCG TGAGCCTGTT CCCCAACTAC GACAGCCGCA CCTACCCCAT CCGCACCGTG
     LeuAspIle ValSerLeu PheProAsnTyr AspSerArg ThrTyrPro IleArgThrVal

781  AGCCAGCTGA CCCGCGAGAT TTACACCAAC CCCGTGCTGG AGAACTTCGA CGGCAGCTTC
     SerGlnLeu ThrArgGlu IleTyrThrAsn ProValLeu GluAsnPhe AspGlySerPhe

841  CGCGGCAGCG CCCAGGGCAT CGAGGGCAGC ATCCGCAGCC CCCACCTGAT GGACATCCTG
     ArgGlySer AlaGlnGly IleGluGlySer IleArgSer ProHisLeu MetAspIleLeu

901  AACAGCATCA CCATCTACAC CGACGCCCAC CGCGGCGAGT ACTACTGGAG CGGCCACCAG
     AsnSerIle ThrIleTyr ThrAspAlaHis ArgGlyGlu TyrTyrTrp SerGlyHisGln
```

Fig. 7B

```
 961   ATCATGGCCA GCCCCGTCGG CTTCAGCGGC CCCGAGTTCA CCTTCCCCCT GTACGGCACC
       IleMetAla SerProVal GlyPheSerGly ProGluPhe ThrPhePro LeuTyrGlyThr

1021   ATGGGCAACG CTGCACCTCA GCAGCGCATC GTGGCACAGC TGGGCCAGGG AGTGTACCGC
       MetGlyAsn AlaAlaPro GlnGlnArgIle ValAlaGln LeuGlyGln GlyValTyrArg

1081   ACCCTGAGCA GCACCCTGTA CCGTCGACCT TTCAACATCG GCATCAACAA CCAGCAGCTG
       ThrLeuSer SerThrLeu TyrArgArgPro PheAsnIle GlyIleAsn AsnGlnGlnLeu

1141   AGCGTGCTGG ACGGCACCGA GTTCGCCTAC GGCACCAGCA GCAACCTGCC CAGCGCCGTG
       SerValLeu AspGlyThr GluPheAlaTyr GlyThrSer SerAsnLeu ProSerAlaVal

1201   TACCGCAAGA GCGGCACCGT GGACAGCCTG GACGAGATCC CCCCTCAGAA CAACAACGTG
       TyrArgLys SerGlyThr ValAspSerLeu AspGluIle ProProGln AsnAsnAsnVal

1261   CCACCTCGAC AGGGCTTCAG CCACCGTCTG AGCCACGTGA GCATGTTCCG CAGTGGCTTC
       ProProArg GlnGlyPhe SerHisArgLeu SerHisVal SerMetPhe ArgSerGlyPhe

1321   AGCAACAGCA GCGTGAGCAT CATCCGTGCA CCTATGTTCA GCTGGATTCA CCGCAGTGCC
       SerAsnSer SerValSer IleIleArgAla ProMetPhe SerTrpIle HisArgSerAla

1381   GAGTTCAACA ACATCATCCC CAGCAGCCAG ATCACCCAGA TCCCCCTGAC CAAGAGCACC
       GluPheAsn AsnIleIle ProSerSerGln IleThrGln IleProLeu ThrLysSerThr

1441   AACCTGGGCA GCGGCACCAG CGTGGTGAAG GGCCCCGGCT TCACCGGCGG CGACATCCTG
       AsnLeuGly SerGlyThr SerValValLys GlyProGly PheThrGly GlyAspIleLeu

1501   CGCCGCACCA GCCCCGGCCA GATCAGCACC CTGCGCGTGA ACATCACCGC CCCCCTGAGC
       ArgArgThr SerProGly GlnIleSerThr LeuArgVal AsnIleThr AlaProLeuSer

1561   CAGCGCTACC GCGTCCGCAT CCGCTACGCC AGCACCACCA ACCTGCAGTT CCACACCAGC
       GlnArgTyr ArgValArg IleArgTyrAla SerThrThr AsnLeuGln PheHisThrSer

1621   ATCGACGGCC GCCCCATCAA CCAGGGCAAC TTCAGCGCCA CCATGAGCAG CGGCAGCAAC
       IleAspGly ArgProIle AsnGlnGlyAsn PheSerAla ThrMetSer SerGlySerAsn

1681   CTGCAGAGCG GCAGCTTCCG CACCGTGGGC TTCACCACCC CCTTCAACTT CAGCAACGGC
       LeuGlnSer GlySerPhe ArgThrValGly PheThrThr ProPheAsn PheSerAsnGly

1741   AGCAGCGTGT TCACCCTGAG CGCCCACGTG TTCAACAGCG GCAACGAGGT GTACATCGAC
       SerSerVal PheThrLeu SerAlaHisVal PheAsnSer GlyAsnGlu ValTyrIleAsp

1801   CGCATCGAGT TCGTGCCCGC CGAGGTGACC TTCGAGGCCG AGTACGACCT GGAGAGGGCT
       ArgIleGlu PheValPro AlaGluValThr PheGluAla GluTyrAsp LeuGluArgAla

1861   CAGAAGGCCG TGAACGAGCT GTTCACCAGC AGCAACCAGA TCGGCCTGAA GACCGACGTG
       GlnLysAla ValAsnGlu LeuPheThrSer SerAsnGln IleGlyLeu LysThrAspVal
```

Fig. 7C

```
1921  ACCGACTACC ACATCGAT/CA AGTATCCAAT TTAGTTGAGT GTTTATCTGATGAATTTTGT
      ThrAspTyr  HisIleAsp/GlnValSerAsn LeuValGlu  CysLeuSer  AspGluPheCys

1981  CTGGATGAAA AAAAAGAATT GTCCGAGAAA GTCAAACATG CGAAGCGACT TAGTGATGAG
      LeuAspGlu  LysLysGlu  LeuSerGluLys ValLysHis AlaLysArg  LeuSerAspGlu

2041  CGGAATTTAC TTCAAGATCC AAACTTTAGA GGGATCAATA GACAACTAGA CCGTGGCTGG
      ArgAsnLeu  LeuGlnAsp  ProAsnPheArg GlyIleAsn ArgGlnLeu  AspArgGlyTrp

2101  AGAGGAAGTA CGGATATTAC CATCCAAGGA GGCGATGACG TATTCAAAGA GAATTACGTT
      ArgGlySer  ThrAspIle  ThrIleGlnGly GlyAspAsp ValPheLys  GluAsnTyrVal

2161  ACGCTATTGG GTACCTTTGA TGAGTGCTAT CCAACGTATT TATATCAAAA AATAGATGAG
      ThrLeuLeu  GlyThrPhe  AspGluCysTyr ProThrTyr LeuTyrGln  LysIleAspGlu

2221  TCGAAATTAA AAGCCTATAC CCGTTACCAA TTAAGAGGGT ATATCGAAGA TAGTCAAGAC
      SerLysLeu  LysAlaTyr  ThrArgTyrGln LeuArgGly TyrIleGlu  AspSerGlnAsp

2281  TTAGAAATCT ATTTAATTCG CTACAATGCC AAACACGAAA CAGTAAATGT GCCAGGTACG
      LeuGluIle  TyrLeuIle  ArgTyrAsnAla LysHisGlu ThrValAsn  ValProGlyThr

2341  GGTTCCTTAT GGCCGCTTTC AGCCCCAAGT CCAATCGGAA AATGTGCCCA TCATTCCCAT
      GlySerLeu  TrpProLeu  SerAlaProSer ProIleGly LysCysAla  HisHisSerHis

2401  CATTTCTCCT TGGACATTGA TGTTGGATGT ACAGACTTAA ATGAGGACTT AGGTGTATGG
      HisPheSer  LeuAspIle  AspValGlyCys ThrAspLeu AsnGluAsp  LeuGlyValTrp

2461  GTGATATTCA AGATTAAGAC GCAAGATGGC CATGCAAGAC TAGGAAATCT AGAATTTCTC
      ValIlePhe  LysIleLys  ThrGlnAspGly HisAlaArg LeuGlyAsn  LeuGluPheLeu

2521  GAAGAGAAAC CATTAGTAGG AGAAGCACTA GCTCGTGTGA AAAGAGCGGA GAAAAAATGG
      GluGluLys  ProLeuVal  GlyGluAlaLeu AlaArgVal LysArgAla  GluLysLysTrp

2581  AGAGACAAAC GTGAAAAATT GGAATGGGAA ACAAATATTG TTTATAAAGA GGCAAAAGAA
      ArgAspLys  ArgGluLys  LeuGluTrpGlu ThrAsnIle ValTyrLys  GluAlaLysGlu

2641  TCTGTAGATG CTTTATTTGT AAACTCTCAA TATGATAGAT TACAAGCGGA TACCAACATC
      SerValAsp  AlaLeuPhe  ValAsnSerGln TyrAspArg LeuGlnAla  AspThrAsnIle

2701  GCGATGATTC ATGCGGCAGA TAAACGCGTT CATAGCATTC GAGAAGCTTA TCTGCCTGAG
      Ala e Ile  HisAlaAla  AspLysArgVal HisSerIle ArgGluAla  TyrLeuProGlu

2761  CTGTCTGTGA TTCCGGGTGT CAATGCGGCT ATTTTTGAAG AATTAGAAGG GCGTATTTTC
      LeuSerVal  IleProGly  ValAsnAlaAla IlePheGlu GluLeuGlu  GlyArgIlePhe

2821  ACTGCATTCT CCCTATATGA TGCGAGAAAT GTCATTAAAA ATGGTGATTT TAATAATGGC
      ThrAlaPhe  SerLeuTyr  AspAlaArgAsn ValIleLys AsnGlyAsp  PheAsnAsnGly
```

Fig. 7D

```
2881  TTATCCTGCT GGAACGTGAA AGGGCATGTA GATGTAGAAG AACAAAACAA CCACCGTTCG
      LeuSerCys  TrpAsnVal  LysGlyHisVal AspValGlu  GluGlnAsn  AsnHisArgSer

2941  GTCCTTGTTG TTCCGGAATG GGAAGCAGAA GTGTCACAAG AAGTTCGTGT CTGTCCGGGT
      ValLeuVal  ValProGlu  TrpGluAlaGlu ValSerGln  GluValArg  ValCysProGly

3001  CGTGGCTATA TCCTTCGTGT CACAGCGTAC AAGGAGGGAT ATGGAGAAGG TTGCGTAACC
      ArgGlyTyr  IleLeuArg  ValThrAlaTyr LysGluGly  TyrGlyGlu  GlyCysValThr

3061  ATTCATGAGA TCGAGAACAA TACAGACGAA CTGAAGTTTA GCAACTGTGT AGAAGAGGAA
      IleHisGlu  IleGluAsn  AsnThrAspGlu LeuLysPhe  SerAsnCys  ValGluGluGlu

3121  GTATATCCAA CAACACGGT AACGTGTAAT GATTATACTG CGACTCAAGA AGAATATGAG
      ValTyrPro  AsnAsnThr  ValThrCysAsn AspTyrThr  AlaThrGln  GluGluTyrGlu

3181  GGTACGTACA CTTCTCGTAA TCGAGGATAT GACGGAGCCT ATGAAAGCAA TTCTTCTGTA
      GlyThrTyr  ThrSerArg  AsnArgGlyTyr AspGlyAla  TyrGluSer  AsnSerSerVal

3241  CCAGCTGATT ATGCATCAGC CTATGAAGAA AAAGCATATA CAGATGGACG AAGAGACAAT
      ProAlaAsp  TyrAlaSer  AlaTyrGluGlu LysAlaTyr  ThrAspGly  ArgArgAspAsn

3301  CCTTGTGAAT CTAACAGAGG ATATGGGGAT TACACACCAC TACCAGCTGG CTATGTGACA
      ProCysGlu  SerAsnArg  GlyTyrGlyAsp TyrThrPro  LeuProAla  GlyTyrValThr

3361  AAAGAATTAG AGTACTTCCC AGAAACCGAT AAGGTATGGA TTGAGATCGG AGAAACGGAA
      LysGluLeu  GluTyrPhe  ProGluThrAsp LysValTrp  IleGluIle  GlyGluThrGlu

3421  GGAACATTCA TCGTGGACAG CGTGGAATTA CTTCTTATGG AGGAATAA
      GlyThrPhe  IleValAsp  SerValGluLeu LeuLeuMet  GluGlu---
```

Fig. 9A

```
  1 ATGGACAACA ACCCCAACAT CAACGAGTGC ATCCCCTACA ACTGCCTGAG CAACCCCGAG
    MetAspAsn AsnProAsn IleAsnGluCys IleProTyr AsnCysLeu SerAsnProGlu

61 GTGGAGGTGC TGGGCGGCGA GCGCATCGAG ACCGGCTACA CCCCCATCGA CATCAGCCTG
    ValGluVal LeuGlyGly GluArgIleGlu ThrGlyTyr ThrProIle AspIleSerLeu

121 AGCCTGACCC AGTTCCTGCT GAGCGAGTTC GTGCCCGGCG CCGGCTTCGT GCTGGGCCTG
    SerLeuThr GlnPheLeu LeuSerGluPhe ValProGly AlaGlyPhe ValLeuGlyLeu

181 GTGGACATCA TCTGGGGCAT CTTCGGCCCC AGCCAGTGGG ACGCCTTCCT GGTGCAGATC
    ValAspIle IleTrpGly IlePheGlyPro SerGlnTrp AspAlaPhe LeuValGlnIle

241 GAGCAGCTGA TCAACCAGCG CATCGAGGAG TTCGCCCGCA ACCAGGCCAT CAGCCGCCTG
    GluGlnLeu IleAsnGln ArgIleGluGlu PheAlaArg AsnGlnAla IleSerArgLeu

301 GAGGGCCTGA GCAACCTGTA CCAAATCTAC GCCGAGAGCT TCCGCGAGTG GGAGGCCGAC
    GluGlyLeu SerAsnLeu TyrGlnIleTyr AlaGluSer PheArgGlu TrpGluAlaAsp

361 CCCACCAACC CCGCCCTGCG CGAGGAGATG CGCATCCAGT TCAACGACAT GAACAGCGCC
    ProThrAsn ProAlaLeu ArgGluGluMet ArgIleGln PheAsnAsp MetAsnSerAla

421 CTGACCACCG CCATCCCCCT GTTCGCCGTG CAGAACTACC AGGTGCCCCT GCTGAGCGTG
    LeuThrThr AlaIlePro LeuPheAlaVal GlnAsnTyr GlnValPro LeuLeuSerVal

481 TACGTGCAGG CCGCCAACCT GCACCTGAGC GTGCTGCGCG ACGTCAGCGT GTTCGGCCAG
    TyrValGln AlaAlaAsn LeuHisLeuSer ValLeuArg AspValSer ValPheGlyGln

541 CGCTGGGGCT TCGACGCCGC CACCATCAAC AGCCGCTACA ACGACCTGAC CCGCCTGATC
    ArgTrpGly PheAspAla AlaThrIleAsn SerArgTyr AsnAspLeu ThrArgLeuIle

601 GGCAACTACA CCGACCACGC CGTGCGCTGG TACAACACCG GCCTGGAGCG CGTGTGGGGT
    GlyAsnTyr ThrAspHis AlaValArgTrp TyrAsnThr GlyLeuGlu ArgValTrpGly

661 CCCGACAGCC GCGACTGGAT CAGGTACAAC CAGTTCCGCC GCGAGCTGAC CCTGACCGTG
    ProAspSer ArgAspTrp IleArgTyrAsn GlnPheArg ArgGluLeu ThrLeuThrVal

721 CTGGACATCG TGAGCCTGTT CCCCAACTAC GACAGCCGCA CCTACCCCAT CCGCACCGTG
    LeuAspIle ValSerLeu PheProAsnTyr AspSerArg ThrTyrPro IleArgThrVal

781 AGCCAGCTGA CCCGCGAGAT TTACACCAAC CCCGTGCTGG AGAACTTCGA CGGCAGCTTC
    SerGlnLeu ThrArgGlu IleTyrThrAsn ProValLeu GluAsnPhe AspGlySerPhe

841 CGCGGCAGCG CCCAGGGCAT CGAGGGCAGC ATCCGCAGCC CCCACCTGAT GGACATCCTG
    ArgGlySer AlaGlnGly IleGluGlySer IleArgSer ProHisLeu MetAspIleLeu

901 AACAGCATCA CCATCTACAC CGACGCCCAC CGCGGCGAGT ACTACTGGAG CGGCCACCAG
    AsnSerIle ThrIleTyr ThrAspAlaHis ArgGlyGlu TyrTyrTrp SerGlyHisGln

961 ATCATGGCCA GCCCCGTCGG CTTCAGCGGC CCCGAGTTCA CCTTCCCCCT GTACGGCACC
    IleMetAla SerProVal GlyPheSerGly ProGluPhe ThrPhePro LeuTyrGlyThr
```

Fig. 9B

```
1021 ATGGGCAACG CTGCACCTCA GCAGCGCATC GTGGCACAGC TGGGCCAGGG AGTGTACCGC
     MetGlyAsn AlaAlaPro GlnGlnArgIle ValAlaGln LeuGlyGln GlyValTyrArg

1081 ACCCTGAGCA GCACCCTGTA CCGTCGACCT TTCAACATCG GCATCAACAA CCAGCAGCTG
     ThrLeuSer SerThrLeu TyrArgArgPro PheAsnIle GlyIleAsn AsnGlnGlnLeu

1141 AGCGTGCTGG ACGGCACCGA GTTCGCCTAC GGCACCAGCA GCAACCTGCC CAGCGCCGTG
     SerValLeu AspGlyThr GluPheAlaTyr GlyThrSer SerAsnLeu ProSerAlaVal

1201 TACCGCAAGA GCGGCACCGT GGACAGCCTG GACGAGATCC CCCCTCAGAA CAACAACGTG
     TyrArgLys SerGlyThr ValAspSerLeu AspGluIle ProProGln AsnAsnAsnVal

1261 CCACCTCGAC AGGGCTTCAG CCACCGTCTG AGCCACGTGA GCATGTTCCG CAGTGGCTTC
     ProProArg GlnGlyPhe SerHisArgLeu SerHisVal SerMetPhe ArgSerGlyPhe

1321 AGCAACAGCA GCGTGAGCAT CATCCGTGCA CCTATGTTCA GCTGGATTCA CCGCAGTGCC
     SerAsnSer SerValSer IleIleArgAla ProMetPhe SerTrpIle HisArgSerAla

1381 GAGTTCAACA ACATCATCCC CAGCAGCCAG ATCACCCAGA TCCCCCTGAC CAAGAGCACC
     GluPheAsn AsnIleIle ProSerSerGln IleThrGln IleProLeu ThrLysSerThr

1441 AACCTGGGCA GCGGCACCAG CGTGGTGAAG GGCCCCGGCT TCACCGGCGG CGACATCCTG
     AsnLeuGly SerGlyThr SerValValLys GlyProGly PheThrGly GlyAspIleLeu

1501 CGCCGCACCA GCCCCGGCCA GATCAGCACC CTGCGCGTGA ACATCACCGC CCCCCTGAGC
     ArgArgThr SerProGly GlnIleSerThr LeuArgVal AsnIleThr AlaProLeuSer

1561 CAGCGCTACC GCGTCCGCAT CCGCTACGCC AGCACCACCA ACCTGCAGTT CCACACCAGC
     GlnArgTyr ArgValArg IleArgTyrAla SerThrThr AsnLeuGln PheHisThrSer

1621 ATCGACGGCC GCCCCATCAA CCAGGGCAAC TTCAGCGCCA CCATGAGCAG CGGCAGCAAC
     IleAspGly ArgProIle AsnGlnGlyAsn PheSerAla ThrMetSer SerGlySerAsn

1681 CTGCAGAGCG GCAGCTTCCG CACCGTGGGC TTCACCACCC CCTTCAACTT CAGCAACGGC
     LeuGlnSer GlySerPhe ArgThrValGly PheThrThr ProPheAsn PheSerAsnGly

1741 AGCAGCGTGT TCACCCTGAG CGCCCACGTG TTCAACAGCG GCAACGAGGT GTACATCGAC
     SerSerVal PheThrLeu SerAlaHisVal PheAsnSer GlyAsnGlu ValTyrIleAsp

1801 CGCATCGAGT TCGTGCCCGC CGAGGTGACC TTCGAGGCCG AGTACGACCT GGAGAGGGCT
     ArgIleGlu PheValPro AlaGluValThr PheGluAla GluTyrAsp LeuGluArgAla

1861 CAGAAGGCCG TGAACGAGCT GTTCACCAGC AGCAACCAGA TCGGCCTGAA GACCGACGTG
     GlnLysAla ValAsnGlu LeuPheThrSer SerAsnGln IleGlyLeu LysThrAspVal

1921 ACCGACTACC ACATCGATCA AGTATCCAAT TTAGTTGAGT GTTTATCTGA TGAATTTTGT
     ThrAspTyr HisIleAsp GlnValSerAsn LeuValGlu CysLeuSer AspGluPheCys

1981 CTGGATGAAA AAAAGAATT GTCCGAGAAA GTCAAACATG CGAAGCGACT TAGTGATGAG
     LeuAspGlu LysLysGlu LeuSerGluLys ValLysHis AlaLysArg LeuSerAspGlu
```

Fig. 9C

```
2041 CGGAATTTAC TTCAAGATCC AAACTTTAGA GGGATCAATA GACAACTAGA CCGTGGCTGG
     ArgAsnLeu  LeuGlnAsp  ProAsnPheArg GlyIleAsn  ArgGlnLeu  AspArgGlyTrp

2101 AGAGGAAGTA CGGATATTAC CATCCAAGGA GGCGATGACG TATTCAAAGA GAATTACGTT
     ArgGlySer  ThrAspIle  ThrIleGlnGly GlyAspAsp  ValPheLys  GluAsnTyrVal

2161 ACGCTATTGG GTACCTTCGA CGAGTGCTAC CCCACCTACC TGTACCAGAA GATCGACGAG
     ThrLeuLeu  GlyThrPhe  AspGluCysTyr ProThrTyr  LeuTyrGln  LysIleAspGlu

2221 AGCAAGCTGA AGGCCTACAC CCGCTACCAG CTGCGCGGCT ACATCGAGGA CAGCCAGGAC
     SerLysLeu  LysAlaTyr  ThrArgTyrGln LeuArgGly  TyrIleGlu  AspSerGlnAsp

2281 CTGGAAATCT ACCTGATCCG CTACAACGCC AAGCACGAGA CCGTGAACGT GCCCGGCACC
     LeuGluIle  TyrLeuIle  ArgTyrAsnAla LysHisGlu  ThrValAsn  ValProGlyThr

2341 GGCAGCCTGT GGCCCCTGAG CGCCCCCAGC CCCATCGGCA AGTGCGGGGA GCCGAATCGA
     GlySerLeu  TrpProLeu  SerAlaProSer ProIleGly  LysCysGly  GluProAsnArg

2401 TGCGCTCCGC ACCTGGAGTG GAACCCGGAC CTAGACTGCA GCTGCAGGGA CGGGGAGAAG
     CysAlaPro  HisLeuGlu  TrpAsnProAsp LeuAspCys  SerCysArg  AspGlyGluLys

2461 TGCGCCCACC ACAGCCACCA CTTCAGCCTG GACATCGACG TGGGCTGCAC CGACCTGAAC
     CysAlaHis  HisSerHis  HisPheSerLeu AspIleAsp  ValGlyCys  ThrAspLeuAsn

2521 GAGGACCTGG GCGTGTGGGT GATCTTCAAG ATCAAGACCC AGGACGGCCA CGCCCGCCTG
     GluAspLeu  GlyValTrp  ValIlePheLys IleLysThr  GlnAspGly  HisAlaArgLeu

2581 GGCAATCTAG AATTTCTCGA AGAGAAACCA TTAGTAGGAG AAGCACTAGC TCGTGTGAAA
     GlyAsnLeu  GluPheLeu  GluGluLysPro LeuValGly  GluAlaLeu  AlaArgValLys

2641 AGAGCGGAGA AAAAATGGAG AGACAAACGT GAAAAATTGG AATGGGAAAC AAATATTGTT
     ArgAlaGlu  LysLysTrp  ArgAspLysArg GluLysLeu  GluTrpGlu  ThrAsnIleVal

2701 TATAAAGAGG CAAAAGAATC TGTAGATGCT TTATTTGTAA ACTCTCAATA TGATAGATTA
     TyrLysGlu  AlaLysGlu  SerValAspAla LeuPheVal  AsnSerGln  TyrAspArgLeu

2761 CAAGCGGATA CCAACATCGC GATGATTCAT GCGGCAGATA AACGCGTTCA TAGCATTCGA
     GlnAlaAsp  ThrAsnIle  AlaMetIleHis AlaAlaAsp  LysArgVal  HisSerIleArg

2821 GAAGCTTATC TGCCTGAGCT GTCTGTGATT CCGGGTGTCA ATGCGGCTAT TTTTGAAGAA
     GluAlaTyr  LeuProGlu  LeuSerValIle ProGlyVal  AsnAlaAla  IlePheGluGlu

2881 TTAGAAGGGC GTATTTTCAC TGCATTCTCC CTATATGATG CGAGAAATGT CATTAAAAAT
     LeuGluGly  ArgIlePhe  ThrAlaPheSer LeuTyrAsp  AlaArgAsn  ValIleLysAsn

2941 GGTGATTTTA ATAATGGCTT ATCCTGCTGG AACGTGAAAG GCATGTAGA TGTAGAAGAA
     GlyAspPhe  AsnAsnGly  LeuSerCysTrp AsnValLys  GlyHisVal  AspValGluGlu

3001 CAAAACAACC ACCGTTCGGT CCTTGTTGTT CCGGAATGGG AAGCAGAAGT GTCACAAGAA
     GlnAsnAsn  HisArgSer  ValLeuValVal ProGluTrp  GluAlaGlu  ValSerGlnGlu
```

Fig. 9D

```
3061 GTTCGTGTCT GTCCGGGTCG TGGCTATATC CTTCGTGTCA CAGCGTACAA GGAGGGATAT
     ValArgVal CysProGly ArgGlyTyrIle LeuArgVal ThrAlaTyr LysGluGlyTyr

3121 GGAGAAGGTT GCGTAACCAT TCATGAGATC GAGAACAATA CAGACGAACT GAAGTTTAGC
     GlyGluGly CysValThr IleHisGluIle GluAsnAsn ThrAspGlu LeuLysPheSer

3181 AACTGTGTAG AAGAGGAAGT ATATCCAAAC AACACGGTAA CGTGTAATGA TTATACTGCG
     AsnCysVal GluGluGlu ValTyrProAsn AsnThrVal ThrCysAsn AspTyrThrAla

3241 ACTCAAGAAG AATATGAGGG TACGTACACT TCTCGTAATC GAGGATATGA CGGAGCCTAT
     ThrGlnGlu GluTyrGlu GlyThrTyrThr SerArgAsn ArgGlyTyr AspGlyAlaTyr

3301 GAAAGCAATT CTTCTGTACC AGCTGATTAT GCATCAGCCT ATGAAGAAAA AGCATATACA
     GluSerAsn SerSerVal ProAlaAspTyr AlaSerAla TyrGluGlu LysAlaTyrThr

3361 GATGGACGAA GAGACAATCC TTGTGAATCT AACAGAGGAT ATGGGATTA CACACCACTA
     AspGlyArg ArgAspAsn ProCysGluSer AsnArgGly TyrGlyAsp TyrThrProLeu

3421 CCAGCTGGCT ATGTGACAAA AGAATTAGAG TACTTCCCAG AAACCGATAA GGTATGGATT
     ProAlaGly TyrValThr LysGluLeuGlu TyrPhePro GluThrAsp LysValTrpIle

3481 GAGATCGGAG AAACGGAAGG AACATTCATC GTGGACAGCG TGGAATTACT TCTTATGGAG
     GluIleGly GluThrGlu GlyThrPheIle ValAspSer ValGluLeu LeuLeuMetGlu

3541 GAATAA
     Glu---
```

Fig. 11A

```
  1  ATGGACAACA ACCCCAACAT CAACGAGTGC ATCCCCTACA ACTGCCTGAG CAACCCCGAG
     MetAspAsn  AsnProAsn  IleAsnGluCys IleProTyr  AsnCysLeu  SerAsnProGlu

61  GTGGAGGTGC TGGGCGGCGA GCGCATCGAG ACCGGCTACA CCCCCATCGA CATCAGCCTG
     ValGluVal  LeuGlyGly  GluArgIleGlu ThrGlyTyr  ThrProIle  AspIleSerLeu

121  AGCCTGACCC AGTTCCTGCT GAGCGAGTTC GTGCCCGGCG CCGGCTTCGT GCTGGGCCTG
     SerLeuThr  GlnPheLeu  LeuSerGluPhe ValProGly  AlaGlyPhe  ValLeuGlyLeu

181  GTGGACATCA TCTGGGGCAT CTTCGGCCCC AGCCAGTGGG ACGCCTTCCT GGTGCAGATC
     ValAspIle  IleTrpGly  IlePheGlyPro SerGlnTrp  AspAlaPhe  LeuValGlnIle

241  GAGCAGCTGA TCAACCAGCG CATCGAGGAG TTCGCCCGCA ACCAGGCCAT CAGCCGCCTG
     GluGlnLeu  IleAsnGln  ArgIleGluGlu PheAlaArg  AsnGlnAla  IleSerArgLeu

301  GAGGGCCTGA GCAACCTGTA CCAAATCTAC GCCGAGAGCT TCCGCGAGTG GGAGGCCGAC
     GluGlyLeu  SerAsnLeu  TyrGlnIleTyr AlaGluSer  PheArgGlu  TrpGluAlaAsp

361  CCCACCAACC CCGCCCTGCG CGAGGAGATG CGCATCCAGT TCAACGACAT GAACAGCGCC
     ProThrAsn  ProAlaLeu  ArgGluGluMet ArgIleGln  PheAsnAsp  MetAsnSerAla

421  CTGACCACCG CCATCCCCCT GTTCGCCGTG CAGAACTACC AGGTGCCCCT GCTGAGCGTG
     LeuThrThr  AlaIlePro  LeuPheAlaVal GlnAsnTyr  GlnValPro  LeuLeuSerVal

481  TACGTGCAGG CCGCCAACCT GCACCTGAGC GTGCTGCGCG ACGTCAGCGT GTTCGGCCAG
     TyrValGln  AlaAlaAsn  LeuHisLeuSer ValLeuArg  AspValSer  ValPheGlyGln

541  CGCTGGGGCT TCGACGCCGC CACCATCAAC AGCCGCTACA ACGACCTGAC CGCCTGATC
     ArgTrpGly  PheAspAla  AlaThrIleAsn SerArgTyr  AsnAspLeu  ThrArgLeuIle

601  GGCAACTACA CCGACCACGC CGTGCGCTGG TACAACACCG GCCTGGAGCG CGTGTGGGGT
     GlyAsnTyr  ThrAspHis  AlaValArgTrp TyrAsnThr  GlyLeuGlu  ArgValTrpGly

661  CCCGACAGCC GCGACTGGAT CAGGTACAAC CAGTTCCGCC GCGAGCTGAC CCTGACCGTG
     ProAspSer  ArgAspTrp  IleArgTyrAsn GlnPheArg  ArgGluLeu  ThrLeuThrVal

721  CTGGACATCG TGAGCCTGTT CCCCAACTAC GACAGCCGCA CCTACCCCAT CCGCACCGTG
     LeuAspIle  ValSerLeu  PheProAsnTyr AspSerArg  ThrTyrPro  IleArgThrVal

781  AGCCAGCTGA CCCGCGAGAT TTACACCAAC CCCGTGCTGG AGAACTTCGA CGGCAGCTTC
     SerGlnLeu  ThrArgGlu  IleTyrThrAsn ProValLeu  GluAsnPhe  AspGlySerPhe

841  CGCGGCAGCG CCCAGGGCAT CGAGGGCAGC ATCCGCAGCC CCACCTGAT GGACATCCTG
     ArgGlySer  AlaGlnGly  IleGluGlySer IleArgSer  ProHisLeu  MetAspIleLeu

901  AACAGCATCA CCATCTACAC CGACGCCCAC CGCGGCGAGT ACTACTGGAG CGGCCACCAG
     AsnSerIle  ThrIleTyr  ThrAspAlaHis ArgGlyGlu  TyrTyrTrp  SerGlyHisGln

961  ATCATGGCCA GCCCCGTCGG CTTCAGCGGC CCCGAGTTCA CCTTCCCCCT GTACGGCACC
     IleMetAla  SerProVal  GlyPheSerGly ProGluPhe  ThrPhePro  LeuTyrGlyThr
```

Fig. 11B

```
1021  ATGGGCAACG CTGCACCTCA GCAGCGCATC GTGGCACAGC TGGGCCAGGG AGTGTACCGC
      MetGlyAsn AlaAlaPro GlnGlnArgIle ValAlaGln LeuGlyGln GlyValTyrArg

1081  ACCCTGAGCA GCACCCTGTA CCGTCGACCT TTCAACATCG GCATCAACAA CCAGCAGCTG
      ThrLeuSer SerThrLeu TyrArgArgPro PheAsnIle GlyIleAsn AsnGlnGlnLeu

1141  AGCGTGCTGG ACGGCACCGA GTTCGCCTAC GGCACCAGCA GCAACCTGCC CAGCGCCGTG
      SerValLeu AspGlyThr GluPheAlaTyr GlyThrSer SerAsnLeu ProSerAlaVal

1201  TACCGCAAGA GCGGCACCGT GGACAGCCTG GACGAGATCC CCCCTCAGAA CAACAACGTG
      TyrArgLys SerGlyThr ValAspSerLeu AspGluIle ProProGln AsnAsnAsnVal

1261  CCACCTCGAC AGGGCTTCAG CCACCGTCTG AGCCACGTGA GCATGTTCCG CAGTGGCTTC
      ProProArg GlnGlyPhe SerHisArgLeu SerHisVal SerMetPhe ArgSerGlyPhe

1321  AGCAACAGCA GCGTGAGCAT CATCCGTGCA CCTATGTTCA GCTGGATTCA CCGCAGTGCC
      SerAsnSer SerValSer IleIleArgAla ProMetPhe SerTrpIle HisArgSerAla

1381  GAGTTCAACA ACATCATCCC CAGCAGCCAG ATCACCCAGA TCCCCCTGAC CAAGAGCACC
      GluPheAsn AsnIleIle ProSerSerGln IleThrGln IleProLeu ThrLysSerThr

1441  AACCTGGGCA GCGGCACCAG CGTGGTGAAG GGCCCCGGCT TCACCGGCGG CGACATCCTG
      AsnLeuGly SerGlyThr SerValValLys GlyProGly PheThrGly GlyAspIleLeu

1501  CGCCGCACCA GCCCCGGCCA GATCAGCACC CTGCGCGTGA ACATCACCGC CCCCCTGAGC
      ArgArgThr SerProGly GlnIleSerThr LeuArgVal AsnIleThr AlaProLeuSer

1561  CAGCGCTACC GCGTCCGCAT CCGCTACGCC AGCACCACCA ACCTGCAGTT CCACACCAGC
      GlnArgTyr ArgValArg IleArgTyrAla SerThrThr AsnLeuGln PheHisThrSer

1621  ATCGACGGCC GCCCCATCAA CCAGGGCAAC TTCAGCGCCA CCATGAGCAG CGGCAGCAAC
      IleAspGly ArgProIle AsnGlnGlyAsn PheSerAla ThrMetSer SerGlySerAsn

1681  CTGCAGAGCG GCAGCTTCCG CACCGTGGGC TTCACCACCC CCTTCAACTT CAGCAACGGC
      LeuGlnSer GlySerPhe ArgThrValGly PheThrThr ProPheAsn PheSerAsnGly

1741  AGCAGCGTGT TCACCCTGAG CGCCCACGTG TTCAACAGCG GCAACGAGGT GTACATCGAC
      SerSerVal PheThrLeu SerAlaHisVal PheAsnSer GlyAsnGlu ValTyrIleAsp

1801  CGCATCGAGT TCGTGCCCGC CGAGGTGACC TTCGAGGCCG AGTACGACCT GGAGAGGGCT
      ArgIleGlu PheValPro AlaGluValThr PheGluAla GluTyrAsp LeuGluArgAla

1861  CAGAAGGCCG TGAACGAGCT GTTCACCAGC AGCAACCAGA TCGGCCTGAA GACCGACGTG
      GlnLysAla ValAsnGlu LeuPheThrSer SerAsnGln IleGlyLeu LysThrAspVal

1921  ACCGACTACC ACATCGATCA GGTGAGCAAC CTGGTGGAGT GCTTAAGCGA CGAGTTCTGC
      ThrAspTyr HisIleAsp GlnValSerAsn LeuValGlu CysLeuSer AspGluPheCys

1981  CTGGACGAGA AGAAGGAGCT GAGCGAGAAG GTGAAGCACG CCAAGCGCCT GAGCGACGAG
      LeuAspGlu LysLysGlu LeuSerGluLys ValLysHis AlaLysArg LeuSerAspGlu
```

Fig. 11C

```
2041  CGCAACCTGC TGCAGGACCC CAACTTCCGC GGCATCAACC GCCAGCTGGA CCGCGGCTGG
      ArgAsnLeu  LeuGlnAsp  ProAsnPheArg GlyIleAsn  ArgGlnLeu  AspArgGlyTrp

2101  CGAGGCAGCA CCGATATCAC CATCCAGGGC GGCGACGACG TGTTCAAGGA GAACTACGTG
      ArgGlySer  ThrAspIle  ThrIleGlnGly GlyAspAsp  ValPheLys  GluAsnTyrVal

2161  ACCCTGCTGG GCACCTTCGA CGAGTGCTAC CCCACCTACC TGTACCAGAA GATCGACGAG
      ThrLeuLeu  GlyThrPhe  AspGluCysTyr ProThrTyr  LeuTyrGln  LysIleAspGlu

2221  AGCAAGCTGA AGGCCTACAC CCGCTACCAG CTGCGCGGCT ACATCGAGGA CAGCCAGGAC
      SerLysLeu  LysAlaTyr  ThrArgTyrGln LeuArgGly  TyrIleGlu  AspSerGlnAsp

2281  CTGGAAATCT ACCTGATCCG CTACAACGCC AAGCACGAGA CCGTGAACGT GCCCGGCACC
      LeuGluIle  TyrLeuIle  ArgTyrAsnAla LysHisGlu  ThrValAsn  ValProGlyThr

2341  GGCAGCCTGT GGCCCCTGAG CGCCCCCAGC CCCATCGGCA AGTGCGGGGA GCCGAATCGA
      GlySerLeu  TrpProLeu  SerAlaProSer ProIleGly  LysCysGly  GluProAsnArg

2401  TGCGCTCCGC ACCTGGAGTG GAACCCGGAC CTAGACTGCA GCTGCAGGGA CGGGGAGAAG
      CysAlaPro  HisLeuGlu  TrpAsnProAsp LeuAspCys  SerCysArg  AspGlyGluLys

2461  TGCGCCCACC ACAGCCACCA CTTCAGCCTG GACATCGACG TGGGCTGCAC CGACCTGAAC
      CysAlaHis  HisSerHis  HisPheSerLeu AspIleAsp  ValGlyCys  ThrAspLeuAsn

2521  GAGGACCTGG GCGTGTGGGT GATCTTCAAG ATCAAGACCC AGGACGGCCA CGCCCGCCTG
      GluAspLeu  GlyValTrp  ValIlePheLys IleLysThr  GlnAspGly  HisAlaArgLeu

2581  GGCAATCTAG AATTTCTCGA AGAGAAACCA TTAGTAGGAG AAGCACTAGC TCGTGTGAAA
      GlyAsnLeu  GluPheLeu  GluGluLysPro LeuValGly  GluAlaLeu  AlaArgValLys

2641  AGAGCGGAGA AAAAATGGAG AGACAAACGT GAAAAATTGG AATGGGAAAC AAATATTGTT
      ArgAlaGlu  LysLysTrp  ArgAspLysArg GluLysLeu  GluTrpGlu  ThrAsnIleVal

2701  TATAAAGAGG CAAAAGAATC TGTAGATGCT TTATTTGTAA ACTCTCAATA TGATAGATTA
      TyrLysGlu  AlaLysGlu  SerValAspAla LeuPheVal  AsnSerGln  TyrAspArgLeu

2761  CAAGCGGATA CCAACATCGC GATGATTCAT GCGGCAGATA AACGCGTTCA TAGCATTCGA
      GlnAlaAsp  ThrAsnIle  AlaMetIleHis AlaAlaAsp  LysArgVal  HisSerIleArg

2821  GAAGCTTATC TGCCTGAGCT GTCTGTGATT CCGGGTGTCA ATGCGGCTAT TTTTGAAGAA
      GluAlaTyr  LeuProGlu  LeuSerValIle ProGlyVal  AsnAlaAla  IlePheGluGlu

2881  TTAGAAGGGC GTATTTTCAC TGCATTCTCC CTATATGATG CGAGAAATGT CATTAAAAAT
      LeuGluGly  ArgIlePhe  ThrAlaPheSer LeuTyrAsp  AlaArgAsn  ValIleLysAsn

2941  GGTGATTTTA ATAATGGCTT ATCCTGCTGG AACGTGAAAG GGCATGTAGA TGTAGAAGAA
      GlyAspPhe  AsnAsnGly  LeuSerCysTrp AsnValLys  GlyHisVal  AspValGluGlu

3001  CAAAACAACC ACCGTTCGGT CCTTGTTGTT CCGGAATGGG AAGCAGAAGT GTCACAAGAA
      GlnAsnAsn  HisArgSer  ValLeuValVal ProGluTrp  GluAlaGlu  ValSerGlnGlu
```

Fig. 11D

```
3061  GTTCGTGTCT GTCCGGGTCG TGGCTATATC CTTCGTGTCA CAGCGTACAA GGAGGGATAT
      ValArgVal CysProGly ArgGlyTyrIle LeuArgVal ThrAlaTyr LysGluGlyTyr

3121  GGAGAAGGTT GCGTAACCAT TCATGAGATC GAGAACAATA CAGACGAACT GAAGTTTAGC
      GlyGluGly CysValThr IleHisGluIle GluAsnAsn ThrAspGlu LeuLysPheSer

3181  AACTGTGTAG AAGAGGAAGT ATATCCAAAC AACACGGTAA CGTGTAATGA TTATACTGCG
      AsnCysVal GluGluGlu ValTyrProAsn AsnThrVal ThrCysAsn AspTyrThrAla

3241  ACTCAAGAAG AATATGAGGG TACGTACACT TCTCGTAATC GAGGATATGA CGGAGCCTAT
      ThrGlnGlu GluTyrGlu GlyThrTyrThr SerArgAsn ArgGlyTyr AspGlyAlaTyr

3301  GAAAGCAATT CTTCTGTACC AGCTGATTAT GCATCAGCCT ATGAAGAAAA AGCATATACA
      GluSerAsn SerSerVal ProAlaAspTyr AlaSerAla TyrGluGlu LysAlaTyrThr

3361  GATGGACGAA GAGACAATCC TTGTGAATCT AACAGAGGAT ATGGGGATTA CACACCACTA
      AspGlyArg ArgAspAsn ProCysGluSer AsnArgGly TyrGlyAsp TyrThrProLeu

3421  CCAGCTGGCT ATGTGACAAA AGAATTAGAG TACTTCCCAG AAACCGATAA GGTATGGATT
      ProAlaGly TyrValThr LysGluLeuGlu TyrPhePro GluThrAsp LysValTrpIle

3481  GAGATCGGAG AAACGGAAGG AACATTCATC GTGGACAGCG TGGAATTACT TCTTATGGAG
      GluIleGly GluThrGlu GlyThrPheIle ValAspSer ValGluLeu LeuLeuMetGlu

3541  GAATAA
      Glu---
```

Fig. 13A

```
  1  ATGGACAACA ACCCCAACAT CAACGAGTGC ATCCCCTACA ACTGCCTGAG CAACCCCGAG
     MetAspAsn  AsnProAsn  IleAsnGluCys IleProTyr  AsnCysLeu  SerAsnProGlu

61  GTGGAGGTGC TGGGCGGCGA GCGCATCGAG ACCGGCTACA CCCCCATCGA CATCAGCCTG
     ValGluVal  LeuGlyGly  GluArgIleGlu ThrGlyTyr  ThrProIle  AspIleSerLeu

121  AGCCTGACCC AGTTCCTGCT GAGCGAGTTC GTGCCCGGCG CCGGCTTCGT GCTGGGCCTG
     SerLeuThr  GlnPheLeu  LeuSerGluPhe ValProGly  AlaGlyPhe  ValLeuGlyLeu

181  GTGGACATCA TCTGGGGCAT CTTCGGCCCC AGCCAGTGGG ACGCCTTCCT GGTGCAGATC
     ValAspIle  IleTrpGly  IlePheGlyPro SerGlnTrp  AspAlaPhe  LeuValGlnIle

241  GAGCAGCTGA TCAACCAGCG CATCGAGGAG TTCGCCCGCA ACCAGGCCAT CAGCCGCCTG
     GluGlnLeu  IleAsnGln  ArgIleGluGlu PheAlaArg  AsnGlnAla  IleSerArgLeu

301  GAGGGCCTGA GCAACCTGTA CCAAATCTAC GCCGAGAGCT TCCGCGAGTG GGAGGCCGAC
     GluGlyLeu  SerAsnLeu  TyrGlnIleTyr AlaGluSer  PheArgGlu  TrpGluAlaAsp

361  CCCACCAACC CCGCCCTGCG CGAGGAGATG CGCATCCAGT TCAACGACAT GAACAGCGCC
     ProThrAsn  ProAlaLeu  ArgGluGluMet ArgIleGln  PheAsnAsp  MetAsnSerAla

421  CTGACCACCG CCATCCCCCT GTTCGCCGTG CAGAACTACC AGGTGCCCCT GCTGAGCGTG
     LeuThrThr  AlaIlePro  LeuPheAlaVal GlnAsnTyr  GlnValPro  LeuLeuSerVal

481  TACGTGCAGG CCGCCAACCT GCACCTGAGC GTGCTGCGCG ACGTCAGCGT GTTCGGCCAG
     TyrValGln  AlaAlaAsn  LeuHisLeuSer ValLeuArg  AspValSer  ValPheGlyGln

541  CGCTGGGGCT TCGACGCCGC CACCATCAAC AGCCGCTACA ACGACCTGAC CCGCCTGATC
     ArgTrpGly  PheAspAla  AlaThrIleAsn SerArgTyr  AsnAspLeu  ThrArgLeuIle

601  GGCAACTACA CCGACCACGC CGTGCGCTGG TACAACACCG GCCTGGAGCG CGTGTGGGGT
     GlyAsnTyr  ThrAspHis  AlaValArgTrp TyrAsnThr  GlyLeuGlu  ArgValTrpGly

661  CCCGACAGCC GCGACTGGAT CAGGTACAAC CAGTTCCGCC GCGAGCTGAC CCTGACCGTG
     ProAspSer  ArgAspTrp  IleArgTyrAsn GlnPheArg  ArgGluLeu  ThrLeuThrVal

721  CTGGACATCG TGAGCCTGTT CCCCAACTAC GACAGCCGCA CCTACCCCAT CCGCACCGTG
     LeuAspIle  ValSerLeu  PheProAsnTyr AspSerArg  ThrTyrPro  IleArgThrVal

781  AGCCAGCTGA CCCGCGAGAT TTACACCAAC CCCGTGCTGG AGAACTTCGA CGGCAGCTTC
     SerGlnLeu  ThrArgGlu  IleTyrThrAsn ProValLeu  GluAsnPhe  AspGlySerPhe

841  CGCGGCAGCG CCCAGGGCAT CGAGGGCAGC ATCCGCAGCC CCCACCTGAT GGACATCCTG
     ArgGlySer  AlaGlnGly  IleGluGlySer IleArgSer  ProHisLeu  MetAspIleLeu

901  AACAGCATCA CCATCTACAC CGACGCCCAC CGCGGCGAGT ACTACTGGAG CGGCCACCAG
     AsnSerIle  ThrIleTyr  ThrAspAlaHis ArgGlyGlu  TyrTyrTrp  SerGlyHisGln

961  ATCATGGCCA GCCCCGTCGG CTTCAGCGGC CCCGAGTTCA CCTTCCCCCT GTACGGCACC
     IleMetAla  SerProVal  GlyPheSerGly ProGluPhe  ThrPhePro  LeuTyrGlyThr
```

Fig. 13B

```
1021  ATGGGCAACG CTGCACCTCA GCAGCGCATC GTGGCACAGC TGGGCCAGGG AGTGTACCGC
      MetGlyAsn AlaAlaPro GlnGlnArgIle ValAlaGln LeuGlyGln GlyValTyrArg

1081  ACCCTGAGCA GCACCCTGTA CCGTCGACCT TTCAACATCG GCATCAACAA CCAGCAGCTG
      ThrLeuSer SerThrLeu TyrArgArgPro PheAsnIle GlyIleAsn AsnGlnGlnLeu

1141  AGCGTGCTGG ACGGCACCGA GTTCGCCTAC GGCACCAGCA GCAACCTGCC CAGCGCCGTG
      SerValLeu AspGlyThr GluPheAlaTyr GlyThrSer SerAsnLeu ProSerAlaVal

1201  TACCGCAAGA GCGGCACCGT GGACAGCCTG GACGAGATCC CCCCTCAGAA CAACAACGTG
      TyrArgLys SerGlyThr ValAspSerLeu AspGluIle ProProGln AsnAsnAsnVal

1261  CCACCTCGAC AGGGCTTCAG CCACCGTCTG AGCCACGTGA GCATGTTCCG CAGTGGCTTC
      ProProArg GlnGlyPhe SerHisArgLeu SerHisVal SerMetPhe ArgSerGlyPhe

1321  AGCAACAGCA GCGTGAGCAT CATCCGTGCA CCTATGTTCA GCTGGATTCA CCGCAGTGCC
      SerAsnSer SerValSer IleIleArgAla ProMetPhe SerTrpIle HisArgSerAla

1381  GAGTTCAACA ACATCATCCC CAGCAGCCAG ATCACCCAGA TCCCCCTGAC CAAGAGCACC
      GluPheAsn AsnIleIle ProSerSerGln IleThrGln IleProLeu ThrLysSerThr

1441  AACCTGGGCA GCGGCACCAG CGTGGTGAAG GGCCCCGGCT TCACCGGCGG CGACATCCTG
      AsnLeuGly SerGlyThr SerValValLys GlyProGly PheThrGly GlyAspIleLeu

1501  CGCCGCACCA GCCCCGGCCA GATCAGCACC CTGCGCGTGA ACATCACCGC CCCCCTGAGC
      ArgArgThr SerProGly GlnIleSerThr LeuArgVal AsnIleThr AlaProLeuSer

1561  CAGCGCTACC GCGTCCGCAT CCGCTACGCC AGCACCACCA ACCTGCAGTT CCACACCAGC
      GlnArgTyr ArgValArg IleArgTyrAla SerThrThr AsnLeuGln PheHisThrSer

1621  ATCGACGGCC GCCCCATCAA CCAGGGCAAC TTCAGCGCCA CCATGAGCAG CGGCAGCAAC
      IleAspGly ArgProIle AsnGlnGlyAsn PheSerAla ThrMetSer SerGlySerAsn

1681  CTGCAGAGCG GCAGCTTCCG CACCGTGGGC TTCACCACCC CCTTCAACTT CAGCAACGGC
      LeuGlnSer GlySerPhe ArgThrValGly PheThrThr ProPheAsn PheSerAsnGly

1741  AGCAGCGTGT TCACCCTGAG CGCCCACGTG TTCAACAGCG GCAACGAGGT GTACATCGAC
      SerSerVal PheThrLeu SerAlaHisVal PheAsnSer GlyAsnGlu ValTyrIleAsp

1801  CGCATCGAGT TCGTGCCCGC CGAGGTGACC TTCGAGGCCG AGTACGACCT GGAGAGGGCT
      ArgIleGlu PheValPro AlaGluValThr PheGluAla GluTyrAsp LeuGluArgAla

1861  CAGAAGGCCG TGAACGAGCT GTTCACCAGC AGCAACCAGA TCGGCCTGAA GACCGACGTG
      GlnLysAla ValAsnGlu LeuPheThrSer SerAsnGln IleGlyLeu LysThrAspVal

1921  ACCGACTACC ACATCGATCA GGTGAGCAAC CTGGTGGAGT GCTTAAGCGA CGAGTTCTGC
      ThrAspTyr HisIleAsp GlnValSerAsn LeuValGlu CysLeuSer AspGluPheCys

1981  CTGGACGAGA AGAAGGAGCT GAGCGAGAAG GTGAAGCACG CCAAGCGCCT GAGCGACGAG
      LeuAspGlu LysLysGlu LeuSerGluLys ValLysHis AlaLysArg LeuSerAspGlu
```

Fig. 13C

```
2041  CGCAACCTGC TGCAGGACCC CAACTTCCGC GGCATCAACC GCCAGCTGGA CCGCGGCTGG
      ArgAsnLeu  LeuGlnAsp  ProAsnPheArg GlyIleAsn  ArgGlnLeu  AspArgGlyTrp

2101  CGAGGCAGCA CCGATATCAC CATCCAGGGC GGCGACGACG TGTTCAAGGA GAACTACGTG
      ArgGlySer  ThrAspIle  ThrIleGlnGly GlyAspAsp  ValPheLys  GluAsnTyrVal

2161  ACCCTGCTGG GCACCTTCGA CGAGTGCTAC CCCACCTACC TGTACCAGAA GATCGACGAG
      ThrLeuLeu  GlyThrPhe  AspGluCysTyr ProThrTyr  LeuTyrGln  LysIleAspGlu

2221  AGCAAGCTGA AGGCCTACAC CCGCTACCAG CTGCGCGGCT ACATCGAGGA CAGCCAGGAC
      SerLysLeu  LysAlaTyr  ThrArgTyrGln LeuArgGly  TyrIleGlu  AspSerGlnAsp

2281  CTGGAAATCT ACCTGATCCG CTACAACGCC AAGCACGAGA CCGTGAACGT GCCCGGCACC
      LeuGluIle  TyrLeuIle  ArgTyrAsnAla LysHisGlu  ThrValAsn  ValProGlyThr

2341  GGCAGCCTGT GGCCCCTGAG CGCCCCCAGC CCCATCGGCA AGTGCGGGGA GCCGAATCGA
      GlySerLeu  TrpProLeu  SerAlaProSer ProIleGly  LysCysGly  GluProAsnArg

2401  TGCGCTCCGC ACCTGGAGTG GAACCCGGAC CTAGACTGCA GCTGCAGGGA CGGGGAGAAG
      CysAlaPro  HisLeuGlu  TrpAsnProAsp LeuAspCys  SerCysArg  AspGlyGluLys

2461  TGCGCCCACC ACAGCCACCA CTTCAGCCTG GACATCGACG TGGGCTGCAC CGACCTGAAC
      CysAlaHis  HisSerHis  HisPheSerLeu AspIleAsp  ValGlyCys  ThrAspLeuAsn

2521  GAGGACCTGG GCGTGTGGGT GATCTTCAAG ATCAAGACCC AGGACGGCCA CGCCCGCCTG
      GluAspLeu  GlyValTrp  ValIlePheLys IleLysThr  GlnAspGly  HisAlaArgLeu

2581  GGCAATCTAG AGTTCCTGGA GGAGAAGCCC CTGGTGGGCG AGGCCCTGGC CCGCGTGAAG
      GlyAsnLeu  GluPheLeu  GluGluLysPro LeuValGly  GluAlaLeu  AlaArgValLys

2641  CGCGCCGAGA AGAAGTGGCG CGACAAGCGC GAGAAGCTGG AGTGGGAGAC CAACATCGTG
      ArgAlaGlu  LysLysTrp  ArgAspLysArg GluLysLeu  GluTrpGlu  ThrAsnIleVal

2701  TACAAGGAGG CCAAGGAGAG CGTGGACGCC CTGTTCGTGA ACAGCCAGTA CGACCGCCTG
      TyrLysGlu  AlaLysGlu  SerValAspAla LeuPheVal  AsnSerGln  TyrAspArgLeu

2761  CAGGCCGACA CCAACATCGC CATGATCCAC GCCGCCGACA AGCGCGTGCA CAGCATTCGC
      GlnAlaAsp  ThrAsnIle  AlaMetIleHis AlaAlaAsp  LysArgVal  HisSerIleArg

2821  GAGGCCTACC TGCCCGAGCT GAGCGTGATC CCCGGCGTGA ACGCCGCCAT CTTCGAGGAA
      GluAlaTyr  LeuProGlu  LeuSerValIle ProGlyVal  AsnAlaAla  IlePheGluGlu

2881  CTCGAGGGCC GCATCTTCAC CGCCTTCAGC CTGTACGACG CCCGCAACGT GATCAAGAAC
      LeuGluGly  ArgIlePhe  ThrAlaPheSer LeuTyrAsp  AlaArgAsn  ValIleLysAsn

2941  GGCGACTTCA ACAACGGCCT GAGCTGCTGG AACGTGAAGG GCCACGTGGA CGTGGAGGAG
      GlyAspPhe  AsnAsnGly  LeuSerCysTrp AsnValLys  GlyHisVal  AspValGluGlu

3001  CAGAACAACC ACCGCAGCGT GCTGGTGGTG CCCGAGTGGG AGGCCGAGGT GAGCCAGGAG
      GlnAsnAsn  HisArgSer  ValLeuValVal ProGluTrp  GluAlaGlu  ValSerGlnGlu
```

Fig. 13D

```
3061  GTGCGCGTGT GCCCCGGCCG CGGCTACATC CTGCGCGTGA CCGCCTACAA GGAGGGCTAC
      ValArgVal  CysProGly  ArgGlyTyrIle LeuArgVal  ThrAlaTyr  LysGluGlyTyr

3121  GGCGAGGGCT GCGTGACCAT CCACGAGATC GAGAACAACA CCGACGAGCT CAAGTTCAGC
      GlyGluGly  CysValThr  IleHisGluIle GluAsnAsn  ThrAspGlu  LeuLysPheSer

3181  AACTGCGTGG AGGAGGAGGT GTACCCCAAC AACACCGTGA CCTGCAACGA CTACACCGCG
      AsnCysVal  GluGluGlu  ValTyrProAsn AsnThrVal  ThrCysAsn  AspTyrThrAla

3241  ACCCAGGAGG AGTACGAGGG CACCTACACC AGCCGCAACC GCGGCTACGA CGGCGCCTAC
      ThrGlnGlu  GluTyrGlu  GlyThrTyrThr SerArgAsn  ArgGlyTyr  AspGlyAlaTyr

3301  GAGAGCAACA GCAGCGTGCC CGCCGACTAC GCCAGCGCCT ACGAGGAGAA GGCCTACACC
      GluSerAsn  SerSerVal  ProAlaAspTyr AlaSerAla  TyrGluGlu  LysAlaTyrThr

3361  GACGGCCGCC GCGACAACCC CTGCGAGAGC AACCGCGGCT ACGGCGACTA CACCCCCCTG
      AspGlyArg  ArgAspAsn  ProCysGluSer AsnArgGly  TyrGlyAsp  TyrThrProLeu

3421  CCCGCCGGCT ACGTGACCAA GGAGCTGGAG TACTTCCCCG AGACCGACAA GGTGTGGATC
      ProAlaGly  TyrValThr  LysGluLeuGlu TyrPhePro  GluThrAsp  LysValTrpIle

3481  GAGATCGGCG AGACCGAGGG CACCTTCATC GTGGACAGCG TGGAGCTGCT GCTGATGGAG
      GluIleGly  GluThrGlu  GlyThrPheIle ValAspSer  ValGluLeu  LeuLeuMetGlu

3541  GAG
      Glu
```

Fig. 15A

```
  1  ATGGACAACA ACCCCAACAT CAACGAGTGC ATCCCCTACA ACTGCCTGAG CAACCCCGAG
     MetAspAsn  AsnProAsn  IleAsnGluCys IleProTyr  AsnCysLeu  SerAsnProGlu

61  GTGGAGGTGC TGGGCGGCGA GCGCATCGAG ACCGGCTACA CCCCCATCGA CATCAGCCTG
     ValGluVal  LeuGlyGly  GluArgIleGlu ThrGlyTyr  ThrProIle  AspIleSerLeu

121  AGCCTGACCC AGTTCCTGCT GAGCGAGTTC GTGCCCGGCG CCGGCTTCGT GCTGGGCCTG
     SerLeuThr  GlnPheLeu  LeuSerGluPhe ValProGly  AlaGlyPhe  ValLeuGlyLeu

181  GTGGACATCA TCTGGGGCAT CTTCGGCCCC AGCCAGTGGG ACGCCTTCCT GGTGCAGATC
     ValAspIle  IleTrpGly  IlePheGlyPro SerGlnTrp  AspAlaPhe  LeuValGlnIle

241  GAGCAGCTGA TCAACCAGCG CATCGAGGAG TTCGCCCGCA ACCAGGCCAT CAGCCGCCTG
     GluGlnLeu  IleAsnGln  ArgIleGluGlu PheAlaArg  AsnGlnAla  IleSerArgLeu

301  GAGGGCCTGA GCAACCTGTA CCAAATCTAC GCCGAGAGCT TCCGCGAGTG GGAGGCCGAC
     GluGlyLeu  SerAsnLeu  TyrGlnIleTyr AlaGluSer  PheArgGlu  TrpGluAlaAsp

361  CCCACCAACC CCGCCCTGCG CGAGGAGATG CGCATCCAGT TCAACGACAT GAACAGCGCC
     ProThrAsn  ProAlaLeu  ArgGluGluMet ArgIleGln  PheAsnAsp  MetAsnSerAla

421  CTGACCACCG CCATCCCCCT GTTCGCCGTG CAGAACTACC AGGTGCCCCT GCTGAGCGTG
     LeuThrThr  AlaIlePro  LeuPheAlaVal GlnAsnTyr  GlnValPro  LeuLeuSerVal

481  TACGTGCAGG CCGCCAACCT GCACCTGAGC GTGCTGCGCG ACGTCAGCGT GTTCGGCCAG
     TyrValGln  AlaAlaAsn  LeuHisLeuSer ValLeuArg  AspValSer  ValPheGlyGln

541  CGCTGGGGCT TCGACGCCGC CACCATCAAC AGCCGCTACA ACGACCTGAC CCGCCTGATC
     ArgTrpGly  PheAspAla  AlaThrIleAsn SerArgTyr  AsnAspLeu  ThrArgLeuIle

601  GGCAACTACA CCGACCACGC CGTGCGCTGG TACAACACCG GCCTGGAGCG CGTGTGGGGT
     GlyAsnTyr  ThrAspHis  AlaValArgTrp TyrAsnThr  GlyLeuGlu  ArgValTrpGly

661  CCCGACAGCC GCGACTGGAT CAGGTACAAC CAGTTCCGCC GCGAGCTGAC CCTGACCGTG
     ProAspSer  ArgAspTrp  IleArgTyrAsn GlnPheArg  ArgGluLeu  ThrLeuThrVal

721  CTGGACATCG TGAGCCTGTT CCCCAACTAC GACAGCCGCA CCTACCCCAT CCGCACCGTG
     LeuAspIle  ValSerLeu  PheProAsnTyr AspSerArg  ThrTyrPro  IleArgThrVal

781  AGCCAGCTGA CCCGCGAGAT TTACACCAAC CCCGTGCTGG AGAACTTCGA CGGCAGCTTC
     SerGlnLeu  ThrArgGlu  IleTyrThrAsn ProValLeu  GluAsnPhe  AspGlySerPhe

841  CGCGGCAGCG CCCAGGGCAT CGAGGGCAGC ATCCGCAGCC CCCACCTGAT GGACATCCTG
     ArgGlySer  AlaGlnGly  IleGluGlySer IleArgSer  ProHisLeu  MetAspIleLeu

901  AACAGCATCA CCATCTACAC CGACGCCCAC CGCGGCGAGT ACTACTGGAG CGGCCACCAG
     AsnSerIle  ThrIleTyr  ThrAspAlaHis ArgGlyGlu  TyrTyrTrp  SerGlyHisGln

961  ATCATGGCCA GCCCCGTCGG CTTCAGCGGC CCCGAGTTCA CCTTCCCCCT GTACGGCACC
     IleMetAla  SerProVal  GlyPheSerGly ProGluPhe  ThrPhePro  LeuTyrGlyThr
```

Fig. 15B

```
1021  ATGGGCAACG CTGCACCTCA GCAGCGCATC GTGGCACAGC TGGGCCAGGG AGTGTACCGC
      MetGlyAsn  AlaAlaPro  GlnGlnArgIle VallAlaGln LeuGlyGln  GlyValTyrArg 1081  ACCCTGAGCA GCACCCTGTA CCGTCGACCT TTCAACATCG GCATCAACAA CCAGCAGCTG
      ThrLeuSer  SerThrLeu  TyrArgArgPro PheAsnIle  GlyIleAsn  AsnGlnGlnLeu 1141  AGCGTGCTGG ACGGCACCGA GTTCGCCTAC GGCACCAGCA GCAACCTGCC CAGCGCCGTG
      SerValLeu  AspGlyThr  GluPheAlaTyr GlyThrSer  SerAsnLeu  ProSerAlaVal 1201  TACCGCAAGA GCGGCACCGT GGACAGCCTG GACGAGATCC CCCCTCAGAA CAACAACGTG
      TyrArgLys  SerGlyThr  ValAspSerLeu AspGluIle  ProProGln  AsnAsnAsnVal 1261  CCACCTCGAC AGGGCTTCAG CCACCGTCTG AGCCACGTGA GCATGTTCCG CAGTGGCTTC
      ProProArg  GlnGlyPhe  SerHisArgLeu SerHisVal  SerMetPhe  ArgSerGlyPhe 1321  AGCAACAGCA GCGTGAGCAT CATCCGTGCA CCTATGTTCA GCTGGATTCA CCGCAGTGCC
      SerAsnSer  SerValSer  IleIleArgAla ProMetPhe  SerTrpIle  HisArgSerAla 1381  GAGTTCAACA ACATCATCCC CAGCAGCCAG ATCACCCAGA TCCCCCTGAC CAAGAGCACC
      GluPheAsn  AsnIleIle  ProSerSerGln IleThrGln  IleProLeu  ThrLysSerThr 1441  AACCTGGGCA GCGGCACCAG CGTGGTGAAG GGCCCCGGCT TCACCGGCGG CGACATCCTG
      AsnLeuGly  SerGlyThr  SerValValLys GlyProGly  PheThrGly  GlyAspIleLeu 1501  CGCCGCACCA GCCCCGGCCA GATCAGCACC CTGCGCGTGA ACATCACCGC CCCCCTGAGC
      ArgArgThr  SerProGly  GlnIleSerThr LeuArgVal  AsnIleThr  AlaProLeuSer 1561  CAGCGCTACC GCGTCCGCAT CCGCTACGCC AGCACCACCA ACCTGCAGTT CCACACCAGC
      GlnArgTyr  ArgValArg  IleArgTyrAla SerThrThr  AsnLeuGln  PheHisThrSer 1621  ATCGACGGCC GCCCCATCAA CCAGGGCAAC TTCAGCGCCA CCATGAGCAG CGGCAGCAAC
      IleAspGly  ArgProIle  AsnGlnGlyAsn PheSerAla  ThrMetSer  SerGlySerAsn 1681  CTGCAGAGCG GCAGCTTCCG CACCGTGGGC TTCACCACCC CCTTCAACTT CAGCAACGGC
      LeuGlnSer  GlySerPhe  ArgThrValGly PheThrThr  ProPheAsn  PheSerAsnGly 1741  AGCAGCGTGT TCACCCTGAG CGCCCACGTG TTCAACAGCG GCAACGAGGT GTACATCGAC
      SerSerVal  PheThrLeu  SerAlaHisVal PheAsnSer  GlyAsnGlu  ValTyrIleAsp 1801  CGCATCGAGT TCGTGCCCGC CGAGGTGACC TTCGAGGCCG AGTACGACCT GGAGAGGGCT
      ArgIleGlu  PheValPro  AlaGluValThr PheGluAla  GluTyrAsp  LeuGluArgAla 1861  CAGAAGGCCG TGAACGAGCT GTTCACCAGC AGCAACCAGA TCGGCCTGAA GACCGACGTG
      GlnLysAla  ValAsnGlu  LeuPheThrSer SerAsnGln  IleGlyLeu  LysThrAspVal 1921  ACCGACTACC ACATCGATCA AGTATCCAAT TTAGTTGAGT GTTTATCTGA TGAATTTTGT
      ThrAspTyr  HisIleAsp  GlnValSerAsn LeuValGlu  CysLeuSer  AspGluPheCys 1981  CTGGATGAAA AAAAAGAATT GTCCGAGAAA GTCAAACATG CGAAGCGACT TAGTGATGAG
      LeuAspGlu  LysLysGlu  LeuSerGluLys ValLysHis  AlaLysArg  LeuSerAspGlu
```

Fig. 15C

```
2041  CGGAATTTAC TTCAAGATCC AAACTTTAGA GGGATCAATA GACAACTAGA CCGTGGCTGG
      ArgAsnLeu  LeuGlnAsp  ProAsnPheArg GlyIleAsn  ArgGlnLeu  AspArgGlyTrp

2101  AGAGGAAGTA CGGATATTAC CATCCAAGGA GGCGATGACG TATTCAAAGA GAATTACGTT
      ArgGlySer  ThrAspIle  ThrIleGlnGly GlyAspAsp  ValPheLys  GluAsnTyrVal

2161  ACGCTATTGG GTACCTTTGA TGAGTGCTAT CCAACGTATT TATATCAAAA AATAGATGAG
      ThrLeuLeu  GlyThrPhe  AspGluCysTyr ProThrTyr  LeuTyrGln  LysIleAspGlu

2221  TCGAAATTAA AAGCCTATAC CCGTTACCAA TTAAGAGGGT ATATCGAAGA TAGTCAAGAC
      SerLysLeu  LysAlaTyr  ThrArgTyrGln LeuArgGly  TyrIleGlu  AspSerGlnAsp

2281  TTAGAAATCT ATTTAATTCG CTACAATGCC AAACACGAAA CAGTAAATGT GCCAGGTACG
      LeuGluIle  TyrLeuIle  ArgTyrAsnAla LysHisGlu  ThrValAsn  ValProGlyThr

2341  GGTTCCTTAT GGCCGCTTTC AGCCCCAAGT CCAATCGGCA AGTGCGGGGA GCCGAATCGA
      GlySerLeu  TrpProLeu  SerAlaProSer ProIleGly  LysCysGly  GluProAsnArg

2401  TGCGCTCCGC ACCTGGAGTG GAACCCGGAC CTAGACTGCA GCTGCAGGGA CGGGGAGAAG
      CysAlaPro  HisLeuGlu  TrpAsnProAsp LeuAspCys  SerCysArg  AspGlyGluLys

2461  TGCGCCCACC ACAGCCACCA CTTCAGCCTG GACATCGACG TGGGCTGCAC CGACCTGAAC
      CysAlaHis  HisSerHis  HisPheSerLeu AspIleAsp  ValGlyCys  ThrAspLeuAsn

2521  GAGGACCTGG GCGTGTGGGT GATCTTCAAG ATCAAGACCC AGGACGGCCA CGCCCGCCTG
      GluAspLeu  GlyValTrp  ValIlePheLys IleLysThr  GlnAspGly  HisAlaArgLeu

2581  GGCAATCTAG AATTTCTCGA AGAGAAACCA TTAGTAGGAG AAGCACTAGC TCGTGTGAAA
      GlyAsnLeu  GluPheLeu  GluGluLysPro LeuValGly  GluAlaLeu  AlaArgValLys

2641  AGAGCGGAGA AAAAATGGAG AGACAAACGT GAAAAATTGG AATGGGAAAC AAATATTGTT
      ArgAlaGlu  LysLysTrp  ArgAspLysArg GluLysLeu  GluTrpGlu  ThrAsnIleVal

2701  TATAAAGAGG CAAAAGAATC TGTAGATGCT TTATTTGTAA ACTCTCAATA TGATAGATTA
      TyrLysGlu  AlaLysGlu  SerValAspAla LeuPheVal  AsnSerGln  TyrAspArgLeu

2761  CAAGCGGATA CCAACATCGC GATGATTCAT GCGGCAGATA AACGCGTTCA TAGCATTCGA
      GlnAlaAsp  ThrAsnIle  AlaMetIleHis AlaAlaAsp  LysArgVal  HisSerIleArg

2821  GAAGCTTATC TGCCTGAGCT GTCTGTGATT CCGGGTGTCA ATGCGGCTAT TTTTGAAGAA
      GluAlaTyr  LeuProGlu  LeuSerValIle ProGlyVal  AsnAlaAla  IlePheGluGlu

2881  TTAGAAGGGC GTATTTTCAC TGCATTCTCC CTATATGATG CGAGAAATGT CATTAAAAAT
      LeuGluGly  ArgIlePhe  ThrAlaPheSer LeuTyrAsp  AlaArgAsn  ValIleLysAsn

2941  GGTGATTTTA ATAATGGCTT ATCCTGCTGG AACGTGAAAG GGCATGTAGA TGTAGAAGAA
      GlyAspPhe  AsnAsnGly  LeuSerCysTrp AsnValLys  GlyHisVal  AspValGluGlu

3001  CAAAACAACC ACCGTTCGGT CCTTGTTGTT CCGGAATGGG AAGCAGAAGT GTCACAAGAA
      GlnAsnAsn  HisArgSer  ValLeuValVal ProGluTrp  GluAlaGlu  ValSerGlnGlu
```

Fig. 15D

```
3061  GTTCGTGTCT GTCCGGGTCG TGGCTATATC CTTCGTGTCA CAGCGTACAA GGAGGGATAT
      ValArgVal CysProGly ArgGlyTyrIle LeuArgVal ThrAlaTyr LysGluGlyTyr

3121  GGAGAAGGTT GCGTAACCAT TCATGAGATC GAGAACAATA CAGACGAACT GAAGTTTAGC
      GlyGluGly CysValThr IleHisGluIle GluAsnAsn ThrAspGlu LeuLysPheSer

3181  AACTGTGTAG AAGAGGAAGT ATATCCAAAC AACACGGTAA CGTGTAATGA TTATACTGCG
      AsnCysVal GluGluGlu ValTyrProAsn AsnThrVal ThrCysAsn AspTyrThrAla

3241  ACTCAAGAAG AATATGAGGG TACGTACACT TCTCGTAATC GAGGATATGA CGGAGCCTAT
      ThrGlnGlu GluTyrGlu GlyThrTyrThr SerArgAsn ArgGlyTyr AspGlyAlaTyr

3301  GAAAGCAATT CTTCTGTACC AGCTGATTAT GCATCAGCCT ATGAAGAAAA AGCATATACA
      GluSerAsn SerSerVal ProAlaAspTyr AlaSerAla TyrGluGlu LysAlaTyrThr

3361  GATGGACGAA GAGACAATCC TTGTGAATCT AACAGAGGAT ATGGGGATTA CACACCACTA
      AspGlyArg ArgAspAsn ProCysGluSer AsnArgGly TyrGlyAsp TyrThrProLeu

3421  CCAGCTGGCT ATGTGACAAA AGAATTAGAG TACTTCCCAG AAACCGATAA GGTATGGATT
      ProAlaGly TyrValThr LysGluLeuGlu TyrPhePro GluThrAsp LysValTrpIle

3481  GAGATCGGAG AAACGGAAGG AACATTCATC GTGGACAGCG TGGAATTACT TCTTATGGAG
      GluIleGly GluThrGlu GlyThrPheIle ValAspSer ValGluLeu LeuLeuMetGlu

3541  GAATAAG
      Glu---
```

Fig. 23A

CryIA(b) Protein Levels in Transgenic Maize

ELISA Bt Values of Field Plants:

| INBRED X PARENT | ABRU PLANT Number | ng Bt/mg protein |
|---|---|---|
| 2ND01X171-4A | 1646 | 29 |
| 5N984X171-4A | 857 | 1705 |
| 5N984X171-4A | 870 | 1760 |
| 5N984X171-13 | 969 | 22 |
| 5N984X171-15 | 1468 | 17 |
| 5N984X171-15 | 1470 | 28 |
| 5N984X171-14A | 1502 | 180 |
| 5N984X171-14A | 1529 | 1500 |
| 5N984X176-11 | 1667 | 408 |
| 5N984X176-11 | 1671 | 1270 |
| 5N984X176-11 | 1673 | 1522 |
| 5N984X176-11 | 1675 | 943 |
| 5N984X176-11 | 1679 | 967 |
| 5N984X171-4B | 1942 | 15 |
| 5N984X171-4B | 1946 | 16 |
| 5NA56X171-16ABX | 1101 | 30 |
| 5NA89X176-11 | 1622 | 959 |
| 5NA89X176-11 | 1630 | 1172 |
| 5NA89X176-11 | 1635 | 1100 |
| 6F010X171-4 | 825 | 103 |
| 6F010X171-4 | 832 | 1298 |

-Bt levels are in ng cryIA(b)/mg total protein.

-Data are from progeny of the described maize transformants expressing the cryIA(b) protein.

-ELISA analysis of transgenic plant material was carried out using standard procedures as described elsewhere.

Fig. 23B
Bioassay of European corn borer, Ostrinia nubilalis, and sugarcane borer, Diatraea saccharalis

| Plasmid | Promoter | Cross | Plant No. | Bt Gene | Percent Mortality | |
|---|---|---|---|---|---|---|
| | | | | | Ostrinia | Diatraea |
| pCIB4431 | PEPC | 5N984 X 176-8B | 21 | + | 100 | 100 |
| | | | 22 | - | 0 | 0 |
| | | | 40 | + | 100 | 100 |
| pCIB4431 | PEPC | 5N984 X 176-11 | 95 | + | 100 | 100 |
| | | | 96 | - | 0 | 0 |
| | | | 98 | + | 100 | 100 |
| pCIB4418 | 35S | 5N984 X 171-14A | 45 | - | 0 | 10 |
| | | | 64 | + | 100 | 90 |
| | | | 68 | + | 100 | 100 |
| pCIB4431 | PEPC | 2N217AF X 176-8B | 1 | - | 0 | 0 |
| | | | 3 | + | 100 | 100 |
| | | | 4 | + | 100 | 100 |
| pCIB4418 | 35S | 2N217AF X 171-15 | 70 | - | 10 | 0 |
| | | | 83 | + | 90 | 80 |
| | | | 88 | + | 90 | 100 |

Fig. 23C

CryIA(b) Protein Levels in Transgenic Maize

Greenhouse plants

| 35S LINE | LEAF | PITH | ROOT | POLLEN |
|---|---|---|---|---|
| 6F010 x 171-4A | -409 + 288 | NT | NT | NT |
| 5N984 x 171-14A | 256 + 159 | 191 | 198 | 30 |
| 6F010 x 171-16AB | 240 + 174 | 221 | 271 | NT |
| 5N984 x 171-13 | 201 + 94 | NT | NT | NT |
| 5NA89 x 171-13 | 37 + 7 | 150 | 0 | NT |
| 5N984 x 171-18 | 7.7 + 3 | NT | NT | NT |
| 6N615 x 171-16AB | 7.5 + 3 | 0 | 0 | NT |
| PEPC LINE | | | | |
| 6N615 x 176-11 | 1126 + 419 | 41 | 19 | NT |
| 6F010 x 176-10 | 774 + 159 | NT | NT | 130 |
| 5N984 x 176-11 | 719 + 128 | 16 | 20 | 186 |

-Bt levels are in ng cryIA(b)/mg total protein.

Data are from progeny of the described maize transformants expressing the cryIA(b) protein.

ELISA analysis of transgenic plant material was carried out using standard procedures as described elsewhere.

Fig. 23D
Bioassay of European corn borer, Ostrinia nubilalis, on Pith:SynBt maize

| Plasmid | Promoter | Event | Plant No. | Percent Mortality |
|---|---|---|---|---|
| pCIB4433 | Pith | JS21A-Top | 1 | 90 |
| | | | 3 | 80 |
| | | | 11 | 90 |
| | | | 13 | 70 |
| | | | 14 | 75 |
| | | | 19 | 85 |
| | | | 28 | 80 |
| pCIB4433 | Pith | JS22D-Mid | 3 | 70 |
| | | | 4 | 65 |
| | | | 7 | 85 |
| | | | 17 | 95 |
| | | Control | 1 | 5 |
| | | | 2 | 0 |
| | | | 3 | 0 |

Fig. 23E

EXPRESSION OF THE CRYIA(b) GENE IN TRANSGENIC MAIZE USING THE PITH-PREFERRED PROMOTER

Leaf samples from small plantlets transformed with pCIB4433 using procedures described elsewhere were analyzed for the presence of the cryIA(b) protein using ELISA. All plants expressing cryIA(b) were found to be insecticidal in the standard European corn borer bioassay.

Note that the pith-preferred promoter has a low, but detectable level of expression in leaf tissue of maize. Detection of CryIA(b) protein is consistent with this pattern of expression.

| PLANT NUMBER | ng cryIA(b)/mg protein |
|---|---|
| JS21A-1 TOP | 169 |
| JS21A-2 TOP | 0 |
| JS21A-3 TOP | 113 |
| JS21A-11 TOP | 127 |
| JS21A-12 TOP | 112 |
| JS21A-13 TOP | 97 |
| JS21A-14 TOP | 118 |
| JS21A-19 TOP | 82 |
| JS21A-24 TOP | 0 |
| JS21A-28 TOP | 154 |
| JS22D-3 MID | 2946 |
| JS22D-4 MID | 5590 |
| JS22D-11 MID | 215 |
| JS22D-17 MID | 3004 |

Fig. 24A

```
   1 GAATTCGGATCCATTAAAGAAGTCTTTGAACAGATTCTAGAGATCTAGTTTAATGAGCTC   60
  61 CCAAAAGTCTTGAAAAAATTCAGCGGGGAGGCCATTAGGGCAGGGGTACTGTTATGTTTT  120
 121 AAAGAGAACACCACTTTCTTGATCTCTTCTAAAGAGAAATGTTTTGTAAGAAGGATCCTG  180
 181 TCCTCCTCATCCAACCTTTTCATCGGCAAATTTTTCATAGAGATATTAGAGGCAAGAGAG  240
 241 GGGCCAAAAAGATCCATGTAAATGGAAGTGGCCACCTGGTTGATACCTCCCTCATCTTCA  300
 301 ACAGAAAATCCATTATGAAAAAGTGAATGGATTTTAAACTCTTCTTTTTCTTCCCTTTTG  360
 361 CAATGAGCTGAAAATATCTGGTATTATTCTCATCACCCTCATTAATGAATCTGTCCCTAG  420
 421 CAATTTGCTTTCTCTTGATCCCTTCTGCAGCCACCATGTTTCTTAAATTCCACTCCATAT  480
 481 CAAGCTTTTCCAATCTATCAGAATCTGAGATGGCTGCAATCTCTCTCATTTTCTCAAGGA  540
 541 TATCGATGTTATCCATAAGGTATTTCTTGAACTTCTTATATTTCCCTTCGACATTTATAT  600
 601 TCCATCCTTTCAACATTTTTTTGTTCAATCTTTTTTGTTTTTTTCCTTTCCAAACATCGA  660
 661 TACATTTCCTGCTCCTCACAGGTAAGGACGAGCTTTCAAAAAACCTTCTGCTTTAAAGTC  720
 721 AGGTCTGAGCCTCCAGCAAAGCTCACATATCTAAAGTCCCTCTTCTTAGTTGGGACAGAG  780
 781 TCAGTGCTAAGACACATGGGAACATGACCAGAAAAAAAAAATCATATTTAGCCCAGAGAC  840
 841 AACAATATTCTTGTACTGCAAGTCTCGTTATGGGCTAGCAAAGGAATCTACCCAACTTCT  900
 901 CAAATGTGTTGGGATGTCAAGTATATAGACTATTCATCAGTTCCAACTCTATCAAACTGT  960
 961 GCAGCTCAATTATAGAGTTGAATAAAGTGCTCCATCTATTTGTTCTTATCCTCATATTTG 1020
1021 GTTAAGATATTAAAATCACCTCCCACCAACATTTAAAGTGCACCATTTAAAGTGGCTCGC 1080
1081 GAGCACCAAACCGCTGAAAACCGGAAATGTTTAGCACGTTGGCAGCGGGACCCTTTTCTA 1140
1141 TCTCATCGTGTTCTTCGTTGTCCACCACGGCCCACGGGCCAACGCTCCTCCATCCTGTAG 1200
1201 TGTAGAGTATATTCCATTTGCGACCGAGCCGAGCATCGATCCAGCCACACTGGCCACTGC 1260
                                                 84
1261 CAGCCAGCCATGTGGCACTCCTACGTATACTACGTGAGGTGAGATTCACTCACATGGAT  1320
-465                                                              -405

1321 GGGACCGAGATATTTTACTGCTGTGGTTGTGTGAGAGATAATAAAGCATTTATGACGATT 1380
1381 GCTGAACAGCACACACCATGCGTCCAGATAGAGAAAGCTTTCTCTCTTTATTCGCATGCA 1440

1441 TGTTTCATTATCTTTTATCATATATATATAACACATATTAAATGATTCTTCGTTCCAATT 1500
-285                                                              -226

1501 TATAATTCATTTGACTTTTTTATCCACCGATGCTCGTTTTATTAAAAAAAAATATTATAAT 1560
-225                                                              -166

1561 TATTGTTACTTTTTGTTGTAATATTGTTTAGCATATAATAAACTTTGATACTAGTATGTT 1620
-165                                                              -106
                                 49
1621 TCCGAGCAAAAAAAAATATTAATATTTAGATTACGAGCCCATTAATTAATTATATTCGAG 1680
-105                                                              -46

83                          +1
1681 ACAAGCGAAGCAAAGCAAAGCAAGCTAATGTTGCCCCTGCTGTGCATGCAGAGGCCCGCT 1740
-45                                                              +15
                                                    73******
1741 CTTGCTATAAACGAGGCAGCTAGACGCGACTCGACTCATCAGCCTCATCAACCTCGACGA 1800
+16                                                              +75
     **************                             ▼
1801 AGGAGGAACGAACGGACAGGTTGTTGCACAGAAGCGACATGGCTTTCGCGCCCAAAACGT 1860
+76                                            M  A  F  A  P  K  T  S +135
```

```
1861 CCTCCTCCTCCTCGCTGTCCTCGGCGTTGCAGGCAGCTCAGTCGCCGCCGCTGCTCCTGA 1920
+126   S  S  S  S  L  S  S  A  L  Q  A  A  Q  S  P  P  L  L  L  R  +195

40 + 41
1921 GGCGGATGTCGTCGACCGCAACACCGAGACGGAGGTACGACGCGGCCGTCGTCGTCACTA 1980
+196   R  M  S  S  T  A  T  P  R  R  R  Y  D  A  A  V  V  V  T  T  +255

1981 CCACCACCACTGCTAGAGCTGCGGCGGCTGCTGTCACGGTTCCCGCCGCCCCGCCGCAGG 2040
+256   T  T  T  A  R  A  A  A  A  V  T  V  P  A  A  P  P  Q  A  +315

75                            $
2041 CGGGCCGCCGCCGCCGGTGCCACCAAAGCAAGCGGCGGCACCCGCAGAGGAGGAGCCGTC 2100
+316   G  R  R  R  R  C  H  Q  S  K  R  R  H  P  Q  R  R  S  R  P  +375

2101 CGGTGTCGGACACCATGGCGGCGCTCATGGCCAAGGGCAAGGTTCGTATAGTACGCGCGC 2160
+376   V  S  D  T  M  A  A  L  M  A  K  G  K

2161 GTGTCGTCGTCGTTATTTTGCGCATAGGCGCGGACATACACGTGCTTTAGCTAGCTAACA 2220
2221 GCTAGATCATCGGTGCAGACGGCGTTCATCCCGTACATCACCGCCGGCGACCCGGACCTA 2280
                    T  A  F  I  P  Y  I  T  A  G  D  P  D  L

2281 GCGACGACGGCCGAGGCGCTGCGTCTGCTGGACGGCTGTGGCGCCGACGTCATCGAGCTG 2340
       A  T  T  A  E  A  L  R  L  L  D  G  C  G  A  D  V  I  E  L

2341 GGGGTACCCTGCTCGGACCCCTACATCGACGGGCCCATCATCCAGGCGTCGGTGGCGCGG 2400
       G  V  P  C  S  D  P  Y  I  D  G  P  I  I  Q  A  S  V  A  R

2401 GCTCTGGCCAGCGGCACCACCATGGACGCCGTGCTGGAGATGCTGAGGGAGGTGACGCCG 2460
       A  L  A  S  G  T  T  M  D  A  V  L  E  M  L  R  E  V  T  P

2461 GAGCTGTCGTGCCCCGTGGTGCTCCTCTCCTACTACAAGCCCATCATGTCTCGCAGCTTG 2520
       E  L  S  C  P  V  V  L  L  S  Y  Y  K  P  I  M  S  R  S  L

2521 GCCGAGATGAAAGAGGCGGGGGTCCACGGTAACTATAGCTAGCTCTTCCGATCCCCCTTC 2580
       A  E  M  K  E  A  G  V  H

2581 AATTAATTAATTTATAGTAGTCCATTCATGTGATGATTTTTGTTTTTCTTTTTACTGACA 2640
2641 GGTCTTATAGTGCCTGATCTCCCGTACGTGGCCGCGCACTCGCTGTGGAGTGAAGCCAAG 2700
                G  L  I  V  P  D  L  P  Y  V  A  A  H  S  L  W  S  E  A  K

2701 AACAACAACCTGGAGCTGGTAGGTTGAATTAAGTTGATGCATGTGATGATTTATGTAGCT 2760
       N  N  N  L  E  L

2761 AGATCGAGCTAGCTATAATTAGGAGCATATCAGGTGCTGCTGACAACACCAGCCATACCA 2820
                                  V  L  L  T  T  P  A  I  P

2821 GAAGACAGGATGAAGGAGATCACCAAGGCTTCAGAAGGCTTCGTCTACCTGGTAGTTATA 2880
       E  D  R  M  K  E  I  T  K  A  S  E  G  F  V  Y  L

2881 TGTATATATAGATGGACGACGTAACTCATTCCAGCCCCATGCATATATGGAGGCTTCAAT 2940
2941 TCTGCAGAGACGACGAAGACCACGACGACGACTAACACTAGCTAGGGGCGTACGTTGCAG 3000

3001 GTGAGCGTGAACGGAGTGACAGGTCCTCGCGCAAACGTGAACCCACGAGTGGAGTCACTC 3060
       V  S  V  N  G  V  T  G  P  R  A  N  V  N  P  R  V  E  S  L
```

Fig. 24C

```
3061 ATCCAGGAGGTTAAGAAGGTGACTAACAAGCCCGTTGCTGTTGGCTTCGGCATATCCAAG 3120
      I  Q  E  V  K  K  V  T  N  K  P  V  A  V  G  F  G  I  S  K

3121 CCCGAGCACGTGAAGCAGGTACGTACGTAGCTGACCAAAAAAAACTGTTAACAAGTTTTG 3180
      P  E  H  V  K
3181 TTTGACAAGCCGGCTACTAGCTAGCTAACAGTGATCAGTGACACACACACACACACAGAT 3240
                                                               Q  I

3241 TGCGCAGTGGGGCGCTGACGGGGTGATCATCGGCAGCGCCATGGTGAGGCAGCTGGGCGA 3300
      A  Q  W  G  A  D  G  V  I  I  G  S  A  M  V  R  Q  L  G  E

3301 AGCGGCTTCTCCCAAGCAAGGCCTGAGGAGGCTGGAGGAGTATGCCAGGGGCATGAAGAA 3360
      A  A  S  P  K  Q  G  L  R  R  L  E  E  Y  A  R  G  M  K  N
                   +++
3361 CGCGCTGCCATGAGTCCATGACAAAGTAAAACGTACAGAGACACTTGATAATATCTATCT 3420
      A  L  P
3421 ATCATCTCGGAGAAGACGACCGACCAATAAAAATAAGCCAAGTGGAAGTGAAGCTTAGCT 3480

3481 GTATATACACCGTACGTCGTCGTCGTCGTTCCGGATCGATCTCGGCCGGCTAGCTAGCAG 3540
3541 AACGTGTACGTAGTAGTATGTAATGCATGGAGTGTGGAGCTACTAGCTAGCTGGCCGTTC 3600
3601 ATTCGATTATAATTCTTCGCTCTGCTGTGGTAGCAGATGTACCTAGTCGATCTTGTACGA 3660

3661 CGAAGAAGCTGGCTAGCTAGCCGTCTCGATCGTATATGTACTGATTAATCTGCAGATTGA 3720
                                                                 $
3721 ATAAAAACTACAGTACGCATATGATGCGTACGTACGTGTGTATAGTTTGTGCTCATATAT 3780
3781 GCTCCTCATCACCTGCCTGATCTGCCCATCGATCTCTCTCGTACTCCTTCCTGTTAAATG 3840
3841 CCTTCTTTGACAGACACACCACCACCAGCAGCAGTGACGCTCTGCACGCCGCCGCTTTAA 3900
3901 GACATGTAAGATATTTTAAGAGGTATAAGATACCAAGGAGCACAAATCTGGAGCACTGGG 3960
3961 ATATTGCAAAGACAAAAAAAAACAAAATTAAAGTCCCACCAAAGTAGAGATAGTAAAGA 4020
4021 GGTGGATGGATTAAAATTATCTCATGATTTTTGGATCTGCTCAAATAGATCGATATGGTA 4080
4081 TTCAGATCTATGTTGTATAGCCTTTTCATTAGCTTTCTGAAAAAAAAATGGTATGATGAG 4140
4141 TGCGGAGTAGCTAGGGCTGTGAAGGAGTCGGATGGGCTTCCACGTACTTGTTTGTGGCCC 4200
4201 TAGTCCGGTTCTATTTAGGTCCGATCCGAGTCCGGCATGGTCCGGTTCCATACGGGCTAG 4260
4261 GACCAAGCTCGGCACGTGAGTTTTAGGCCCGTCGGCTAGCCCGAGCACGACCCGTTTTTA 4320
4321 AACTGGCTAGGACTCGCCCATTTAATAAGACAAACATTGCAAAAAATAGCTCTATTTTTT 4380
4381 ATTTAAAATATATTGTTTATTTGTGAAATGTGTATTATTTGTAATATATATTATTGTATA 4440
4441 TAGTTATATCTTCAATTATGATTTATAAATATGTTTTTTATTATGAACTCAATTTTAAGT 4500
4501 TTGATTTATGCGTTGGCGGGCTCGAGGAGGCACGGTGAACATTTTGGGTCGGGCTTAAC 4560
4561 GGGTCGGCCCGGCCCGGTTCGGCCCATCCACGGCCCATCCCGTGTCGGCCTCGTTCGGTG 4620
4621 AGTTCAGCCCGTCGGACAACCCGTCCCCGGCCCGGATAATTAATCGGGCCTAACCGTGGC 4680
4681 GTGCTTAAACGGTCCGTGCCTCAACGGACCGGGCCGCGGGCGGCCCGTTTGACATCTCTA 4740
4741 GTGGTGTGATTAGAGATGGCGATGGGAACCGATCACTGATTCCGTGTGGAGAATTCGATA 4800
4801 TCAAGCTTATCGATACC                                           4817
```

Entire sequence of the maize TrpA gene, with introns
and exons, transcription and translation strats, start and
stop of cDNA.
$ = start and end of cDNA; +1 = transcription start; 73******* =
primer extension primer; ▼ = start of translation; +++ = stop
codon; _____ = CCAAT Box, TATAA Box, poly A addition site.
above underlined sequences are PCR primers.

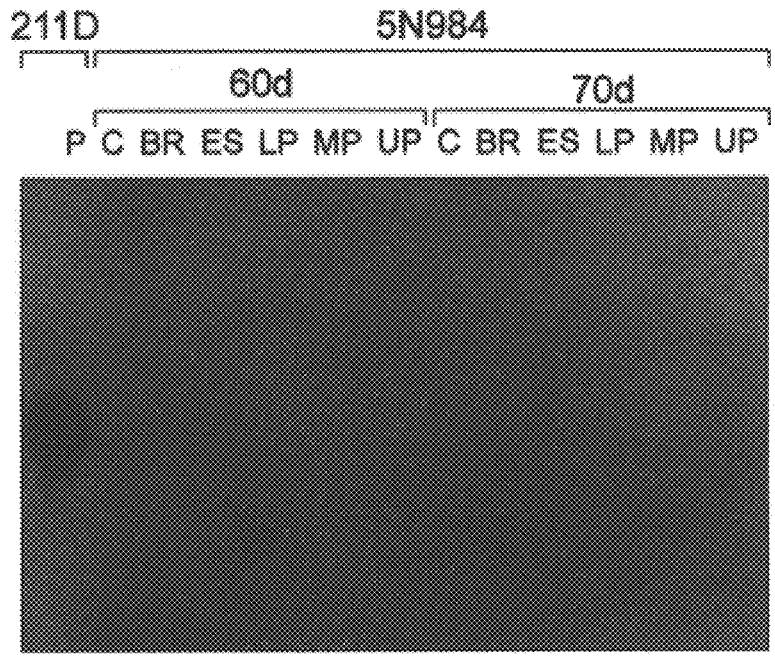
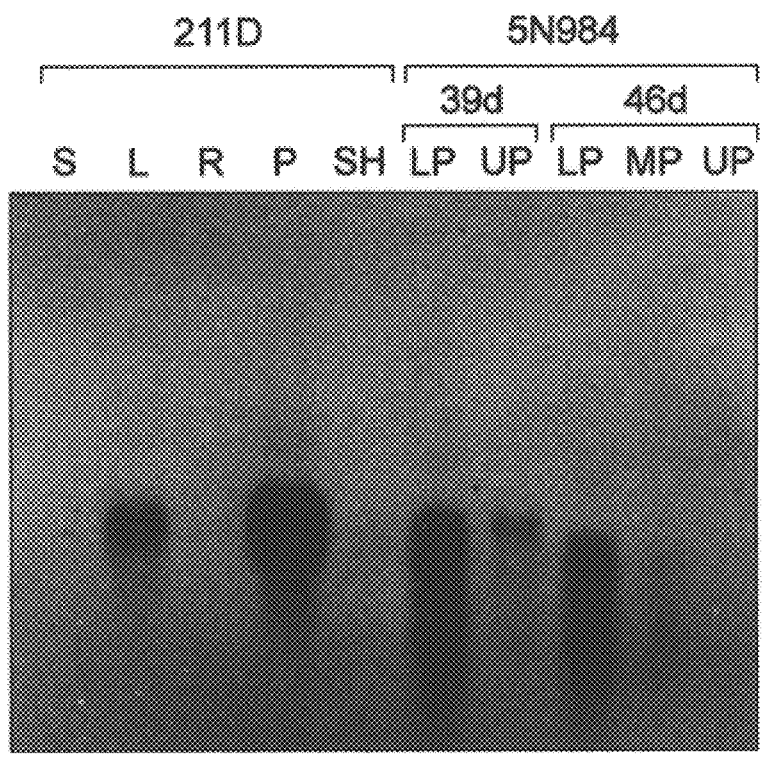
Northern blot showing differential expression of TrpA gene in maize tissues. 2 hour exposure against film at -80C with Dupont Cronex intensifying screens.
Fig. 25A Northern blot showing differential expression of TrpA gene in maize tissues. 4 hour exposure against film at -80C with Dupont Cronex intensifying screens.

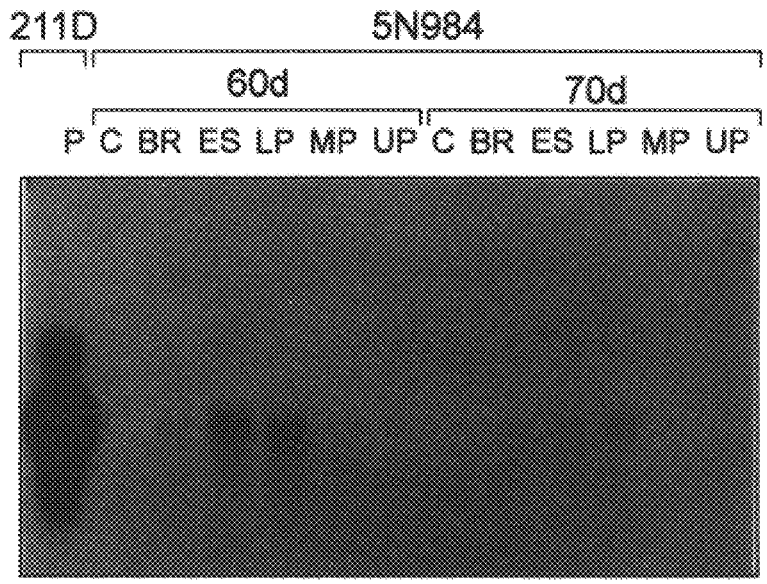
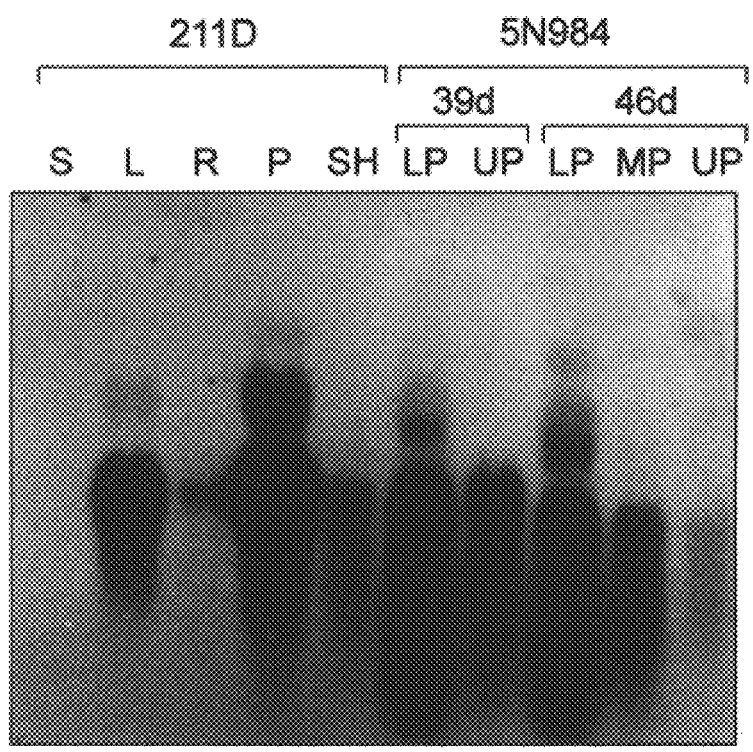
Northern blot showing differential expression of TrpA gene in maize tissues. 18 hour exposure against film at -80C with Dupont Cronex intensifying screens.
Fig. 25C Northern blot showing differential expression of TrpA gene in maize tissues. 48 hour exposure against film at -80C with Dupont Cronex intensifying screens.

Northern blot showing maize TrpA gene expression in Funk lines 211D and 5N984 leaf and pith and the absense of expression in 211D seed total RNA.
65 hour exposure against film at -80C with Dupont Cronex intensifying screens.

Genomic southern of Funk line 211D probed with the TrpA cDNA 8-2. B = BamHI, E = EcoRI, EV = EcoRV, H = HindIII and S = SacI.
120 hour exposure against film at -80C with Dupont Cronex intensifying screens.

Primer extension showing the transcription start of TrpA gene and sequencing ladder.
1 hour exposure against film at -80C with Dupont Cronex intensifying screens.

RNase protection of region from +2 bp to +387 bp with three annealing temperatures.
16 hour exposure against film at -80C with Dupont Cronex intensifying screens.

Fig. 30A
Maize Pollen CDPK cDNA sequence
sequence contained in clones pCIB3168 and pCIB3169

```
  1 TG CAG ATC ATG CAC CAC CTC TCC GGC CAG CCC AAC GTG GTG GGC CTC CGC GGC GCG
  1▶Gln Ile Met His His Leu Ser Gly Gln Pro Asn Val Val Gly Leu Arg Gly Ala

57 TAC GAG GAC AAG CAG AGC GTG CAC CTC GTC ATG GAG CTG TGC GCG GGC GGG GAG CTC
 19▶Tyr Glu Asp Lys Gln Ser Val His Leu Val Met Glu Leu Cys Ala Gly Gly Glu Leu
                                                     AvaI
114 TTC GAC CGC ATC ATC GCC CGG GGC CAG TAC ACG GAG CGC GGC GCC GCG GAG CTG CTG
 38▶Phe Asp Arg Ile Ile Ala Arg Gly Gln Tyr Thr Glu Arg Gly Ala Ala Glu Leu Leu

171 CGC GCC ATC GTG CAG ATC GTG CAC ACC TGC CAC TCC ATG GGG GTG ATG CAC CGG GAC
 57▶Arg Ala Ile Val Gln Ile Val His Thr Cys His Ser Met Gly Val Met His Arg Asp
         AvaI
228 ATC AAG CCC GAG AAC TTC CTG CTG CTC AGC AAG GAC GAG GAC GCG CCG CTC AAG GCC
 76▶Ile Lys Pro Glu Asn Phe Leu Leu Leu Ser Lys Asp Glu Asp Ala Pro Leu Lys Ala

285 ACC GAC TTC GGC CTC TCC GTC TTC TTC AAG GAG GGC GAG CTG CTC AGG GAC ATC GTC
 95▶Thr Asp Phe Gly Leu Ser Val Phe Phe Lys Glu Gly Glu Leu Leu Arg Asp Ile Val
                                            AvaI
342 GGC AGC GCC TAC TAC ATC GCG CCC GAG GTG CTC AAG AGG AAG TAC GGC CCG GAG GCC
114▶Gly Ser Ala Tyr Tyr Ile Ala Pro Glu Val Leu Lys Arg Lys Tyr Gly Pro Glu Ala

399 GAC ATC TGG AGC GTC GGC GTC ATG CTC TAC ATC TTC CTC GCC GGC GTG CCT CCC TTC
133▶Asp Ile Trp Ser Val Gly Val Met Leu Tyr Ile Phe Leu Ala Gly Val Pro Pro Phe

456 TGG GCA GAG AAC GAG AAC GGC ATC TTC ACC GCC ATC CTG CGA GGG CAG CTT GAC CTC
152▶Trp Ala Glu Asn Glu Asn Gly Ile Phe Thr Ala Ile Leu Arg Gly Gln Leu Asp Leu

513 TCC AGC GAG CCA TGG CCA CAC ATC TCG CCG GGA GCC AAG GAT CTC GTC AAG AAG ATG
171▶Ser Ser Glu Pro Trp Pro His Ile Ser Pro Gly Ala Lys Asp Leu Val Lys Lys Met

570 CTC AAC ATC AAC CCC AAG GAG CGG CTC ACG GCG TTC CAG GTC CTC AAT CAC CCA TGG
190▶Leu Asn Ile Asn Pro Lys Glu Arg Leu Thr Ala Phe Gln Val Leu Asn His Pro Trp

627 ATC AAA GAA GAC GGA GAC GCG CCT GAC ACG CCG CTT GAC AAC GTT GTT CTC GAC AGG
209▶Ile Lys Glu Asp Gly Asp Ala Pro Asp Thr Pro Leu Asp Asn Val Val Leu Asp Arg

684 CTC AAG CAG TTC AGG GCC ATG AAC CAG TTC AAG AAA GCA GCA TTG AGG ATC ATA GCT
228▶Leu Lys Gln Phe Arg Ala Met Asn Gln Phe Lys Lys Ala Ala Leu Arg Ile Ile Ala

741 GGG TGC CTA TCC GAA GAG GAG ATC ACA GGG CTG AAG GAG ATG TTC AAG AAC ATT GAC
247▶Gly Cys Leu Ser Glu Glu Glu Ile Thr Gly Leu Lys Glu Met Phe Lys Asn Ile Asp

798 AAG GAT AAC AGC GGG ACC ATT ACC CTC GAC GAG CTC AAA CAC GGG TTG GCA AAG CAC
266▶Lys Asp Asn Ser Gly Thr Ile Thr Leu Asp Glu Leu Lys His Gly Leu Ala Lys His

855 GGG CCC AAG CTG TCA GAC AGC GAA ATG GAG AAA CTA ATG GAA GCA GCT GAC GCT GAC
285▶Gly Pro Lys Leu Ser Asp Ser Glu Met Glu Lys Leu Met Glu Ala Ala Asp Ala Asp
                                                         EcoRI
912 GGC AAC GGG TTA ATT GAC TAC GAC GAA TTC GTC ACC GCA ACA GTG CAT ATG AAC AAA
304▶Gly Asn Gly Leu Ile Asp Tyr Asp Glu Phe Val Thr Ala Thr Val His Met Asn Lys
```

Fig. 30B

```
969  CTG GAT AGA GAA GAG CAC CTT TAC ACA GCA TTC CAG TAT TTC GAC AAG GAC AAC AGC
323▶Leu Asp Arg Glu Glu His Leu Tyr Thr Ala Phe Gln Tyr Phe Asp Lys Asp Asn Ser

1026 GGG TAC ATT ACT AAA GAA GAG CTT GAG CAC GCC TTG AAG GAG CAA GGG TTG TAT GAC
342▶Gly Tyr Ile Thr Lys Glu Glu Leu Glu His Ala Leu Lys Glu Gln Gly Leu Tyr Asp

1083 GCC GAT AAA ATC AAA GAC ATC ATC TCC GAT GCC GAC TCT GAC AAT GAT GGA AGG ATA
361▶Ala Asp Lys Ile Lys Asp Ile Ile Ser Asp Ala Asp Ser Asp Asn Asp Gly Arg Ile

1140 GAT TAT TCA GAG TTT GTG GCG ATG ATG AGG AAA GGG ACG GCT GGT GCC GAG CCA ATG
380▶Asp Tyr Ser Glu Phe Val Ala Met Met Arg Lys Gly Thr Ala Gly Ala Glu Pro Met

1197 AAC ATC AAG AAG AGG CGA GAC ATA GTC CTA TAG TGAAGTGAAGCAGCAAGTGTGTAATGTAATGTG
399▶Asn Ile Lys Lys Arg Arg Asp Ile Val Leu ...

1263 TATAGCAGCTCAAACAAGCAAATTTGTACATCTGTACACAAATGCAATGGGGTTACTTTTGCAAAAAAAAAAAAAAA
                  Ⓙ
1340 AAAAAAAAA
```

Fig. 32

```
Lipman-Pearson Protein Alignment
Gap Penalty: 2;  Gap Length Penalty: 12
Seq1            Seq2           Similarity    Gap     Gap    Consensus
pol CDPK ptn    rat pk2 ptn    Index         Number  Length Length
1>551           1>528          36.5          4       4      297
```

```
pol CDPK ptn   YSMGKELGRGQFGVTHLCTHRTSGEKLACKTIAKRKLAAREDVDDVRREVQIMHHLSGQPNVVGLRGAYE 162
               Y : .ELG:G.F:V.: C...TS.:. A K.I..:KL:AR:: :..: RE.:I : L. :PN:V L::: .
rat pk2  ptn   YQLFEELGKGAFSVVRRCVKKTSTQEYAAKIINTKKLSARDH-QKLEREARICRLLK-HPNIVRLHDSIS  81 pol CDPK ptn   DKQSVHLVMELCAGGELFDRIIARGQYTERGAAELLRAIVQIVHTCHSMGVMHRDIKPENFLLLSKDEDA 232
               :.    .LV.:.  :GGELF: I:AR. Y:E :A:: :::.I:: V:  H  :::HRD:KPEN:LL SK .:A
rat pk2  ptn   EEGFHYLVFDLVTGGELFEDIVAREYYSEADASHCIHQILESVNHIHQHDIVHRDLKPENLLLASKCKGA 151 pol CDPK ptn   PLKATDFGLSVFFK-EGELLRDIVGSAYYIAPEVL-KRKYGPEADIWSVGVMLYIFLAGVPPFWAENENG 300
               ::K :DFGL::     :...: : :...G:: Y::PEVL::.. YG  .DIW: GV:LYI:L.G PPFW.E:::
rat pk2  ptn   AVKLADFGLAIEVQGEQQAWFGFAGTPGYLSPEVLRKDPYGKPVDIWACGVILYILLVGYPPFWDEDQHK 221 pol CDPK ptn   IFTAILRGQLDLSSEPWPHISPGAKDLVKKMLNINPKERLTAFQVLNHPWIKEDGDAPDTPLDNVVLDRL 370
               :: .I  G. D::S W   ::.P.AK:L:::ML.INP .R:TA Q.L:HPW: : :...:.      : .:: L
rat pk2  ptn   LYQQIKAGAYDFPSPEWDTVTPEAKNLINQMLTINPAKRITADQALKHPWVCQRSTVASMMHRQETVECL 291 pol CDPK ptn   KQFRAMNQFKKAALRII 387
               ::F.A..::K A L .:
rat pk2  ptn   RKFNARRKLKGAILTTM 308
```

Fig. 33

```
Lipman-Pearson Protein Alignment
Gap Penalty: 2;  Gap Length Penalty: 12
Seq1              Seq2             Similarity    Gap      Gap     Consensus
pol CDPK ptn      humcama ptn          Index   Number   Length    Length
1>551             1>150                 40.3      2        2        142 pol CDPK ptn    LSEEEITGLKEMFKNIDKDNSGTITLDELKHGLAKHGPKLSDSEMEKLMEAADADGNGLIDYDEFVTATV 460
                L:EE:I:.:KE F. :DKD..GTIT .EL    : . G.: :::E::.:::..DADGNG ID: EF:T  .
humcama ptn     LTEEQIAEFKEAFSLFDKDGDGTITTKELGTVMRSLGQNPTEAELQDMINEVDADGNGTIDFPEFLTMMA 74 pol CDPK ptn    HMNKL-DREEHLYTAFQYFDKDNSGYITKEELEHALKEQGLYDADKIKDI-ISDADSDNDGRIDYSEFVA 528
                : M:.. D.EE:: .AF: FDKD.:GYI: .EL H.:.: G    ..:.:.:::I.:AD D.DG:::Y.EFV.
humcama ptn     RKMKDTDSEEEIREAFRVKDKDGNGYISAAELRHVMTNLGEKLTDEEVDEMIREADIDGDGQVNYEEFVQ 144 pol CDPK ptn    MM 530
                MM
humcama ptn     MM 146
```

Fig. 34

```
Lipman-Pearson Protein Alignment
Gap Penalty: 2;  Gap Length Penalty: 12
Seq1          Seq2           Similarity   Gap     Gap     Consensus
pol CDPK ptn  soybean CDPK ptn  Index    Number  Length   Length
1>551         1>509           62.4        1       1       464
```

```
pol CDPK ptn     VLGRPMEDVRATYSMGKELGRGQFGVTHLCTHRTSGEKLACKTIAKRKLAAREDVDDVRREVQIMHHLSG 150
                 || :. :::|..|.:|:.||:||||.|  ||:|:||.|:|||:|:||||  :||  :||:||:||||||.
soybean CDPK ptn VLPQRTQNIREVYEVGRKLGQGQFGTTFECTRRASGGKFACKSIPKRKLLCKEDYEDVWREIQIMHHLSE  91 pol CDPK ptn     QPNVVGLRGAYEDKQSVHLVMELCAGGELFDRIIARGQYTERGAAELLRAIVQIVHTCHSMGVMHRDIKP 220
                 ::|||  : |:|||. :||||||||.|||||||||:..|:|:|| ||  |:::||::|:::|||:|||||:||
soybean CDPK ptn HANVVRIEGTYEDSTAVHLVMELCEGGELFDRIVQKGHYSERQAARLIKTIVEVVEACHSLGVMHRDLKP 161 pol CDPK ptn     ENFLLLSKDEDAPLKATDFGLSVFFKEGELLRDIVGSAYYIAPEVLKRKYGPEADIWSVGVMLYIFLAGV 290
                 ||||: :  ||||  ||||||||||||:| ||  : |:||:||:|||||::  ||||:|:||.||:|||:|:||
soybean CDPK ptn ENFLFDTIDEDAKLKATDFGLSVFYKPGESFCDVVGSPYYVAPEVLRKLYGPESDVWSAGVILYILLSGV 231 pol CDPK ptn     PPFWAENENGIFTAILRGQLDLSSEPWPHISPGAKDLVKKMLNINPKERLTAFQVLNHPWIKEDGDAPDT 360
                 ||||||:| ||| .|| |:||: ||||| || :||||::|||: |||.|||| :||.||||  |.  |||.
soybean CDPK ptn PPFWAESEPGIFRQILLGKLDFHSEPWPSISDSAKDLIRKMLDQNPKTRLTAHEVLRHPWIVDDNIAPDK 301 pol CDPK ptn     PLDNVVLDRLKQFRAMNQFKKAALRIIAGCLSEEEITGLKEMFKNIDKDNSGTITLDELKHGLAKHGPKL 430
                 |||:.||.|||||.|||::||  |||:||.  ||||||.|||||:||  ||.||||||||:||||:|| :  |:.|
soybean CDPK ptn PLDSAVLSRLKQFSAMNKLKKMALRVIAERLSEEEIGGLKELFKMIDTDNSGTITFDELKDGLKRVGSEL 371 pol CDPK ptn     SDSEMEKLMEAADADGNGLIDYDEFVTATVHMNKLDREEHLYTAFQYFDKDNSGYITKEELEHALKEQGL 500
                 :||:..||:|||  | :|  |||:||::|||||:|||:|||:|  :||  ||||||.|||||  :|:::|  |: ||
soybean CDPK ptn MESEIKDLMDAADIDKSGTIDYGEFIAATVHLNKLEREENLVSAFSYFDKDGSGYITLDEIQQACKDFGL 441 pol CDPK ptn     YDADKIKDIISDADSDNDGRIDYSEFVAMMRKGTAGAEPMNIKK 544
                 |.. .|.|.:|.:  |  ||||:|||||:||.||||||..:|  ....::|
soybean CDPK ptn -DDIHIDDMIKEIDQDNDGQIDYGEFAAMMRKGNGGIGRRTMRK 484
```

Fig. 35A pol CDPK gene Map (1 > 4165)      Site and Sequence
Enzymes :      6 of 198 enzymes (Filtered)
Settings :      Circular, Certain Sites Only, Standard Genetic Code

```
TTAGTAACACCTCTCCAATCGCTTGGGTTGGCACATTCTTAGCTTTTATCACATTTTAAGAAATAGAGTTCACCACCTTC
                                                                                 80

AAAATATGCCTATACAATGAATGATGCTTGGATGCAATATAGCTAGATTCAACTAGCTATATATGGTCAATAGAACCCTG
                                                                                 160

TGAGCACCTCACAAACACGACTTCAATTTTGAGACCCTAAGCGAGTAAATGGTTAAAGTCCTCTTATTATTAGTCTTAGG
                                                                                 240

ACTTCTCCTTGCTAAATGCTTGTCAGCGATCTATATATCTTCCCCACTGCGGGAGATACTATATATAGGGCCTTGGACCT
                                                                                 320

CTAGGGTATCTCAAAGGCCTAGTCACAACAATTCTCAACAGTATTTAATTTTATACATGTATGAACAGTGTAGGAATTTG
                                                                                 400

AGTGCCCAACCCAAGAGTGGGAGGTGTAAATTGGGTAGCTAAACTTAAATAGGGCTCTTCTTATTTAGGTTTATCTAGTC
                                                                                 480

TCTACTTAGACTAATTCAGAAAGAATTTTACAACCTATGGTTAATCATATCTCTAGTCTAAGCAAATTTAGGAAAGTTAA
                                                                                 560

AAGCACACAATTAGGCACATGTGAAAGATGTGTATGGTAAGTAAAAGACTTATAAGGAAAAAGTGGGTGAATCCTCAAGA
                                                                                 640

TGTGGTGGTATATCCCAATGATATTAGATGCCAGAATATAGGGGGGAAATCGATGTATACCATCTCTACCAGGATACCTG
                                                                                 720

TGCGGACTGTGCAACTGACACATGGACCATGGTGTCTTCTTAGATTTGGTTATTAGCTAATTGCGCTACAACTTGTTCAA
                                                                                 800

GGCTAGACCAAATTAAAAAACTAATATTAAACATAAAAAGTTAGGCAAACTATAGTAAATTATGCAGCGATCCAACAACA
                                                                                 880

AGCCATGTCTCGTGGGTCATGAGCCACGCGTCGGCCATACACCCACATGATGTTTCCATACGGATGGTCCTTATGCAATT
                                                                                 960

TTGTCTGCAAAACACAAGCCTTAATACAGCCACGCGACAATCATGGAAGTGGTCGTTTTAGGTCCTCATCATGAAGTTCA
                                                                                 1040

GGGAAAACGCATCAAATGTAATGCAGAGAAATGGTATTTCTTCTCTTGTAAATCAGGGAGAGGAGTACCATCAGTACAGA
                                                                                 1120

EcoR I
TTCAGAATCAGAATTCAGTCTTCCAACGACAATAATCGCAGCATCTTGTAAAAATTTGCAGAAACTTCTGTTTGACTTGT
                                                                                 1200

AGCCCTGACCTTTGCAAATATTTGAAGTTGTGCCTGCTGACACAACTTCAATCTGGAAGTGCTGTTGATCAGTTTTGCCA
                                                                                 1280

GAAACAGCAAGCAGCCTATATATATCTGTCACGAGACACCCTGCCGCCCTCTTCTTTCCCGCCATTCCCTCCCTACCCTT
                                                                                 1360
```

Fig. 35C pol CDPK gene Map (1 > 4165)   Site and Sequence

```
                                               Ava I
CGTGCAGATCGTGCACACCTGCCACTCCATGGGGGTGATGCACCGGGACATCAAGCCCGAGAACTTCCTGCTGCTCAGCA
                                                                                 2160
——————————————————————— EXON 1 ———————————————————————

AGGACGAGGACGCGCCGCTCAAGGCCACCGACTTCGGCCTCTCCGTCTTCTTCAAGGAGGGCGAGCTGCTCAGGGACATC
                                                                                 2240
——————————————————————— EXON 1 ———————————————————————

Ava I
GTCGGCAGCGCCTACTACATCGCGCCCGAGGTGCTCAAGAGGAAGTACGGCCCGGAGGCCGACATCTGGAGCGTCGGCGT
                                                                                 2320
——————————————————————— EXON 1 ———————————————————————

Bam H I
CATGCTCTACATCTTCCTCGCCGGCGTGCCTCCCTTCTGGGCAGGTCGGATCCGTCCGTGTTCGTCCTAGACGATATACA
                                                                                 2400
——————————— EXON 1 ———————————         ——————————— INTRON 1 ———————————

GAACCCGACGATGGATTTGCTTCTCAGCCCTGTTCTTGCATCACCAGAGAACGAGAACGGCATCTTCACCGCCATCCTGC
                                                                                 2480
——————————— INTRON 1 ———————————       ——————————— EXON 2 ———————————

GAGGGCAGCTTGACCTCTCCAGCGAGCCATGGCCACACATCTCGCCGGGAGCCAAGGATCTCGTCAAGAAGATGCTCAAC
                                                                                 2560
——————————————————————— EXON 2 ———————————————————————

ATCAACCCCAAGGAGCGGCTCACGGCGTTCCAGGTCCTCAGTAAGTACCCAGATCGTTGCTGTCATACACTCATATGAAT
                                                                                 2640
——————————— EXON 2 ———————————         ——————————— INTRON 2 ———————————

TGTATCGTTCATGAGCAACGATCGAGCGGATTTGGTGAACTTGTAGATCACCCATGGATCAAAGAAGACGGAGACGCGCC
                                                                                 2720
——————————— INTRON 2 ———————————       ——————————— EXON 3 ———————————

TGACACGCCGCTTGACAACGTTGTTCTCGACAGGCTCAAGCAGTTCAGGGCCATGAACCAGTTCAAGAAAGCAGCATTGA
                                                                                 2800
——————————————————————— EXON 3 ———————————————————————
```

Fig. 35E

```
pol CDPK gene Map (1 > 4165)          Site and Sequence
TCAGCCGACAAACTAAACTATAGAAACCACATCATGATATCAAATTTTGAGGTGGCGGTGCTACAGAAATAGAACCCAGT
                                                                                 3600
━━━━━━━━━━━━━━━━━━━━━━━━━━━━━━━━━━━━━━━━━━━━━━━━━━━━━━━━━━━━━━━━━━━━━━━━━━━━━━━━
─────────────────────────── INTRON 6 ───────────────────────────

ACACCAAAATGACTAACTTGTCATGATTAGTTGTTCCTCGTAACTGAACATTTGTGTTCTTAGTTTCTTATTGTTAAACC
                                                                                 3680
━━━━━━━━━━━━━━━━━━━━━━━━━━━━━━━━━━━━━━━━━━━━━━━━━━━━━━━━━━━━━━━━━━━━━━━━━━━━━━━━
─────────────────────────── INTRON 6 ───────────────────────────

AAAGACTTAAATTCACTTTTGCACATGCAGGATGGAAGGATAGATTATTCAGAGTTTGTGGCGATGATGAGGAAAGGGAC
                                                                                 3760
━━━━━━━━━━━━━━━━━━━━━━━┃┌──────────────────────────────────
──────── INTRON 6 ──────┘└────────────── EXON 7 ──────────────

GGCTGGTGCCGAGCCAATGAACATCAAGAAGAGGCGAGACATAGTCCTATAGTGAAGTGAAGCAGWAAGTGTGTAATGTA
                                                                                 3840
───────────────────────────────────────────────────>┐
──────────────── EXON 7 ────────────────────────────┘

ATGTGTATAGCAGCTCAAACAAGCAAATTTGTACATCTGTACACAAATGCAATGGGGTTACTTTTGCAACTTAGTTCATG
                                                                                 3920

GATGGTTGTGTACGTTGTGCTATTGATTGCAAGTGATTTGAAAGACATGCATACTTAGGAACTGAGAAAGATAGATCTAC
                                                                                 4000

TACTGCTAGAGACAGAACAATAGGATKKYAATTCAGYAAGTGYGTATTTCAGAAGACTACAGCTGGCÁTCTATTATTCTC
                                                                                 4080

ATTGTCCTCGCAAAAATACTGATGATGCATTTGAGAGAACAATATGCAACAAGATCGAGCTCCCTATAGTGAGTCGTATT
                                                                                 4160

AGGCC
────> 4165
```

Fig. 37A

```
   1 ATGGACAACA ACCCCAACAT CAACGAGTGC ATCCCCTACA ACTGCCTGAG CAACCCCGAG
     NetAspAsn AsnProAsn IleAsnGluCys IleProTyr AsnCysLeu SerAsnProGlu

61 GTGGAGGTGC TGGGCGGCGA GCGCATCGAG ACCGGCTACA CCCCCATCGA CATCAGCCTG
     ValGluVal LeuGlyGly GluArgIleGlu ThrGlyTyr ThrProIle AspIleSerLeu

121 AGCCTGACCC AGTTCCTGCT GAGCGAGTTC GTGCCCGGCG CCGGCTTCGT GCTGGGCCTG
     SerLeuThr GlnPheLeu LeuSerGluPhe ValProGly AlaGlyPhe ValLeuGlyLeu

181 GTGGACATCA TCTGGGGCAT CTTCGGCCCC AGCCAGTGGG ACGCCTTCCT GGTGCAGATC
     ValAspIle IleTrpGly IlePheGlyPro SerGlnTrp AspAlaPhe LeuValGlnIle

241 GAGCAGCTGA TCAACCAGCG CATCGAGGAG TTCGCCCGCA ACCAGGCCAT CAGCCGCCTG
     GluGlnLeu IleAsnGln ArgIleGluGlu PheAlaArg AsnGlnAla IleSerArgLeu

301 GAGGGCCTGA GCAACCTGTA CCAAATCTAC GCCGAGAGCT TCCGCGAGTG GGAGGCCGAC
     GluGlyLeu SerAsnLeu TyrGlnIleTyr AlaGluSer PheArgGlu TrpGluAlaAsp

361 CCCACCAACC CCGCCCTGCG CGAGGAGATG CGCATCCAGT TCAACGACAT GAACAGCGCC
     ProThrAsn ProAlaLeu ArgGluGluMet ArgIleGln PheAsnAsp MetAsnSerAla

421 CTGACCACCG CCATCCCCCT GTTCGCCGTG CAGAACTACC AGGTGCCCCT GCTGAGCGTG
     LeuThrThr AlaIlePro LeuPheAlaVal GlnAsnTyr GlnValPro LeuLeuSerVal

481 TACGTGCAGG CCGCCAACCT GCACCTGAGC GTGCTGCGCG ACGTCAGCGT GTTCGGCCAG
     TyrValGln AlaAlaAsn LeuHisLeuSer ValLeuArg AspValSer ValPheGlyGln

541 CGCTGGGGCT TCGACGCCGC CACCATCAAC AGCCGCTACA ACGACCTGAC CCGCCTGATC
     ArgTrpGly PheAspAla AlaThrIleAsn SerArgTyr AsnAspLeu ThrArgLeuIle

601 GGCAACTACA CCGACCACGC CGTGCGCTGG TACAACACCG GCCTGGAGCG CGTGTGGGGT
     GlyAsnTyr ThrAspHis AlaValArgTrp TyrAsnThr GlyLeuGlu ArgValTrpGly

661 CCCGACAGCC GCGACTGGAT CAGGTACAAC CAGTTCCGCC GCGAGCTGAC CCTGACCGTG
     ProAspSer ArgAspTrp IleArgTyrAsn GlnPheArg ArgGluLeu ThrLeuThrVal

721 CTGGACATCG TGAGCCTGTT CCCCAACTAC GACAGCCGCA CCTACCCCAT CCGCACCGTG
     LeuAspIle ValSerLeu PheProAsnTyr AspSerArg ThrTyrPro IleArgThrVal

781 AGCCAGCTGA CCCGCGAGAT TTACACCAAC CCCGTGCTGG AGAACTTCGA CGGCAGCTTC
     SerGlnLeu ThrArgGlu IleTyrThrAsn ProValLeu GluAsnPhe AspGlySerPhe

841 CGCGGCAGCG CCCAGGGCAT CGAGGGCAGC ATCCGCAGCC CCACCTGAT GGACATCCTG
     ArgGlySer AlaGlnGly IleGluGlySer IleArgSer ProHisLeu MetAspIleLeu

901 AACAGCATCA CCATCTACAC CGACGCCCAC CGCGGCGAGT ACTACTGGAG CGGCCACCAG
     AsnSerIle ThrIleTyr ThrAspAlaHis ArgGlyGlu TyrTyrTrp SerGlyHisGln

961 ATCATGGCCA GCCCCGTCGG CTTCAGCGGC CCCGAGTTCA CCTTCCCCCT GTACGGCACC
     IleMetAla SerProVal GlyPheSerGly ProGluPhe ThrPhePro LeuTyrGlyThr

1021 ATGGGCAACG CTGCACCTCA GCAGCGCATC GTGGCACAGC TGGGCCAGGG AGTGTACCGC
     MetGlyAsn AlaAlaPro GlnGlnArgIle ValAlaGln LeuGlyGln GlyValTyrArg

1081 ACCCTGAGCA GCACCCTGTA CCGTCGACCT TCAACATCG GCATCAACAA CCAGCAGCTG
     ThrLeuSer SerThrLeu TyrArgArgPro PheAsnIle GlyIleAsn AsnGlnGlnLeu

1141 AGCGTGCTGG ACGGCACCGA GTTCGCCTAC GGCACCAGCA GCAACCTGCC CAGCGCCGTG
     SerValLeu AspGlyThr GluPheAlaTyr GlyThrSer SerAsnLeu ProSerAlaVal

1201 TACCGCAAGA GCGGCACCGT GGACAGCCTG GACGAGATCC CCCCTCAGAA CAACAACGTG
     TyrArgLys SerGlyThr ValAspSerLeu AspGluIle ProProGln AsnAsnAsnVal
```

Fig. 37B

```
1261 CCACCTCGAC AGGGCTTCAG CCACCGTCTG AGCCACGTGA CCATGTTCCG CAGTGGCTTC
     ProProArg GlnGlyPhe  SerHisArgLeu SerHisVal  SerMetPhe  ArgSerGlyPhe

1321 AGCAACAGCA GCGTGAGCAT CATCCGTGCA CCTATGTTCA GCTGGATTCA CCGCAGTGCC
     SerAsnSer  SerValSer  IleIleArgAla ProMetPhe SerTrpIle  HisArgSerAla

1381 GAGTTCAACA ACATCATCCC CAGCAGCCAG ATCACCCAGA TCCCCCTGAC CAAGAGCACC
     GluPheAsn  AsnIleIle  ProSerSerGln IleThrGln IleProLeu  ThrLysSerThr

1441 AACCTGGGCA GCGGCACCAG CGTGGTGAAG GGCCCCGGCT TCACCGGCGG CGACATCCTG
     AsnLeuGly  SerGlyThr  SerValValLys GlyProGly PheThrGly  GlyAspIleLeu

1501 CGCCGCACCA GCCCCGGCCA GATCAGCACC CTGCGCGTGA ACATCACCGC CCCCCTGAGC
     ArgArgThr  SerProGly  GlnIleSerThr LeuArgVal AsnIleThr  AlaProLeuSer

1561 CAGCGCTACC GCGTCCGCAT CCGCTACGCC AGCACCACCA ACCTGCAGTT CCACACCAGC
     GlnArgTyr  ArgValArg  IleArgTyrAla SerThrThr AsnLeuGln  PheHisThrSer

1621 ATCGACGGCC GCCCCATCAA CCAGGGCAAC TTCAGCGCCA CCATGAGCAG CGGCAGCAAC
     IleAspGly  ArgProIle  AsnGlnGlyAsn PheSerAla ThrMetSer  SerGlySerAsn

1681 CTGCAGAGCG GCAGCTTCCG CACCGTGGGC TTCACCACCC CCTTCAACTT CAGCAACGGC
     LeuGlnSer  GlySerPhe  ArgThrValGly PheThrThr ProPheAsn  PheSerAsnGly

1741 AGCAGCGTGT TCACCCTGAG CGCCCACGTG TTCAACAGCG GCAACGAGGT GTACATCGAC
     SerSerVal  PheThrLeu  SerAlaHisVal PheAsnSer GlyAsnGlu  ValTyrIleAsp

1801 CGCATCGAGT TCGTGCCCGC CGAGGTGACC TTCGAGGCCG AGTACGACCT GGAGAGGGCT
     ArgIleGlu  PheValPro  AlaGluValThr PheGluAla GluTyrAsp  LeuGluArgAla

1861 CAGAAGGCCG TGAACGAGCT GTTCACCAGC AGCAACCAGA TCGGCCTGAA GACCGACGTG
     GlnLysAla  ValAsnGlu  LeuPheThrSer SerAsnGln IleGlyLeu  LysThrAspVal

1921 ACCGACTACC ACATCGATCA AGTATCCAAT TTAGTTGAGT GTTTATCTGA TGAATTTGT
     ThrAspTyr  HisIleAsp  GlnValSerAsn LeuValGlu CysLeuSer  AspGluPheCys

1981 CTGGATGAAA AAAAGAATT GTCCGAGAAA GTCAAACATG CGAAGCGACT TAGTGATGAG
     LeuAspGlu  LysLysGlu  LeuSerGluLys ValLysHis AlaLysArg  LeuSerAspGlu

2041 CGGAATTTAC TTCAAGATCC AAACTTTAGA GGGATCAATA GACAACTAGA CCGTGGCTGG
     ArgAsnLeu  LeuGlnAsp  ProAsnPheArg GlyIleAsn ArgGlnLeu  AspArgGlyTrp

2101 AGAGGAAGTA CGGATATTAC CATCCAAGGA GGCGATGACG TATTCAAAGA GAATTACGTT
     ArgGlySer  ThrAspIle  ThrIleGlnGly GlyAspAsp ValPheLys  GluAsnTyrVal

2161 ACGCTATTGG GTACCTTTGA TGAGTGCTAT CCAACGTATT TATATCAAAA AATAGATGAG
     ThrLeuLeu  GlyThrPhe  AspGluCysTyr ProThrTyr LeuTyrGln  LysIleAspGlu

2221 TCGAAATTAA AAGCCTATAC CCGTTACCAA TTAAGAGGGT ATATCGAAGA TAGTCAAGAC
     SerLysLeu  LysAlaTyr  ThrArgTyrGln LeuArgGly TyrIleGlu  AspSerGlnAsp

2281 TTAGAAATCT ATTTAATTCG CTACAATGCC AAACACGAAA CAGTAAATGT GCCAGGTACG
     LeuGluIle  TyrLeuIle  ArgTyrAsnAla LysHisGlu ThrValAsn  ValProGlyThr

2341 GGTTCCTTAT GGCCGCTTTC AGCCCCAAGT CCAATCGGAA AATGTGGGGA GCCGAATCGA
     GlySerLeu  TrpProLeu  SerAlaProSer ProIleGly LysCysGly  GluProAsnArg

2401 TGCGCTCCGC ACCTGGAGTG GAACCCGGAC CTAGACTGCA GCTGCAGGGA CGGGGAGAAG
     CysAlaPro  HisLeuGlu  TrpAsnProAsp LeuAspCys SerCysArg  AspGlyGluLys

2461 TGCGCCCATC ATTCCCATCA TTTCTCCTTG GACATTGATG TTGGATGTAC AGACTTAAAT
     CysAlaHis  HisSerHis  HisPheSerLeu AspIleAsp ValGlyCys  ThrAspLeuAsn

2521 GAGGACTTAG GTGTATGGGT GATATTCAAG ATTAAGACGC AAGATGGCCA TGCAAGACTA
     GluAspLeu  GlyValTrp  ValIlePheLys IleLysThr GlnAspGly  HisAlaArgLeu

2581 GGAAATCTAG AATTTCTCGA AGAGAAACCA TTAGTAGGAG AAGCACTAGC TCGTGTGAAA
     GlyAsnLeu  GluPheLeu  GluGluLysPro LeuValGly GluAlaLeu  AlaArgValLys
```

Fig. 37C

```
2641 AGAGCGGAGA 2VGWkTGGAG AGACAAACGT GAAAAATTGG AATGGGAAAC AAATATTGTT
     ArgAlaGlu  LysLysTrp  ArgAspLysArg GluLysLeu GluTrpGlu  ThrAsnIleVal

2701 TATAAAGAGG CAAAAGAATC TGTAGATGCT TTATTTGTAA ACTCTCAATA TGATAGATTA
     TyrLysGlu  AlaLysGlu  SerValAspAla LeuPheVal AsnSerGln  TyrAspArgLeu

2761 CAAGCGGATA CCAACATCGC GATGATTCAT GCGGCAGATA AACGCGTTCA TAGCATTCGA
     GlnAlaAsp  ThrAsnIle  AlaMetIleHis AlaAlaAsp LysArgVal  HisSerIleArg

2821 GAAGCTTATC TGCCTGAGCT GTCTGTGATT CCGGGTGTCA ATGCGGCTAT TTTTGAAGAA
     GluAlaTyr  LeuProGlu  LeuSerValIle ProGlyVal AsnAlaAla  IlePheGluGlu

2881 TTAGAAGGGC GTATTTTCAC TGCATTCTCC CTATATGATG CGAGAAATGT CATTAAAAAT
     LeuGluGly  ArgIlePhe  ThrAlaPheSer LeuTyrAsp AlaArgAsn  ValIleLysAsn

2941 GGTGATTTTA ATAATGGCTT ATCCTGCTGG AACGTGAAAG GGCATGTAGA TGTAGAAGAA
     GlyAspPhe  AsnAsnGly  LeuSerCysTrp AsnValLys GlyHisVal  AspValGluGlu

3001 CAAAACAACC ACCGTTCGGT CCTTGTTGTT CCGGAATGGG AAGCAGAAGT GTCACAAGAA
     GlnAsnAsn  HisArgSer  ValLeuValVal ProGluTrp GluAlaGlu  ValSerGlnGlu

3061 GTTCGTGTCT GTCCGGGTCG TGGCTATATC CTTCGTGTCA CAGCGTACAA GGAGGGATAT
     ValArgVal  CysProGly  ArgGlyTyrIle LeuArgVal ThrAlaTyr  LysGluGlyTyr

3121 GGAGAAGGTT GCGTAACCAT TCATGAGATC GAGAACAATA CAGACGAACT GAAGTTTAGC
     GlyGluGly  CysValThr  IleHisGluIle GluAsnAsn ThrAspGlu  LeuLysPheSer

3181 AACTGTGTAG AAGAGGAAGT ATATCCAAAC AACACGGTAA CGTGTAATGA TTATACTGCG
     AsnCysVal  GluGluGlu  ValTyrProAsn AsnThrVal ThrCysAsn  AspTyrThrAla

3241 ACTCAAGAAG AATATGAGGG TACGTACACT TCTCGTAATC GAGGATATGA CGGAGCCTAT
     ThrGlnGlu  GluTyrGlu  GlyThrTyrThr SerArgAsn ArgGlyTyr  AspGlyAlaTyr

3301 GAAAGCAATT CTTCTGTACC AGCTGATTAT GCATCAGCCT ATGAAGAAAA AGCATATACA
     GluSerAsn  SerSerVal  ProAlaAspTyr AlaSerAla TyrGluGlu  LysAlaTyrThr

3361 GATGGACGAA GAGACAATCC TTGTGAATCT AACAGAGGAT ATGGGATTA CACACCACTA
     AspGlyArg  ArgAspAsn  ProCysGluSer AsnArgGly TyrGlyAsp  TyrThrProLeu

3421 CCAGCTGGCT ATGTGACAAA AGAATTAGAG TACTTCCCAG AAACCGATAA GGTATGGATT
     ProAlaGly  TyrValThr  LysGluLeuGlu TyrPhePro GluThrAsp  LysValTrpIle

3481 GAGATCGGAG AAACGGAAGG AACATTCATC GTGGACAGCG TGGAATTACT TCTTATGGAG
     GluIleGly  GluThrGlu  GlyThrPheIle ValAspSer ValGluLeu  LeuLeuMetGlu

3541 GAATAA
     Glu---
``` ary of the present invention to provide synthetic Bt insecticidal protein genes which have been optimized for expression in pl According to the above objects, we have synthesized Bt insecticidal crystal protein genes in which the codon usage has been altered in order to increase expression in plants, particularly maize. However, rather than alter the codon usage to resemble a maize gene in terms of overall codon distribution, we have optimized the codon usage by using the codons which are most preferred in maize (maize preferred codons) in the synthesis of the synthetic gene. The optimized maize preferred codon usage is effective for expression of high levels of the Bt insecticidal protein. This might be the result of maximizing the amount of Bt insecticidal protein translated from a given population of messenger RNAs. The synthesis of a Bt IP gene using maize preferred codons also tends to eliminate fortuitous processing sites that might occur in the native coding sequence. The expression of this synthetic gene is significantly higher in maize cells than that of the native IP Bt gene.

Preferred synthetic, maize optimized DNA sequences of the present invention derive from the protein encoded by the cryIA(b) gene in *Bacillus thuringiensis* var. kurstaki, HD-1; Geiser et al., Gene, 48:109–118 (1986) or the cryIB gene (AKA Crya4 gene) described by Brizzard and Whiteley, Nuc. Acids. Res., 16:2723 (1988). The DNA sequence of the native kurstaki HD-1 cryIA(b) gene is shown as SEQ ID NO: 1. These proteins are active against various lepidopteran insects, including *Ostrinia nubilalis*, the European Corn Borer.

While the present invention has been exemplified by the synthesis of maize optimized Bt protein genes, it is recognized that the method can be utilized to optimize expression of any protein in plants.

The instant optimized genes can be fused with a variety of promoters, including constitutive, inducible, temporally regulated, developmentally regulated, tissue-preferred and tissue-specific promoters to prepare recombinant DNA molecules, i.e., chimeric genes. The maize optimized gene (coding sequence) provides substantially higher levels of expression in a transformed plant, when compared with a non-maize optimized gene. Accordingly, plants resistant to Coleopteran or Lepidopteran pests, such as European corn borer and sugarcane borer, can be produced.

It is another object of the present invention to provide tissue-preferred and tissue-specific promoters which drive the expression of an operatively associated structural gene of interest in a specific part or parts of a plant to the substantial exclusion of other parts.

It is another object of the present invention to provide pith-preferred promoters. By "pith-preferred," it is intended that the promoter is capable of directing the expression of an operatively associated structural gene in greater abundance in the pith of a plant than in the roots, outer sheath, and brace roots, and with substantially no expression in seed.

It is yet another object of this invention to provide pollen-specific promoters. By "pollen-specific," it is intended that the promoter is capable of directing the expression of an operatively associated structural gene of interest substantially exclusively in the pollen of a plant, with negligible expression in any other plant part. By "negligible," it is meant functionally insignificant.

It is yet another object of the present invention to provide recombinant DNA molecules comprising a tissue-preferred promoter or tissue-specific promoter operably associated or linked to a structural gene of interest, particularly a structural gene encoding an insecticidal protein, and expression of the recombinant molecule in a plant.

It is a further object of the present invention to provide transgenic plants which express at least one structural gene of interest operatively in a tissue-preferred or tissue-specific expression pattern.

In one specific embodiment of the invention disclosed and claimed herein, the tissue-preferred or tissue-specific promoter is operably linked to a structural gene encoding an insecticidal protein, and a plant is stably transformed with at least one such recombinant molecule. The resultant plant will be resistant to particular insects which feed on those parts of the plant in which the gene(s) is(are) expressed. Preferred structural genes encode B.t. insecticidal proteins. More preferred are maize optimized B.t. IP genes.

BRIEF DESCRIPTION OF THE FIGURES

FIG. 1 is a comparison of the full-length native Bt cryIA(b) gene (BTHKURHD; SEQ ID NO: 1), a full-length synthetic maize optimized Bt cryIA(b) gene (flsynbt.fin; SEQ ID NO: 4) and a truncated synthetic maize optimized Bt cryIA(b) gene (bssyn; SEQ ID NO: 3). This figure shows that the full-length synthetic maize optimized cryIA(b) gene sequence matches that of the native cryIA(b) gene at about 2354 out of 3468 nucleotides (approximately 68% homology).

FIG. 2 is a comparison of the truncated native Bt cryIA(b) gene (nucleotides 1 to 1947 of BTHKURHD; SEQ ID NO: 1) and a truncated synthetic maize optimized Bt gene (bssyn; SEQ ID NO: 3). This figure shows that the truncated synthetic maize optimized cryIA(b) gene sequence matches that of the native cryIA(b) gene at about 1278 out of 1947 nucleotides (approximately 66% homology).

FIG. 3 is a comparison of the pure maize optimized Bt gene sequence (syn1T.mze; SEQ ID NO: 2) with a truncated synthetic maize optimized Bt gene (bssyn; SEQ ID NO: 3) and a full-length synthetic maize optimized Bt gene modified to include restriction sites for facilitating construction of the gene (synful.mod; SEQ ID NO: 4). This figure shows that the truncated synthetic maize optimized cryIA(b) gene sequence matches that of the pure maize optimized cryIA(b) gene at 1913 out of 1947 nucleotides (approximately 98% homology).

FIG. 4 is a comparison of a native truncated Bt cryIA(b) gene (nucleotides 1 to 1845 of BTHKURHD SEQ ID NO: 1) with a truncated synthetic cryIA(b) gene described in Perlak et al., PNAS USA, 88:3324–3328 (1991) (PMONBT SEQ ID NO: 5) and a truncated synthetic maize optimized Bt gene (bssyn SEQ ID NO: 3). This figure shows that the PMONBT gene sequence matches that of the native cryIA (b) gene at about 1453 out of 1845 nucleotides (approximately 79% homology), while the truncated synthetic maize optimized Bt cryIA(b) gene matches the native cryIA(b) gene at about 1209 out of 1845 nucleotides (approximately 66% homology).

FIG. 5 is a comparison of a truncated synthetic cryIA(b) gene described in Perlak et al., PNAS USA, 88:3324–3328 (1991) (PMONBT SEQ ID NO: 5) and a truncated synthetic maize optimized Bt cryIA(b) gene (bssyn SEQ ID NO: 3). This figure shows that the PMONBT gene sequence matches that of the truncated synthetic maize optimized Bt cryIA(b) gene at about 1410 out of 1845 nucleotides (approximately 77% homology).

FIG. 6 is a full-length, maize optimized CryIB gene (SEQ ID NO: 6) encoding the CryIB protein (SEQ ID NO: 7).

FIG. 7 is a full-length, hybrid, partially maize optimized DNA sequence of a CryIA(b) gene (SEQ ID NO: 8) which is contained in pCIB4434. The synthetic region is from nucleotides 1–1938 (amino acids 1–646 SEQ ID NO: 9), and the native region is from nucleotides 1939–3468 (amino acids 647–1155 SEQ ID NO: 9). The fusion point between the synthetic and native coding sequences is indicated by a slash (/) in the sequence.

FIG. 9 is a full-length, hybrid, maize optimized DNA sequence (SEQ ID NO: 10) encoding a heat stable CryIA(b) protein (SEQ ID NO: 11), contained in pCIB5511.

FIG. 11 is a full-length, hybrid, maize optimized DNA sequence (SEQ ID NO: 12) encoding a heat stable CryIA(b) protein (SEQ ID NO: 13), contained in pCIB5512.

FIG. 13 is a full-length, maize optimized DNA sequence (SEQ ID NO: 14) encoding a heat stable CryIA(b) protein (SEQ ID NO: 15), contained in pCIB5513.

FIG. 15 is a full-length, maize optimized DNA sequence (SEQ ID NO: 16) encoding a heat-stable CryIA(b) protein (SEQ ID NO: 17), contained in pCIB5514.

FIG. 23A is a table containing data of cryIA(b) protein levels in transgenic maize.

FIG. 23B is a table which summarizes results of bioassays of Ostrinia and Diatraea on leaf material from maize progeny containing a maize optimized CryIA(b) gene.

FIG. 23C is a table containing data of cryIA(b) protein levels in transgenic maize.

FIG. 23D is a table which summarizes the results of bioassays of Ostrinia and Diatraea on leaf material from maize progeny containing a synthetic Bt. maize gene operably linked to a pith promoter.

FIG. 23E is a table containing data on expression of the cryIA(b) gene in transgenic maize using the pith-preferred promoter. Leaf samples from small plantlets transformed with pCIB4433 using procedures described elsewhere were analyzed for the presence of the cryIA(b) protein using ELISA. All plants expressing cryIA(b) were found to be insecticidal in the standard European corn borer bioassay. Note that the pith-preferred promoter has a low, but detectable level of expression in leaf tissue of maize. Detection of CryIA(b) protein is consistent with this pattern of expression.

FIG. 24 is a complete genomic DNA sequence (SEQ ID NO: 18) encoding a maize tryptophan synthase-alpha subunit (TrpA) protein (SEQ ID NO: 19). Introns, exons, transcription and translation starts, start and stop of cDNA are shown. $=start and end of cDNA; +1=transcription start; 73*******=primer extension primer; +1=start of translation; +++=stop codon; bp 1495–99=CCAAT Box; bp 1593–1598=TATAA Box; bp 3720–3725=poly A addition site;
above underlined sequences are PCR primers.

FIGS. 25A, 25B, 25C and 25D are Northern blot analyses which show differential expression of the maize TrpA subunit gene in maize tissue at 2 hour, 4 hour, 18 hour, and 48 hour intervals, respectively, at −80° C. with DuPont Cronex intensifying screens. P=pith; C=cob; BR=brace roots; ES=ear shank; LP=lower pith; MP=middle pith; UP=upper pith; S=seed; L=leaf; R=root; SH=sheath; and P(upper left)= total pith.

FIG. 30 shows the DNA sequence of the maize pollen-specific calcium dependent protein kinase gene cDNA (SEQ ID NO: 20), as contained in the 1.0 kb and 0.5 kb fragments of the original Type II cDNA clone. The EcoRI site that divides the 1.0 kb and 0.5 kb fragments is indicated. This cDNA is not full length, as the mRNA start site maps 490 bp upstream of the end of the cDNA clone. The translated protein is disclosed as SEQ ID NO: 21.

FIG. 32 is an amino acid sequence (sequence line 1, amino acids 13 to 307 of SEQ ID NO: 22) comparison of the pollen CDPK derived protein sequence and the rat calmodulin-dependent protein kinase 2 protein sequence (sequence line 3; SEQ ID NO: 23) disclosed in Tobimatsu et al., J. Biol. Chem. 263:16082–16086 (1988). The Align program of the DNAstar software package was used to evaluate the sequences. The homology to protein kinases occurs in the 5' two thirds of the gene, i.e. in the 1.0 kb fragment.

FIG. 33 is an amino acid sequence comparison of the pollen CDPK derived protein sequence (sequence line 1; amino acids 311 to 450 of SEQ ID NO: 22) and the human calmodulin protein sequence (sequence line 3; SEQ ID NO: 24) disclosed in Fischer et al., J. Biol. Chem. 263:17055–17062 (1988). The homology to calmodulin occurs in the 3' one third of the gene, i.e. in the 0.5 kb fragment.

FIG. 34 is an amino acid sequence comparison of the pollen CDPK derived protein sequence (sequence line 1; SEQ ID NO: 22) and soybean CDPK (SEQ ID NO: 25). The homology occurs over the entire gene.

FIG. 37 is a full-length, hybrid, maize-optimized DNA sequence (SEQ ID NO: 27) encoding a heat stable cryIA(b) protein (SEQ ID NO: 28).

DESCRIPTION OF THE SEQUENCES

Figure 8:
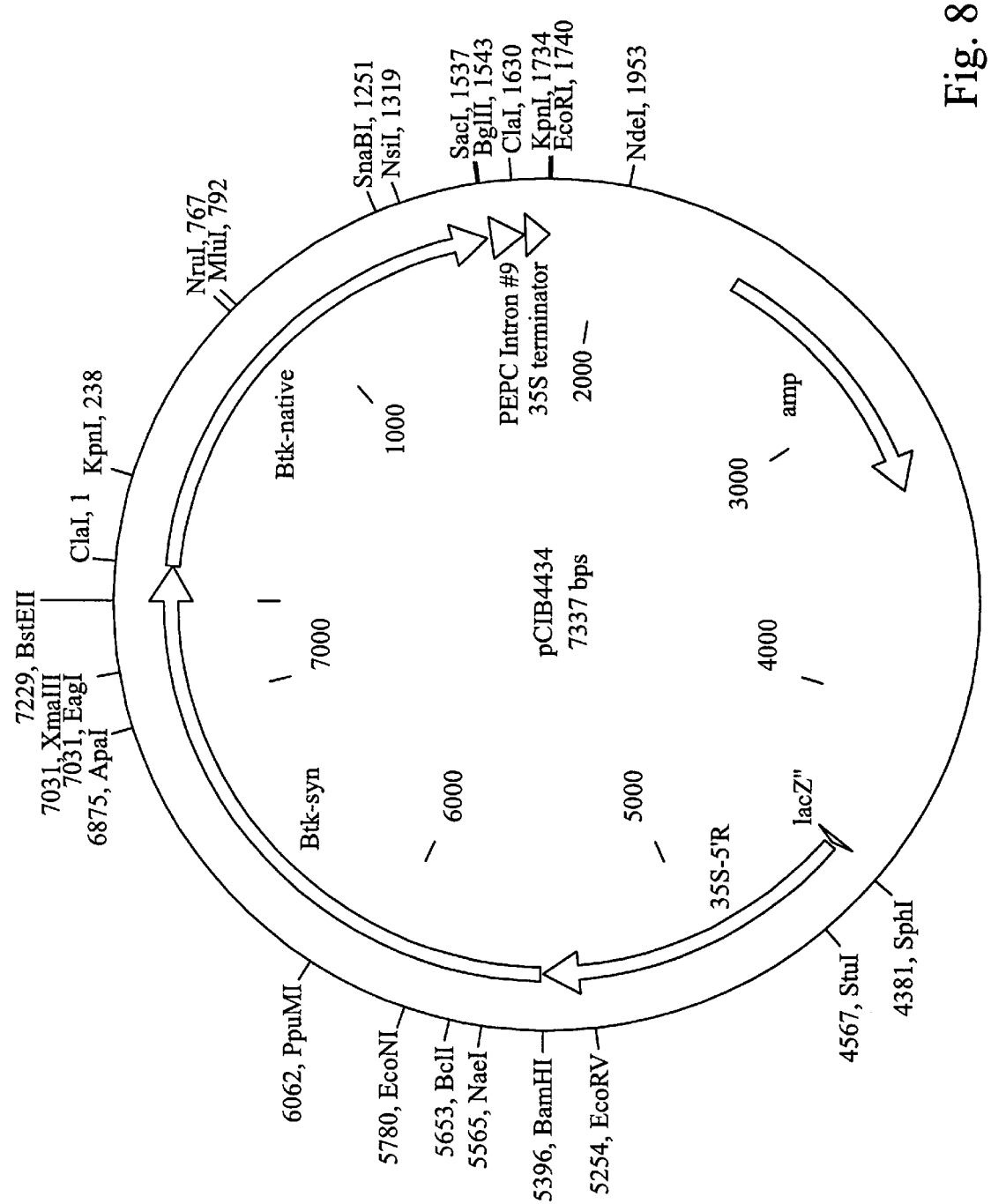
FIG. 8 is a map of pCIB4434.
Figure 10:
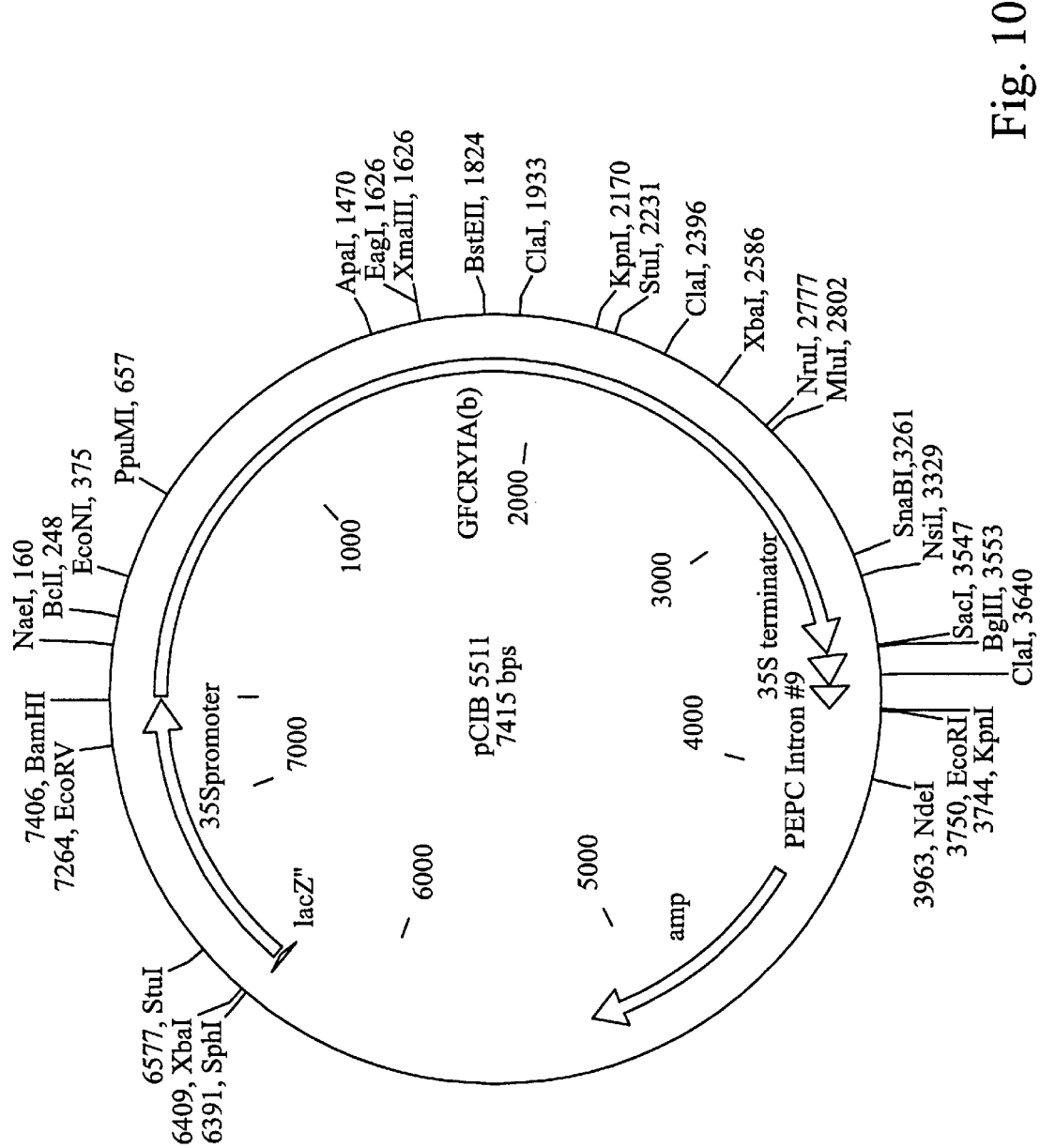
FIG. 10 is a map of pCIB5511.
Figure 12:
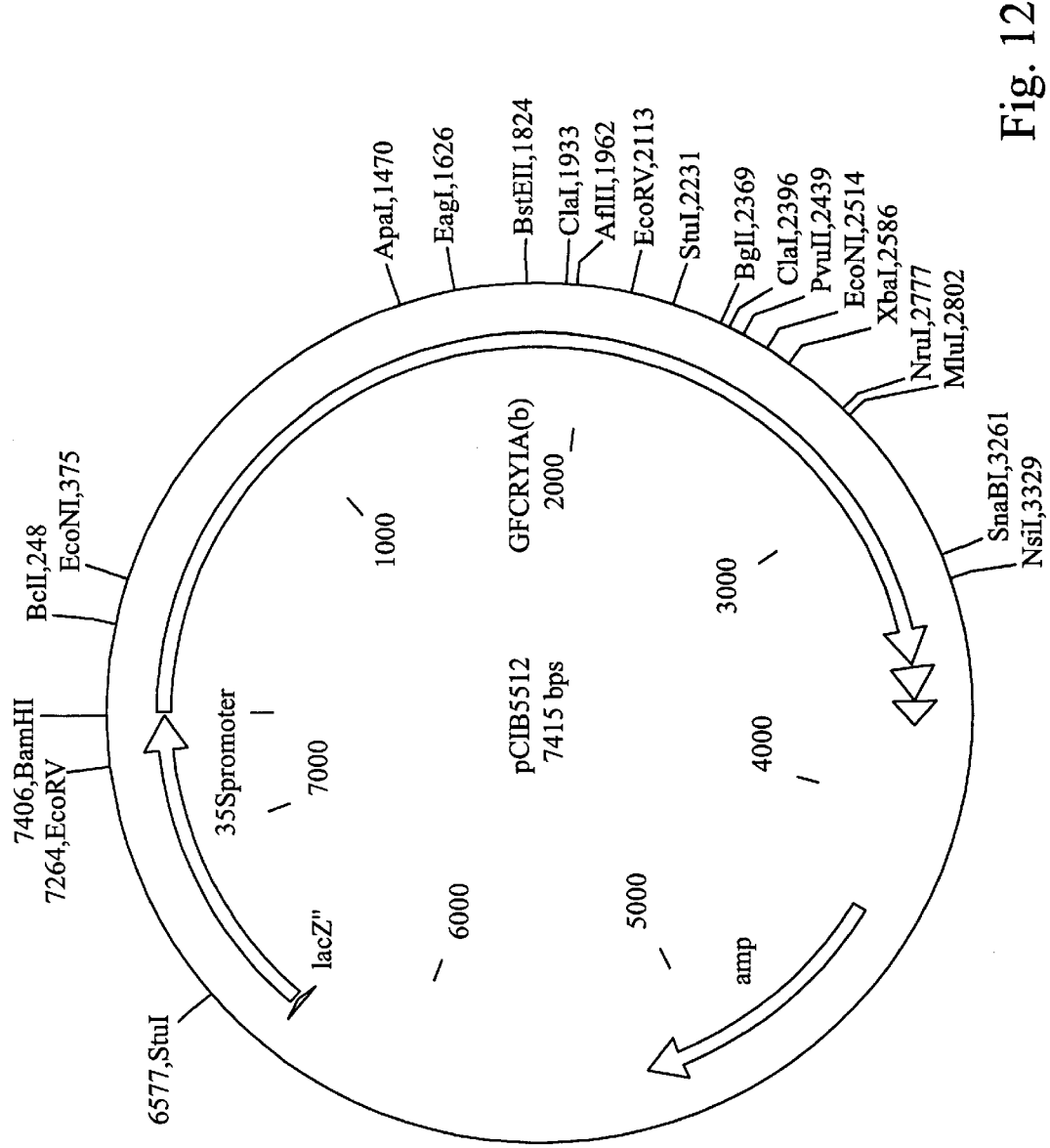
FIG. 12 is a map of pCIB5512.
Figure 14:
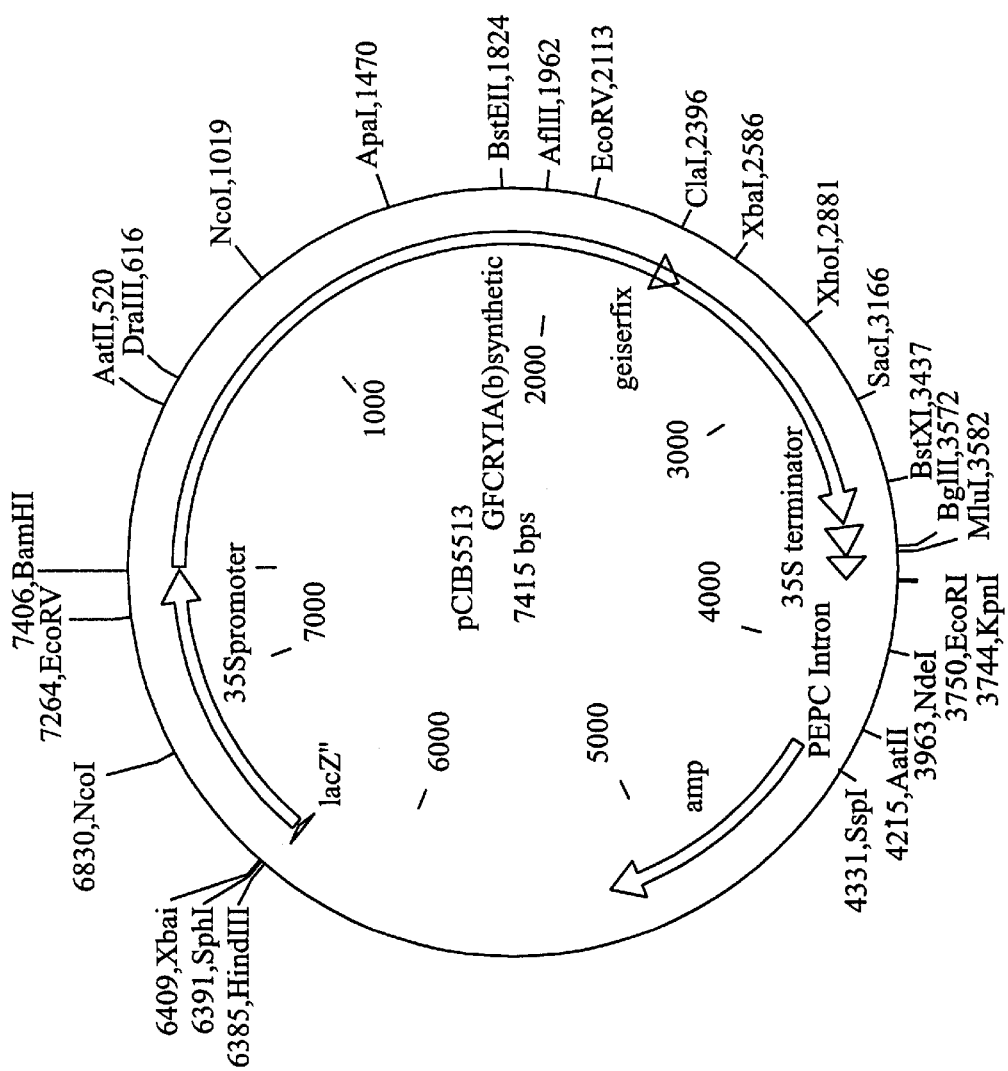
FIG. 14 is a map of pCIB5513.
Figure 16:
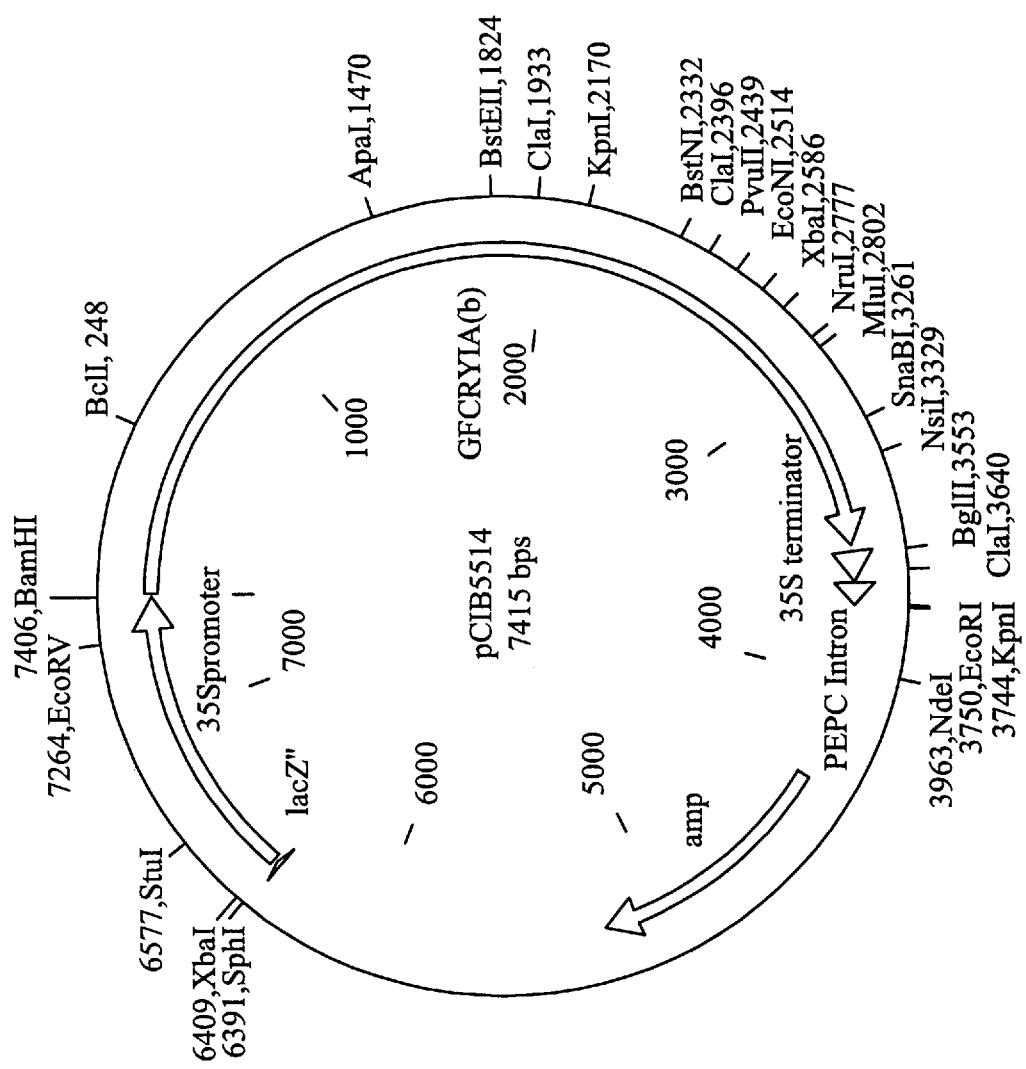
FIG. 16 is a map of pCIB5514.
Figure 17:
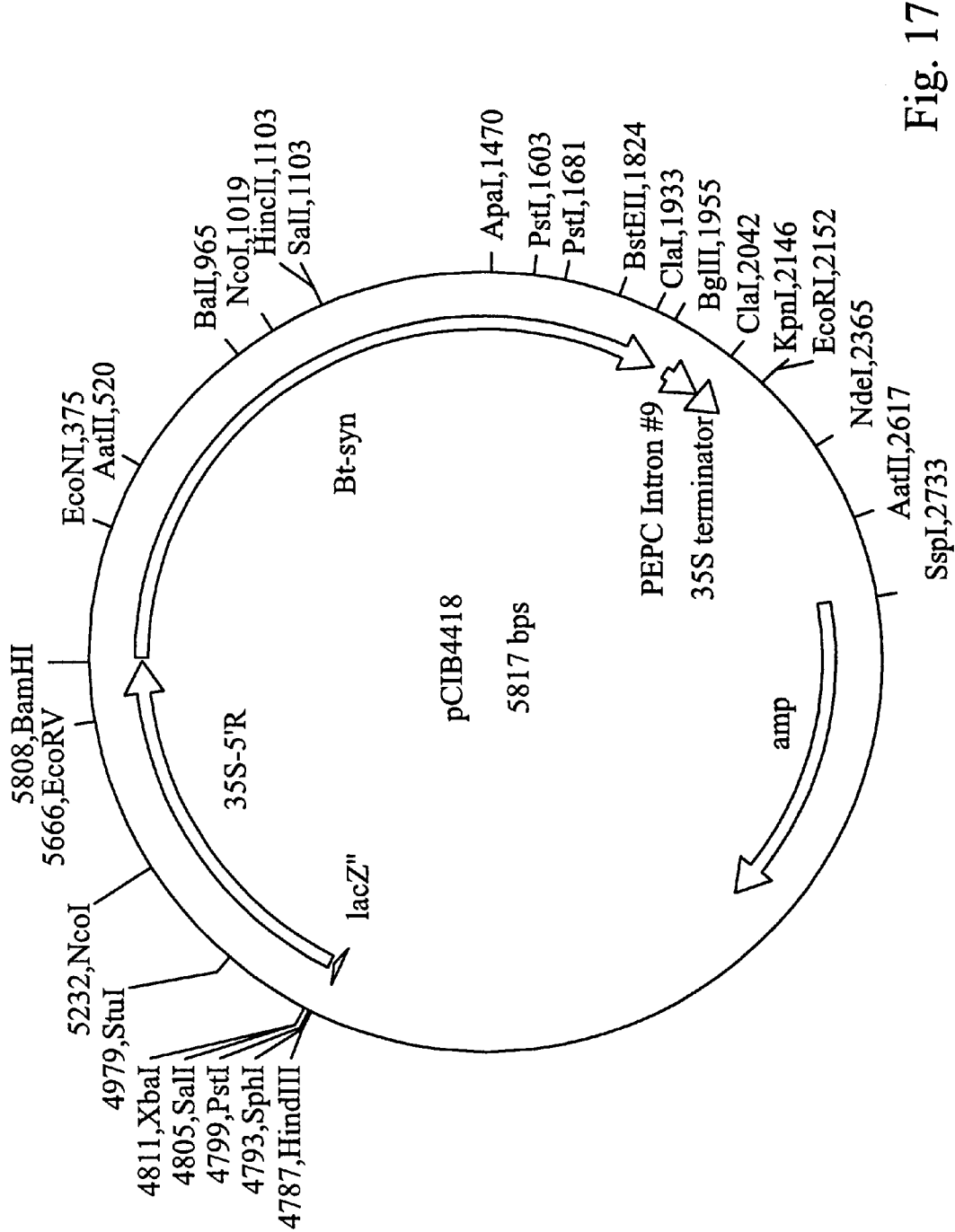
FIG. 17 is a map of pCIB4418.
Figure 18:
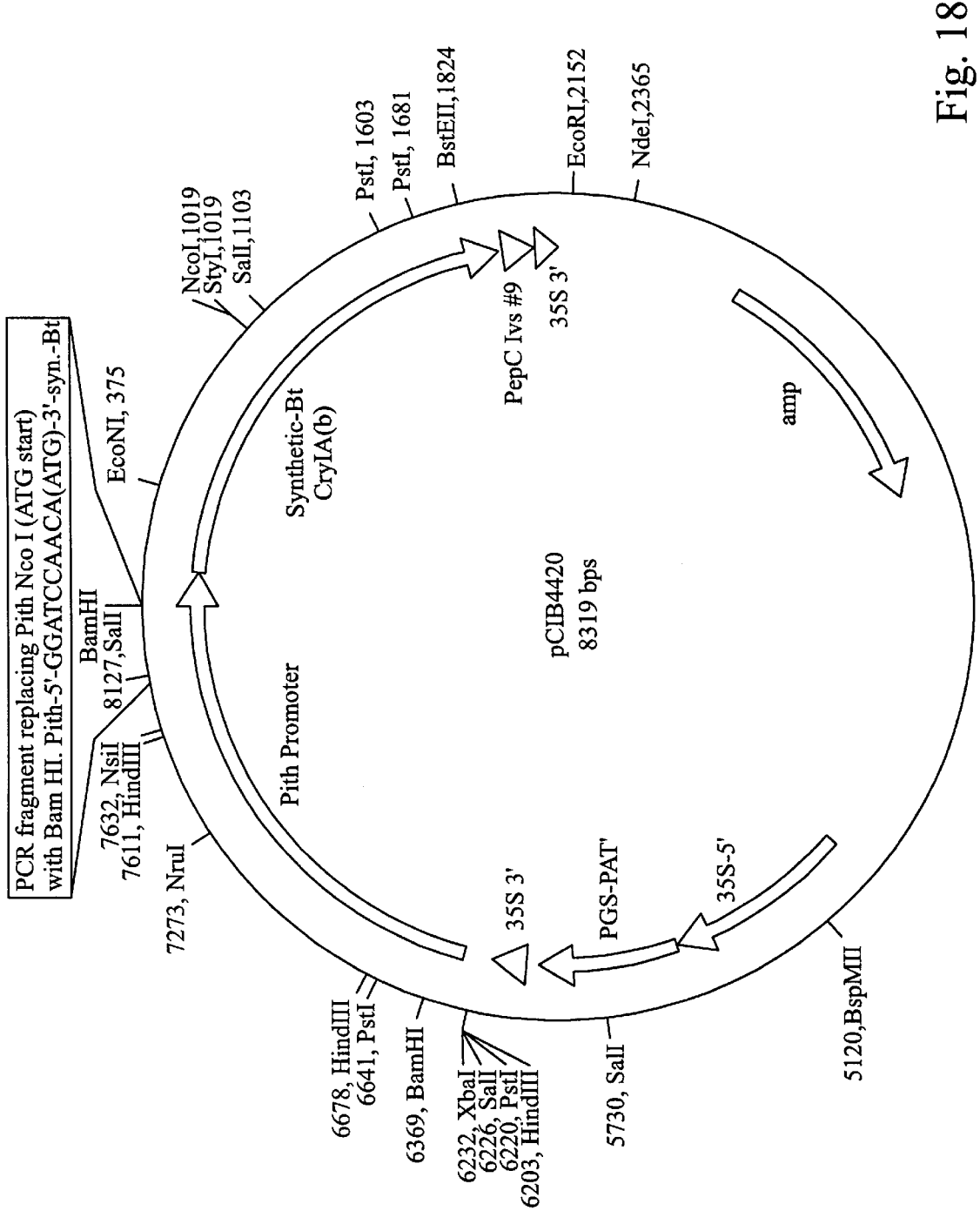
FIG. 18 is a map of pCIB4420.
Figure 19:
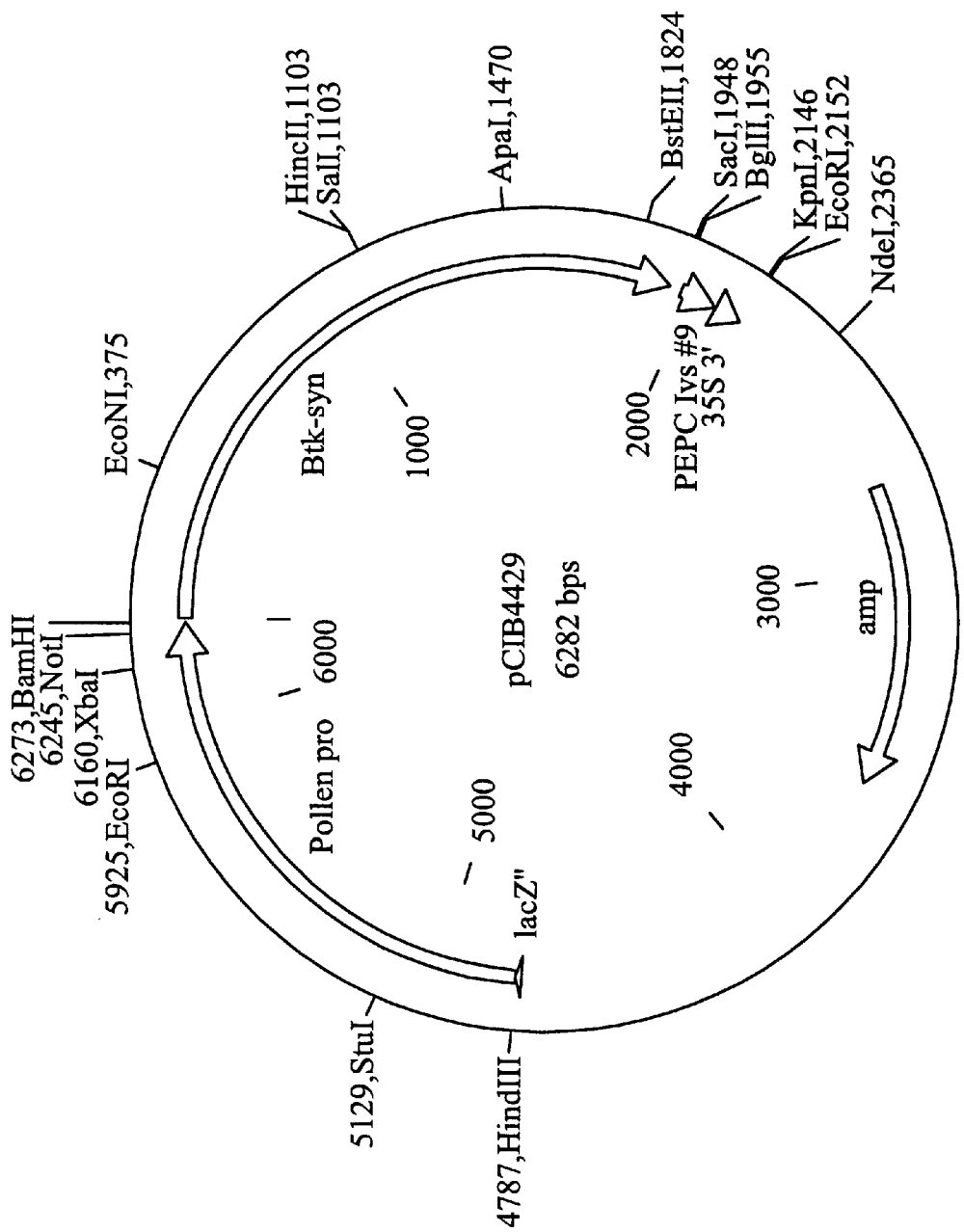
FIG. 19 is a map of pCIB4429.

SEQ ID NO: 1 is the DNA sequence of a full-length native Bt cryIA(b) gene.

SEQ ID NO: 2 is the DNA sequence of a full-length pure maize optimized synthetic Bt cryIA(b) gene.

SEQ ID NO: 3 is the DNA sequence of an approximately 2 Kb truncated synthetic maize optimized Bt cryIA(b) gene.

SEQ ID NO: 4 is the DNA sequence of a full-length synthetic maize optimized Bt cryIA(b) gene.

SEQ ID NO: 5 is the DNA sequence of an approximately 2 Kb synthetic Bt gene according to Perlak et al.

DETAILED DESCRIPTION OF THE INVENTION

The following definitions are provided in order to provide clarity with respect to the terms as they are used in the specification and claims to describe the present invention.

Maize preferred codon: Preferred codon refers to the preference exhibited by a specific host cell in the usage of nucleotide codons to specify a given amino acid. The preferred codon for an amino acid for a particular host is the single codon which most frequently encodes that amino acid in that host. The maize preferred codon for a particular amino acid may be derived from known gene sequences from maize. For example, maize codon usage for 28 genes from maize plants are listed in Table 4 of Murray et al., Nucleic Acids Research, 17:477–498 (1989), the disclosure of which is incorporated herein by reference. For instance, the maize preferred codon for alanine is GCC, since, according to pooled sequences of 26 maize genes in Murray et al., supra, that codon encodes alanine 36% of the time, compared to GCG (24%), GCA (13%), and GCT (27%).

Pure maize optimized sequence: An optimized gene or DNA sequence refers to a gene in which the nucleotide sequence of a native gene has been modified in order to utilize preferred codons for maize. For example, a synthetic maize optimized Bt cryIA(b) gene is one wherein the nucleotide sequence of the native Bt cryIA(b) gene has been modified such that the codons used are the maize preferred codons, as described above. A pure maize optimized gene is one in which the nucleotide sequence comprises 100 percent of the maize preferred codon sequences for a particular polypeptide. For example, the pure maize optimized Bt cryIA(b) gene is one in which the nucleotide sequence comprises 100 percent maize preferred codon sequences and encodes a polypeptide with the same amino acid sequence as that produced by the native Bt cryIA(b) gene. The pure nucleotide sequence of the optimized gene may be varied to permit manipulation of the gene, such as by altering a nucleotide to create or eliminate restriction sites. The pure nucleotide sequence of the optimized gene may also be varied to eliminate potentially deleterious processing sites, such as potential polyadenylation sites or intron recognition sites.

It is recognized that "partially maize optimized," sequences may also be utilized. By partially maize optimized, it is meant that the coding region of the gene is a chimeric (hybrid), being comprised of sequences derived from a native insecticidal gene and sequences which have been optimized for expression in maize. A partially optimized gene expresses the insecticidal protein at a level sufficient to control insect pests, and such expression is at a higher level than achieved using native sequences only. Partially maize optimized sequences include those which contain at least about 5% optimized sequences.

Full-length Bt Genes: Refers to DNA sequences comprising the full nucleotide sequence necessary to encode the polypeptide produced by a native Bt gene. For example, the native Bt cryLA(b) gene is approximately 3.5 Kb in length and encodes a polypeptide which is approximately 1150 amino acids in length. A full-length synthetic cryIA(b) Bt gene would be at least approximately 3.5 Kb in length.

Truncated Bt Genes: Refers to DNA sequences comprising less than the full nucleotide sequence necessary to encode the polypeptide produced by a native Bt gene, but which encodes the active toxin portion of the polypeptide. For example, a truncated synthetic Bt gene of approximately 1.9 Kb encodes the active toxin portion of the polypeptide such that the protein product exhibits insecticidal activity.

Tissue-preferred promoter: The term "tissue-preferred promoter" is used to indicate that a given regulatory DNA sequence will promote a higher level of transcription of an associated structural gene or DNA coding sequence, or of expression of the product of the associated gene as indicated by any conventional RNA or protein assay, or that a given DNA sequence will demonstrate some differential effect; i.e., that the transcription of the associated DNA sequences or the expression of a gene product is greater in some tissue than in all other tissues of the plant.

"Tissue-specific promoter" is used to indicate that a given regulatory DNA sequence will promote transcription of an associated coding DNA sequence essentially entirely in one or more tissues of a plant, or in one type of tissue, e.g. green tissue, while essentially no transcription of that associated coding DNA sequence will occur in all other tissues or types of tissues of the plant.

The present invention provides DNA sequences optimized for expression in plants, especially in maize plants. In a preferred embodiment of the present invention, the DNA sequences encode the production of an insecticidal toxin, preferably a polypeptide sharing substantially the amino acid sequence of an insecticidal crystal protein toxin normally produced by *Bacillus thuringiensis*. The synthetic gene may encode a truncated or full-length insecticidal protein. Especially preferred are synthetic DNA sequences which encode a polypeptide effective against insects of the order Lepidoptera and Coleoptera, and synthetic DNA sequences which encode a polypeptide having an amino acid sequence essentially the same as one of the crystal protein toxins of *Bacillus thuringiensis* variety kurstaki, HD-1.

The present invention provides synthetic DNA sequences effective to yield high expression of active insecticidal proteins in plants, preferably maize protoplasts, plant cells and plants. The synthetic DNA sequences of the present invention have been modified to resemble a maize gene in terms of codon usage and G+C content. As a result of these modifications, the synthetic DNA sequences of the present invention do not contain the potential processing sites which are present in the native gene. The resulting synthetic DNA sequences (synthetic Bt IP coding sequences) and plant transformation vectors containing this synthetic DNA sequence (synthetic Bt IP genes) result in surprisingly increased expression of the synthetic Bt IP gene, compared to the native Bt IP gene, in terms of insecticidal protein production in plants, particularly maize. The high level of expression results in maize cells and plants that exhibit resistance to lepidopteran insects, preferably European Corn Borer and *Diatrea saccharalis*, the Sugarcane Borer.

The synthetic DNA sequences of the present invention are designed to encode insecticidal proteins from *Bacillus thuringiensis*, but are optimized for expression in maize in terms of G+C content and codon usage. For example, the maize codon usage table described in Murray et al., supra, is used to reverse translate the amino acid sequence of the toxin produced by the *Bacillus thuringiensis* subsp. kurstaki HD-1 cryIA(b) gene, using only the most preferred maize codons. The reverse translated DNA sequence is referred to as the pure maize optimized sequence and is shown as Sequence 4. This sequence is subsequently modified to eliminate unwanted restriction endonuclease sites, and to create desired restriction endonuclease sites. These modifications are designed to facilitate cloning of the gene without appreciably altering the codon usage or the maize optimized sequence. During the cloning procedure, in order to facilitate cloning of the gene, other modifications are made in a region that appears especially susceptible to errors induced during cloning by the polymerase chain reaction (PCR). The final sequence of the maize optimized synthetic Bt IP gene is shown in Sequence 2. A comparison of the maize optimized synthetic Bt IP gene with the native kurstaki cryIA(b) Bt gene is shown in FIG. 1.

In a preferred embodiment of the present invention, the protein produced by the synthetic DNA sequence is effective against insects of the order Lepidoptera or Coleoptera. In a more preferred embodiment, the polypeptide encoded by the synthetic DNA sequence consists essentially of the full-length or a truncated amino acid sequence of an insecticidal protein normally produced by *Bacillus thuringiensis* var. kurstaki HD-1. In a particular embodiment, the synthetic DNA sequence encodes a polypeptide consisting essentially of a truncated amino acid sequence of the Bt CryIA(b) protein.

The insecticidal proteins of the invention are expressed in a plant in an amount sufficient to control insect pests, i.e. insect controlling amounts. It is recognized that the amount of expression of insecticidal protein in a plant necessary to control insects may vary depending upon species of plant, type of insect, environmental factors and the like. Generally, the insect population will be kept below the economic threshold which varies from plant to plant. For example, to control European corn borer in maize, the economic threshold is .5 eggmass/plant which translates to about 10 larvae/plant.

The methods of the invention are useful for controlling a wide variety of insects including but not limited to rootworms, cutworms, armyworms, particularly fall and beet armyworms, wireworms, aphids, corn borers, particularly European corn borers, sugarcane borer, lesser corn stalk borer, Southwestern corn borer, etc.

In a preferred embodiment of the present invention, the synthetic coding DNA sequence optimized for expression in maize comprises a G+C percentage greater than that of the native cryIA(b) gene. It is preferred that the G+C percentage be at least about 50 percent, and more preferably at least about 60 percent. It is especially preferred that the G+C percent be about 64 percent.

In another preferred embodiment of the present invention, the synthetic coding DNA sequence optimized for expression in maize comprises a nucleotide sequence having at least about 90 percent homology with the "pure" maize optimized nucleotide sequence of the native *Bacillus thuringiensis* cryLA(b) protein, more preferably at least about 95 percent homology, and most preferably at least about 98 percent.

Other preferred embodiments of the present invention include synthetic DNA sequences having essentially the DNA sequence of SEQ ID NO: 4, as well as mutants or variants thereof; transformation vectors comprising essentially the DNA sequence of SEQ ID NO: 4; and isolated DNA sequences derived from the plasmids pCIB4406, pCIB4407, pCIB4413, pCIB4414, pCIB4416, pCIB4417, pCIB4418, pCIB4419, pCIB4420, pCIB4421, pCIB4423, pCIB4434, pCIB4429, pCIB4431, pCIB4433. Most preferred are isolated DNA sequences derived from the plasmids pCIB4418 and pCIB4420, pCIB4434, pCIB4429, pCIB4431, and pCIB4433.

In order to construct one of the maize optimized DNA sequences of the present invention, synthetic DNA oligonucleotides are made with an average length of about 80 nucleotides. These oligonucleotides are designed to hybridize to produce fragments comprising the various quarters of the truncated toxin gene. The oligonucleotides for a given quarter are hybridized and amplified using PCR. The quarters are then cloned and the cloned quarters are sequenced to find those containing the desired sequences. In one instance, the fourth quarter, the hybridized oligonucleotides are cloned directly without PCR amplification. Once all clones of four quarters are found which contain open reading frames, an intact gene encoding the active insecticidal protein is assembled. The assembled gene may then be tested for insecticidal activity against any insect of interest including the European Corn Borer (ECB) and the sugarcane borer. (Examples 5A and 5B, respectively). When a fully functional gene is obtained, it is again sequenced to confirm its primary structure. The fully functional gene is found to give 100% mortality when bioassayed against ECB. The fully functional gene is also modified for expression in maize.

The maize optimized gene is tested in a transient expression assay, e.g. a maize transient expression assay. The native Bt cryIA(b) coding sequence for the active insecticidal toxin is not expressed at a detectable level in a maize transient expression system. Thus, the level of expression of the synthesized gene can be determined. By the present methods, expression of a protein in a transformed plant can be increased at least about 100 fold to about 50,000 fold, more specifically at least about 1,000 fold to at least about 20,000 fold.

Increasing expression of an insecticial gene to an effective level does not require manipulation of a native gene along the entire sequence. Effective expression can be achieved by manipulating only a portion of the sequences necessary to obtain increased expression. A full-length, maize optimized CryIA(b) gene may be prepared which contains a protein of the native CryIA(b) sequence. For example, FIG. 7 illustrates a full-length, maize optimized CryIA(b) gene which is a synthetic-native hybrid. That is, about 2 kb of the gene (nucleotides 1–1938 SEQ ID NO: 8) is maize optimized, i.e. synthetic. The remainder, C-terminal nucleotides 647–1155 SEQ ID NO: 8, are identical to the corresponding sequence native of the CryIA(b) gene. Construction of the illustrated gene is described in Example 6, below.

It is recognized that by using the methods described herein, a variety of synthetic/native hybrids may be constructed and tested for expression. The important aspect of hybrid construction is that the protein is produced in sufficient amounts to control insect pests. In this manner, critical regions of the gene may be identified and such regions synthesized using preferred codons. The synthetic sequences can be linked with native sequences as demonstrated in the Examples below. Generally, N-terminal portions or processing sites can be synthesized and substituted in the native coding sequence for enhanced expression in plants.

In another embodiment of the present invention, the maize optimized genes encoding cryIA(b) protein may be manipulated to render the encoded protein more heat stable or temperature stable compared to the native cryIA(b) protein. It has been shown that the cryIA(b) gene found in *Bacillus thuringiensis* kurstaki HD-1 contains a 26 amino acid deletion, when compared with the cryIA(a) and cryIA (c) proteins, in the —COOH half of the protein. This deletion leads to a temperature-sensitive cryIA(b) protein. See M. Geiser, EP 0 440 581, entitled "Temperaturstabiles *Bacillus thuringiensis*-Toxin". Repair of this deletion with the corresponding region from the cryIA(a) or cryIA(c) protein improves the temperature stability of the repaired protein. Constructs of the full-length modified cryIA(b) synthetic gene are designed to insert sequences coding for the missing amino acids at the appropriate place in the sequence without altering the reading frame and without changing the rest of the protein sequence. The full-length synthetic version of the gene is assembled by synthesizing a series of double-stranded DNA cassettes, each approximately 300 bp in size, using standard techniques of DNA synthesis and enzymatic reactions. The repaired gene is said to encode a "heat stable" or "temperature-stable" cryIA(b) protein, since it retains more biological activity than its native counterpart when exposed to high temperatures. Specific sequences of maize optimized, heat stable cryIA(b) genes encoding temperature stable proteins are set forth in FIGS. 9 (SEQ ID NO: 10), 11 (SEQ ID NO: 12), 13 (SEQ ID NO: 14), and 15 (SEQ ID NO: 16), and are also described in Example 7, below.

The present invention encompasses maize optimized coding sequences encoding other polypeptides, including those of other *Bacillus thuringiensis* insecticidal polypeptides or insecticidal proteins from other sources. For example, cryIB genes can be maize optimized, and then stably introduced into plants, particularly maize. The sequence of a maize optimized cryIB gene constructed in accordance with the present invention is set forth in FIG. 6 (SEQ ID NO: 6).

Optimizing a Bt IP gene for expression in maize using the maize preferred codon usage according to the present invention results in a significant increase in the expression of the insecticidal gene. It is anticipated that other genes can be synthesized using plant codon preferences to improve their expression in maize or other plants. Use of maize codon preference is a likely method of optimizing and maximizing expression of foreign genes in maize. Such genes include genes used as selectable or scoreable markers in maize transformation, genes which confer herbicide resistance, genes which confer disease resistance, and other genes which confer insect resistance.

The synthetic cryIA(b) gene is also inserted into Agrobacterium vectors which are useful for transformation of a large variety of dicotyledenous plant species. (Example 44). Plants stably transformed with the synthetic cryIA(b) Agrobacterium vectors exhibit insecticidal activity.

The native Bt cryIA(b) gene is quite A+T rich. The G+C content of the full-length native Bt cryIA(b) gene is approximately 39%. The G+C content of a truncated native Bt cryIA(b) gene of about 2 Kb in length is approximately 37%. In general, maize coding regions tend to be predominantly G+C rich. The modifications made to the Bt cryIA(b) gene result in a synthetic IP coding region which has greater than 50% G+C content, and has about 65% homology at the DNA level with the native cryIA(b) gene. The protein encoded by this synthetic CryIA(b) gene is 100% homologous with the native protein, and thus retains full function in terms of insect activity. The truncated synthetic CryIA(b) IP gene is about 2 Kb in length and the gene encodes the active toxin region of the native Bt kurstaki CryIA(b) insecticidal protein. The length of the protein encoded by the truncated synthetic CryIA(b) gene is 648 amino acids.

The synthetic genes of the present invention are useful for enhanced expression in transgenic plants, most preferably in transformed maize. The transgenic plants of the present invention may be used to express the insecticidal CryIA(b) protein at a high level, resulting in resistance to insect pests, preferably coleopteran or lepidopteran insects, and most preferably European Corn Borer (ECB) and Sugarcane Borer.

In the present invention, the DNA coding sequence of the synthetic maize optimized gene may be under the control of regulatory elements such as promoters which direct expression of the coding sequence. Such regulatory elements, for example, include monocot or maize and other monocot functional promoters to provide expression of the gene in various parts of the maize plant. The regulatory element may be constitutive. That is, it may promote continuous and stable expression of the gene. Such promoters include but are not limited to the CaMV 35S promoter; the CaMV 19S promoter; *A. tumefaciens* promoters such as octopine synthase promoters, mannopine synthase promoters, nopaline synthase promoters, or other opine synthase promoters; ubiquitin promoters, actin promoters, histone promoters and tubulin promoters. The regulatory element may be a tissue-preferential promoter, that is, it may promote higher expression in some tissues of a plant than in others. Preferably, the tissue-preferential promoter may direct higher expression of the synthetic gene in leaves, stems, roots and/or pollen than in seed. The regulatory element may also be inducible, such as by heat stress, water stress, insect feeding or chemical induction, or may be developmentally regulated. Numerous promoters whose expression are known to vary in a tissue specific manner are known in the art. One such example is the maize phosphoenol pyruvate carboxylase (PEPC), which is green tissue-specific. See, for example, Hudspeth, R. L. and Grula, J. W., Plant Molecular Biology 12:579–589, 1989). Other green tissue-specific promoters include chlorophyll a/b binding protein promoters and RubisCO small subunit promoters.

The present invention also provides isolated and purified pith-preferred promoters. Preferred pith-preferred promoters are isolated from graminaceous monocots such as sugarcane, rice, wheat, sorghum, barley, rye and maize; more preferred are those isolated from maize plants.

In a preferred embodiment, the pith-preferred promoter is isolated from a plant TrpA gene; in a most preferred embodiment, it is isolated from a maize TrpA gene. That is, the promoter in its native state is operatively associated with a maize tryptophan synthase-alpha subunit gene (hereinafter "TrpA"). The encoded protein has a molecular mass of about 38 kD. Together with another alpha subunit and two beta subunits, TrpA forms a multimeric enzyme, tryptophan synthase. Each subunit can operate separately, but they function more efficiently together. TrpA catalyzes the conversion of indole glycerol phosphate to indole. Neither the maize TrpA gene nor the encoded protein had been isolated from any plant before Applicants' invention. The *Arabidopsis thaliana* tryptophan synthase beta subunit gene has been cloned as described Wright et al., The Plant Cell, 4:711–719 (1992). The instant maize TrpA gene has no homology to the beta subunit encoding gene. The present invention also provides purified pollen-specific promoters obtainable from a plant calcium-dependent phosphate kinase (CDPK) gene. That is, in its native state, the promoter is operably linked to a plant CDPK gene. In a preferred embodiment, the promoter is isolated from a maize CDPK gene. By "pollen-specific," it is meant that the expression of an operatively associated structural gene of interest is substantially exclusively (i.e. essentially entirely) in the pollen of a plant, and is negligible in all other plant parts. By "CDPK," it is meant a plant protein kinase which has a high affinity for calcium, but not calmodulin, and requires calcium, but not calmodulin, for its catalytic activity.

To obtain tissue-preferred or tissue specific promoters, genes encoding tissue specific messenger RNA (mRNA) can be obtained by differential screening of a cDNA library. For example, a pith-preferred cDNA can be obtained by subjecting a pith cDNA library to differential screening using cDNA probes obtained from pith and seed mRNA. See, *Molecular Cloning, A Laboratory Manual*, Sambrook et al. eds. Cold Spring Harbor Press: New York (1989).

Alternately, tissue specific promoters may be obtained by obtaining tissue specific proteins, sequencing the N-terminus, synthesizing oligonucleotide probes and using the probes to screen a cDNA library. Such procedures are exemplified in the Experimental section for the isolation of a pollen specific promoter.

The scope of the present invention in regard to the pith-preferred and pollen-specific promoters encompasses functionally active fragments of a full-length promoter that also are able to direct pith-preferred or pollen-specific transcription, respectively, of associated structural genes. Functionally active fragments of a promoter DNA sequence may be derived from a promoter DNA sequence, by several art-recognized procedures, such as, for example, by cleaving the promoter DNA sequence using restriction enzymes, synthesizing in accordance with the sequence of the promoter DNA sequence, or may be obtained through the use of PCR technology. See, e.g. Mullis et al., Meth. Enzymol. 155:335–350 (1987); Erlich (ed.), PCR Technology, Stockton Press (New York 1989).

Further included within the scope of the instant invention are pith-preferred and pollen-specific promoters "equivalent" to the full-length promoters. That is, different nucleotides, or groups of nucleotides may be modified, added or deleted in a manner that does not abolish promoter activity in accordance with known procedures.

A pith-preferred promoter obtained from a maize TrpA gene is shown in FIG. 24 (SEQ ID NO: 18). Those skilled in the art, with this sequence information in hand, will recognize that pith-preferred promoters included within the scope of the present invention can be obtained from other plants by probing pith libraries from these plants with probes derived from the maize TrpA structural gene. Probes designed from sequences that are highly conserved among TrpA subunit genes of various species, as discussed generally in Example 17, are preferred. Other pollen-specific promoters, which in their native state are linked to plant CDPK genes other than maize, can be isolated in similar fashion using probes derived from the conserved regions of the maize CDPK gene to probe pollen libraries.

In another embodiment of the present invention, the pith-preferred or pollen-specific promoter is operably linked to a DNA sequence, i.e. structural gene, encoding a protein of interest, to form a recombinant DNA molecule or chimeric gene. The phrase "operably linked to" has an art-recognized meaning; it may be used interchangeably with "operatively associated with," "linked to," or "fused to".

The structural gene may be homologous or heterologous with respect to origin of the promoter and/or a target plant into which it is transformed. Regardless of relative origin, the associated DNA sequence will be expressed in the transformed plant in accordance with the expression properties of the promoter to which it is linked. Thus, the choice of associated DNA sequence should flow from a desire to have the sequence expressed in this fashion. Examples of heterologous DNA sequences include those which encode insecticidal proteins, e.g. proteins or polypeptides toxic or inhibitory to insects or other plant parasitic arthropods, or plant pathogens such as fungi, bacteria and nematodes. These heterologous DNA sequences encode proteins such as magainins, Zasloff, PNAS USA, 84:5449–5453 (1987); cecropins, Hultmark et al., Eur. J. Biochem. 127:207–217 (1982); attacins, Hultmark et al., EMBO J. 2:571–576 (1983); melittin, gramicidin S, Katsu et al., Biochem. Biophys. Acta, 939:57–63 (1988); sodium channel proteins and synthetic fragments, Oiki et al. PNAS USA, 85:2395–2397 (1988); the alpha toxin of *Staphylococcus aureusm* Tobkes et al., Biochem., 24:1915–1920 (1985); apolipoproteins and fragments thereof, Knott et al., Science 230:37 (1985); Nakagawa et al., J. Am. Chem. Soc., 107:7087 (1985); alamethicin and a variety of synthetic amphipathic peptides, Kaiser et al., Ann. Rev. Biophys. Biophys. Chem. 16:561–581 (1987); lectins, Lis et al., Ann. Rev. Biochem., 55:35–68 (1986); protease and amylase inhibitors; and insecticidal proteins from *Bacillus thuringiensis*, particularly the delta-endotoxins from *B. thuringiensis*; and from other bacteria or fungi.

In a preferred embodiment of the invention, a pith-preferred promoter obtained from a maize TrpA subunit gene or pollen-specific promoter obtained from a maize CDPK gene is operably linked to a heterologous DNA sequence encoding a *Bacillus thuringiensis* ("B.t.") insecticidal protein. These proteins and the corresponding structural genes are well known in the art. See, Hofte and Whiteley, Microbiol. Reviews, 53:242–255 (1989).

While it is recognized that any promoter capable of directing expression can be utilized, it may be preferable to use heterologous promoters rather than the native promoter of the protein of interest. In this manner, chimeric nucleotide sequences can be constructed which can be determined based on the plant to be transformed as well as the insect pest. For example, to control insect pests in maize, a monocot or maize promoter can be operably linked to a Bt protein. The maize promoter can be selected from tissue-preferred and tissue-specific promoters such as pith-preferred and pollen-specific promoters, respectively as disclosed herein.

In some instances, it may be preferred to transform the plant cell with more than one chimeric gene construct. Thus, for example, a single plant could be transformed with a pith-preferred promoter operably linked to a Bt protein as well as a pollen-specific promoter operably linked to a Bt protein. The transformed plants would express Bt proteins in the plant pith and pollen and to a lesser extent the roots, outer sheath and brace roots.

For various other reasons, particularly management of potential insect resistance developing to plant expressed insecticidal proteins, it is beneficial to express more than one insecticidal protein (IP) in the same plant. One could express two different genes (such as two different *Bacillus thuringiensis* derived delta-endotoxins which bind different receptors in the target insect's midgut) in the same tissues, or one can selectively express the two toxins in different tissues of the same plant using tissue specific promoters. Expressing two Bt genes (or any two insecticidal genes) in the same plant using three different tissue specific promoters presents a problem for production of a plant expressing the desired phenotype. Three different promoters driving two different genes yields six different insecticidal genes that need to be introduced into the plant at the same time. Also needed for the transformation is a selectable marker to aid in identification of transformed plants. This means introducing seven different genes into the plant at the same time. It is most desired that all genes, especially the insecticidal genes, integrate into the plant genome at the same locus so they will behave as a single gene trait and not as a multiple gene trait that will be harder to track during breeding of commercial hybrids. The total number of genes can be reduced by using differential tissue specific expression of the different insecticidal proteins.

For example, by fusing cryIA(b) with the pollen and PEP carboxylase promoters, one would obtain expression of this gene in green tissues and pollen. Fusing a pith-preferred promoter with the cryIB delta endotoxin from *Bacillus thuringiensis* would produce expression of this insecticidal protein most abundantly in the pith of a transformed plant, but not in seed tissues. Transformation of a plant with three genes, PEP carboxylase/cryIA(b), pollen/cryIA(b), and pith/cryIB produces a plant expressing two different Bt insecticidal endotoxins in different tissues of the same plant. CryIA(b) would be expressed in the "outside" tissues of a plant (particularly maize), that is, in those tissues which European corn borer feeds on first after hatching. Should ECB prove resistant to cryIA(b) and be able to burrow into the stalk of the plant after feeding on leaf tissue and/or pollen, it would then encounter the cryIB delta-endotoxin and be exposed to a second insecticidal component. In this manner, one can differentially express two different insecticidal components in the same plant and decrease the total number of genes necessary to introduce as a single genetic unit while at the same time providing protection against development of resistance to a single insecticidal component.

Likewise, a plant may be transformed with constructs encoding more than one type of insecticidal protein to control various insects. Thus, a number of variations may be constructed by one of skill in the art.

The recombinant DNA molecules of the invention may be prepared by manipulating the various elements to place them in proper orientation. Thus, adapters or linkers may be employed to join the DNA fragments. Other manipulations may be performed to provide for convenient restriction sites, removal of restriction sites or superfluous DNA. These manipulations can be performed by art-recognized methods. See, Sambrook et al., Molecular Cloning: A Laboratory Manual, Cold Spring Harbor Laboratory Press, second edition, 1989. For example, methods such as restriction, chewing back or filling in overhangs to provide blunt ends, ligation of linkers, complementary ends of the DNA fragments can be provided for joining and ligation. See, Sambrook et al., supra.

Other functional DNA sequences may be included in the recombinant DNA molecule, depending upon the way in which the molecule is to be incorporated into the target plant genome. For instance, in the case of Agrobacterium-mediated transformation, if Ti- or the Ri-plasmid is used to transform the plant cells, the right and left borders of the T-DNA of the Ti- and Ri-plasmid will be joined as flanking regions to the expression cassette. *Agrobacterium tumefaciens*-mediated transformation of plants has been described in Horsch et al., Science, 225:1229 (1985); Marton, Cell Culture Somatic Cell Genetics of Plants, 1:514–521 (1984); Hoekema, In: The Binary Plant Vector System Offset-Drukkerij Kanters B.V., Alblasserdam, 1985, Chapter V Fraley, et al., Crit. Rev. Plant Sci., 4:1–46; and An et al., EMBO J., 4:277–284 (1985).

The recombinant DNA molecules of the invention also can include a marker gene to facilitate selection in recombinant plant cells. Examples of markers include resistance to a biocide such as an antibiotic, e.g. kanamycin, hygromycin, chloramphenicol, paramomycin, methotrexate and bleomycin, or a herbicide such as imidazolones, sulfonylureas, glyphosate, phosphinothricin, or bialaphos. Marker genes are well known in the art.

In another embodiment of the present invention, plants stably transformed with a recombinant DNA molecule or chimeric gene as described hereinabove are provided. The resultant transgenic plant contains the transformed gene stably incorporated into its genome, and will express the structural gene operably associated to the promoter in the respective fashion.

Transgenic plants encompassed by the instant invention include both monocots and dicots. Representative examples include maize, tobacco, tomato, cotton, rape seed, soybean, wheat, rice, alfalfa, potato and sunflower. Preferred plants include maize, particularly inbred maize plants.

All transformed plants encompassed by the instant invention may be prepared by several methods known in the art. *A. tumefaciens*-mediated transformation has been disclosed above. Other methods include direct gene transfer into protoplasts, Paszkowski et al., EMBO J., 12:2717 (1984); Loerz et al., Mol. Gen. & Genet., 1199:178 (1985); Fromm et al., Nature 319:719 (1986); microprojectile bombardment, Klein et al., Bio/Technology, 6:559–563 (1988); injection into protoplasts, cultured cells and tissues, Reich et al., Bio/Technology, 4:1001–1004 (1986); or injection into meristematic tissues or seedlings and plants as described by De La Pena et al., Nature, 325:274–276 (1987); Graves et al., Plant Mol. Biol., 7:43–50 (1986); Hooykaas-Van Slogteren et al., Nature, 311:763–764 (1984); Grimsley et al., Bio/Technology, 6:185 (1988); and Grimsley et al., Nature, 325:177 (1988); and electroporation, WO92/09696.

The expression pattern of a structural gene operatively associated with an instant tissue-preferred or tissue-specific promoter in a transformed plant containing the same is critical in the case where the structural gene encodes an insecticidal protein. For example, the instantly disclosed pith-preferred expression pattern will allow the transgenic plant to tolerate and withstand pathogens and herbivores that attack primarily the pith, but also the brace roots, outer sheath and leaves of the plant since the protein will be expressed to a lesser extent but still in an insect controlling amount in these plant parts, but yet in the case of both types of promoters, will leave the seed of the plant unaffected.

EXAMPLES

The following examples further describe the materials and methods used in carrying out the invention. They are offered by way of illustration, and not by way of limitation.

Example 1

General Methods

DNA manipulations were done using procedures that are standard in the art. These procedures can often be modified and/or substituted without substantively changing the result. Except where other references are identified, most of these procedures are described in Sambrook et al., Molecular Cloning: A Laboratory Manual, Cold Spring Harbor Laboratory Press, second edition, 1989.

Synthesis of DNA Oligomers:

DNA oligomers which are from about twenty to about ninety, preferably from about sixty to about eighty nucleotides in length, are synthesized using an Applied Biosystems model 380B DNA synthesizer and standard procedures. The oligomers are made using the updated SSCAF3 cycle on a 0.2 μmole, wide pore, small scale ABI column. The end procedure is run trityl off and the oligomer is cleaved from the column using the 380B's automatic cleavage cycle. The oligomers are then deblocked in excess ammonium hydroxide ($NH_4OH$) at 55° C. for 8–12 hours. The oligomers are then dried in an evaporator using nitrogen gas. After completion, the oligomers are resuspended in 0.25–0.5 ml of deionized water.

Purification of Synthetic Oligomers:

An aliquot of each oligomer is mixed with an equal volume of blue dyeformamide mix with the final solution containing 0.05% bromophenol blue, 0.05% xylene cyanol FF, and 25% formamide. This mixture is heated at 95° C. for 10 minutes to denature the oligomers. Samples are then applied to a 12% polyacrylamide-urea gel containing 7 M urea (Sambrook et al.). After electrophoresis at 300–400 volts for 34 hours using a Vertical Slab Gel Unit (Hoefer Scientific Instruments, San Francisco, calif.), UV shadowing is used to locate the correct sized fragment in the gel which was then excised using a razor blade. The purified gel fragment is minced and incubated in 0.4 M LiCl, 1 mM EDTA (pH 8) buffer overnight at 37° C.

Either of two methods is used to separate the oligomers from the polyacrylamide gel remnants: Gene\X 25 μM porous polyethylene filter units or Millipore's ultrafree-MC 0.45 μM filter units. The purified oligomers are ethanol precipitated, recovered by centrifuging in a microfuge for 20 min at 4° C., and finally resuspended in TE (10 mM Tris, 1 mM EDTA, pH 8.0). Concentrations are adjusted to 50 ng\|H 251 based on absorption readings at 260 nm.

Kinasing Oligomers for Size Determinations:

To check the size of some of the oligomers on a sequencing gel, kinase labeling reactions are carried out using purified synthetic oligomers of each representative size: 40 mers, 60 mers, 70 mers, 80 mers, and 90 mers. In each 20 μl kinasing reaction, one pmole of purified oligomer is used in a buffer of 7.0 mM Tris pH 7.5, 10 mM KCl, 1 mM MgCl2), 0.5 mM DTT, 50 μg/ml BSA, 3000 μCi (3 pmoles) of 32P-gammaATP, and 8 units of T4 polynucleotide kinase. The kinase reaction is incubated for 1 hour at 37° C., followed by a phenol\chloroform extraction and three ethanol precipitations with glycogen as carrier (Tracy, Prep. Biochem. 11:251–268 (1981).

Two gel loadings (one containing 1000 cpm, the other containing 2000 cpm) of each reaction are prepared with 25% formamide, 0.05% bromophenol blue, and 0.05% xylene cyanol FF. The kinased oligomers are boiled for 5 minutes before loading on a 6% polyacrylamide, 7 M urea sequencing gel (BRL Gel Mix TM6, BRL, Gaithersburg, Md.). A sequencing reaction of plasmid pUC18 is run on the same gel to provide size markers. After electrophoresis, the gel is dried and exposed to diagnostic X-ray film (Kodak, X-OMAT AR). The resulting autoradiograph shows all purified oligomers tested to be of the correct size. Oligomers which had not been sized directly on the sequencing gel are run on a 6% polyacrylamide, 7 M urea gel (BRL Gel Mix TM6), using the sized oligomers as size markers. All oligomers are denatured first with 25% formamide at 100° C. for 5 minutes before loading on the gel. Ethidium bromide staining of the polyacrylamide gel allows all the oligomers to be visualized for size determination.

Hybridizing Oligomers for Direct Cloning:

Oligomers to be hybridized are pooled together (from 1 μg to 20 μg total DNA) and kinased at 37° C. for 1 hour in 1×Promega ligation buffer containing 30 mM Tris-HCl pH 7.8, 10 mM MgCl2, 10 mM DTT, and 1 mM dATP. One to 20 units of T4 polynucleotide kinase is used in the reaction, depending on the amount of total DNA present. The kinasing reactions are stopped by placing the reaction in a boiling water bath for five minutes. Oligomers to form the 5' termini of the hybridized molecules are not kinased but are added to the kinased oligomers along with additional hybridization buffer after heating. The pooled oligomers are in a volume of 50–100 ul with added hybridization buffer used to adjust the final salt conditions to 100 mM NaCl, 120 mM Tris pH 7.5, and 10 mM MgCl2. The kinased and non-kinased oligomers are pooled together and heated in a boiling water bath for five minutes and allowed to slowly cool to room temperature over a period of about four hours. The hybridized oligomers are then phenol\chloroform extracted, ethanol precipitated, and resuspended in 17 μl of TE (10 mM Tris, 1 mM EDTA, pH 8.0). Using this 17 μl, a ligation reaction with a final volume of 20 μl is assembled (final conditions=30 mM Tris-HCl pH 7.8, 10 mM MgCl2, 10 mM DTT, 1 mM ATP, and 3 units of T4 DNA ligase (Promega, Madison Wiss.). The ligation is allowed to incubate for about 2 hours at room temperature. The hybridized\ligated fragments are generally purified on 2% Nusieve gels before andor after cutting with restriction enzymes prior to cloning into vectors. A 20 μl volume ligation reaction is assembled using 100 ng to 500 ng of each fragment with approximate equimolar amounts of DNA in 30 mM Tris-HCl pH 7.8, 10 mM MgCl2, 10 mM DTT, 1 mM ATP, and 3 units of T4 DNA ligase (Promega, Madison, Wiss.). Ligations are incubated at room temperature for 2 hours. After ligation, DNA is transformed into frozen competent *E. coli* cells using standard procedures (Sambrook et al.) and transformants are selected on LB-agar (Sambrook et al.) containing 100 μg/ml ampicillin (see below).

PCR Reactions for Screening Clones in *E. coli*:

*E. coli* colonies which contain the correct DNA insert are identified using PCR (see generally, Sandhu et al., BioTechniques 7:689–690 (1989)). Using a toothpick, colonies are scraped from an overnight plate and added to a 20 μl to 45 μl PCR reaction mix containing about 50 pmoles of each hybridizing primer (see example using primers MK23A28 and MK25A28 to select orientation of SacII fragment in pHYB2#6), 200 μm to 400 mM of each dNTP, and 1×reaction buffer (Perkin Elmer Cetus, Norwalk, Conn.). After boiling the *E. coli*\PCR mix in a boiling water bath for 10 minutes, 5 μl of Taq polymerase (0.5 units)(Perkin Elmer Cetus, Norwalk, Conn.) in 1×reaction buffer is added. The PCR reaction parameters are generally set with a denaturing step of 94° C. for 30 seconds, annealing at 55° C. for 45 seconds, and extension at 72° C. for 45 seconds for 30 to 36 cycles. PCR reaction products are run on agarose or Nusieve agarose (FMC) gels to detect the correct fragment size amplified.

Ligations:

Restriction enzyme digested fragments are either purified in 1% LGT (low gelling temperature agarose, FMC), 2% Nusieve (FMC), or 0.75% agarose using techniques standard in the art. DNA bands are visualized with ethidium bromide and bands are recovered from gels by excision with a razor blade. Fragments isolated from LGT are ligated directly in the LGT. Ten microliters of each recovered DNA fragment is used to assemble the ligation reactions, producing final ligation reaction volumes of about 23 µl. After excision with a razor blade, the recovered gel bands containing the desired DNA fragments are melted and brought to 1×ligase buffer and 3 units of T4 DNA ligase (Promega) are added as described above. Fragments isolated from either regular agarose or Nusieve agarose are purified from the agarose using ultrafree-MC 0.45 µM filter units (Millipore) and the fragments are ligated as described above. Ligation reactions are incubated at room temperature for two hours before transforming into frozen competent $E.\ coli$ cells using standard procedures (Sambrook et al.).

Transformations:

Frozen competent $E.\ coli$ cells of the strain DH5alpha or HB101 are prepared and transformed using standard procedures (Sambrook et al.). $E.\ Coli$ "SURE" competent cells are obtained from Stratagene (La Jolla, Calif.). For ligations carried out in LGT agarose, after ligation reactions are complete, 50 mM CaCl2 is added to a final volume of about 150 µl and the solution heated at approximately 65° C. for about 10 minutes to completely melt the agarose. The solution is then mixed and chilled on ice for about 10 minutes before the addition of about 200 µl of competent cells which had been thawed on ice. This mixture is allowed to incubate for 30 minutes on ice. The mixture is next heat shocked at 42° C. for 60 seconds before chilling on ice for two minutes. Next, 800 µl of SOC media (20% tryptone, 0.5% yeast extract, 10 mM NaCl, 2.5 mM KCl, adjusted to pH 8 with 5 N NaOH, 20 mM MgCl2:MgSO4 mix, and 20 mM glucose; Sambrook et al.) is added and the cells are incubated at 37° C. with shaking for about one hour before plating on selective media plates. Plates typically are L-agar (Sambrook et al.) containing 100 µg/ml ampicillin.

When ligations are carried out in a solution without agarose, typically 200 µl of frozen competent $E.\ coli$ cells (strain DH5alpha (BRL, Gaithersburg, Md. or Sure cells, Stratagene, La Jolla, Calif.) are thawed on ice and 5 µl of the ligation mixture added. The reaction is incubated on ice for about 45 to 60 minutes, the cells are then heat shocked at 42° for about 90 seconds. After recovery at room temperature for about 10 minutes, 800 µl of SOC medium is added and the cells are then incubated 1 hour at 37° C. with shaking and plated as above.

When screening for inserts into the beta-galactosidase gene in some of the standard vectors used, 200 µl of the recovered transformation mixture is plated on LB-agar plates containing 0.008% X-gal, 80 µM IPTG, and 100 µg/ml ampicillin (Sambrook et al.). The plates are incubated at 37° overnight to allow selection and growth of transformants.

Miniscreening DNA:

Transformants from the selective media plates are grown and their plasmid structure is examined and confirmed using standard plasmid mini-screen procedures (Sambrook et al.). Typically, the "boiling" procedure is used to produce small amounts of plasmid DNA for analysis (Sambrook et al.). Alternatively, an ammonium acetate procedure is used in some cases. This procedure is a modification of that reported by Shing-yi Lee et al., Biotechniques 9:676–679 (1990).

1) Inoculate a single bacterial colony from the overnight selection plates into 5 ml (can be scaled down to 1 ml) of TB (Sambrook et al.) medium and grow in the presence of the appropriate antibiotic.

2) Incubate on a roller at 37° C. overnight.

3) Collect 5 ml of bacterial cells in a plastic Oakridge tube and spin for 5 min. at 5000 rpm in a Sorvall SS-34 rotor at 4° C.

4) Remove the supernatant.

5) Resuspend the pellet in 1 ml of lysis buffer (50 mM glucose, 25 mM Tris-HCl(pH 8.0), 10 mM EDTA and 5 mg/ml lysozyme), vortex for 5 seconds, and incubate at room temperature for 5 min.

6) Add 2 ml of freshly prepared alkaline solution (0.2 N NaOH, 1% sodium dodecyl sulfate), tightly secure lid, mix by inverting 5 times and place tube in an ice-water bath for 5 min.

7) Add 1.5 ml of ice-cold 7.5 M ammonium acetate (pH 7.6) to the solution, mix by inverting the tube gently 5 times and place on an ice-water bath for 5 min.

8) Centrifuge mixture at 9000 rpm for 10 min. at room temperature.

9) Transfer clear supernatant to a 15 ml Corex tube and add 0.6 volumes of isopropanol (approx. 2.5 ml). Let sit at room temperature for 10 min.

10) Centrifuge the mixture at 9000 rpm for 10 min. at room temperature and discard the supernatant.

11) Resuspend the pellet in 300 ul of TE buffer. Add 6 ul of a stock of RNase A & T1 (made as a 200 ul solution by adding 180 ul of RNase A (3254 Units/mg protein, 5.6 mg protein/ml) and 20 ul of RNase T1(481 Units/ug protein, 1.2 mg protein/ml)). These stocks may be purchased from USB(US Biochemical). Transfer to a microcentrifuge tube and incubate at 37° C. for 15 min.

12) Add 75 ul of distilled water and 100 ul of 7.5 M ammonium acetate and incubate in an ice-water bath for 10 min.

13) Centrifuge the mixture at 14,000 rpm for 10 min. in a Beckman microfuge at 4° C.

14) Precipitate by adding 2.5 volumes of 100% EtOH (approx. 1 ml) and incubate in an ice-water bath for 10 min.

15) Spin at 14,000 rpm for 10 min. in a microfuge.

16) Wash pellet with 70% ethanol (using 0.5 ml–1 ml). Dry the pellet and resuspend in 100 µl of 1×New England Biolabs restriction enzyme Buffer 4 (20 mM Tris-HCl(pH 7.9), 10 mM magnesium acetate, 50 mM potassium acetate, 1 mM DTT). Measure concentration and check purity by spectrophotometry at absorbances 260 and 280 nm.

For a more rapid determination as to whether or not a particular bacterial colony harbored a recombinant plasmid, a PCR miniscreen procedure is carried out using a modification of the method described by (Sandhu, G. S. et al., 1989, BioTechniques, 7:689–690). Briefly, the following mixture is prepared:

100 µl primer mix above, 20 µM each primer,

100 µl dNTP mix (2.5 mM each)

100 µl 10×AmpliTaq buffer (Perkin-Elmer Cetus, 1×buffer=10 mM Tris-HCl pH 8.3, 50 mM KCl, 1.5 mM MgCl2, and 0.01% gelatin)

700 µl deionized water.

20 µl of the above mixture is put into a a 0.5 ml polyproplyene PCR tube. A transformed bacterial colony is picked with a toothpick and resuspended in the mixture. The tube is put in a boiling water bath for 10 minutes and then cooled to room temperature before adding 5 μl of the mix described below:

265 μl deionized water

30 μl 10×Amplitaq buffer (Perkin-Elmer Cetus, 1×buffer=10 mM Tris-HCl pH 8.3, 50 mM KCl, 1.5 mM MgCl2, and 0.01% gelatin)

7.5 μl Taq polymerase

The samples are overlaid with 50 μl of mineral oil and PCR is carried out for 30 cycles using the following parameters:

denature: 94° for 1 min anneal: 55° for 1 min extend: 72° for 45 seconds.

After PCR amplification, 1 μl of loading dye (30% glycerol, 0.25% Bromophenol blue, 0.25% xylene cyanol) is added to the whole reaction and 20 μl of the mixture is loaded on a 2% Nusieve, 1% agarose gel to see if there is a PCR product of the expected size.

This procedure is used as an initial screen. Minipreps are subsequently carried out to confirm the structure of the plasmid and its insert prior to sequencing.

Example 2

AMPLIFICATION AND ASSEMBLY OF EACH QUARTER

Cloning fragments of the synthetic Bt cryIA(b) gene:

The synthetic gene was designed to be cloned in four pieces, each roughly one quarter of the gene. The oligomers for each quarter were pooled to either be assembled by PCR, hybridization, or a combination of hybridization followed by PCR amplification as described elsewhere. Synthetic quarters were pieced together with overlapping restriction sites Aat II, NcoI, and Apa I between the 1st and 2nd, 2nd and 3rd, and 3rd and 4th quarters respectively.

Each quarter of the gene (representing about 500 bp) was assembled by hybridizing the appropriate oligomers and amplifying the desired fragment using PCR primers specific for the ends of that quarter. Two different sets of PCR reactions employing two sets of slightly different primers were used. The PCR products of the two reactions were designed to be identical except that in the first reaction there was an additional AATT sequence at the 5' end of the coding region and in the second reaction there was an AGCT sequence at the 3' end of a given quarter. When the products of the two reactions for a particular quarter were mixed (after removing the polymerase, primers and incomplete products), denatured, and subsequently re-annealed, a certain ratio (theoretically 50%) of the annealed product should have non-homologous overhanging ends. These ends were designed to correspond to the "sticky ends" formed during restriction digestion with EcoRI at the 5' end and Hind III at the 3' end of the molecule. The resulting molecules were phosphorylated, ligated into an EcoRI/HindIII digested and phosphatased Bluescript vector, and transformed into frozen competent E. coli strain DH5alpha. After selection, the E. coli colonies containing the desired fragment are identified by restriction digest patterns of the DNA. Inserts representing parts of the synthetic gene are subsequently purified and sequenced using standard procedures. In all cases, clones from multiple PCR reactions are generated and sequenced. The quarters are then joined together using the unique restriction sites at the junctions to obtain the complete gene.

Cloned quarters are identified by mini-screen procedures and the gene fragment sequenced. It is found that errors are frequently introduced into the sequence, most probably during the PCR amplification steps. To correct such errors in clones that contain only a few such errors, hybridized oligomers are used. Hybridized fragments are digested at restriction enzyme recognition sites within the fragment and cloned to replace the mutated region in the synthetic gene. Hybridized fragments range from 90 bp in length (e.g. the region that replaces the fragment between the Sac II sites in the 2nd quarter) to the about 350 bp 4th quarter fragment that replaces two PCR induced mutations in the 4th quarter of the gene.

Due to the high error rate of PCR, a plasmid is designed and constructed which allows the selection of a cloned gene fragment that contains an open reading frame. This plasmid is designed in such a manner that if an open reading frame is introduced into the cloning sites, the transformed bacteria could grow in the presence of kanamycin. The construction of this vector is described in detail below. This selection system greatly expedites the progress by allowing one to rapidly identify clones with open reading frames without having to sequence a large number of independent clones. The synthetic quarters are assembled in various plasmids, including BSSK (Stratagene; La Jolla, Calif.), pUC18 (Sambrook et al.), and the Km-expression vector. Other suitable plasmids, including pUC based plasmids, are known in the art and may also be used. Complete sequencing of cloned fragments, western blot analysis of cloned gene products, and insect bioassays using European corn borer as the test insect verify that fully functional synthetic Bt cryIA(b) genes have been obtained.

Construction of the Km-expression vector to select open reading frames: The Km-expression vector is designed to select for fragments of the synthetic gene which contain open-reading frames. PCR oligomers are designed which allow the fusion of the NPTII gene from Tn5 starting at nucleotide 13 (Reiss et al., EMBO J. 3:3317–3322 (1984)) with pUC18 and introduce useful restriction sites between the DNA segments. The polylinker region contains restriction sites to allow cloning various synthetic Bt IP fragments in-frame with the Km gene. The 88 bp 5' oligomer containing the polylinker region is purified on a 6% polyacrylamide gel as described above for the oligomer PAGE purification. A PCR reaction is assembled with a 1 Kb Bgl II\Sma I template fragment which contains the NPT II gene derived from Tn5. The PCR reaction mix contains 100 ng of template with 100 pmols of oligomers KE72A28 and KE74A28 (see sequences below), 200 nM dNTP, and 2.5 Units of Taq polymerase all in a 50 μl volume with an equal volume of mineral oil overlaid. Sequences of the primers are:

KE74A28

5'-GCAGATCTGG ATCCATGCAC GCCGTGAAGG GCCCTTCTAG AAGGCCTATC GATAAAGAGC TCCCCGGGGA TGGATTGCAC GCAGGTTC-3' (SEQ ID NO: 29)

KE72A28

5'-GCGTTAACAT GTCGACTCAG AAGAACTCGT CAAGAAGGCG-3' (SEQ ID NO: 30)

The PCR parameters used are: 94° C. for 45 seconds (sec), 55° C. for 45 sec, and 72° C. for 55 sec with the extension at step 3 for 3 sec for 20 cycles. All PCR reactions are carried out in a Perkin-Elmer Cetus thermocycler. The amplified PCR product is 800 bp and contains the polylinker region with a translational start site followed by unique restriction sites fused in-frame with the Km gene from base #13 running through the translational terminator. pUC:KM74 is the Km-expression cassette that was assembled from the 800 bp Bgl II\Sal I polylinker/Km fragment cloned in the PUC18 vector. The lacZ promoter allows the Km gene to be expressed in E. coli. pUC:KM74 derivatives has to first be plated on LB-agar plates containing 100 µg/ml ampicillin to select transformants which can subsequently be screened on LB-agar plates containing 25 µg/ml kanamycin/IPTG. Synthetic Bt IP gene fragments are assembled from each quarter in the Km-cassette to verify cloning of open-reading-frame containing fragments pieces. The first ECB active synthetic Bt IP gene fragment, pBt:Km#6, is a Bt IP gene that shows Km resistance. This fragment is subsequently discovered to contain mutations in the 3rd and 4th quarter which are later repaired.

Example 2A

SYNTHESIS AND CLONING OF THE FIRST QUARTER OF THE SYNTHETIC GENE (base pairs 1 to 550)

The following procedures are followed in order to clone the first quarter of the synthetic DNA sequence encoding a synthetic Bt cryIA(b) gene. The same procedures are essentially followed for synthesis and cloning of the other quarters, except as noted for primers and restriction sites.

Template for Quarter 1: Mixture of equal amounts of purified oligomers U1–U7 and L1 to L7

PCR Primers:

Forward:

P1 (a): 5'-GTCGACAAGG ATCCAACAAT GG-3' (SEQ ID NO: 31)

P1 (b): 5'-AATTGTCGAC AAGGATCCAA CAATGG-3' (SEQ ID NO: 32)

Reverse:

P2 (a): 5'-ACACGCTGAC GTCGCGCAGC ACG-3' (SEQ ID NO: 33)

P2 (b): 5'-AGCTACACGC TGACGTCGCG CAG-3' (SEQ ID NO: 34)

Primer pair A1: P1(b)+P2(a)

Primer pair A2: P1(a)+P2(b)

The PCR reaction containing the oligomers comprising the first quarter of the synthetic maize-optimized Bt IP gene is set up as follows:

- 200 ng oligo mix (all oligos for the quarter mixed in equal amounts based on weight)
- 10 μl of primer mix (1:1 mix of each at 20 μM; primers are described above)
- 5 μl of 10×PCR buffer
- PCR buffer used may be either
- (a) 1×concentration=10 mM KCl, 10 mM (NH4)2SO4, 20 mM Tris-HCl, pH 8.0, 2 mM MgSO4, and 0.1% Triton X-100), or
- (b) 1×concentration=10 mM Tris-HCl pH 8.3, 50 mM KCl 1.5 mM MgCl2, 0.01% wt/vol gelatin.

Components are mixed, heated in a boiling water bath for 5 minutes, and incubated at 65° C. for 10 minutes.

Next, the following reagents are added:

- 8 μl of dNTPs mixture (final concentration in the reaction=0.2 mM each)
- 5 units polymerase.

The Final Reaction Volume is 50 Microliters.

Oligomers are then incubated for 3 min at 72° C. and then a PCR cycle is run. The PCR reaction is run in a Perkin Elmer thermocycler on a step cycle protocol as follows:

- denaturation cycle: 94° for 1 minute
- annealing cycle: 60° for 1 minute
- extension cycle: 72° for 45 seconds (+3 sec per cycle)
- number of cycles: 15

After the reaction is complete, 10 μl of the PCR reaction is loaded on a 2% Nusieve-GTG (FMC), 1% agarose analytical gel to monitor the reaction. The remaining 40 μl is used to clone the gene fragments as described below.

PCR Products

The termini of the double stranded PCR product corresponding to the various primer pairs are shown (only upper strand):

```
A1 AATTGTCGAC(SEQ ID NO:35)________________GCGTGT   (554 bp) first qtr.
A2  GTCGAC__________________GCGTGTAGCT(SEQ ID NO:36)(554 bp) first qtr.
```

Hybridization

40 μl of each of the PCR reactions described above is purified using a chromaspin 400 column (Clonetech, Palo Alto, Calif.) according to manufacturers directions. Five μg of carrier DNA was added to the reactions before loading on the column. (This is done for most of the cloning. However, in some reactions the PCR reactions are phenol:chloroform extracted using standard procedures (Sambrook et al.) to remove the Taq polymerase and the PCR generated DNA is recovered from the aqueous phase using a standard ethanol precipitation procedure.) The carrier DNA does not elute with the PCR generated fragments. The A1 and A2 reaction counterparts for each quarter are mixed, heated in a boiling water bath for 10 minutes and then incubated at 65° C. overnight. The reactions are then removed from the 65° bath and ethanol precipitated with 1 μl (20 μg) of nuclease free glycogen (Tracy, Prep. Biochem. 11:251–268 (1981) as carrier. The pellet is resuspended in 40 μl of deionized water.

Phosphorylation Reaction

The phosphorylation reaction is carried out as follows:

- 40 μl DNA
- 2.5 μl 20 mM ATP
- 0.5 μl 10×BSA/DTT (1×=5 mM DTT, 0.5 mg/ml BSA)
- 1.0 μl 10×polynucleotide kinase buffer (1×=70 mM Tris.HCl,
- pH 7.6, 0.1 M KCl, 10 mM $MgCl_2$)
- 2.0 μl polynucleotide kinase (New England Biolabs, 20 units).

Incubation is for 2 hours at 37° C.

The reaction is then extracted one time with a 1:1 phenol:chloroform mixture, then once with chloroform and the aqueous phase ethanol precipitated using standard procedures. The pellet is resuspended in 10 μl of TE.

Restriction Digests

- 20 μg of Bluescript vector (BSSK+, Stratagene, La Jolla, Calif.)
- 10 μl 10×restriction buffer (1×=20 mM Tris-HCl pH 8.0, 10 mM MgCl2, 100 mM NaCl)
- 5 μl Eco RI (New England Biolabs) 100 units
- 5 μl Hind III (New England Biolabs) 100 units Final reaction volume is 100 μl.

Incubation is for 3 hours at 37°.

When completed, the reaction is extracted with an equal volume of phenol saturated with TE (10 mM Tris.HCl pH 8.0 and 10 mM EDTA). After centrifugation, the aqueous phase was extracted with an equal volume of 1:1 mixture of (TE saturated) phenol:chloroform (the "chloroform" is mixed in a ratio of 24:1 chloroform:isoamyl alcohol), and finally the aqueous phase from this extraction is extracted with an equal volume of chloroform. The final aqueous phase is ethanol precipitated (by adding 10 µl of 3 M sodium acetate and 250 ||l of absolute ethanol, left at 4° for 10 min and centrifuged in a microfuge at maximum speed for 10 minutes. The pellet is rinsed in 70% ethanol and dried at room temperature for 5–10 minutes and resuspended in 100 µl of 10 mM Tris.HCl (pH 8.3).

Phosphatase Reaction

Vector DNA is routinely treated with phosphatase to reduce the number of colonies obtained without an insert. Calf intestinal alkaline phosphatase is typically used (Sambrook et al.), but other phosphatase enzymes can also be used for this step.

Typical phosphatase reactions are set up as below:

90 µl of digested DNA described above

10 µl of 10×Calf intestinal alkaline phosphatase buffer (1×=50 mM Tris-HCl (pH 8.3), 10 mM MgCl2, 1 mM ZnCl2, 10 mM spermidine)

1 µl (1 unit) of calf intestinal alkaline phosphatase (CIP, Boehringer Mannheim, Indianapolis, Ind.)

Incubation is at 37° C. for 1 hour.

The DNA is then gel purified (on a 1% low gelling temperature (LGT) agarose gel) and the pellet resuspended in 50 µl TE. After electrophoresis, the appropriate band is excised from the gel using a razor blade, melted at 65° for 5 minutes and diluted 1:1 with TE. This solution is extracted twice with phenol, once with the above phenol:chloroform mixture, and once with chloroform. The final aqueous phase is ethanol precipitated and resuspended in TE buffer.

Ligation:

To ligate fragments of the synthetic gene into vectors, the following conditions are typically used.

5 µl of phosphorylated insert DNA

2 µl of phosphatased Eco RI/Hind III digested Bluescript vector heated at 65° for 5 minutes, then cooled 1 µl 10×ligase buffer (1×buffer=30 mM Tris.HCl (pH 7.8), 10 mM MgCl2, 10 mM DTT, 1 mM ATP)

1 µl BSA (1 mg/ml)

1 µl ligase (3 units, Promega, Madison, Wis.)

Ligase reactions are typically incubated at 16° overnight or at room temperature for two hours.

Transformation:

Transformation of ligated DNA fragments into E. coli is performed using standard procedures (Sambrook et al.) as described above.

Identification of recombinants

White or light blue colonies resulting from overnight incubation of transformation plates are selected. Plasmids in the transformants are characterized using standard mini-screen procedures (Sambrook et al.) or as described above. One of the three procedures listed below are typically employed:

(1) boiling DNA miniprep method
(2) PCR miniscreen
(3) Ammonium acetate miniprep.

The restriction digest of recombinant plasmids believed to contain the first quarter is set up as follows:

(a) Bam HI/Aat II digest: 10 µl DNA+10 µl 1×New England Biolabs restriction enzyme Buffer 4

0.5 µl Bam HI (10 units)

0.5 µl Aat II (5 units)

Incubation is for about 2 hours at 37° C.

Clones identified as having the desired restriction pattern are next digested with Pvu II and with Bgl II in separate reactions. Only clones with the desired restriction patterns with all three enzyme digestions are carried further for sequencing.

Sequencing of cloned gene fragments:

Sequencing is performed using a modification of Sanger's dideoxy chain termination method (Sambrook et al.) using double stranded DNA with the Sequenase 2 kit (United States Biochemical Corp., Cleveland, Ohio). In all, six first quarter clones are sequenced. Of the clones sequenced, only two clones designated pQA1 and pQA5 are found to contain only one deletion each. These deletions are of one base pair each located at position 452 in pQA1 and position 297 in pQA5.

Plasmid pQA1 is used with pP1–8 (as described below) to obtain a first quarter with the expected sequence.

Example 2B

SYNTHESIS AND CLONING OF THE SECOND QUARTER (base pairs 531 to 1050)

Template: oligomers U8–U14 and L8–L14

PCR Primers:

forward:

P3 (a): 5'-GCTGCGCGAC GTCAGCGTGT TCGG-3' (SEQ ID NO: 37)

P3 (b): 5'-AATTGCTGCG CGACGTCAGC GTG-3' (SEQ ID NO: 38)

Reverse:

P4 (a): 5'-GGCGTTGCCC ATGGTGCCGT ACAGG-3' (SEQ ID NO: 39)

P4 (b): 5'-AGCTGGCGT TGCCCATGGT GCCG-3' (SEQ ID NO: 40)

Primer pair B1: P3(b)+P4(a)

Primer pair B2: P3(a)+P4(b)

PCR Products

B1 AATTGCTGCG(SEQ ID NO:41)_____AACGCC   (524 bp) second quarter

B2  GCTGCG_____AACGCCAGCT(SEQ ID NO:42)(524 bp)

Hybridization, PCR amplification, spin column size fractionation, and cloning of this gene fragment in Bluescript digested with Eco RI/Hind III are performed as described above for the first quarter (Example 2A). The PCR product for this quarter is about 529 bp in size representing the second quarter of the gene (nucleotides 531 to 1050). Transformation is into frozen competent E. coli cells (DH5alpha) using standard procedures described above (Sambrook et al.)

Miniscreen of pQB clones:

Miniprep DNA is prepared as described above and digested with (a) Aat II/Nco I, (b) Pvu II and (c) with Bgl I to confirm the structure insert in the vector before sequencing.

Sequencing is performed as described above using the dideoxy method of Sanger (Sambrook et al.).

A total of thirteen clones for this quarter are sequenced. The second quarter consistently contains one or more deletions between position 884 and 887. In most cases the G at position 884 is deleted.

Plasmid pQB5 had only one deletion at position 884. This region lies between two Sac II sites (positions 859 and 949). Correction of this deletion is described in Example 3.
Clones of the first half (1–1050 bp).

A fragment for cloning the first half (quarters 1 and 2) of the synthetic Bt maize gene as a single DNA fragment is obtained by restriction digestion of the product of a PCR reaction comprising the first quarter and the second quarter. Restriction endonuclease Aat II is used to cut the DNA (following phenol extraction and ethanol precipitation) in a 20 μl reaction. 15 μl of each of the Aat II digested quarters is mixed and ligated (in a 50 μl volume by adding 5 μl of 10×ligase buffer, (1×=30 mM Tris-HCl pH 7.8, 10 mM MgCl2, 10 mM DTT, 1 mM ATP) 14 μl of deionized water and 1 μl of T4 DNA ligase, 3 units, Promega, Madison, Wis.) at room temperature for 2 hr. The result is an about 1 kb fragment as judged by electrophoresis on a 1% agarose gel run using standard conditions (Sambrook et al.) Ten μl of the ligation product is amplified by PCR using conditions described previously except that only 5 cycles were run.

Primer Pair: HA=P1(a)+P4(b)

Primer Pair: HB=P1(b)+P4(a)

The product of these reactions is cloned into Bluescript (Stratagene, La Jolla, Calif.) as described for the individual quarters. This procedure is only done once i.e., all insert DNA is obtained in a particular region from a single PCR reaction.

Thirty-six colonies are miniscreened with Sal I digests and Pvu II digests. All except 4 contain an insert of approximately 1 kb in size of which at least 20 contain the correct Pvu II digestion pattern. Eight of these clones are selected for sequence analysis. One of the clones, P1–8, has the desired sequence between the Eco NI site (396 bp) and the Dra III site (640 bp). This clone is used to obtain a plasmid with the desired sequence up to the Dra III site (640 bp) in the second quarter with pQA1 (first quarter with a deletion at position 452 bp described previously.)

Example 2C

CLONING AND SYNTHESIS OF THIRD QUARTER (base pairs 1021 to 1500)

Template: Oligos U15–U20 and L15–L21

PCR primers:

forward

P5 (a): 5'-TTCCCCCTGT ACGGCACCAT GGGCAACGCC GC-3' (SEQ ID NO: 43)

P5 (b): 5'-AATTGTACGG CACCATGGGC AAC-3' (SEQ ID NO: 44)

reverse

P6 (a): 5'-GAAGCCGGGG CCCTTCACCA CGCTGG-3' (SEQ ID NO: 45)

P6 (b): 5'-AGCTGAAGCC GGGGCCCTTC ACC-3' (SEQ ID NO: 46)

Primer pair C1: P5(b)+P6(a)

Primer pair C2: P5(a)+P6(b)

PCR Product:

PCR reactions, spin column recovery of the correct sized DNA fragment, and ligation into vectors are performed as described above (Example 2A) using a Bluescript vector cut with Eco RI and Hind III. The approximately 479 base pair PCR product represents the third quarter of the synthetic gene (NT 1021–1500).

Transformation into frozen competent *E. coli* strain DH5alpha cells, selection and identification of transformants, characterization of transformants by mini-screen procedures, and sequencing of the synthetic gene fragment in the vector are all as described above.

Mini screen of pQC clones:

The third quarter is miniscreened using standard procedures (Sambrook et al.). Miniprep DNA is cut with (a) Nco I/Apa I and (b) with Pvu II. Clones containing the correct restriction digest patterns are sequenced using standard procedures. A total of 22 clones of the third quarter are sequenced. Three major deletion "hotspots" in the third quarter are identified (a) at position 1083 (b) between position 1290–1397 and (c) between positions 1356–1362. In all clones except one, pQC8, there is also consistently an insertion of a C at position 1365. In addition to these mutations, the third quarter clones contain a large number of other apparently random deletions. The common factor to the three mutational "hotspots" in the third quarter and the one in the second quarter is that these regions are all flanked on either side by sequences that are about 80% C+G. Other regions containing 5 to 9 C–Gs in a row are not affected. The oligomers in U15, U16, U18, U19, L15, L16, L18 and L19 are redesigned to reduce the C+G content in these regions. Five clones each from PCR reaction using the modified oligomers are sequenced.

Plasmid pQCN103 has the correct sequence for the third quarter except for a change at position 1326. This change, which substitutes a G for a C, results in the substitution of one amino acid (leucine) for the original (phenylalanine).

Example 2D

SYNTHESIS AND CLONING OF FOURTH QUARTER (base pairs 1480 to 1960)

The fourth quarter of the gene is obtained from a clone which is originally designed to comprise the third and fourth quarters of the gene. The "second half" of the synthetic gene is obtained from PCR reactions to fuse the third and fourth quarters. These reactions are run with PCR primers P5(a) and P6(a) described above for the third quarter and primers P7(a) and P8(a) (described below). The reverse primer is modified to include a Sac I site and a termination codon. Separate reactions for each quarter are run for 30 cycles using the conditions described above. The two quarters are joined together by overlapping PCR and subsequently digested with restriction enzymes Nco I and Sac I. The resulting 953 bp fragment is cloned directionally into pCIB3054, which has been cut with Nco I/Sac I and treated with alkaline phosphatase.

pCIB3054 is constructed by inserting intron #9 of PEP-carboxylase (PEPC ivs #9) in the unique Hpa I site of pCIB246 (described in detail in Example 4) pCIB246 is cut with HpaI and phosphatased with CIP using standard procedures described in Example 2A. PEPC ivs #9 is obtained

```
C1  AATTGTACGG(SEQ ID NO:47)__________GGCTTC  (475 bp) 3d qtr

C2 TTCCCCTGTACGG(SEQ ID NO:48)__________GGCTTCAGCT(SEQ ID NO:49)(484 bp) 3d qtr
```

65 by PCR using pPEP-10 as the template. pPEP-10 is a genomic subclone containing the entire maize PEP carboxylase gene encoding the $C_4$ photosynthetic enzyme, plus about 2.2 Kb of 5'-flanking and 1.8 Kb of 3'-flanking DNA. The 10 Kb DNA is ligated in the HindIII site of pUC18. (Hudspeth et al., Plant Molecular Biology, 12: 576–589 (1989). The forward PCR primer used to obtain the PEP-Civs#9 is GTACAAAAACCAGCAACTC (SEQ ID NO: 50) and the reverse primer is CTGCACAAAGTGGAG-TAGT (SEQ ID NO: 51). The PCR product is a 108 bp fragment containing only the PEPcarboxylase intron #9 sequences. The PCR reaction is extracted with phenol and chloroform, ethanol precipitated phosphorylated with polynucleotide kinase and treated with T4 polymerase to fill in the 3' nontemplated base addition found in PCR products (Clark, J. M., Nucleic Acid Research, 16: 9677–9686 (1988)) using standard procedures.

The kinased fragment is blunt-end cloned into the HpaI site of pCIB246, using standard
procedures described earlier.
Amplification and Assembly of the Fourth Quarter
Template: U21 –U26 and L22–L28
PCR primers
FORWARD
P7 (a): 5'-TGGTGAAGGG CCCCGGCTTC ACCGG-3' (SEQ ID NO: 52)
REVERSE
P8 (a): 5'-ATCATCGATG AGCTCCTACA CCTGATCGAT GTGGTA-3' (SEQ ID NO: 53)
PRIMER PAIR 4: P7(a)+P8(a)
PRIMER PAIR 3: P5(A)+P6(a)
Primer pair for overlapping PCR: P7(a)+P8(a)
PCR Product

```
                                               (SEQ ID NO:54)
fourth quarter:GGTGAA_____ATCAGGAGCTCATCGATGAT
```

(484 bp) third quarter: TTCCCCCTGTA (SEQ ID NO: 55)--------------TTCACCGG
(484 bp) second half: GGTGAA-------CATGATGAT (953 bp)

Four positive clones are identified by plasmid miniscreen and are subsequently sequenced using standard procedures.

Plasmid Bt.P2 #1 contains approximately the correct fourth quarter sequence except for two mutations. These mutations are at position 1523 (substituting an A for a G, resulting in an amino acid change which substitutes a His for an Arg) and at position 1634 (substituting a T for a C, resulting in an amino acid substitution of a Ser for a Thr).

Plasmid Bt.P2 #1 is used in the construction of pCIB4414 described below. (The mistakes are ultimately corrected by hybridizing all the oligos of the fourth quarter, digesting with Apa I/Bst E II and replacing that region in pCIB4414. Therefore, only sequences from position 1842–1960 remain of Bt.P2#1 in the final construct.)

Example 3

ASSEMBLY AND REPAIR OF THE FINAL SYNTHETIC GENE

The synthetic maize optimized Bt cryIA(b) gene is designed to be cloned in quarters. Using the PCR technique, however, results in mutations, which in most cases are deletions resulting in frameshift mutations. Plasmids containing individual quarters are therefore sequenced and the correct parts ligated together using standard procedures.

After obtaining first and second quarter clones with almost the desired sequence, plasmids pEB 1Q#4 and pEB 1Q#5 are constructed to obtain the desired sequence of the synthetic Bt gene up to the Dra III site at the base pair position 634 (this mutation destroys the Dra III site). The pEB1Q constructs are made by ligating a 3.9 Kb Eco NI\Bam HI fragment from pP1–8 with a 400 bp fragment from pQA1. pEB 1Q#5 has the desired sequence up to the Dra III site, but pEB 1Q#4 has a mutation at base pair position 378.

Plasmids p1H1M4 and p1H1M5 are constructed to repair the Dra III site in pEB1Q#4 and pEB1Q#5. Plasmids p1H1M#4 and #5 are made by ligating a 3.5 Kb Nco I\Aat II fragment from pEB1Q#4 and #5 respectively, with a 500 bp Nco I\Aat II fragment from pQB5. Plasmid p1H1M5 contains a mutation between the Sac II sites at position 884 in the second quarter of the synthetic Bt gene. Plasmid p1H1M4 contains the additional mutation as described in its precursor construct pEB1Q#4.

The Sac II site in the Bluescript vector region of p1H1M4 is deleted by cutting p1H1M4 with Not I and Sac I and converting these sites to blunt ends using T4 DNA polymerase under standard conditions before ligating this 3.9 Kb fragment to make p1H1M4^S. Deleting the Sac II site in the vector region allows the 90 bp Sac II fragment with the mutation at position 884 in the 2nd quarter of p1H1M4^S to be removed prior to replacement with a 90 bp Sac II fragment. Oligomers U\L 12 and 13 are kinased and hybridized (described above) before cutting with Sac II and isolating a 90 bp fragment on a 2% Nusieve gel. The Sac II fragment is ligated into the about 3.8 Kb Sac II cut p1H1M4^S vector which has been phosphatased with CIP. The repaired Sac II construct is called pHYB2#6. The orientation of the Sac II fragment in pHYB2#6 is detected by PCR screening as described earlier using the following primers:

MK23A28=5'-GGGGCTGCGGATGCTGCCCT-3' (SEQ ID NO: 56)

MK25A28=5'-GAGCTGACCCTGACCGTGCT-3' (SEQ ID NO: 57)

MK26A28=5'-CACCTGATGGACATCCTGAA-3' (SEQ ID NO: 58)

Running the PCR reactions with 50 pmoles of primers MK23A28 and MK25A28 produces an approximate 180 bp fragment, indicating the inserted fragment bounded by the Sac II sites in pHYB2#6 is in the correct orientation. Using primers MK25A28 and MK26A28 in the PCR screening acts as the negative control producing an approximate 180 bp fragment only in constructs containing the Sac II bounded fragment in the wrong orientation. pHYB2#6 sequence is determined using standard procedures.

pHYB2#6 has one mutation at position 378 which needed to be repaired to obtain a first quarter containing the desired sequence.

Plasmid p1HG#6 contains the desired sequence for the entire first half of the synthetic Bt gene. p1HG#6 is made from a 3.4 Kb Aat II\Nco I fragment of p1H1M5#2 ligated to a 500 bp Aat II\Nco I fragment from pHYB2#6.

To identify clones or partial clones of the synthetic gene which contain open reading frames, the kanamycin selection vector (described above) is used. The fourth quarter of the synthetic Bt gene is the first put into the kanamycin cassette. pKM74-4 contains the approximately 500 bp Apa I\Cla I fragment from plasmid BtP2 (which had been previously transformed into a dam- *E. coli* strain (PO-100) to be able to cut with Cla I), ligated to pUC:KM74 cut with Apa I\Cla I. Plasmid pKM74-4 displays kanamycin resistance but is later found to contain two substitution mutations at positions 1523 and 1634 (mutations are described above in the section on cloning the fourth quarter; they are substitutions, not deletions or insertions). The correct first half of the synthetic Bt gene from plasmid p1HG#6 is inserted into plasmid pKM74–4. The resulting plasmid, called pKm124, is made from the about 3.9 Kb Apa I\Bam HI fragment derived from pKM74–4 ligated to 1 Kb Apa I\Bam HI fragment from p1HG#6. pKm124 shows kanamycin resistance. This plasmid contains the first, second, and fourth quarters of the synthetic gene forming a single open reading frame.

The third quarter of the synthetic gene is next cloned into pKM124. The first functional clone, in plasmid pBt:Km#6, is a functional copy of the truncated synthetic cryIA(b) gene in the Km-cassette which displays kanamycin resistance but which contains deletion mutations between the third and fourth quarters. Plasmid pBt:Km#6 is made from the approximately 5 Kb Apa I\Nco I pKM124 vector fragment ligated to the approximately 500 bp Apa I\Nco I fragment from pQCN103 (pQCN103 contains a mismatch mutation at position 1326 which is repaired later). Contaminating nuclease activity appears to have deleted the Apa I site between the third and fourth quarters in pBt:Km#6. The Bt gene encoded by the synthetic gene in plasmid pBT:Km#6 has about 50–60% of the native proteins' activity against ECB. The 2 Kb Sma I\Bam HI fragment from pBt:Km#6 is inserted into a 35S:expression cassette to make a plasmid called 35S:Bt6.

Two functional synthetic Bt clones, each with mutations, are initially obtained: plasmids pBT:KM#6 and pCIB4414. pCIB4414, which is 100% active in insect bioassays against European corn borer compared with the native gene, contains substitution mutations in the third and fourth quarters at positions 1323, 1523, and 1634.

pCIB4414 is constructed from two plasmids, MG3.G4#18 and 1HG which is described above. MG3.G4#18 is obtained by cloning the Apa I/Kpn I fragment in plasmid Bt.P2#1 into pQCN103 (using those same restriction sites). This produces a plasmid containing the third and fourth quarters of the gene. The first half of the synthetic gene from plasmid 1HG is cut with Bam HI and Nco I and moved into MG3.G4#18 (containing the third and fourth quarters of the gene). The resulting plasmid, pCIB4414, contains a functional version of the synthetic gene. While being functional, the synthetic gene in this plasmid contains three errors; position 1326 (G substituted for a C), position 1523 (substitute A for a G), and at position 1634 (substitution of a T for a C).

The fourth quarter in pCIB4414 is replaced with a 354 bp fourth quarter Apa I\Bst E II fragment obtained from hybridizing, ligating, and restriction cleaving fourth quarter oligomers as described earlier, and isolating the fragment from a 2% Nusieve agarose gel. pCIB4408 is a synthetic Bt gene clone obtained by replacing the fourth quarter fragment in pCIB4414 with the hybridized fourth quarter fragment. To insert the CaMV 35S promoter in front of the synthetic Bt gene, pCIB4406 is made from a 4 Kb Eco N\Kpn I fragment from plasmid p35SBt6 and 1.8 Kb Eco N\Kpn I fragment from pCIB4408.

pCIB4406 is 100% active (as compared with the protein from the native gene) against ECB but contains the substitution mutation in the third quarter of the synthetic gene at position 1323 resulting in an amino acid substitution of a leucine for a phenylalanine. Plasmid pBS 123#13 is used to repair this mutation.

The third quarter fragment in plasmid pBS 123#13 is made from an approximately 479 bp hybridized oligomer generated fragment. Third quarter oligomers U15–U20 and L15–L21 are kinased, hybridized, and ligated as described above. PCR reactions are carried out as described above with primers P5(a) and P6(b) for 15 cycles. The PCR product is treated with proteinase K at a final concentration of about 50 $\mu$g\ml in an approximate 95 $\mu$l volume for 30 minutes at 37° C. followed by 10 minutes at 65° C. (Crowe et al., Nucleic Acid Research 19:184, 1991.) Subsequently, the product is phenol\chloroform extracted and ethanol precipitated using standard procedures before cutting with restriction enzymes Apa I and Nco I.

The approximate 450 bp Apa I\Nco I PCR fragment is ligated to the 3.8 Kb Apa I\Nco I vector fragment from p1HG#6 to make pBS123#13. Plasmid pBS123#13 contains the desired sequence for the third quarter of the maize optimized cryIA(b) gene from position 1319 at the Nsp I site through the Apa I site at position 1493. This 170 bp Nsp I\Apa I fragment from pBS 123#13 is used in the fully active synthetic cryIA(b) gene in plasmid pCIB4418.

Western Blot Analysis:

Western blot analyses of various transformants are performed using crude extracts obtained from *E. coli* grown on selective plates. Using a toothpick, cultures are scraped from fresh plates containing the transformants of interest which have been grown overnight at 37° C. The positive control for expression of the Bt gene in *E. coli* was a construct called pCIB3069 which contains the native Bt-k gene fused with the plant expressible CaMV 35S promoter. pCIB3069 also contains the 35S promoter operably linked to the hygromycin resistance gene, 35S promoter, with Adh intron #1 operably linked to the GUS gene, and 35S promoter operably linked to a gene coding for the production of the native Bt cryIA(b) IP. A negative control of *E. coli* which does not contain a Bt gene is also included in the analyses. Cultures are resuspended in 100 $\mu$l of loading buffer containing 62 mM Tris-HCl pH 6.8, 1% SDS, 0.0025% bromophenol blue, 10% glycerol and 7.5% mercaptoethanol. After heating the mixtures at 95° C. for 10 minutes, the preparations are sonicated for 1–3 seconds. The debris is centrifuged in a microfuge at room temperature for about 5 minutes and 10 to 15 $\mu$l of each sample is loaded onto an acrylamide gel with a 10% running gel below a 6% stacking gel (Laemmli, Nature 227;680–685(1970)). After electrophoresis overnight at 10 mAmps, proteins are transferred from the gel to an Immobilon membrane (Millipore). The transfer is done using an electrophoretic Blotting Unit (American BioNuclear, Emeryville, Calif.) in transfer buffer (20 mM Tris, 150 mM glycine, and 20% methanol) for 1.5 hours at 450 mAmps.

Buffers for western blotting included:

| | |
|---|---|
| Blocking buffer: | 2% Tween-20 |
| | 30 mM Tris-HCl pH 10.2 |
| | 150 nM NaCl |
| Wash buffer: | 0.05% Tween-20 |
| | 30 mM Tris-HCl pH 10.2 |
| | 150 mM NaCl |
| Developing buffer: | 100 mM Tris-HCl pH 9.6 |
| | 100 mM NaCl |
| | 10 mM MgCl2 |

After transfer is complete, the membrane is incubated for about ten minutes in the blocking buffer. Three 15 minute washes with wash buffer are done before the first antibody treatment. The first antibody is an immunoaffinity purified rabbit or goat antibody prepared using the CryIA(b) protein as the antigen (Ciba-Geigy, RTP, N.C.; Rockland Inc., Gilbertsville, Pa.; and Berkeley Antibody CO., Richmond, Calif.). The cryIA(b) specific antibody is treated immediately before use with *E. coli* lysate from Bio-Rad in a 1 ml volume with 5 $\mu$g of antibody, 50 $\mu$l of *E. coli* lysate in the wash buffer solution. This mixture is incubated for 1 hour at room temperature before diluting it 1 to 30 for a final dilution of 1:6000 with wash buffer. Incubation of the membrane with the first antibody is at room temperature for 1.5 hours.

Three 10 minute washes are done between the 1st and 2nd antibody treatments. The second antibody is either rabbit anti-goat or goat anti-rabbit/alkaline phosphatase conjugate (Sigma, St. Louis, Mo.). Incubation with the alkaline phosphatase conjugate is carried out at room temperature for one hour using a 1 to 6000 dilution in wash buffer. Six 10 minute washes are done between the second antibody treatment and developing the western blot. The western blot is developed in 100 ml of developing buffer with 440 μl of nitroblue tetrazolium in 70% dimethyl formamide (75 mg\ml), and 330 μl of 5-bromo-4-chloro-indolyl-phosphate in 100% dimethyl formamide (50 mg\ml). After developing for 15 to 30 minutes, the membrane is washed in water and air dried.

Example 4
CONSTRUCTION OF TRANSFORMATION VECTORS
Construction of pCIB710 and derivatives.

CaMV 35S Promoter Cassette Plasmids pCIB709 and pCIB710 are constructed as shown in Rothstein et al., Gene 53:153–161 (1987). pCIB710 contains CaMV promoter and transcription termination sequences for the 35S RNA transcript (Covey et al., Nucl. Acids. Res., 9:6735–6747 (1981)). A 1149 bp BglII restriction fragment of CaMV DNA (bp 6494–7643 in Hohn et al., Current Topics in Microbiology and Immunology, 96:194–220 and Appendices A to G (1982)) is isolated from CaMV DNA by preparative agarose gel electrophoresis as described earlier The fragment is mixed with BamHI-cleaved plasmid pUC19 DNA, treated with T4 DNA ligase, and transformed into E. coli. (Note the BamHI restriction site in the resulting plasmid is destroyed by ligation of the BglII cohesive ends to the BamHI cohesive ends.)

The resulting plasmid, called pUC19/35S, is then used in oligonucleotide-directed in-vitro mutagenesis to insert the BamHI recognition sequence GGATCC immediately following CaMV nucleotide 7483 in the Hohn reference. The resulting plasmid, pCIB710, contains the CaMV 35S promoter region and transcription termination region separated by a BamHI restriction site. DNA sequences inserted into this BamHI site will be expressed in plants by these CaMV transcription regulation sequences. (Also note that pCIB710 does not contain any ATG translation initiation codons between the start of transcription and the BamHI site). pCIB710 is modified to produce pCIB709 by inserting a Bam HI fragment containing the coding sequence for hygromycin phosphotransferase from pLG90 (Rothstein et al., Gene, 53:153–161 (1987)) in the Bam HI site.

pCIB709 is modified to produce pCIB996 by removing the ATG just upstream from the initiation codon of the hygromycin phosphotranserase gene using standard mutagenesis techniques while inserting a Bgl II restriction site at this location. The resulting plasmid, pCIB996, is further modified to remove the Bam HI, Sma I and Bgl II sites in the 5' untranslated leader region located 5' of the initiation codon for the initiation codon. The result is a change of DNA base sequence from -TATAAGGATC CCGGGGGCA AGATCTGAGA TATG (SEQ ID NO: 59)-Hyg to -TATAAGGATC TGAGATATG (SEQ ID NO: 59 with nucleotides 11–24 deleted)-Hyg. The resulting plasmid is known as pCIB3073.

Alternatively, pCIB710 is modified to produce pCIB900, by inserting the Bam HI—Bcl I fragment of pCIB 10/35SBt, which contains the 645 amino acid Bt coding sequence, described in Part C4 below, into the Bam HI site of pCIB710 to create pCIB710/35SBt. To introduce an antibiotic resistance marker, pCIB709 is cut with Sal I, a Kpn I/Sal I adaptor is ligated and the resulting ligation product is cut with Kpn I. The Kpn fragment of pCIB709 containing the 35S/hygromycin resistance gene is inserted into the Kpn I site of pCIB710/35SBt to produce pCIB900.

Genes useful as the selectable marker gene include the hygromycin resistance gene described in Rothstein et al., Gene 53: 153–161 (1987). The hygromycin gene described in this reference is moved into a pUC plasmid such as pCIB710 or pCIB709 and the "extra" ATG upstream from the hygromycin phosphotransferase coding sequence is removed to create pCIB996. This modified pCIB996 gene is further modified to remove a BglII, BamfHI and SmaI sites from the 5' region of the gene using standard techniques of molecular biology to make pCIB3073.

pCIB932 is a pUC19-based plasmid containing the chimeric gene Pep-C:promoter\Bt\Pep-C:terminator. It is composed of fragments derived from pPEP-10, a HindIII subclone of a genomic clone, H1-lambda-14, PNAS USA, 83:2884–2888 (1986), of the maize gene encoding the PEP carboxylase enzyme active in photosynthesis, and from pCIB930, which is a BamHI fragment containing the 645 amino acid truncated form of the the cryIAb endotoxin gene in the BamHI site of pUC18.

The 2.6 kb EcoRI-XhoI fragment from pPEP-10, containing the polyA addition site from the PEP carboxylase gene, is isolated and digested with PstI and HincII. The restriction digest is ligated with PstI/HincII digested pUC18, transformed into E. coli and transformants screened for those containing a 412 bp PstI-HincII insert in pUC18 and the insert verified by sequencing. The resulting plasmid is called pCIB931.

The nuclear gene encoding the phosphoenolpyruvate carboxylase isozyme ("Pep-C") is described in Hudspeth et al., Plant Molecular Biology, 12: 579–589 (1989). pCIB932 is constructed by the ligation of three fragments. The first fragment, containing the PEP-C transcription terminator, is produced by digesting pCIB931 to completion with HindIII, partially with SphI and the 3098 bp fragment isolated. The second fragment, containing the Bt endotoxin coding sequence, is produced by digesting pCIB930 with NcoI and SphI and isolating the 1950 bp fragment. The third fragment, containing the PEP-C promoter, is produced by digesting pPEP-10 to completion with HindIII, partially with NcoI and isolating the 2.3 kb fragment. The ligation mix is transformed into E. coli, transformants with the correct insertion identified and the insert verified by sequencing.

pCIB932 is cut with PvuII to generate a 4.9 Kb fragment containing the maize Pep-C:promoter\Bt\Pep-C:terminator and purified on a 1% LGT agarose gel in 1×TAE. The linearized pCIB3079 vector and the 4.9 Kb insert from pCIB932 are ligated using T4 DNA ligase in LGT to make pCIB4401. pCIB4401 is a maize transformation vector containing the chimeric genes: 35S:promoter\PAT\35S:terminator, Pep-C:promoter\Bt\Pep-C: terminator, and 35S:promoter\AdhI #1 intron\GUS\35S: terminator.

Construction of pCIB246 (35S-GUS-35S)

A CaMV 35S promoter cassette, pCIB246, is constructed as follows.

The DdeI restriction site at nucleotide position 7482 of the CaMV genome (Franck et al., Cell, 21:285–294 (1980)) is modified by insertion of a 48 bp oligonucleotide containing several restriction enzyme sites including an NcoI (CCATGG) site, a SalI (GTCGAC) site, and an SstI (GAGCTC) site. This altered CaMV 35S promoter is inserted into a pUC19 vector that had been modified to destroy the vector's SstI and SalI sites. Thus, the CaMV 35S promoter of pCIB 1500 contains unique SstI and SalI sites for cloning.

pCIB 1500 is digested with SstI/NcoI and ligated with the GUS gene obtained from pBI221 (Clontech Laboratories, Inc., Palo Alto, Calif.). The NcoI site is fused to the GUS gene such that the ATG of the NcoI site functions as the start codon for the translation of the GUS gene. The CaMV 35S polyadenylation and termination signals are used for the 3' end of the chimeric gene.

Construction of pCIB3069 (35S-Adh1-GUS-35S)

pCIB246 is modified by adding the maize alcohol dehydrogenase gene Adh1 intron number 1 (Adh1) (Dennis et al., Nucleic Acids Research, 12:3983–4000 (1984)) into the Sal I site of pCIB246 to produce plasmid pCIB3007. The Adh1 intron is excised from the maize Adh1 gene as a Bal I/Pst I fragment and subcloned into pUC 18 that was cut with Sma I/Pst I to make a plasmid called Adh 1026. Adh 1026 is cut with Pvu II/Sac II, the fragments are made blunt ended with T4 DNA polymerase, Sal I linkers are added using standard procedures and a fragment of about 560 bp is recovered from a 3% NuSeive gel and ligated into Sal I cut/phosphatase treated pUC18. The Sal I linkered Adh intron #1 in the resulting plasmid is cut out with Sal I, gel purified, and ligated into Sal I cut/phosphatase treated pCIB246 to make plasmid pCIB3007.

pCIB3007 is cut with PstI and the ends made blunt by using T4 DNA polymerase (NEW England Biolabs) according to the suppliers' specifications. The resulting blunt ended molecules are cut with Sph I and the approximately 5.8 Kb fragment with one blunt end and one Sph I end is purified on a low gelling temperature (LGT) agarose gel using standard procedures. pCIB900 is cut with Sma I/Sph I and the fragment containing the 35S/Bt gene is purified on a LGT agarose gel. The two gel purified fragments are ligated in LGT agarose using T4 DNA ligase according to standard conditions. The resulting ligated fragments are transformed into E. coli using standard procedures and the resulting plasmid is called pCIB3062. There are two versions of pCIB3062. pCIB3062#1 has a Sma I site regenerated where the Sma I site and the T4 polymerase blunted ends are ligated. This most likely results from the T4 polymerase nibbling a few base pairs from the Pst I site during the blunting reaction. pCIB3062#3 does not have this SmaI site.

pCIB3062#3 is cut with KpnI and made blunt-ended using T4 DNA polymerase, and subsequently cut with Pvu II to yield a 6.4 Kb fragment with blunt ends containing the 35S/GUS and 35S/Bt genes. This blunt-end fragment is ligated into Sma I cut pCIB3073 to produce pCIB3063 or pCIB3069. pCIB3069 contains the same fragment used to make pCIB3063, but the chimeric genes in pCIB3069 are all in the same relative orientation, unlike those in pCIB3063. These plasmids contain a) a 35S promoter operably linked to the hygromycin resistance gene; b) a 35S promoter, with Adh intron #1, operably linked to the GUS gene; and c) a 35S promoter operably linked to a gene coding for the production of the synthetic cryIA(b) insecticidal protein from Bacillus thuringiensis, as described above. GUS Assays:

GUS assays are done essentially as described in Jefferson, Plant Mol. Bio. Reporter, 5:387–405 (1987). As shown above, plasmid pCIB246 contains a CaMV 35S promoter fused with the GUS gene. The 5' untranslated leader of this chimeric gene contains a copy of the maize Adh 1 intron #1. It is used here as a transformation control. Although the same amount of pCIB246 is added to each transformation, the calculated activity varied among Bt constructs tested. The values reported below are averages of 3 replicates. pCIB4407 was tested twice.

| | |
|---|---|
| pCIB3069 | 28 nM MU/ug/min |
| pCIB4407 | 0.7 nM MU/ug/min, 2.3 nM MU/ug/min |

Example 5A

ASSAY OF SYNTHETIC cryIA(b) gene FOR INSECTICIDAL ACTIVITY AGAINST EUROPEAN CORN BORER The synthetic cryIA(b) gene in pCIB4414 in *E. coli* is assayed for insecticidal activity against European corn borer according to the following protocol.

Molten artifical insect diet is poured into a 60 mm Gellman snap-cap petri dish. After solidification, *E. coli* cells, suspended in 0.1% Triton X-100, are spread over the surface at a concentration of 3×107 cells/cm2. The plates are air dried. Ten first instar European corn borer, *Ostrinia nubilalis*, which are less than 12 hours old are then placed onto the diet surface. The test is incubated at 30° C. in complete darkness for 2–5 days. At the end of the test percent mortality is recorded. A positive clone has been defined as one giving 50% or higher mortality when control *E. coli* cells give 0–10% background mortality.

For comparison, the native cryIA(b) gene in pCIB3069 is tested at the same concentration. Clones are tested at 3×107 cells/$cm^2$ diet; 20 insects per clone.

The following results are observed:

| Clone | Percent Mortality |
|---|---|
| Control | 0 |
| pCIB3069 | 100 |
| pCIB4414 | 100 |

Thses results indicate that the insecticidal crystal protein produced by the synthetic cryIA(b) gene demonstrates activity against European corn borer comparable to that of the IP produced by the native cryIA(b). Other plasmids containing a synthetic cryIA(b) gene were assayed in a similar manner.

Example 5AB

ASSAY OF CRYIA(b) PROTEIN FOR INSECTICIDAL ACTIVITY AGAINST SUGARCANE BORER.

CryIA(b) was expressed in *E. coli* and assayed for insecticidal activity against Sugarcane borer (*Diatrea saccharalis*) according to the same protocol used for European corn borer, described immediately above. The results are summarized in the Table.

TABLE

SUGARCANE BORER ASSAY WITH Bt PROTEIN FROM *E. COLI*

| Protein Concentration (ng/g) | Percent Mortality CryIA(b) |
|---|---|
| 10 | 0 |
| 25 | 0 |
| 50 | 7 |
| 100 | 13 |
| 250 | 40 |
| 500 | 53 |
| 1000 | 80 |

TABLE-continued

SUGARCANE BORER ASSAY WITH Bt PROTEIN FROM *E. COLI*

| Protein Concentration (ng/g) | Percent Mortality CryIA(b) |
|---|---|
| LC50 | 380 |
| 95%Cl | 249–646 |

The results indicate that the insecticidal protein produced by a maize optimized Bt gene is effective against Sugarcane borer. The upper concentrations of CryIA(b) protein, 250 ng/g-1000 ng/g, are achievable in transgenic maize plants produced in accordance with the instant invention.

Example 6
MAIZE PROTOPLAST ISOLATION AND TRANSFORMATION WITH THE SYNTHETIC BT GENE Expression of the synthetic Bt gene is assayed in transiently transformed maize protoplasts.

Protoplast Isolation Procedure:

1. The contents of 10 two day old maize 2717 Line 6 suspension cultures are pipetted into 50 ml sterile tubes and allowed to settle. All culture media is then removed and discarded.
2. Cells (3–5 ml Packed Cell Volume) are resuspended in 30 ml protoplast enzyme solution. Recipe follows:

3% Cellulase RS

1% Macerozyme R10 in KMC Buffer

KMC Buffer (recipe for 1 liter)

| | |
|---|---|
| KCl | 8.65 g |
| $MgCl_2$—$6H_2O$ | 16.47 g |
| $CaCl_2$—$2H_2O$ | 12.50 g |
| MES | 5.0 g | pH 5.6, filter sterilize

3. Mix cells well and aliquot into 100×25 mm petri dishes, about 15 ml per plate. Shake on a gyratory shaker for 4 hours to digest.

4. Pipette 10 ml KMC through each 100 micron sieve to be used. Filter contents of dishes through sieve. Wash sieve with an equal volume KMC.

5. Pipette sieved protoplasts carefully into 50 ml tubes and spin in a Beckman TJ-6 centrifuge for 10 minutes at 1000 rpm (500×g).

6. Remove supernatant and resuspend pellet carefully in 10 ml KMC. Combine contents of 3 tubes into one and bring volume to 50 ml with KMC.

7. Spin and wash again by repeating the above step.

8. Resuspend all washed protoplasts in 50 ml KMC. Count in a hemocytometer. Spin protoplasts and resuspend at $8\times10^6$/ml in resuspending buffer (RS Buffer).

RS Buffer (recipe for 500 ml)

mannitol 27.33 g

CaCl2 (0.1 M stock) 75 ml

MES 0.5 g pH 5.8, filter sterilize

Protoplast Transformation Procedure:

1. Aliquot 50 μg plasmid DNA (Bt IP constructs, both synthetic (pCIB4407) and native (pCIB3069)) to 15 ml polystyrene culture tubes. Also aliquot 25 μg GUS-containing plasmid DNA (which does not contain Bt IP (pCIB246) to all tubes. 3 replications are used per construct to be tested, with 1 rep containing no DNA as a control.

| Bt constructs: | GUS construct: |
|---|---|
| pCIB3069<br>pCIB4407 | pCIB246 |

2. Gently mix protoplasts well and aliquot 0.5 ml per tube.

3. Add 0.5 ml PEG-40 to each tube.

PEG-40:

0.4 M mannitol 0.1 M $Ca(NO_3)_2$-$4H_2O$ pH 8.0, filter sterilize

4. Mix gently to combine protoplasts with PEG. Wait 30 minutes.

5. Sequentially add 1 ml, 2 ml, and 5 ml W5 solution at 5 minute intervals.

W5 Solution:

154 mM NaCl 125 mM $CaCl_2$-$H_2O$

5mM KCl 5 mM glucose pH 7.0, filter sterilize

6. Spin for 10 minutes in a Beckman TJ-6 centrifuge at about 1000 rpm (500 g).

Remove supernatant.

7. Gently resuspend pellet in 1.5 ml FW media and plate carefully in 35×10 mm petri dishes.

FW media (recipe for 1 liter):

| | |
|---|---|
| MS salts | 4.3 g |
| 200X B5 vits. | 5 ml |
| sucrose | 30 g |
| proline | 1.5 g |
| mannitol | 54 g |
| 2,4 D | 3 mg | pH 5.7, filter sterilize

8. Incubate overnight in the dark at room temperature.

9. Perform GUS assays, insect bioassays, and ELISA's on protoplast extracts as described below.

Example 7

CONSTRUCTION OF A FULL-LENGTH SYNTHETIC MAIZE OPTIMIZED CRYIA(b) GENE (SEQ ID NO: 4) shows the synthetic maize optimized sequence encoding the full-length cryIA(b) insecticidal protein from *B. thuringiensis*. The truncated version described above represents the first approximately 2 Kb of this gene. The remainder of the full-length gene is cloned using the procedures described above. Briefly, this procedure entails synthesizing DNA oligomers of 40 to 90 NT in length, typically using 80 mers as an average size. The oligomers are purified using standard procedures of HPLC or recovery from a polyacrylamide gel. Purified oligomers are kinased and hybridized to form fragments of about 500 bp. The hybridized oligomers can be amplified using PCR under standard conditions. The 500 bp fragments, either directly from hybridizations, from PCR amplification, or recovered from agarose gels after either hybridization or PCR amplification, are then cloned into a plasmid and transformed into *E. coli* using standard procedures. Recombinant plasmids containing the desired inserts are identified, as described above, using PCR and/or standard miniscreen procedures. Inserts that appear correct based upon their PCR and/or restriction enzyme profile are then sequenced to identify those clones containing the desired open reading frame. The fragments are then ligated together with the approximately 2 Kb synthetic sequence described in Example 2 to produce a full-length maize optimized synthetic cryIA(b) gene useful for expression of high levels of CryIA(b) protein in maize.

G+C Content of native and synthetic Bt genes:

| | |
|---|---|
| Full-length native | 38.8% |
| Truncated native | 37.2% |
| Full-length synthetic | 64.8% |
| Truncated synthetic | 64.6% |

% homology of the final truncated version of the Bt gene relative to a "pure" maize codon usage gene: 98.25%

Example 8

Construction of a Plant Expressible, Full-length, Hybrid Partially Maize Optimized CryIA(b) Gene.

pCIB4434 contains a full length CryIA(b) gene (SEQ ID NO: 8) comprised of about 2 Kb of the synthetic maize optimized cryIA(b) gene with the remainder (COOH terminal encoding portion) of the gene derived from the native gene. Thus, the coding region is a chimera between the synthetic gene and the native gene, but the resulting protein is identical to the native cryIA(b) protein. The synthetic region is from nucleotide 1–1938 (amino acids 1 to 646) and the native coding sequence is from nucleotide 1939–3468 (amino acids 647 to 1155). The sequence of this gene is set forth in FIG. 7. A map of pCIB4434 is shown in FIG. 8.

The following oligos were designed to make pCIB4434:

KE134A28=5'-CGTGACCGAC TACCACATCG ATCAAGTATC CAATTTAGTT GAGT-3' (SEQ ID NO: 60)

KE135A28=5'-ACTCAACTAA ATTGGATACT TGATCGATGT GGTAGTCGGTC ACG-3' (SEQ ID NO: 61)

KE136A28=5'-GCAGATCTGA GCTCTTAGGT ACCCAATAGC GTAACGT-3' (SEQ ID NO: 62)

KE137A28=5'-GCTGATTATG CATCAGCCTAT-3' (SEQ ID NO: 63)

KE138A28=5'-GCAGATCTGA GCTCTTATTC CTCCATAAGA AGTAATTC-3' (SEQ ID NO: 64)

MK05A28=5'-CAAAGGTACC CAATAGCGTA ACG-3' (SEQ ID NO: 65)

MK35A28=5'-AACGAGGTGT ACATCGACCG-3' (SEQ ID NO: 66)

pCIB4434 is made using a four-way ligation with a 5.7 kb fragment from pCIB4418, a 346 bp Bst E II\Kpn I PCR-generated synthetic:native fusion fragment, a 108 bp Kpn I\Nsi I native CryIA(b) fragment from pCIB 1315, and a 224 bp Nsi I\Bgl II PCR-generated fragment. Standard conditions for ligation and transformation are as described previously.

A synthetic:native gene fusion fragment is made in two steps using PCR. The first 253 bp of the PCR fusion fragment is made using 100 pmols of oligos KE134A28 and MK04A28 with approximately 200 ng of native cryIA(b) template in a 100 ul volume with 200 nm of each dNTP, 1×PCR buffer (Perkin Elmer Cetus), 20% glycerol, and 5 units of Taq polymerase (Perkin Elmer Cetus). The PCR reaction is run with the following parameters: 1 minute at 94° C., 1 minute at 55° C., 45 seconds at 72° C., with extension 3 for 3 seconds for 25 cycles. A fraction (1%) of this first PCR reaction is used as a template along with 200 ng of the synthetic cryIA(b) DNA to make the complete 351 bp synthetic:native fusion fragment. Oligos used as PCR primers in this second PCR reaction are 50 pmols of MK35A28, 50 pmols of MK04A28, and 25 pmols of KE135A28. The PCR reaction mix and parameters are the same as those listed above. The resultant 351 bp synthetic:native fusion fragment is treated with Proteinase K at 50 ugm\nl total concentration and phenol\chloroform extraction followed by ethanol precipitation before cutting with Bst E II\Kpn I using standard conditions.

The 224 bp Nsi I\Bgl II PCR fragment used in making pCIB4434 is made using 100 pmols of oligos KE137A28 and KE138A28 and 200 ng of the native cryIA(b) gene as template in 100 ul volume with the same PCR reaction mix and parameters as listed above. The 230 bp PCR native cryIA(b) fragment is treated with Proteinase K, phenol\chloroform extracted, and ethanol precipitated as described above, before cutting with Nsi I\Bgl II.

pCIB4434 was transformed into maize protoplasts as described above. Line 6 2717 protoplasts were used with pCIB4434 and pCIB4419 as a control for comparison. The results are shown below:

| | ng Bt/mg protein |
|---|---|
| 4419(35S) | 14,400 ± 2,100 |
| 434(full-length) | 2,200 ± 900 |

Background = 13 ng Bt/mg protein for untransformed protoplasts

The results indicate that pCIB4434 expresses at a level of about 15% of pCIB4419.

Western blot analysis shows at least one-third of the cryLA(b) protein produced by pCIB4434 in this system is about 130 kD in size. Therefore, a significant amount of full-length cryIA(b) protein is produced in maize cells from the expression of pCIB4434.

Example 7

Construction of a Full-Length, CryIA(b) Genes Encoding a Temperature-Stable CryIA(b) Protein.

Constructs pCIB5511–5515, each containing a full-length, cryIA(b) gene are described below. In these sequences, the 26 amino acid deletion between amino acids 793 and 794, KCGEPNRCAPHLEWNPDLDCSCRDGE (see: SEQ ID NOS: 8, 10, 12, 14, 16), present in cryIA(a) and cryIA(c) but not in cryIA(b), has been repaired. The gene in pCIB5513 is synthetic; the other four genes are hybrids, and thus are partially maize optimized.

Construction of pCIB5511

This plasmid is a derivative of pCIB4434. A map of pCIB5511 is shown in FIG. 10. A 435 bp segment of DNA between bp 2165 and 2590 was constructed by hybridization of synthetic oligomers designed to represent the upper and lower strand as described above for the construction of the truncated cryIA(b) gene. This segment of synthetic DNA is synthesized using standard techniques known in the art and includes the 26 amino acid deletion found to occur naturally in the cryIA(b) protein in *Bacillus thuringiensis* kurstaki HD-1. The entire inserted segment of DNA uses maize optimized codon preferences to encode amino acids. The 26 amino acids used to repair the naturally occurring deletion are contained within this fragment. They are inserted starting at position 2387 between the KpnI site at nt 2170 and the XbaI site at nt 2508 (2586 in pCIB551 1) of pCIB4434. pCIB5511 is constructed via a three way ligation using a 3.2 Kb fragment obtained by restriction digestion of pCIB4434 with SphI and KpnI, a 3.8 Kb fragment obtained by digestion of pCIB4434 with SphI and XbaI, and a 416 bp fragment obtained by digestion of the synthetic DNA described above, with KpnI and XbaI. Enzymatic reactions are carried out under standard conditions. After ligation, the DNA mixture is transformed into competent E. coli cells using standard procedures. Transformants are selected on L-agar containing 100 μg/ml ampicillin. Plasmids in transformants are characterized using standard mini-screen procedures. The sequence of the repaired cryIA(b) gene encoding the cryIA(b) temperature (heat) stable protein is set forth in FIG. 9 (SEQ ID NO: 10).

Construction of pCIB5512

This plasmid construct is a derivative of pCIB4434. A map of pCIB5512 is shown in FIG. 12. DNA to repair the 26 amino acid deletion is prepared using standard techniques of DNA synthesis and enzymatic reaction. Three double stranded DNA cassettes, pGFcas1, pGFcas2 and pGFcas3, each about 300 bp in size, are prepared. These cassettes are designed to contain the maize optimized codons while maintaining 100% amino acid identity with the insecticidal protein. These cassettes are used to replace the region between restriction site BstEII at position 1824 and XbaI at position 2508 and include the insertion of the additional 78 bp which encode the missing 26 amino acids (described above for pCIB5511 in pCIB4434). Each of these cassettes is cloned into the EcoRV site of the vector Bluescript (Stratagene) by standard techniques. The three cassettes are designed to contain overlapping restriction sites. Cassette 1 has restriction sites BstEII at the 5' end and EcoRV at the 3' end: cassette 2 has EcoRV at the 5' end and ClaI at the 3' end and cassette 3 has ClaI at the 5' end and Xba I at the 3' end. They are cloned individually in Bluescript and the the complete 762 bp fragment is subsequently assembled by ligation using standard techniques. pCIB5512 is assembled using this 762 bp fragment and ligating it with a 6.65 Kb fragment obtained by a complete digestion of pCIB4434 with BstEI and a partial digestion with XbaI. Alternatively, a four way ligation using the same vector and the three cassettes digested with the specific enzymes can be employed. Enzymatic reactions are carried out under standard conditions. After ligation, the DNA mixture is transformed into competent *E. coli* cells using standard procedures. Transformants are selected on L-agar containing 100 μg/ml ampicillin. Plasmids in transformants are characterized using standard mini-screen procedures. The resulting plasmid is pCIB5512. The sequence of the repaired cryIA(b) gene is illustrated in FIG. 11 (SEQ ID NO: 12). This repaired cryIA(b) differs from that carried in pCIB5511 in that a larger region of the cryIA(b) coding region is optimized for maize expression by using maize preferred codons.

Construction of pCIB5513

This plasmid contains a repaired cryIA(b) gene derived from pCIB5512. A map of pCIB5513 is shown in FIG. 14. The region 3' from the XbaI site at position 2586 to the end of the gene (BglII site at position 3572) is replaced entirely with maize optimized codons. This region is synthesized, using standard techniques of DNA synthesis and enzymatic reaction, well known in the art, as four double stranded DNA cassettes (cassettes # 4, 5, 6, 7). Adjacent cassettes have overlapping restriction sites to facilitate assembly between cassettes. These are XbaI and XhoI at the 5' and 3' ends of cassette 4; XhoI and SacI at the 5' and 3' ends, respectively, of cassette 5; SacI and BstXI at the 5' and 3' ends, respectively, of cassette 6; and BstXI and BglII at the 5' and 3' ends, respectively, of cassette 7. As described for pCIB5512, the cassettes are cloned into the blunt-end EcoRV site of the Bluescript vector (Stratagene) and the full-length "repaired" cryIA(b) gene cloned either by sequential assembly of the above cassettes in Bluescript followed by ligation of the complete 967 bp synthetic region with a 6448 bp fragment obtained by a complete digestion of pCIB5512 with BglII and a partial digestion with XbaI. Alternately, the plasmid containing the full-length genes is obtained by a 5-way ligation of each of the four cassettes (after cleavage with the appropriate enzymes) and the same vector as above. The sequence of the full-length, "repaired" cryIA(b) gene is set forth in FIG. 13 (SEQ ID NO: 14). The protein encoded by the various synthetic and synthetic/native coding region chimeras encode the same protein. This protein is the heat-stable version of cryIA(b) produced by repairing the naturally occurring 26 amino acid deletion found in the cryIA(b) gene from *Bacillus thuringiensis* kurstaki HD-1 when the homologous region is compared with either cryIA(a) or cryIA(c) *Bacillus thuringiensis* delta-endotoxins.

Construction of pCIB5514

This plasmid is a derivative of pCIB4434. A map of pCIB5514 is shown in FIG. 16. It is made using synthetic DNA cassette #3 (see above) which contains a maize optimized sequence of the region between the ClaI site (position 2396) found in the 26 amino acid thermostable region and the XbaI site at position 2508 in pCIB4434 (2586 in pCIB5511). The region between nt 2113 of pCIB4434 and the junction of the thermostable region is PCR amplified by using pCIB4434 as template with the following primers:

forward: 5'GCACCGATATCACCATCCAAGGAGGCG ATGACGTATTCAAAG-3' (SEQ ID NO: 67)

reverse:

5'-AGCGCATCGATTCGGCTCCCCGCACTTGCCG ATTGGACTTGGGGCTGAAAG-3' (SEQ ID NO: 68).

The PCR product is then digested with restriction enzymes KpnI and ClaI and ligated in a four part reaction with a 189 bp fragment obtained by digestion of cassette 3 with ClaI and XbaI, a 3.2 Kb fragment of pCIB4434 digested with SphI and KpnI, and a 3.8 Kb fragment of pCIB4434 obtained by digestion with SphI and Xba. Enzymatic reactions are carried out under standard conditions. The ligation product is transformed into competent *E coli* cells, selected with ampicillin and screened using standard procedures described above. The sequence of the repaired cryIA(b) gene contained in pCIB5514 is shown in FIG. 15 (SEQ ID NO: 16).

pCIB4434 was modified by adding the 78bp Geiser thermostable element (Geiser TSE), described above, between the Kpn I site (2170 bp) and the Xba I site (2508 bp) in the native Btk region. The exact insertion site starts at the nucleotide #2379. The region containing the Geiser TSE was amplified by two sets of PCR reactions, i.e. the Kpn I-Geiser TSE fragment and the Geiser TSE-Xba I fragment.

PCR primer# 1: (Kpn I site)

5'-ATTACGTTAC GCTATTGGGT ACCTTTGATG-3' (SEQ ID NO: 69)

PCR primer#2: (Geiser TSE bottom)

```
                                        (SEQ ID NO:70)
5'-TCCCCGTCCC TGCAGCTGCA GTCTAGGTCC GGGTTCCACT
         CCAGGTGCGG AGCGCATCGA TTCGGCTCCC CGCACTTGCC
         GATTGGACTT GGGGCTGA-3'
```

PCR primer#3: (Geiser TSE top)

(SEQ ID NO:71)
5'CAAGTGCGGG GAGCCGAATC GATGCGCTCC GCACCTGGAG

TGGAACCCGG ACCTAGACTG CAGCTGCAGG GACGGGGAAA

AATGTGCCCA TCATTCCC-3'

PCR primer#4: (Xba I site)
5'-TGGTTTCTCT TCGAGAAATT CTAGATTTCC-3' (SEQ ID NO: 72)

Figure 38:
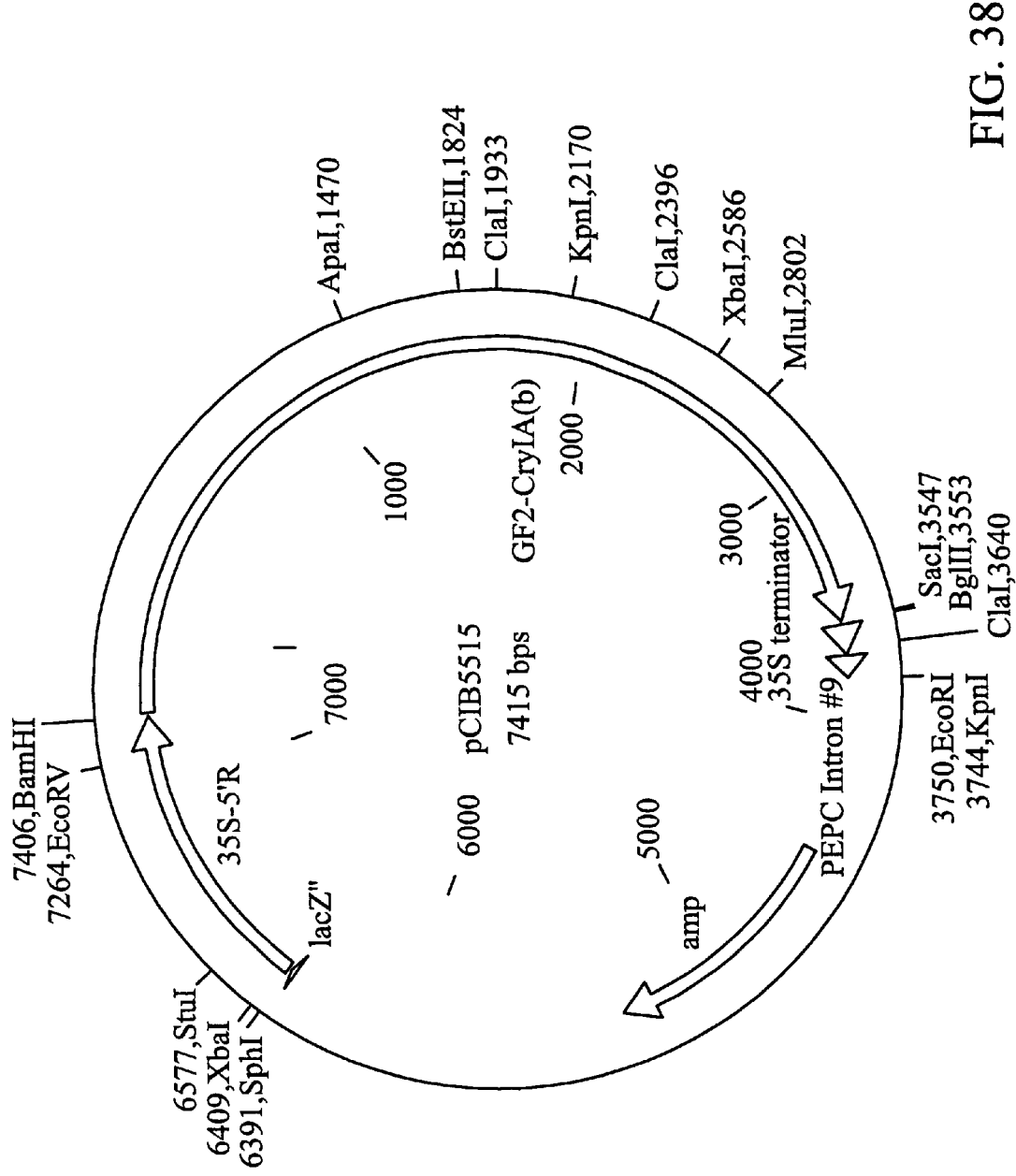
FIG. 38 is a map of pCIB5515.

After the amplification, the PCR fragments were digested with (Kpn I+Cla I) and (Cla I+Xba I), respectively. These two fragments were ligated to the Kpn I and Xba I digested pCIB4434. The resulting construct pCIB5515 is pCIB4434 with a Geiser TSE and an extra Cla I site flanked by Kpn I and Xba I. A map of pCIB5515 is illustrated in FIG. 38. The cryIA(b) gene contained herein, which encodes a temperature stable cryIA(b) protein, is shown in FIG. 37 (SEQ ID NO: 27).

Examples 9–20 set forth below are directed to the isolation and characterization of a pith-preferred promoter.

Example 9
RNA Isolation and Northern Blots

All RNA was isolated from plants grown under greenhouse conditions. Total RNA was isolated as described in Kramer et al., Plant Physiol., 90:1214–1220 (1990) from the following tissues of Funk maize line 5N984: 8, 11, 15, 25, 35, 40, and 60 day old green leaves; 8, 11, 15, 25, 35, 39, 46, 60 and 70 day old pith; 60 and 70 day old brace roots from Funk maize line 5N984; 60 and 70 day 5N984 sheath and ear stock. RNA was also isolated from 14 day 211D roots and from developing seed at weekly intervals for weeks one through five post-pollenation. Poly A+RNA was isolated using oligo-dT as described by Sambrook et al., Molecular Cloning: A Laboratory Manual (2nd ed.), 1989, and Northern blots were carried out, also as per Sambrook et al. using either total RNA (30 µg) or poly A+RNA (2–10 µg). After electrophoresis, RNA was blotted onto Nitroplus 2000 membranes (Micron Separations Inc). The RNA was linked to the filter using the Stratalinker (Stratagene) at 0.2 mjoules. The northerns were probed with the 1200 bp EcoRI pith (TRpA) 8-2 cDNA fragment, isolated by using 0.8% low melting temperature agarose in a TBE buffer system. Northerns were hybridized and washed and the filters exposed to film as described in Isolation of cDNA clones.

Example 10
Isolation of cDNA Clones

First strand cDNA synthesis was carried out using the BRL AMV reverse transcriptase system I using conditions specified by the supplier (Life Technologies, Inc., Gaithersburg, Md.). Specifically, 25 µl reactions containing 50 mM Tris-HCl pH 8.3, 20 mM KCl, 1 mM DTT, 6 mM MgCl2, 1 mM each of each dNTP, 0.1 mM oligo (dT)12–18, 2 µg pith poly(A+) RNA, 100 µg/ml BSA, 50 µg/ml actinomycin D, 8 units placental RNase inhibitor, 1 µl (10 mM Ci/ml) 32P dCTP>3000 mCi/mM as tracer, and 30 units AMV reverse transcriptase were incubated at 42° C. for 30 min. Additional KCl was added to a concentration of 50 mM and incubation continued a further 30 min. at 42° C. KCl was added again to yield a final concentration of 100 mM. Additional AMV reverse transcriptase reaction buffer was added to maintain starting concentrations of the other components plus an additional 10 units, and the incubation continued at 42° C. for another 30 min. Second strand synthesis was completed using the Riboclone cDNA synthesis system with Eco RI linkers (Promega, Madison, Wis.). Double stranded cDNA was sized on an 1% agarose gel using Tris-borate-EDTA buffer as disclosed in Sambrook et al., and showed an average size of about 1.2 Kb. The cDNA was size fractionated using NA45 DEAE membrane so as to retain those molecules of about 1000 bp or larger using conditions specified by the supplier (Schleicher and Schuell). Size fractionated cDNA was ligated into the Lambda ZapII vector (Stratagene, La Jolla, Calif.) and packaged into lambda particles using Gigapack II Plus (Stratagene, La Jolla, Calif.). The unamplified library had a titer of 315,000 pfu while the amplified library had a titer of 3.5 billion/ml using PLK-F cells.

Recombinant phage were plated at a density of 5000 pfu on 150×15 mm L-agar plates. A total of 50,000 phage were screened using duplicate lifts from each plate and probes of first strand cDNA generated from either pith derived mRNA or seed derived mRNA. The lifts were done as described in Sambrook et al. using nitrocellulose filters. DNA was fixed to the filters by UV crosslinking using a Stratalinker (Stratagene, La Jolla, Calif.) at 0.2 mJoule. Prehybridization and hybridization of the filter were carried out in a solution of 10×Denhardts solution, 150 µg/ml sheared salmon sperm DNA, 1% SDS, 50 mM sodium phosphate pH 7, 5 mM EDTA, 6×SSC, 0.05% sodium pyrophosphate. Prehybridization was at 62° C. for 4 hours and hybridization was at 62° C. for 18 hours (overnight) with 1 million cpm/ml in a volume of 40 ml. Filters were washed in 500 ml of 2×SSC, 0.5% SDS at room temperature for 15 min. then at 63° C. in 0.1×SSC, 0.5% SDS for 30 min. for each wash. Radiolabeled DNA probes were made using a BRL random prime labeling system and unincorporated counts removed using Nick Columns (Pharmacia). Filters were exposed overnight to Kodak X-Omat AR X-ray film with (DuPont) Cronex Lightning Plus intensifying screens at −80° C. Plaques showing hybridization with the pith-derived probe and not the seed-derived probe were plaque purified for further characterization.

Example 11
Isolation of Genomic Clones

Genomic DNA from Funk inbred maize line 211D was isolated as described by Shure et al., Cell, 35:225–233 (1988). The DNA was partially digested with Sau 3A and subsequently size fractionated on 10–40% sucrose gradients centrifuged in a Beckman SW40 rotor at 22,000 rpm for 20 hours at 20° C. Fractions in the range of 9–23 Kb were pooled and ethanol precipitated. Lambda Dash II (Stratagene) cut with Bam HI was used as described by the supplier. The library was screened unamplified and a total of 300,000 pfu were screened using the conditions described above. The library was probed using pith-specific (TrpA) cDNA clone 8-2, pCIB5600 which was identified in the differential screen of the cDNA library. Isolated clones were plaque purified and a large scale phage preparation was made using Lambdasorb (Promega) as described by the supplier. Isolated genomic clones were digested with Eco RI and the 4.8 kb EcoRI fragment was subcloned into Bluescript vector (Stratagene).

Example 12
DNA Sequence and Computer Analysis

Nucleotide sequencing was performed using the dideoxy chain-termination method disclosed in Sanger et al., PNAS, 74:5463–5467 (1977). Sequencing primers were synthesized on an Applied Biosystems model 380B DNA synthesizer using standard conditions. Sequencing reactions were carried out using the Sequenase system (US Biochemical Corp.). Gel analysis was performed on 40 cm gels of 6% polyacrylamide with 7 M urea in Tris-Borate-EDTA buffer (BRL Gel-Mix 6). Analysis of sequences and comparison with sequences in GenBank were done using the U. of Wisconsin Genetic Computer Group Sequence Analysis Software (UWGCG).

Example 13
Mapping the Transcriptional Start Site

Figure 29:
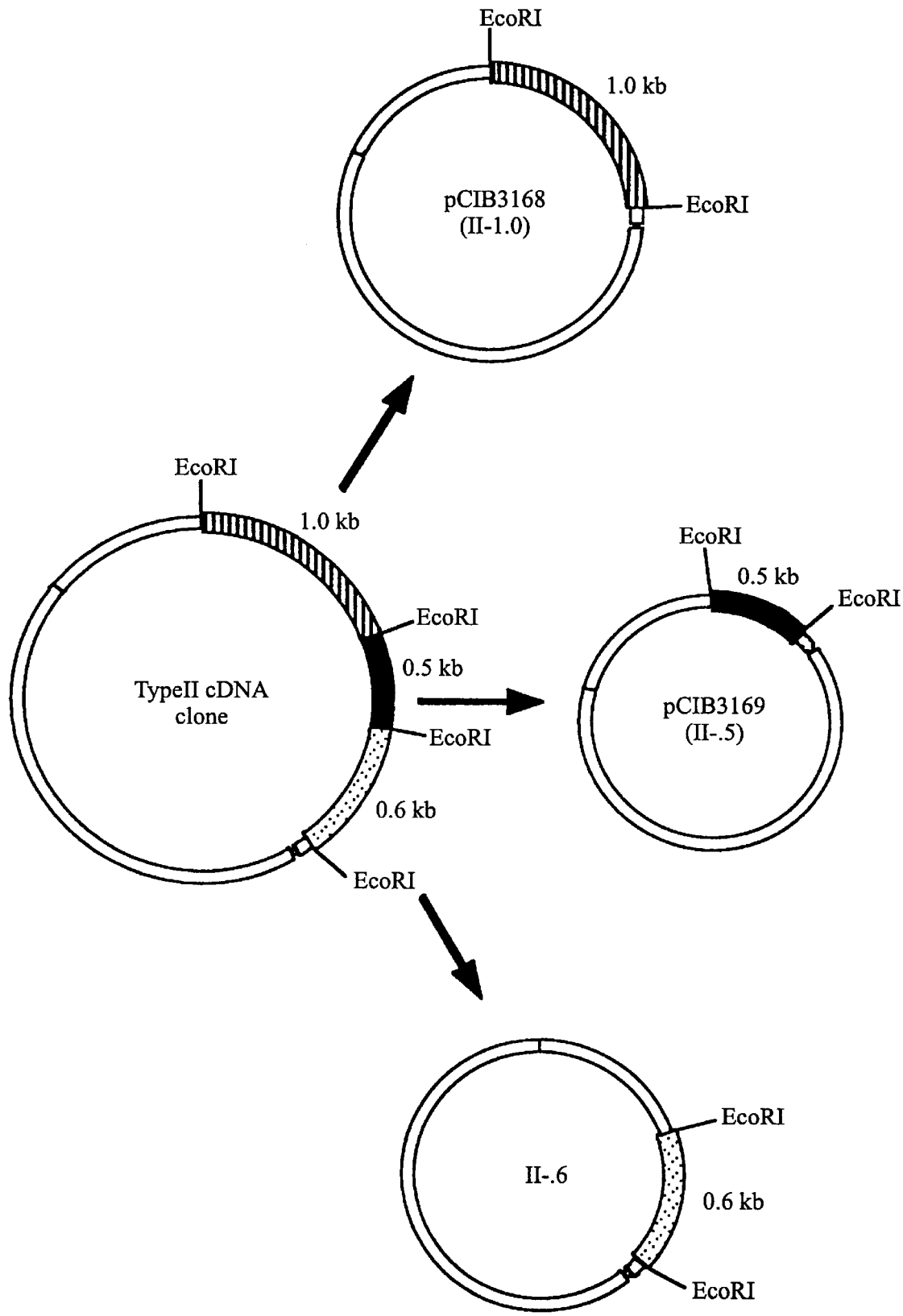
FIG. 29 is A map of the original Type II pollen-specific cDNA clone. The subcloning of the three EcoRI fragments into pBluescript vectors to create pCIB3168, pCIB3169 and II-.6 is illustrated.

Primer extension was carried according to the procedure of Metraux et al., PNAS,86:896–900 (1988). Briefly, 30 μg of maize pith total RNA were annealed with the primer in 50 mM Tris pH 7.5,40 mM KCl, 3 mM MgCl2 (RT buffer) by heating to 80° C. for 10 minutes and slow cooling to 42° C. The RNA/primer mix was allowed to hybridize overnight. Additional RT buffer, DTT to 6 mM, BSA to 0.1 mg/ml, RNAsin at 4 U/ml and dNTP's at 1 mM each were added. Then 8 units AMV reverse transcriptase were added and reaction placed at 37° C. for one hour. The primer used was 5'-CCGTTCGTTC CTCCTTCGTC GAGG-3' (SEQ ID NO: 73), which starts at +90 bp relative to the transcription start. See FIG. 29A. A sequencing ladder using the same primer as in the primer extension reaction was generated using the 4.8 Kb genomic clone to allow determination of the transcriptional start site. The sequencing reaction was carried out as described in Example 12.

RNase protection was used to determine if the the 371 bp sequence from +2 bp to +373 bp (start of cDNA) was contiguous or if it contained one or more introns. A 385 bp SphI-NcoI fragment spanning +2 bp to +387 bp relative to transcriptional start see FIG. 29B was cloned into pGEM-5Zf(+) (Promega) and transcribed using the Riboprobe Gemini system (Promega) from the SP6 promoter to generate radioactive antisense RNA probes as described by the supplier. RNase protection was carried out as described in Sambrook et al. pBR322 (cut with HpaII and end labelled with 32P-dCTP) and Klenow fragment were used molecular weight markers. Gels were 6% acrylamidene/7M urea (BRL Gel-Mix 6) and were run at 60 watts constant power.

Example 14
Genomic Southern Blots

Genomic DNA was isolated from maize line 211D using the procedure of Shure et al., supra. 8 μg of genomic DNA were used for each restriction enzyme digest. The following enzymes were used in the buffer suggested by the supplier: BamHI, EcoRI, EcoRV, HindIII, and SacI. Pith cDNA clone number 8-2 was used for estimating gene copy number. The digested DNA was run on a 0.7% agarose gel using Tris-Borate-EDTA buffer system. The gel was pretreated with 250 mM HCl for 15 min. to facilitate transfer of high molecular weight DNA. The DNA was transferred to Nitroplus 2000 membrane and subsequently probed with the pith cDNA 8-2. The blot was washed as described in Example 10.

Example 15
PCR Material and Methods

PCR reactions were preformed using the GeneAmp DNA Amplication reagent kit and AmpliTaq recombinant Taq DNA polmerase (Perkin Elmer Cetus). Reaction condition were as follows: 0.1 to 0.5 uM of each of the two primers used per reaction, 25 ng of the pith 4.8 Kb EcoRI fragment in Bluescript, plus the PCR reaction mix described by the supplier for a total volume of 50 uL in 0.5 mL GeneAmp reaction tube (Perkin Elmer Cetus). The DNA Thermal Cycler (Perkin Elmer Cetus) using the Step-Cycle program set to denature at 94° C. for 60 s, anneal at 55° C. for 60 s, and extend at 72° C. for 45 s followed by a 3-s-per-cycle extension for a total of 30 cycles. The following primer sets were used: I. 83×84, −429 bp to −2 bp; II. 49×73, −69 bp to +91 bp; III. 38×41, +136 bp to +258 bp; and IV. 40×75, +239 bp to +375 bp. These are marked on FIG. 24.

Example 16
Isolation of a Pith-Preferred Gene.

A cDNA library derived from pith mRNA cloned into Lambda Zap and screened using first strand cDNA derived from either pith or seed mRNA. Clones which hybridized with only the pith probe were plaque purified and again screened. Clones passing the second screen were used as probes in northern blots containing RNA from various maize tissues.

Example 17
Gene Structure and Sequence Analysis.

The 1.2 Kb insert of the cDNA clone 8-2 was sequenced using the dideoxy method of Sanger et al., supra. Likewise, the genomic equivalent contained on a 4.8 Kb EcoRI fragment in Bluescript denoted as pCIB5601, was sequenced. This information revealed that the genomic copy of the coding region spans 1.7 Kb and contains five introns. The mRNA transcript represents six exons. This is shown in FIG. 24. The exons range in size from 43 bp to 313 bp and the introns vary in size from 76 bp to 130 bp. The entire sequence of the gene and its corresponding deduced amino acid sequence are shown in FIG. 24 (SEQ ID NOS: 18 and 19).

This gene encodes a protein of 346 amino acids with a molecular mass of about 38 kD. As illustrated in Table 1, the predicted protein shows 62% similarity and 41% identity with the subunit protein of *Pseudomonas aeruginosa* and has high homology with trpA proteins from other organisms.

TABLE 1

Conservation of TrpA sequences between a maize TrpA gene and other organisms.

| Organisms compared | % amino acid Similarity | % amino acid Identity |
|---|---|---|
| Haloferax volancii | 56.4 | 36.1 |
| Methanococcus voltae | 58.1 | 35.1 |
| Pseudomonas aeruginosa | 62.5 | 41.8 |
| Neurospora crassa | 61.4 | 39.3 |
| Saccharomyces cerevisiae | 56.7 | 36.1 |

Similarity groupings, I = L = M = V, D = E, F = Y, K = R, N = Q, S = T
Similarities and identities were done using the GAP program from UWGCG.

Crawford et al., Ann. Rev. Microbiol., 43:567–600 (1989), incorporated herein by reference, found regions of conserved amino acids in bacterial trpA genes. These are amino acids 49 to 58, amino acids 181 to 184, and amino acids 213 to 216, with the rest of the gene showing greater variability than is seen in the TrpB sequence. An alignment of known trpA proteins with the maize TrpA protein (not shown) illustrates that the homology between the maize gene and other trpA proteins is considerable. Also, it is comparable to the level of homology observed when other TrpA proteins are compared to each other as described in Crawford et al., supra.

Figure 28A:
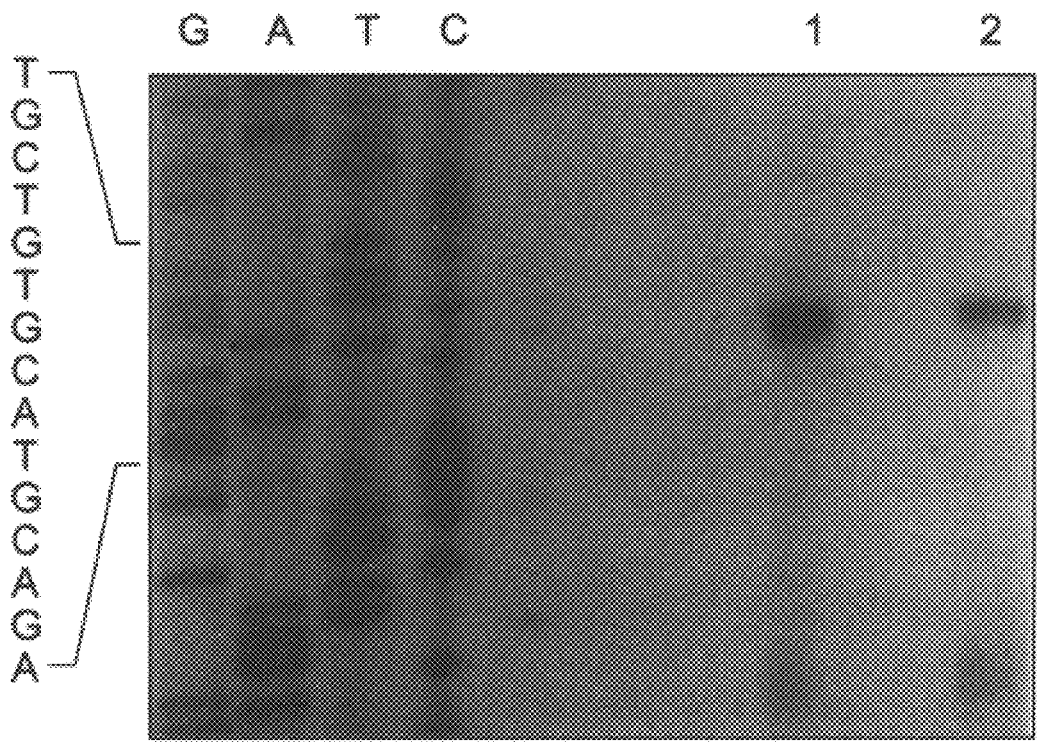
FIG. 28A is a primer extension analysis which shows the transcriptional start of the maize TrpA subunit gene and sequencing ladder at a 1 hour exposure against film at −80° C. with Dupont Cronex intensifying screens. Lane+1 and +2 are 1X+0.5X samples of primer extension reaction.

To determine the location of the transcription start site and whether or not there were introns present in this region, four polymerase chain reaction (PCR) generated fragments of about 122 bp to 427 bp from the region −429 bp to +372 bp were used for northern analysis. The results of the northerns showed that PCR probes II, III, IV hybridized to pith total RNA and PCR probe I did not hybridize. This indicated that the transcription start was in the −69 bp to +90 bp region. To more precisely locate the transcriptional start site, primer extension was employed. FIG. 28A shows that when a primer (#73) located at +90 bp relative to the transcriptional start is used for primer extension, the transcriptional start site is located at +1, 1726 bp on the genomic sequence.

The first ATG from the transcriptional start site is at +114 bp. This is the ATG that would be expected to serve as the site for translational initiation. This ATG begins an open reading that runs into the open reading frame found in the cDNA clone. The first 60 amino acids of this predicted open reading frame strongly resemble a chloroplast transit peptide. See Berlyn et al. PNAS, 86:4604–4608 (1989) and Neumann-Karlin et al., EMBO J., 5:9–13 (1986). This result suggests that this protein is targeted to a plastid and is likely processed to yield the active protein. Transient expression assays in a maize mesophyll protoplast system using a maize optimized B.t. gene driven by the trpA promoter showed that when the ATG at +114 bp is used as the fusion point, the highest levels of expression are obtained. Using either of the next two ATGs in the sequence substantially reduces the level of expression of the reporter gene. The ATG at +390 bp gave some activity, but at a much lower level than the +114 ATG, and the ATG at +201 bp gave no activity.

Athough a number of TATA like boxes are located upstream of the upstream of the transcriptional start site at +1 bp, the TATAAT at −132 bp is most like the plant consensus of TATAAA. See Joshi, Nuc. Acids Res., 15:6643–6653 (1987). The presumptive CCAAT like box was found at −231 bp . The nucleotide sequence surrounding the ATG start (GCGACATGGC; see SEQ ID NO: 18) has homology to other maize translation starts as described in Messing et al., Genetic Engineering of Plants: An Agricultural Perspective, Plenum Press, pp. 211–227 (1983), but differs from that considered a consensus sequence in plants (ANNATGGC). See, Joshi, above. The presumptive poly(A) addition signal is located at 3719 bp (AATAAA) on the genomic sequence, 52 bp from the end of the cDNA. The sequence matches known sequences for maize as described in Dean et al., Nuc. Acids Res., 14:2229–2240 (1986), and is located 346 bp downstream from the end of protein translation. See Dean et al., Nuc. Acids Res., 14:2229–2240 (1986). The 3' untranslated sequence of the cDNA ends at 3775 bp on the genomic sequence.

Figure 27:
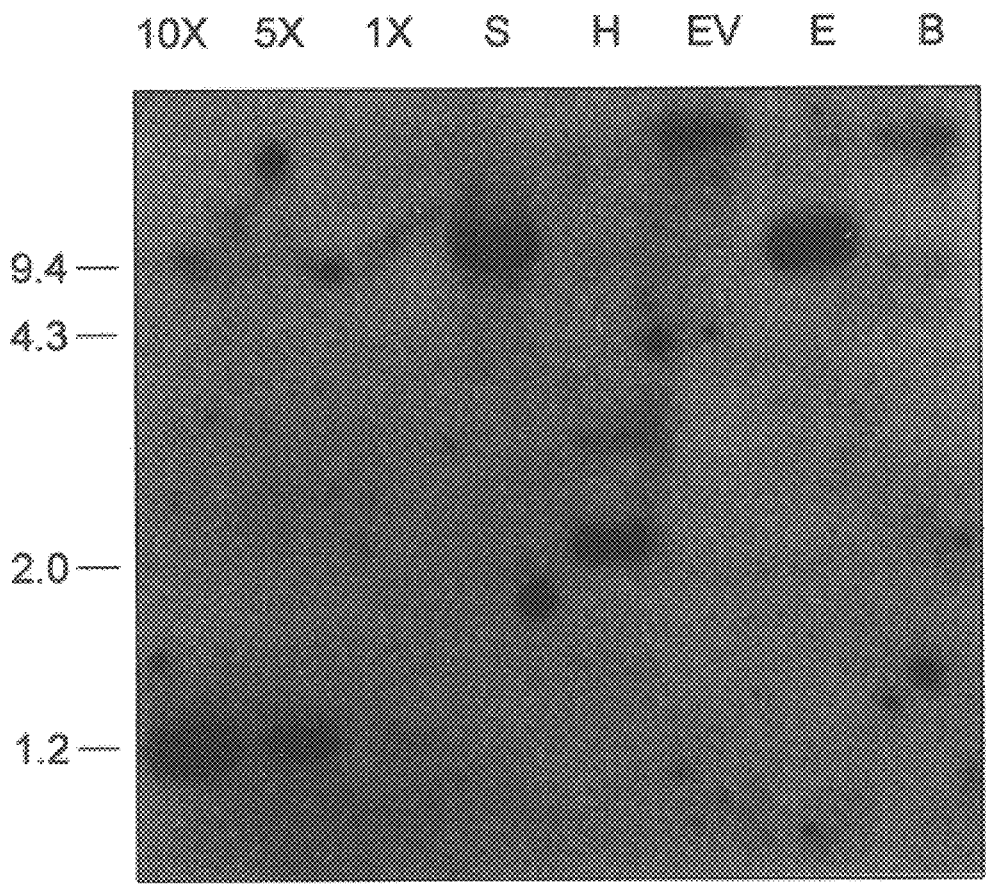
FIG. 27 is a Southern blot analysis of genomic DNA Funk line 211D, probed with maize TrpA cDNA 8-2 (pCIB5600), wherein B denotes BamHI, E denotes EcoRI, EV denotes EcoRV, H denotes HINDIII, and S denotes SacI. 1X, 5X and 10X denote reconstructed gene copy equivalents.

FIG. 27 shows a Southern blot of maize 211D genomic DNA with the approximate gene copy number as reconstructed using pith gene 8-2 cDNA. From the restriction digests and reconstruction there appear to be 1–2 copies of the gene present per haploid genome. There do not appear to be other genes with lower levels of homology with this gene. Therefore, this represents a unique or small member gene family in maize.

Example 18
RNase Protection

Figure 28B:
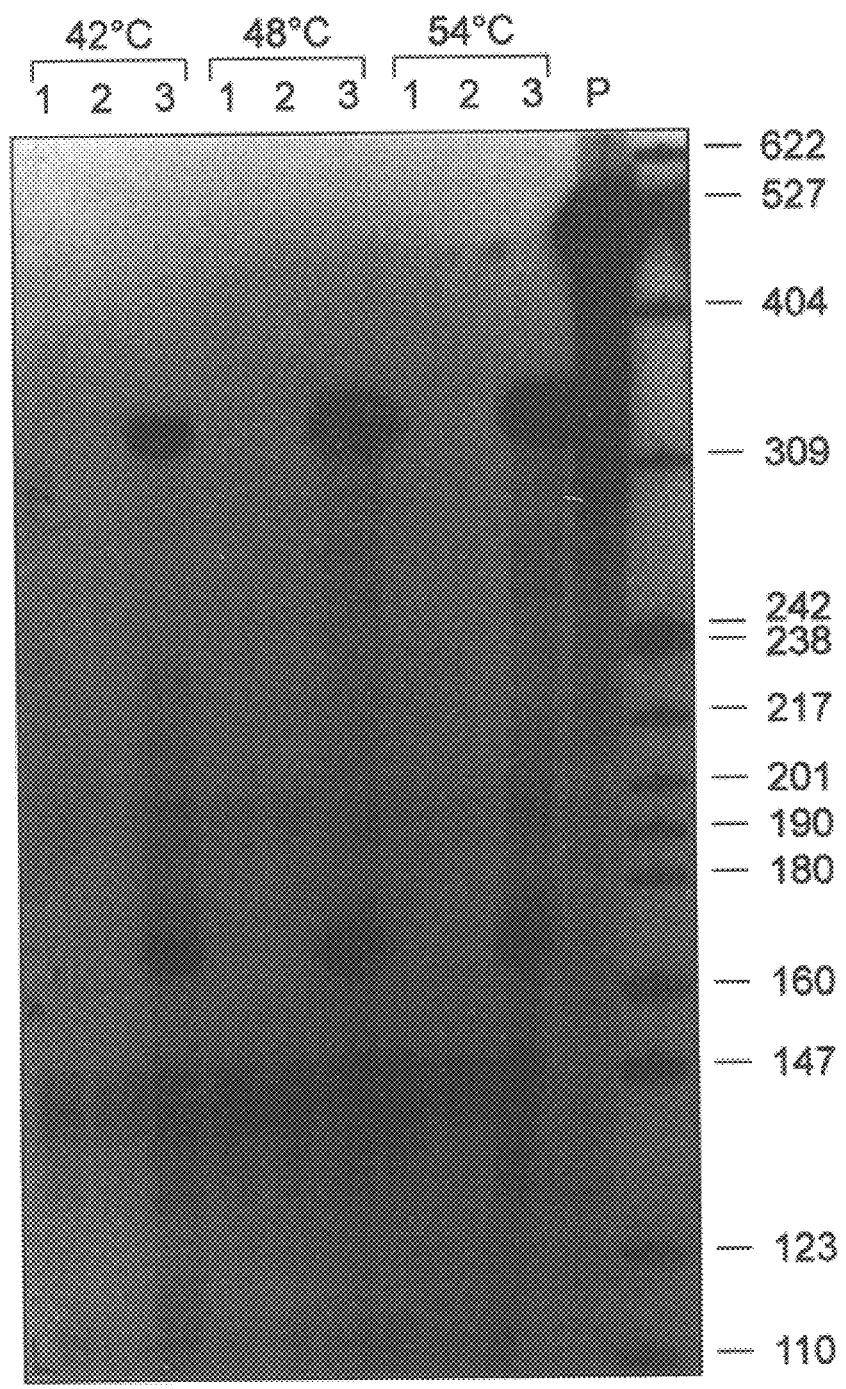
FIG. 28B is an analysis of RNase protection from +2 bp to +387 bp at annealing temperatures of 42° C., 48° C. and 54° C., at a 16 hour exposure against film at −80° C. with DuPont Cronex intensifying screens.

The structure of the 5' end of the mRNA was determined using RNase protection. The RNase protection was carried out using a probe representing 385 nt from +2 bp to +387 bp. This region from the genomic clone was placed in the RNA transcription vector pGEM-5Zf(+) and a 32P labelled RNA probe generated using SP6 polymerase. The probe and the extra bases from the multiple cloning site produce a transcript of 461 nt. The probe was hybridized with total pith RNA and subsequently digested with a mixture of RNase A and T1 and the protected fragments analyzed on denaturing polyacrylamide gels. Analysis of the gels shows a protected fragment of about 355 nt and another fragment of about 160 nt. See FIG. 28B.

The fact that primer extension using a primer (#73) at +80 bp produces a product of 90 NT in length argues that the 5' end of the transcript is located at position +1 bp. Primer extension from a primer in this region produces a product, so one would expect this also to be detected by the RNase protection assay. This primer is located in the 5' region of the RNase protection probe. The cDNA clone contains sequences present in the 3' end of the RNase protection probe and hence were expected to be protected in this assay. Since only one band is present on the gel which could account for both of these sequences, we are confident that the protected fragment is indeed the larger band and that the smaller single band is an artifact. If there were an intron in this region, fragments from each end would be present in the probe, and hence would be detectable on the gel. Of the two bands seen, one of them appears to represent the entire 5' region, therefore we do not believe that there is an intron located in this region.

Example 19
Complementation of E. coli TrpA Mutant with the Pith cDNA 8-2

E. coli strain CGSC strain 5531 from the E. coli Genetic Stock Center, Yale University (O. H. Smith lab strain designation, #M5004) with chromosomal markers glnA3, TrpA9825, 1-,IN(rrnD-rrnE), thi-1 as described in Mayer et al., Mol. Gen. Gentet., 137:131–142 (1975), was transformed with either the pith (TRpA) cDNA 8-2 or Bluescript plasmid (Stratagene) as described in Sambrook et al., supra. The transformants containing the TrpA cDNA 8-2 had the ability to grow without the presence of tryptophan on minimal medium whereas the transformants with the Bluescript (Stratagene) plasmid or untransformed control were not able to grow without tryptophan. The cells transformed with the maize TrpA gene grew very slowly with colonies visible after seven days growth at room temperature. All strains were grown on M9 minimal medium supplemented with 200 ug/ml glutamine, 0.01 ug/ml thiamine and with or without 20 ug/ml tryptophan. All transformants were checked for the presence of the appropriate plasmid by restriction enzyme analysis. Colonies growing in the absence of tryptophan all contained clone 8-2 containing the cDNA for the putative maize TrpA gene, as confirmed by Southern hybridization (data not shown). These results support the conclusion that this is the maize tryptophan synthase subunit A protein.

Example 20
Gene Expression

Figure 25B:
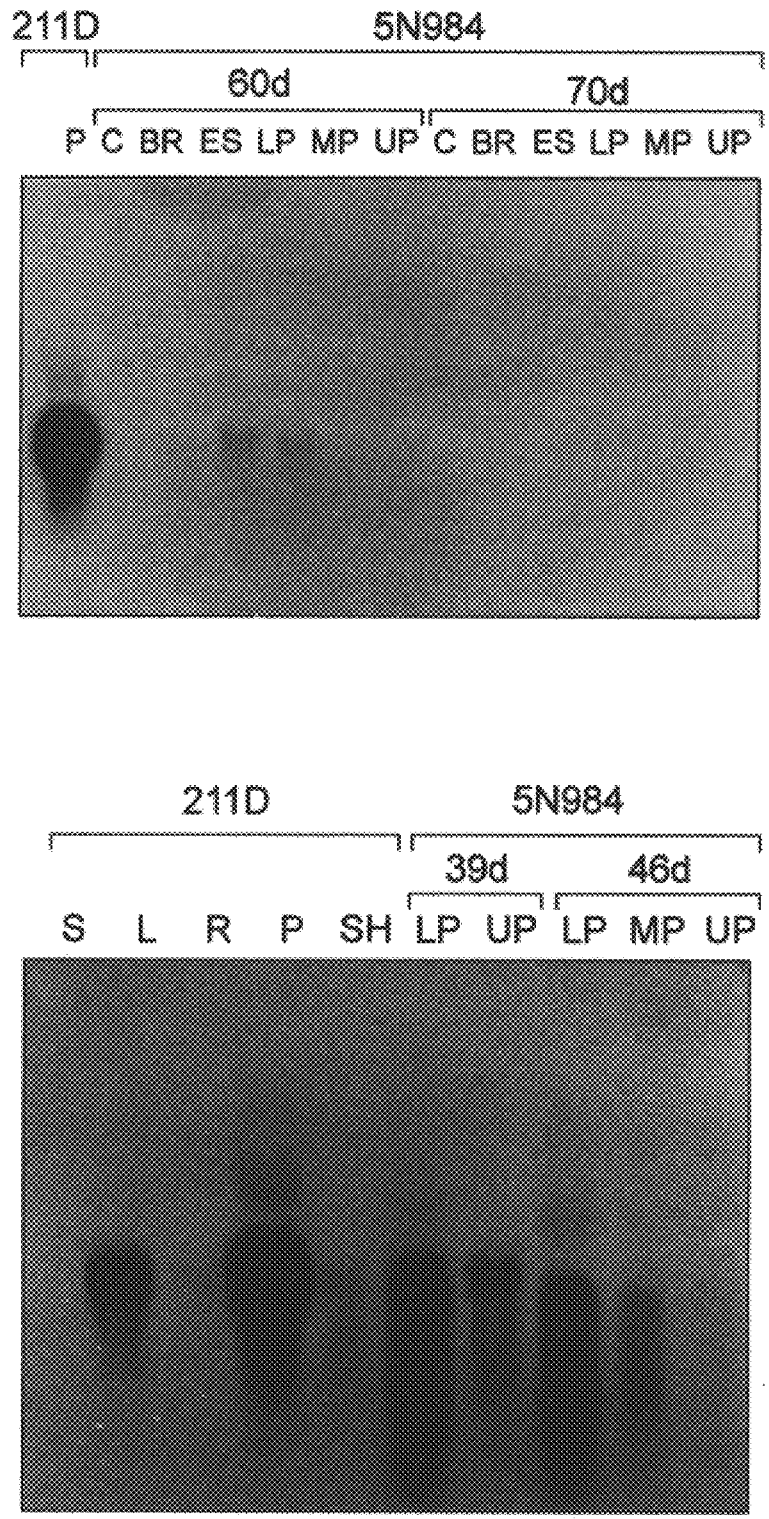
Figure 25D:
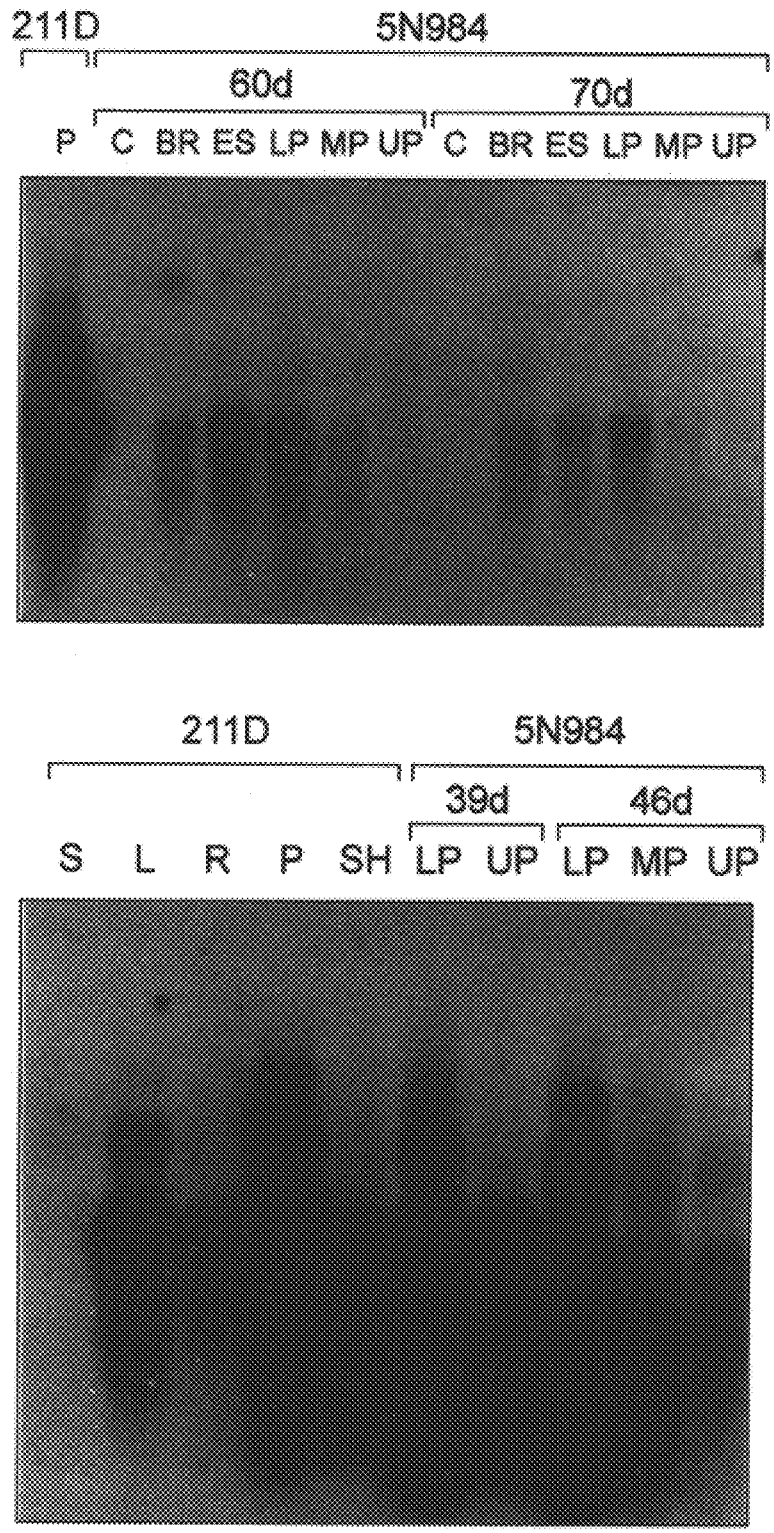
Figure 26:
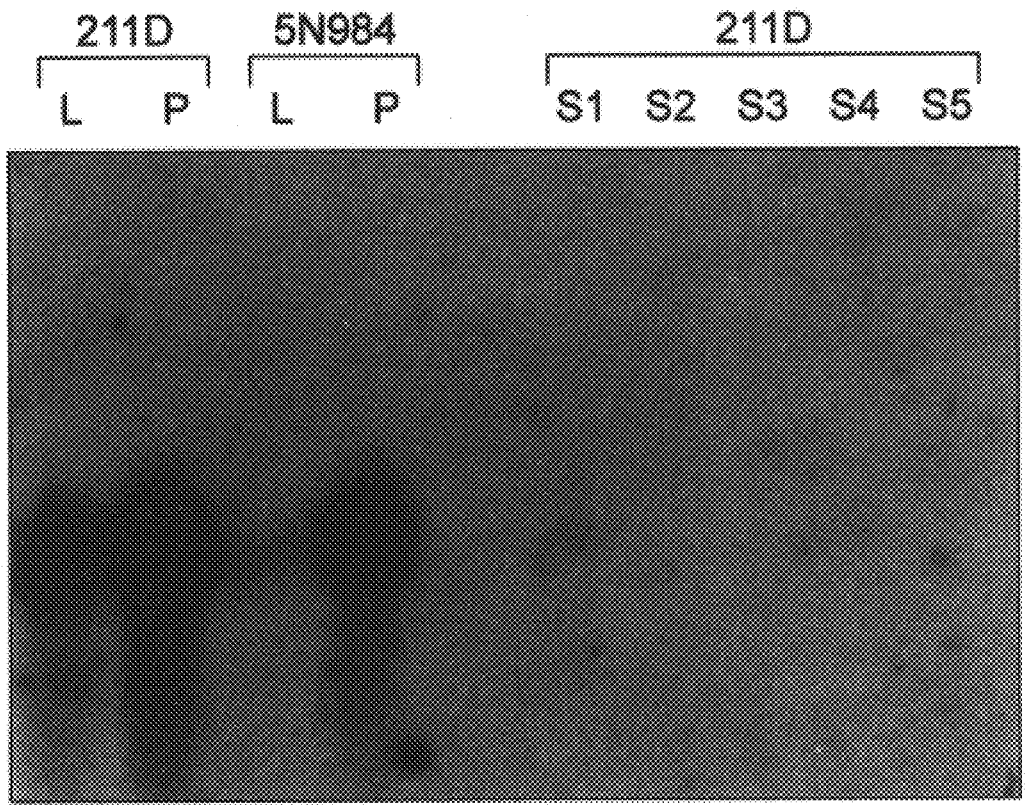
FIG. 26 is a Northern blot analysis, the two left lanes of which show the maize TrpA gene expression in the leaf (L) and pith (P) of Funk inbred lines 211D and 5N984. The five right lanes indicate the absence of expression in Funk 211D seed total RNA. S(1, 2,3, 4 and 5)=seed at 1, 2, 3, 4 and 5 weeks post pollenation. L=leaf; P=pith; S#=seed # weeks post pollenation.

The expression pattern of the pith-preferential gene throughout the plant was examined. Different maize genotypes were also examined for patterns of expression of this gene. The following tissues were used as the source of RNA for these studies: upper, middle, and lower pith, brace roots, ear shank, cob in genotype 5N984; upper, middle, lower pith, 10 day old leaves, 14 day old roots and pith from the entire plant in genotype 211D, and seed from genotype 211D which had been harvested at weekly intervals one to five weeks post-pollination. Lower pith is derived from, i.e. constitutes the two internodes above brace roots; middle pith is derived from the next three internodes; upper pith represents the last two internodes before the tassel in 60 and 70 day plants. Only two internodes were present in 39 day old plants and three internodes for 46 day old plants. Northern blot analysis shows that transcripts hybridizing with a probe derived from the pith cDNA accumulate rapidly in young pith and young leaf. As the age of the plant increases and one moves up the stalk, there is a significant decrease in the amount of transcript detected. See FIGS. 25A–D. At no time is message from this gene detected in seed derived RNA, either total RNA or poly A+RNA. See FIG. 26. Transcript is also detected in root, earshank, and sheath but not at the high levels detected in the pith and young leaf tissues. See FIGS. 25B, 25C. Some message is detected in brace roots, but only at a very low level. See FIG. 25D. Six maize undifferentiated callus lines were analyzed by northern blot analysis and no expression was found for this gene (data not shown) in any callus sample. The level of expression of this gene is extremely high since a very strong signal to a probe from TrpA gene 8-2 can be detected in pith and leaf as little as two hours after exposure of the blot to film (FIG. 25A). The amount of mRNA made is comparable to that derived from the maize phosphoenolpyruvate carboxylase gene disclosed in Hudspeth et al., Plant Mol. Biology, 12:579–589 (1989), another highly expressed maize gene. Hudspeth is incorporated herein by reference.

The expression pattern of this gene is not temporally constant. Expression is very high in the lower and middle pith of plants less than 60 days old and decreases rapidly near the top of the plant. As the plant reaches maturity, e.g. over 70 days old, the expression drops to nearly undetectable levels except in the lower pith and earshank. The accumulation of transcript in young leaf is nearly as high as that seen in lower pith but expression decreases rapidly and is undetectable in leaves over 40 days of age. Expression in leaf was found to be variable depending on the season when it is grown.

Examples 21–39 set forth below are directed to the isolation, characterization and expression analysis of a pollen-specific promoter according to the present invention.

Identification of Pollen-Specific Proteins

Example 21

Maize Plant Growth

Maize plants (*Zea mays* Funk inbred 211D) were grown from seed in a vermiculite/sand mixture in a greenhouse under a 16 hour light/8 hour dark regime.

Example 22

Total Pollen Protein Isolation

Mature pollen was isolated from maize plants at the time of maximum pollen shed. It was sieved to remove debris, frozen in liquid nitrogen, and a 3–4 ml volume of frozen pollen was ground in a mortar and pestle with an equal volume of 75–150 µm glass beads. 40 ml of grinding buffer (2 mM EDTA, 5 mM DTT, 0.1% SDS, 100 mM Hepes pH 8) was added and the mixture was ground again. The glass beads and intact pollen grains were pelleted by low speed centrifugation, and mixture was clarified by centrifugation at 10,000 g for 15 minutes. Protein was precipitated from the supernatant by addition of acetone to 90%.

Example 23

Pollen Exine Protein Isolation

Exine Protein was isolated from maize 211D shed pollen as described in Matousek and Tupy, J., Plant Physiology 119:169–178 (1985).

Example 24

Leaf Protein Isolation

Young leaves (about 60% expanded) were cut from the maize plant the midrib removed. Total protein was isolated as for pollen, except that the material was not frozen and grinding was in a Waring blender without glass beads.

Example 25

Kernel Protein Isolation

Ears with fully developed, but still moist kernels were removed from the plant and the kernels cut off with a scalpel. Total protein was isolated as for leaves.

Example 26

Gel Electrophoresis of Maize Proteins

Pollen, leaf and kernel proteins were separated on SDS polyacrylamide gels as described in Sambrook et al, Molecular Cloning, A Laboratory Manual, Cold Spring Harbor Laboratory Press: New York (1989). Following staining by Coomasie blue, protein bands from pollen, leaf and kernel were compared and abundant proteins of approximately 10 kD, 13 kD, 20 kD, 45 kD, 55 kD and 57 kD were determined to be pollen specific.

Identification of Pollen-Specific cDNA Clones

Example 27

Partial Sequence Determination of Pollen-Specific Proteins

Protein bands determined to be pollen-specific were purified by electroblotting from the polyacrylamide gel onto PVDF membrane (Matsudaira, P., J. Biol. Chem. 261:10035–10038 (1987)) or by reverse phase HPLC. N-terminal sequence of the purified proteins was determined by automated Edman egradation with an Applied Biosystems 470A gas-phase sequencer. Phenylthiohydantoin (PTH) amino acids were identified using an Applied Biosystems 120A PTH analyzer. To obtain internal sequence, proteins were digested with endoproteinase Lys-C (Boehringer Mannheim) in 0.1 M Tris-HCl, pH 8.5, for 24 hours at room temperature using an enzyme:substrate ratio of 1:10. Resulting peptides were isolated by HPLC using an Aquapore C-8 column eluted with a linear acetonitrile/isopropanol (1 :1 ratio) gradient (0 to 60%) in 0.1% TFA. Sequence of isolated Lys-C peptides was determined as above. The following sequences were determined for the 13 kD pollen-specific protein:

N-terminus: TTPLTFQVGKGSKPGHLILTPNVATI (SEQ ID NO: 74)
LysC 61: KPGHLILTPNVATISDVVIK (SEQ ID NO: 75)
LysC 54: SGGTRIADDVIPADFK (SEQ ID NO: 76)
LysC 49: EHGGDDFSFFLK (SEQ ID NO: 77)
LysC 43: EGPTGTWTLDTK (SEQ ID NO: 78)

Example 28

Synthesis of Oligonucleotide Probes for Pollen-Specific cDNAs

Regions of peptide sequence in the 13 kD protein with low codon redundancy were selected, and suitable oligonucleotide probes for the gene encoding these regions were synthesized on an Applied Biosystems 380A synthesizer. The following oligonucleotides were synthesized:

```
                                              (SEQ ID NO:79)
Oligo #51 5'-AA RTC RTC ABC ACC RTG YTC-3'
```

```
                                              (SEQ ID
                                              NO:80)
Oligo #58 5'-CC YTT NCC CAC YTG RAA-3'
``` where the columns of nucleotides represent bases that were incorporated randomly in equal proportions at the indicated position in the oligo. Oligo #51 encodes the amino acid sequence EHGGDDF (amino acids 1 to 7 of SEQ ID NO: 77) found in peptide LysC 49, and Oligo #58 encodes the amino acid sequence FQVGKG (amino acids 6 to 11 of SEQ ID NO: 74) found in peptide N-terminus. Use of these mixed oligonucleotides to screen a cDNA library for the pollen-specific gene will be described below.

Example 29
Construction of a Maize Pollen cDNA Library

Total maize RNA from maize 211D shed pollen was isolated as described in Glisen et al, Biochemistry 13:2633–2637 (1974). Poly A+mRNA was purified from total RNA as described in Sambrook et al. Using this mRNA, cDNA was prepared using a cDNA synthesis kit purchased from Promega, following protocols supplied with the kit. The EcoRI linkers were added to the cDNA and it was ligated into arms of the cloning vector lambda Zap, purchased from Stratagene and using the protocol supplied by the manufacturer. The ligation product was packaged in a lambda packaging extract also purchased from Stratagene, and used to infect E. coli BB4 cells.

Example 30
Isolation of Pollen-Specific cDNA Clones

The maize pollen cDNA library was probed using the synthetic oligonucleotides probes specific for the 13 kD protein gene, as described in Sambrook et al. Briefly, about 100,000 phage plaques of the pollen cDNA library were plated and lifted to nitrocellulose filters. The filters were probed using oligonucleotides #51 and #58 which had been 32P end-labeled using polynucleotide kinase. The probes were hybridized to the filters at low stringency (50 degrees C. in 1M NaCl, 10% dextran sulfate, 0.5% SDS), washed 30 minutes at room temperature and then 30 minutes at 45 degrees C. in 6×SSC, 0.1% SDS, and exposed to X-ray film to identify positive clones. Putative clones were purified through four rounds of plaque hybridization. Three classes of cDNA clones were isolated. Type I contained EcoRI fragments of 0.2 kb and 1.8 kb. Type II contained EcoRI fragments of 0.6 kb, 0.5 kb and 1.0 kb, and Type III contained an EcoRI fragment of 2.3 kb.

Example 31
Characterization of Pollen-Specific cDNA Clones

The EcoRI fragments of the Type II cDNA clone were subcloned into the plasmid vector pBluescript SK+, purchased from Stratagene. See FIG. 29. The 0.6 kb fragment in pBluescript was named II-.6, the 0.5 kb fragment in pBluescript was named II-.5 (later renamed pCIB3169) and the 1.0 kb fragment in pBluescript was named II-1.0 (later renamed pCIB3168). As will be described below, the 0.5 kb and 1.0 kb fragments encode the maize pollen-specific CDPK gene. RNA from anthers, pollen, leaf, root and silk was denatured with glyoxal, electrophoresed on a 1% agarose gel, transferred to nitrocellulose, and probed separately with the three EcoRI fragments that had been labeled with 32P by random primer extension as described in Sambrook et al, Molecular Cloning, A Laboratory Manual, Cold Spring Harbor Laboratory Press: New York (1989). The blots were exposed to X-ray film, and an mRNA band of approximately 1.5 kb was identified with the 0.6 kb fragment probe, while the 0.5 and 1.0 kb fragments hybridized to an approximately 2.0 kb mRNA. In all cases hybridization was only seen in the pollen RNA lane, with the exception that the 0.6 kb fragment showed a slight signal in anther mRNA. The conclusion from these data was that the original cDNA clone was a fusion cDNA molecules derived from two different mRNAs. The 0.6 kb fragment was a partial cDNA of a 1.5 kb pollen-specific mRNA, and this mRNA encodes the peptides LysC 49 and N-terminus. The 1.0 and 0.5 kb fragments comprise a partial cDNA of a 2.0 kb pollen-specific mRNA unrelated to the peptides and oligonucleotide probes used for probes. This conclusion was verified when the fragments were sequenced using the dideoxy chain termination method as described in Sambrook et al. The cDNA sequence is shown in FIG. 30 (SEQ ID NO: 20).

Example 32
Determination of Specificity of mRNA Expression

Figure 31:
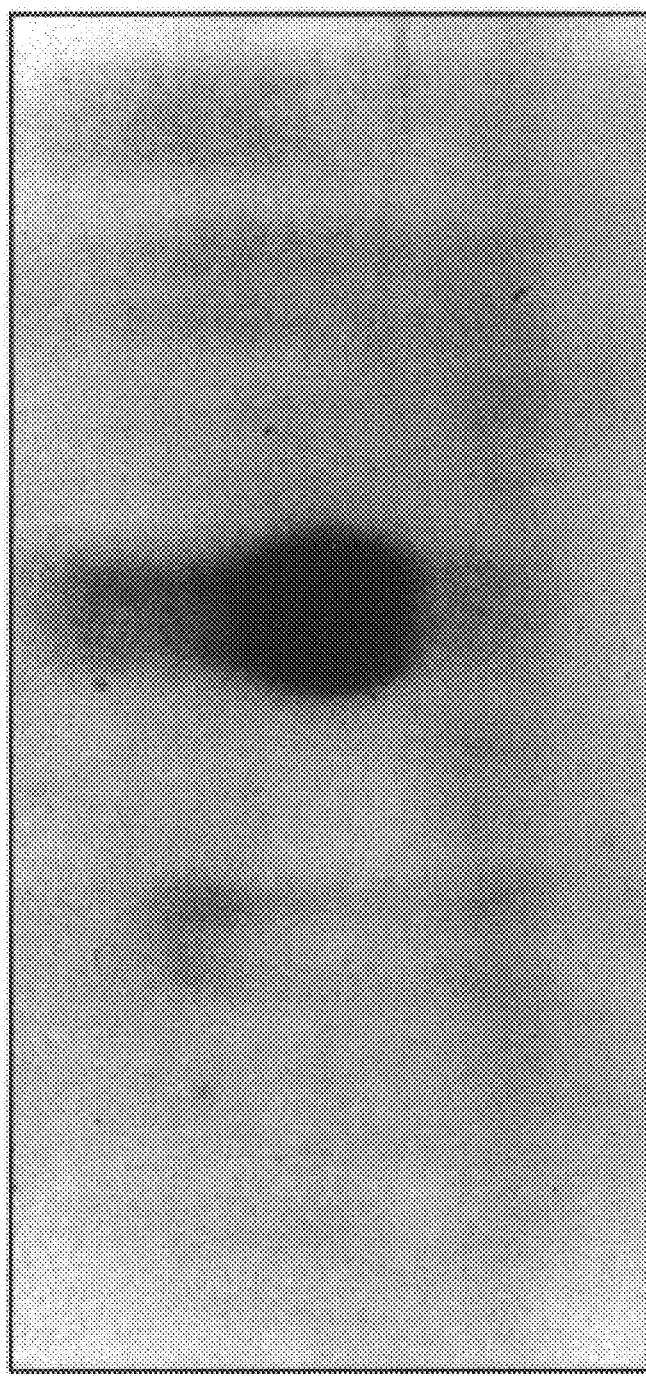
FIG. 31 illustrates the tissue-specific expression of the pollen CDPK mRNA. RNA from the indicated maize 211D tissues was denatured, electrophoresed on an agarose gel, transferred to nitrocellulose, and probed with the pollen CDPK cDNA 0.5 kb fragment. The mRNA is detectable only in the pollen, where a strong signal is seen.

To determine if the 2.0 kb RNA represented by cDNA clones pCIB3169 and pCIB3168 were present only in pollen, total RNA was isolated from maize 211D roots, leaves, pollen, anthers or silks. The RNAs were denatured with glyoxal, electrophoresed on a 1% agarose gel, transferred to nitrocellulose, and probed with 32P-labeled EcoRI insert from plasmid pCIB3168 or pCIB3169, all using standard techniques as described in Sambrook et al, Molecular Cloning, A Laboratory Manual, Cold Spring Harbor Laboratory Press: New York (1989). Exposure of this blot to photographic film demonstrates that the gene represented by these two clones is only transcriptionally active in the pollen (FIG. 31).

Identification of a Pollen-Specific Promoter

Example 33
Construction of a Maize Genomic DNA Library

Genomic DNA from maize line 211D young shoots was isolated as described in Shure et 1, Cell 35:225–233 (1983). The DNA was provided to Stratagene, where a genomic DNA library was constructed by cloning Sau3AI partially digested DNA into Stratagene's Lambda Dash cloning vector.

Example 34
Genomic DNA Blot Hybridization to Determine Gene Copy Number.

Genomic DNA from maize line 211 D was digested with a number of restriction enzymes, the individual digests electrophoresed on an agarose gel, transferred to nitrocellulose, and probed with 32P-labeled EcoRI insert from plasmid pCIB3168 (1.0 kb fragment), pCIB3169 (0.5 kb fragment) or clone II-.6 using standard techniques described in Sambrook et al. More than 10 bands were detected by the II-.6 probe on most digests, indicating that this cDNA is derived from a large, multigene family. Probing with the 1.0 kb fragment detected from 3 to 6 bands, and probing with the 0.5 kb fragment detected only from 1 to 3 bands which were a subset of those detected by the 1.0 kb fragment. Due to the smaller gene family size detected by the 1.0 kb and 0.5 kb fragments, it was decided to attempt to isolate the genomic clone corresponding to them.

Example 35
Isolation of a Pollen-Specific Genomic Clone

The Stratagene maize 211D genomic library was screened by probing plaque lifts with 32P labeled inserts from plasmid pCIB3168 (1.0 kb fragment) and pCIB3169 (0.5 kb fragment) using standard procedures as described in the Stratagene manual accompanying the library. Using this strategy, Lambda clone MG14 was isolated, and it hybridized to both probes. The 9.0 kb BamHI fragment of MG14, which also hybridized to both probes, was subcloned into the BamHI site of pBluescript SK+ to create plasmid pCIB379. 1800 bp of pCIB379, in the region corresponding to the cDNA sequence, was sequenced as described above. Comparison of the cDNA and genomic sequences showed only 91% identity. pCIB379 insert represents a related pollen-specific gene.

Figure 35B:
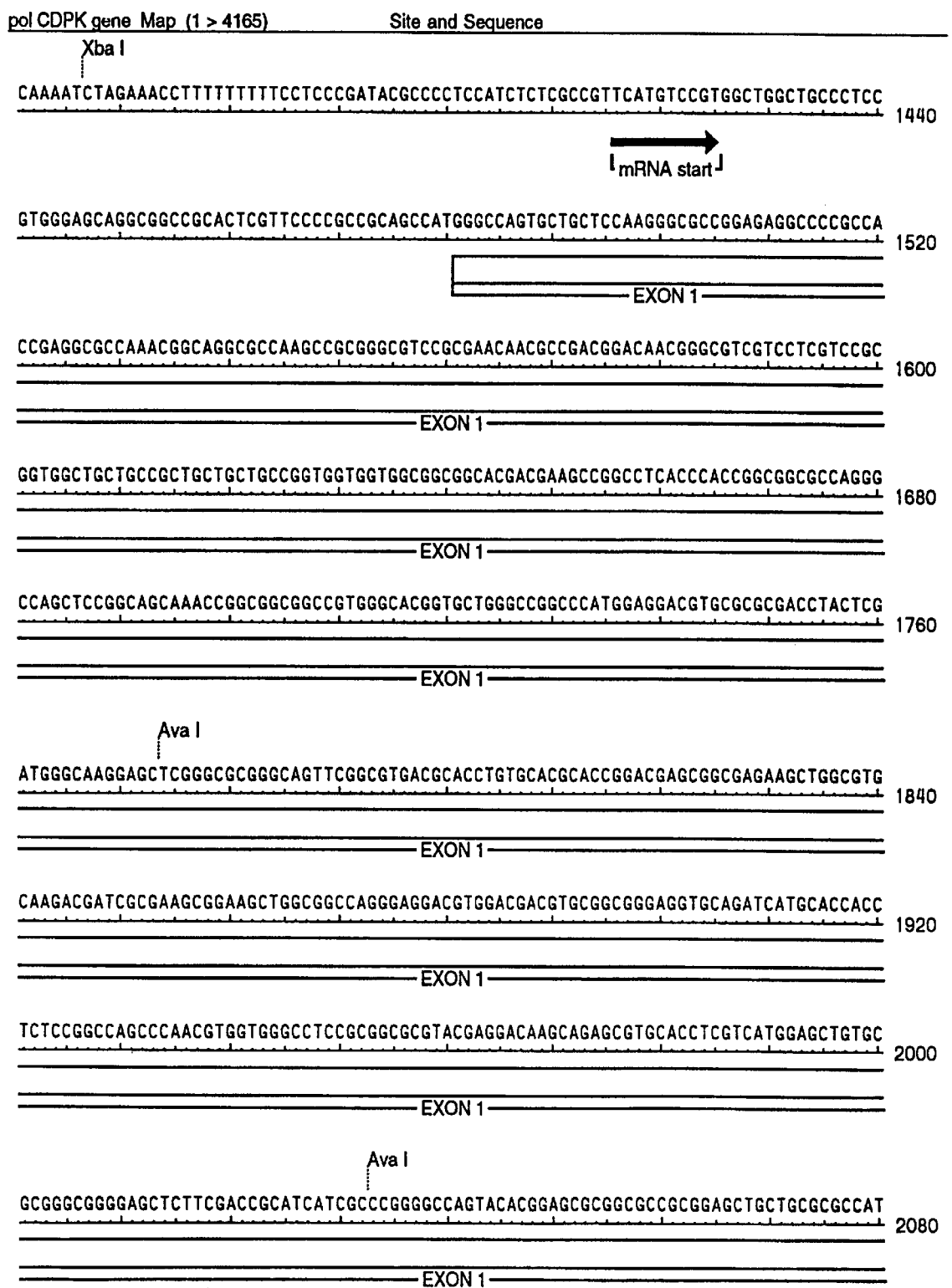
FIG. 35 illustrates the sequence of the maize pollen-specific CDPK gene (SEQ ID NO: 26). 1.4 kb of sequence prior to the mRNA start site is shown. The positions of the seven exons and six introns are depicted under the corresponding DNA sequence. The site of polyadenylation in the cDNA clone is indicated.
Figure 35D:
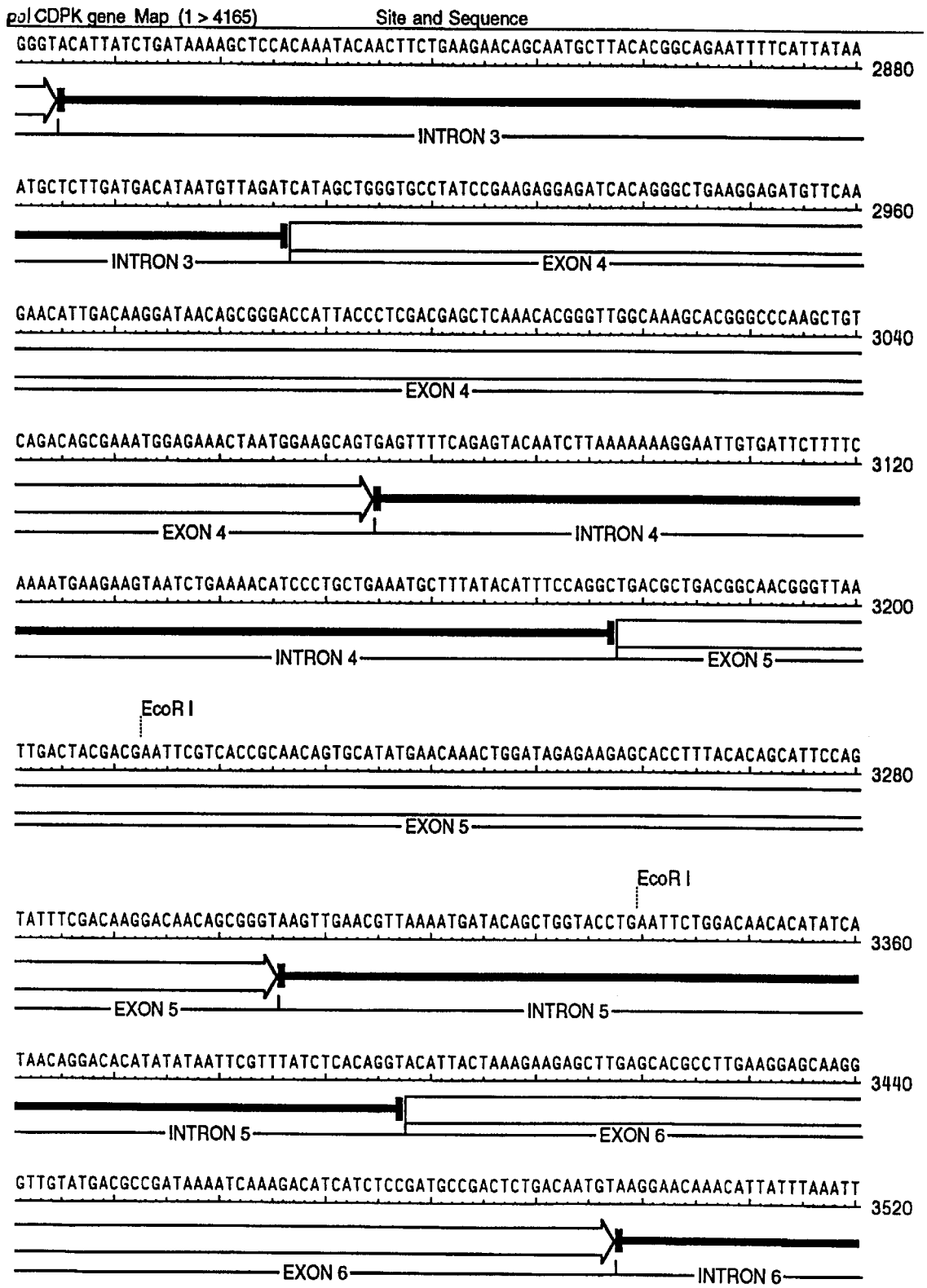

A second maize 211D genomic library was constructed in the vector lambda GEM-11, purchased from Promega, using the procedures described in the Promega manual. Screening this un-amplified library as above yielded clone GEM11–1, which hybridized to both 0.5 and 1.0 kb probes. The 20 kb HindIII fragment of GEM11–1, which also hybridized to both probes, was subcloned into the HindIII site of pBlue script SK+ to yield pCIB3166. The DNA sequence of 41. kb of pCIB3166 was determined (FIG. 35; SEQ ID NO: 26) and after accounting for six introns in the genomic clone, was 100% identical to the cDNA sequence of pCIB3168 and pCIB3169. Comparison of the pCIB3166 sequence to the Genbank/EMBL database revealed that the 5' portion, through the 3 exon, was 34.6% identical to rat calmodulin-dependent protein kinase II at the amino acid level (FIG. 32), while the fourth through seventh exons were 39.4% identical to human calmodulin. See FIG. 33. No other pollen-specific kinase has been described, and at the time this a protein combining kinase and calmodulin domains was unknown. Subsequently, Harper et al., Science 252:951–954 (1991) have disclosed the cDNA sequence of a similar protein from soybean, although this gene is not pollen-specific in expression. Comparison of the soybean calcium-Dependent Protein Kinase (CDPK) and the maize pollen CDPK reveals 38% identity at the amino acid level. See FIG. 34.

Example 36
Identification of the Promoter's Transcriptional Start Site by Primer Extension Oligonucleotide PE51, with the following sequence was synthesized as a primer.

5'-TGGCCCATGGCTGCGGCGGGGAACGAGTGCGGC-3' (SEQ ID NO: 81)

Primer extension analysis was carried out on polyA+ pollen mRNA as described in Metraux et al., PNAS USA 86:896–890 (1989). The transcription initiation site was determined to be between bases 1415 and 1425 on the partial sequence of pCIB3166 shown in FIG. 35.

Testing Promoter Function in Transgenic Plants

Example 37
Construction of Promoter Vectors for Plant Transformation

To demonstrate that the pollen CDPK promoter can drive expression of a linked gene in transgenic plants, a gene fusion of the pollen CDPK promoter to the Beta-glucuronidase gene of E. coli was constructed as follows. The 10 kb BamHI fragment from lambda GEM11-1 containing the first exon and part of the first intron of the pollen CDPK gene plus 9 kb upstream of the gene was subcloned into the BamHI site of pBluescript SK+ to create plasmid pCIB3167. The 2.3 kb BamHI-HindIII fragment from pCIB3167 was subcloned into the BamHI and HindIII sites of pBluescript SK+ to create plasmid pSK105. The pSK105 was digested with AvaI and HindIII, and the 1.75 kb HindIII-AvaI fragment was isolated on an agarose gel. A PCR reaction was run under standard conditions as described in Sambrook et al. using intact pSK105 as a template and the following primers:

42: 5'-AGCGGTCGACCTGCAGGCATGCGATCTG CACCTCCCGCCG-3' (SEQ ID NO: 82)
43: 5'-ATGGGCAAGGAGCTCGGG-3 (SEQ ID NO: 83)

The PCR reaction products were digested with AvaI and SalI and the resulting fragment isolated on an agarose gel. pBluescript SK+ was digested with HindIII and SalI. The 1.75 kb HindIII-AvaI fragment, PCR derived AvaI-SalI fragment, and pBluescript vector with HindIII and SalI ends were ligated in a three way ligation to create plasmid pSK 110.

A fusion of the promoter fragment in pSK110 to the Beta-glucuronidase (GUS) gene was created by digesting pSK 110 with HindIII and SalI, isolating the 1.9 kb fragment on an agarose gel and ligating it into HindIII and SalI sites of pCIB3054, to create plasmid pKL2, a plasmid derived from pUC19 containing the GUS gene followed by plant intron from the maize PEPC gene and a polyA signal from cauliflower mosaic virus. This promoter fusion was inactive in plants, probably due to the presence of out of frame ATG codons in the leader sequence preceding the GUS gene ATG.

A function fusion of the promoter was created by digesting pKL2 with XbaI and SalI to remove the previous fusion junction. A new fusion junction was produced in a PCR reaction using pSK105 as a template and the following primers:

SK50: 5'-CCCTTCAAAATCTAGAAACCT-3' (SEQ ID NO: 84)
SK49: 5'-TAATGTCGACGAACGGCGAGAGATGGA-3' (SEQ ID NO: 85)

The PCR product was digested with XbaI and SalI and purified on an agarose gel. The purified fragment was ligated into the XbaI and SalI sites of pKL2 to created plasmid pCIB3171. This plasmid contains a functional fusion of pollen CDPK promoter and GUS which directs expression the GUS gene exclusively in pollen.

To create a vector containing the pollen CDPK promoter-GUS fusion suitable for use in Agrobacterium tumefaciens-mediated plant transformation, the fusion gene was isolated from pCIB3171 by digestion with HindIII and SalI. The resulting fragment was ligated into the HindIII and SalI sites of pBI101 (purchased from Clontech) to create plasmid pCIB3175.

Example 38
Production of Transgenic Plants pCIB3175 was transformed into Agrobacterium tumefaciens containing the helper plasmid pCIB542, and the resulting culture used to transform leaf disks from tobacco shoot tip cultures as described by Horsch et al., Science 227:1229–1231 (1985) except that nurse cultures were omitted and selection was on 100 mg/l kanamycin. Transgenic plants were regenerated and verified for presence of the transgene by PCR.

Example 39
GUS Gene Expression Analysis

Pollen from primary transformants and their progeny were analyzed histochemically for expression of the GUS gene as described by Guerrero et al., Mol. Gen. Genet. 224:161–168 (1990). The percentage of pollen grains expressing the GUS gene, as demonstrated by blue staining in the X-gluc buffer, is shown in the table below.

| Plant Number | % Blue Pollen |
| --- | --- |
| PP1-51 | 28% |
| PP1-54 | 54% |
| PP1-55 | none |
| PP1-61 | very few |
| PP1-63 | 51% |
| PP1-67 | 15% |
| PP1-80 | 10% |
| PP1-83 | 12% |

Primary transformants in which a single pollen CDPK promoter-GUS gene was integrated would produce a maximum 50% GUS positive pollen due to segregation of the single gene. Flouometric GUS assays were done on pollen, stem, root, leaf and pistil tissue of selected plants to demonstrate the specificity of pollen CDPK promoter expression. Assays were performed as described in Jefferson, Plant Mol. Biol. 14:995–1006(1990), and GUS activity values are expressed as nmoles MU/ug protein/minute.

| Plant number | Tissue | GUS Activity | Untransformed Net GUS Activity | Plant GUS Activity |
|---|---|---|---|---|
| PP1-51 | stem | 0.01 | 0.02 | 0 |
|  | leaf | 0 | 0 | 0 |
|  | root | 0.15 | 0.10 | 0.05 |
|  | pistil | 0.02 | 0.01 | 0.01 |
|  | pollen | 0.24 | 0.02 | 0.22 |
| PP1-54 | stem | 0.01 | 0.02 | 0 |
|  | leaf | 0 | 0 | 0 |
|  | root | 0.13 | 0.1 | 0.03 |
|  | pistil | 0.01 | 0.01 | 0 |
|  | pollen | 0.60 | 0.02 | 0.58 |
| PP1-63 | stem | 0.01 | 0.02 | 0 |
|  | leaf | 0 | 0 | 0 |
|  | root | 0.07 | 0.1 | 0 |
|  | pistil | 0.01 | 0.01 | 0 |
|  | pollen | 0.57 | 0.02 | 0.55 |

Examples 40–50 are directed primarily to the preparation of chimeric constructs, i.e. recombinant DNA molecules, containing constitutive, tissue-preferred, or tissue-specific promoters operably linked to an instant B.t. gene, insertion of same into vectors, production of transgenic platns containing the vectors, and analysis of expression levels of B.t. proteins of the transgenic plants.

Example 40

CONSTRUCTION OF MAIZE OPTIMIZED BT TRANSFORMATION VECTORS

To demonstrate the effectiveness of the synthetic Bt cryIA(b) gene in maize, the PepC and pith specific promoters are fused to the synthetic Bt cryIA(b) gene using PCR. Oligomers designed for the PCR fusions were:

(PEPC)

KE99A28=5'-TGCGGTTACC GCCGATCACATG-3' (SEQ ID NO: 86)

KE97A28=5'-GCGGTACCGC GTCGACGCGG ATCCCGCGGC GGGAAGCTAAG-3' (SEQ ID NO: 87)

(PITH)

KE100A28=5'-GTCGTCGACC GCAACA-3' (SEQ ID NO: 88)

KE98A28=5'-GCGGTACCGC GTTAACGCGG ATCCTGTCCG ACACCGGAC-3' (SEQ ID NO: 89)

KE104A28=5'-GATGTCGTCG ACCGCAACAC-3' (SEQ ID NO: 90)

KE103A28=5'-GCGGTACCGC GGATCCTGTC CGACACCGGA CGGCT-3' (SEQ ID NO: 91)

PCR primers are designed to replace the Nco I sites in the 5' untranslated leader region of each of these tissue specific genes (containing ATG translational start sites) with Bam HI sites to facilitate cloning of the synthetic cryIA(b) gene into this Bam HI site. Subsequent construction of vectors containing the tissue specific promoters fused to the synthetic cryIA(b) gene and also containing the 35S:PAT:35S marker gene involves several intermediate constructs.

1. pCIB4406 (35S:synthetic-cryIA(b):pepC ivs#9:35S)

pCIB4406 contains the 2 Kb Bam HI\Cla I synthetic cryIA(b) gene fused with the CaMV 35S promoter (Rothstein et al., Gene 53:153–161 (1987)). The gene also contains intron #6 derived from the maize PEP carboxylase gene (ivs#9) in the 3' untranslated region of the gene, which uses the CaMV 3' end. (PNAS USA, 83:2884–2888 (1986), Hudspeth et al., Plant Molecular Biology, 12: 579–589 (1989)). pCIB4406 is ligated and transformed into the "SURE" strain of *E. coli* cells (Stratagene, La Jolla, Calif.) as described above. One mutation is found in pCIB4406's cryIA(b) gene at amino acid #436 which resulted in the desired the being changed to a Leu. pCIB4406 is fully active against European corn borer when tested in insect bioassays and produces a CryIA(b) protein of the expected size as determined by western blot analysis.

2. pCIB4407 (35S:synthetic-cryIA(b):pepC ivs#9:35S +35S:PAT:35S)

pCIB4407 is made from an approximately 4 Kb Hind III\Eco RI fragment containing the 35S:PAT:35S gene, and the 3.1 Kb\Hind HIII\Eco RI 35S:synthetic-cryLA(b):35S gene from pCIB4406. pCIB4407 is ligated and transformed into "SURE", DH5alpha, and HB101 strains of *E. coli* using standard procedures (Sambrook et al.). The synthetic cryIA (b) gene has the same properties as its precursor pCIB4406.

3. pCIB4416 (35S:synthetic-cryIA(b):pepC ivs#9:35S +35S:PAT:35S+35S:Adh intron:GUS:35S.)

pCIB4407 is cut with Eco RI and treated with calf intestinal alkaline phosphatase (CIP) under standard conditions (Sambrook et al.) to produce an about 7.2 Kb fragment that is ligated with a 3.4 Kb Eco RI 35S:Adh\GUS:35S fragment to produce pCIB4416. Ligations and transformations into "SURE" cells is as described above. The synthetic cryIA(b) gene in pCIB4416 has the same properties as the gene in pCIB4406.

4. pCIB4418 (35S:synthetic-cryIA(b):pepC ivs#9:35S)

pCIB4406 is digested with Apa I and Bam HI and treated with CIP. pCIB4406 is digested with Bam HI and Nsp I. pBS123#13 is digested with Nsp I and Apa I. A three-way ligation is made consisting of a 4.3 Kb Apa I\Bam HI fragment from pCIB4406, a 1.3 Kb Bam HI\Nsp I fragment from pCIB4406, and a 170 bp Nsp I\Apa I fragment from pBS 123#13 to form pCIB4418. The host *E. coli* strain for pCIB4418 is HB 101.

5. pCIB4419 (35S:synthetic-cryIA(b):pepC ivs#9:35S+ 35S:PAT:35S+35S:Adh intron:GUS:35S.)

pCIB4416 and pCIB4418 are digested with Bst E II and Eco NI and fragments of pClB4416 are treated with CIP. A 9.1 Kb fragment from pCIB4416 ligated to a 1.4 Kb fragment from pCIB4418 to form pCIB4419. pCIB4419 transformed in HB101 competent *E. coli* cells demonstrates full activity in insect bioassays against European corn borer.

6. pCIB4420 (Pith:synthetic-cryIA(b):PEPC ivs#9:35S+ 35S:PAT:35S)

Intermediate constructs in making pCIB4420 are pBTin1, pBtin2, p4420A and pBtin3. pBtin1 (pith promoter:second half of the synthetic Bt gene+35S:PAT:35S) is made by ligating the 2.1 Kb Xba I\Nco I pith promoter fragment from plasmid pith(3-1) with a 5.2 Kb Xba I\Nco I fragment from pCIB4407. pBtin2 is an intermediate construct containing the pith promoter modified with a 210 bp PCR fragment made using primers KE100A28 and KE98A28 listed above. The PCR reaction mix contains approximately 100 ng of a 2.1 Kb Bam HI\Nco I pith promoter fragment with 100 pmol of each oligomer, 200 nM of each dNTP, 1×buffer (Cetus) and 2.5 units of thermal stable polymerase. Since the Tm is relatively low (between 40° and 50° C.), PCR reactions are run with the following parameters:

denaturation cycle: 94° C. for 1 minute annealing cycle: 37° C. for 1 minute extension cycle: 72° C. for 45 seconds (+3 seconds per cycle)

number of cycles: 25

PCR reactions are treated with proteinase K as described above prior to cutting with Sal I\Kpn I followed by phenol\chloroform extraction and ethanol precipitation as described above. The 210 bp fragment is purified on a 2% Nusieve gel and extracted from the gel using Millipore's filter units. The 210 bp Sal I\Kpn I fragment is ligated to the 4.9 Kb Sal I\Kpn I fragment from pith(3–1) to make pBtin2. p4420A (pith:synthetic-Bt:Pep intron:35S+35S:PAT:35S) is made with a three-way ligation consisting of a 700 bp Nsi I\Bam HI fragment from pBtin2, a 1.8 Kb Bam HI\Bst E II fragment from pCIB4418, and a 5.9 Kb Bst E II\Nsi I fragment from pBtin 1. After p4420A is made three mutations are discovered in pBtin2. A second PCR fragment is made to modify the Nco I site in the pith leader using primers KE104A28 and KE103A28 with Tm values around 65° C. The PCR reaction mix is identical to that listed above with the addition of glycerol to 20% to reduce mutations in G+C rich areas (Henry et al., Plant Molecular Biology Reporter 9(2):139–144, 1991). PCR parameters are as follows:

File I: 94° C.: 3 minutes, 1 cycle

File II: 60° C.: 1 minute

94° C.: 1 minute 25 cycles

File III: 72° C.: 5 minutes, 1 cycle

PCR reactions are treated as above and cut with restriction endonucleases Sal I and Kpn I. The 210 bp Sal I\Kpn I PCR (glycerol in the reaction) fragment is ligated to the 4.9 Kb Sal I\Kpn I fragment from plasmid pith(3–1) to make pBtin3. Sequence data on pBtin3-G#1 shows this PCR generated fragment to be correct.

pBtin3-G#1 is used to make pCIB4420 (also called p4420B "G#6"). pCIB4420 is constructed with a three-way ligation using the 700 bp Nsi I\Bam HI fragment from pBtin3-G#1, a 1.8 Kb Bam HI\Bst E II fragment from pCIB4418, and a 5.9 Kb Bst E II\Nsi I fragment from pBtin1. pCIB4420 is used in mesophyll protoplast experiments and demonstrates full activity of the synthetic cryIA (b) gene against European corn borer.

7. pCIB4413 (PEPC:synthetic-Bt (Phe mutation):PEPC intron:35S.) A fusion fragment is generated by PCR using primers KE99A28 and KE97A28 with a 2.3 KB Hind III\Sal I template from pGUS4.5. The PCR mix contains the same concentration of primers, template, dNTPs, salts, and thermal stable polymerase as described above. PCR reaction parameters are:

denaturation cycle: 94° C. for 1 minute annealing cycle: 55° C. for 1 minute extension cycle: 72° C. for 45 seconds (+3 seconds per cycle)

number of cycles: 30

After completion, PCR reactions are treated with proteinase K followed by phenol\chloroform extraction and ethanol precipitation as described above prior to cutting with restriction endonucleases Bam HI and Bst E II.

pCIB4413 is made with a three-way ligation using the 210 bp Bam HI\Bst E II PCR fragment, a 4.7 Kb Bam HI\Hind III fragment from pCIB4406, and a 2.2 Kb Hind III\Bst E II fragment from pGUS4.5.

8. pCIB4421 (PEPC:synthetic-cryIA(b):PEPC intron:35S.) pCIB4421 is made to replace the synthetic cryIA(b) gene containing the Phe mutation in pCIB4413 with the synthetic cryIA(b) gene from pCIB4419. pCIB4421 is made by ligating a 5.2 Kb Bam HI\Sac I fragment from pCIB4413 with a 1.9 Kb Bam HI\Sac I fragment from pCIB4419.

9. pCIB4423 (PEPC:synthetic-cryIA(b):PepC intron:35S+35S:PAT:35S)

The 2.4 Kb Bam HI\Hind III PEPC promoter fragment from pCIB4421 is ligated to the 6.2 Kb Bam HI\Hind III fragment in pCIB4420 to make pCIB4423. The Hind III site is deleted by exonucleases in the cloning of pCIB4423. pCIB4423 contains the synthetic cryIA(b) gene under the control of the PEPC promoter, and the PAT gene under the control of the 35S promoter.

10. Synthetic cryIA(b) gene in Agrobacterium strains:

Agrobacterium strains made with the synthetic cryIA(b) gene allow transfer of this gene in a range of dicotyledenous plants. Agrobacterium vector pCIB4417 contains the 3.3 Kb Hind III\Eco RI 35S:synthetic-CryIA(b):PepC:ivs#9:35S fragment from pCIB4406 (Phe mutation) ligated to the 14 Kb Hind III\Eco RI fragment from pBI101 (Clontech). Using electroporation, pCIB4417 is transferred into the *A. tumefaciens* strain LBA4404 (Diethard et al., Nucleic Acids Research, Vol 17:#16:6747, 1989.).

200 ng of pCIB4417 and 40 ul of thawed on ice LBA4404 competent cell are electroporated in a pre-cooled 0.2 cm electroporation cuvette (Bio-Rad Laboratories Ltd.). Using Gene Pulser-TM with the Pulse Controller unit (Bio-Rad), an electric pulse is applied immediately with the voltage set at 2.5 kV, and the capacity set at 25 uF. After the pulse, cells are immediately transferred to 1 ml of YEB medium and shaken at 27° C. for 3 hours before plating 10 ul on ABmin:Km50 plates. After incubating at 28° C. for approximately 60 hours colonies are selected for miniscreen preparation to do restriction enzyme analysis. The final Agrobacterium strain is called pCIB4417:LBA4404.

Example 41

ELISA ANALYSIS OF TRANSFORMED MAIZE PROTOPLASTS

The presence of the cryIA(b) toxin protein is detected by utilizing enzyme-linked immunosorbent assay (ELISA). ELISAS are very sensitive, specific assays for antigenic material. ELISA assays are useful to determine the expression of polypeptide gene products. Antiserum for these assays is produced in response to immunizing rabbits with gradient-purified Bt crystals (Ang et al., Applied Environ. Microbiol., 36:625–626 (1978)) solubilized with sodium dodecyl sulfate. ELISA analysis of extracts from transiently transformed maize cells is carried out using standard procedures (see for example Harlow, E., and Lane, D. in "Antibodies: A Laboratory Manual", Cold Spring Harbor Laboratory Press, 1988). ELISA techniques are further described in Clark et al., Methods in Enzymology, 118:742–766 (1986); and Bradford, Anal. Biochem., 72:248 (1976). Thus, these procedures are well-known to those skilled in the art. The disclosure of these references is hereby incorporated herein by reference.

ELISA assays are performed to detect the production of CryIA(b) protein in maize protoplasts. Protein produced is reported below as ng of Bt per mg total protein (ng Bt/mg). Each construct was tested twice.

| | |
|---|---|
| pCIB3069 | No detectable Bt (both tests) |
| pCIB4407 | 21,900 ng Bt/mg total protein,<br>21,000 ng Bt/mg total protein |

The transformed maize cells produce high levels, on the order of approximately 20,000 ng of Bt CryIA(b) protein per mg total soluble protein, of the Bt IP when transformed with the maize optimized Bt gene. The level of detection of these ELISA based assays is about 1 to 5 ng CryIA(b) protein per mg protein. Therefore, the maize optimized Bt gene produces as much as approximately a 20,000 fold increase in expression of this protein in maize cells.

Example 42

ASSAY OF EXTRACT FROM TRANSFORMED PROTOPLASTS FOR INSECTICIDAL ACTIVITY AGAINST EUROPEAN CORN BORER

Western blot analysis is also performed using extracts obtained from maize cells which had been transiently transformed with DNA to express the maize optimized gene. When examined by western blots, this protein appears identical with the protein produced in *E. coli*. In contrast, as demonstrated in Example 6 above, no detectable Bt cryIA(b) insecticidal protein is produced by maize cells transformed with comparable vectors attempting to express the native Bt derived coding region.

Qualitative insect toxicity testing can be carried out using harvested protoplasts. Suspensions are prepared for each replicate tested in all bioassays. A replicate is considered positive if it causes significantly higher mortality than the controls. For example, replicates are tested for their activity against insects in the order Lepidoptera by using the European corn borer, *Ostrinia nubilalis*. One-hundred μl of a protoplast suspension in 0.1% Triton X-100 is pipetted onto the surface of artificial Black cutworm diet, (Bioserv, Inc., Frenchtown, N.J.; F9240) in 50 mm×10 mm snap-cap petri dishes. After air drying 10 neonatal larvae are added to each plate. Mortality is recorded after about 4 days. When this protein is fed to European corn borers, it produces 100% mortality.

Example 43

EXPRESSION OF SYNTHETIC BT IN MAIZE MESOPHYLL PROTOPLASTS

The general procedure for the isolation of corn mesophyll protoplasts is adapted from Sheen et al., The Plant Cell, 2:1027–1038 (1990). The protoplast transformation system used in Sheen et al. is modified by using PEG mediated transformation, rather than electroporation. That procedure, as well as changes made in the isolation procedure, is described below. Maize Mesophyll Protoplast Isolation/Fransformation 1. Sterilize and germinate corn seeds for leaf material. Seedlings are grown in the light at 25° C.
2. Surface sterilize leaf pieces of 10–12 day old seedlings with 5% Clorox for 5 minutes followed by several washes with sterile distilled water.
3. Aliquot enzyme solution (see recipe below); 25 ml/dish (100×25 mm petri dish).
4. Remove any excess water from leaves and place 6–8 2 inch pieces in each dish of enzyme. 14 plates are usually set up with the leaf material from about 100 seedlings.
5. Cut leaves in longitudinal strips as thin as possible (2–5 mm).
6. Shake slowly at 25° C. for 6.5 to 7 hours. Cover plates so that incubation takes place in the dark.
7. Before filtering protoplasts, wash 100 um sieves with 10 ml 0.6 M mannitol. Pipet protoplasts slowly through sieves. Wash plates with 0.6 M mannitol to gather any protoplasts left in the dishes.
8. Pipet filtered liquid carefully into 50 ml sterile tubes. Add equal volumes of 0.6 M mannitol to dilute.
9. Spin for 10 minutes at 1000 rpm/500 g in table-top centrifuge (Beckman Model TJ-6).
10. Remove enzyme solution and discard. Resuspend pellets carefully in 5 ml mannitol. Pool several pellets. Bring volume to 50 ml with 0.6 M mannitol and spin.
11. Resuspend to a known volume (50 ml) and count.
12. After counting and pelleting, resuspend protoplasts at 2 million/ml in resuspending buffer (recipe below). Allow ppts to incubate in the resuspending buffer for at least 30 min before transformation.

Transformation:

1. Aliquot plasmids to tubes (Fisherbrand polystyrene 17×100 mm Snap Cap culture tubes); at least three replicates per treatment; use equimolar amounts of plasmids so that equal gene copy numbers are compared.
2. Add 0.5 ml protoplasts and 0.5 ml 40% PEG made with 0.6 M mannitol.
3. Shake gently to mix and incubate at 25° C. for 30 min.
4. Add protoplast culture media at 5 min intervals: 1,2,5 ml
5. Spin for 10 min at 1000 rpm/500 g.
6. Remove liquid from pellet and resuspend in 1 ml culture media (BMV media)
7. Incubate overnight at 25° C. in the dark.

Recipes:

Enzyme Solution
0.6 M mannitol
10 mM MES, pH 5.7
1mM $CaCL_2$
1mM $MgCl_2$
0.1% BSA
filter-sterilize To this solution, add the following enzymes:

1% Cellulase RS, and 0.1% Macerozyme R10

Wash Buffer: 0.6 M mannitol, filter-sterilize

Resuspending Buffer: 0.6 M mannitol, 20 mM KCl, filter-sterilize

Culture Media: BMV media recipe from:

Okuno et al., Phytopathology 67:610–615 (1977).
0.6 M mannitol
4 mM MES, pH5.7
0.2mM $KH_2PO_4$
1 mM $KNO_3$
1 mM $MgSO_4$
10 mM $CaCI_2$
1×K3 micronutrients
filter-sterilize ELISA analysis of transformed protoplasts is done one day after transformation. ELISA's are done as previously described. The following three experiments are done with maize inbred line 211D. Of course, other lines of maize may be used. 50 ug of plasmid pCIB4419 and equimolar amounts of other plasmids are used. Total soluble protein is determined using the BioRad protein assay. (Bradford, Anal.Biochem, 72:248 (1976).

Transformation Experiment:

Constructs tested:

1. pCIB4419 (Construct contains synthetic Bt under control of CaMV 35S promoter and 35S/PAT and 35S/GUS marker genes)
2. pCIB4420 (Construct contains synthetic Bt under control of Pith promoter and PAT marker gene)
3. pCIB4421 (Construct contains synthetic Bt under control of PEPC promoter)
4. pCIB4423 (Construct contains synthetic Bt under control of PEPC promoter and PAT marker gene) (PEPC:synthetic-cryIA(b):PepC intron:35S+35S:PAT:35S)

In the following experiments, 10 or 11 day old 211D seedlings are analyzed for production of the Bt CryIA(b) protein in the Biorad protein assay:

Experiment 1 (11 day seedlings):

| | |
|---|---|
| pCIB4419 | 15,000 ± 3,000 ng Bt/mg protein |
| pCIB4420 | 280 ± 65 ng Bt/mg protein |
| pCIB4421 | 9,000 ± 800 ng Bt/mg protein |

Experiment 2 (10 day seedlings):

| | |
|---|---|
| pCIB4419 | 5,000 ± 270 ng Bt/mg protein |
| pCIB4420 | 80 ± 14 ng Bt/mg protein |
| pCIB4421 | 1,600 ± 220 ng Bt/mg protein |

Experiment 3 (11 day seedlings):

| | |
|---|---|
| pCIB4419 | 21,500 ± 1,800 ng Bt/mg protein |
| pCIB4420 | 260 ± 50 ng Bt/mg protein |
| pCIB4421 | 11,900 ± 4,000 ng Bt/mg protein |
| pCIB4423 | 7,200 ± 3,400 ng Bt/mg protein |

The above experiments confirm that both the CaMV 35S and PEPC promoters express the synthetic Bt CryIA(b) protein at very high levels. The pith promoter, while less efficient, is also effective for the expression of synthetic CryIA(b) protein.

Example 44

STABLE EXPRESSION OF SYNTHETIC BT IN LETTUCE

The synthetic Bt gene in the Agrobacterium vector pCIB4417 is transformed into *Lactuca sativa* cv. Redprize (lettuce). The transformation procedure used is described in Enomoto et al., Plant Cell Reports, 9:6–9 (1990).

Transformation procedure:

Lettuce seeds are suface sterilized in 5% Clorox for 5 minutes followed by several washes in sterile distilled water. Surface-sterilized seeds are plated on half strength MS media (Murashige and Skoog, Physiol. Plant. 15:473–497 (1962)). Cotyledons of 6-day-old Redprize seedlings, grown under illumination of 3,000 l×16 hr at 25° C., are used as the explants for Agrobacterium infection. The base and tip of each cotyledon are removed with a scalpel. The explants are soaked for 10 minutes in the bacterial solution which have been cultured for 48 hours in AB minimal media with the apropriate antibiotics at 28° C. After blotting excess bacterial solution on sterile filter paper, the explants are plated on MS media (0.1 mg/l BA and 0.1 mg/l NAA) for 2 days. Explants are then transferred to selective media containing 500 mg/l carbenicillin and 50 mg/l kanamycin. The explants are subcultured to fresh media weekly. The growth chamber conditions are 16 hour 2,000 l×light at 25° C. After approximately 4 weeks, an ELISA is done on healthy looking callus from each of four plates being subcultured. The ELISA procedure is the same as described above for protoplasts; soluble protein is again determined by the Biorad assay described above.

Results:

| | |
|---|---|
| pCIB3021 (kan control) | 0 |
| pCIB4417 (plate 1) | 0 |
| pCIB4417 (plate 2) | 505 ng Bt/mg protein |

-continued

| | |
|---|---|
| pCIB4417 (plate 3) | 45 ng Bt/mg protein |
| pCIB4417 (plate 4) | 1,200 ng Bt/mg protein |

This example demonstrates that dicot plants can also show increased expression of the optimized insecticidal gene.

Example 45

Construction of pCIB4429.

pCIB4429 contains a preferred maize pollen-specific promoter fused with the maize optimized cryIA(b) gene. The pollen-specific maize promoter used in this construct was obtained from the plasmid pKL2, described in Example 37. The maize optimized cryIA(b) gene was obtained from plasmid pCIB4418, also described in Example 37.

pKL2 is a plasmid that contains a preferred maize pollen-specific promoter fused with the *E. coli* beta-glucuronidase gene. It was constructed from plasmids pSK1 10 and pCIB3054. pSK110 contains the pollen specific maize promoter. pCIB3054, a pUC19 derivative, contains the *E. coli* beta-glucuronidase (GUS) gene fused with the cauliflower mosaic virus (CaMV) 35S promoter. It's construction is described elsewhere in this application. This promoter can be removed from this plasmid by cutting with SalI/HindIII to yield a fragment containing the GUS gene, a bacterial ampicillin resistance gene and a ColEI origin of replication. A second fragment contains the CaMV 35S promoter.

pCIB3054 was cut with the restriction enzymes SalI and HindIII, using standard conditions, for 2 hours at room temperature. The reaction was then extracted with phenol/chloroform using standard conditions and the DNA recovered by ethanol precipitation using standard conditions. The recovered DNA was resuspended in buffer appropriate for reaction with calf intestinal alkaline phosphatase (CIP) and reacted with 2.5 units of CIP at 37° C. overnight. After the CIP reaction, the DNA was purified on an agarose gel using standard conditions described elsewhere in this application. pSK10 was cut with SalI/HindIII under standard conditions for 2 hours at room temperature and the DNA subsequently purified on an agarose gel using standard conditions. The recovered DNA fragments were ligated using standard conditions for two hours at room temperature and subsequently transformed into competent *E. coli* strain HB 101 cells using standard conditions. Transformants were selected on L-agar containing 100 μg ampicillin/ml. Transformants were characterized for the desired plasmid construct using standard plasmid mini-screen procedures. The correct construct was named pKL2.

To make pCIB4429, a three way ligation was performed using standard conditions known to those in the art. The three fragments ligated were:

1) a HindIII/(BamHI fragment from pCIB4418, of about 4.7 kb in size, containing the cryIA(b) gene, the bacterial ampicillin resistance gene, and the ColEI origin of replication
2) a HindIII/XbaI fragment from pKL2 of about 1.3 kb in size and containing the pollen specific promoter from maize
3) a PCR generated fragment derived from the pollen promoter with a BamHI site introduced downstream from the start of transcription. This fragment is approximately 120 bp and has ends cut with the restriction enzymes XbaI/BamHI.

The PCR fragment was generated using a 100 μl reaction volume and standard conditions described above. The primers used were:

SK50: 5'-CCC TTC AAA ATC TAG AAA CCT-3' (SEQ ID NO: 84)

KE127: 5'-GCG GAT CCG GCT GCG GCG GGG AAC GA-3' (SEQ ID NO: 92)

The above primers were mixed in a PCR reaction with plasmid pSK105, a plasmid that contains the pollen specific promoter from maize.

After the PCR reaction was complete, 10 μl of the reaction was run on an agarose gel, using standard condition, to make sure the reaction produced the expected size product. The remaining 90 μl was treated with proteinase K at a final concentration of 50 μg/ml for 30 min. at 37° C. The reaction was then heated at 65° C. for 10 min., then phenol/chloroform extracted using standard procedures. The DNA was recovered from the supernatant by precipitating with two volumes of ethanol using standard conditions. After precipitation, the DNA was recovered by centrifuging in a microfuge. The pellet was rinsed one time with 70% ethanol (as is standard in the art), briefly dried to remove all ethanol, and the pellet resuspended in 17 μl TE buffer. 2 μl of 10×restriction enzyme buffer was added as were 0.5 μl BamHI and 0.5 μl XbaI. The DNA was digested for 1 hour at 37° C. to produce a DNA fragment cut with XbaI/BamHI. After digestion with the restriction enzymes, this fragment was purified on an agarose gel composed of 2% NuSieve (FMC)/1% agarose gel. Millipore filter units were used to elute the DNA from the agarose using the manufacturer's specifications. After elution, the DNA was used in the three-way ligation described above.

After ligation, the DNA was transformed into competent E. coli strain HB 101 cells using standard techniques. Transformants were selected on L-agar plates containing ampicillin at 100 μg/ml. Colonies that grew under selective conditions were characterized for plasmid inserts using techniques standard in the art.

Figure 20:
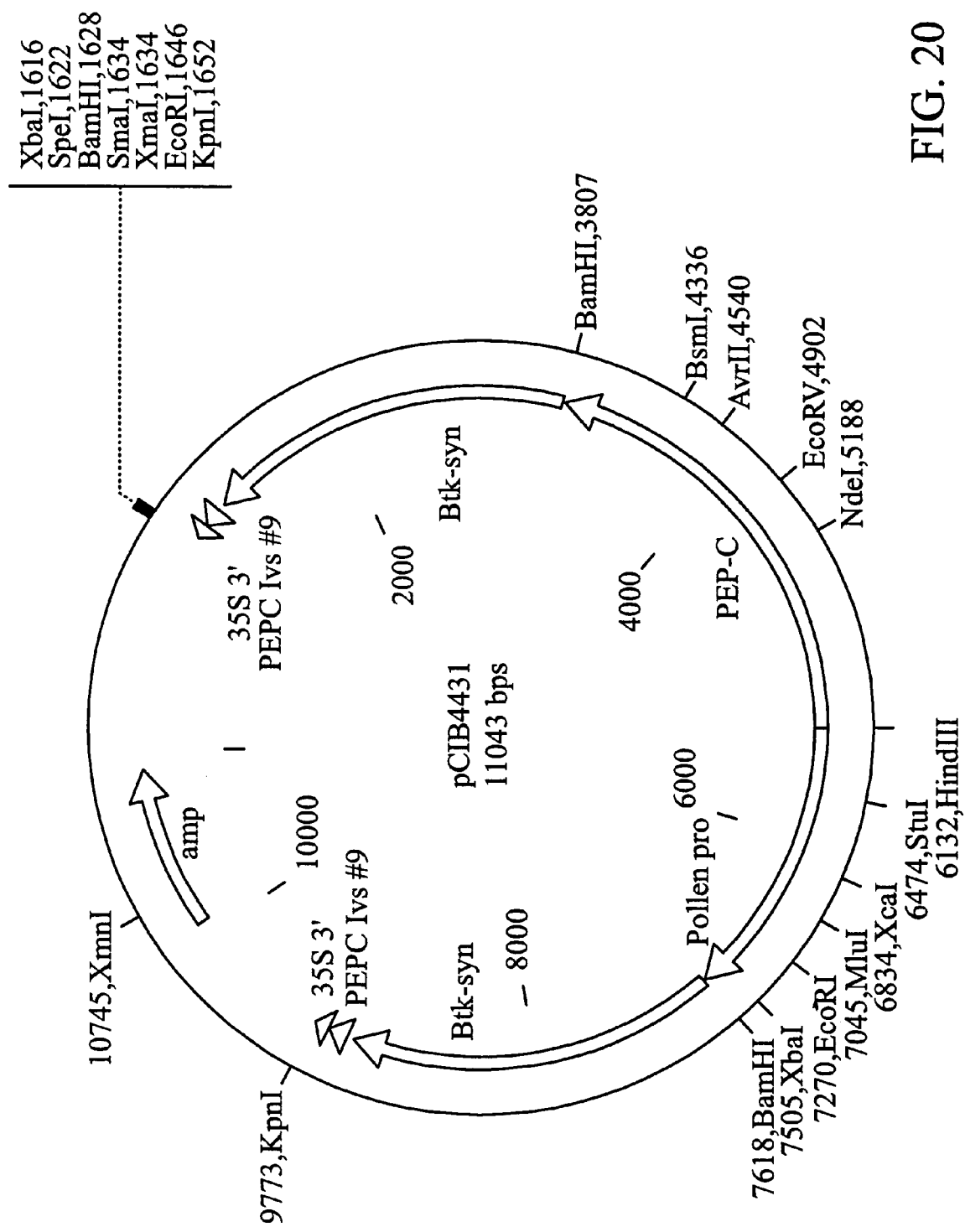
FIG. 20 is a map of pCIB4431.

Example 46
Construction of pCIB4431, a Vector for Tissue Specific Expression of the Synthetic CryIA(b) Gene in Plants.

pCIB4431 is a vector designed to transform maize. It contains two chimeric Bt endotoxin genes expressible in maize. These genes are the PEP carboxylase promoter/synthetic-cryIA(b) and a pollen promoter/synthetic-cryLA (b). The PEP carboxylase/cryIA(b) gene in this vector is derived from pCIB4421 described above. The pollen promoter is also described above. FIG. 20 is a map of plasmid pCIB4431. pCIB4431 was constructed via a three part ligation using the about 3.5 Kb Kpn I/Hind III fragment (containing pollen/synthetic-cryIA(b)from pCIB4429, the about 4.5 Kb Hind III/Eco RI (PEPC/synthetic-cryIA(b) and the about 2.6 Kb Kpn I/Eco RI fragment from the vector Bluescript.

Figure 21:
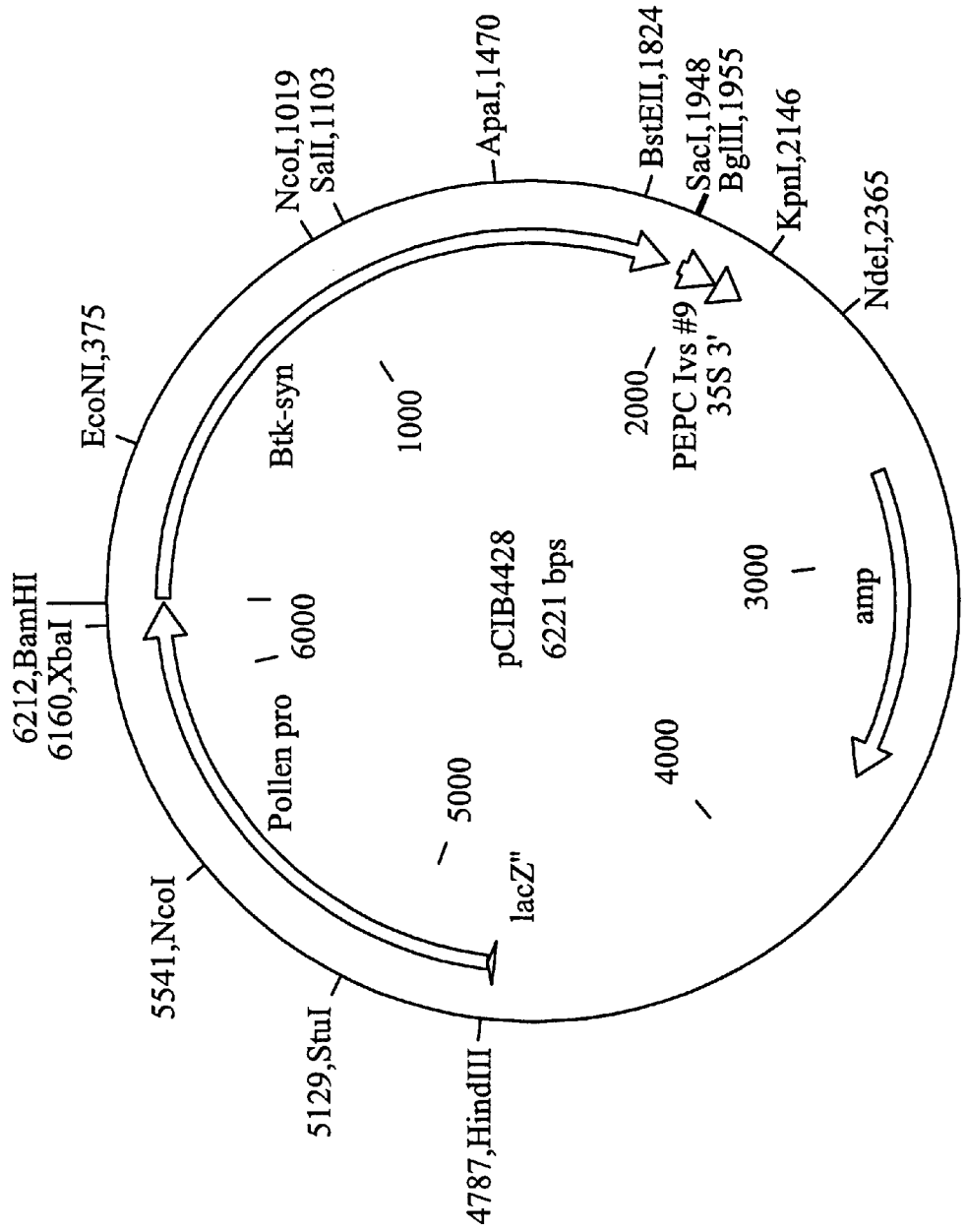
FIG. 21 is a map of pCIB4428.
Figure 22:
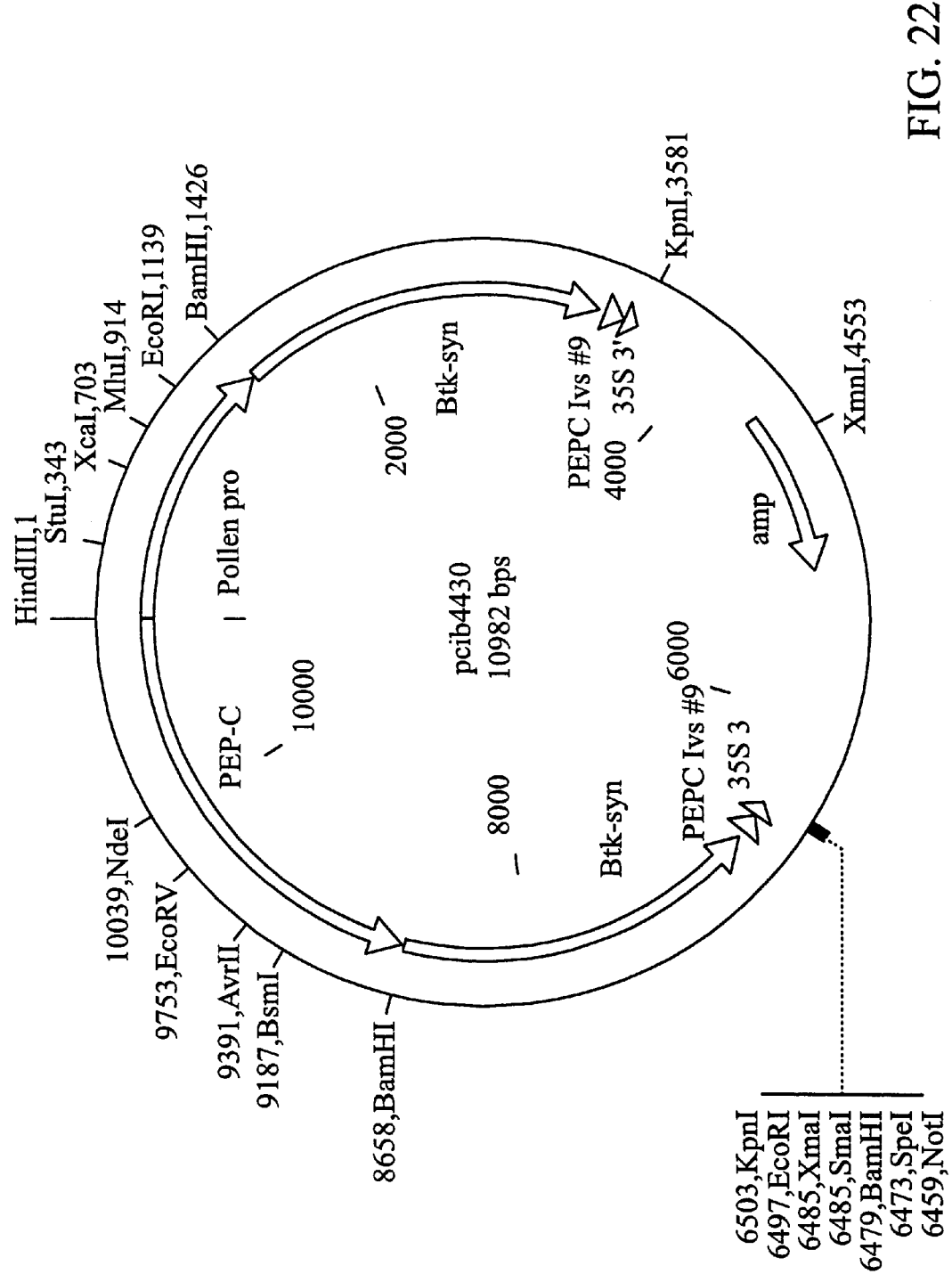
FIG. 22 is a map of pCIB4430.

Other vectors including the pollen promoter/synthetic CryIA(b) chimeric gene include pCIB4428 and pCIB4430. See FIGS. 21 and 22. pCIB4430 also contains the PEPC/synthetic-Bt gene described above.

Example 47
Production of Transgenic Maize Plants Containing the Synthetic Maize Optimized CryIA(b) Gene The example below utilizes Biolistics to introduce DNA coated particles into maize cells, from which transformed plants are generated.

Experiment KC-65

Production of transgenic maize plants expressing the synthetic cryIA(b) gene using a tissue-specific promoter.

Tissue

Immature maize embryos, approximately 1.5–2.5 mm in length, were excised from an ear of genotype 6N615 14–15 days after pollination. The mother plant was grown in the greenhouse. Before excision, the ear was surface sterilized with 20% Clorox for 20 minutes and rinse 3 times with sterile water. Individual embryos were plated scutellum side in a 2 cm square area, 36 embryos to a plate, on the callus initiation medium, 2DG4+5 chloramben medium (N6 major salts, B5 minor salts, MS iron, 2% sucrose, with 5 mg/l chloramben, 20 mg/l glucose, and 10 ml G4 additions (Table 1) added after autoclaving.

TABLE 1

| G4 Additions | |
|---|---|
| Ingredient | per liter medium |
| Casein hydrolysate | 0.5 gm |
| Proline | 1.38 gm |
| Nicotinic acid | .2 mg |
| Pyridoxine-HCl | .2 mg |
| Thiamine-HCl | .5 mg |
| Choline-HCl | .1 mg |
| Riboflavin | .05 mg |
| Biotin | .1 mg |
| Folic acid | .05 mg |
| Ca pantothenate | .1 mg |
| p-aminobenzoic acid | .05 mg |
| B12 | .136 μg |

Bombardment

Tissue was bombarded using the PDS-1000He Biolistics device. The tissue was placed on the shelf 8 cm below the stopping screen shelf. The tissue was shot one time with the DNA/gold microcarrier solution, 10 μl dried onto the macrocarrier. The stopping screen used was hand punched at ABRU using 10×10 stainless steel mesh screen. Rupture discs of 1550 psi value were used. After bombardment, the embryos were cultured in the dark at 25° C.

Preparation of DNA for Delivery

The microcarrier was prepared essentially according to the instructions supplied with the Biolistic device. While vortexing 50 μl 1.0 μgold microcarrier, added 5 μl pCIB4431 (1.23 μg/μl) (#898)+2 μl pCIB3064 0.895 μg/μl) (#456) followed by 50 μl 2.5 M CaCl$_2$, then 20 μl 0.1 M spermidine (free base, TC grade). The resulting mixture was vortexed 3 minutes and microfuged for 10 sec. The supernatant was removed and the icrocarriers washed 2 times with 250 μl of 100% EtOH (HPLC grade) by vortexing briefly, centrifuging and removing the supernatant. The microcarriers are resuspended in 65 μl 100% EtOH.

Callus formation

Embryos were transferred to callus initiation medium with 3 mg/l PPT 1 day after bombardment. Embryos were scored for callus initiation at 2 and 3 weeks after bombardment. Any responses were transferred to callus maintenance medium, 2DG4+0.5 2,4-D medium with 3 mg/L PPT. Callus maintenance medium is N6 major salts, B5 minor salts, MS iron, 2% sucrose, with 0.5 mg/l 2,4-D, 20 mg/l glucose, and 10 ml G4 additions added after autoclaving. Embryogenic callus was subcultured every 2 weeks to fresh maintenance medium containing 3 mg/L PPT. All callus was incubated in the dark at 25° C.

The Type I callus formation response was 15%. Every embryo which produced callus was cultured as an individual event giving rise to an individual line.

Regeneration

After 12 weeks on selection, the tissue was removed from callus maintenance edium with PPT and was placed on regeneration medium. Regeneration medium is 0.25MS3S5BA (0.25 mg/l 2,4 D, 5 mg/l BAP, MS salts, 3% sucrose) for 2 weeks followed by subculture to MS3S medium for regeneration of plants. After 4 to 10 weeks, plants were removed and put into GA 7's. Our line KC65 0–6, which became the #176 BT event, produced a total of 38 plants.

Assays

All plants, as they became established in the GA7's, were tested by the chlorophenol red (CR) test for resistance to PPT as described in U.S. patent application Ser. No. 07/759, 243, filed Sep. 13, 1991, the relevant portions of which are hereby incorporated herein by reference. This assay utilizes a pH sensitive indicator dye to show which cells are growing in the presence of PPT. Cells which grow produce a pH change in the media and turn the indicator yellow (from red). Plants expressing the resistance gene to PPT are easily seen in this test. (#176=8 positive/30 negative) Plants positive by the CR test were assayed by PCR for the presence of the synthetic BT gene. (#176=5 positive/2 negative/1 dead)

Plants positive by PCR for the syn-BT gene were sent to the phytotron. Once established in the phytotron, they were characterized using insect bioassays and ELISA analysis. Plants were insect bioassayed using a standard European Corn Borer assay (described in Example 5A) in which small pieces of leaf of clipped from a plant and placed in a small petri dish with a number of ECB neonate larvae. Plants are typically assayed at a height of about 6 inches. Plants showing 100% mortality to ECB in this assay are characterized further. ELISA data are shown below. Positive plants are moved to the greenhouse.

Greenhouse/Fertility

Plant number #176–11 was pollinated with wild-type 6N615 pollen. One tassel ear and one ear shoot were produced. All of the embryos from the tassel ear (11) and 56 kernels from Ear 1 were rescued. 294 kernels remained on the ear and dried down naturally.

Pollen from #176–11 was outcrossed to various maize genotypes 5N984, 5NA89, and 3N961. Embryos have been rescued from all 3 outcrosses (5N984=45; 5NA89=30; 3N961=8). Most of the kernels remained on the ears on the plants in the greenhouse and were dried down naturally. DNA was isolated from plant #176–11 using standard techniques and analysed by Southern blot analysis. It was found to contain sequences which hybridize with probes generated from the synthetic cryIA(b) gene and with a probe generated from the PAT gene. These results showed integration of these genes into the genome of maize.

Experiment KC-64

Production of transgenic maize plants expressing the synthetic cryIA(b) gene using a constitutive promoter.

Tissue

Immature maize embryos, approximately 1.5–2.5 mm in length, were excised from an ear of genotype 6N615 14–15 days after pollination. The mother plant was grown in the greenhouse. Before excision, the ear was surface sterilized with 20% Clorox for 20 minutes and rinse 3 times with sterile water. Individual embryos were plated scutellum side in a 2 cm square area, 36 embryos to a plate, on the callus initiation medium, 2DG4+5 chloramben medium (N6 major salts, B5 minor salts, MS iron, 2% sucrose, with 5 mg/l chloramben, 20 mg/l glucose, and 10 ml G4 additions Table 1) added after autoclaving.

TABLE 1

| Ingredient | per liter medium |
|---|---|
| G4 Additions | |
| Casein hydrolysate | 0.5 gm |
| Proline | 1.38 gm |
| Nicotinic acid | .2 mg |
| Pyridoxine-HCl | .2 mg |
| Thiamine-HCl | .5 mg |
| Choline-HCl | .1 mg |
| Riboflavin | .05 mg |
| Biotin | .1 mg |
| Folic acid | .05 mg |
| Ca pantothenate | .1 mg |
| p-aminobenzoic acid | .05 mg |
| B12 | .136 µg |

Bombardment

Tissue was bombarded using the PDS-1000He Biolistics device. The tissue was placed on the shelf 8 cm below the stopping screen shelf. The tissue was shot one time with the DNA/gold microcarrier solution, 10 µl dried onto the macrocarrier. The stopping screen used was hand punched at ABRU using 10×10 stainless steel mesh screen. Rupture discs of 1550 psi value were used. After bombardment, the embryos were cultured in the dark at 25° C.

Preparation of DNA for Delivery

The microcarrier was prepared essentially according to the instructions supplied with the Biolistic device. While vortexing 50 µl 1.0 µl gold microcarrier, added 3.2 µl pCIB4418 (0.85 µg/µl) (#905)+2 µl pCIB3064 0.895 µg/µl) (#456)+1.6 µl pCIB3007A (1.7 µg/µl) (#152) followed by 50 µl 2.5 M CaCl$_2$, then 20 µl 0.1 M spermidine (free base, TC grade). The resulting mixture was vortexed 3 minutes and microfuged for 10 sec. The supernatant was removed and the microcarriers washed 2 times with 250 µl of 100% EtOH (HPLC grade) by vortexing briefly, centrifuging and removing the supernatant. The microcarriers are resuspended in 65 µl 100% EtOH.

Callus Formation

Embryos were transferred to callus initiation medium with 3 mg/l PPT 1 day after bombardment. Embryos were scored for callus initiation at 2 and 3 weeks after bombardment. Any responses were transferred to callus maintenance medium, 2DG4+0.5 2,4-D medium with 3 mg/L PPT. Callus maintenance medium is N6 major salts, B5 minor salts, MS iron, 2% sucrose, with 0.5 mg/l 2,4-D, 20 mg/l glucose, and 10 ml G4 additions added after utoclaving. Embryogenic callus was subcultured every 2 weeks to fresh maintenance medium containing 3 mg/L PPT. All callus was incubated in the dark at 25° C.

The Type I callus formation response was 18%. Every embryo which produced callus was cultured as an individual event giving rise to an individual line.

Regeneration

After 12 weeks on selection, the tissue was removed from callus maintenance medium with PPT and was placed on regeneration medium and incubated at 250° C. using a 16 hour light (50 µE .m−2. s−1)/8 hour dark photoperiod. Regeneration medium is 0.25MS3S5BA (0.25 mg/l 2,4 D, 5 mg/l BAP, MS salts, 3% sucrose) for 2 weeks followed by subculture to MS3S medium for regeneration of plants. After 4 to 10 weeks, plants were removed and put into GA 7's. Our line KC64 0–1, which became the #170 BT event, produced 55 plants. Our line KC64 0–7, which became the #171 BT event, produced a total of 33 plants.

Assays

Eleven plants, as they became established in the GA7's, were tested by the chlorophenol red (CR) test for resistance to PPT as per Shillito, et al, above. This assay utilizes a pH sensitive indicator dye to show which cells are growing in the presence of PPT. Cells which grow produce a pH change in the media and turn the indicator yellow (from red). Plants expressing the resistance gene to PPT are easily seen in this test. Plants positive by the CR test were assayed by PCR for the presence of the synthetic BT gene. (Event 170=37 positive/18 negative; #171=25 positive/8 negative).

Plants positive by PCR for the syn-Bt gene were sent to the phytotron. Once established in the phytotron, they were characterized using insect bioassays and ELISA analysis. Plants were insect bioassayed using a standard European corn borer assay (see below) in which small pieces of leaf of clipped from a lant and placed in a small petri dish with a number of ECB neonate larvae. Plants are typically assayed at a height of about 6 inches. Plants showing 100% mortality to ECB in this assay are characterized further. ELISA data are shown below. Positive plants are moved to the greenhouse.

Basta screening

Eight of the mature plants from the #170 event were selected for evaluation of Basta (Hoechst) resistance. On one middle leaf per plant, an area approximately 10–14 cm long×the leaf width was painted with 0, 0.4, 1.0 or 2.0% (10 ml of 200 g/L diluted to 100 ml with deionized water) aqueous Basta containing 2 drops of Tween 20/100 ml. Two plants were tested per level. Eight wild-type 6N615 plants of the same approximate age were treated as controls. All plants were observed at 4 and 7 days. All of the control plants eventually died. Throughout the study, none of the #170 plants displayed any damage due to the herbicide.

Pollination

All tassel ears, first ear and, if available, the second ear on the #170 and #171 plants were pollinated with wild-type 6N615 pollen. At least 90% of the plants were female fertile.

Pollen from #171 plants was outcrossed to genotypes 6N615, 5NA984, 5NA89, 6F010, 5NA56, 2N217AF, 2NDO 1 and 3N961. At least 90% of the plants were shown to be male fertile.

Embryo Rescue

Embryos from the #171 event have been "rescued." Fourteen to 16 days after pollination, the ear tip with 25–50 kernels was cut from the ear with a coping saw. Prior to cutting, the husks were gently peeled away to expose the upper portion of the ear. The cut end of the ear on the plant was painted with Captan fungicide and the husks replaced. The seed remaining on the plant was allowed to dry naturally.

The excised ear piece was surface sterilized with 20% Clorox for 20 minutes and rinsed 3 times with sterile water. Individual embryos were excised and plated scutellum side up on B5 medium (Gamborg) containing 2% sucrose. B5 vitamins are added to the medium after autoclaving. Four embryos were plated per GA7 container and the containers incubated in the dark. When germination occurred, the containers were moved to a light culture room and incubated at 25° C. using a 16 hour light (50 µE .m−2. s−1)/8 hour dark photoperiod. The germination frequency is 94%.

Progeny from 15 plants of the #171 event and 2 of the #176 event were rescued using standard embryo rescue techniques and evaluated. All plants were evaluated by insect assay. Plants from the #171 event were also tested in the histochemical GUS assay. In both the insect assay and the GUS assay, the ratio of segregation of the transgenes was 1:1, as expected for a single locus insertion event.

Example 48

Analysis of Transgenic Maize Plants

ELISA ASSAY

Detection of cryIA(b) gene expression in transgenic maize is monitored using European corn borer(ECB) insect bioassays and ELISA analysis for a quantitative determination of the level of cryIA(b) protein obtained. Quantitative determination of cryIA(b) IP in the leaves of transgenic plants was performed using enzyme-linked immunosorbant assays (ELISA) as disclosed in Clark M F, Lister R M, Bar-Joseph M: ELISA Techniques. In: Weissbach A, Weissbach H (eds) Methods in Enzymology 118:742–766, Academic Press, Florida (1986). Immunoaffinity purified polyclonal rabbit and goat antibodies specific for the *B. thuringiensis* subsp. kurstaki IP were used to determine ng IP per mg soluble protein from crude extracts of leaf samples. The sensitivity of the double sandwich ELISA is 1–5 ng IP per mg soluble protein using 50 ug of total protein per ELISA microtiter dish well.

Corn extracts were made by grinding leaf tissue in gauze lined plastic bags using a hand held ball-bearing homogenizer (AGDIA, Elkart Ind.) in the presence of extraction buffer (50 mM $Na_2CO_3$ pH 9.5, 100 mM NaCl, 0.05% Triton, 0.05% Tween, 1 mM PMSF and 1 µM leupeptin). Protein determination was performed using the Bio-Rad (Richmond, Calif.) protein assay.

Using the above procedure, the primary maize transformants described above were analyzed for the presence of cryIA(b) protein using ELISA. These plants varied in height from 6 inches to about three feet at the time of analysis.

| Plant | Bt ng/ml soluble protein | 5/27/91 |
|---|---|---|
| 176-8 | 0 | 0 |
| 176-10 | 700 | 1585 |
| 176-11 | 760 | 2195 |
| 171-4A | 59 | |
| 171-6 | 50 | |
| 171-8 | 60 | |
| 171-9 | 280 | |
| 171-13 | 77 | |
| 171-14A | 43 | |
| 171-14B | 60 | |
| 171-15 | 55 | |
| 171-16A | 13 | |
| 171-16B | 19 | |
| 171-18 | 19 | |
| 176-30 | 1160 | |
| 171-32 | 980 | |
| 171-31 | 166 | |
| 171-30 | 370 | |
| 71-14 | | |
| #10 leaf | 26 | |
| 1 leaf | 17 | |
| plant | 171–16 | |
| #leaf | 40 | |
| #1 leaf | 120 | |

EUROPEAN CORN BORER ASSAY

1. One to four 4 cm sections are cut from an extended leaf of a corn plant.
2. Each leaf piece is placed on a moistened filter disc in a 50×9 mm petri dish.
3. Five neonate European corn borer larvae are placed on each leaf piece. (Making a total of 5–20 larvae per plant.)
4. The petri dishes are incubated at 29.5° C.
5. Leaf feeding damage and mortality data are scored at 24, 48, and 72 hours.

Example 49
Expression of Bt Endotoxin in Progeny of Transformed Maize Plants The transformed maize plants were fully fertile and were crossed with several genotypes of maize. Progeny from these crosses were analyzed for their ability to kill European corn borer (ECB) in a standard ECB bioassay (described immediately above) as well as for the presence of the cryIA(b) protein using ELISA as described above. The ability to kill ECB and the production of cryIA(b) protein correlated. These traits segregated to the progeny with a 1:1 ratio, indicating a single site of insertion for the active copy of the synthetic gene. This 1:1 ratio was true for both the constitutive promoter/synthetic-cryIA(b) plants and the tissue specific promoter/synthetic-cryIA(b) plants (data not shown).

FIG. 23A is a table containing a small subset of the total number of progeny analyzed. This table is representative of a number of different crosses.

Insect assays were done with *Diatrea saccharalis* and *Ostrinia nubilalis* using leaf material (as described above) of transgenic progeny containing a maize optimized CryIA(b) gene. The results of these assays are shown in FIG. 23B. They demonstrate that the maize optimized CryIA(b) gene functions in transformed maize to provide resistance to Sugarcane borer and *Ostrinia nubilalis*.

Example 50
EXPRESSION OF THE CRYIA(b) GENE IN MAIZE POLLEN

Progeny of the transformed maize plants containing the chimeric pollen promoter/synthetic cryIA(b) gene derived from pCIB4431 were grown in the field to maturity. Pollen was collected and analyzed for the presence of the cryIA(b) protein using standard ELISA techniquesd as described elsewhere. High levels of cryIA(b) protein were detected in the pollen. Progeny from the 35S promoter/synthetic cryIA (b) transformed plant were grown in the greenhouse. Pollen from these plants was analyzed using ELISA, and cryIA(b) protein was detected. Results are shown below in FIG. 23C.

It is recognized that factors including selection of plant lines, plant genotypes, synthetic sequences and the like, may also affect expression.

Figure 36:
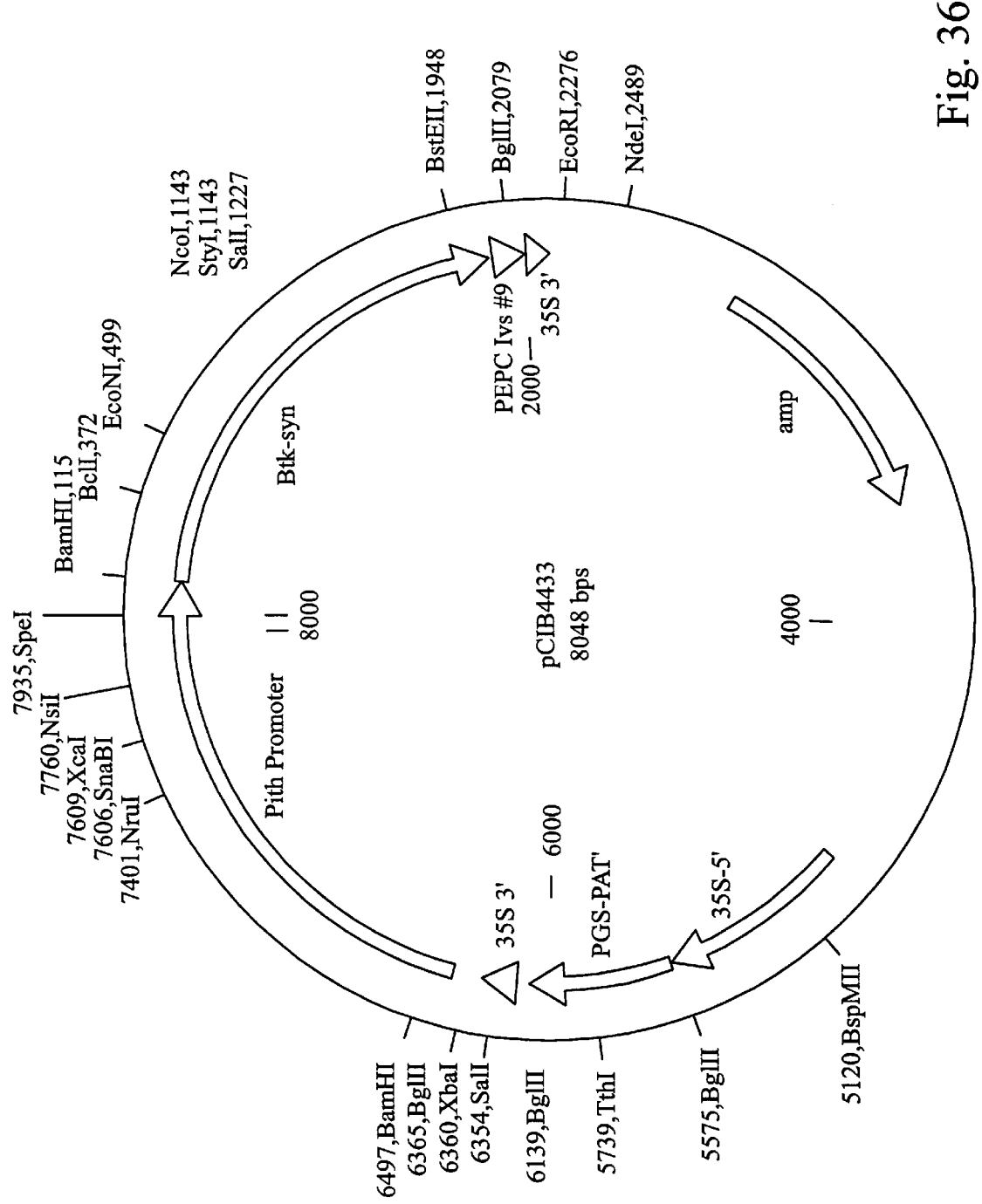
FIG. 36 is a map of pCIB4433.

Example 51
EXPRESSION OF THE CRYIA(b) GENE FUSED TO A PITH-PREFERRED PROMOTER.

pCIB4433 (FIG. 36) is a plasmid containing the maize optimized CryIA(b) gene fused with the pith-preferred promoter isolated from maize. This plasmid was constructed using a three-way ligation consisting of:

1) pCIB4418, cut with BstEH and BamHI; 1.8 Kb fragment
2) pBtin1, cut with NsiI and BstEII; 5.9 Kb fragment; pBtinl is described elsewhere in this application
3) PCR fragment VI-151 was generated in a PCR reaction using standard conditions as described elsewhere in this application.

PCR primers utilized were:

KE150A28: 5'-ATT CGC ATG CAT GTT TCA TTA TC-3' (SEQ ID NO: 93)

KE151A28: 5'-GCT GGT ACC ACG GAT CCG TCG CTT CTG TGC AAC AAC C-3' (SEQ ID NO: 94)

After the PCR reaction, the DNA was checked on an agarose gel to make sure the reaction had proceeded properly. DNA was recovered from the PCR reaction using standard conditions described elsewhere and subsequently cut with the restriction enzymes NsiI and BamHI using standard condition. After cutting, the fragment was run on a 2% NuSieve gel and the desired band recovered as described elsewhere. The DNA was used in the ligation described above.

After ligation (under standard condition), the DNA was transformed into competent *E. coli* cell.

Transformation was carried out using microprojectile bombardment essentially as described elsewhere in this application. Embryos were transferred to medium containing 10 µg/ml PPT 24 hours after microprojectile bombardment. Resulting callus was transferred to medium containing 40 µg/ml PPT after four weeks. Plants were regenerated without selection.

A small sample of plants (3–5) was assayed by PCR for each event. Further codes were added to indicate different positions and distances of embryos with respect to the microprojectile bombardment device. Plants were sent to the greenhouse having the following codes:

| | |
|---|---|
| JS21A TOP | Plants B.t. PCR Positive |
| JS21A MID | Plants B.t. PCR Positive |
| JS21C BOT | Plants B.t. PCR Positive |
| JS22D MID | Plants B.t. PCR Positive |
| JS23B MID | Plants B.t. PCR Negative (for control) |

Leaf samples from the regenerated plants were bioassayed for insecticidal activity against European corn borer as described in Example 48 with the results shown in FIG. 23D.

ELISA analysis of leaf samples to quantify the level of CryIA(b) protein expressed in the leaves was carried out as described in Example 48 with the results shown in FIG. 23E.

DEPOSITS

The following plasmids have been deposited with the Agricultural Research Culture Collection (NRRL)(1818 N. University St., Peoria, Ill. 61604) under the provisions of the Budapest Treaty: pCIB4418, pCIB4420, pCIB4429, pCIB4431, pCIB4433, pCIB5601, pCIB3166 and pCIB3171.

The present invention has been described with reference to specific embodiments thereof; however it will be appreciated that numerous variations, modifications, and embodiments are possible. Accordingly, all such variations, modifications and embodiments are to be regarded as being within the spirit and scope of the present invention.

SEQUENCE LISTING (1) GENERAL INFORMATION:

(iii) NUMBER OF SEQUENCES: 94

(2) INFORMATION FOR SEQ ID NO:1:

(i) SEQUENCE CHARACTERISTICS:
        (A) LENGTH: 3468 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: Bacillus thuringiensis kurstaki
        (B) STRAIN: HD-1

(ix) FEATURE:
        (A) NAME/KEY: misc_feature
        (B) LOCATION: 1..3468
        (D) OTHER INFORMATION: /product= "Full-length native
           cryIA(b)"
           /note= "Appears in Figures 1 and 4 as BTHKURHD."

(xi) SEQUENCE DESCRIPTION: SEQ ID NO:1:

```
ATGGATAACA ATCCGAACAT CAATGAATGC ATTCCTTATA ATTGTTTAAG TAACCCTGAA      60

GTAGAAGTAT TAGGTGGAGA AAGAATAGAA ACTGGTTACA CCCCAATCGA TATTTCCTTG     120

TCGCTAACGC AATTTCTTTT GAGTGAATTT GTTCCCGGTG CTGGATTTGT GTTAGGACTA     180

GTTGATATAA TATGGGGAAT TTTTGGTCCC TCTCAATGGG ACGCATTTCT TGTACAAATT     240

GAACAGTTAA TTAACCAAAG AATAGAAGAA TTCGCTAGGA ACCAAGCCAT TTCTAGATTA     300

GAAGGACTAA GCAATCTTTA TCAAATTTAC GCAGAATCTT TTAGAGAGTG GAAGCAGAT      360

CCTACTAATC CAGCATTAAG AGAAGAGATG CGTATTCAAT TCAATGACAT GAACAGTGCC     420

CTTACAACCG CTATTCCTCT TTTTGCAGTT CAAAATTATC AAGTTCCTCT TTTATCAGTA     480

TATGTTCAAG CTGCAAATTT ACATTTATCA GTTTTGAGAG ATGTTTCAGT GTTTGGACAA     540

AGGTGGGGAT TTGATGCCGC GACTATCAAT AGTCGTTATA ATGATTTAAC TAGGCTTATT     600

GGCAACTATA CAGATCATGC TGTACGCTGG TACAATACGG GATTAGAGCG TGTATGGGGA     660

CCGGATTCTA GAGATTGGAT AAGATATAAT CAATTTAGAA GAGAATTAAC ACTAACTGTA     720

TTAGATATCG TTTCTCTATT TCCGAACTAT GATAGTAGAA CGTATCCAAT TCGAACAGTT     780

TCCCAATTAA CAAGAGAAAT TTATACAAAC CCAGTATTAG AAAATTTTGA TGGTAGTTTT     840

CGAGGCTCGG CTCAGGGCAT AGAAGGAAGT ATTAGGAGTC CACATTTGAT GGATATACTT     900

AACAGTATAA CCATCTATAC GGATGCTCAT AGAGGAGAAT ATTATTGGTC AGGGCATCAA     960

ATAATGGCTT CTCCTGTAGG GTTTTCGGGG CCAGAATTCA CTTTTCCGCT ATATGGAACT    1020

ATGGGAAATG CAGCTCCACA ACAACGTATT GTTGCTCAAC TAGGTCAGGG CGTGTATAGA    1080

ACATTATCGT CCACTTTATA TAGAAGACCT TTTAATATAG GGATAAATAA TCAACAACTA    1140

TCTGTTCTTG ACGGGACAGA ATTTGCTTAT GGAACCTCCT CAAATTTGCC ATCCGCTGTA    1200

TACAGAAAAA GCGAACGGT AGATTCGCTG GATGAAATAC CGCCACAGAA TAACAACGTG     1260

CCACCTAGGC AAGGATTTAG TCATCGATTA AGCCATGTTT CAATGTTTCG TTCAGGCTTT    1320

AGTAATAGTA GTGTAAGTAT AATAAGAGCT CCTATGTTCT CTTGGATACA TCGTAGTGCT    1380

GAATTTAATA ATATAATTCC TTCATCACAA ATTACACAAA TACCTTTAAC AAAATCTACT    1440

AATCTTGGCT CTGGAACTTC TGTCGTTAAA GGACCAGGAT TTACAGGAGG AGATATTCTT    1500

CGAAGAACTT CACCTGGCCA GATTTCAACC TTAAGAGTAA ATATTACTGC ACCATTATCA    1560

CAAAGATATC GGGTAAGAAT TCGCTACGCT TCTACCACAA ATTTACAATT CCATACATCA    1620
```

```
ATTGACGGAA GACCTATTAA TCAGGGGAAT TTTTCAGCAA CTATGAGTAG TGGGAGTAAT    1680

TTACAGTCCG GAAGCTTTAG GACTGTAGGT TTTACTACTC CGTTTAACTT TTCAAATGGA    1740

TCAAGTGTAT TTACGTTAAG TGCTCATGTC TTCAATTCAG GCAATGAAGT TTATATAGAT    1800

CGAATTGAAT TTGTTCCGGC AGAAGTAACC TTTGAGGCAG AATATGATTT AGAAAGAGCA    1860

CAAAAGGCGG TGAATGAGCT GTTTACTTCT TCCAATCAAA TCGGGTTAAA AACAGATGTG    1920

ACGGATTATC ATATTGATCA AGTATCCAAT TTAGTTGAGT GTTTATCTGA TGAATTTTGT    1980

CTGGATGAAA AAAAGAATT GTCCGAGAAA GTCAAACATG CGAAGCGACT TAGTGATGAG     2040

CGGAATTTAC TTCAAGATCC AAACTTTAGA GGGATCAATA GACAACTAGA CCGTGGCTGG    2100

AGAGGAAGTA CGGATATTAC CATCCAAGGA GGCGATGACG TATTCAAAGA GAATTACGTT    2160

ACGCTATTGG GTACCTTTGA TGAGTGCTAT CCAACGTATT TATATCAAAA AATAGATGAG    2220

TCGAAATTAA AAGCCTATAC CCGTTACCAA TTAAGAGGGT ATATCGAAGA TAGTCAAGAC    2280

TTAGAAATCT ATTTAATTCG CTACAATGCC AAACACGAAA CAGTAAATGT GCCAGGTACG    2340

GGTTCCTTAT GGCCGCTTTC AGCCCCAAGT CCAATCGGAA AATGTGCCCA TCATTCCCAT    2400

CATTTCTCCT TGGACATTGA TGTTGGATGT ACAGACTTAA ATGAGGACTT AGGTGTATGG    2460

GTGATATTCA AGATTAAGAC GCAAGATGGC CATGCAAGAC TAGGAAATCT AGAATTTCTC    2520

GAAGAGAAAC CATTAGTAGG AGAAGCACTA GCTCGTGTGA AAAGAGCGGA GAAAAAATGG    2580

AGAGACAAAC GTGAAAAATT GGAATGGGAA ACAAATATTG TTTATAAAGA GGCAAAAGAA    2640

TCTGTAGATG CTTTATTTGT AAACTCTCAA TATGATAGAT TACAAGCGGA TACCAACATC    2700

GCGATGATTC ATGCGGCAGA TAAACGCGTT CATAGCATTC GAGAAGCTTA TCTGCCTGAG    2760

CTGTCTGTGA TTCCGGGTGT CAATGCGGCT ATTTTTGAAG AATTAGAAGG GCGTATTTTC    2820

ACTGCATTCT CCCTATATGA TGCGAGAAAT GTCATTAAAA ATGGTGATTT TAATAATGGC    2880

TTATCCTGCT GGAACGTGAA AGGGCATGTA GATGTAGAAG AACAAAACAA CCACCGTTCG    2940

GTCCTTGTTG TTCCGGAATG GGAAGCAGAA GTGTCACAAG AAGTTCGTGT CTGTCCGGGT    3000

CGTGGCTATA TCCTTCGTGT CACAGCGTAC AAGGAGGGAT ATGGAGAAGG TTGCGTAACC    3060

ATTCATGAGA TCGAGAACAA TACAGACGAA CTGAAGTTTA GCAACTGTGT AGAAGAGGAA    3120

GTATATCCAA ACAACACGGT AACGTGTAAT GATTATACTG CGACTCAAGA AGAATATGAG    3180

GGTACGTACA CTTCTCGTAA TCGAGGATAT GACGGAGCCT ATGAAAGCAA TTCTTCTGTA    3240

CCAGCTGATT ATGCATCAGC CTATGAAGAA AAAGCATATA CAGATGGACG AAGAGACAAT    3300

CCTTGTGAAT CTAACAGAGG ATATGGGGAT TACACACCAC TACCAGCTGG CTATGTGACA    3360

AAAGAATTAG AGTACTTCCC AGAAACCGAT AAGGTATGGA TTGAGATCGG AGAAACGGAA    3420

GGAACATTCA TCGTGGACAG CGTGGAATTA CTTCTTATGG AGGAATAA                3468
```

(2) INFORMATION FOR SEQ ID NO:2:

(i) SEQUENCE CHARACTERISTICS:
        (A) LENGTH: 3468 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(iii) HYPOTHETICAL: NO (ix) FEATURE:
        (A) NAME/KEY: misc_feature
        (B) LOCATION: 1..3468

(D) OTHER INFORMATION: /product= "Full-length pure maize
    optimized synthetic Bt"
    /note= "Disclosed in Figure 3 as syn1T.mze"

(xi) SEQUENCE DESCRIPTION: SEQ ID NO:2:

```
ATGGACAACA ACCCCAACAT CAACGAGTGC ATCCCCTACA ACTGCCTGAG CAACCCCGAG     60
GTGGAGGTGC TGGGCGGCGA GCGCATCGAG ACCGGCTACA CCCCCATCGA CATCAGCCTG    120
AGCCTGACCC AGTTCCTGCT GAGCGAGTTC GTGCCCGGCG CCGGCTTCGT GCTGGGCCTG    180
GTGGACATCA TCTGGGGCAT CTTCGGCCCC AGCCAGTGGG ACGCCTTCCT GGTGCAGATC    240
GAGCAGCTGA TCAACCAGCG CATCGAGGAG TTCGCCCGCA ACCAGGCCAT CAGCCGCCTG    300
GAGGGCCTGA GCAACCTGTA CCAGATCTAC GCCGAGAGCT TCCGCGAGTG GGAGGCCGAC    360
CCCACCAACC CCGCCCTGCG CGAGGAGATG CGCATCCAGT TCAACGACAT GAACAGCGCC    420
CTGACCACCG CCATCCCCCT GTTCGCCGTG CAGAACTACC AGGTGCCCCT GCTGAGCGTG    480
TACGTGCAGG CCGCCAACCT GCACCTGAGC GTGCTGCGCG ACGTGAGCGT GTTCGGCCAG    540
CGCTGGGGCT TCGACGCCGC CACCATCAAC AGCCGCTACA ACGACCTGAC CCGCCTGATC    600
GGCAACTACA CCGACCACGC CGTGCGCTGG TACAACACCG GCCTGGAGCG CGTGTGGGGC    660
CCCGACAGCC GCGACTGGAT CCGCTACAAC CAGTTCCGCC GCGAGCTGAC CCTGACCGTG    720
CTGGACATCG TGAGCCTGTT CCCCAACTAC GACAGCCGCA CCTACCCCAT CCGCACCGTG    780
AGCCAGCTGA CCCGCGAGAT CTACACCAAC CCCGTGCTGG AGAACTTCGA CGGCAGCTTC    840
CGCGGCAGCG CCCAGGGCAT CGAGGGCAGC ATCCGCAGCC CCCACCTGAT GGACATCCTG    900
AACAGCATCA CCATCTACAC CGACGCCCAC CGCGGCGAGT ACTACTGGAG CGGCCACCAG    960
ATCATGGCCA GCCCCGTGGG CTTCAGCGGC CCCGAGTTCA CCTTCCCCCT GTACGGCACC   1020
ATGGGCAACG CCGCCCCCCA GCAGCGCATC GTGGCCCAGC TGGGCCAGGG CGTGTACCGC   1080
ACCCTGAGCA GCACCCTGTA CCGCCGCCCC TTCAACATCG GCATCAACAA CCAGCAGCTG   1140
AGCGTGCTGG ACGGCACCGA GTTCGCCTAC GGCACCAGCA GCAACCTGCC CAGCGCCGTG   1200
TACCGCAAGA GCGGCACCGT GGACAGCCTG GACGAGATCC CCCCCCAGAA CAACAACGTG   1260
CCCCCCCGCC AGGGCTTCAG CCACCGCCTG AGCCACGTGA GCATGTTCCG CAGCGGCTTC   1320
AGCAACAGCA GCGTGAGCAT CATCCGCGCC CCCATGTTCA GCTGGATCCA CCGCAGCGCC   1380
GAGTTCAACA ACATCATCCC CAGCAGCCAG ATCACCCAGA TCCCCCTGAC CAAGAGCACC   1440
AACCTGGGCA GCGGCACCAG CGTGGTGAAG GGCCCCGGCT TCACCGGCGG CGACATCCTG   1500
CGCCGCACCA GCCCCGGCCA GATCAGCACC CTGCGCGTGA ACATCACCGC CCCCCTGAGC   1560
CAGCGCTACC GCGTGCGCAT CCGCTACGCC AGCACCACCA ACCTGCAGTT CCACACCAGC   1620
ATCGACGGCC GCCCCATCAA CCAGGGCAAC TTCAGCGCCA CCATGAGCAG CGGCAGCAAC   1680
CTGCAGAGCG GCAGCTTCCG CACCGTGGGC TTCACCACCC CCTTCAACTT CAGCAACGGC   1740
AGCAGCGTGT TCACCCTGAG CGCCCACGTG TTCAACAGCG GCAACGAGGT GTACATCGAC   1800
CGCATCGAGT TCGTGCCCGC CGAGGTGACC TTCGAGGCCG AGTACGACCT GGAGCGCGCC   1860
CAGAAGGCCG TGAACGAGCT GTTCACCAGC AGCAACCAGA TCGGCCTGAA GACCGACGTG   1920
ACCGACTACC ACATCGACCA GGTGAGCAAC CTGGTGGAGT GCCTGAGCGA CGAGTTCTGC   1980
CTGGACGAGA AGAAGGAGCT GAGCGAGAAG GTGAAGCACG CCAAGCGCCT GAGCGACGAG   2040
CGCAACCTGC TGCAGGACCC CAACTTCCGC GGCATCAACC GCCAGCTGGA CCGCGGCTGG   2100
CGCGGCAGCA CCGACATCAC CATCCAGGGC GGCGACGACG TGTTCAAGGA GAACTACGTG   2160
ACCCTGCTGG GCACCTTCGA CGAGTGCTAC CCCACCTACC TGTACCAGAA GATCGACGAG   2220
```

```
AGCAAGCTGA AGGCCTACAC CCGCTACCAG CTGCGCGGCT ACATCGAGGA CAGCCAGGAC      2280

CTGGAGATCT ACCTGATCCG CTACAACGCC AAGCACGAGA CCGTGAACGT GCCCGGCACC      2340

GGCAGCCTGT GGCCCCTGAG CGCCCCCAGC CCCATCGGCA AGTGCGCCCA CCACAGCCAC      2400

CACTTCAGCC TGGACATCGA CGTGGGCTGC ACCGACCTGA ACGAGGACCT GGGCGTGTGG      2460

GTGATCTTCA AGATCAAGAC CCAGGACGGC ACGCCCGCC TGGGCAACCT GGAGTTCCTG       2520

GAGGAGAAGC CCCTGGTGGG CGAGGCCCTG GCCCGCGTGA AGCGCGCCGA GAAGAAGTGG      2580

CGCGACAAGC GCGAGAAGCT GGAGTGGGAG ACCAACATCG TGTACAAGGA GGCCAAGGAG      2640

AGCGTGGACG CCCTGTTCGT GAACAGCCAG TACGACCGCC TGCAGGCCGA CACCAACATC      2700

GCCATGATCC ACGCCGCCGA CAAGCGCGTG CACAGCATCC GCGAGGCCTA CCTGCCCGAG      2760

CTGAGCGTGA TCCCCGGCGT GAACGCCGCC ATCTTCGAGG AGCTGGAGGG CCGCATCTTC      2820

ACCGCCTTCA GCCTGTACGA CGCCCGCAAC GTGATCAAGA ACGGCGACTT CAACAACGGC      2880

CTGAGCTGCT GGAACGTGAA GGGCCACGTG GACGTGGAGG AGCAGAACAA CCACCGCAGC      2940

GTGCTGGTGG TGCCCGAGTG GGAGGCCGAG GTGAGCCAGG AGGTGCGCGT GTGCCCCGGC      3000

CGCGGCTACA TCCTGCGCGT GACCGCCTAC AAGGAGGGCT ACGGCGAGGG CTGCGTGACC      3060

ATCCACGAGA TCGAGAACAA CACCGACGAG CTGAAGTTCA GCAACTGCGT GGAGGAGGAG      3120

GTGTACCCCA ACAACACCGT GACCTGCAAC GACTACACCG CCACCCAGGA GGAGTACGAG      3180

GGCACCTACA CCAGCCGCAA CCGCGGCTAC GACGGCGCCT ACGAGAGCAA CAGCAGCGTG      3240

CCCGCCGACT ACGCCAGCGC CTACGAGGAG AAGGCCTACA CCGACGGCCG CCGCGACAAC      3300

CCCTGCGAGA GCAACCGCGG CTACGGCGAC TACACCCCCC TGCCCGCCGG CTACGTGACC      3360

AAGGAGCTGG AGTACTTCCC CGAGACCGAC AAGGTGTGGA TCGAGATCGG CGAGACCGAG      3420

GGCACCTTCA TCGTGGACAG CGTGGAGCTG CTGCTGATGG AGGAGTAG                   3468

(2) INFORMATION FOR SEQ ID NO:3:

(i) SEQUENCE CHARACTERISTICS:
        (A) LENGTH: 1947 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(iii) HYPOTHETICAL: NO (ix) FEATURE:
        (A) NAME/KEY: misc_feature
        (B) LOCATION: 1..1947
        (D) OTHER INFORMATION: /product= "Truncated synthetic
            maize optimized cryIA(b) gene"
            /note= "Disclosed in Figures 1, 2, 3, 4 and 5 as bssyn."

(xi) SEQUENCE DESCRIPTION: SEQ ID NO:3:

ATGGACAACA ACCCCAACAT CAACGAGTGC ATCCCCTACA ACTGCCTGAG CAACCCCGAG        60

GTGGAGGTGC TGGGCGGCGA GCGCATCGAG ACCGGCTACA CCCCCATCGA CATCAGCCTG       120

AGCCTGACCC AGTTCCTGCT GAGCGAGTTC GTGCCCGGCG CCGGCTTCGT GCTGGGCCTG       180

GTGGACATCA TCTGGGGCAT CTTCGGCCCC AGCCAGTGGG ACGCCTTCCT GGTGCAGATC       240

GAGCAGCTGA TCAACCAGCG CATCGAGGAG TTCGCCCGCA ACCAGGCCAT CAGCCGCCTG       300

GAGGGCCTGA GCAACCTGTA CCAAATCTAC GCCGAGAGCT TCCGCGAGTG GGAGGCCGAC       360

CCCACCAACC CCGCCCTGCG CGAGGAGATG CGCATCCAGT TCAACGACAT GAACAGCGCC       420

CTGACCACCG CCATCCCCCT GTTCGCCGTG CAGAACTACC AGGTGCCCCT GCTGAGCGTG       480
```

-continued

```
TACGTGCAGG CCGCCAACCT GCACCTGAGC GTGCTGCGCG ACGTCAGCGT GTTCGGCCAG      540

CGCTGGGGCT TCGACGCCGC CACCATCAAC AGCCGCTACA ACGACCTGAC CCGCCTGATC      600

GGCAACTACA CCGACCACGC CGTGCGCTGG TACAACACCG GCCTGGAGCG CGTGTGGGGT      660

CCCGACAGCC GCGACTGGAT CAGGTACAAC CAGTTCCGCC GCGAGCTGAC CCTGACCGTG      720

CTGGACATCG TGAGCCTGTT CCCCAACTAC GACAGCCGCA CCTACCCCAT CCGCACCGTG      780

AGCCAGCTGA CCCGCGAGAT TTACACCAAC CCCGTGCTGG AGAACTTCGA CGGCAGCTTC      840

CGCGGCAGCG CCCAGGGCAT CGAGGGCAGC ATCCGCAGCC CCCACCTGAT GGACATCCTG      900

AACAGCATCA CCATCTACAC CGACGCCCAC CGCGGCGAGT ACTACTGGAG CGGCCACCAG      960

ATCATGGCCA GCCCCGTCGG CTTCAGCGGC CCCGAGTTCA CCTTCCCCCT GTACGGCACC     1020

ATGGGCAACG CTGCACCTCA GCAGCGCATC GTGGCACAGC TGGGCCAGGG AGTGTACCGC     1080

ACCCTGAGCA GCACCCTGTA CCGTCGACCT TTCAACATCG GCATCAACAA CCAGCAGCTG     1140

AGCGTGCTGG ACGGCACCGA GTTCGCCTAC GGCACCAGCA GCAACCTGCC CAGCGCCGTG     1200

TACCGCAAGA GCGGCACCGT GGACAGCCTG GACGAGATCC CCCTCAGAA CAACAACGTG      1260

CCACCTCGAC AGGGCTTCAG CCACCGTCTG AGCCACGTGA GCATGTTCCG CAGTGGCTTC     1320

AGCAACAGCA GCGTGAGCAT CATCCGTGCA CCTATGTTCA GCTGGATTCA CCGCAGTGCC     1380

GAGTTCAACA ACATCATCCC CAGCAGCCAA ATCACCCAGA TCCCCCTGAC CAAGAGCACC     1440

AACCTGGGCA GCGGCACCAG CGTGGTGAAG GGCCCCGGCT TCACCGGCGG CGACATCCTG     1500

CGCCGCACCA GCCCCGGCCA GATCAGCACC CTGCGCGTGA ACATCACCGC CCCCCTGAGC     1560

CAGCGCTACC GCGTCCGCAT CCGCTACGCC AGCACCACCA ACCTGCAGTT CCACACCAGC     1620

ATCGACGGCC GCCCCATCAA CCAGGGCAAC TTCAGCGCCA CCATGAGCAG CGGCAGCAAC     1680

CTGCAGAGCG GCAGCTTCCG CACCGTGGGC TTCACCACCC CCTTCAACTT CAGCAACGGC     1740

AGCAGCGTGT TCACCCTGAG CGCCCACGTG TTCAACAGCG GCAACGAGGT GTACATCGAC     1800

CGCATCGAGT TCGTGCCCGC CGAGGTGACC TTCGAGGCCG AGTACGACCT GGAGAGGGCT     1860

CAGAAGGCCG TGAACGAGCT GTTCACCAGC AGCAACCAGA TCGGCCTGAA GACCGACGTG     1920

ACCGACTACC ACATCGATCA GGTGTAG                                        1947
```

(2) INFORMATION FOR SEQ ID NO:4:

(i) SEQUENCE CHARACTERISTICS:
        (A) LENGTH: 3468 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(iii) HYPOTHETICAL: NO (ix) FEATURE:
        (A) NAME/KEY: misc_feature
        (B) LOCATION: 1..3468
        (D) OTHER INFORMATION: /product= "Full length synthetic
            maize optimized"
            /note= "Disclosed in Figure 3 as synful.mod. This
            sequence is identical to flsynbt.fin as disclosed in
            Figure 1."

(xi) SEQUENCE DESCRIPTION: SEQ ID NO:4:

```
ATGGACAACA ACCCCAACAT CAACGAGTGC ATCCCCTACA ACTGCCTGAG CAACCCCGAG       60

GTGGAGGTGC TGGGCGGCGA GCGCATCGAG ACCGGCTACA CCCCCATCGA CATCAGCCTG      120
```

-continued

| | |
|---|---|
| AGCCTGACCC AGTTCCTGCT GAGCGAGTTC GTGCCCGGCG CCGGCTTCGT GCTGGGCCTG | 180 |
| GTGGACATCA TCTGGGGCAT CTTCGGCCCC AGCCAGTGGG ACGCCTTCCT GGTGCAGATC | 240 |
| GAGCAGCTGA TCAACCAGCG CATCGAGGAG TTCGCCCGCA ACCAGGCCAT CAGCCGCCTG | 300 |
| GAGGGCCTGA GCAACCTGTA CCAAATCTAC GCCGAGAGCT TCCGCGAGTG GGAGGCCGAC | 360 |
| CCCACCAACC CCGCCCTGCG CGAGGAGATG CGCATCCAGT TCAACGACAT GAACAGCGCC | 420 |
| CTGACCACCG CCATCCCCCT GTTCGCCGTG CAGAACTACC AGGTGCCCCT GCTGAGCGTG | 480 |
| TACGTGCAGG CCGCCAACCT GCACCTGAGC GTGCTGCGCG ACGTCAGCGT GTTCGGCCAG | 540 |
| CGCTGGGGCT TCGACGCCGC CACCATCAAC AGCCGCTACA ACGACCTGAC CCGCCTGATC | 600 |
| GGCAACTACA CCGACCACGC CGTGCGCTGG TACAACACCG GCCTGGAGCG CGTGTGGGGT | 660 |
| CCCGACAGCC GCGACTGGAT CAGGTACAAC CAGTTCCGCC GCGAGCTGAC CCTGACCGTG | 720 |
| CTGGACATCG TGAGCCTGTT CCCCAACTAC GACAGCCGCA CCTACCCCAT CCGCACCGTG | 780 |
| AGCCAGCTGA CCCGCGAGAT TTACACCAAC CCCGTGCTGG AGAACTTCGA CGGCAGCTTC | 840 |
| CGCGGCAGCG CCCAGGGCAT CGAGGGCAGC ATCCGCAGCC CCCACCTGAT GGACATCCTG | 900 |
| AACAGCATCA CCATCTACAC CGACGCCCAC CGCGGCGAGT ACTACTGGAG CGGCCACCAG | 960 |
| ATCATGGCCA GCCCCGTCGG CTTCAGCGGC CCCGAGTTCA CCTTCCCCCT GTACGGCACC | 1020 |
| ATGGGCAACG CTGCACCTCA GCAGCGCATC GTGGACAGC TGGGCCAGGG AGTGTACCGC | 1080 |
| ACCCTGAGCA GCACCCTGTA CCGTCGACCT TTCAACATCG GCATCAACAA CCAGCAGCTG | 1140 |
| AGCGTGCTGG ACGGCACCGA GTTCGCCTAC GGCACCAGCA GCAACCTGCC CAGCGCCGTG | 1200 |
| TACCGCAAGA GCGGCACCGT GGACAGCCTG GACGAGATCC CCCCTCAGAA CAACAACGTG | 1260 |
| CCACCTCGAC AGGGCTTCAG CCACCGTCTG AGCCACGTGA GCATGTTCCG CAGTGGCTTC | 1320 |
| AGCAACAGCA GCGTGAGCAT CATCCGTGCA CCTATGTTCA GCTGGATTCA CCGCAGTGCC | 1380 |
| GAGTTCAACA ACATCATCCC CAGCAGCCAG ATCACCCAGA TCCCCCTGAC CAAGAGCACC | 1440 |
| AACCTGGGCA GCGGCACCAG CGTGGTGAAG GGCCCCGGCT TCACCGGCGG CGACATCCTG | 1500 |
| CGCCGCACCA GCCCCGGCCA GATCAGCACC CTGCGCGTGA ACATCACCGC CCCCCTGAGC | 1560 |
| CAGCGCTACC GCGTCCGCAT CCGCTACGCC AGCACCACCA ACCTGCAGTT CCACACCAGC | 1620 |
| ATCGACGGCC GCCCCATCAA CCAGGGCAAC TTCAGCGCCA CCATGAGCAG CGGCAGCAAC | 1680 |
| CTGCAGAGCG GCAGCTTCCG CACCGTGGGC TTCACCACCC CCTTCAACTT CAGCAACGGC | 1740 |
| AGCAGCGTGT TCACCCTGAG CGCCCACGTG TTCAACAGCG GCAACGAGGT GTACATCGAC | 1800 |
| CGCATCGAGT TCGTGCCCGC CGAGGTGACC TTCGAGGCCG AGTACGACCT GGAGAGGGCT | 1860 |
| CAGAAGGCCG TGAACGAGCT GTTCACCAGC AGCAACCAGA TCGGCCTGAA GACCGACGTG | 1920 |
| ACCGACTACC ACATCGATCA GGTGAGCAAC CTGGTGGAGT GCCTGAGCGA CGAGTTCTGC | 1980 |
| CTGGACGAGA GAAGGAGCT GAGCGAGAAG GTGAAGCACG CCAAGCGCCT GAGCGACGAG | 2040 |
| CGCAACCTGC TGCAGGACCC CAACTTCCGC GGCATCAACC GCCAGCTGGA CCGCGGCTGG | 2100 |
| CGCGGCAGCA CCGACATCAC CATCCAGGGC GGCGACGACG TGTTCAAGGA GAACTACGTG | 2160 |
| ACCCTGCTGG GCACCTTCGA CGAGTGCTAC CCCACCTACC TGTACCAGAA GATCGACGAG | 2220 |
| AGCAAGCTGA AGGCCTACAC CCGCTACCAG CTGCGCGGCT ACATCGAGGA CAGCCAGGAC | 2280 |
| CTGGAGATCT ACCTGATCCG CTACAACGCC AAGCACGAGA CCGTGAACGT GCCCGGCACC | 2340 |
| GGCAGCCTGT GGCCCCTGAG CGCCCCCAGC CCCATCGGCA AGTGCGCCCA CCACAGCCAC | 2400 |
| CACTTCAGCC TGGACATCGA CGTGGGCTGC ACCGACCTGA ACGAGGACCT GGGCGTGTGG | 2460 |
| GTGATCTTCA AGATCAAGAC CCAGGACGGC CACGCCCGCC TGGGCAACCT GGAGTTCCTG | 2520 |

| | | | | |
|---|---|---|---|---|
| GAGGAGAAGC | CCCTGGTGGG | CGAGGCCCTG | GCCCGCGTGA | AGCGCGCCGA GAAGAAGTGG | 2580 |
| CGCGACAAGC | GCGAGAAGCT | GGAGTGGGAG | ACCAACATCG | TGTACAAGGA GGCCAAGGAG | 2640 |
| AGCGTGGACG | CCCTGTTCGT | GAACAGCCAG | TACGACCGCC | TGCAGGCCGA CACCAACATC | 2700 |
| GCCATGATCC | ACGCCGCCGA | CAAGCGCGTG | CACAGCATTC | GCGAGGCCTA CCTGCCCGAG | 2760 |
| CTGAGCGTGA | TCCCCGGCGT | GAACGCCGCC | ATCTTCGAGG | AGCTGGAGGG CCGCATCTTC | 2820 |
| ACCGCCTTCA | GCCTGTACGA | CGCCCGCAAC | GTGATCAAGA | ACGGCGACTT CAACAACGGC | 2880 |
| CTGAGCTGCT | GGAACGTGAA | GGGCCACGTG | GACGTGGAGG | AGCAGAACAA CCACCGCAGC | 2940 |
| GTGCTGGTGG | TGCCCGAGTG | GGAGGCCGAG | GTGAGCCAGG | AGGTGCGCGT GTGCCCCGGC | 3000 |
| CGCGGCTACA | TCCTGCGCGT | GACCGCCTAC | AAGGAGGGCT | ACGGCGAGGG CTGCGTGACC | 3060 |
| ATCCACGAGA | TCGAGAACAA | CACCGACGAG | CTCAAGTTCA | GCAACTGCGT GGAGGAGGAG | 3120 |
| GTGTACCCCA | ACAACACCGT | GACCTGCAAC | GACTACACCG | CCACCCAGGA GGAGTACGAG | 3180 |
| GGCACCTACA | CCAGCCGCAA | CCGCGGCTAC | GACGGCGCCT | ACGAGAGCAA CAGCAGCGTG | 3240 |
| CCCGCCGACT | ACGCCAGCGC | CTACGAGGAG | AAGGCCTACA | CCGACGGCCG CCGCGACAAC | 3300 |
| CCCTGCGAGA | GCAACCGCGG | CTACGGCGAC | TACACCCCCC | TGCCCGCCGG CTACGTGACC | 3360 |
| AAGGAGCTGG | AGTACTTCCC | CGAGACCGAC | AAGGTGTGGA | TCGAGATCGG CGAGACCGAG | 3420 |
| GGCACCTTCA | TCGTGGACAG | CGTGGAGCTG | CTGCTGATGG | AGGAGTAG | 3468 |

(2) INFORMATION FOR SEQ ID NO:5:

(i) SEQUENCE CHARACTERISTICS:
        (A) LENGTH: 1845 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(iii) HYPOTHETICAL: NO (ix) FEATURE:
        (A) NAME/KEY: misc_feature
        (B) LOCATION: 1..1845
        (D) OTHER INFORMATION: /note= "This is the synthetic Bt
            gene according to Perlak et al. as shown in Figures 4 and 5 as PMONBT."

(xi) SEQUENCE DESCRIPTION: SEQ ID NO:5:

```
ATGGACAACA ACCCAAACAT CAACGAATGC ATTCCATACA ACTGCTTGAG TAACCCAGAA     60

GTTGAAGTAC TTGGTGGAGA ACGCATTGAA ACCGGTTACA CTCCCATCGA CATCTCCTTG    120

TCCTTGACAC AGTTTCTGCT CAGCGAGTTC GTGCCAGGTG CTGGGTTCGT TCTCGGACTA    180

GTTGACATCA TCTGGGGTAT CTTTGGTCCA TCTCAATGGG ATGCATTCCT GGTGCAAATT    240

GAGCAGTTGA TCAACCAGAG GATCGAAGAG TTCGCCAGGA ACCAGGCCAT CTCTAGGTTG    300

GAAGGATTGA GCAATCTCTA CCAAATCTAT GCAGAGAGCT TCAGAGAGTG GGAAGCCGAT    360

CCTACTAACC CAGCTCTCCG CGAGGAAATG CGTATTCAAT TCAACGACAT GAACAGCGCC    420

TTGACCACAG CTATCCCATT GTTCGCAGTC CAGAACTACC AAGTTCCTCT CTTGTCCGTG    480

TACGTTCAAG CAGCTAATCT TCACCTCAGC GTGCTTCGAG ACGTTAGCGT GTTTGGGCAA    540

AGGTGGGGAT TCGATGCTGC AACCATCAAT AGCCGTTACA ACGACCTTAC TAGGCTGATT    600

GGAAACTACA CCGACCACGC TGTTCGTTGG TACAACACTG GCTTGGAGCG TGTCTGGGGT    660

CCTGATTCTA GAGATTGGAT TAGATACAAC CAGTTCAGGA GAGAATTGAC CCTCACAGTT    720

TTGGACATTG TGTCTCTCTT CCCGAACTAT GACTCCAGAA CCTACCCTAT CCGTACAGTG    780
```

```
TCCCAACTTA CCAGAGAAAT CTATACTAAC CCAGTTCTTG AGAACTTCGA CGGTAGCTTC      840

CGTGGTTCTG CCCAAGGTAT CGAAGGCTCC ATCAGGAGCC CACACTTGAT GGACATCTTG      900

AACAGCATAA CTATCTACAG CGATGCTCAC AGAGGAGAGT ATTACTGGTC TGGACACCAG      960

ATCATGGCCT CTCCAGTTGG ATTCAGCGGG CCCGAGTTTA CCTTTCCTCT CTATGGAACT     1020

ATGGGAAACG CCGCTCCACA ACAACGTATC GTTGCTCAAC TAGGTCAGGG TGTCTACAGA     1080

ACCTTGTCTT CCACCTTGTA CAGAAGACCC TTCAATATCG GTATCAACAA CCAGCAACTT     1140

TCCGTTCTTG ACGGAACAGA GTTCGCCTAT GGAACCTCTT CTAACTTGCC ATCCGCTGTT     1200

TACAGAAAGA GCGGAACCGT TGATTCCTTG GACGAAATCC CACCACAGAA CAACAATGTG     1260

CCACCCAGGC AAGGATTCTC CCACAGGTTG AGCCACGTGT CCATGTTCCG TTCCGGATTC     1320

AGCAACAGTT CCGTGAGCAT CATCAGAGCT CCTATGTTCT CATGGATTCA TCGTAGTGCT     1380

GAGTTCAACA ATATCATTCC TTCCTCTCAA ATCACCCAAA TCCCATTGAC CAAGTCTACT     1440

AACCTTGGAT CTGGAACTTC TGTCGTGAAA GGACCAGGCT TCACAGGAGG TGATATTCTT     1500

AGAAGAACTT CTCCTGGCCA GATTAGCACC CTCAGAGTTA ACATCACTGC ACCACTTTCT     1560

CAAAGATATC GTGTCAGGAT TCGTTACGCA TCTACCACTA ACTTGCAATT CCACACCTCC     1620

ATCGACGGAA GGCCTATCAA TCAGGGTAAC TTCTCCGCAA CCATGTCAAG CGGCAGCAAC     1680

TTGCAATCCG GCAGCTTCAG AACCGTCGGT TTCACTACTC CTTTCAACTT CTCTAACGGA     1740

TCAAGCGTTT TCACCCTTAG CGCTCATGTG TTCAATTCTG GCAATGAAGT GTACATTGAC     1800

CGTATTGAGT TTGTGCCTGC CGAAGTTACC TTCGAGGCTG AGTAC                     1845

(2) INFORMATION FOR SEQ ID NO:6:

(i) SEQUENCE CHARACTERISTICS:
        (A) LENGTH: 3624 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(iii) HYPOTHETICAL: NO (ix) FEATURE:
        (A) NAME/KEY: CDS
        (B) LOCATION: 1..3621
        (D) OTHER INFORMATION: /product= "Full-length, maize
            optmized cryIB"
            /note= "Disclosed in Figure 6."

(xi) SEQUENCE DESCRIPTION: SEQ ID NO:6:

ATG GAC CTG CTG CCC GAC GCC CGC ATC GAG GAC AGC CTG TGC ATC GCC         48
Met Asp Leu Leu Pro Asp Ala Arg Ile Glu Asp Ser Leu Cys Ile Ala
 1               5                  10                  15

GAG GGC AAC AAC ATC GAC CCC TTC GTG AGC GCC AGC ACC GTG CAG ACC         96
Glu Gly Asn Asn Ile Asp Pro Phe Val Ser Ala Ser Thr Val Gln Thr
             20                  25                  30

GGC ATC AAC ATC GCC GGC CGC ATC CTG GGC GTG CTG GGC GTG CCC TTC        144
Gly Ile Asn Ile Ala Gly Arg Ile Leu Gly Val Leu Gly Val Pro Phe
         35                  40                  45

GCC GGC CAG CTG GCC AGC TTC TAC AGC TTC CTG GTG GGC GAG CTG TGG        192
Ala Gly Gln Leu Ala Ser Phe Tyr Ser Phe Leu Val Gly Glu Leu Trp
     50                  55                  60

CCC CGC GGC CGC GAC CAG TGG GAG ATC TTC CTG GAG CAC GTG GAG CAG        240
Pro Arg Gly Arg Asp Gln Trp Glu Ile Phe Leu Glu His Val Glu Gln
 65                  70                  75                  80
```

| | |
|---|---|
| CTG ATC AAC CAG CAG ATC ACC GAG AAC GCC CGC AAC ACC GCC CTG GCC<br>Leu Ile Asn Gln Gln Ile Thr Glu Asn Ala Arg Asn Thr Ala Leu Ala<br>85                        90                     95 | 288 |
| CGC CTG CAG GGC CTG GGC GAC AGC TTC CGC GCC TAC CAG CAG AGC CTG<br>Arg Leu Gln Gly Leu Gly Asp Ser Phe Arg Ala Tyr Gln Gln Ser Leu<br>        100                     105                110 | 336 |
| GAG GAC TGG CTG GAG AAC CGC GAC GAC GCC CGC ACC CGC AGC GTG CTG<br>Glu Asp Trp Leu Glu Asn Arg Asp Asp Ala Arg Thr Arg Ser Val Leu<br>     115                    120                125 | 384 |
| TAC ACC CAG TAC ATC GCC CTG GAG CTG GAC TTC CTG AAC GCC ATG CCC<br>Tyr Thr Gln Tyr Ile Ala Leu Glu Leu Asp Phe Leu Asn Ala Met Pro<br>130                     135                140 | 432 |
| CTG TTC GCC ATC CGC AAC CAG GAG GTG CCC CTG CTG ATG GTG TAC GCC<br>Leu Phe Ala Ile Arg Asn Gln Glu Val Pro Leu Leu Met Val Tyr Ala<br>145              150                155             160 | 480 |
| CAG GCC GCC AAC CTG CAC CTG CTG CTG CTG CGC GAC GCC AGC CTG TTC<br>Gln Ala Ala Asn Leu His Leu Leu Leu Leu Arg Asp Ala Ser Leu Phe<br>            165                170              175 | 528 |
| GGC AGC GAG TTC GGC CTG ACC AGC CAG GAG ATC CAG CGC TAC TAC GAG<br>Gly Ser Glu Phe Gly Leu Thr Ser Gln Glu Ile Gln Arg Tyr Tyr Glu<br>        180                    185                190 | 576 |
| CGC CAG GTG GAG CGC ACC CGC GAC TAC AGC GAC TAC TGC GTG GAG TGG<br>Arg Gln Val Glu Arg Thr Arg Asp Tyr Ser Asp Tyr Cys Val Glu Trp<br>     195                    200                205 | 624 |
| TAC AAC ACC GGC CTG AAC AGC CTG CGC GGC ACC AAC GCC GCC AGC TGG<br>Tyr Asn Thr Gly Leu Asn Ser Leu Arg Gly Thr Asn Ala Ala Ser Trp<br>210                     215                220 | 672 |
| GTG CGC TAC AAC CAG TTC CGC CGC GAC CTG ACC CTG GGC GTG CTG GAC<br>Val Arg Tyr Asn Gln Phe Arg Arg Asp Leu Thr Leu Gly Val Leu Asp<br>225              230                235             240 | 720 |
| CTG GTG GCC CTG TTC CCC AGC TAC GAC ACC CGC ACC TAC CCC ATC AAC<br>Leu Val Ala Leu Phe Pro Ser Tyr Asp Thr Arg Thr Tyr Pro Ile Asn<br>            245                250              255 | 768 |
| ACC AGC GCC CAG CTG ACC CGC GAG GTG TAC ACC GAC GCC ATC GGC GCC<br>Thr Ser Ala Gln Leu Thr Arg Glu Val Tyr Thr Asp Ala Ile Gly Ala<br>        260                    265                270 | 816 |
| ACC GGC GTG AAC ATG GCC AGC ATG AAC TGG TAC AAC AAC AAC GCC CCC<br>Thr Gly Val Asn Met Ala Ser Met Asn Trp Tyr Asn Asn Asn Ala Pro<br>     275                    280                285 | 864 |
| AGC TTC AGC GCC ATC GAG GCC GCC GCC ATC CGC AGC CCC CAC CTG CTG<br>Ser Phe Ser Ala Ile Glu Ala Ala Ala Ile Arg Ser Pro His Leu Leu<br>290                     295                300 | 912 |
| GAC TTC CTG GAG CAG CTG ACC ATC TTC AGC GCC AGC AGC CGC TGG AGC<br>Asp Phe Leu Glu Gln Leu Thr Ile Phe Ser Ala Ser Ser Arg Trp Ser<br>305              310                315             320 | 960 |
| AAC ACC CGC CAC ATG ACC TAC TGG CGC GGC CAC ACC ATC CAG AGC CGC<br>Asn Thr Arg His Met Thr Tyr Trp Arg Gly His Thr Ile Gln Ser Arg<br>            325                330              335 | 1008 |
| CCC ATC GGC GGC GGC CTG AAC ACC AGC ACC CAC GGC GCC ACC AAC ACC<br>Pro Ile Gly Gly Gly Leu Asn Thr Ser Thr His Gly Ala Thr Asn Thr<br>        340                    345                350 | 1056 |
| AGC ATC AAC CCC GTG ACC CTG CGC TTC GCC AGC CGC GAC GTG TAC CGC<br>Ser Ile Asn Pro Val Thr Leu Arg Phe Ala Ser Arg Asp Val Tyr Arg<br>     355                    360                365 | 1104 |
| ACC GAG AGC TAC GCC GGC GTG CTG CTG TGG GGC ATC TAC CTG GAG CCC<br>Thr Glu Ser Tyr Ala Gly Val Leu Leu Trp Gly Ile Tyr Leu Glu Pro<br>370                     375                380 | 1152 |
| ATC CAC GGC GTG CCC ACC GTG CGC TTC AAC TTC ACC AAC CCC CAG AAC<br>Ile His Gly Val Pro Thr Val Arg Phe Asn Phe Thr Asn Pro Gln Asn<br>385              390                395             400 | 1200 |

```
ATC AGC GAC CGC GGC ACC GCC AAC TAC AGC CAG CCC TAC GAG AGC CCC       1248
Ile Ser Asp Arg Gly Thr Ala Asn Tyr Ser Gln Pro Tyr Glu Ser Pro
            405                 410                 415

GGC CTG CAG CTG AAG GAC AGC GAG ACC GAG CTG CCC CCC GAG ACC ACC       1296
Gly Leu Gln Leu Lys Asp Ser Glu Thr Glu Leu Pro Pro Glu Thr Thr
420                 425                 430

GAG CGC CCC AAC TAC GAG AGC TAC AGC CAC CGC CTG AGC CAC ATC GGC       1344
Glu Arg Pro Asn Tyr Glu Ser Tyr Ser His Arg Leu Ser His Ile Gly
            435                 440                 445

ATC ATC CTG CAG AGC CGC GTG AAC GTG CCC GTG TAC AGC TGG ACC CAC       1392
Ile Ile Leu Gln Ser Arg Val Asn Val Pro Val Tyr Ser Trp Thr His
450                 455                 460

CGC AGC GCC GAC CGC ACC AAC ACC ATC GGC CCC AAC CGC ATC ACC CAG       1440
Arg Ser Ala Asp Arg Thr Asn Thr Ile Gly Pro Asn Arg Ile Thr Gln
465                 470                 475                 480

ATC CCC ATG GTG AAG GCC AGC GAG CTG CCC CAG GGC ACC ACC GTG GTG       1488
Ile Pro Met Val Lys Ala Ser Glu Leu Pro Gln Gly Thr Thr Val Val
            485                 490                 495

CGC GGC CCC GGC TTC ACC GGC GGC GAC ATC CTG CGC CGC ACC AAC ACC       1536
Arg Gly Pro Gly Phe Thr Gly Gly Asp Ile Leu Arg Arg Thr Asn Thr
            500                 505                 510

GGC GGC TTC GGC CCC ATC CGC GTG ACC GTG AAC GGC CCC CTG ACC CAG       1584
Gly Gly Phe Gly Pro Ile Arg Val Thr Val Asn Gly Pro Leu Thr Gln
            515                 520                 525

CGC TAC CGC ATC GGC TTC CGC TAC GCC AGC ACC GTG GAC TTC GAC TTC       1632
Arg Tyr Arg Ile Gly Phe Arg Tyr Ala Ser Thr Val Asp Phe Asp Phe
530                 535                 540

TTC GTG AGC CGC GGC GGC ACC ACC GTG AAC AAC TTC CGC TTC CTG CGC       1680
Phe Val Ser Arg Gly Gly Thr Thr Val Asn Asn Phe Arg Phe Leu Arg
545                 550                 555                 560

ACC ATG AAC AGC GGC GAC GAG CTG AAG TAC GGC AAC TTC GTG CGC CGC       1728
Thr Met Asn Ser Gly Asp Glu Leu Lys Tyr Gly Asn Phe Val Arg Arg
            565                 570                 575

GCC TTC ACC ACC CCC TTC ACC TTC ACC CAG ATC CAG GAC ATC ATC CGC       1776
Ala Phe Thr Thr Pro Phe Thr Phe Thr Gln Ile Gln Asp Ile Ile Arg
            580                 585                 590

ACC AGC ATC CAG GGC CTG AGC GGC AAC GGC GAG GTG TAC ATC GAC AAG       1824
Thr Ser Ile Gln Gly Leu Ser Gly Asn Gly Glu Val Tyr Ile Asp Lys
            595                 600                 605

ATC GAG ATC ATC CCC GTG ACC GCC ACC TTC GAG GCC GAG TAC GAC CTG       1872
Ile Glu Ile Ile Pro Val Thr Ala Thr Phe Glu Ala Glu Tyr Asp Leu
610                 615                 620

GAG CGC GCC CAG GAG GCC GTG AAC GCC CTG TTC ACC AAC ACC AAC CCC       1920
Glu Arg Ala Gln Glu Ala Val Asn Ala Leu Phe Thr Asn Thr Asn Pro
625                 630                 635                 640

CGC CGC CTG AAG ACC GAC GTG ACC GAC TAC CAC ATC GAC CAG GTG AGC       1968
Arg Arg Leu Lys Thr Asp Val Thr Asp Tyr His Ile Asp Gln Val Ser
            645                 650                 655

AAC CTG GTG GCC TGC CTG AGC GAC GAG TTC TGC CTG GAC GAG AAG CGC       2016
Asn Leu Val Ala Cys Leu Ser Asp Glu Phe Cys Leu Asp Glu Lys Arg
            660                 665                 670

GAG CTG CTG GAG AAG GTG AAG TAC GCC AAG CGC CTG AGC GAC GAG CGC       2064
Glu Leu Leu Glu Lys Val Lys Tyr Ala Lys Arg Leu Ser Asp Glu Arg
            675                 680                 685

AAC CTG CTG CAG GAC CCC AAC TTC ACC AGC ATC AAC AAG CAG CCC GAC       2112
Asn Leu Leu Gln Asp Pro Asn Phe Thr Ser Ile Asn Lys Gln Pro Asp
            690                 695                 700

TTC ATC AGC ACC AAC GAG CAG AGC AAC TTC ACC AGC ATC CAC GAG CAG       2160
Phe Ile Ser Thr Asn Glu Gln Ser Asn Phe Thr Ser Ile His Glu Gln
705                 710                 715                 720
```

-continued

| | | |
|---|---|---|
| AGC GAG CAC GGC TGG TGG GGC AGC GAG AAC ATC ACC ATC CAG GAG GGC<br>Ser Glu His Gly Trp Trp Gly Ser Glu Asn Ile Thr Ile Gln Glu Gly<br>            725                      730                      735 | 2208 |
| AAC GAC GTG TTC AAG GAG AAC TAC GTG ACC CTG CCC GGC ACC TTC AAC<br>Asn Asp Val Phe Lys Glu Asn Tyr Val Thr Leu Pro Gly Thr Phe Asn<br>      740                      745                      750 | 2256 |
| GAG TGC TAC CCC ACC TAC CTG TAC CAG AAG ATC GGC GAG AGC GAG CTG<br>Glu Cys Tyr Pro Thr Tyr Leu Tyr Gln Lys Ile Gly Glu Ser Glu Leu<br>            755                      760                      765 | 2304 |
| AAG GCC TAC ACC CGC TAC CAG CTG CGC GGC TAC ATC GAG GAC AGC CAG<br>Lys Ala Tyr Thr Arg Tyr Gln Leu Arg Gly Tyr Ile Glu Asp Ser Gln<br>770                      775                      780 | 2352 |
| GAC CTG GAG ATC TAC CTG ATC CGC TAC AAC GCC AAG CAC GAG ACC CTG<br>Asp Leu Glu Ile Tyr Leu Ile Arg Tyr Asn Ala Lys His Glu Thr Leu<br>785                      790                      795                      800 | 2400 |
| GAC GTG CCC GGC ACC GAG AGC CTG TGG CCC CTG AGC GTG GAG AGC CCC<br>Asp Val Pro Gly Thr Glu Ser Leu Trp Pro Leu Ser Val Glu Ser Pro<br>                  805                      810                      815 | 2448 |
| ATC GGC CGC TGC GGC GAG CCC AAC CGC TGC GCC CCC CAC TTC GAG TGG<br>Ile Gly Arg Cys Gly Glu Pro Asn Arg Cys Ala Pro His Phe Glu Trp<br>            820                      825                      830 | 2496 |
| AAC CCC GAC CTG GAC TGC AGC TGC CGC GAC GGC GAG AAG TGC GCC CAC<br>Asn Pro Asp Leu Asp Cys Ser Cys Arg Asp Gly Glu Lys Cys Ala His<br>                  835                      840                      845 | 2544 |
| CAC AGC CAC CAC TTC AGC CTG GAC ATC GAC GTG GGC TGC ACC GAC CTG<br>His Ser His His Phe Ser Leu Asp Ile Asp Val Gly Cys Thr Asp Leu<br>850                      855                      860 | 2592 |
| CAC GAG AAC CTG GGC GTG TGG GTG GTG TTC AAG ATC AAG ACC CAG GAG<br>His Glu Asn Leu Gly Val Trp Val Val Phe Lys Ile Lys Thr Gln Glu<br>865                      870                      875                      880 | 2640 |
| GGC CAC GCC CGC CTG GGC AAC CTG GAG TTC ATC GAG GAG AAG CCC CTG<br>Gly His Ala Arg Leu Gly Asn Leu Glu Phe Ile Glu Glu Lys Pro Leu<br>                  885                      890                      895 | 2688 |
| CTG GGC GAG GCC CTG AGC CGC GTG AAG CGC GCC GAG AAG AAG TGG CGC<br>Leu Gly Glu Ala Leu Ser Arg Val Lys Arg Ala Glu Lys Lys Trp Arg<br>            900                      905                      910 | 2736 |
| GAC AAG CGC GAG AAG CTG CAG CTG GAG ACC AAG CGC GTG TAC ACC GAG<br>Asp Lys Arg Glu Lys Leu Gln Leu Glu Thr Lys Arg Val Tyr Thr Glu<br>                  915                      920                      925 | 2784 |
| GCC AAG GAG GCC GTG GAC GCC CTG TTC GTG GAC AGC CAG TAC GAC CGC<br>Ala Lys Glu Ala Val Asp Ala Leu Phe Val Asp Ser Gln Tyr Asp Arg<br>930                      935                      940 | 2832 |
| CTG CAG GCC GAC ACC AAC ATC GGC ATG ATC CAC GCC GCC GAC AAG CTG<br>Leu Gln Ala Asp Thr Asn Ile Gly Met Ile His Ala Ala Asp Lys Leu<br>945                      950                      955                      960 | 2880 |
| GTG CAC CGC ATC CGC GAG GCC TAC CTG AGC GAG CTG CCC GTG ATC CCC<br>Val His Arg Ile Arg Glu Ala Tyr Leu Ser Glu Leu Pro Val Ile Pro<br>                965                      970                      975 | 2928 |
| GGC GTG AAC GCC GAG ATC TTC GAG GAG CTG GAG GGC CAC ATC ATC ACC<br>Gly Val Asn Ala Glu Ile Phe Glu Glu Leu Glu Gly His Ile Ile Thr<br>                  980                      985                      990 | 2976 |
| GCC ATC AGC CTG TAC GAC GCC CGC AAC GTG GTG AAG AAC GGC GAC TTC<br>Ala Ile Ser Leu Tyr Asp Ala Arg Asn Val Val Lys Asn Gly Asp Phe<br>            995                      1000                      1005 | 3024 |
| AAC AAC GGC CTG ACC TGC TGG AAC GTG AAG GGC CAC GTG GAC GTG CAG<br>Asn Asn Gly Leu Thr Cys Trp Asn Val Lys Gly His Val Asp Val Gln<br>      1010                      1015                      1020 | 3072 |
| CAG AGC CAC CAC CGC AGC GAC CTG GTG ATC CCC GAG TGG GAG GCC GAG<br>Gln Ser His His Arg Ser Asp Leu Val Ile Pro Glu Trp Glu Ala Glu<br>1025                      1030                      1035                      1040 | 3120 |

-continued

```
GTG AGC CAG GCC GTG CGC GTG TGC CCC GGC TGC GGC TAC ATC CTG CGC          3168
Val Ser Gln Ala Val Arg Val Cys Pro Gly Cys Gly Tyr Ile Leu Arg
             1045                1050                1055

GTG ACC GCC TAC AAG GAG GGC TAC GGC GAG GGC TGC GTG ACC ATC CAC          3216
Val Thr Ala Tyr Lys Glu Gly Tyr Gly Glu Gly Cys Val Thr Ile His
         1060                1065                1070

GAG ATC GAG AAC AAC ACC GAC GAG CTG AAG TTC AAG AAC CGC GAG GAG          3264
Glu Ile Glu Asn Asn Thr Asp Glu Leu Lys Phe Lys Asn Arg Glu Glu
         1075                1080                1085

GAG GAG GTG TAC CCC ACC GAC ACC GGC ACC TGC AAC GAC TAC ACC GCC          3312
Glu Glu Val Tyr Pro Thr Asp Thr Gly Thr Cys Asn Asp Tyr Thr Ala
         1090                1095                1100

CAC CAG GGC ACC GCC GGC TGC GCC GAC GCC TGC AAC AGC CGC AAC GCC          3360
His Gln Gly Thr Ala Gly Cys Ala Asp Ala Cys Asn Ser Arg Asn Ala
1105                1110                1115                1120

GGC TAC GAG GAC GCC TAC GAG GTG GAC ACC ACC GCC AGC GTG AAC TAC          3408
Gly Tyr Glu Asp Ala Tyr Glu Val Asp Thr Thr Ala Ser Val Asn Tyr
             1125                1130                1135

AAG CCC ACC TAC GAG GAG GAG ACC TAC ACC GAC GTG CGC CGC GAC AAC          3456
Lys Pro Thr Tyr Glu Glu Glu Thr Tyr Thr Asp Val Arg Arg Asp Asn
             1140                1145                1150

CAC TGC GAG TAC GAC CGC GGC TAC GTG AAC TAC CCC CCC GTG CCC GCC          3504
His Cys Glu Tyr Asp Arg Gly Tyr Val Asn Tyr Pro Pro Val Pro Ala
             1155                1160                1165

GGC TAC GTG ACC AAG GAG CTG GAG TAC TTC CCC GAG ACC GAC ACC GTG          3552
Gly Tyr Val Thr Lys Glu Leu Glu Tyr Phe Pro Glu Thr Asp Thr Val
         1170                1175                1180

TGG ATC GAG ATC GGC GAG ACC GAG GGC AAG TTC ATC GTG GAC AGC GTG          3600
Trp Ile Glu Ile Gly Glu Thr Glu Gly Lys Phe Ile Val Asp Ser Val
1185                1190                1195                1200

GAG CTG CTG CTG ATG GAG GAG TAG                                          3624
Glu Leu Leu Leu Met Glu Glu
             1205
```

(2) INFORMATION FOR SEQ ID NO:7:

(i) SEQUENCE CHARACTERISTICS:
        (A) LENGTH: 1207 amino acids
        (B) TYPE: amino acid
        (D) TOPOLOGY: linear (ii) MOLECULE TYPE: protein (xi) SEQUENCE DESCRIPTION: SEQ ID NO:7:

```
Met Asp Leu Leu Pro Asp Ala Arg Ile Glu Asp Ser Leu Cys Ile Ala
 1               5                  10                  15

Glu Gly Asn Asn Ile Asp Pro Phe Val Ser Ala Ser Thr Val Gln Thr
             20                  25                  30

Gly Ile Asn Ile Ala Gly Arg Ile Leu Gly Val Leu Gly Val Pro Phe
         35                  40                  45

Ala Gly Gln Leu Ala Ser Phe Tyr Ser Phe Leu Val Gly Glu Leu Trp
     50                  55                  60

Pro Arg Gly Arg Asp Gln Trp Glu Ile Phe Leu Glu His Val Glu Gln
 65                  70                  75                  80

Leu Ile Asn Gln Gln Ile Thr Glu Asn Ala Arg Asn Thr Ala Leu Ala
                 85                  90                  95

Arg Leu Gln Gly Leu Gly Asp Ser Phe Arg Ala Tyr Gln Gln Ser Leu
            100                 105                 110

Glu Asp Trp Leu Glu Asn Arg Asp Asp Ala Arg Thr Arg Ser Val Leu
        115                 120                 125
```

-continued

```
Tyr Thr Gln Tyr Ile Ala Leu Glu Leu Asp Phe Leu Asn Ala Met Pro
130                 135                 140

Leu Phe Ala Ile Arg Asn Gln Glu Val Pro Leu Leu Met Val Tyr Ala
145                 150                 155                 160

Gln Ala Ala Asn Leu His Leu Leu Leu Arg Asp Ala Ser Leu Phe
                165                 170                 175

Gly Ser Glu Phe Gly Leu Thr Ser Gln Glu Ile Gln Arg Tyr Tyr Glu
                180                 185                 190

Arg Gln Val Glu Arg Thr Arg Asp Tyr Ser Asp Tyr Cys Val Glu Trp
                195                 200                 205

Tyr Asn Thr Gly Leu Asn Ser Leu Arg Gly Thr Asn Ala Ala Ser Trp
210                 215                 220

Val Arg Tyr Asn Gln Phe Arg Arg Asp Leu Thr Leu Gly Val Leu Asp
225                 230                 235                 240

Leu Val Ala Leu Phe Pro Ser Tyr Asp Thr Arg Thr Tyr Pro Ile Asn
                245                 250                 255

Thr Ser Ala Gln Leu Thr Arg Glu Val Tyr Thr Asp Ala Ile Gly Ala
                260                 265                 270

Thr Gly Val Asn Met Ala Ser Met Asn Trp Tyr Asn Asn Ala Pro
                275                 280                 285

Ser Phe Ser Ala Ile Glu Ala Ala Ile Arg Ser Pro His Leu Leu
                290                 295                 300

Asp Phe Leu Glu Gln Leu Thr Ile Phe Ser Ala Ser Ser Arg Trp Ser
305                 310                 315                 320

Asn Thr Arg His Met Thr Tyr Trp Arg Gly His Thr Ile Gln Ser Arg
                325                 330                 335

Pro Ile Gly Gly Gly Leu Asn Thr Ser Thr His Gly Ala Thr Asn Thr
                340                 345                 350

Ser Ile Asn Pro Val Thr Leu Arg Phe Ala Ser Arg Asp Val Tyr Arg
                355                 360                 365

Thr Glu Ser Tyr Ala Gly Val Leu Leu Trp Gly Ile Tyr Leu Glu Pro
370                 375                 380

Ile His Gly Val Pro Thr Val Arg Phe Asn Phe Thr Asn Pro Gln Asn
385                 390                 395                 400

Ile Ser Asp Arg Gly Thr Ala Asn Tyr Ser Gln Pro Tyr Glu Ser Pro
                405                 410                 415

Gly Leu Gln Leu Lys Asp Ser Glu Thr Glu Leu Pro Pro Glu Thr Thr
                420                 425                 430

Glu Arg Pro Asn Tyr Glu Ser Tyr Ser His Arg Leu Ser His Ile Gly
                435                 440                 445

Ile Ile Leu Gln Ser Arg Val Asn Val Pro Val Tyr Ser Trp Thr His
450                 455                 460

Arg Ser Ala Asp Arg Thr Asn Thr Ile Gly Pro Asn Arg Ile Thr Gln
465                 470                 475                 480

Ile Pro Met Val Lys Ala Ser Glu Leu Pro Gln Gly Thr Thr Val Val
                485                 490                 495

Arg Gly Pro Gly Phe Thr Gly Gly Asp Ile Leu Arg Arg Thr Asn Thr
                500                 505                 510

Gly Gly Phe Gly Pro Ile Arg Val Thr Val Asn Gly Pro Leu Thr Gln
                515                 520                 525

Arg Tyr Arg Ile Gly Phe Arg Tyr Ala Ser Thr Val Asp Phe Asp Phe
                530                 535                 540

Phe Val Ser Arg Gly Gly Thr Thr Val Asn Asn Phe Arg Phe Leu Arg
545                 550                 555                 560
```

-continued

```
Thr Met Asn Ser Gly Asp Glu Leu Lys Tyr Gly Asn Phe Val Arg Arg
            565                 570                 575

Ala Phe Thr Thr Pro Phe Thr Phe Thr Gln Ile Gln Asp Ile Ile Arg
            580                 585                 590

Thr Ser Ile Gln Gly Leu Ser Gly Asn Gly Glu Val Tyr Ile Asp Lys
            595                 600                 605

Ile Glu Ile Ile Pro Val Thr Ala Thr Phe Glu Ala Glu Tyr Asp Leu
            610                 615                 620

Glu Arg Ala Gln Glu Ala Val Asn Ala Leu Phe Thr Asn Thr Asn Pro
625                 630                 635                 640

Arg Arg Leu Lys Thr Asp Val Thr Asp Tyr His Ile Asp Gln Val Ser
            645                 650                 655

Asn Leu Val Ala Cys Leu Ser Asp Glu Phe Cys Leu Asp Glu Lys Arg
            660                 665                 670

Glu Leu Leu Glu Lys Val Lys Tyr Ala Lys Arg Leu Ser Asp Glu Arg
            675                 680                 685

Asn Leu Leu Gln Asp Pro Asn Phe Thr Ser Ile Asn Lys Gln Pro Asp
690                 695                 700

Phe Ile Ser Thr Asn Glu Gln Ser Asn Phe Thr Ser Ile His Glu Gln
705                 710                 715                 720

Ser Glu His Gly Trp Trp Gly Ser Glu Asn Ile Thr Ile Gln Glu Gly
            725                 730                 735

Asn Asp Val Phe Lys Glu Asn Tyr Val Thr Leu Pro Gly Thr Phe Asn
            740                 745                 750

Glu Cys Tyr Pro Thr Tyr Leu Tyr Gln Lys Ile Gly Glu Ser Glu Leu
            755                 760                 765

Lys Ala Tyr Thr Arg Tyr Gln Leu Arg Gly Tyr Ile Glu Asp Ser Gln
            770                 775                 780

Asp Leu Glu Ile Tyr Leu Ile Arg Tyr Asn Ala Lys His Glu Thr Leu
785                 790                 795                 800

Asp Val Pro Gly Thr Glu Ser Leu Trp Pro Leu Ser Val Glu Ser Pro
            805                 810                 815

Ile Gly Arg Cys Gly Glu Pro Asn Arg Cys Ala Pro His Phe Glu Trp
            820                 825                 830

Asn Pro Asp Leu Asp Cys Ser Cys Arg Asp Gly Glu Lys Cys Ala His
            835                 840                 845

His Ser His His Phe Ser Leu Asp Ile Asp Val Gly Cys Thr Asp Leu
            850                 855                 860

His Glu Asn Leu Gly Val Trp Val Phe Lys Ile Lys Thr Gln Glu
865                 870                 875                 880

Gly His Ala Arg Leu Gly Asn Leu Glu Phe Ile Glu Glu Lys Pro Leu
            885                 890                 895

Leu Gly Glu Ala Leu Ser Arg Val Lys Arg Ala Glu Lys Lys Trp Arg
            900                 905                 910

Asp Lys Arg Glu Lys Leu Gln Leu Glu Thr Lys Arg Val Tyr Thr Glu
            915                 920                 925

Ala Lys Glu Ala Val Asp Ala Leu Phe Val Asp Ser Gln Tyr Asp Arg
            930                 935                 940

Leu Gln Ala Asp Thr Asn Ile Gly Met Ile His Ala Ala Asp Lys Leu
945                 950                 955                 960

Val His Arg Ile Arg Glu Ala Tyr Leu Ser Glu Leu Pro Val Ile Pro
            965                 970                 975

Gly Val Asn Ala Glu Ile Phe Glu Glu Leu Glu Gly His Ile Ile Thr
```

-continued

```
                       980                 985                 990
Ala Ile Ser Leu Tyr Asp Ala Arg Asn Val Val Lys Asn Gly Asp Phe
                995                1000               1005

Asn Asn Gly Leu Thr Cys Trp Asn Val Lys Gly His Val Asp Val Gln
        1010                1015               1020

Gln Ser His His Arg Ser Asp Leu Val Ile Pro Glu Trp Glu Ala Glu
1025                1030               1035               1040

Val Ser Gln Ala Val Arg Val Cys Pro Gly Cys Gly Tyr Ile Leu Arg
                1045               1050               1055

Val Thr Ala Tyr Lys Glu Gly Tyr Gly Glu Gly Cys Val Thr Ile His
        1060                1065               1070

Glu Ile Glu Asn Asn Thr Asp Glu Leu Lys Phe Lys Asn Arg Glu Glu
        1075                1080               1085

Glu Glu Val Tyr Pro Thr Asp Thr Gly Thr Cys Asn Asp Tyr Thr Ala
        1090                1095               1100

His Gln Gly Thr Ala Gly Cys Ala Asp Ala Cys Asn Ser Arg Asn Ala
1105                1110               1115               1120

Gly Tyr Glu Asp Ala Tyr Glu Val Asp Thr Thr Ala Ser Val Asn Tyr
                1125               1130               1135

Lys Pro Thr Tyr Glu Glu Glu Thr Tyr Thr Asp Val Arg Arg Asp Asn
                1140               1145               1150

His Cys Glu Tyr Asp Arg Gly Tyr Val Asn Tyr Pro Pro Val Pro Ala
        1155                1160               1165

Gly Tyr Val Thr Lys Glu Leu Glu Tyr Phe Pro Glu Thr Asp Thr Val
        1170                1175               1180

Trp Ile Glu Ile Gly Glu Thr Glu Gly Lys Phe Ile Val Asp Ser Val
1185                1190               1195               1200

Glu Leu Leu Leu Met Glu Glu
                1205

(2) INFORMATION FOR SEQ ID NO:8:

(i) SEQUENCE CHARACTERISTICS:
        (A) LENGTH: 3468 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(iii) HYPOTHETICAL: NO (ix) FEATURE:
        (A) NAME/KEY: CDS
        (B) LOCATION: 1..3465
        (D) OTHER INFORMATION: /product= "Full-length, hybrid,
            partially maize optimized cryIA(b)"
            /note= "Disclosed in Figure 7 as contained in pCIB4434."

(xi) SEQUENCE DESCRIPTION: SEQ ID NO:8:

ATG GAC AAC AAC CCC AAC ATC AAC GAG TGC ATC CCC TAC AAC TGC CTG      48
Met Asp Asn Asn Pro Asn Ile Asn Glu Cys Ile Pro Tyr Asn Cys Leu
        1210                1215               1220

AGC AAC CCC GAG GTG GAG GTG CTG GGC GGC GAG CGC ATC GAG ACC GGC      96
Ser Asn Pro Glu Val Glu Val Leu Gly Gly Glu Arg Ile Glu Thr Gly
        1225                1230               1235

TAC ACC CCC ATC GAC ATC AGC CTG AGC CTG ACC CAG TTC CTG CTG AGC     144
Tyr Thr Pro Ile Asp Ile Ser Leu Ser Leu Thr Gln Phe Leu Leu Ser
1240                1245               1250               1255

GAG TTC GTG CCC GGC GCC GGC TTC GTG CTG GGC CTG GTG GAC ATC ATC     192
```

-continued

```
                Glu Phe Val Pro Gly Ala Gly Phe Val Leu Gly Leu Val Asp Ile Ile
                                    1260                1265                1270

TGG GGC ATC TTC GGC CCC AGC CAG TGG GAC GCC TTC CTG GTG CAG ATC              240
Trp Gly Ile Phe Gly Pro Ser Gln Trp Asp Ala Phe Leu Val Gln Ile
        1275                1280                1285

GAG CAG CTG ATC AAC CAG CGC ATC GAG GAG TTC GCC CGC AAC CAG GCC              288
Glu Gln Leu Ile Asn Gln Arg Ile Glu Glu Phe Ala Arg Asn Gln Ala
    1290                1295                1300

ATC AGC CGC CTG GAG GGC CTG AGC AAC CTG TAC CAA ATC TAC GCC GAG              336
Ile Ser Arg Leu Glu Gly Leu Ser Asn Leu Tyr Gln Ile Tyr Ala Glu
        1305                1310                1315

AGC TTC CGC GAG TGG GAG GCC GAC CCC ACC AAC CCC GCC CTG CGC GAG              384
Ser Phe Arg Glu Trp Glu Ala Asp Pro Thr Asn Pro Ala Leu Arg Glu
1320                1325                1330                1335

GAG ATG CGC ATC CAG TTC AAC GAC ATG AAC AGC GCC CTG ACC ACC GCC              432
Glu Met Arg Ile Gln Phe Asn Asp Met Asn Ser Ala Leu Thr Thr Ala
        1340                1345                1350

ATC CCC CTG TTC GCC GTG CAG AAC TAC CAG GTG CCC CTG CTG AGC GTG              480
Ile Pro Leu Phe Ala Val Gln Asn Tyr Gln Val Pro Leu Leu Ser Val
        1355                1360                1365

TAC GTG CAG GCC GCC AAC CTG CAC CTG AGC GTG CTG CGC GAC GTC AGC              528
Tyr Val Gln Ala Ala Asn Leu His Leu Ser Val Leu Arg Asp Val Ser
        1370                1375                1380

GTG TTC GGC CAG CGC TGG GGC TTC GAC GCC GCC ACC ATC AAC AGC CGC              576
Val Phe Gly Gln Arg Trp Gly Phe Asp Ala Ala Thr Ile Asn Ser Arg
        1385                1390                1395

TAC AAC GAC CTG ACC CGC CTG ATC GGC AAC TAC ACC GAC CAC GCC GTG              624
Tyr Asn Asp Leu Thr Arg Leu Ile Gly Asn Tyr Thr Asp His Ala Val
1400                1405                1410                1415

CGC TGG TAC AAC ACC GGC CTG GAG CGC GTG TGG GGT CCC GAC AGC CGC              672
Arg Trp Tyr Asn Thr Gly Leu Glu Arg Val Trp Gly Pro Asp Ser Arg
        1420                1425                1430

GAC TGG ATC AGG TAC AAC CAG TTC CGC CGC GAG CTG ACC CTG ACC GTG              720
Asp Trp Ile Arg Tyr Asn Gln Phe Arg Arg Glu Leu Thr Leu Thr Val
        1435                1440                1445

CTG GAC ATC GTG AGC CTG TTC CCC AAC TAC GAC AGC CGC ACC TAC CCC              768
Leu Asp Ile Val Ser Leu Phe Pro Asn Tyr Asp Ser Arg Thr Tyr Pro
        1450                1455                1460

ATC CGC ACC GTG AGC CAG CTG ACC CGC GAG ATT TAC ACC AAC CCC GTG              816
Ile Arg Thr Val Ser Gln Leu Thr Arg Glu Ile Tyr Thr Asn Pro Val
1465                1470                1475

CTG GAG AAC TTC GAC GGC AGC TTC CGC GGC AGC GCC CAG GGC ATC GAG              864
Leu Glu Asn Phe Asp Gly Ser Phe Arg Gly Ser Ala Gln Gly Ile Glu
1480                1485                1490                1495

GGC AGC ATC CGC AGC CCC CAC CTG ATG GAC ATC CTG AAC AGC ATC ACC              912
Gly Ser Ile Arg Ser Pro His Leu Met Asp Ile Leu Asn Ser Ile Thr
                1500                1505                1510

ATC TAC ACC GAC GCC CAC CGC GGC GAG TAC TAC TGG AGC GGC CAC CAG              960
Ile Tyr Thr Asp Ala His Arg Gly Glu Tyr Tyr Trp Ser Gly His Gln
        1515                1520                1525

ATC ATG GCC AGC CCC GTC GGC TTC AGC GGC CCC GAG TTC ACC TTC CCC             1008
Ile Met Ala Ser Pro Val Gly Phe Ser Gly Pro Glu Phe Thr Phe Pro
        1530                1535                1540

CTG TAC GGC ACC ATG GGC AAC GCT GCA CCT CAG CAG CGC ATC GTG GCA             1056
Leu Tyr Gly Thr Met Gly Asn Ala Ala Pro Gln Gln Arg Ile Val Ala
        1545                1550                1555

CAG CTG GGC CAG GGA GTG TAC CGC ACC CTG AGC AGC ACC CTG TAC CGT             1104
Gln Leu Gly Gln Gly Val Tyr Arg Thr Leu Ser Ser Thr Leu Tyr Arg
1560                1565                1570                1575

CGA CCT TTC AAC ATC GGC ATC AAC AAC CAG CAG CTG AGC GTG CTG GAC             1152
```

```
                                        -continued

Arg Pro Phe Asn Ile Gly Ile Asn Asn Gln Gln Leu Ser Val Leu Asp
            1580                1585                1590

GGC ACC GAG TTC GCC TAC GGC ACC AGC AGC AAC CTG CCC AGC GCC GTG      1200
Gly Thr Glu Phe Ala Tyr Gly Thr Ser Ser Asn Leu Pro Ser Ala Val
        1595                1600                1605

TAC CGC AAG AGC GGC ACC GTG GAC AGC CTG GAC GAG ATC CCC CCT CAG      1248
Tyr Arg Lys Ser Gly Thr Val Asp Ser Leu Asp Glu Ile Pro Pro Gln
        1610                1615                1620

AAC AAC AAC GTG CCA CCT CGA CAG GGC TTC AGC CAC CGT CTG AGC CAC      1296
Asn Asn Asn Val Pro Pro Arg Gln Gly Phe Ser His Arg Leu Ser His
        1625                1630                1635

GTG AGC ATG TTC CGC AGT GGC TTC AGC AAC AGC AGC GTG AGC ATC ATC      1344
Val Ser Met Phe Arg Ser Gly Phe Ser Asn Ser Ser Val Ser Ile Ile
1640            1645                1650                1655

CGT GCA CCT ATG TTC AGC TGG ATT CAC CGC AGT GCC GAG TTC AAC AAC      1392
Arg Ala Pro Met Phe Ser Trp Ile His Arg Ser Ala Glu Phe Asn Asn
            1660                1665                1670

ATC ATC CCC AGC AGC CAG ATC ACC CAG ATC CCC CTG ACC AAG AGC ACC      1440
Ile Ile Pro Ser Ser Gln Ile Thr Gln Ile Pro Leu Thr Lys Ser Thr
            1675                1680                1685

AAC CTG GGC AGC GGC ACC AGC GTG GTG AAG GGC CCC GGC TTC ACC GGC      1488
Asn Leu Gly Ser Gly Thr Ser Val Val Lys Gly Pro Gly Phe Thr Gly
            1690                1695                1700

GGC GAC ATC CTG CGC CGC ACC AGC CCC GGC CAG ATC AGC ACC CTG CGC      1536
Gly Asp Ile Leu Arg Arg Thr Ser Pro Gly Gln Ile Ser Thr Leu Arg
        1705                1710                1715

GTG AAC ATC ACC GCC CCC CTG AGC CAG CGC TAC CGC GTC CGC ATC CGC      1584
Val Asn Ile Thr Ala Pro Leu Ser Gln Arg Tyr Arg Val Arg Ile Arg
1720            1725                1730                1735

TAC GCC AGC ACC ACC AAC CTG CAG TTC CAC ACC AGC ATC GAC GGC CGC      1632
Tyr Ala Ser Thr Thr Asn Leu Gln Phe His Thr Ser Ile Asp Gly Arg
            1740                1745                1750

CCC ATC AAC CAG GGC AAC TTC AGC GCC ACC ATG AGC AGC GGC AGC AAC      1680
Pro Ile Asn Gln Gly Asn Phe Ser Ala Thr Met Ser Ser Gly Ser Asn
            1755                1760                1765

CTG CAG AGC GGC AGC TTC CGC ACC GTG GGC TTC ACC ACC CCC TTC AAC      1728
Leu Gln Ser Gly Ser Phe Arg Thr Val Gly Phe Thr Thr Pro Phe Asn
        1770                1775                1780

TTC AGC AAC GGC AGC AGC GTG TTC ACC CTG AGC GCC CAC GTG TTC AAC      1776
Phe Ser Asn Gly Ser Ser Val Phe Thr Leu Ser Ala His Val Phe Asn
    1785                1790                1795

AGC GGC AAC GAG GTG TAC ATC GAC CGC ATC GAG TTC GTG CCC GCC GAG      1824
Ser Gly Asn Glu Val Tyr Ile Asp Arg Ile Glu Phe Val Pro Ala Glu
1800            1805                1810                1815

GTG ACC TTC GAG GCC GAG TAC GAC CTG GAG AGG GCT CAG AAG GCC GTG      1872
Val Thr Phe Glu Ala Glu Tyr Asp Leu Glu Arg Ala Gln Lys Ala Val
            1820                1825                1830

AAC GAG CTG TTC ACC AGC AGC AAC CAG ATC GGC CTG AAG ACC GAC GTG      1920
Asn Glu Leu Phe Thr Ser Ser Asn Gln Ile Gly Leu Lys Thr Asp Val
        1835                1840                1845

ACC GAC TAC CAC ATC GAT CAA GTA TCC AAT TTA GTT GAG TGT TTA TCT      1968
Thr Asp Tyr His Ile Asp Gln Val Ser Asn Leu Val Glu Cys Leu Ser
            1850                1855                1860

GAT GAA TTT TGT CTG GAT GAA AAA AAA GAA TTG TCC GAG AAA GTC AAA      2016
Asp Glu Phe Cys Leu Asp Glu Lys Lys Glu Leu Ser Glu Lys Val Lys
            1865                1870                1875

CAT GCG AAG CGA CTT AGT GAT GAG CGG AAT TTA CTT CAA GAT CCA AAC      2064
His Ala Lys Arg Leu Ser Asp Glu Arg Asn Leu Leu Gln Asp Pro Asn
1880            1885                1890                1895

TTT AGA GGG ATC AAT AGA CAA CTA GAC CGT GGC TGG AGA GGA AGT ACG      2112
```

```
          Phe Arg Gly Ile Asn Arg Gln Leu Asp Arg Gly Trp Arg Gly Ser Thr
                      1900                1905                1910

GAT ATT ACC ATC CAA GGA GGC GAT GAC GTA TTC AAA GAG AAT TAC GTT                2160
Asp Ile Thr Ile Gln Gly Gly Asp Asp Val Phe Lys Glu Asn Tyr Val
            1915                1920                1925

ACG CTA TTG GGT ACC TTT GAT GAG TGC TAT CCA ACG TAT TTA TAT CAA                2208
Thr Leu Leu Gly Thr Phe Asp Glu Cys Tyr Pro Thr Tyr Leu Tyr Gln
        1930                1935                1940

AAA ATA GAT GAG TCG AAA TTA AAA GCC TAT ACC CGT TAC CAA TTA AGA                2256
Lys Ile Asp Glu Ser Lys Leu Lys Ala Tyr Thr Arg Tyr Gln Leu Arg
        1945                1950                1955

GGG TAT ATC GAA GAT AGT CAA GAC TTA GAA ATC TAT TTA ATT CGC TAC                2304
Gly Tyr Ile Glu Asp Ser Gln Asp Leu Glu Ile Tyr Leu Ile Arg Tyr
1960                1965                1970                1975

AAT GCC AAA CAC GAA ACA GTA AAT GTG CCA GGT ACG GGT TCC TTA TGG                2352
Asn Ala Lys His Glu Thr Val Asn Val Pro Gly Thr Gly Ser Leu Trp
                1980                1985                1990

CCG CTT TCA GCC CCA AGT CCA ATC GGA AAA TGT GCC CAT CAT TCC CAT                2400
Pro Leu Ser Ala Pro Ser Pro Ile Gly Lys Cys Ala His His Ser His
            1995                2000                2005

CAT TTC TCC TTG GAC ATT GAT GTT GGA TGT ACA GAC TTA AAT GAG GAC                2448
His Phe Ser Leu Asp Ile Asp Val Gly Cys Thr Asp Leu Asn Glu Asp
        2010                2015                2020

TTA GGT GTA TGG GTG ATA TTC AAG ATT AAG ACG CAA GAT GGC CAT GCA                2496
Leu Gly Val Trp Val Ile Phe Lys Ile Lys Thr Gln Asp Gly His Ala
        2025                2030                2035

AGA CTA GGA AAT CTA GAA TTT CTC GAA GAG AAA CCA TTA GTA GGA GAA                2544
Arg Leu Gly Asn Leu Glu Phe Leu Glu Glu Lys Pro Leu Val Gly Glu
2040                2045                2050                2055

GCA CTA GCT CGT GTG AAA AGA GCG GAG AAA AAA TGG AGA GAC AAA CGT                2592
Ala Leu Ala Arg Val Lys Arg Ala Glu Lys Lys Trp Arg Asp Lys Arg
                2060                2065                2070

GAA AAA TTG GAA TGG GAA ACA AAT ATT GTT TAT AAA GAG GCA AAA GAA                2640
Glu Lys Leu Glu Trp Glu Thr Asn Ile Val Tyr Lys Glu Ala Lys Glu
            2075                2080                2085

TCT GTA GAT GCT TTA TTT GTA AAC TCT CAA TAT GAT AGA TTA CAA GCG                2688
Ser Val Asp Ala Leu Phe Val Asn Ser Gln Tyr Asp Arg Leu Gln Ala
        2090                2095                2100

GAT ACC AAC ATC GCG ATG ATT CAT GCG GCA GAT AAA CGC GTT CAT AGC                2736
Asp Thr Asn Ile Ala Met Ile His Ala Ala Asp Lys Arg Val His Ser
        2105                2110                2115

ATT CGA GAA GCT TAT CTG CCT GAG CTG TCT GTG ATT CCG GGT GTC AAT                2784
Ile Arg Glu Ala Tyr Leu Pro Glu Leu Ser Val Ile Pro Gly Val Asn
2120                2125                2130                2135

GCG GCT ATT TTT GAA GAA TTA GAA GGG CGT ATT TTC ACT GCA TTC TCC                2832
Ala Ala Ile Phe Glu Glu Leu Glu Gly Arg Ile Phe Thr Ala Phe Ser
                2140                2145                2150

CTA TAT GAT GCG AGA AAT GTC ATT AAA AAT GGT GAT TTT AAT AAT GGC                2880
Leu Tyr Asp Ala Arg Asn Val Ile Lys Asn Gly Asp Phe Asn Asn Gly
            2155                2160                2165

TTA TCC TGC TGG AAC GTG AAA GGG CAT GTA GAT GTA GAA GAA CAA AAC                2928
Leu Ser Cys Trp Asn Val Lys Gly His Val Asp Val Glu Glu Gln Asn
        2170                2175                2180

AAC CAC CGT TCG GTC CTT GTT GTT CCG GAA TGG GAA GCA GAA GTG TCA                2976
Asn His Arg Ser Val Leu Val Val Pro Glu Trp Glu Ala Glu Val Ser
        2185                2190                2195

CAA GAA GTT CGT GTC TGT CCG GGT CGT GGC TAT ATC CTT CGT GTC ACA                3024
Gln Glu Val Arg Val Cys Pro Gly Arg Gly Tyr Ile Leu Arg Val Thr
2200                2205                2210                2215

GCG TAC AAG GAG GGA TAT GGA GAA GGT TGC GTA ACC ATT CAT GAG ATC                3072
```

```
Ala Tyr Lys Glu Gly Tyr Gly Glu Gly Cys Val Thr Ile His Glu Ile
        2220                2225                    2230

GAG AAC AAT ACA GAC GAA CTG AAG TTT AGC AAC TGT GTA GAA GAG GAA    3120
Glu Asn Asn Thr Asp Glu Leu Lys Phe Ser Asn Cys Val Glu Glu Glu
            2235                2240                    2245

GTA TAT CCA AAC AAC ACG GTA ACG TGT AAT GAT TAT ACT GCG ACT CAA    3168
Val Tyr Pro Asn Asn Thr Val Thr Cys Asn Asp Tyr Thr Ala Thr Gln
            2250                2255                    2260

GAA GAA TAT GAG GGT ACG TAC ACT TCT CGT AAT CGA GGA TAT GAC GGA    3216
Glu Glu Tyr Glu Gly Thr Tyr Thr Ser Arg Asn Arg Gly Tyr Asp Gly
        2265                2270                    2275

GCC TAT GAA AGC AAT TCT TCT GTA CCA GCT GAT TAT GCA TCA GCC TAT    3264
Ala Tyr Glu Ser Asn Ser Ser Val Pro Ala Asp Tyr Ala Ser Ala Tyr
2280                2285                2290                2295

GAA GAA AAA GCA TAT ACA GAT GGA CGA AGA GAC AAT CCT TGT GAA TCT    3312
Glu Glu Lys Ala Tyr Thr Asp Gly Arg Arg Asp Asn Pro Cys Glu Ser
            2300                2305                    2310

AAC AGA GGA TAT GGG GAT TAC ACA CCA CTA CCA GCT GGC TAT GTG ACA    3360
Asn Arg Gly Tyr Gly Asp Tyr Thr Pro Leu Pro Ala Gly Tyr Val Thr
            2315                2320                    2325

AAA GAA TTA GAG TAC TTC CCA GAA ACC GAT AAG GTA TGG ATT GAG ATC    3408
Lys Glu Leu Glu Tyr Phe Pro Glu Thr Asp Lys Val Trp Ile Glu Ile
            2330                2335                    2340

GGA GAA ACG GAA GGA ACA TTC ATC GTG GAC AGC GTG GAA TTA CTT CTT    3456
Gly Glu Thr Glu Gly Thr Phe Ile Val Asp Ser Val Glu Leu Leu Leu
        2345                2350                    2355

ATG GAG GAA TAA                                                    3468
Met Glu Glu
2360
```

(2) INFORMATION FOR SEQ ID NO:9:

(i) SEQUENCE CHARACTERISTICS:
        (A) LENGTH: 1155 amino acids
        (B) TYPE: amino acid
        (D) TOPOLOGY: linear (ii) MOLECULE TYPE: protein (xi) SEQUENCE DESCRIPTION: SEQ ID NO:9:

```
Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65              70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160
```

```
Tyr Val Gln Ala Ala Asn Leu His Leu Ser Val Leu Arg Asp Val Ser
                165                 170                 175

Val Phe Gly Gln Arg Trp Gly Phe Asp Ala Thr Ile Asn Ser Arg
            180                 185                 190

Tyr Asn Asp Leu Thr Arg Leu Ile Gly Asn Tyr Thr Asp His Ala Val
            195                 200                 205

Arg Trp Tyr Asn Thr Gly Leu Glu Arg Val Trp Gly Pro Asp Ser Arg
            210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
                260                 265                 270

Leu Glu Asn Phe Asp Gly Ser Phe Arg Gly Ser Ala Gln Gly Ile Glu
                275                 280                 285

Gly Ser Ile Arg Ser Pro His Leu Met Asp Ile Leu Asn Ser Ile Thr
            290                 295                 300

Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
                340                 345                 350

Gln Leu Gly Gln Gly Val Tyr Arg Thr Leu Ser Ser Thr Leu Tyr Arg
                355                 360                 365

Arg Pro Phe Asn Ile Gly Ile Asn Asn Gln Gln Leu Ser Val Leu Asp
            370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
            435                 440                 445

Arg Ala Pro Met Phe Ser Trp Ile His Arg Ser Ala Glu Phe Asn Asn
            450                 455                 460

Ile Ile Pro Ser Ser Gln Ile Thr Gln Ile Pro Leu Thr Lys Ser Thr
465                 470                 475                 480

Asn Leu Gly Ser Gly Thr Ser Val Val Lys Gly Pro Gly Phe Thr Gly
                485                 490                 495

Gly Asp Ile Leu Arg Arg Thr Ser Pro Gly Gln Ile Ser Thr Leu Arg
                500                 505                 510

Val Asn Ile Thr Ala Pro Leu Ser Gln Arg Tyr Arg Val Arg Ile Arg
            515                 520                 525

Tyr Ala Ser Thr Thr Asn Leu Gln Phe His Thr Ser Ile Asp Gly Arg
            530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
                565                 570                 575

Phe Ser Asn Gly Ser Ser Val Phe Thr Leu Ser Ala His Val Phe Asn
```

-continued

```
                580                 585                 590
Ser Gly Asn Glu Val Tyr Ile Asp Arg Ile Glu Phe Val Pro Ala Glu
            595                 600                 605
Val Thr Phe Glu Ala Glu Tyr Asp Leu Glu Arg Ala Gln Lys Ala Val
610                 615                 620
Asn Glu Leu Phe Thr Ser Ser Asn Gln Ile Gly Leu Lys Thr Asp Val
625                 630                 635                 640
Thr Asp Tyr His Ile Asp Gln Val Ser Asn Leu Val Glu Cys Leu Ser
                645                 650                 655
Asp Glu Phe Cys Leu Asp Glu Lys Lys Glu Leu Ser Glu Lys Val Lys
            660                 665                 670
His Ala Lys Arg Leu Ser Asp Glu Arg Asn Leu Leu Gln Asp Pro Asn
        675                 680                 685
Phe Arg Gly Ile Asn Arg Gln Leu Asp Arg Gly Trp Arg Gly Ser Thr
690                 695                 700
Asp Ile Thr Ile Gln Gly Gly Asp Asp Val Phe Lys Glu Asn Tyr Val
705                 710                 715                 720
Thr Leu Leu Gly Thr Phe Asp Glu Cys Tyr Pro Thr Tyr Leu Tyr Gln
                725                 730                 735
Lys Ile Asp Glu Ser Lys Leu Lys Ala Tyr Thr Arg Tyr Gln Leu Arg
            740                 745                 750
Gly Tyr Ile Glu Asp Ser Gln Asp Leu Glu Ile Tyr Leu Ile Arg Tyr
        755                 760                 765
Asn Ala Lys His Glu Thr Val Asn Val Pro Gly Thr Gly Ser Leu Trp
    770                 775                 780
Pro Leu Ser Ala Pro Ser Pro Ile Gly Lys Cys Ala His His Ser His
785                 790                 795                 800
His Phe Ser Leu Asp Ile Asp Val Gly Cys Thr Asp Leu Asn Glu Asp
                805                 810                 815
Leu Gly Val Trp Val Ile Phe Lys Ile Lys Thr Gln Asp Gly His Ala
            820                 825                 830
Arg Leu Gly Asn Leu Glu Phe Leu Glu Glu Lys Pro Leu Val Gly Glu
        835                 840                 845
Ala Leu Ala Arg Val Lys Arg Ala Glu Lys Lys Trp Arg Asp Lys Arg
850                 855                 860
Glu Lys Leu Glu Trp Glu Thr Asn Ile Val Tyr Lys Glu Ala Lys Glu
865                 870                 875                 880
Ser Val Asp Ala Leu Phe Val Asn Ser Gln Tyr Asp Arg Leu Gln Ala
                885                 890                 895
Asp Thr Asn Ile Ala Met Ile His Ala Ala Asp Lys Arg Val His Ser
            900                 905                 910
Ile Arg Glu Ala Tyr Leu Pro Glu Leu Ser Val Ile Pro Gly Val Asn
        915                 920                 925
Ala Ala Ile Phe Glu Glu Leu Glu Gly Arg Ile Phe Thr Ala Phe Ser
    930                 935                 940
Leu Tyr Asp Ala Arg Asn Val Ile Lys Asn Gly Asp Phe Asn Asn Gly
945                 950                 955                 960
Leu Ser Cys Trp Asn Val Lys Gly His Val Asp Val Glu Glu Gln Asn
                965                 970                 975
Asn His Arg Ser Val Leu Val Val Pro Glu Trp Glu Ala Glu Val Ser
            980                 985                 990
Gln Glu Val Arg Val Cys Pro Gly Arg Gly Tyr Ile Leu Arg Val Thr
        995                 1000                1005
```

-continued

```
Ala Tyr Lys Glu Gly Tyr Gly Glu Gly Cys Val Thr Ile His Glu Ile
    1010                1015                1020
Glu Asn Asn Thr Asp Glu Leu Lys Phe Ser Asn Cys Val Glu Glu Glu
1025            1030            1035                1040
Val Tyr Pro Asn Asn Thr Val Thr Cys Asn Asp Tyr Thr Ala Thr Gln
                1045            1050                1055
Glu Glu Tyr Glu Gly Thr Tyr Thr Ser Arg Asn Arg Gly Tyr Asp Gly
            1060            1065            1070
Ala Tyr Glu Ser Asn Ser Ser Val Pro Ala Asp Tyr Ala Ser Ala Tyr
        1075            1080            1085
Glu Glu Lys Ala Tyr Thr Asp Gly Arg Arg Asp Asn Pro Cys Glu Ser
    1090            1095            1100
Asn Arg Gly Tyr Gly Asp Tyr Thr Pro Leu Pro Ala Gly Tyr Val Thr
1105            1110            1115                1120
Lys Glu Leu Glu Tyr Phe Pro Glu Thr Asp Lys Val Trp Ile Glu Ile
                1125            1130            1135
Gly Glu Thr Glu Gly Thr Phe Ile Val Asp Ser Val Glu Leu Leu Leu
            1140            1145            1150
Met Glu Glu
    1155
```

(2) INFORMATION FOR SEQ ID NO:10:

(i) SEQUENCE CHARACTERISTICS:
        (A) LENGTH: 3546 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(iii) HYPOTHETICAL: NO (ix) FEATURE:
        (A) NAME/KEY: CDS
        (B) LOCATION: 1..3543
        (D) OTHER INFORMATION: /product= "Full-length, hybrid,
           maize optimized heat stable cryIA(b)"
           /note= "Disclosed in Figure 9 as contained in pCIB5511."

(xi) SEQUENCE DESCRIPTION: SEQ ID NO:10:

```
ATG GAC AAC AAC CCC AAC ATC AAC GAG TGC ATC CCC TAC AAC TGC CTG       48
Met Asp Asn Asn Pro Asn Ile Asn Glu Cys Ile Pro Tyr Asn Cys Leu
                1160                1165                1170

AGC AAC CCC GAG GTG GAG GTG CTG GGC GGC GAG CGC ATC GAG ACC GGC       96
Ser Asn Pro Glu Val Glu Val Leu Gly Gly Glu Arg Ile Glu Thr Gly
            1175                1180                1185

TAC ACC CCC ATC GAC ATC AGC CTG AGC CTG ACC CAG TTC CTG CTG AGC      144
Tyr Thr Pro Ile Asp Ile Ser Leu Ser Leu Thr Gln Phe Leu Leu Ser
        1190                1195                1200

GAG TTC GTG CCC GGC GCC GGC TTC GTG CTG GGC CTG GTG GAC ATC ATC      192
Glu Phe Val Pro Gly Ala Gly Phe Val Leu Gly Leu Val Asp Ile Ile
    1205                1210                1215

TGG GGC ATC TTC GGC CCC AGC CAG TGG GAC GCC TTC CTG GTG CAG ATC      240
Trp Gly Ile Phe Gly Pro Ser Gln Trp Asp Ala Phe Leu Val Gln Ile
1220                1225                1230                1235

GAG CAG CTG ATC AAC CAG CGC ATC GAG GAG TTC GCC CGC AAC CAG GCC      288
Glu Gln Leu Ile Asn Gln Arg Ile Glu Glu Phe Ala Arg Asn Gln Ala
                1240                1245                1250

ATC AGC CGC CTG GAG GGC CTG AGC AAC CTG TAC CAA ATC TAC GCC GAG      336
Ile Ser Arg Leu Glu Gly Leu Ser Asn Leu Tyr Gln Ile Tyr Ala Glu
            1255                1260                1265
```

```
AGC TTC CGC GAG TGG GAG GCC GAC CCC ACC AAC CCC GCC CTG CGC GAG       384
Ser Phe Arg Glu Trp Glu Ala Asp Pro Thr Asn Pro Ala Leu Arg Glu
        1270            1275            1280

GAG ATG CGC ATC CAG TTC AAC GAC ATG AAC AGC GCC CTG ACC ACC GCC       432
Glu Met Arg Ile Gln Phe Asn Asp Met Asn Ser Ala Leu Thr Thr Ala
    1285            1290            1295

ATC CCC CTG TTC GCC GTG CAG AAC TAC CAG GTG CCC CTG CTG AGC GTG       480
Ile Pro Leu Phe Ala Val Gln Asn Tyr Gln Val Pro Leu Leu Ser Val
1300            1305            1310            1315

TAC GTG CAG GCC GCC AAC CTG CAC CTG AGC GTG CTG CGC GAC GTC AGC       528
Tyr Val Gln Ala Ala Asn Leu His Leu Ser Val Leu Arg Asp Val Ser
        1320            1325            1330

GTG TTC GGC CAG CGC TGG GGC TTC GAC GCC GCC ACC ATC AAC AGC CGC       576
Val Phe Gly Gln Arg Trp Gly Phe Asp Ala Ala Thr Ile Asn Ser Arg
    1335            1340            1345

TAC AAC GAC CTG ACC CGC CTG ATC GGC AAC TAC ACC GAC CAC GCC GTG       624
Tyr Asn Asp Leu Thr Arg Leu Ile Gly Asn Tyr Thr Asp His Ala Val
1350            1355            1360

CGC TGG TAC AAC ACC GGC CTG GAG CGC GTG TGG GGT CCC GAC AGC CGC       672
Arg Trp Tyr Asn Thr Gly Leu Glu Arg Val Trp Gly Pro Asp Ser Arg
        1365            1370            1375

GAC TGG ATC AGG TAC AAC CAG TTC CGC CGC GAG CTG ACC CTG ACC GTG       720
Asp Trp Ile Arg Tyr Asn Gln Phe Arg Arg Glu Leu Thr Leu Thr Val
1380            1385            1390            1395

CTG GAC ATC GTG AGC CTG TTC CCC AAC TAC GAC AGC CGC ACC TAC CCC       768
Leu Asp Ile Val Ser Leu Phe Pro Asn Tyr Asp Ser Arg Thr Tyr Pro
        1400            1405            1410

ATC CGC ACC GTG AGC CAG CTG ACC CGC GAG ATT TAC ACC AAC CCC GTG       816
Ile Arg Thr Val Ser Gln Leu Thr Arg Glu Ile Tyr Thr Asn Pro Val
    1415            1420            1425

CTG GAG AAC TTC GAC GGC AGC TTC CGC GGC AGC GCC CAG GGC ATC GAG       864
Leu Glu Asn Phe Asp Gly Ser Phe Arg Gly Ser Ala Gln Gly Ile Glu
        1430            1435            1440

GGC AGC ATC CGC AGC CCC CAC CTG ATG GAC ATC CTG AAC AGC ATC ACC       912
Gly Ser Ile Arg Ser Pro His Leu Met Asp Ile Leu Asn Ser Ile Thr
    1445            1450            1455

ATC TAC ACC GAC GCC CAC CGC GGC GAG TAC TAC TGG AGC GGC CAC CAG       960
Ile Tyr Thr Asp Ala His Arg Gly Glu Tyr Tyr Trp Ser Gly His Gln
1460            1465            1470            1475

ATC ATG GCC AGC CCC GTC GGC TTC AGC GGC CCC GAG TTC ACC TTC CCC      1008
Ile Met Ala Ser Pro Val Gly Phe Ser Gly Pro Glu Phe Thr Phe Pro
        1480            1485            1490

CTG TAC GGC ACC ATG GGC AAC GCT GCA CCT CAG CAG CGC ATC GTG GCA      1056
Leu Tyr Gly Thr Met Gly Asn Ala Ala Pro Gln Gln Arg Ile Val Ala
    1495            1500            1505

CAG CTG GGC CAG GGA GTG TAC CGC ACC CTG AGC AGC ACC CTG TAC CGT      1104
Gln Leu Gly Gln Gly Val Tyr Arg Thr Leu Ser Ser Thr Leu Tyr Arg
        1510            1515            1520

CGA CCT TTC AAC ATC GGC ATC AAC AAC CAG CAG CTG AGC GTG CTG GAC      1152
Arg Pro Phe Asn Ile Gly Ile Asn Asn Gln Gln Leu Ser Val Leu Asp
    1525            1530            1535

GGC ACC GAG TTC GCC TAC GGC ACC AGC AGC AAC CTG CCC AGC GCC GTG      1200
Gly Thr Glu Phe Ala Tyr Gly Thr Ser Ser Asn Leu Pro Ser Ala Val
1540            1545            1550            1555

TAC CGC AAG AGC GGC ACC GTG GAC AGC CTG GAC GAG ATC CCC CCT CAG      1248
Tyr Arg Lys Ser Gly Thr Val Asp Ser Leu Asp Glu Ile Pro Pro Gln
        1560            1565            1570

AAC AAC AAC GTG CCA CCT CGA CAG GGC TTC AGC CAC CGT CTG AGC CAC      1296
Asn Asn Asn Val Pro Pro Arg Gln Gly Phe Ser His Arg Leu Ser His
    1575            1580            1585
```

```
GTG AGC ATG TTC CGC AGT GGC TTC AGC AAC AGC AGC GTG AGC ATC ATC      1344
Val Ser Met Phe Arg Ser Gly Phe Ser Asn Ser Ser Val Ser Ile Ile
        1590                1595                1600

CGT GCA CCT ATG TTC AGC TGG ATT CAC CGC AGT GCC GAG TTC AAC AAC      1392
Arg Ala Pro Met Phe Ser Trp Ile His Arg Ser Ala Glu Phe Asn Asn
1605                1610                1615

ATC ATC CCC AGC AGC CAG ATC ACC CAG ATC CCC CTG ACC AAG AGC ACC      1440
Ile Ile Pro Ser Ser Gln Ile Thr Gln Ile Pro Leu Thr Lys Ser Thr
1620                1625                1630                1635

AAC CTG GGC AGC GGC ACC AGC GTG GTG AAG GGC CCC GGC TTC ACC GGC      1488
Asn Leu Gly Ser Gly Thr Ser Val Val Lys Gly Pro Gly Phe Thr Gly
        1640                1645                1650

GGC GAC ATC CTG CGC CGC ACC AGC CCC GGC CAG ATC AGC ACC CTG CGC      1536
Gly Asp Ile Leu Arg Arg Thr Ser Pro Gly Gln Ile Ser Thr Leu Arg
        1655                1660                1665

GTG AAC ATC ACC GCC CCC CTG AGC CAG CGC TAC CGC GTC CGC ATC CGC      1584
Val Asn Ile Thr Ala Pro Leu Ser Gln Arg Tyr Arg Val Arg Ile Arg
        1670                1675                1680

TAC GCC AGC ACC ACC AAC CTG CAG TTC CAC ACC AGC ATC GAC GGC CGC      1632
Tyr Ala Ser Thr Thr Asn Leu Gln Phe His Thr Ser Ile Asp Gly Arg
        1685                1690                1695

CCC ATC AAC CAG GGC AAC TTC AGC GCC ACC ATG AGC AGC GGC AGC AAC      1680
Pro Ile Asn Gln Gly Asn Phe Ser Ala Thr Met Ser Ser Gly Ser Asn
1700                1705                1710                1715

CTG CAG AGC GGC AGC TTC CGC ACC GTG GGC TTC ACC ACC CCC TTC AAC      1728
Leu Gln Ser Gly Ser Phe Arg Thr Val Gly Phe Thr Thr Pro Phe Asn
        1720                1725                1730

TTC AGC AAC GGC AGC AGC GTG TTC ACC CTG AGC GCC CAC GTG TTC AAC      1776
Phe Ser Asn Gly Ser Ser Val Phe Thr Leu Ser Ala His Val Phe Asn
        1735                1740                1745

AGC GGC AAC GAG GTG TAC ATC GAC CGC ATC GAG TTC GTG CCC GCC GAG      1824
Ser Gly Asn Glu Val Tyr Ile Asp Arg Ile Glu Phe Val Pro Ala Glu
        1750                1755                1760

GTG ACC TTC GAG GCC GAG TAC GAC CTG GAG AGG GCT CAG AAG GCC GTG      1872
Val Thr Phe Glu Ala Glu Tyr Asp Leu Glu Arg Ala Gln Lys Ala Val
        1765                1770                1775

AAC GAG CTG TTC ACC AGC AGC AAC CAG ATC GGC CTG AAG ACC GAC GTG      1920
Asn Glu Leu Phe Thr Ser Ser Asn Gln Ile Gly Leu Lys Thr Asp Val
1780                1785                1790                1795

ACC GAC TAC CAC ATC GAT CAA GTA TCC AAT TTA GTT GAG TGT TTA TCT      1968
Thr Asp Tyr His Ile Asp Gln Val Ser Asn Leu Val Glu Cys Leu Ser
        1800                1805                1810

GAT GAA TTT TGT CTG GAT GAA AAA AAA GAA TTG TCC GAG AAA GTC AAA      2016
Asp Glu Phe Cys Leu Asp Glu Lys Lys Glu Leu Ser Glu Lys Val Lys
        1815                1820                1825

CAT GCG AAG CGA CTT AGT GAT GAG CGG AAT TTA CTT CAA GAT CCA AAC      2064
His Ala Lys Arg Leu Ser Asp Glu Arg Asn Leu Leu Gln Asp Pro Asn
        1830                1835                1840

TTT AGA GGG ATC AAT AGA CAA CTA GAC CGT GGC TGG AGA GGA AGT ACG      2112
Phe Arg Gly Ile Asn Arg Gln Leu Asp Arg Gly Trp Arg Gly Ser Thr
        1845                1850                1855

GAT ATT ACC ATC CAA GGA GGC GAT GAC GTA TTC AAA GAG AAT TAC GTT      2160
Asp Ile Thr Ile Gln Gly Gly Asp Asp Val Phe Lys Glu Asn Tyr Val
1860                1865                1870                1875

ACG CTA TTG GGT ACC TTC GAC GAG TGC TAC CCC ACC TAC CTG TAC CAG      2208
Thr Leu Leu Gly Thr Phe Asp Glu Cys Tyr Pro Thr Tyr Leu Tyr Gln
        1880                1885                1890

AAG ATC GAC GAG AGC AAG CTG AAG GCC TAC ACC CGC TAC CAG CTG CGC      2256
Lys Ile Asp Glu Ser Lys Leu Lys Ala Tyr Thr Arg Tyr Gln Leu Arg
        1895                1900                1905
```

```
GGC TAC ATC GAG GAC AGC CAG GAC CTG GAA ATC TAC CTG ATC CGC TAC    2304
Gly Tyr Ile Glu Asp Ser Gln Asp Leu Glu Ile Tyr Leu Ile Arg Tyr
        1910                1915                1920

AAC GCC AAG CAC GAG ACC GTG AAC GTG CCC GGC ACC GGC AGC CTG TGG    2352
Asn Ala Lys His Glu Thr Val Asn Val Pro Gly Thr Gly Ser Leu Trp
1925                1930                1935

CCC CTG AGC GCC CCC AGC CCC ATC GGC AAG TGC GGG GAG CCG AAT CGA    2400
Pro Leu Ser Ala Pro Ser Pro Ile Gly Lys Cys Gly Glu Pro Asn Arg
1940                1945                1950                1955

TGC GCT CCG CAC CTG GAG TGG AAC CCG GAC CTA GAC TGC AGC TGC AGG    2448
Cys Ala Pro His Leu Glu Trp Asn Pro Asp Leu Asp Cys Ser Cys Arg
            1960                1965                1970

GAC GGG GAG AAG TGC GCC CAC CAC AGC CAC CAC TTC AGC CTG GAC ATC    2496
Asp Gly Glu Lys Cys Ala His His Ser His His Phe Ser Leu Asp Ile
        1975                1980                1985

GAC GTG GGC TGC ACC GAC CTG AAC GAG GAC CTG GGC GTG TGG GTG ATC    2544
Asp Val Gly Cys Thr Asp Leu Asn Glu Asp Leu Gly Val Trp Val Ile
    1990                1995                2000

TTC AAG ATC AAG ACC CAG GAC GGC CAC GCC CGC CTG GGC AAT CTA GAA    2592
Phe Lys Ile Lys Thr Gln Asp Gly His Ala Arg Leu Gly Asn Leu Glu
2005                2010                2015

TTT CTC GAA GAG AAA CCA TTA GTA GGA GAA GCA CTA GCT CGT GTG AAA    2640
Phe Leu Glu Glu Lys Pro Leu Val Gly Glu Ala Leu Ala Arg Val Lys
2020                2025                2030                2035

AGA GCG GAG AAA AAA TGG AGA GAC AAA CGT GAA AAA TTG GAA TGG GAA    2688
Arg Ala Glu Lys Lys Trp Arg Asp Lys Arg Glu Lys Leu Glu Trp Glu
            2040                2045                2050

ACA AAT ATT GTT TAT AAA GAG GCA AAA GAA TCT GTA GAT GCT TTA TTT    2736
Thr Asn Ile Val Tyr Lys Glu Ala Lys Glu Ser Val Asp Ala Leu Phe
        2055                2060                2065

GTA AAC TCT CAA TAT GAT AGA TTA CAA GCG GAT ACC AAC ATC GCG ATG    2784
Val Asn Ser Gln Tyr Asp Arg Leu Gln Ala Asp Thr Asn Ile Ala Met
    2070                2075                2080

ATT CAT GCG GCA GAT AAA CGC GTT CAT AGC ATT CGA GAA GCT TAT CTG    2832
Ile His Ala Ala Asp Lys Arg Val His Ser Ile Arg Glu Ala Tyr Leu
2085                2090                2095

CCT GAG CTG TCT GTG ATT CCG GGT GTC AAT GCG GCT ATT TTT GAA GAA    2880
Pro Glu Leu Ser Val Ile Pro Gly Val Asn Ala Ala Ile Phe Glu Glu
2100                2105                2110                2115

TTA GAA GGG CGT ATT TTC ACT GCA TTC TCC CTA TAT GAT GCG AGA AAT    2928
Leu Glu Gly Arg Ile Phe Thr Ala Phe Ser Leu Tyr Asp Ala Arg Asn
            2120                2125                2130

GTC ATT AAA AAT GGT GAT TTT AAT AAT GGC TTA TCC TGC TGG AAC GTG    2976
Val Ile Lys Asn Gly Asp Phe Asn Asn Gly Leu Ser Cys Trp Asn Val
        2135                2140                2145

AAA GGG CAT GTA GAT GTA GAA GAA CAA AAC AAC CAC CGT TCG GTC CTT    3024
Lys Gly His Val Asp Val Glu Glu Gln Asn Asn His Arg Ser Val Leu
    2150                2155                2160

GTT GTT CCG GAA TGG GAA GCA GAA GTG TCA CAA GAA GTT CGT GTC TGT    3072
Val Val Pro Glu Trp Glu Ala Glu Val Ser Gln Glu Val Arg Val Cys
2165                2170                2175

CCG GGT CGT GGC TAT ATC CTT CGT GTC ACA GCG TAC AAG GAG GGA TAT    3120
Pro Gly Arg Gly Tyr Ile Leu Arg Val Thr Ala Tyr Lys Glu Gly Tyr
2180                2185                2190                2195

GGA GAA GGT TGC GTA ACC ATT CAT GAG ATC GAG AAC AAT ACA GAC GAA    3168
Gly Glu Gly Cys Val Thr Ile His Glu Ile Glu Asn Asn Thr Asp Glu
            2200                2205                2210

CTG AAG TTT AGC AAC TGT GTA GAA GAG GAA GTA TAT CCA AAC AAC ACG    3216
Leu Lys Phe Ser Asn Cys Val Glu Glu Glu Val Tyr Pro Asn Asn Thr
        2215                2220                2225
```

```
GTA ACG TGT AAT GAT TAT ACT GCG ACT CAA GAA GAA TAT GAG GGT ACG     3264
Val Thr Cys Asn Asp Tyr Thr Ala Thr Gln Glu Glu Tyr Glu Gly Thr
            2230                2235                2240

TAC ACT TCT CGT AAT CGA GGA TAT GAC GGA GCC TAT GAA AGC AAT TCT     3312
Tyr Thr Ser Arg Asn Arg Gly Tyr Asp Gly Ala Tyr Glu Ser Asn Ser
        2245                2250                2255

TCT GTA CCA GCT GAT TAT GCA TCA GCC TAT GAA GAA AAA GCA TAT ACA     3360
Ser Val Pro Ala Asp Tyr Ala Ser Ala Tyr Glu Glu Lys Ala Tyr Thr
2260                2265                2270                2275

GAT GGA CGA AGA GAC AAT CCT TGT GAA TCT AAC AGA GGA TAT GGG GAT     3408
Asp Gly Arg Arg Asp Asn Pro Cys Glu Ser Asn Arg Gly Tyr Gly Asp
            2280                2285                2290

TAC ACA CCA CTA CCA GCT GGC TAT GTG ACA AAA GAA TTA GAG TAC TTC     3456
Tyr Thr Pro Leu Pro Ala Gly Tyr Val Thr Lys Glu Leu Glu Tyr Phe
        2295                2300                2305

CCA GAA ACC GAT AAG GTA TGG ATT GAG ATC GGA GAA ACG GAA GGA ACA     3504
Pro Glu Thr Asp Lys Val Trp Ile Glu Ile Gly Glu Thr Glu Gly Thr
    2310                2315                2320

TTC ATC GTG GAC AGC GTG GAA TTA CTT CTT ATG GAG GAA TAA             3546
Phe Ile Val Asp Ser Val Glu Leu Leu Leu Met Glu Glu
    2325                2330                2335

(2) INFORMATION FOR SEQ ID NO:11:

(i) SEQUENCE CHARACTERISTICS:
        (A) LENGTH: 1181 amino acids
        (B) TYPE: amino acid
        (D) TOPOLOGY: linear (ii) MOLECULE TYPE: protein (xi) SEQUENCE DESCRIPTION: SEQ ID NO:11:

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65              70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
        195                 200                 205
```

-continued

```
Arg Trp Tyr Asn Thr Gly Leu Glu Arg Val Trp Gly Pro Asp Ser Arg
    210                 215                 220
Asp Trp Ile Arg Tyr Asn Gln Phe Arg Glu Leu Thr Leu Thr Val
225                 230                 235                 240
Leu Asp Ile Val Ser Leu Phe Pro Asn Tyr Asp Ser Arg Thr Tyr Pro
                245                 250                 255
Ile Arg Thr Val Ser Gln Leu Thr Arg Glu Ile Tyr Thr Asn Pro Val
            260                 265                 270
Leu Glu Asn Phe Asp Gly Ser Phe Arg Gly Ser Ala Gln Gly Ile Glu
        275                 280                 285
Gly Ser Ile Arg Ser Pro His Leu Met Asp Ile Leu Asn Ser Ile Thr
    290                 295                 300
Ile Tyr Thr Asp Ala His Arg Gly Glu Tyr Tyr Trp Ser Gly His Gln
305                 310                 315                 320
Ile Met Ala Ser Pro Val Gly Phe Ser Gly Pro Glu Phe Thr Phe Pro
                325                 330                 335
Leu Tyr Gly Thr Met Gly Asn Ala Ala Pro Gln Gln Arg Ile Val Ala
            340                 345                 350
Gln Leu Gly Gln Gly Val Tyr Arg Thr Leu Ser Ser Thr Leu Tyr Arg
        355                 360                 365
Arg Pro Phe Asn Ile Gly Ile Asn Asn Gln Gln Leu Ser Val Leu Asp
    370                 375                 380
Gly Thr Glu Phe Ala Tyr Gly Thr Ser Ser Asn Leu Pro Ser Ala Val
385                 390                 395                 400
Tyr Arg Lys Ser Gly Thr Val Asp Ser Leu Asp Glu Ile Pro Pro Gln
                405                 410                 415
Asn Asn Asn Val Pro Pro Arg Gln Gly Phe Ser His Arg Leu Ser His
            420                 425                 430
Val Ser Met Phe Arg Ser Gly Phe Ser Asn Ser Ser Val Ser Ile Ile
        435                 440                 445
Arg Ala Pro Met Phe Ser Trp Ile His Arg Ser Ala Glu Phe Asn Asn
    450                 455                 460
Ile Ile Pro Ser Ser Gln Ile Thr Gln Ile Pro Leu Thr Lys Ser Thr
465                 470                 475                 480
Asn Leu Gly Ser Gly Thr Ser Val Val Lys Gly Pro Gly Phe Thr Gly
                485                 490                 495
Gly Asp Ile Leu Arg Arg Thr Ser Pro Gly Gln Ile Ser Thr Leu Arg
            500                 505                 510
Val Asn Ile Thr Ala Pro Leu Ser Gln Arg Tyr Arg Val Arg Ile Arg
        515                 520                 525
Tyr Ala Ser Thr Thr Asn Leu Gln Phe His Thr Ser Ile Asp Gly Arg
    530                 535                 540
Pro Ile Asn Gln Gly Asn Phe Ser Ala Thr Met Ser Ser Gly Ser Asn
545                 550                 555                 560
Leu Gln Ser Gly Ser Phe Arg Thr Val Gly Phe Thr Thr Pro Phe Asn
                565                 570                 575
Phe Ser Asn Gly Ser Ser Val Phe Thr Leu Ser Ala His Val Phe Asn
            580                 585                 590
Ser Gly Asn Glu Val Tyr Ile Asp Arg Ile Glu Phe Val Pro Ala Glu
        595                 600                 605
Val Thr Phe Glu Ala Glu Tyr Asp Leu Glu Arg Ala Gln Lys Ala Val
    610                 615                 620
Asn Glu Leu Phe Thr Ser Ser Asn Gln Ile Gly Leu Lys Thr Asp Val
625                 630                 635                 640
```

-continued

```
Thr Asp Tyr His Ile Asp Gln Val Ser Asn Leu Val Glu Cys Leu Ser
            645                 650                 655
Asp Glu Phe Cys Leu Asp Glu Lys Lys Glu Leu Ser Glu Lys Val Lys
            660                 665                 670
His Ala Lys Arg Leu Ser Asp Glu Arg Asn Leu Leu Gln Asp Pro Asn
            675                 680                 685
Phe Arg Gly Ile Asn Arg Gln Leu Asp Arg Gly Trp Arg Gly Ser Thr
690                 695                 700
Asp Ile Thr Ile Gln Gly Gly Asp Asp Val Phe Lys Glu Asn Tyr Val
705                 710                 715                 720
Thr Leu Leu Gly Thr Phe Asp Glu Cys Tyr Pro Thr Tyr Leu Tyr Gln
                725                 730                 735
Lys Ile Asp Glu Ser Lys Leu Lys Ala Tyr Thr Arg Tyr Gln Leu Arg
                740                 745                 750
Gly Tyr Ile Glu Asp Ser Gln Asp Leu Glu Ile Tyr Leu Ile Arg Tyr
                755                 760                 765
Asn Ala Lys His Glu Thr Val Asn Val Pro Gly Thr Gly Ser Leu Trp
770                 775                 780
Pro Leu Ser Ala Pro Ser Pro Ile Gly Lys Cys Gly Glu Pro Asn Arg
785                 790                 795                 800
Cys Ala Pro His Leu Glu Trp Asn Pro Asp Leu Asp Cys Ser Cys Arg
                805                 810                 815
Asp Gly Glu Lys Cys Ala His Ser His His Phe Ser Leu Asp Ile
                820                 825                 830
Asp Val Gly Cys Thr Asp Leu Asn Glu Asp Leu Gly Val Trp Val Ile
                835                 840                 845
Phe Lys Ile Lys Thr Gln Asp Gly His Ala Arg Leu Gly Asn Leu Glu
850                 855                 860
Phe Leu Glu Glu Lys Pro Leu Val Gly Glu Ala Leu Ala Arg Val Lys
865                 870                 875                 880
Arg Ala Glu Lys Lys Trp Arg Asp Lys Arg Glu Lys Leu Glu Trp Glu
                885                 890                 895
Thr Asn Ile Val Tyr Lys Glu Ala Lys Glu Ser Val Asp Ala Leu Phe
                900                 905                 910
Val Asn Ser Gln Tyr Asp Arg Leu Gln Ala Asp Thr Asn Ile Ala Met
                915                 920                 925
Ile His Ala Ala Asp Lys Arg Val His Ser Ile Arg Glu Ala Tyr Leu
930                 935                 940
Pro Glu Leu Ser Val Ile Pro Gly Val Asn Ala Ala Ile Phe Glu Glu
945                 950                 955                 960
Leu Glu Gly Arg Ile Phe Thr Ala Phe Ser Leu Tyr Asp Ala Arg Asn
                965                 970                 975
Val Ile Lys Asn Gly Asp Phe Asn Asn Gly Leu Ser Cys Trp Asn Val
                980                 985                 990
Lys Gly His Val Asp Val Glu Glu Gln Asn Asn His Arg Ser Val Leu
                995                 1000                1005
Val Val Pro Glu Trp Glu Ala Glu Val Ser Gln Glu Val Arg Val Cys
        1010                1015                1020
Pro Gly Arg Gly Tyr Ile Leu Arg Val Thr Ala Tyr Lys Glu Gly Tyr
1025                1030                1035                1040
Gly Glu Gly Cys Val Thr Ile His Glu Ile Glu Asn Asn Thr Asp Glu
                1045                1050                1055
Leu Lys Phe Ser Asn Cys Val Glu Glu Glu Val Tyr Pro Asn Asn Thr
```

-continued

```
                1060                1065                1070
    Val Thr Cys Asn Asp Tyr Thr Ala Thr Gln Glu Tyr Glu Gly Thr
                1075                1080                1085

Tyr Thr Ser Arg Asn Arg Gly Tyr Asp Gly Ala Tyr Glu Ser Asn Ser
                1090                1095                1100

Ser Val Pro Ala Asp Tyr Ala Ser Ala Tyr Glu Glu Lys Ala Tyr Thr
    1105                1110                1115                1120

Asp Gly Arg Arg Asp Asn Pro Cys Glu Ser Asn Arg Gly Tyr Gly Asp
                1125                1130                1135

Tyr Thr Pro Leu Pro Ala Gly Tyr Val Thr Lys Glu Leu Glu Tyr Phe
                1140                1145                1150

Pro Glu Thr Asp Lys Val Trp Ile Glu Ile Gly Glu Thr Glu Gly Thr
                1155                1160                1165

Phe Ile Val Asp Ser Val Glu Leu Leu Leu Met Glu Glu
                1170                1175                1180
```

(2) INFORMATION FOR SEQ ID NO:12:

(i) SEQUENCE CHARACTERISTICS:
        (A) LENGTH: 3546 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(iii) HYPOTHETICAL: NO (ix) FEATURE:
        (A) NAME/KEY: CDS
        (B) LOCATION: 1..3543
        (D) OTHER INFORMATION: /product= "Full-length, hybrid,
            maize optimized heat stable cryIA(b)"
            /note= "Disclosed in Figure 11 as contained in pCIB5512"

(xi) SEQUENCE DESCRIPTION: SEQ ID NO:12:

```
ATG GAC AAC AAC CCC AAC ATC AAC GAG TGC ATC CCC TAC AAC TGC CTG     48
Met Asp Asn Asn Pro Asn Ile Asn Glu Cys Ile Pro Tyr Asn Cys Leu
            1185                1190                1195

AGC AAC CCC GAG GTG GAG GTG CTG GGC GGC GAG CGC ATC GAG ACC GGC     96
Ser Asn Pro Glu Val Glu Val Leu Gly Gly Glu Arg Ile Glu Thr Gly
        1200                1205                1210

TAC ACC CCC ATC GAC ATC AGC CTG AGC CTG ACC CAG TTC CTG CTG AGC    144
Tyr Thr Pro Ile Asp Ile Ser Leu Ser Leu Thr Gln Phe Leu Leu Ser
    1215                1220                1225

GAG TTC GTG CCC GGC GCC GGC TTC GTG CTG GGC CTG GTG GAC ATC ATC    192
Glu Phe Val Pro Gly Ala Gly Phe Val Leu Gly Leu Val Asp Ile Ile
1230                1235                1240                1245

TGG GGC ATC TTC GGC CCC AGC CAG TGG GAC GCC TTC CTG GTG CAG ATC    240
Trp Gly Ile Phe Gly Pro Ser Gln Trp Asp Ala Phe Leu Val Gln Ile
        1250                1255                1260

GAG CAG CTG ATC AAC CAG CGC ATC GAG GAG TTC GCC CGC AAC CAG GCC    288
Glu Gln Leu Ile Asn Gln Arg Ile Glu Glu Phe Ala Arg Asn Gln Ala
    1265                1270                1275

ATC AGC CGC CTG GAG GGC CTG AGC AAC CTG TAC CAA ATC TAC GCC GAG    336
Ile Ser Arg Leu Glu Gly Leu Ser Asn Leu Tyr Gln Ile Tyr Ala Glu
        1280                1285                1290

AGC TTC CGC GAG TGG GAG GCC GAC CCC ACC AAC CCC GCC CTG CGC GAG    384
Ser Phe Arg Glu Trp Glu Ala Asp Pro Thr Asn Pro Ala Leu Arg Glu
    1295                1300                1305

GAG ATG CGC ATC CAG TTC AAC GAC ATG AAC AGC GCC CTG ACC ACC GCC    432
Glu Met Arg Ile Gln Phe Asn Asp Met Asn Ser Ala Leu Thr Thr Ala
```

-continued

| | |
|---|---|
| 1310                 1315                 1320                 1325 | |
| ATC CCC CTG TTC GCC GTG CAG AAC TAC CAG GTG CCC CTG CTG AGC GTG<br>Ile Pro Leu Phe Ala Val Gln Asn Tyr Gln Val Pro Leu Leu Ser Val<br>                1330                      1335                    1340 | 480 |
| TAC GTG CAG GCC GCC AAC CTG CAC CTG AGC GTG CTG CGC GAC GTC AGC<br>Tyr Val Gln Ala Ala Asn Leu His Leu Ser Val Leu Arg Asp Val Ser<br>                    1345                    1350                    1355 | 528 |
| GTG TTC GGC CAG CGC TGG GGC TTC GAC GCC GCC ACC ATC AAC AGC CGC<br>Val Phe Gly Gln Arg Trp Gly Phe Asp Ala Ala Thr Ile Asn Ser Arg<br>          1360                    1365                    1370 | 576 |
| TAC AAC GAC CTG ACC CGC CTG ATC GGC AAC TAC ACC GAC CAC GCC GTG<br>Tyr Asn Asp Leu Thr Arg Leu Ile Gly Asn Tyr Thr Asp His Ala Val<br>          1375                    1380                    1385 | 624 |
| CGC TGG TAC AAC ACC GGC CTG GAG CGC GTG TGG GGT CCC GAC AGC CGC<br>Arg Trp Tyr Asn Thr Gly Leu Glu Arg Val Trp Gly Pro Asp Ser Arg<br>1390                    1395                    1400                    1405 | 672 |
| GAC TGG ATC AGG TAC AAC CAG TTC CGC CGC GAG CTG ACC CTG ACC GTG<br>Asp Trp Ile Arg Tyr Asn Gln Phe Arg Arg Glu Leu Thr Leu Thr Val<br>                    1410                    1415                    1420 | 720 |
| CTG GAC ATC GTG AGC CTG TTC CCC AAC TAC GAC AGC CGC ACC TAC CCC<br>Leu Asp Ile Val Ser Leu Phe Pro Asn Tyr Asp Ser Arg Thr Tyr Pro<br>          1425                    1430                    1435 | 768 |
| ATC CGC ACC GTG AGC CAG CTG ACC CGC GAG ATT TAC ACC AAC CCC GTG<br>Ile Arg Thr Val Ser Gln Leu Thr Arg Glu Ile Tyr Thr Asn Pro Val<br>                1440                    1445                    1450 | 816 |
| CTG GAG AAC TTC GAC GGC AGC TTC CGC GGC AGC GCC CAG GGC ATC GAG<br>Leu Glu Asn Phe Asp Gly Ser Phe Arg Gly Ser Ala Gln Gly Ile Glu<br>          1455                    1460                    1465 | 864 |
| GGC AGC ATC CGC AGC CCC CAC CTG ATG GAC ATC CTG AAC AGC ATC ACC<br>Gly Ser Ile Arg Ser Pro His Leu Met Asp Ile Leu Asn Ser Ile Thr<br>1470                    1475                    1480                    1485 | 912 |
| ATC TAC ACC GAC GCC CAC CGC GGC GAG TAC TAC TGG AGC GGC CAC CAG<br>Ile Tyr Thr Asp Ala His Arg Gly Glu Tyr Tyr Trp Ser Gly His Gln<br>                1490                    1495                    1500 | 960 |
| ATC ATG GCC AGC CCC GTC GGC TTC AGC GGC CCC GAG TTC ACC TTC CCC<br>Ile Met Ala Ser Pro Val Gly Phe Ser Gly Pro Glu Phe Thr Phe Pro<br>          1505                    1510                    1515 | 1008 |
| CTG TAC GGC ACC ATG GGC AAC GCT GCA CCT CAG CAG CGC ATC GTG GCA<br>Leu Tyr Gly Thr Met Gly Asn Ala Ala Pro Gln Gln Arg Ile Val Ala<br>                1520                    1525                    1530 | 1056 |
| CAG CTG GGC CAG GGA GTG TAC CGC ACC CTG AGC AGC ACC CTG TAC CGT<br>Gln Leu Gly Gln Gly Val Tyr Arg Thr Leu Ser Ser Thr Leu Tyr Arg<br>          1535                    1540                    1545 | 1104 |
| CGA CCT TTC AAC ATC GGC ATC AAC AAC CAG CAG CTG AGC GTG CTG GAC<br>Arg Pro Phe Asn Ile Gly Ile Asn Asn Gln Gln Leu Ser Val Leu Asp<br>1550                    1555                    1560                    1565 | 1152 |
| GGC ACC GAG TTC GCC TAC GGC ACC AGC AGC AAC CTG CCC AGC GCC GTG<br>Gly Thr Glu Phe Ala Tyr Gly Thr Ser Ser Asn Leu Pro Ser Ala Val<br>                1570                    1575                    1580 | 1200 |
| TAC CGC AAG AGC GGC ACC GTG GAC AGC CTG GAC GAG ATC CCC CCT CAG<br>Tyr Arg Lys Ser Gly Thr Val Asp Ser Leu Asp Glu Ile Pro Pro Gln<br>          1585                    1590                    1595 | 1248 |
| AAC AAC AAC GTG CCA CCT CGA CAG GGC TTC AGC CAC CGT CTG AGC CAC<br>Asn Asn Asn Val Pro Pro Arg Gln Gly Phe Ser His Arg Leu Ser His<br>1600                    1605                    1610 | 1296 |
| GTG AGC ATG TTC CGC AGT GGC TTC AGC AAC AGC AGC GTG AGC ATC ATC<br>Val Ser Met Phe Arg Ser Gly Phe Ser Asn Ser Ser Val Ser Ile Ile<br>          1615                    1620                    1625 | 1344 |
| CGT GCA CCT ATG TTC AGC TGG ATT CAC CGC AGT GCC GAG TTC AAC AAC<br>Arg Ala Pro Met Phe Ser Trp Ile His Arg Ser Ala Glu Phe Asn Asn | 1392 |

-continued

|  |  |
|---|---|
| 1630    1635    1640    1645 | |
| ATC ATC CCC AGC AGC CAG ATC ACC CAG ATC CCC CTG ACC AAG AGC ACC<br>Ile Ile Pro Ser Ser Gln Ile Thr Gln Ile Pro Leu Thr Lys Ser Thr<br>            1650              1655              1660 | 1440 |
| AAC CTG GGC AGC GGC ACC AGC GTG GTG AAG GGC CCC GGC TTC ACC GGC<br>Asn Leu Gly Ser Gly Thr Ser Val Val Lys Gly Pro Gly Phe Thr Gly<br>            1665              1670              1675 | 1488 |
| GGC GAC ATC CTG CGC CGC ACC AGC CCC GGC CAG ATC AGC ACC CTG CGC<br>Gly Asp Ile Leu Arg Arg Thr Ser Pro Gly Gln Ile Ser Thr Leu Arg<br>            1680              1685              1690 | 1536 |
| GTG AAC ATC ACC GCC CCC CTG AGC CAG CGC TAC CGC GTC CGC ATC CGC<br>Val Asn Ile Thr Ala Pro Leu Ser Gln Arg Tyr Arg Val Arg Ile Arg<br>            1695              1700              1705 | 1584 |
| TAC GCC AGC ACC ACC AAC CTG CAG TTC CAC ACC AGC ATC GAC GGC CGC<br>Tyr Ala Ser Thr Thr Asn Leu Gln Phe His Thr Ser Ile Asp Gly Arg<br>1710              1715              1720              1725 | 1632 |
| CCC ATC AAC CAG GGC AAC TTC AGC GCC ACC ATG AGC AGC GGC AGC AAC<br>Pro Ile Asn Gln Gly Asn Phe Ser Ala Thr Met Ser Ser Gly Ser Asn<br>            1730              1735              1740 | 1680 |
| CTG CAG AGC GGC AGC TTC CGC ACC GTG GGC TTC ACC ACC CCC TTC AAC<br>Leu Gln Ser Gly Ser Phe Arg Thr Val Gly Phe Thr Thr Pro Phe Asn<br>            1745              1750              1755 | 1728 |
| TTC AGC AAC GGC AGC AGC GTG TTC ACC CTG AGC GCC CAC GTG TTC AAC<br>Phe Ser Asn Gly Ser Ser Val Phe Thr Leu Ser Ala His Val Phe Asn<br>            1760              1765              1770 | 1776 |
| AGC GGC AAC GAG GTG TAC ATC GAC CGC ATC GAG TTC GTG CCC GCC GAG<br>Ser Gly Asn Glu Val Tyr Ile Asp Arg Ile Glu Phe Val Pro Ala Glu<br>            1775              1780              1785 | 1824 |
| GTG ACC TTC GAG GCC GAG TAC GAC CTG GAG AGG GCT CAG AAG GCC GTG<br>Val Thr Phe Glu Ala Glu Tyr Asp Leu Glu Arg Ala Gln Lys Ala Val<br>1790              1795              1800              1805 | 1872 |
| AAC GAG CTG TTC ACC AGC AGC AAC CAG ATC GGC CTG AAG ACC GAC GTG<br>Asn Glu Leu Phe Thr Ser Ser Asn Gln Ile Gly Leu Lys Thr Asp Val<br>            1810              1815              1820 | 1920 |
| ACC GAC TAC CAC ATC GAT CAG GTG AGC AAC CTG GTG GAG TGC TTA AGC<br>Thr Asp Tyr His Ile Asp Gln Val Ser Asn Leu Val Glu Cys Leu Ser<br>            1825              1830              1835 | 1968 |
| GAC GAG TTC TGC CTG GAC GAG AAG AAG GAG CTG AGC GAG AAG GTG AAG<br>Asp Glu Phe Cys Leu Asp Glu Lys Lys Glu Leu Ser Glu Lys Val Lys<br>            1840              1845              1850 | 2016 |
| CAC GCC AAG CGC CTG AGC GAC GAG CGC AAC CTG CTG CAG GAC CCC AAC<br>His Ala Lys Arg Leu Ser Asp Glu Arg Asn Leu Leu Gln Asp Pro Asn<br>            1855              1860              1865 | 2064 |
| TTC CGC GGC ATC AAC CGC CAG CTG GAC CGC GGC TGG CGA GGC AGC ACC<br>Phe Arg Gly Ile Asn Arg Gln Leu Asp Arg Gly Trp Arg Gly Ser Thr<br>1870              1875              1880              1885 | 2112 |
| GAT ATC ACC ATC CAG GGC GGC GAC GAC GTG TTC AAG GAG AAC TAC GTG<br>Asp Ile Thr Ile Gln Gly Gly Asp Asp Val Phe Lys Glu Asn Tyr Val<br>            1890              1895              1900 | 2160 |
| ACC CTG CTG GGC ACC TTC GAC GAG TGC TAC CCC ACC TAC CTG TAC CAG<br>Thr Leu Leu Gly Thr Phe Asp Glu Cys Tyr Pro Thr Tyr Leu Tyr Gln<br>            1905              1910              1915 | 2208 |
| AAG ATC GAC GAG AGC AAG CTG AAG GCC TAC ACC CGC TAC CAG CTG CGC<br>Lys Ile Asp Glu Ser Lys Leu Lys Ala Tyr Thr Arg Tyr Gln Leu Arg<br>            1920              1925              1930 | 2256 |
| GGC TAC ATC GAG GAC AGC CAG GAC CTG GAA ATC TAC CTG ATC CGC TAC<br>Gly Tyr Ile Glu Asp Ser Gln Asp Leu Glu Ile Tyr Leu Ile Arg Tyr<br>            1935              1940              1945 | 2304 |
| AAC GCC AAG CAC GAG ACC GTG AAC GTG CCC GGC ACC GGC AGC CTG TGG<br>Asn Ala Lys His Glu Thr Val Asn Val Pro Gly Thr Gly Ser Leu Trp | 2352 |

-continued

```
       1950               1955                1960                1965

CCC CTG AGC GCC CCC AGC CCC ATC GGC AAG TGC GGG GAG CCG AAT CGA      2400
Pro Leu Ser Ala Pro Ser Pro Ile Gly Lys Cys Gly Glu Pro Asn Arg
                1970                1975                1980

TGC GCT CCG CAC CTG GAG TGG AAC CCG GAC CTA GAC TGC AGC TGC AGG      2448
Cys Ala Pro His Leu Glu Trp Asn Pro Asp Leu Asp Cys Ser Cys Arg
                1985                1990                1995

GAC GGG GAG AAG TGC GCC CAC CAC AGC CAC CAC TTC AGC CTG GAC ATC      2496
Asp Gly Glu Lys Cys Ala His His Ser His His Phe Ser Leu Asp Ile
                2000                2005                2010

GAC GTG GGC TGC ACC GAC CTG AAC GAG GAC CTG GGC GTG TGG GTG ATC      2544
Asp Val Gly Cys Thr Asp Leu Asn Glu Asp Leu Gly Val Trp Val Ile
                2015                2020                2025

TTC AAG ATC AAG ACC CAG GAC GGC CAC GCC CGC CTG GGC AAT CTA GAA      2592
Phe Lys Ile Lys Thr Gln Asp Gly His Ala Arg Leu Gly Asn Leu Glu
2030                2035                2040                2045

TTT CTC GAA GAG AAA CCA TTA GTA GGA GAA GCA CTA GCT CGT GTG AAA      2640
Phe Leu Glu Glu Lys Pro Leu Val Gly Glu Ala Leu Ala Arg Val Lys
                2050                2055                2060

AGA GCG GAG AAA AAA TGG AGA GAC AAA CGT GAA AAA TTG GAA TGG GAA      2688
Arg Ala Glu Lys Lys Trp Arg Asp Lys Arg Glu Lys Leu Glu Trp Glu
                2065                2070                2075

ACA AAT ATT GTT TAT AAA GAG GCA AAA GAA TCT GTA GAT GCT TTA TTT      2736
Thr Asn Ile Val Tyr Lys Glu Ala Lys Glu Ser Val Asp Ala Leu Phe
                2080                2085                2090

GTA AAC TCT CAA TAT GAT AGA TTA CAA GCG GAT ACC AAC ATC GCG ATG      2784
Val Asn Ser Gln Tyr Asp Arg Leu Gln Ala Asp Thr Asn Ile Ala Met
                2095                2100                2105

ATT CAT GCG GCA GAT AAA CGC GTT CAT AGC ATT CGA GAA GCT TAT CTG      2832
Ile His Ala Ala Asp Lys Arg Val His Ser Ile Arg Glu Ala Tyr Leu
2110                2115                2120                2125

CCT GAG CTG TCT GTG ATT CCG GGT GTC AAT GCG GCT ATT TTT GAA GAA      2880
Pro Glu Leu Ser Val Ile Pro Gly Val Asn Ala Ala Ile Phe Glu Glu
                2130                2135                2140

TTA GAA GGG CGT ATT TTC ACT GCA TTC TCC CTA TAT GAT GCG AGA AAT      2928
Leu Glu Gly Arg Ile Phe Thr Ala Phe Ser Leu Tyr Asp Ala Arg Asn
                2145                2150                2155

GTC ATT AAA AAT GGT GAT TTT AAT AAT GGC TTA TCC TGC TGG AAC GTG      2976
Val Ile Lys Asn Gly Asp Phe Asn Asn Gly Leu Ser Cys Trp Asn Val
                2160                2165                2170

AAA GGG CAT GTA GAT GTA GAA GAA CAA AAC AAC CAC CGT TCG GTC CTT      3024
Lys Gly His Val Asp Val Glu Glu Gln Asn Asn His Arg Ser Val Leu
                2175                2180                2185

GTT GTT CCG GAA TGG GAA GCA GAA GTG TCA CAA GAA GTT CGT GTC TGT      3072
Val Val Pro Glu Trp Glu Ala Glu Val Ser Gln Glu Val Arg Val Cys
2190                2195                2200                2205

CCG GGT CGT GGC TAT ATC CTT CGT GTC ACA GCG TAC AAG GAG GGA TAT      3120
Pro Gly Arg Gly Tyr Ile Leu Arg Val Thr Ala Tyr Lys Glu Gly Tyr
                2210                2215                2220

GGA GAA GGT TGC GTA ACC ATT CAT GAG ATC GAG AAC AAT ACA GAC GAA      3168
Gly Glu Gly Cys Val Thr Ile His Glu Ile Glu Asn Asn Thr Asp Glu
                2225                2230                2235

CTG AAG TTT AGC AAC TGT GTA GAA GAG GAA GTA TAT CCA AAC AAC ACG      3216
Leu Lys Phe Ser Asn Cys Val Glu Glu Glu Val Tyr Pro Asn Asn Thr
                2240                2245                2250

GTA ACG TGT AAT GAT TAT ACT GCG ACT CAA GAA GAA TAT GAG GGT ACG      3264
Val Thr Cys Asn Asp Tyr Thr Ala Thr Gln Glu Glu Tyr Glu Gly Thr
                2255                2260                2265

TAC ACT TCT CGT AAT CGA GGA TAT GAC GGA GCC TAT GAA AGC AAT TCT      3312
Tyr Thr Ser Arg Asn Arg Gly Tyr Asp Gly Ala Tyr Glu Ser Asn Ser
```

-continued

```
                    2270                2275                2280                2285
TCT GTA CCA GCT GAT TAT GCA TCA GCC TAT GAA GAA AAA GCA TAT ACA              3360
Ser Val Pro Ala Asp Tyr Ala Ser Ala Tyr Glu Glu Lys Ala Tyr Thr
            2290                2295                2300

GAT GGA CGA AGA GAC AAT CCT TGT GAA TCT AAC AGA GGA TAT GGG GAT              3408
Asp Gly Arg Arg Asp Asn Pro Cys Glu Ser Asn Arg Gly Tyr Gly Asp
            2305                2310                2315

TAC ACA CCA CTA CCA GCT GGC TAT GTG ACA AAA GAA TTA GAG TAC TTC              3456
Tyr Thr Pro Leu Pro Ala Gly Tyr Val Thr Lys Glu Leu Glu Tyr Phe
            2320                2325                2330

CCA GAA ACC GAT AAG GTA TGG ATT GAG ATC GGA GAA ACG GAA GGA ACA              3504
Pro Glu Thr Asp Lys Val Trp Ile Glu Ile Gly Glu Thr Glu Gly Thr
            2335                2340                2345

TTC ATC GTG GAC AGC GTG GAA TTA CTT CTT ATG GAG GAA TAA                      3546
Phe Ile Val Asp Ser Val Glu Leu Leu Leu Met Glu Glu
2350                2355                2360
```

(2) INFORMATION FOR SEQ ID NO:13:

(i) SEQUENCE CHARACTERISTICS:
        (A) LENGTH: 1181 amino acids
        (B) TYPE: amino acid
        (D) TOPOLOGY: linear (ii) MOLECULE TYPE: protein (xi) SEQUENCE DESCRIPTION: SEQ ID NO:13:

```
Met Asp Asn Asn Pro Asn Ile Asn Glu Cys Ile Pro Tyr Asn Cys Leu
 1               5                  10                  15

Ser Asn Pro Glu Val Glu Val Leu Gly Gly Glu Arg Ile Glu Thr Gly
                20                  25                  30

Tyr Thr Pro Ile Asp Ile Ser Leu Ser Leu Thr Gln Phe Leu Leu Ser
            35                  40                  45

Glu Phe Val Pro Gly Ala Gly Phe Val Leu Gly Leu Val Asp Ile Ile
        50                  55                  60

Trp Gly Ile Phe Gly Pro Ser Gln Trp Asp Ala Phe Leu Val Gln Ile
 65                  70                  75                  80

Glu Gln Leu Ile Asn Gln Arg Ile Glu Glu Phe Ala Arg Asn Gln Ala
                 85                  90                  95

Ile Ser Arg Leu Glu Gly Leu Ser Asn Leu Tyr Gln Ile Tyr Ala Glu
                100                 105                 110

Ser Phe Arg Glu Trp Glu Ala Asp Pro Thr Asn Pro Ala Leu Arg Glu
            115                 120                 125

Glu Met Arg Ile Gln Phe Asn Asp Met Asn Ser Ala Leu Thr Thr Ala
        130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
            195                 200                 205

Arg Trp Tyr Asn Thr Gly Leu Glu Arg Val Trp Gly Pro Asp Ser Arg
        210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
```

-continued

```
                245                 250                 255
Ile Arg Thr Val Ser Gln Leu Thr Arg Glu Ile Tyr Thr Asn Pro Val
                260                 265                 270
Leu Glu Asn Phe Asp Gly Ser Phe Arg Gly Ser Ala Gln Gly Ile Glu
                275                 280                 285
Gly Ser Ile Arg Ser Pro His Leu Met Asp Ile Leu Asn Ser Ile Thr
            290                 295                 300
Ile Tyr Thr Asp Ala His Arg Gly Glu Tyr Tyr Trp Ser Gly His Gln
305                 310                 315                 320
Ile Met Ala Ser Pro Val Gly Phe Ser Gly Pro Glu Phe Thr Phe Pro
                325                 330                 335
Leu Tyr Gly Thr Met Gly Asn Ala Ala Pro Gln Gln Arg Ile Val Ala
                340                 345                 350
Gln Leu Gly Gln Gly Val Tyr Arg Thr Leu Ser Ser Thr Leu Tyr Arg
                355                 360                 365
Arg Pro Phe Asn Ile Gly Ile Asn Asn Gln Gln Leu Ser Val Leu Asp
            370                 375                 380
Gly Thr Glu Phe Ala Tyr Gly Thr Ser Ser Asn Leu Pro Ser Ala Val
385                 390                 395                 400
Tyr Arg Lys Ser Gly Thr Val Asp Ser Leu Asp Glu Ile Pro Pro Gln
                405                 410                 415
Asn Asn Asn Val Pro Pro Arg Gln Gly Phe Ser His Arg Leu Ser His
                420                 425                 430
Val Ser Met Phe Arg Ser Gly Phe Ser Asn Ser Ser Val Ser Ile Ile
            435                 440                 445
Arg Ala Pro Met Phe Ser Trp Ile His Arg Ser Ala Glu Phe Asn Asn
450                 455                 460
Ile Ile Pro Ser Ser Gln Ile Thr Gln Ile Pro Leu Thr Lys Ser Thr
465                 470                 475                 480
Asn Leu Gly Ser Gly Thr Ser Val Val Lys Gly Pro Gly Phe Thr Gly
                485                 490                 495
Gly Asp Ile Leu Arg Arg Thr Ser Pro Gly Gln Ile Ser Thr Leu Arg
            500                 505                 510
Val Asn Ile Thr Ala Pro Leu Ser Gln Arg Tyr Arg Val Arg Ile Arg
            515                 520                 525
Tyr Ala Ser Thr Thr Asn Leu Gln Phe His Thr Ser Ile Asp Gly Arg
530                 535                 540
Pro Ile Asn Gln Gly Asn Phe Ser Ala Thr Met Ser Ser Gly Ser Asn
545                 550                 555                 560
Leu Gln Ser Gly Ser Phe Arg Thr Val Gly Phe Thr Thr Pro Phe Asn
                565                 570                 575
Phe Ser Asn Gly Ser Ser Val Phe Thr Leu Ser Ala His Val Phe Asn
            580                 585                 590
Ser Gly Asn Glu Val Tyr Ile Asp Arg Ile Glu Phe Val Pro Ala Glu
            595                 600                 605
Val Thr Phe Glu Ala Glu Tyr Asp Leu Glu Arg Ala Gln Lys Ala Val
            610                 615                 620
Asn Glu Leu Phe Thr Ser Ser Asn Gln Ile Gly Leu Lys Thr Asp Val
625                 630                 635                 640
Thr Asp Tyr His Ile Asp Gln Val Ser Asn Leu Val Glu Cys Leu Ser
                645                 650                 655
Asp Glu Phe Cys Leu Asp Glu Lys Lys Glu Leu Ser Glu Lys Val Lys
            660                 665                 670
```

```
His Ala Lys Arg Leu Ser Asp Glu Arg Asn Leu Leu Gln Asp Pro Asn
            675                 680                 685

Phe Arg Gly Ile Asn Arg Gln Leu Asp Arg Gly Trp Arg Gly Ser Thr
        690                 695                 700

Asp Ile Thr Ile Gln Gly Asp Val Phe Lys Glu Asn Tyr Val
705                 710                 715                 720

Thr Leu Leu Gly Thr Phe Asp Glu Cys Tyr Pro Thr Tyr Leu Tyr Gln
                725                 730                 735

Lys Ile Asp Glu Ser Lys Leu Lys Ala Tyr Thr Arg Tyr Gln Leu Arg
                740                 745                 750

Gly Tyr Ile Glu Asp Ser Gln Asp Leu Glu Ile Tyr Leu Ile Arg Tyr
            755                 760                 765

Asn Ala Lys His Glu Thr Val Asn Val Pro Gly Thr Gly Ser Leu Trp
770                 775                 780

Pro Leu Ser Ala Pro Ser Pro Ile Gly Lys Cys Gly Glu Pro Asn Arg
785                 790                 795                 800

Cys Ala Pro His Leu Glu Trp Asn Pro Asp Leu Asp Cys Ser Cys Arg
                805                 810                 815

Asp Gly Glu Lys Cys Ala His His Ser His His Phe Ser Leu Asp Ile
                820                 825                 830

Asp Val Gly Cys Thr Asp Leu Asn Glu Asp Leu Gly Val Trp Val Ile
            835                 840                 845

Phe Lys Ile Lys Thr Gln Asp Gly His Ala Arg Leu Gly Asn Leu Glu
850                 855                 860

Phe Leu Glu Glu Lys Pro Leu Val Gly Glu Ala Leu Ala Arg Val Lys
865                 870                 875                 880

Arg Ala Glu Lys Lys Trp Arg Asp Lys Arg Glu Lys Leu Glu Trp Glu
                885                 890                 895

Thr Asn Ile Val Tyr Lys Glu Ala Lys Glu Ser Val Asp Ala Leu Phe
            900                 905                 910

Val Asn Ser Gln Tyr Asp Arg Leu Gln Ala Asp Thr Asn Ile Ala Met
        915                 920                 925

Ile His Ala Ala Asp Lys Arg Val His Ser Ile Arg Glu Ala Tyr Leu
    930                 935                 940

Pro Glu Leu Ser Val Ile Pro Gly Val Asn Ala Ala Ile Phe Glu Glu
945                 950                 955                 960

Leu Glu Gly Arg Ile Phe Thr Ala Phe Ser Leu Tyr Asp Ala Arg Asn
                965                 970                 975

Val Ile Lys Asn Gly Asp Phe Asn Asn Gly Leu Ser Cys Trp Asn Val
            980                 985                 990

Lys Gly His Val Asp Val Glu Glu Gln Asn Asn His Arg Ser Val Leu
        995                 1000                1005

Val Val Pro Glu Trp Glu Ala Glu Val Ser Gln Glu Val Arg Val Cys
    1010                1015                1020

Pro Gly Arg Gly Tyr Ile Leu Arg Val Thr Ala Tyr Lys Glu Gly Tyr
1025                1030                1035                1040

Gly Glu Gly Cys Val Thr Ile His Glu Ile Glu Asn Asn Thr Asp Glu
                1045                1050                1055

Leu Lys Phe Ser Asn Cys Val Glu Glu Val Tyr Pro Asn Asn Thr
            1060                1065                1070

Val Thr Cys Asn Asp Tyr Thr Ala Thr Gln Glu Glu Tyr Glu Gly Thr
        1075                1080                1085

Tyr Thr Ser Arg Asn Arg Gly Tyr Asp Gly Ala Tyr Glu Ser Asn Ser
    1090                1095                1100
```

-continued

```
Ser Val Pro Ala Asp Tyr Ala Ser Ala Tyr Glu Glu Lys Ala Tyr Thr
1105                1110                1115                1120

Asp Gly Arg Arg Asp Asn Pro Cys Glu Ser Asn Arg Gly Tyr Gly Asp
                1125                1130                1135

Tyr Thr Pro Leu Pro Ala Gly Tyr Val Thr Lys Glu Leu Glu Tyr Phe
            1140                1145                1150

Pro Glu Thr Asp Lys Val Trp Ile Glu Ile Gly Glu Thr Glu Gly Thr
        1155                1160                1165

Phe Ile Val Asp Ser Val Glu Leu Leu Leu Met Glu Glu
1170                1175                1180
```

(2) INFORMATION FOR SEQ ID NO:14:

(i) SEQUENCE CHARACTERISTICS:
        (A) LENGTH: 3546 base pairs
        (B) TYPE: nucleic acid
        (C) STRANDEDNESS: single
        (D) TOPOLOGY: linear (ii) MOLECULE TYPE: other nucleic acid
       (A) DESCRIPTION: /desc = "Synthetic DNA"

(iii) HYPOTHETICAL: NO (ix) FEATURE:
       (A) NAME/KEY: CDS
       (B) LOCATION: 1..3543
       (D) OTHER INFORMATION: /product= "Full-length, hybrid,
          maize optimized heat stable cryIA(b)"
          /note= "Disclosed in Figure 13 as contained in pCIB5513."

(xi) SEQUENCE DESCRIPTION: SEQ ID NO:14:

```
ATG GAC AAC AAC CCC AAC ATC AAC GAG TGC ATC CCC TAC AAC TGC CTG        48
Met Asp Asn Asn Pro Asn Ile Asn Glu Cys Ile Pro Tyr Asn Cys Leu
            1185                1190                1195

AGC AAC CCC GAG GTG GAG GTG CTG GGC GGC GAG CGC ATC GAG ACC GGC        96
Ser Asn Pro Glu Val Glu Val Leu Gly Gly Glu Arg Ile Glu Thr Gly
        1200                1205                1210

TAC ACC CCC ATC GAC ATC AGC CTG AGC CTG ACC CAG TTC CTG CTG AGC       144
Tyr Thr Pro Ile Asp Ile Ser Leu Ser Leu Thr Gln Phe Leu Leu Ser
    1215                1220                1225

GAG TTC GTG CCC GGC GCC GGC TTC GTG CTG GGC CTG GTG GAC ATC ATC       192
Glu Phe Val Pro Gly Ala Gly Phe Val Leu Gly Leu Val Asp Ile Ile
1230                1235                1240                1245

TGG GGC ATC TTC GGC CCC AGC CAG TGG GAC GCC TTC CTG GTG CAG ATC       240
Trp Gly Ile Phe Gly Pro Ser Gln Trp Asp Ala Phe Leu Val Gln Ile
            1250                1255                1260

GAG CAG CTG ATC AAC CAG CGC ATC GAG GAG TTC GCC CGC AAC CAG GCC       288
Glu Gln Leu Ile Asn Gln Arg Ile Glu Glu Phe Ala Arg Asn Gln Ala
        1265                1270                1275

ATC AGC CGC CTG GAG GGC CTG AGC AAC CTG TAC CAA ATC TAC GCC GAG       336
Ile Ser Arg Leu Glu Gly Leu Ser Asn Leu Tyr Gln Ile Tyr Ala Glu
    1280                1285                1290

AGC TTC CGC GAG TGG GAG GCC GAC CCC ACC AAC CCC GCC CTG CGC GAG       384
Ser Phe Arg Glu Trp Glu Ala Asp Pro Thr Asn Pro Ala Leu Arg Glu
1295                1300                1305

GAG ATG CGC ATC CAG TTC AAC GAC ATG AAC AGC GCC CTG ACC ACC GCC       432
Glu Met Arg Ile Gln Phe Asn Asp Met Asn Ser Ala Leu Thr Thr Ala
            1310                1315                1320                1325

ATC CCC CTG TTC GCC GTG CAG AAC TAC CAG GTG CCC CTG CTG AGC GTG       480
Ile Pro Leu Phe Ala Val Gln Asn Tyr Gln Val Pro Leu Leu Ser Val
        1330                1335                1340

TAC GTG CAG GCC GCC AAC CTG CAC CTG AGC GTG CTG CGC GAC GTC AGC       528
```

-continued

```
                Tyr Val Gln Ala Ala Asn Leu His Leu Ser Val Leu Arg Asp Val Ser
                                1345                1350                1355

GTG TTC GGC CAG CGC TGG GGC TTC GAC GCC GCC ACC ATC AAC AGC CGC             576
Val Phe Gly Gln Arg Trp Gly Phe Asp Ala Ala Thr Ile Asn Ser Arg
    1360                1365                1370

TAC AAC GAC CTG ACC CGC CTG ATC GGC AAC TAC ACC GAC CAC GCC GTG             624
Tyr Asn Asp Leu Thr Arg Leu Ile Gly Asn Tyr Thr Asp His Ala Val
    1375                1380                1385

CGC TGG TAC AAC ACC GGC CTG GAG CGC GTG TGG GGT CCC GAC AGC CGC             672
Arg Trp Tyr Asn Thr Gly Leu Glu Arg Val Trp Gly Pro Asp Ser Arg
1390                1395                1400                1405

GAC TGG ATC AGG TAC AAC CAG TTC CGC CGC GAG CTG ACC CTG ACC GTG             720
Asp Trp Ile Arg Tyr Asn Gln Phe Arg Arg Glu Leu Thr Leu Thr Val
                1410                1415                1420

CTG GAC ATC GTG AGC CTG TTC CCC AAC TAC GAC AGC CGC ACC TAC CCC             768
Leu Asp Ile Val Ser Leu Phe Pro Asn Tyr Asp Ser Arg Thr Tyr Pro
            1425                1430                1435

ATC CGC ACC GTG AGC CAG CTG ACC CGC GAG ATT TAC ACC AAC CCC GTG             816
Ile Arg Thr Val Ser Gln Leu Thr Arg Glu Ile Tyr Thr Asn Pro Val
        1440                1445                1450

CTG GAG AAC TTC GAC GGC AGC TTC CGC GGC AGC GCC CAG GGC ATC GAG             864
Leu Glu Asn Phe Asp Gly Ser Phe Arg Gly Ser Ala Gln Gly Ile Glu
    1455                1460                1465

GGC AGC ATC CGC AGC CCC CAC CTG ATG GAC ATC CTG AAC AGC ATC ACC             912
Gly Ser Ile Arg Ser Pro His Leu Met Asp Ile Leu Asn Ser Ile Thr
1470                1475                1480                1485

ATC TAC ACC GAC GCC CAC CGC GGC GAG TAC TAC TGG AGC GGC CAC CAG             960
Ile Tyr Thr Asp Ala His Arg Gly Glu Tyr Tyr Trp Ser Gly His Gln
                1490                1495                1500

ATC ATG GCC AGC CCC GTC GGC TTC AGC GGC CCC GAG TTC ACC TTC CCC            1008
Ile Met Ala Ser Pro Val Gly Phe Ser Gly Pro Glu Phe Thr Phe Pro
            1505                1510                1515

CTG TAC GGC ACC ATG GGC AAC GCT GCA CCT CAG CAG CGC ATC GTG GCA            1056
Leu Tyr Gly Thr Met Gly Asn Ala Ala Pro Gln Gln Arg Ile Val Ala
        1520                1525                1530

CAG CTG GGC CAG GGA GTG TAC CGC ACC CTG AGC AGC ACC CTG TAC CGT            1104
Gln Leu Gly Gln Gly Val Tyr Arg Thr Leu Ser Ser Thr Leu Tyr Arg
    1535                1540                1545

CGA CCT TTC AAC ATC GGC ATC AAC AAC CAG CAG CTG AGC GTG CTG GAC            1152
Arg Pro Phe Asn Ile Gly Ile Asn Asn Gln Gln Leu Ser Val Leu Asp
1550                1555                1560                1565

GGC ACC GAG TTC GCC TAC GGC ACC AGC AGC AAC CTG CCC AGC GCC GTG            1200
Gly Thr Glu Phe Ala Tyr Gly Thr Ser Ser Asn Leu Pro Ser Ala Val
                1570                1575                1580

TAC CGC AAG AGC GGC ACC GTG GAC AGC CTG GAC GAG ATC CCC CCT CAG            1248
Tyr Arg Lys Ser Gly Thr Val Asp Ser Leu Asp Glu Ile Pro Pro Gln
            1585                1590                1595

AAC AAC AAC GTG CCA CCT CGA CAG GGC TTC AGC CAC CGT CTG AGC CAC            1296
Asn Asn Asn Val Pro Pro Arg Gln Gly Phe Ser His Arg Leu Ser His
        1600                1605                1610

GTG AGC ATG TTC CGC AGT GGC TTC AGC AAC AGC AGC GTG AGC ATC ATC            1344
Val Ser Met Phe Arg Ser Gly Phe Ser Asn Ser Ser Val Ser Ile Ile
    1615                1620                1625

CGT GCA CCT ATG TTC AGC TGG ATT CAC CGC AGT GCC GAG TTC AAC AAC            1392
Arg Ala Pro Met Phe Ser Trp Ile His Arg Ser Ala Glu Phe Asn Asn
1630                1635                1640                1645

ATC ATC CCC AGC AGC CAG ATC ACC CAG ATC CCC CTG ACC AAG AGC ACC            1440
Ile Ile Pro Ser Ser Gln Ile Thr Gln Ile Pro Leu Thr Lys Ser Thr
                1650                1655                1660

AAC CTG GGC AGC GGC ACC AGC GTG GTG AAG GGC CCC GGC TTC ACC GGC            1488
```

```
             Asn Leu Gly Ser Gly Thr Ser Val Val Lys Gly Pro Gly Phe Thr Gly
                         1665                1670                1675

GGC GAC ATC CTG CGC CGC ACC AGC CCC GGC CAG ATC AGC ACC CTG CGC              1536
Gly Asp Ile Leu Arg Arg Thr Ser Pro Gly Gln Ile Ser Thr Leu Arg
        1680                1685                1690

GTG AAC ATC ACC GCC CCC CTG AGC CAG CGC TAC CGC GTC CGC ATC CGC              1584
Val Asn Ile Thr Ala Pro Leu Ser Gln Arg Tyr Arg Val Arg Ile Arg
        1695                1700                1705

TAC GCC AGC ACC ACC AAC CTG CAG TTC CAC ACC AGC ATC GAC GGC CGC              1632
Tyr Ala Ser Thr Thr Asn Leu Gln Phe His Thr Ser Ile Asp Gly Arg
1710                1715                1720                1725

CCC ATC AAC CAG GGC AAC TTC AGC GCC ACC ATG AGC AGC GGC AGC AAC              1680
Pro Ile Asn Gln Gly Asn Phe Ser Ala Thr Met Ser Ser Gly Ser Asn
                1730                1735                1740

CTG CAG AGC GGC AGC TTC CGC ACC GTG GGC TTC ACC ACC CCC TTC AAC              1728
Leu Gln Ser Gly Ser Phe Arg Thr Val Gly Phe Thr Thr Pro Phe Asn
                1745                1750                1755

TTC AGC AAC GGC AGC AGC GTG TTC ACC CTG AGC GCC CAC GTG TTC AAC              1776
Phe Ser Asn Gly Ser Ser Val Phe Thr Leu Ser Ala His Val Phe Asn
            1760                1765                1770

AGC GGC AAC GAG GTG TAC ATC GAC CGC ATC GAG TTC GTG CCC GCC GAG              1824
Ser Gly Asn Glu Val Tyr Ile Asp Arg Ile Glu Phe Val Pro Ala Glu
        1775                1780                1785

GTG ACC TTC GAG GCC GAG TAC GAC CTG GAG AGG GCT CAG AAG GCC GTG              1872
Val Thr Phe Glu Ala Glu Tyr Asp Leu Glu Arg Ala Gln Lys Ala Val
1790                1795                1800                1805

AAC GAG CTG TTC ACC AGC AGC AAC CAG ATC GGC CTG AAG ACC GAC GTG              1920
Asn Glu Leu Phe Thr Ser Ser Asn Gln Ile Gly Leu Lys Thr Asp Val
                1810                1815                1820

ACC GAC TAC CAC ATC GAC CAG GTG AGC AAC CTG GTG GAG TGC TTA AGC              1968
Thr Asp Tyr His Ile Asp Gln Val Ser Asn Leu Val Glu Cys Leu Ser
            1825                1830                1835

GAC GAG TTC TGC CTG GAC GAG AAG AAG GAG CTG AGC GAG AAG GTG AAG              2016
Asp Glu Phe Cys Leu Asp Glu Lys Lys Glu Leu Ser Glu Lys Val Lys
        1840                1845                1850

CAC GCC AAG CGC CTG AGC GAC GAG CGC AAC CTG CTG CAG GAC CCC AAC              2064
His Ala Lys Arg Leu Ser Asp Glu Arg Asn Leu Leu Gln Asp Pro Asn
1855                1860                1865

TTC CGC GGC ATC AAC CGC CAG CTG GAC CGC GGC TGG CGA GGC AGC ACC              2112
Phe Arg Gly Ile Asn Arg Gln Leu Asp Arg Gly Trp Arg Gly Ser Thr
1870                1875                1880                1885

GAT ATC ACC ATC CAG GGC GGC GAC GAC GTG TTC AAG GAG AAC TAC GTG              2160
Asp Ile Thr Ile Gln Gly Gly Asp Asp Val Phe Lys Glu Asn Tyr Val
                1890                1895                1900

ACC CTG CAG GGC ACC TTC GAC GAG TGC TAC CCC ACC TAC CTG TAC CAG              2208
Thr Leu Gln Gly Thr Phe Asp Glu Cys Tyr Pro Thr Tyr Leu Tyr Gln
            1905                1910                1915

CCG ATC GAC GAG AGC AAG CTG AAG GCC TAC ACC CGC TAC CAG CTG CGC              2256
Pro Ile Asp Glu Ser Lys Leu Lys Ala Tyr Thr Arg Tyr Gln Leu Arg
        1920                1925                1930

GGC TAC ATC GAG GAC AGC CAG GAC CTG GAA ATC TAC CTG ATC CGC TAC              2304
Gly Tyr Ile Glu Asp Ser Gln Asp Leu Glu Ile Tyr Leu Ile Arg Tyr
        1935                1940                1945

AAC GCC AAG CAC GAG ACC GTG AAC GTG CCC GGC ACC GGC AGC CTG TGG              2352
Asn Ala Lys His Glu Thr Val Asn Val Pro Gly Thr Gly Ser Leu Trp
1950                1955                1960                1965

CCC CTG AGC GCC CCC AGC CCC ATC GGC AAG TGC GGG GAG CCG AAT CGA              2400
Pro Leu Ser Ala Pro Ser Pro Ile Gly Lys Cys Gly Glu Pro Asn Arg
                1970                1975                1980

TGC GCT CCG CAC CTG GAG TGG AAC CCG GAC CTA GAC TGC AGC TGC AGG              2448
```

```
Cys Ala Pro His Leu Glu Trp Asn Pro Asp Leu Asp Cys Ser Cys Arg
        1985                1990                1995

GAC GGG GAG AAG TGC GCC CAC CAC AGC CAC CAC TTC AGC CTG GAC ATC         2496
Asp Gly Glu Lys Cys Ala His His Ser His His Phe Ser Leu Asp Ile
        2000                2005                2010

GAC GTG GGC TGC ACC GAC CTG AAC GAG GAC CTG GGC GTG TGG GTG ATC         2544
Asp Val Gly Cys Thr Asp Leu Asn Glu Asp Leu Gly Val Trp Val Ile
        2015                2020                2025

TTC AAG ATC AAG ACC CAG GAC GGC CAC GCC CGC CTG GGC AAT CTA GAG         2592
Phe Lys Ile Lys Thr Gln Asp Gly His Ala Arg Leu Gly Asn Leu Glu
2030                2035                2040                2045

TTC CTG GAG GAG AAG CCC CTG GTG GGC GAG GCC CTG GCC CGC GTG AAG         2640
Phe Leu Glu Glu Lys Pro Leu Val Gly Glu Ala Leu Ala Arg Val Lys
        2050                2055                2060

CGC GCC GAG AAG AAG TGG CGC GAC AAG CGC GAG AAG CTG GAG TGG GAG         2688
Arg Ala Glu Lys Lys Trp Arg Asp Lys Arg Glu Lys Leu Glu Trp Glu
        2065                2070                2075

ACC AAC ATC GTG TAC AAG GAG GCC AAG GAG AGC GTG GAC GCC CTG TTC         2736
Thr Asn Ile Val Tyr Lys Glu Ala Lys Glu Ser Val Asp Ala Leu Phe
        2080                2085                2090

GTG AAC AGC CAG TAC GAC CGC CTG CAG GCC GAC ACC AAC ATC GCC ATG         2784
Val Asn Ser Gln Tyr Asp Arg Leu Gln Ala Asp Thr Asn Ile Ala Met
        2095                2100                2105

ATC CAC GCC GCC GAC AAG CGC GTG CAC AGC ATT CGC GAG GCC TAC CTG         2832
Ile His Ala Ala Asp Lys Arg Val His Ser Ile Arg Glu Ala Tyr Leu
2110                2115                2120                2125

CCC GAG CTG AGC GTG ATC CCC GGC GTG AAC GCC GCC ATC TTC GAG GAA         2880
Pro Glu Leu Ser Val Ile Pro Gly Val Asn Ala Ala Ile Phe Glu Glu
        2130                2135                2140

CTC GAG GGC CGC ATC TTC ACC GCC TTC AGC CTG TAC GAC GCC CGC AAC         2928
Leu Glu Gly Arg Ile Phe Thr Ala Phe Ser Leu Tyr Asp Ala Arg Asn
        2145                2150                2155

GTG ATC AAG AAC GGC GAC TTC AAC AAC GGC CTG AGC TGC TGG AAC GTG         2976
Val Ile Lys Asn Gly Asp Phe Asn Asn Gly Leu Ser Cys Trp Asn Val
        2160                2165                2170

AAG GGC CAC GTG GAC GTG GAG GAG CAG AAC AAC CAC CGC AGC GTG CTG         3024
Lys Gly His Val Asp Val Glu Glu Gln Asn Asn His Arg Ser Val Leu
        2175                2180                2185

GTG GTG CCC GAG TGG GAG GCC GAG GTG AGC CAG GAG GTG CGC GTG TGC         3072
Val Val Pro Glu Trp Glu Ala Glu Val Ser Gln Glu Val Arg Val Cys
2190                2195                2200                2205

CCC GGC CGC GGC TAC ATC CTG CGC GTG ACC GCC TAC AAG GAG GGC TAC         3120
Pro Gly Arg Gly Tyr Ile Leu Arg Val Thr Ala Tyr Lys Glu Gly Tyr
        2210                2215                2220

GGC GAG GGC TGC GTG ACC ATC CAC GAG ATC GAG AAC AAC ACC GAC GAG         3168
Gly Glu Gly Cys Val Thr Ile His Glu Ile Glu Asn Asn Thr Asp Glu
        2225                2230                2235

CTC AAG TTC AGC AAC TGC GTG GAG GAG GAG GTT TAC CCC AAC AAC ACC         3216
Leu Lys Phe Ser Asn Cys Val Glu Glu Glu Val Tyr Pro Asn Asn Thr
        2240                2245                2250

GTG ACC TGC AAC GAC TAC ACC GCG ACC CAG GAG GAG TAC GAA GGC ACC         3264
Val Thr Cys Asn Asp Tyr Thr Ala Thr Gln Glu Glu Tyr Glu Gly Thr
        2255                2260                2265

TAC ACC TCT CGC AAC AGG GGT TAC GAC GGC GCC TAC GAG TCC AAC AGC         3312
Tyr Thr Ser Arg Asn Arg Gly Tyr Asp Gly Ala Tyr Glu Ser Asn Ser
2270                2275                2280                2285

TCC GTG CCA GCC GAC TAC GCC AGC GCC TAC GAG GAG AAA GCC TAC ACC         3360
Ser Val Pro Ala Asp Tyr Ala Ser Ala Tyr Glu Glu Lys Ala Tyr Thr
        2290                2295                2300

GAC GGT AGA CGC GAC AAC CCA TGT GAG AGC AAC AGA GGC TAC GGC GAC         3408
```

| | | | | | | | | | | | | |
|---|---|---|---|---|---|---|---|---|---|---|---|---|
| Asp | Gly | Arg | Arg | Asp | Asn | Pro | Cys | Glu | Ser | Asn | Arg | Gly | Tyr | Gly | Asp |
| | | 2305 | | | | 2310 | | | | 2315 | | |

```
TAC ACC CCC CTG CCC GCT GGA TAC GTG ACC AAG GAG CTG GAG TAC TTC      3456
Tyr Thr Pro Leu Pro Ala Gly Tyr Val Thr Lys Glu Leu Glu Tyr Phe
        2320                2325                2330

CCC GAG ACC GAC AAG GTG TGG ATC GAG ATT GGC GAG ACC GAG GGC ACC      3504
Pro Glu Thr Asp Lys Val Trp Ile Glu Ile Gly Glu Thr Glu Gly Thr
    2335                2340                2345

TTC ATC GTG GAC AGC GTG GAG CTG CTG CTG ATG GAG GAG TAG              3546
Phe Ile Val Asp Ser Val Glu Leu Leu Leu Met Glu Glu
2350                2355                2360
```

(2) INFORMATION FOR SEQ ID NO:15:

(i) SEQUENCE CHARACTERISTICS:
        (A) LENGTH: 1181 amino acids
        (B) TYPE: amino acid
        (D) TOPOLOGY: linear (ii) MOLECULE TYPE: protein (xi) SEQUENCE DESCRIPTION: SEQ ID NO:15:

```
Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
                20                  25                  30

Tyr Thr Pro Ile Asp Ile Ser Leu Ser Leu Thr Gln Phe Leu Leu Ser
            35                  40                  45

Glu Phe Val Pro Gly Ala Gly Phe Val Leu Gly Leu Val Asp Ile Ile
        50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
        195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285
```

-continued

```
Gly Ser Ile Arg Ser Pro His Leu Met Asp Ile Leu Asn Ser Ile Thr
290                 295                 300

Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
450                 455                 460

Ile Ile Pro Ser Ser Gln Ile Thr Gln Ile Pro Leu Thr Lys Ser Thr
465                 470                 475                 480

Asn Leu Gly Ser Gly Thr Ser Val Val Lys Gly Pro Gly Phe Thr Gly
                485                 490                 495

Gly Asp Ile Leu Arg Arg Thr Ser Pro Gly Gln Ile Ser Thr Leu Arg
            500                 505                 510

Val Asn Ile Thr Ala Pro Leu Ser Gln Arg Tyr Arg Val Arg Ile Arg
        515                 520                 525

Tyr Ala Ser Thr Thr Asn Leu Gln Phe His Thr Ser Ile Asp Gly Arg
530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
                565                 570                 575

Phe Ser Asn Gly Ser Ser Val Phe Thr Leu Ser Ala His Val Phe Asn
            580                 585                 590

Ser Gly Asn Glu Val Tyr Ile Asp Arg Ile Glu Phe Val Pro Ala Glu
        595                 600                 605

Val Thr Phe Glu Ala Glu Tyr Asp Leu Glu Arg Ala Gln Lys Ala Val
610                 615                 620

Asn Glu Leu Phe Thr Ser Ser Asn Gln Ile Gly Leu Lys Thr Asp Val
625                 630                 635                 640

Thr Asp Tyr His Ile Asp Gln Val Ser Asn Leu Val Glu Cys Leu Ser
                645                 650                 655

Asp Glu Phe Cys Leu Asp Glu Lys Lys Glu Leu Ser Glu Lys Val Lys
            660                 665                 670

His Ala Lys Arg Leu Ser Asp Glu Arg Asn Leu Leu Gln Asp Pro Asn
        675                 680                 685

Phe Arg Gly Ile Asn Arg Gln Leu Asp Arg Gly Trp Arg Gly Ser Thr
690                 695                 700

Asp Ile Thr Ile Gln Gly Gly Asp Asp Val Phe Lys Glu Asn Tyr Val
```

-continued

```
705                 710                 715                 720
Thr Leu Gln Gly Thr Phe Asp Glu Cys Tyr Pro Thr Tyr Leu Tyr Gln
                    725                 730                 735
Pro Ile Asp Glu Ser Lys Leu Lys Ala Tyr Thr Arg Tyr Gln Leu Arg
                740                 745                 750
Gly Tyr Ile Glu Asp Ser Gln Asp Leu Glu Ile Tyr Leu Ile Arg Tyr
            755                 760                 765
Asn Ala Lys His Glu Thr Val Asn Val Pro Gly Thr Gly Ser Leu Trp
770                 775                 780
Pro Leu Ser Ala Pro Ser Pro Ile Gly Lys Cys Gly Glu Pro Asn Arg
785                 790                 795                 800
Cys Ala Pro His Leu Glu Trp Asn Pro Asp Leu Asp Cys Ser Cys Arg
                805                 810                 815
Asp Gly Glu Lys Cys Ala His His Ser His Phe Ser Leu Asp Ile
                820                 825                 830
Asp Val Gly Cys Thr Asp Leu Asn Glu Asp Leu Gly Val Trp Val Ile
            835                 840                 845
Phe Lys Ile Lys Thr Gln Asp Gly His Ala Arg Leu Gly Asn Leu Glu
        850                 855                 860
Phe Leu Glu Glu Lys Pro Leu Val Gly Glu Ala Leu Ala Arg Val Lys
865                 870                 875                 880
Arg Ala Glu Lys Lys Trp Arg Asp Lys Arg Glu Lys Leu Glu Trp Glu
                885                 890                 895
Thr Asn Ile Val Tyr Lys Glu Ala Lys Glu Ser Val Asp Ala Leu Phe
                900                 905                 910
Val Asn Ser Gln Tyr Asp Arg Leu Gln Ala Asp Thr Asn Ile Ala Met
            915                 920                 925
Ile His Ala Ala Asp Lys Arg Val His Ser Ile Arg Glu Ala Tyr Leu
        930                 935                 940
Pro Glu Leu Ser Val Ile Pro Gly Val Asn Ala Ala Ile Phe Glu Glu
945                 950                 955                 960
Leu Glu Gly Arg Ile Phe Thr Ala Phe Ser Leu Tyr Asp Ala Arg Asn
                965                 970                 975
Val Ile Lys Asn Gly Asp Phe Asn Asn Gly Leu Ser Cys Trp Asn Val
            980                 985                 990
Lys Gly His Val Asp Val Glu Glu Gln Asn Asn His Arg Ser Val Leu
        995                 1000                1005
Val Val Pro Glu Trp Glu Ala Glu Val Ser Gln Glu Val Arg Val Cys
        1010                1015                1020
Pro Gly Arg Gly Tyr Ile Leu Arg Val Thr Ala Tyr Lys Glu Gly Tyr
1025                1030                1035                1040
Gly Glu Gly Cys Val Thr Ile His Glu Ile Glu Asn Asn Thr Asp Glu
                1045                1050                1055
Leu Lys Phe Ser Asn Cys Val Glu Glu Val Tyr Pro Asn Asn Thr
            1060                1065                1070
Val Thr Cys Asn Asp Tyr Thr Ala Thr Gln Glu Glu Tyr Glu Gly Thr
        1075                1080                1085
Tyr Thr Ser Arg Asn Arg Gly Tyr Asp Gly Ala Tyr Glu Ser Asn Ser
        1090                1095                1100
Ser Val Pro Ala Asp Tyr Ala Ser Ala Tyr Glu Glu Lys Ala Tyr Thr
1105                1110                1115                1120
Asp Gly Arg Arg Asp Asn Pro Cys Glu Ser Asn Arg Gly Tyr Gly Asp
                1125                1130                1135
```

-continued

```
Tyr Thr Pro Leu Pro Ala Gly Tyr Val Thr Lys Glu Leu Glu Tyr Phe
        1140                1145                1150

Pro Glu Thr Asp Lys Val Trp Ile Glu Ile Gly Glu Thr Glu Gly Thr
        1155                1160                1165

Phe Ile Val Asp Ser Val Glu Leu Leu Leu Met Glu Glu
    1170                1175                1180
```

(2) INFORMATION FOR SEQ ID NO:16:

(i) SEQUENCE CHARACTERISTICS:
        (A) LENGTH: 3547 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(iii) HYPOTHETICAL: NO (ix) FEATURE:
        (A) NAME/KEY: CDS
        (B) LOCATION: 1..3543
        (D) OTHER INFORMATION: /product= "Full-length, hybrid,
            maize optimized heat stable cryIA(b)"
            /note= "Disclosed in Figure 15 as contained in pCIB5514."

(xi) SEQUENCE DESCRIPTION: SEQ ID NO:16:

```
ATG GAC AAC AAC CCC AAC ATC AAC GAG TGC ATC CCC TAC AAC TGC CTG        48
Met Asp Asn Asn Pro Asn Ile Asn Glu Cys Ile Pro Tyr Asn Cys Leu
                1185                1190                1195

AGC AAC CCC GAG GTG GAG GTG CTG GGC GGC GAG CGC ATC GAG ACC GGC        96
Ser Asn Pro Glu Val Glu Val Leu Gly Gly Glu Arg Ile Glu Thr Gly
            1200                1205                1210

TAC ACC CCC ATC GAC ATC AGC CTG AGC CTG ACC CAG TTC CTG CTG AGC       144
Tyr Thr Pro Ile Asp Ile Ser Leu Ser Leu Thr Gln Phe Leu Leu Ser
        1215                1220                1225

GAG TTC GTG CCC GGC GCC GGC TTC GTG CTG GGC CTG GTG GAC ATC ATC       192
Glu Phe Val Pro Gly Ala Gly Phe Val Leu Gly Leu Val Asp Ile Ile
1230                1235                1240                1245

TGG GGC ATC TTC GGC CCC AGC CAG TGG GAC GCC TTC CTG GTG CAG ATC       240
Trp Gly Ile Phe Gly Pro Ser Gln Trp Asp Ala Phe Leu Val Gln Ile
                1250                1255                1260

GAG CAG CTG ATC AAC CAG CGC ATC GAG GAG TTC GCC CGC AAC CAG GCC       288
Glu Gln Leu Ile Asn Gln Arg Ile Glu Glu Phe Ala Arg Asn Gln Ala
            1265                1270                1275

ATC AGC CGC CTG GAG GGC CTG AGC AAC CTG TAC CAA ATC TAC GCC GAG       336
Ile Ser Arg Leu Glu Gly Leu Ser Asn Leu Tyr Gln Ile Tyr Ala Glu
        1280                1285                1290

AGC TTC CGC GAG TGG GAG GCC GAC CCC ACC AAC CCC GCC CTG CGC GAG       384
Ser Phe Arg Glu Trp Glu Ala Asp Pro Thr Asn Pro Ala Leu Arg Glu
    1295                1300                1305

GAG ATG CGC ATC CAG TTC AAC GAC ATG AAC AGC GCC CTG ACC ACC GCC       432
Glu Met Arg Ile Gln Phe Asn Asp Met Asn Ser Ala Leu Thr Thr Ala
1310                1315                1320                1325

ATC CCC CTG TTC GCC GTG CAG AAC TAC CAG GTG CCC CTG CTG AGC GTG       480
Ile Pro Leu Phe Ala Val Gln Asn Tyr Gln Val Pro Leu Leu Ser Val
                1330                1335                1340

TAC GTG CAG GCC GCC AAC CTG CAC CTG AGC GTG CTG CGC GAC GTC AGC       528
Tyr Val Gln Ala Ala Asn Leu His Leu Ser Val Leu Arg Asp Val Ser
            1345                1350                1355

GTG TTC GGC CAG CGC TGG GGC TTC GAC GCC GCC ACC ATC AAC AGC CGC       576
Val Phe Gly Gln Arg Trp Gly Phe Asp Ala Ala Thr Ile Asn Ser Arg
        1360                1365                1370
```

```
                                              -continued

TAC AAC GAC CTG ACC CGC CTG ATC GGC AAC TAC ACC GAC CAC GCC GTG            624
Tyr Asn Asp Leu Thr Arg Leu Ile Gly Asn Tyr Thr Asp His Ala Val
    1375                1380                1385

CGC TGG TAC AAC ACC GGC CTG GAG CGC GTG TGG GGT CCC GAC AGC CGC            672
Arg Trp Tyr Asn Thr Gly Leu Glu Arg Val Trp Gly Pro Asp Ser Arg
1390                1395                1400                1405

GAC TGG ATC AGG TAC AAC CAG TTC CGC CGC GAG CTG ACC CTG ACC GTG            720
Asp Trp Ile Arg Tyr Asn Gln Phe Arg Arg Glu Leu Thr Leu Thr Val
            1410                1415                1420

CTG GAC ATC GTG AGC CTG TTC CCC AAC TAC GAC AGC CGC ACC TAC CCC            768
Leu Asp Ile Val Ser Leu Phe Pro Asn Tyr Asp Ser Arg Thr Tyr Pro
        1425                1430                1435

ATC CGC ACC GTG AGC CAG CTG ACC CGC GAG ATT TAC ACC AAC CCC GTG            816
Ile Arg Thr Val Ser Gln Leu Thr Arg Glu Ile Tyr Thr Asn Pro Val
    1440                1445                1450

CTG GAG AAC TTC GAC GGC AGC TTC CGC GGC AGC GCC CAG GGC ATC GAG            864
Leu Glu Asn Phe Asp Gly Ser Phe Arg Gly Ser Ala Gln Gly Ile Glu
1455                1460                1465

GGC AGC ATC CGC AGC CCC CAC CTG ATG GAC ATC CTG AAC AGC ATC ACC            912
Gly Ser Ile Arg Ser Pro His Leu Met Asp Ile Leu Asn Ser Ile Thr
1470                1475                1480                1485

ATC TAC ACC GAC GCC CAC CGC GGC GAG TAC TAC TGG AGC GGC CAC CAG            960
Ile Tyr Thr Asp Ala His Arg Gly Glu Tyr Tyr Trp Ser Gly His Gln
            1490                1495                1500

ATC ATG GCC AGC CCC GTC GGC TTC AGC GGC CCC GAG TTC ACC TTC CCC           1008
Ile Met Ala Ser Pro Val Gly Phe Ser Gly Pro Glu Phe Thr Phe Pro
        1505                1510                1515

CTG TAC GGC ACC ATG GGC AAC GCT GCA CCT CAG CAG CGC ATC GTG GCA           1056
Leu Tyr Gly Thr Met Gly Asn Ala Ala Pro Gln Gln Arg Ile Val Ala
    1520                1525                1530

CAG CTG GGC CAG GGA GTG TAC CGC ACC CTG AGC AGC ACC CTG TAC CGT           1104
Gln Leu Gly Gln Gly Val Tyr Arg Thr Leu Ser Ser Thr Leu Tyr Arg
1535                1540                1545

CGA CCT TTC AAC ATC GGC ATC AAC AAC CAG CAG CTG AGC GTG CTG GAC           1152
Arg Pro Phe Asn Ile Gly Ile Asn Asn Gln Gln Leu Ser Val Leu Asp
1550                1555                1560                1565

GGC ACC GAG TTC GCC TAC GGC ACC AGC AGC AAC CTG CCC AGC GCC GTG           1200
Gly Thr Glu Phe Ala Tyr Gly Thr Ser Ser Asn Leu Pro Ser Ala Val
            1570                1575                1580

TAC CGC AAG AGC GGC ACC GTG GAC AGC CTG GAC GAG ATC CCC CCT CAG           1248
Tyr Arg Lys Ser Gly Thr Val Asp Ser Leu Asp Glu Ile Pro Pro Gln
        1585                1590                1595

AAC AAC AAC GTG CCA CCT CGA CAG GGC TTC AGC CAC CGT CTG AGC CAC           1296
Asn Asn Asn Val Pro Pro Arg Gln Gly Phe Ser His Arg Leu Ser His
    1600                1605                1610

GTG AGC ATG TTC CGC AGT GGC TTC AGC AAC AGC AGC GTG AGC ATC ATC           1344
Val Ser Met Phe Arg Ser Gly Phe Ser Asn Ser Ser Val Ser Ile Ile
1615                1620                1625

CGT GCA CCT ATG TTC AGC TGG ATT CAC CGC AGT GCC GAG TTC AAC AAC           1392
Arg Ala Pro Met Phe Ser Trp Ile His Arg Ser Ala Glu Phe Asn Asn
1630                1635                1640                1645

ATC ATC CCC AGC AGC CAG ATC ACC CAG ATC CCC CTG ACC AAG AGC ACC           1440
Ile Ile Pro Ser Ser Gln Ile Thr Gln Ile Pro Leu Thr Lys Ser Thr
            1650                1655                1660

AAC CTG GGC AGC GGC ACC AGC GTG GTG AAG GGC CCC GGC TTC ACC GGC           1488
Asn Leu Gly Ser Gly Thr Ser Val Val Lys Gly Pro Gly Phe Thr Gly
        1665                1670                1675

GGC GAC ATC CTG CGC CGC ACC AGC CCC GGC CAG ATC AGC ACC CTG CGC           1536
Gly Asp Ile Leu Arg Arg Thr Ser Pro Gly Gln Ile Ser Thr Leu Arg
    1680                1685                1690
```

-continued

| | |
|---|---|
| GTG AAC ATC ACC GCC CCC CTG AGC CAG CGC TAC CGC GTC CGC ATC CGC<br>Val Asn Ile Thr Ala Pro Leu Ser Gln Arg Tyr Arg Val Arg Ile Arg<br>1695                      1700                      1705 | 1584 |
| TAC GCC AGC ACC ACC AAC CTG CAG TTC CAC ACC AGC ATC GAC GGC CGC<br>Tyr Ala Ser Thr Thr Asn Leu Gln Phe His Thr Ser Ile Asp Gly Arg<br>1710                      1715                      1720                      1725 | 1632 |
| CCC ATC AAC CAG GGC AAC TTC AGC GCC ACC ATG AGC AGC GGC AGC AAC<br>Pro Ile Asn Gln Gly Asn Phe Ser Ala Thr Met Ser Ser Gly Ser Asn<br>                1730                      1735                      1740 | 1680 |
| CTG CAG AGC GGC AGC TTC CGC ACC GTG GGC TTC ACC ACC CCC TTC AAC<br>Leu Gln Ser Gly Ser Phe Arg Thr Val Gly Phe Thr Thr Pro Phe Asn<br>                1745                      1750                      1755 | 1728 |
| TTC AGC AAC GGC AGC AGC GTG TTC ACC CTG AGC GCC CAC GTG TTC AAC<br>Phe Ser Asn Gly Ser Ser Val Phe Thr Leu Ser Ala His Val Phe Asn<br>                1760                      1765                      1770 | 1776 |
| AGC GGC AAC GAG GTG TAC ATC GAC CGC ATC GAG TTC GTG CCC GCC GAG<br>Ser Gly Asn Glu Val Tyr Ile Asp Arg Ile Glu Phe Val Pro Ala Glu<br>1775                      1780                      1785 | 1824 |
| GTG ACC TTC GAG GCC GAG TAC GAC CTG GAG AGG GCT CAG AAG GCC GTG<br>Val Thr Phe Glu Ala Glu Tyr Asp Leu Glu Arg Ala Gln Lys Ala Val<br>1790                      1795                      1800                      1805 | 1872 |
| AAC GAG CTG TTC ACC AGC AGC AAC CAG ATC GGC CTG AAG ACC GAC GTG<br>Asn Glu Leu Phe Thr Ser Ser Asn Gln Ile Gly Leu Lys Thr Asp Val<br>                1810                      1815                      1820 | 1920 |
| ACC GAC TAC CAC ATC GAT CAA GTA TCC AAT TTA GTT GAG TGT TTA TCT<br>Thr Asp Tyr His Ile Asp Gln Val Ser Asn Leu Val Glu Cys Leu Ser<br>                1825                      1830                      1835 | 1968 |
| GAT GAA TTT TGT CTG GAT GAA AAA AAA GAA TTG TCC GAG AAA GTC AAA<br>Asp Glu Phe Cys Leu Asp Glu Lys Lys Glu Leu Ser Glu Lys Val Lys<br>                1840                      1845                      1850 | 2016 |
| CAT GCG AAG CGA CTT AGT GAT GAG CGG AAT TTA CTT CAA GAT CCA AAC<br>His Ala Lys Arg Leu Ser Asp Glu Arg Asn Leu Leu Gln Asp Pro Asn<br>1855                      1860                      1865 | 2064 |
| TTT AGA GGG ATC AAT AGA CAA CTA GAC CGT GGC TGG AGA GGA AGT ACG<br>Phe Arg Gly Ile Asn Arg Gln Leu Asp Arg Gly Trp Arg Gly Ser Thr<br>1870                      1875                      1880                      1885 | 2112 |
| GAT ATT ACC ATC CAA GGA GGC GAT GAC GTA TTC AAA GAG AAT TAC GTT<br>Asp Ile Thr Ile Gln Gly Gly Asp Asp Val Phe Lys Glu Asn Tyr Val<br>                1890                      1895                      1900 | 2160 |
| ACG CTA TTG GGT ACC TTT GAT GAG TGC TAT CCA ACG TAT TTA TAT CAA<br>Thr Leu Leu Gly Thr Phe Asp Glu Cys Tyr Pro Thr Tyr Leu Tyr Gln<br>                1905                      1910                      1915 | 2208 |
| AAA ATA GAT GAG TCG AAA TTA AAA GCC TAT ACC CGT TAC CAA TTA AGA<br>Lys Ile Asp Glu Ser Lys Leu Lys Ala Tyr Thr Arg Tyr Gln Leu Arg<br>1920                      1925                      1930 | 2256 |
| GGG TAT ATC GAA GAT AGT CAA GAC TTA GAA ATC TAT TTA ATT CGC TAC<br>Gly Tyr Ile Glu Asp Ser Gln Asp Leu Glu Ile Tyr Leu Ile Arg Tyr<br>                1935                      1940                      1945 | 2304 |
| AAT GCC AAA CAC GAA ACA GTA AAT GTG CCA GGT ACG GGT TCC TTA TGG<br>Asn Ala Lys His Glu Thr Val Asn Val Pro Gly Thr Gly Ser Leu Trp<br>1950                      1955                      1960                      1965 | 2352 |
| CCG CTT TCA GCC CCA AGT CCA ATC GGC AAG TGC GGG GAG CCG AAT CGA<br>Pro Leu Ser Ala Pro Ser Pro Ile Gly Lys Cys Gly Glu Pro Asn Arg<br>                1970                      1975                      1980 | 2400 |
| TGC GCT CCG CAC CTG GAG TGG AAC CCG GAC CTA GAC TGC AGC TGC AGG<br>Cys Ala Pro His Leu Glu Trp Asn Pro Asp Leu Asp Cys Ser Cys Arg<br>                1985                      1990                      1995 | 2448 |
| GAC GGG GAG AAG TGC GCC CAC CAC AGC CAC CAC TTC AGC CTG GAC ATC<br>Asp Gly Glu Lys Cys Ala His His Ser His His Phe Ser Leu Asp Ile<br>                2000                      2005                      2010 | 2496 |

| | | | | | | | | | | | | | | |
|---|---|---|---|---|---|---|---|---|---|---|---|---|---|---|
| GAC | GTG | GGC | TGC | ACC | GAC | CTG | AAC | GAG | GAC | CTG | GGC | GTG | TGG | GTG | ATC | 2544 |
| Asp | Val | Gly | Cys | Thr | Asp | Leu | Asn | Glu | Asp | Leu | Gly | Val | Trp | Val | Ile |
| | 2015 | | | | 2020 | | | | 2025 | | | | |

```
GAC GTG GGC TGC ACC GAC CTG AAC GAG GAC CTG GGC GTG TGG GTG ATC          2544
Asp Val Gly Cys Thr Asp Leu Asn Glu Asp Leu Gly Val Trp Val Ile
    2015                2020                2025

TTC AAG ATC AAG ACC CAG GAC GGC CAC GCC CGC CTG GGC AAT CTA GAA          2592
Phe Lys Ile Lys Thr Gln Asp Gly His Ala Arg Leu Gly Asn Leu Glu
2030                2035                2040                2045

TTT CTC GAA GAG AAA CCA TTA GTA GGA GAA GCA CTA GCT CGT GTG AAA          2640
Phe Leu Glu Glu Lys Pro Leu Val Gly Glu Ala Leu Ala Arg Val Lys
                2050                2055                2060

AGA GCG GAG AAA AAA TGG AGA GAC AAA CGT GAA AAA TTG GAA TGG GAA          2688
Arg Ala Glu Lys Lys Trp Arg Asp Lys Arg Glu Lys Leu Glu Trp Glu
            2065                2070                2075

ACA AAT ATT GTT TAT AAA GAG GCA AAA GAA TCT GTA GAT GCT TTA TTT          2736
Thr Asn Ile Val Tyr Lys Glu Ala Lys Glu Ser Val Asp Ala Leu Phe
        2080                2085                2090

GTA AAC TCT CAA TAT GAT AGA TTA CAA GCG GAT ACC AAC ATC GCG ATG          2784
Val Asn Ser Gln Tyr Asp Arg Leu Gln Ala Asp Thr Asn Ile Ala Met
    2095                2100                2105

ATT CAT GCG GCA GAT AAA CGC GTT CAT AGC ATT CGA GAA GCT TAT CTG          2832
Ile His Ala Ala Asp Lys Arg Val His Ser Ile Arg Glu Ala Tyr Leu
2110                2115                2120                2125

CCT GAG CTG TCT GTG ATT CCG GGT GTC AAT GCG GCT ATT TTT GAA GAA          2880
Pro Glu Leu Ser Val Ile Pro Gly Val Asn Ala Ala Ile Phe Glu Glu
                2130                2135                2140

TTA GAA GGG CGT ATT TTC ACT GCA TTC TCC CTA TAT GAT GCG AGA AAT          2928
Leu Glu Gly Arg Ile Phe Thr Ala Phe Ser Leu Tyr Asp Ala Arg Asn
            2145                2150                2155

GTC ATT AAA AAT GGT GAT TTT AAT AAT GGC TTA TCC TGC TGG AAC GTG          2976
Val Ile Lys Asn Gly Asp Phe Asn Asn Gly Leu Ser Cys Trp Asn Val
        2160                2165                2170

AAA GGG CAT GTA GAT GTA GAA GAA CAA AAC AAC CAC CGT TCG GTC CTT          3024
Lys Gly His Val Asp Val Glu Glu Gln Asn Asn His Arg Ser Val Leu
    2175                2180                2185

GTT GTT CCG GAA TGG GAA GCA GAA GTG TCA CAA GAA GTT CGT GTC TGT          3072
Val Val Pro Glu Trp Glu Ala Glu Val Ser Gln Glu Val Arg Val Cys
2190                2195                2200                2205

CCG GGT CGT GGC TAT ATC CTT CGT GTC ACA GCG TAC AAG GAG GGA TAT          3120
Pro Gly Arg Gly Tyr Ile Leu Arg Val Thr Ala Tyr Lys Glu Gly Tyr
                2210                2215                2220

GGA GAA GGT TGC GTA ACC ATT CAT GAG ATC GAG AAC AAT ACA GAC GAA          3168
Gly Glu Gly Cys Val Thr Ile His Glu Ile Glu Asn Asn Thr Asp Glu
            2225                2230                2235

CTG AAG TTT AGC AAC TGT GTA GAA GAG GAA GTA TAT CCA AAC AAC ACG          3216
Leu Lys Phe Ser Asn Cys Val Glu Glu Glu Val Tyr Pro Asn Asn Thr
        2240                2245                2250

GTA ACG TGT AAT GAT TAT ACT GCG ACT CAA GAA GAA TAT GAG GGT ACG          3264
Val Thr Cys Asn Asp Tyr Thr Ala Thr Gln Glu Glu Tyr Glu Gly Thr
    2255                2260                2265

TAC ACT TCT CGT AAT CGA GGA TAT GAC GGA GCC TAT GAA AGC AAT TCT          3312
Tyr Thr Ser Arg Asn Arg Gly Tyr Asp Gly Ala Tyr Glu Ser Asn Ser
2270                2275                2280                2285

TCT GTA CCA GCT GAT TAT GCA TCA GCC TAT GAA GAA AAA GCA TAT ACA          3360
Ser Val Pro Ala Asp Tyr Ala Ser Ala Tyr Glu Glu Lys Ala Tyr Thr
                2290                2295                2300

GAT GGA CGA AGA GAC AAT CCT TGT GAA TCT AAC AGA GGA TAT GGG GAT          3408
Asp Gly Arg Arg Asp Asn Pro Cys Glu Ser Asn Arg Gly Tyr Gly Asp
            2305                2310                2315

TAC ACA CCA CTA CCA GCT GGC TAT GTG ACA AAA GAA TTA GAG TAC TTC          3456
Tyr Thr Pro Leu Pro Ala Gly Tyr Val Thr Lys Glu Leu Glu Tyr Phe
        2320                2325                2330
```

```
CCA GAA ACC GAT AAG GTA TGG ATT GAG ATC GGA GAA ACG GAA GGA ACA    3504
Pro Glu Thr Asp Lys Val Trp Ile Glu Ile Gly Glu Thr Glu Gly Thr
    2335                2340                2345

TTC ATC GTG GAC AGC GTG GAA TTA CTT CTT ATG GAG GAA TAAG           3547
Phe Ile Val Asp Ser Val Glu Leu Leu Leu Met Glu Glu
2350                2355                2360
```

(2) INFORMATION FOR SEQ ID NO:17:

(i) SEQUENCE CHARACTERISTICS:
        (A) LENGTH: 1181 amino acids
        (B) TYPE: amino acid
        (D) TOPOLOGY: linear (ii) MOLECULE TYPE: protein (xi) SEQUENCE DESCRIPTION: SEQ ID NO:17:

```
Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
                20                  25                  30

Tyr Thr Pro Ile Asp Ile Ser Leu Ser Leu Thr Gln Phe Leu Leu Ser
            35                  40                  45

Glu Phe Val Pro Gly Ala Gly Phe Val Leu Gly Leu Val Asp Ile Ile
        50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
        195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Gly Ser Ile Arg Ser Pro His Leu Met Asp Ile Leu Asn Ser Ile Thr
    290                 295                 300

Ile Tyr Thr Asp Ala His Arg Gly Glu Tyr Tyr Trp Ser Gly His Gln
305                 310                 315                 320
```

-continued

```
Ile Met Ala Ser Pro Val Gly Phe Ser Gly Pro Glu Phe Thr Phe Pro
            325                 330                 335
Leu Tyr Gly Thr Met Gly Asn Ala Ala Pro Gln Gln Arg Ile Val Ala
        340                 345                 350
Gln Leu Gly Gln Gly Val Tyr Arg Thr Leu Ser Ser Thr Leu Tyr Arg
    355                 360                 365
Arg Pro Phe Asn Ile Gly Ile Asn Asn Gln Gln Leu Ser Val Leu Asp
370                 375                 380
Gly Thr Glu Phe Ala Tyr Gly Thr Ser Ser Asn Leu Pro Ser Ala Val
385                 390                 395                 400
Tyr Arg Lys Ser Gly Thr Val Asp Ser Leu Asp Glu Ile Pro Pro Gln
                405                 410                 415
Asn Asn Asn Val Pro Pro Arg Gln Gly Phe Ser His Arg Leu Ser His
            420                 425                 430
Val Ser Met Phe Arg Ser Gly Phe Ser Asn Ser Ser Val Ser Ile Ile
        435                 440                 445
Arg Ala Pro Met Phe Ser Trp Ile His Arg Ser Ala Glu Phe Asn Asn
    450                 455                 460
Ile Ile Pro Ser Ser Gln Ile Thr Gln Ile Pro Leu Thr Lys Ser Thr
465                 470                 475                 480
Asn Leu Gly Ser Gly Thr Ser Val Val Lys Gly Pro Gly Phe Thr Gly
                485                 490                 495
Gly Asp Ile Leu Arg Arg Thr Ser Pro Gly Gln Ile Ser Thr Leu Arg
            500                 505                 510
Val Asn Ile Thr Ala Pro Leu Ser Gln Arg Tyr Arg Val Arg Ile Arg
        515                 520                 525
Tyr Ala Ser Thr Thr Asn Leu Gln Phe His Thr Ser Ile Asp Gly Arg
    530                 535                 540
Pro Ile Asn Gln Gly Asn Phe Ser Ala Thr Met Ser Ser Gly Ser Asn
545                 550                 555                 560
Leu Gln Ser Gly Ser Phe Arg Thr Val Gly Phe Thr Thr Pro Phe Asn
                565                 570                 575
Phe Ser Asn Gly Ser Ser Val Phe Thr Leu Ser Ala His Val Phe Asn
            580                 585                 590
Ser Gly Asn Glu Val Tyr Ile Asp Arg Ile Glu Phe Val Pro Ala Glu
        595                 600                 605
Val Thr Phe Glu Ala Glu Tyr Asp Leu Glu Arg Ala Gln Lys Ala Val
    610                 615                 620
Asn Glu Leu Phe Thr Ser Ser Asn Gln Ile Gly Leu Lys Thr Asp Val
625                 630                 635                 640
Thr Asp Tyr His Ile Asp Gln Val Ser Asn Leu Val Glu Cys Leu Ser
                645                 650                 655
Asp Glu Phe Cys Leu Asp Glu Lys Lys Glu Leu Ser Glu Lys Val Lys
            660                 665                 670
His Ala Lys Arg Leu Ser Asp Glu Arg Asn Leu Leu Gln Asp Pro Asn
        675                 680                 685
Phe Arg Gly Ile Asn Arg Gln Leu Asp Arg Gly Trp Arg Gly Ser Thr
    690                 695                 700
Asp Ile Thr Ile Gln Gly Gly Asp Asp Val Phe Lys Glu Asn Tyr Val
705                 710                 715                 720
Thr Leu Leu Gly Thr Phe Asp Glu Cys Tyr Pro Thr Tyr Leu Tyr Gln
                725                 730                 735
Lys Ile Asp Glu Ser Lys Leu Lys Ala Tyr Thr Arg Tyr Gln Leu Arg
            740                 745                 750
```

-continued

Gly Tyr Ile Glu Asp Ser Gln Asp Leu Glu Ile Tyr Leu Ile Arg Tyr
        755                 760                 765

Asn Ala Lys His Glu Thr Val Asn Val Pro Gly Thr Gly Ser Leu Trp
        770                 775                 780

Pro Leu Ser Ala Pro Ser Pro Ile Gly Lys Cys Gly Glu Pro Asn Arg
785                 790                 795                 800

Cys Ala Pro His Leu Glu Trp Asn Pro Asp Leu Asp Cys Ser Cys Arg
                805                 810                 815

Asp Gly Glu Lys Cys Ala His His Ser His His Phe Ser Leu Asp Ile
            820                 825                 830

Asp Val Gly Cys Thr Asp Leu Asn Glu Asp Leu Gly Val Trp Val Ile
            835                 840                 845

Phe Lys Ile Lys Thr Gln Asp Gly His Ala Arg Leu Gly Asn Leu Glu
        850                 855                 860

Phe Leu Glu Glu Lys Pro Leu Val Gly Glu Ala Leu Ala Arg Val Lys
865                 870                 875                 880

Arg Ala Glu Lys Lys Trp Arg Asp Lys Arg Glu Lys Leu Glu Trp Glu
                885                 890                 895

Thr Asn Ile Val Tyr Lys Glu Ala Lys Glu Ser Val Asp Ala Leu Phe
            900                 905                 910

Val Asn Ser Gln Tyr Asp Arg Leu Gln Ala Asp Thr Asn Ile Ala Met
            915                 920                 925

Ile His Ala Ala Asp Lys Arg Val His Ser Ile Arg Glu Ala Tyr Leu
        930                 935                 940

Pro Glu Leu Ser Val Ile Pro Gly Val Asn Ala Ala Ile Phe Glu Glu
945                 950                 955                 960

Leu Glu Gly Arg Ile Phe Thr Ala Phe Ser Leu Tyr Asp Ala Arg Asn
                965                 970                 975

Val Ile Lys Asn Gly Asp Phe Asn Asn Gly Leu Ser Cys Trp Asn Val
            980                 985                 990

Lys Gly His Val Asp Val Glu Glu Gln Asn Asn His Arg Ser Val Leu
            995                 1000                1005

Val Val Pro Glu Trp Glu Ala Glu Val Ser Gln Glu Val Arg Val Cys
        1010                1015                1020

Pro Gly Arg Gly Tyr Ile Leu Arg Val Thr Ala Tyr Lys Glu Gly Tyr
1025                1030                1035                1040

Gly Glu Gly Cys Val Thr Ile His Glu Ile Glu Asn Asn Thr Asp Glu
                1045                1050                1055

Leu Lys Phe Ser Asn Cys Val Glu Glu Glu Val Tyr Pro Asn Asn Thr
            1060                1065                1070

Val Thr Cys Asn Asp Tyr Thr Ala Thr Gln Glu Glu Tyr Glu Gly Thr
            1075                1080                1085

Tyr Thr Ser Arg Asn Arg Gly Tyr Asp Gly Ala Tyr Glu Ser Asn Ser
        1090                1095                1100

Ser Val Pro Ala Asp Tyr Ala Ser Ala Tyr Glu Glu Lys Ala Tyr Thr
1105                1110                1115                1120

Asp Gly Arg Arg Asp Asn Pro Cys Glu Ser Asn Arg Gly Tyr Gly Asp
                1125                1130                1135

Tyr Thr Pro Leu Pro Ala Gly Tyr Val Thr Lys Glu Leu Glu Tyr Phe
            1140                1145                1150

Pro Glu Thr Asp Lys Val Trp Ile Glu Ile Gly Glu Thr Glu Gly Thr
            1155                1160                1165

Phe Ile Val Asp Ser Val Glu Leu Leu Leu Met Glu Glu 1170            1175            1180

(2) INFORMATION FOR SEQ ID NO:18:

(i) SEQUENCE CHARACTERISTICS:
        (A) LENGTH: 4817 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (ix) FEATURE:
        (A) NAME/KEY: CDS
        (B) LOCATION: join(1839..2141, 2239..2547, 2641..2718, 2794
            ..2871, 3001..3135, 3236..3370)
        (D) OTHER INFORMATION: /product= "maize TrpA"
            /note= "Maize TrpA sequence as disclosed in Figure 24."

(ix) FEATURE:
        (A) NAME/KEY: TATA_signal
        (B) LOCATION: 1594..1599

(ix) FEATURE:
        (A) NAME/KEY: CAAT_signal
        (B) LOCATION: 1495..1499

(ix) FEATURE:
        (A) NAME/KEY: promoter
        (B) LOCATION: 39..1838
        (D) OTHER INFORMATION: /function= "Promoter sequence used
            in pCIB4433"

(xi) SEQUENCE DESCRIPTION: SEQ ID NO:18:

```
GAATTCGGAT CCATTAAAGA AGTCTTTGAA CAGATTCTAG AGATCTAGTT TAATGAGCTC      60

CCAAAAGTCT TGAAAAAATT CAGCGGGGAG GCCATTAGGG CAGGGGTACT GTTATGTTTT     120

AAAGAGAACA CCACTTTCTT GATCTCTTCT AAAGAGAAAT GTTTTGTAAG AAGGATCCTG     180

TCCTCCTCAT CCAACCTTTT CATCGGCAAA TTTTTCATAG AGATATTAGA GGCAAGAGAG     240

GGGCCAAAAA GATCCATGTA AATGGAAGTG GCCACCTGGT TGATACCTCC CTCATCTTCA     300

ACAGAAAATC CATTATGAAA AAGTGAATGG ATTTTAAACT CTTCTTTTTC TTCCCTTTTG     360

CAATGAGCTG AAAATATCTG GTATTATTCT CATCACCCTC ATTAATGAAT CTGTCCCTAG     420

CAATTTGCTT TCTCTTGATC CCTTCTGCAG CCACCATGTT TCTTAAATTC CACTCCATAT     480

CAAGCTTTTC CAATCTATCA GAATCTGAGA TGGCTGCAAT CTCTCTCATT TTCTCAAGGA     540

TATCGATGTT ATCCATAAGG TATTTCTTGA ACTTCTTATA TTTCCCTTCG ACATTTATAT     600

TCCATCCTTT CAACATTTTT TTGTTCAATC TTTTTTGTTT TTTTCCTTTC CAAACATCGA     660

TACATTTCCT GCTCCTCACA GGTAAGGACG AGCTTTCAAA AAACCTTCTG CTTTAAAGTC     720

AGGTCTGAGC CTCCAGCAAA GCTCACATAT CTAAAGTCCC TCTTCTTAGT TGGGACAGAG     780

TCAGTGCTAA GACACATGGG AACATGACCA GAAAAAAAAA ATCATATTTA GCCCAGAGAC     840

AACAATATTC TTGTACTGCA AGTCTCGTTA TGGGCTAGCA AAGGAATCTA CCCAACTTCT     900

CAAATGTGTT GGGATGTCAA GTATATAGAC TATTCATCAG TTCCAACTCT ATCAAACTGT     960

GCAGCTCAAT TATAGAGTTG AATAAAGTGC TCCATCTATT TGTTCTTATC CTCATATTTG    1020

GTTAAGATAT TAAAATCACC TCCCACCAAC ATTTAAAGTG CACCATTTAA AGTGGCTCGC    1080

GAGCACCAAA CCGCTGAAAA CCGGAAATGT TTAGCACGTT GGCAGCGGGA CCCTTTTCTA    1140

TCTCATCGTG TTCTTCGTTG TCCACCACGG CCCACGGGCC AACGCTCCTC CATCCTGTAG    1200

TGTAGAGTAT ATTCCATTTG CGACCGAGCC GAGCATCGAT CCAGCCACAC TGGCCACTGC    1260
```

```
CAGCCAGCCA TGTGGCACTC CTACGTATAC TACGTGAGGT GAGATTCACT CACATGGGAT       1320

GGGACCGAGA TATTTTACTG CTGTGGTTGT GTGAGAGATA ATAAAGCATT TATGACGATT       1380

GCTGAACAGC ACACACCATG CGTCCAGATA GAGAAAGCTT TCTCTCTTTA TTCGCATGCA       1440

TGTTTCATTA TCTTTTATCA TATATATATA ACACATATTA AATGATTCTT CGTTCCAATT       1500

TATAATTCAT TTGACTTTTT TATCCACCGA TGCTCGTTTT ATTAAAAAAA ATATTATAAT       1560

TATTGTTACT TTTTGTTGTA ATATTGTTTA GCATATAATA AACTTTGATA CTAGTATGTT       1620

TCCGAGCAAA AAAAAATATT AATATTTAGA TTACGAGCCC ATTAATTAAT TATATTCGAG       1680

ACAAGCGAAG CAAAGCAAAG CAAGCTAATG TTGCCCCTGC TGTGCATGCA GAGGCCCGCT       1740

CTTGCTATAA ACGAGGCAGC TAGACGCGAC TCGACTCATC AGCCTCATCA ACCTCGACGA       1800

AGGAGGAACG AACGGACAGG TTGTTGCACA GAAGCGAC ATG GCT TTC GCG CCC          1853
                                          Met Ala Phe Ala Pro
                                            1               5

AAA ACG TCC TCC TCC TCC TCG CTG TCC TCG GCG TTG CAG GCA GCT CAG        1901
Lys Thr Ser Ser Ser Ser Ser Leu Ser Ser Ala Leu Gln Ala Ala Gln
            10                  15                  20

TCG CCG CCG CTG CTC CTG AGG CGG ATG TCG TCG ACC GCA ACA CCG AGA        1949
Ser Pro Pro Leu Leu Leu Arg Arg Met Ser Ser Thr Ala Thr Pro Arg
        25                  30                  35

CGG AGG TAC GAC GCG GCC GTC GTC GTC ACT ACC ACC ACC ACT GCT AGA        1997
Arg Arg Tyr Asp Ala Ala Val Val Val Thr Thr Thr Thr Thr Ala Arg
    40                  45                  50

GCT GCG GCG GCT GCT GTC ACG GTT CCC GCC GCC CCG CCG CAG GCG GGC        2045
Ala Ala Ala Ala Ala Val Thr Val Pro Ala Ala Pro Pro Gln Ala Gly
55                  60                  65

CGC CGC CGC CGG TGC CAC CAA AGC AAG CGG CGG CAC CCG CAG AGG AGG        2093
Arg Arg Arg Arg Cys His Gln Ser Lys Arg Arg His Pro Gln Arg Arg
70                  75                  80                  85

AGC CGT CCG GTG TCG GAC ACC ATG GCG GCG CTC ATG GCC AAG GGC AAG        2141
Ser Arg Pro Val Ser Asp Thr Met Ala Ala Leu Met Ala Lys Gly Lys
                90                  95                 100

GTTCGTATAG TACGCGCGCG TGTCGTCGTC GTTATTTTGC GCATAGGCGC GGACATACAC      2201

GTGCTTTAGC TAGCTAACAG CTAGATCATC GGTGCAG ACG GCG TTC ATC CCG TAC      2256
                                        Thr Ala Phe Ile Pro Tyr
                                                        105

ATC ACC GCC GGC GAC CCG GAC CTA GCG ACG ACG GCC GAG GCG CTG CGT        2304
Ile Thr Ala Gly Asp Pro Asp Leu Ala Thr Thr Ala Glu Ala Leu Arg
            110                 115                 120

CTG CTG GAC GGC TGT GGC GCC GAC GTC ATC GAG CTG GGG GTA CCC TGC        2352
Leu Leu Asp Gly Cys Gly Ala Asp Val Ile Glu Leu Gly Val Pro Cys
        125                 130                 135

TCG GAC CCC TAC ATC GAC GGG CCC ATC ATC CAG GCG TCG GTG GCG CGG        2400
Ser Asp Pro Tyr Ile Asp Gly Pro Ile Ile Gln Ala Ser Val Ala Arg
140                 145                 150                 155

GCT CTG GCC AGC GGC ACC ACC ATG GAC GCC GTG CTG GAG ATG CTG AGG        2448
Ala Leu Ala Ser Gly Thr Thr Met Asp Ala Val Leu Glu Met Leu Arg
                160                 165                 170

GAG GTG ACG CCG GAG CTG TCG TGC CCC GTG GTG CTC CTC TCC TAC TAC        2496
Glu Val Thr Pro Glu Leu Ser Cys Pro Val Val Leu Leu Ser Tyr Tyr
            175                 180                 185

AAG CCC ATC ATG TCT CGC AGC TTG GCC GAG ATG AAA GAG GCG GGG GTC        2544
Lys Pro Ile Met Ser Arg Ser Leu Ala Glu Met Lys Glu Ala Gly Val
        190                 195                 200

CAC GGTAACTATA GCTAGCTCTT CCGATCCCCC TTCAATTAAT TAATTTATAG             2597
His

TAGTCCATTC ATGTGATGAT TTTTGTTTTT CTTTTTACTG ACA GGT CTT ATA GTG        2652
```

```
                                   Gly Leu Ile Val
                                                205

CCT GAT CTC CCG TAC GTG GCC GCG CAC TCG CTG TGG AGT GAA GCC AAG      2700
Pro Asp Leu Pro Tyr Val Ala Ala His Ser Leu Trp Ser Glu Ala Lys
    210                 215                 220

AAC AAC AAC CTG GAG CTG GTAGGTTGAA TTAAGTTGAT GCATGTGATG              2748
Asn Asn Asn Leu Glu Leu
225             230

ATTTATGTAG CTAGATCGAG CTAGCTATAA TTAGGAGCAT ATCAG GTG CTG CTG         2802
                                                 Val Leu Leu

ACA ACA CCA GCC ATA CCA GAA GAC AGG ATG AAG GAG ATC ACC AAG GCT      2850
Thr Thr Pro Ala Ile Pro Glu Asp Arg Met Lys Glu Ile Thr Lys Ala
        235                 240                 245

TCA GAA GGC TTC GTC TAC CTG GTAGTTATAT GTATATATAG ATGGACGACG          2901
Ser Glu Gly Phe Val Tyr Leu
250                 255

TAACTCATTC CAGCCCCATG CATATATGGA GGCTTCAATT CTGCAGAGAC GACGAAGACC     2961

ACGACGACGA CTAACACTAG CTAGGGGCGT ACGTTGCAG GTG AGC GTG AAC GGA       3015
                                           Val Ser Val Asn Gly
                                                           260

GTG ACA GGT CCT CGC GCA AAC GTG AAC CCA CGA GTG GAG TCA CTC ATC      3063
Val Thr Gly Pro Arg Ala Asn Val Asn Pro Arg Val Glu Ser Leu Ile
            265                 270                 275

CAG GAG GTT AAG AAG GTG ACT AAC AAG CCC GTT GCT GTT GGC TTC GGC      3111
Gln Glu Val Lys Lys Val Thr Asn Lys Pro Val Ala Val Gly Phe Gly
                280                 285                 290

ATA TCC AAG CCC GAG CAC GTG AAG CAGGTACGTA CGTAGCTGAC CAAAAAAAC      3165
Ile Ser Lys Pro Glu His Val Lys
                295                 300

TGTTAACAAG TTTTGTTTGA CAAGCCGGCT ACTAGCTAGC TAACAGTGAT CAGTGACACA    3225

CACACACACA CAG ATT GCG CAG TGG GGC GCT GAC GGG GTG ATC ATC GGC       3274
               Gln Ile Ala Gln Trp Gly Ala Asp Gly Val Ile Ile Gly
                                    305                 310

AGC GCC ATG GTG AGG CAG CTG GGC GAA GCG GCT TCT CCC AAG CAA GGC      3322
Ser Ala Met Val Arg Gln Leu Gly Glu Ala Ala Ser Pro Lys Gln Gly
315                 320                 325                 330

CTG AGG AGG CTG GAG GAG TAT GCC AGG GGC ATG AAG AAC GCG CTG CCA      3370
Leu Arg Arg Leu Glu Glu Tyr Ala Arg Gly Met Lys Asn Ala Leu Pro
                335                 340                 345

TGAGTCCATG ACAAAGTAAA ACGTACAGAG ACACTTGATA ATATCTATCT ATCATCTCGG    3430

AGAAGACGAC CGACCAATAA AAATAAGCCA AGTGGAAGTG AAGCTTAGCT GTATATACAC    3490

CGTACGTCGT CGTCGTCGTT CCGGATCGAT CTCGGCCGGC TAGCTAGCAG AACGTGTACG    3550

TAGTAGTATG TAATGCATGG AGTGTGGAGC TACTAGCTAG CTGGCCGTTC ATTCGATTAT    3610

AATTCTTCGC TCTGCTGTGG TAGCAGATGT ACCTAGTCGA TCTTGTACGA CGAAGAAGCT    3670

GGCTAGCTAG CCGTCTCGAT CGTATATGTA CTGATTAATC TGCAGATTGA ATAAAAACTA    3730

CAGTACGCAT ATGATGCGTA CGTACGTGTG TATAGTTTGT GCTCATATAT GCTCCTCATC    3790

ACCTGCCTGA TCTGCCCATC GATCTCTCTC GTACTCCTTC CTGTTAAATG CCTTCTTTGA    3850

CAGACACACC ACCACCAGCA GCAGTGACGC TCTGCACGCC GCCGCTTTAA GACATGTAAG    3910

ATATTTTAAG AGGTATAAGA TACCAAGGAG CACAAATCTG GAGCACTGGG ATATTGCAAA    3970

GACAAAAAAA AAACAAAATT AAAGTCCCAC CAAAGTAGAG ATAGTAAAGA GGTGGATGGA    4030

TTAAAATTAT CTCATGATTT TTGGATCTGC TCAAATAGAT CGATATGGTA TTCAGATCTA    4090

TGTTGTATAG CCTTTTCATT AGCTTTCTGA AAAAAAAATG GTATGATGAG TGCGGAGTAG    4150
```

```
CTAGGGCTGT GAAGGAGTCG GATGGGCTTC CACGTACTTG TTTGTGGCCC TAGTCCGGTT    4210

CTATTTAGGT CCGATCCGAG TCCGGCATGG TCCGGTTCCA TACGGGCTAG GACCAAGCTC    4270

GGCACGTGAG TTTTAGGCCC GTCGGCTAGC CCGAGCACGA CCCGTTTTTA AACTGGCTAG    4330

GACTCGCCCA TTTAATAAGA CAAACATTGC AAAAAATAGC TCTATTTTTT ATTTAAAATA    4390

TATTGTTTAT TTGTGAAATG TGTATTATTT GTAATATATA TTATTGTATA TAGTTATATC    4450

TTCAATTATG ATTTATAAAT ATGTTTTTTA TTATGAACTC AATTTTAAGT TTGATTTATG    4510

CGTTGGCGGG CTCGAGGAGG CACGGTGAAC ATTTTTGGGT CGGGCTTAAC GGGTCGGCCC    4570

GGCCCGGTTC GGCCCATCCA CGGCCCATCC CGTGTCGGCC TCGTTCGGTG AGTTCAGCCC    4630

GTCGGACAAC CCGTCCCCGG CCCGGATAAT TAATCGGGCC TAACCGTGGC GTGCTTAAAC    4690

GGTCCGTGCC TCAACGGACC GGGCCGCGGG CGGCCCGTTT GACATCTCTA GTGGTGTGAT    4750

TAGAGATGGC GATGGGAACC GATCACTGAT TCCGTGTGGA GAATTCGATA TCAAGCTTAT    4810

CGATACC                                                              4817
```

(2) INFORMATION FOR SEQ ID NO:19:

(i) SEQUENCE CHARACTERISTICS:
        (A) LENGTH: 346 amino acids
        (B) TYPE: amino acid
        (D) TOPOLOGY: linear (ii) MOLECULE TYPE: protein (xi) SEQUENCE DESCRIPTION: SEQ ID NO:19:

```
Met Ala Phe Ala Pro Lys Thr Ser Ser Ser Ser Leu Ser Ser Ala
 1               5                  10                  15

Leu Gln Ala Ala Gln Ser Pro Leu Leu Arg Arg Met Ser Ser
            20                  25                  30

Thr Ala Thr Pro Arg Arg Arg Tyr Asp Ala Ala Val Val Thr Thr
        35                  40                  45

Thr Thr Thr Ala Arg Ala Ala Ala Ala Val Thr Val Pro Ala Ala
        50                  55                  60

Pro Pro Gln Ala Gly Arg Arg Arg Cys His Gln Ser Lys Arg Arg
65                  70                  75                  80

His Pro Gln Arg Arg Ser Arg Pro Val Ser Asp Thr Met Ala Leu
                85                  90                  95

Met Ala Lys Gly Lys Thr Ala Phe Ile Pro Tyr Ile Thr Ala Gly Asp
                100                 105                 110

Pro Asp Leu Ala Thr Thr Ala Glu Ala Leu Arg Leu Leu Asp Gly Cys
                115                 120                 125

Gly Ala Asp Val Ile Glu Leu Gly Val Pro Cys Ser Asp Pro Tyr Ile
130                 135                 140

Asp Gly Pro Ile Ile Gln Ala Ser Val Ala Arg Ala Leu Ala Ser Gly
145                 150                 155                 160

Thr Thr Met Asp Ala Val Leu Glu Met Leu Arg Glu Val Thr Pro Glu
                165                 170                 175

Leu Ser Cys Pro Val Val Leu Ser Tyr Tyr Lys Pro Ile Met Ser
                180                 185                 190

Arg Ser Leu Ala Glu Met Lys Glu Ala Gly Val His Gly Leu Ile Val
                195                 200                 205

Pro Asp Leu Pro Tyr Val Ala Ala His Ser Leu Trp Ser Glu Ala Lys
                210                 215                 220

Asn Asn Asn Leu Glu Leu Val Leu Leu Thr Thr Pro Ala Ile Pro Glu
225                 230                 235                 240
```

```
Asp Arg Met Lys Glu Ile Thr Lys Ala Ser Glu Gly Phe Val Tyr Leu
                245                 250                 255

Val Ser Val Asn Gly Val Thr Gly Pro Arg Ala Asn Val Asn Pro Arg
            260                 265                 270

Val Glu Ser Leu Ile Gln Glu Val Lys Lys Val Thr Asn Lys Pro Val
        275                 280                 285

Ala Val Gly Phe Gly Ile Ser Lys Pro Glu His Val Lys Gln Ile Ala
    290                 295                 300

Gln Trp Gly Ala Asp Gly Val Ile Ile Gly Ser Ala Met Val Arg Gln
305                 310                 315                 320

Leu Gly Glu Ala Ala Ser Pro Lys Gln Gly Leu Arg Arg Leu Glu Glu
                325                 330                 335

Tyr Ala Arg Gly Met Lys Asn Ala Leu Pro
                340                 345

(2) INFORMATION FOR SEQ ID NO:20:

(i) SEQUENCE CHARACTERISTICS:
        (A) LENGTH: 1349 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (ix) FEATURE:
        (A) NAME/KEY: CDS
        (B) LOCATION: 3..1226
        (D) OTHER INFORMATION: /note= "cDNA sequence for maize
            pollen-specific calcium dependent protein kinase gene as
            disclosed in Figure 30."

(xi) SEQUENCE DESCRIPTION: SEQ ID NO:20:

TG CAG ATC ATG CAC CAC CTC TCC GGC CAG CCC AAC GTG GTG GGC CTC          47
   Gln Ile Met His His Leu Ser Gly Gln Pro Asn Val Val Gly Leu
               350                 355                 360

CGC GGC GCG TAC GAG GAC AAG CAG AGC GTG CAC CTC GTC ATG GAG CTG         95
Arg Gly Ala Tyr Glu Asp Lys Gln Ser Val His Leu Val Met Glu Leu
            365                 370                 375

TGC GCG GGC GGG GAG CTC TTC GAC CGC ATC ATC GCC CGG GGC CAG TAC        143
Cys Ala Gly Gly Glu Leu Phe Asp Arg Ile Ile Ala Arg Gly Gln Tyr
        380                 385                 390

ACG GAG CGC GGC GCC GCG GAG CTG CTG CGC GCC ATC GTG CAG ATC GTG        191
Thr Glu Arg Gly Ala Ala Glu Leu Leu Arg Ala Ile Val Gln Ile Val
    395                 400                 405

CAC ACC TGC CAC TCC ATG GGG GTG ATG CAC CGG GAC ATC AAG CCC GAG        239
His Thr Cys His Ser Met Gly Val Met His Arg Asp Ile Lys Pro Glu
410                 415                 420                 425

AAC TTC CTG CTG CTC AGC AAG GAC GAG GAC GCG CCG CTC AAG GCC ACC        287
Asn Phe Leu Leu Leu Ser Lys Asp Glu Asp Ala Pro Leu Lys Ala Thr
                430                 435                 440

GAC TTC GGC CTC TCC GTC TTC TTC AAG GAG GGC GAG CTG CTC AGG GAC        335
Asp Phe Gly Leu Ser Val Phe Phe Lys Glu Gly Glu Leu Leu Arg Asp
            445                 450                 455

ATC GTC GGC AGC GCC TAC TAC ATC GCG CCC GAG GTG CTC AAG AGG AAG        383
Ile Val Gly Ser Ala Tyr Tyr Ile Ala Pro Glu Val Leu Lys Arg Lys
        460                 465                 470

TAC GGC CCG GAG GCC GAC ATC TGG AGC GTC GGC GTC ATG CTC TAC ATC        431
Tyr Gly Pro Glu Ala Asp Ile Trp Ser Val Gly Val Met Leu Tyr Ile
    475                 480                 485
```

```
                                                          -continued

TTC CTC GCC GGC GTG CCT CCC TTC TGG GCA GAG AAC GAG AAC GGC ATC         479
Phe Leu Ala Gly Val Pro Pro Phe Trp Ala Glu Asn Glu Asn Gly Ile
490             495                 500                 505

TTC ACC GCC ATC CTG CGA GGG CAG CTT GAC CTC TCC AGC GAG CCA TGG         527
Phe Thr Ala Ile Leu Arg Gly Gln Leu Asp Leu Ser Ser Glu Pro Trp
                510                 515                 520

CCA CAC ATC TCG CCG GGA GCC AAG GAT CTC GTC AAG AAG ATG CTC AAC         575
Pro His Ile Ser Pro Gly Ala Lys Asp Leu Val Lys Lys Met Leu Asn
                525                 530                 535

ATC AAC CCC AAG GAG CGG CTC ACG GCG TTC CAG GTC CTC AAT CAC CCA         623
Ile Asn Pro Lys Glu Arg Leu Thr Ala Phe Gln Val Leu Asn His Pro
                540                 545                 550

TGG ATC AAA GAA GAC GGA GAC GCG CCT GAC ACG CCG CTT GAC AAC GTT         671
Trp Ile Lys Glu Asp Gly Asp Ala Pro Asp Thr Pro Leu Asp Asn Val
555                 560                 565

GTT CTC GAC AGG CTC AAG CAG TTC AGG GCC ATG AAC CAG TTC AAG AAA         719
Val Leu Asp Arg Leu Lys Gln Phe Arg Ala Met Asn Gln Phe Lys Lys
570                 575                 580                 585

GCA GCA TTG AGG ATC ATA GCT GGG TGC CTA TCC GAA GAG GAG ATC ACA         767
Ala Ala Leu Arg Ile Ile Ala Gly Cys Leu Ser Glu Glu Glu Ile Thr
                590                 595                 600

GGG CTG AAG GAG ATG TTC AAG AAC ATT GAC AAG GAT AAC AGC GGG ACC         815
Gly Leu Lys Glu Met Phe Lys Asn Ile Asp Lys Asp Asn Ser Gly Thr
                605                 610                 615

ATT ACC CTC GAC GAG CTC AAA CAC GGG TTG GCA AAG CAC GGG CCC AAG         863
Ile Thr Leu Asp Glu Leu Lys His Gly Leu Ala Lys His Gly Pro Lys
                620                 625                 630

CTG TCA GAC AGC GAA ATG GAG AAA CTA ATG GAA GCA GCT GAC GCT GAC         911
Leu Ser Asp Ser Glu Met Glu Lys Leu Met Glu Ala Ala Asp Ala Asp
635                 640                 645

GGC AAC GGG TTA ATT GAC TAC GAC GAA TTC GTC ACC GCA ACA GTG CAT         959
Gly Asn Gly Leu Ile Asp Tyr Asp Glu Phe Val Thr Ala Thr Val His
650                 655                 660                 665

ATG AAC AAA CTG GAT AGA GAA GAG CAC CTT TAC ACA GCA TTC CAG TAT        1007
Met Asn Lys Leu Asp Arg Glu Glu His Leu Tyr Thr Ala Phe Gln Tyr
                670                 675                 680

TTC GAC AAG GAC AAC AGC GGG TAC ATT ACT AAA GAA GAG CTT GAG CAC        1055
Phe Asp Lys Asp Asn Ser Gly Tyr Ile Thr Lys Glu Glu Leu Glu His
                685                 690                 695

GCC TTG AAG GAG CAA GGG TTG TAT GAC GCC GAT AAA ATC AAA GAC ATC        1103
Ala Leu Lys Glu Gln Gly Leu Tyr Asp Ala Asp Lys Ile Lys Asp Ile
                700                 705                 710

ATC TCC GAT GCC GAC TCT GAC AAT GAT GGA AGG ATA GAT TAT TCA GAG        1151
Ile Ser Asp Ala Asp Ser Asp Asn Asp Gly Arg Ile Asp Tyr Ser Glu
715                 720                 725

TTT GTG GCG ATG ATG AGG AAA GGG ACG GCT GGT GCC GAG CCA ATG AAC        1199
Phe Val Ala Met Met Arg Lys Gly Thr Ala Gly Ala Glu Pro Met Asn
730                 735                 740                 745

ATC AAG AAG AGG CGA GAC ATA GTC CTA TAGTGAAGTG AAGCAGCAAG              1246
Ile Lys Lys Arg Arg Asp Ile Val Leu
                750

TGTGTAATGT AATGTGTATA GCAGCTCAAA CAAGCAAATT TGTACATCTG TACACAAATG      1306

CAATGGGGTT ACTTTTGCAA AAAAAAAAAA AAAAAAAAAA AAA                        1349

(2) INFORMATION FOR SEQ ID NO:21:

(i) SEQUENCE CHARACTERISTICS:
        (A) LENGTH: 408 amino acids
        (B) TYPE: amino acid
        (D) TOPOLOGY: linear
```

(ii) MOLECULE TYPE: protein (xi) SEQUENCE DESCRIPTION: SEQ ID NO:21:

```
Gln Ile Met His His Leu Ser Gly Gln Pro Asn Val Val Gly Leu Arg
 1               5                  10                  15

Gly Ala Tyr Glu Asp Lys Gln Ser Val His Leu Val Met Glu Leu Cys
             20                  25                  30

Ala Gly Gly Glu Leu Phe Asp Arg Ile Ile Ala Arg Gly Gln Tyr Thr
         35                  40                  45

Glu Arg Gly Ala Ala Glu Leu Leu Arg Ala Ile Val Gln Ile Val His
 50                  55                  60

Thr Cys His Ser Met Gly Val Met His Arg Asp Ile Lys Pro Glu Asn
 65                  70                  75                  80

Phe Leu Leu Leu Ser Lys Asp Glu Asp Ala Pro Leu Lys Ala Thr Asp
                 85                  90                  95

Phe Gly Leu Ser Val Phe Phe Lys Glu Gly Glu Leu Leu Arg Asp Ile
            100                 105                 110

Val Gly Ser Ala Tyr Tyr Ile Ala Pro Glu Val Leu Lys Arg Lys Tyr
            115                 120                 125

Gly Pro Glu Ala Asp Ile Trp Ser Val Gly Val Met Leu Tyr Ile Phe
130                 135                 140

Leu Ala Gly Val Pro Pro Phe Trp Ala Glu Asn Glu Asn Gly Ile Phe
145                 150                 155                 160

Thr Ala Ile Leu Arg Gly Gln Leu Asp Leu Ser Ser Glu Pro Trp Pro
                165                 170                 175

His Ile Ser Pro Gly Ala Lys Asp Leu Val Lys Lys Met Leu Asn Ile
            180                 185                 190

Asn Pro Lys Glu Arg Leu Thr Ala Phe Gln Val Leu Asn His Pro Trp
            195                 200                 205

Ile Lys Glu Asp Gly Asp Ala Pro Asp Thr Pro Leu Asp Asn Val Val
        210                 215                 220

Leu Asp Arg Leu Lys Gln Phe Arg Ala Met Asn Gln Phe Lys Lys Ala
225                 230                 235                 240

Ala Leu Arg Ile Ile Ala Gly Cys Leu Ser Glu Glu Ile Thr Gly
                245                 250                 255

Leu Lys Glu Met Phe Lys Asn Ile Asp Lys Asp Asn Ser Gly Thr Ile
                260                 265                 270

Thr Leu Asp Glu Leu Lys His Gly Leu Ala Lys His Gly Pro Lys Leu
            275                 280                 285

Ser Asp Ser Glu Met Glu Lys Leu Met Glu Ala Ala Asp Ala Asp Gly
            290                 295                 300

Asn Gly Leu Ile Asp Tyr Asp Glu Phe Val Thr Ala Thr Val His Met
305                 310                 315                 320

Asn Lys Leu Asp Arg Glu Glu His Leu Tyr Thr Ala Phe Gln Tyr Phe
                325                 330                 335

Asp Lys Asp Asn Ser Gly Tyr Ile Thr Lys Glu Glu Leu Glu His Ala
            340                 345                 350

Leu Lys Glu Gln Gly Leu Tyr Asp Ala Asp Lys Ile Lys Asp Ile Ile
            355                 360                 365

Ser Asp Ala Asp Ser Asp Asn Asp Gly Arg Ile Asp Tyr Ser Glu Phe
        370                 375                 380

Val Ala Met Met Arg Lys Gly Thr Ala Gly Ala Glu Pro Met Asn Ile
385                 390                 395                 400

Lys Lys Arg Arg Asp Ile Val Leu
```

405

(2) INFORMATION FOR SEQ ID NO:22:

(i) SEQUENCE CHARACTERISTICS:
        (A) LENGTH: 464 amino acids
        (B) TYPE: amino acid
        (C) STRANDEDNESS: single
        (D) TOPOLOGY: linear (ii) MOLECULE TYPE: protein (iii) HYPOTHETICAL: NO (ix) FEATURE:
        (A) NAME/KEY: Protein
        (B) LOCATION: 1..464
        (D) OTHER INFORMATION: /note= "derived protein sequence of
            pollen specific CDPK as disclosed in Figure 34."

(xi) SEQUENCE DESCRIPTION: SEQ ID NO:22:

```
Val Leu Gly Arg Pro Met Glu Asp Val Arg Ala Thr Tyr Ser Met Gly
 1               5                  10                  15

Lys Glu Leu Gly Arg Gly Gln Phe Gly Val Thr His Leu Cys Thr His
            20                  25                  30

Arg Thr Ser Gly Glu Lys Leu Ala Cys Lys Thr Ile Ala Lys Arg Lys
        35                  40                  45

Leu Ala Ala Arg Glu Asp Val Asp Val Arg Arg Glu Val Gln Ile
 50                  55                  60

Met His His Leu Ser Gly Gln Pro Asn Val Val Gly Leu Arg Gly Ala
 65                  70                  75                  80

Tyr Glu Asp Lys Gln Ser Val His Leu Val Met Glu Leu Cys Ala Gly
                85                  90                  95

Gly Glu Leu Phe Asp Arg Ile Ile Ala Arg Gly Gln Tyr Thr Glu Arg
            100                 105                 110

Gly Ala Ala Glu Leu Leu Arg Ala Ile Val Gln Ile Val His Thr Cys
        115                 120                 125

His Ser Met Gly Val Met His Arg Asp Ile Lys Pro Glu Asn Phe Leu
130                 135                 140

Leu Leu Ser Lys Asp Glu Asp Ala Pro Leu Lys Ala Thr Asp Phe Gly
145                 150                 155                 160

Leu Ser Val Phe Phe Lys Glu Gly Glu Leu Leu Arg Asp Ile Val Gly
                165                 170                 175

Ser Ala Tyr Tyr Ile Ala Pro Glu Val Leu Lys Arg Lys Tyr Gly Pro
            180                 185                 190

Glu Ala Asp Ile Trp Ser Val Gly Val Met Leu Tyr Ile Phe Leu Ala
        195                 200                 205

Gly Val Pro Pro Phe Trp Ala Glu Asn Glu Asn Gly Ile Phe Thr Ala
210                 215                 220

Ile Leu Arg Gly Gln Leu Asp Leu Ser Ser Glu Pro Trp Pro His Ile
225                 230                 235                 240

Ser Pro Gly Ala Lys Asp Leu Val Lys Lys Met Leu Asn Ile Asn Pro
                245                 250                 255

Lys Glu Arg Leu Thr Ala Phe Gln Val Leu Asn His Pro Trp Ile Lys
            260                 265                 270

Glu Asp Gly Asp Ala Pro Asp Thr Pro Leu Asp Asn Val Val Leu Asp
        275                 280                 285

Arg Leu Lys Gln Phe Arg Ala Met Asn Gln Phe Lys Lys Ala Ala Leu
290                 295                 300
```

```
Arg Ile Ile Ala Gly Cys Leu Ser Glu Glu Ile Thr Gly Leu Lys
305                 310                 315                 320

Glu Met Phe Lys Asn Ile Asp Lys Asp Asn Ser Gly Thr Ile Thr Leu
            325                 330                 335

Asp Glu Leu Lys His Gly Leu Ala Lys His Gly Pro Lys Leu Ser Asp
            340                 345                 350

Ser Glu Met Glu Lys Leu Met Glu Ala Ala Asp Ala Asp Gly Asn Gly
            355                 360                 365

Leu Ile Asp Tyr Asp Glu Phe Val Thr Ala Thr Val His Met Asn Lys
370                 375                 380

Leu Asp Arg Glu Glu His Leu Tyr Thr Ala Phe Gln Tyr Phe Asp Lys
385                 390                 395                 400

Asp Asn Ser Gly Tyr Ile Thr Lys Glu Glu Leu Glu His Ala Leu Lys
                405                 410                 415

Glu Gln Gly Leu Tyr Asp Ala Asp Lys Ile Lys Asp Ile Ile Ser Asp
                420                 425                 430

Ala Asp Ser Asp Asn Asp Gly Arg Ile Asp Tyr Ser Glu Phe Val Ala
            435                 440                 445

Met Met Arg Lys Gly Thr Ala Gly Ala Glu Pro Met Asn Ile Lys Lys
450                 455                 460
```

(2) INFORMATION FOR SEQ ID NO:23:

(i) SEQUENCE CHARACTERISTICS:
    (A) LENGTH: 295 amino acids
    (B) TYPE: amino acid
    (C) STRANDEDNESS: single
    (D) TOPOLOGY: linear (ii) MOLECULE TYPE: protein (iii) HYPOTHETICAL: NO (ix) FEATURE:
    (A) NAME/KEY: Protein
    (B) LOCATION: 1..295
    (D) OTHER INFORMATION: /note= "rat protein kinase II
     protein sequence as shown in Figure 32."

(xi) SEQUENCE DESCRIPTION: SEQ ID NO:23:

```
Tyr Gln Leu Phe Glu Glu Leu Gly Lys Gly Ala Phe Ser Val Val Arg
1               5                   10                  15

Arg Cys Val Lys Lys Thr Ser Thr Gln Glu Tyr Ala Ala Lys Ile Ile
            20                  25                  30

Asn Thr Lys Lys Leu Ser Ala Arg Asp His Gln Lys Leu Glu Arg Glu
            35                  40                  45

Ala Arg Ile Cys Arg Leu Leu Lys His Pro Asn Ile Val Arg Leu His
50                  55                  60

Asp Ser Ile Ser Glu Glu Gly Phe His Tyr Leu Val Phe Asp Leu Val
65                  70                  75                  80

Thr Gly Gly Glu Leu Phe Glu Asp Ile Val Ala Arg Glu Tyr Tyr Ser
                85                  90                  95

Glu Ala Asp Ala Ser His Cys Ile His Gln Ile Leu Glu Ser Val Asn
                100                 105                 110

His Ile His Gln His Asp Ile Val His Arg Asp Leu Lys Pro Glu Asn
            115                 120                 125

Leu Leu Leu Ala Ser Lys Cys Lys Gly Ala Ala Val Lys Leu Ala Asp
            130                 135                 140

Phe Gly Leu Ala Ile Glu Val Gln Gly Glu Gln Gln Ala Trp Phe Gly
145                 150                 155                 160
```

```
Phe Ala Gly Thr Pro Gly Tyr Leu Ser Pro Glu Val Leu Arg Lys Asp
                165                 170                 175

Pro Tyr Gly Lys Pro Val Asp Ile Trp Ala Cys Gly Val Ile Leu Tyr
            180                 185                 190

Ile Leu Leu Val Gly Tyr Pro Pro Phe Trp Asp Glu Asp Gln His Lys
            195                 200                 205

Leu Tyr Gln Gln Ile Lys Ala Gly Ala Tyr Asp Phe Pro Ser Pro Glu
            210                 215                 220

Trp Asp Thr Val Thr Pro Glu Ala Lys Asn Leu Ile Asn Gln Met Leu
225                 230                 235                 240

Thr Ile Asn Pro Ala Lys Arg Ile Thr Ala Asp Gln Ala Leu Lys His
            245                 250                 255

Pro Trp Val Cys Gln Arg Ser Thr Val Ala Ser Met Met His Arg Gln
            260                 265                 270

Glu Thr Val Glu Cys Leu Arg Lys Phe Asn Ala Arg Arg Lys Leu Lys
            275                 280                 285

Gly Ala Ile Leu Thr Thr Met
            290             295
```

(2) INFORMATION FOR SEQ ID NO:24:

(i) SEQUENCE CHARACTERISTICS:
        (A) LENGTH: 142 amino acids
        (B) TYPE: amino acid
        (C) STRANDEDNESS: single
        (D) TOPOLOGY: linear (ii) MOLECULE TYPE: protein (iii) HYPOTHETICAL: NO (ix) FEATURE:
        (A) NAME/KEY: Protein
        (B) LOCATION: 1..142
        (D) OTHER INFORMATION: /note= "human calmodulin protein
            sequence as shown in Figure 33."

(xi) SEQUENCE DESCRIPTION: SEQ ID NO:24:

```
Leu Thr Glu Glu Gln Ile Ala Glu Phe Lys Glu Ala Phe Ser Leu Phe
1               5                   10                  15

Asp Lys Asp Gly Asp Gly Thr Ile Thr Thr Lys Glu Leu Gly Thr Val
            20                  25                  30

Met Arg Ser Leu Gly Gln Asn Pro Thr Glu Ala Glu Leu Gln Asp Met
            35                  40                  45

Ile Asn Glu Val Asp Ala Asp Gly Asn Gly Thr Ile Asp Phe Pro Glu
50                  55                  60

Phe Leu Thr Met Met Ala Arg Lys Met Lys Asp Thr Asp Ser Glu Glu
65                  70                  75                  80

Glu Ile Arg Glu Ala Phe Arg Val Lys Asp Lys Asp Gly Asn Gly Tyr
            85                  90                  95

Ile Ser Ala Ala Glu Leu Arg His Val Met Thr Asn Leu Gly Glu Lys
            100                 105                 110

Leu Thr Asp Glu Glu Val Asp Glu Met Ile Arg Glu Ala Asp Ile Asp
            115                 120                 125

Gly Asp Gly Gln Val Asn Tyr Glu Glu Phe Val Gln Met Met
            130                 135                 140
```

(2) INFORMATION FOR SEQ ID NO:25:

(i) SEQUENCE CHARACTERISTICS:

(A) LENGTH: 463 amino acids
(B) TYPE: amino acid
(C) STRANDEDNESS: single
(D) TOPOLOGY: linear (ii) MOLECULE TYPE: protein (iii) HYPOTHETICAL: NO (ix) FEATURE:
(A) NAME/KEY: Protein
(B) LOCATION: 1..463
(D) OTHER INFORMATION: /note= "protein sequence for soybean CDPK as shown in Figure 34."

(xi) SEQUENCE DESCRIPTION: SEQ ID NO:25:

```
Val Leu Pro Gln Arg Thr Gln Asn Ile Arg Glu Val Tyr Glu Val Gly
  1               5                  10                  15

Arg Lys Leu Gly Gln Gly Gln Phe Gly Thr Thr Phe Glu Cys Thr Arg
             20                  25                  30

Arg Ala Ser Gly Gly Lys Phe Ala Cys Lys Ser Ile Pro Lys Arg Lys
         35                  40                  45

Leu Leu Cys Lys Glu Asp Tyr Glu Asp Val Trp Arg Glu Ile Gln Ile
 50                  55                  60

Met His His Leu Ser Glu His Ala Asn Val Val Arg Ile Glu Gly Thr
 65                  70                  75                  80

Tyr Glu Asp Ser Thr Ala Val His Leu Val Met Glu Leu Cys Glu Gly
                 85                  90                  95

Gly Glu Leu Phe Asp Arg Ile Val Gln Lys Gly His Tyr Ser Glu Arg
            100                 105                 110

Gln Ala Ala Arg Leu Ile Lys Thr Ile Val Glu Val Val Glu Ala Cys
        115                 120                 125

His Ser Leu Gly Val Met His Arg Asp Leu Lys Pro Glu Asn Phe Leu
130                 135                 140

Phe Asp Thr Ile Asp Glu Asp Ala Lys Leu Lys Ala Thr Asp Phe Gly
145                 150                 155                 160

Leu Ser Val Phe Tyr Lys Pro Gly Glu Ser Phe Cys Asp Val Val Gly
                165                 170                 175

Ser Pro Tyr Tyr Val Ala Pro Glu Val Leu Arg Lys Leu Tyr Gly Pro
            180                 185                 190

Glu Ser Asp Val Trp Ser Ala Gly Val Ile Leu Tyr Ile Leu Leu Ser
        195                 200                 205

Gly Val Pro Pro Phe Trp Ala Glu Ser Glu Pro Gly Ile Phe Arg Gln
210                 215                 220

Ile Leu Leu Gly Lys Leu Asp Phe His Ser Glu Pro Trp Pro Ser Ile
225                 230                 235                 240

Ser Asp Ser Ala Lys Asp Leu Ile Arg Lys Met Leu Asp Gln Asn Pro
                245                 250                 255

Lys Thr Arg Leu Thr Ala His Glu Val Leu Arg His Pro Trp Ile Val
            260                 265                 270

Asp Asp Asn Ile Ala Pro Asp Lys Pro Leu Asp Ser Ala Val Leu Ser
        275                 280                 285

Arg Leu Lys Gln Phe Ser Ala Met Asn Lys Leu Lys Lys Met Ala Leu
290                 295                 300

Arg Val Ile Ala Glu Arg Leu Ser Glu Glu Ile Gly Gly Leu Lys
305                 310                 315                 320

Glu Leu Phe Lys Met Ile Asp Thr Asp Asn Ser Gly Thr Ile Thr Phe
                325                 330                 335
```

```
Asp Glu Leu Lys Asp Gly Leu Lys Arg Val Gly Ser Glu Leu Met Glu
            340                 345                 350

Ser Glu Ile Lys Asp Leu Met Asp Ala Ala Asp Ile Asp Lys Ser Gly
            355                 360                 365

Thr Ile Asp Tyr Gly Glu Phe Ile Ala Ala Thr Val His Leu Asn Lys
370                 375                 380

Leu Glu Arg Glu Glu Asn Leu Val Ser Ala Phe Ser Tyr Phe Asp Lys
385                 390                 395                 400

Asp Gly Ser Gly Tyr Ile Thr Leu Asp Glu Ile Gln Gln Ala Cys Lys
                405                 410                 415

Asp Phe Gly Leu Asp Asp Ile His Ile Asp Asp Met Ile Lys Glu Ile
            420                 425                 430

Asp Gln Asp Asn Asp Gly Gln Ile Asp Tyr Gly Glu Phe Ala Ala Met
            435                 440                 445

Met Arg Lys Gly Asn Gly Gly Ile Gly Arg Arg Thr Met Arg Lys
450                 455                 460
```

(2) INFORMATION FOR SEQ ID NO:26:

(i) SEQUENCE CHARACTERISTICS:
        (A) LENGTH: 4162 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (ix) FEATURE:
        (A) NAME/KEY: misc_feature
        (B) LOCATION: 1418..1427
        (D) OTHER INFORMATION: /note= "start of mRNA"

(ix) FEATURE:
        (A) NAME/KEY: exon
        (B) LOCATION: 1481..2366

(ix) FEATURE:
        (A) NAME/KEY: intron
        (B) LOCATION: 2367..2451

(ix) FEATURE:
        (A) NAME/KEY: exon
        (B) LOCATION: 2452..2602

(ix) FEATURE:
        (A) NAME/KEY: intron
        (B) LOCATION: 2603..2690

(ix) FEATURE:
        (A) NAME/KEY: exon
        (B) LOCATION: 2691..2804

(ix) FEATURE:
        (A) NAME/KEY: intron
        (B) LOCATION: 2805..2906

(ix) FEATURE:
        (A) NAME/KEY: exon
        (B) LOCATION: 2907..3075

(ix) FEATURE:
        (A) NAME/KEY: intron
        (B) LOCATION: 3076..3177

(ix) FEATURE:
        (A) NAME/KEY: exon
        (B) LOCATION: 3178..3304

(ix) FEATURE:
        (A) NAME/KEY: intron (B) LOCATION: 3305..3398

(ix) FEATURE:
                    (A) NAME/KEY: exon
                    (B) LOCATION: 3399..3498

(ix) FEATURE:
                    (A) NAME/KEY: intron
                    (B) LOCATION: 3499..3713

(ix) FEATURE:
                    (A) NAME/KEY: exon
                    (B) LOCATION: 3714..3811

(ix) FEATURE:
                    (A) NAME/KEY: promoter
                    (B) LOCATION: 1..1477
                    (C) IDENTIFICATION METHOD: experimental
                    (D) OTHER INFORMATION: /partial
                        /function= "pollen-specific promoter region"
                        /evidence= EXPERIMENTAL (xi) SEQUENCE DESCRIPTION: SEQ ID NO:26:

```
TTAGTAACAC CTCTCCAATC GCTTGGGTTG GCACATTCTT AGCTTTTATC ACATTTTAAG       60

AAATAGAGTT CACCACCTTC AAAATAATGC CTATACAATG AATGATCGCT TGGATGCAAT      120

ATAGCTAGAT TCAACTAGCT ATATATGGTC AATAGAACCC TGTGAGCACC TCACAAACAC      180

GACTTCAATT TTGAGACCCT AAGCGAGTAA ATGGTTAAAG TCCTCTTATT ATTAGTCTTA      240

GGACTTCTCC TTGCTAAATG CTTGTCAGCG ATCTATATAT CTTCCCCACT GCGGGAGATA      300

CTATATATAG GGCCTTGGAC CTCTAGGGTA TCTCAAAGGC CTAGTCACAA CAATTCTCAA      360

CAGTATTTAA TTTTATACAT GTATGAACAG TGTAGGAATT TGAGTGCCCA ACCCAAGAGT      420

GGGAGGTGTA AATTGGGTAG CTAAACTTAA ATAGGGCTCT TCTTATTTAG GTTTATCTAG      480

TCTCTACTTA GACTAATTCA GAAAGAATTT TACAACCTAT GGTTAATCAT ATCTCTAGTC      540

TAAGCAAATT TAGGAAAGTT AAAAGCACAC AATTAGGCAC ATGTGAAAGA TGTGTATGGT      600

AAGTAAAAGA CTTATAAGGA AAAAGTGGGT GAATCCTCAA GATGTGGTGG TATATCCCAA      660

TGATATTAGA TGCCAGAATA TAGGGGGGAA ATCGATGTAT ACCATCTCTA CCAGGATACC      720

TGTGCGGACT GTGCAACTGA CACATGGACC ATGGTGTCTT CTTAGATTTG GTTATTAGCT      780

AATTGCGCTA CAACTTGTTC AAGGCTAGAC CAAATTAAAA AACTAATATT AAACATAAAA      840

AGTTAGGCAA ACTATAGTAA ATTATGCAGC GATCCAACAA CAAGCCATGT CTCGTGGGTC      900

ATGAGCCACG CGTCGGCCAT ACACCCACAT GATGTTTCCA TACGGATGGT CCTTATGCAA      960

TTTTGTCTGC AAAACACAAG CCTTAATACA GCCACGCGAC AATCATGGAA GTGGTCGTTT     1020

TAGGTCCTCA TCATGAAGTT CAGGGAAAAC GCATCAAATG TAATGCAGAG AAATGGTATT     1080

TCTTCTCTTG TAAATCAGGG AGAGGAGTAC CATCAGTACA GATTCAGAAT CAGAATTCAG     1140

TCTTCCAACG ACAATAATCG CAGCATCTTG TAAAAATTTG CAGAAACTTC TGTTTGACTT     1200

GTAGCCCTGA CCTTTGCAAA TATTTGAAGT TGTGCCTGCT GACACAACTT CAATCTGGAA     1260

GTGCTGTTGA TCAGTTTTGC CAGAAACAGC AAGCAGCCTA TATATATCTG TCACGAGACA     1320

CCCTGCCGCC CTCTTCTTTC CCGCCATTCC CTCCCTACCC TTCAAAATCT AGAAACCTTT     1380

TTTTTTCCTC CCGATACGCC CCTCCATCTC TCGCCGTTCA TGTCCGTGGC TGGCTGCCCT     1440

CCGTGGGAGC AGGCGGCCGC ACTCGTTCCC CGCCGCAGCC ATGGGCCAGT GCTGCTCCAA     1500

GGGCGCCGGA GAGGCCCCGC CACCGAGGCG CCAAACGGCA GGCGCCAAGC CGCGGGCGTC     1560

CGCGAACAAC GCCGACGGAC AACGGGCGTC GTCCTCGTCC GCGGTGGCTG CTGCCGCTGC     1620

TGCTGCCGGT GGTGGTGGCG GCGGCACGAC GAAGCCGGCC TCACCCACCG GCGGCGCCAG     1680
```

```
GGCCAGCTCC GGCAGCAAAC CGGCGGCGGC CGTGGGCACG GTGCTGGGCC GGCCCATGGA      1740

GGACGTGCGC GCGACCTACT CGATGGGCAA GGAGCTCGGG CGCGGGCAGT TCGGCGTGAC      1800

GCACCTGTGC ACGCACCGGA CGAGCGGCGA GAAGCTGGCG TGCAAGACGA TCGCGAAGCG      1860

GAAGCTGGCG GCCAGGGAGG ACGTGGACGA CGTGCGGCGG GAGGTGCAGA TCATGCACCA      1920

CCTCTCCGGC CAGCCCAACG TGGTGGGCCT CCGCGGCGCG TACGAGGACA AGCAGAGCGT      1980

GCACCTCGTC ATGGAGCTGT GCGCGGGCGG GGAGCTCTTC GACCGCATCA TCGCCCGGGG      2040

CCAGTACACG GAGCGCGGCG CCGCGGAGCT GCTGCGCGCC ATCGTGCAGA TCGTGCACAC      2100

CTGCCACTCC ATGGGGGTGA TGCACCGGGA CATCAAGCCC GAGAACTTCC TGCTGCTCAG      2160

CAAGGACGAG GACGCGCCGC TCAAGGCCAC CGACTTCGGC CTCTCCGTCT TCTTCAAGGA      2220

GGGCGAGCTG CTCAGGGACA TCGTCGGCAG CGCCTACTAC ATCGCGCCCG AGGTGCTCAA      2280

GAGGAAGTAC GGCCCGGAGG CCGACATCTG GAGCGTCGGC GTCATGCTCT ACATCTTCCT      2340

CGCCGGCGTG CCTCCCTTCT GGGCAGGTCG GATCCGTCCG TGTTCGTCCT AGACGATATA      2400

CAGAACCCGA CGATGGATTT GCTTCTCAGC CCTGTTCTTG CATCACCAGA GAACGAGAAC      2460

GGCATCTTCA CCGCCATCCT GCGAGGGCAG CTTGACCTCT CCAGCGAGCC ATGGCCACAC      2520

ATCTCGCCGG GAGCCAAGGA TCTCGTCAAG AAGATGCTCA ACATCAACCC CAAGGAGCGG      2580

CTCACGGCGT TCCAGGTCCT CAGTAAGTAC CCAGATCGTT GCTGTCATAC ACTCATATGA      2640

ATTGTATCGT TCATGAGCAA CGATCGAGCG GATTTGGTGA ACTTGTAGAT CACCCATGGA      2700

TCAAAGAAGA CGGAGACGCG CCTGACACGC CGCTTGACAA CGTTGTTCTC GACAGGCTCA      2760

AGCAGTTCAG GGCCATGAAC CAGTTCAAGA AAGCAGCATT GAGGGTACAT TATCTGATAA      2820

AAGCTCCACA AATACAACTT CTGAAGAACA GCAATGCTTA CACGGCAGAA TTTTCATTAT      2880

AAATGCTCTT GATGACATAA TGTTAGATCA TAGCTGGGTG CCTATCCGAA GAGGAGATCA      2940

CAGGGCTGAA GGAGATGTTC AAGAACATTG ACAAGGATAA CAGCGGGACC ATTACCCTCG      3000

ACGAGCTCAA ACACGGGTTG GCAAAGCACG GGCCCAAGCT GTCAGACAGC GAAATGGAGA      3060

AACTAATGGA AGCAGTGAGT TTTCAGAGTA CAATCTTAAA AAAAGGAATT GTGATTCTTT      3120

TCAAAATGAA GAAGTAATCT GAAAACATCC CTGCTGAAAT GCTTTATACA TTTCCAGGCT      3180

GACGCTGACG GCAACGGGTT AATTGACTAC GACGAATTCG TCACCGCAAC AGTGCATATG      3240

AACAAACTGG ATAGAGAAGA GCACCTTTAC ACAGCATTCC AGTATTTCGA CAAGGACAAC      3300

AGCGGGTAAG TTGAACGTTA AAATGATACA GCTGGTACCT GAATTCTGGA CAACACATAT      3360

CATAACAGGA CACATATATA ATTCGTTTAT CTCACAGGTA CATTACTAAA GAAGAGCTTG      3420

AGCACGCCTT GAAGGAGCAA GGGTTGTATG ACGCCGATAA AATCAAAGAC ATCATCTCCG      3480

ATGCCGACTC TGACAATGTA AGGAACAAAC ATTATTTAAA TTTCAGCCGA CAAACTAAAC      3540

TATAGAAACC ACATCATGAT ATCAAATTTT GAGGTGGCGG TGCTACAGAA ATAGAACCCA      3600

GTACACCAAA ATGACTAACT TGTCATGATT AGTTGTTCCT CGTAACTGAA CATTTGTGTT      3660

CTTAGTTTCT TATTGTTAAA CCAAAGACTT AAATTCACTT TTGCACATGC AGGATGGAAG      3720

GATAGATTAT TCAGAGTTTG TGGCGATGAT GAGGAAAGGG ACGGCTGGTG CCGAGCCAAT      3780

GAACATCAAG AAGAGGCGAG ACATAGTCCT ATAGTGAAGT GAAGCAGAAG TGTGTAATGT      3840

AATGTGTATA GCAGCTCAAA CAAGCAAATT TGTACATCTG TACACAAATG CAATGGGGTT      3900

ACTTTTGCAA CTTAGTTCAT GGATGGTTGT GTACGTTGTG CTATTGATTG CAAGTGATTT      3960

GAAAGACATG CATACTTAGG AACTGAGAAA GATAGATCTA CTACTGCTAG AGACAGAACA      4020

ATAGGATAAT TCAGAAGTGG TATTTCAGAA GACTACAGCT GGCATCTATT ATTCTCATTG      4080
```

```
TCCTCGCAAA AATACTGATG ATGCATTTGA GAGAACAATA TGCAACAAGA TCGAGCTCCC      4140

TATAGTGAGT CGTATTAGGC CA                                               4162
```

(2) INFORMATION FOR SEQ ID NO:27:

(i) SEQUENCE CHARACTERISTICS:
        (A) LENGTH: 3546 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(iii) HYPOTHETICAL: NO (ix) FEATURE:
        (A) NAME/KEY: CDS
        (B) LOCATION: 1..3543
        (D) OTHER INFORMATION: /product= "Full-length, hybrid
            maize optimized heat stable cryIA(b)"
            /note= "DNA sequence as disclosed in Figure 37 as
            contained in pCIB5515."

(xi) SEQUENCE DESCRIPTION: SEQ ID NO:27:

```
ATG GAC AAC AAC CCC AAC ATC AAC GAG TGC ATC CCC TAC AAC TGC CTG        48
Met Asp Asn Asn Pro Asn Ile Asn Glu Cys Ile Pro Tyr Asn Cys Leu
410             415                 420

AGC AAC CCC GAG GTG GAG GTG CTG GGC GGC GAG CGC ATC GAG ACC GGC        96
Ser Asn Pro Glu Val Glu Val Leu Gly Gly Glu Arg Ile Glu Thr Gly
425                 430                 435                 440

TAC ACC CCC ATC GAC ATC AGC CTG AGC CTG ACC CAG TTC CTG CTG AGC       144
Tyr Thr Pro Ile Asp Ile Ser Leu Ser Leu Thr Gln Phe Leu Leu Ser
                445                 450                 455

GAG TTC GTG CCC GGC GCC GGC TTC GTG CTG GGC CTG GTG GAC ATC ATC       192
Glu Phe Val Pro Gly Ala Gly Phe Val Leu Gly Leu Val Asp Ile Ile
            460                 465                 470

TGG GGC ATC TTC GGC CCC AGC CAG TGG GAC GCC TTC CTG GTG CAG ATC       240
Trp Gly Ile Phe Gly Pro Ser Gln Trp Asp Ala Phe Leu Val Gln Ile
        475                 480                 485

GAG CAG CTG ATC AAC CAG CGC ATC GAG GAG TTC GCC CGC AAC CAG GCC       288
Glu Gln Leu Ile Asn Gln Arg Ile Glu Glu Phe Ala Arg Asn Gln Ala
    490                 495                 500

ATC AGC CGC CTG GAG GGC CTG AGC AAC CTG TAC CAA ATC TAC GCC GAG       336
Ile Ser Arg Leu Glu Gly Leu Ser Asn Leu Tyr Gln Ile Tyr Ala Glu
505                 510                 515                 520

AGC TTC CGC GAG TGG GAG GCC GAC CCC ACC AAC CCC GCC CTG CGC GAG       384
Ser Phe Arg Glu Trp Glu Ala Asp Pro Thr Asn Pro Ala Leu Arg Glu
                525                 530                 535

GAG ATG CGC ATC CAG TTC AAC GAC ATG AAC AGC GCC CTG ACC ACC GCC       432
Glu Met Arg Ile Gln Phe Asn Asp Met Asn Ser Ala Leu Thr Thr Ala
            540                 545                 550

ATC CCC CTG TTC GCC GTG CAG AAC TAC CAG GTG CCC CTG CTG AGC GTG       480
Ile Pro Leu Phe Ala Val Gln Asn Tyr Gln Val Pro Leu Leu Ser Val
        555                 560                 565

TAC GTG CAG GCC GCC AAC CTG CAC CTG AGC GTG CTG CGC GAC GTC AGC       528
Tyr Val Gln Ala Ala Asn Leu His Leu Ser Val Leu Arg Asp Val Ser
    570                 575                 580

GTG TTC GGC CAG CGC TGG GGC TTC GAC GCC GCC ACC ATC AAC AGC CGC       576
Val Phe Gly Gln Arg Trp Gly Phe Asp Ala Ala Thr Ile Asn Ser Arg
585                 590                 595                 600

TAC AAC GAC CTG ACC CGC CTG ATC GGC AAC TAC ACC GAC CAC GCC GTG       624
Tyr Asn Asp Leu Thr Arg Leu Ile Gly Asn Tyr Thr Asp His Ala Val
                605                 610                 615
```

-continued

| | | |
|---|---|---|
| CGC TGG TAC AAC ACC GGC CTG GAG CGC GTG TGG GGT CCC GAC AGC CGC<br>Arg Trp Tyr Asn Thr Gly Leu Glu Arg Val Trp Gly Pro Asp Ser Arg<br>620                625                630 | 672 | |
| GAC TGG ATC AGG TAC AAC CAG TTC CGC CGC GAG CTG ACC CTG ACC GTG<br>Asp Trp Ile Arg Tyr Asn Gln Phe Arg Arg Glu Leu Thr Leu Thr Val<br>635                640                645 | 720 | |
| CTG GAC ATC GTG AGC CTG TTC CCC AAC TAC GAC AGC CGC ACC TAC CCC<br>Leu Asp Ile Val Ser Leu Phe Pro Asn Tyr Asp Ser Arg Thr Tyr Pro<br>650                655                660 | 768 | |
| ATC CGC ACC GTG AGC CAG CTG ACC CGC GAG ATT TAC ACC AAC CCC GTG<br>Ile Arg Thr Val Ser Gln Leu Thr Arg Glu Ile Tyr Thr Asn Pro Val<br>665                670                675                680 | 816 | |
| CTG GAG AAC TTC GAC GGC AGC TTC CGC GGC AGC GCC CAG GGC ATC GAG<br>Leu Glu Asn Phe Asp Gly Ser Phe Arg Gly Ser Ala Gln Gly Ile Glu<br>685                690                695 | 864 | |
| GGC AGC ATC CGC AGC CCC CAC CTG ATG GAC ATC CTG AAC AGC ATC ACC<br>Gly Ser Ile Arg Ser Pro His Leu Met Asp Ile Leu Asn Ser Ile Thr<br>700                705                710 | 912 | |
| ATC TAC ACC GAC GCC CAC CGC GGC GAG TAC TAC TGG AGC GGC CAC CAG<br>Ile Tyr Thr Asp Ala His Arg Gly Glu Tyr Tyr Trp Ser Gly His Gln<br>715                720                725 | 960 | |
| ATC ATG GCC AGC CCC GTC GGC TTC AGC GGC CCC GAG TTC ACC TTC CCC<br>Ile Met Ala Ser Pro Val Gly Phe Ser Gly Pro Glu Phe Thr Phe Pro<br>730                735                740 | 1008 | |
| CTG TAC GGC ACC ATG GGC AAC GCT GCA CCT CAG CAG CGC ATC GTG GCA<br>Leu Tyr Gly Thr Met Gly Asn Ala Ala Pro Gln Gln Arg Ile Val Ala<br>745                750                755                760 | 1056 | |
| CAG CTG GGC CAG GGA GTG TAC CGC ACC CTG AGC AGC ACC CTG TAC CGT<br>Gln Leu Gly Gln Gly Val Tyr Arg Thr Leu Ser Ser Thr Leu Tyr Arg<br>765                770                775 | 1104 | |
| CGA CCT TTC AAC ATC GGC ATC AAC AAC CAG CAG CTG AGC GTG CTG GAC<br>Arg Pro Phe Asn Ile Gly Ile Asn Asn Gln Gln Leu Ser Val Leu Asp<br>780                785                790 | 1152 | |
| GGC ACC GAG TTC GCC TAC GGC ACC AGC AGC AAC CTG CCC AGC GCC GTG<br>Gly Thr Glu Phe Ala Tyr Gly Thr Ser Ser Asn Leu Pro Ser Ala Val<br>795                800                805 | 1200 | |
| TAC CGC AAG AGC GGC ACC GTG GAC AGC CTG GAC GAG ATC CCC CCT CAG<br>Tyr Arg Lys Ser Gly Thr Val Asp Ser Leu Asp Glu Ile Pro Pro Gln<br>810                815                820 | 1248 | |
| AAC AAC AAC GTG CCA CCT CGA CAG GGC TTC AGC CAC CGT CTG AGC CAC<br>Asn Asn Asn Val Pro Pro Arg Gln Gly Phe Ser His Arg Leu Ser His<br>825                830                835                840 | 1296 | |
| GTG AGC ATG TTC CGC AGT GGC TTC AGC AAC AGC AGC GTG AGC ATC ATC<br>Val Ser Met Phe Arg Ser Gly Phe Ser Asn Ser Ser Val Ser Ile Ile<br>845                850                855 | 1344 | |
| CGT GCA CCT ATG TTC AGC TGG ATT CAC CGC AGT GCC GAG TTC AAC AAC<br>Arg Ala Pro Met Phe Ser Trp Ile His Arg Ser Ala Glu Phe Asn Asn<br>860                865                870 | 1392 | |
| ATC ATC CCC AGC AGC CAG ATC ACC CAG ATC CCC CTG ACC AAG AGC ACC<br>Ile Ile Pro Ser Ser Gln Ile Thr Gln Ile Pro Leu Thr Lys Ser Thr<br>875                880                885 | 1440 | |
| AAC CTG GGC AGC GGC ACC AGC GTG GTG AAG GGC CCC GGC TTC ACC GGC<br>Asn Leu Gly Ser Gly Thr Ser Val Val Lys Gly Pro Gly Phe Thr Gly<br>890                895                900 | 1488 | |
| GGC GAC ATC CTG CGC CGC ACC AGC CCC GGC CAG ATC AGC ACC CTG CGC<br>Gly Asp Ile Leu Arg Arg Thr Ser Pro Gly Gln Ile Ser Thr Leu Arg<br>905                910                915                920 | 1536 | |
| GTG AAC ATC ACC GCC CCC CTG AGC CAG CGC TAC CGC GTC CGC ATC CGC<br>Val Asn Ile Thr Ala Pro Leu Ser Gln Arg Tyr Arg Val Arg Ile Arg<br>925                930                935 | 1584 | |

| | |
|---|---|
| TAC GCC AGC ACC ACC AAC CTG CAG TTC CAC ACC AGC ATC GAC GGC CGC<br>Tyr Ala Ser Thr Thr Asn Leu Gln Phe His Thr Ser Ile Asp Gly Arg<br>            940                    945                  950 | 1632 |
| CCC ATC AAC CAG GGC AAC TTC AGC GCC ACC ATG AGC AGC GGC AGC AAC<br>Pro Ile Asn Gln Gly Asn Phe Ser Ala Thr Met Ser Ser Gly Ser Asn<br>            955                    960                  965 | 1680 |
| CTG CAG AGC GGC AGC TTC CGC ACC GTG GGC TTC ACC ACC CCC TTC AAC<br>Leu Gln Ser Gly Ser Phe Arg Thr Val Gly Phe Thr Thr Pro Phe Asn<br>            970                    975                  980 | 1728 |
| TTC AGC AAC GGC AGC AGC GTG TTC ACC CTG AGC GCC CAC GTG TTC AAC<br>Phe Ser Asn Gly Ser Ser Val Phe Thr Leu Ser Ala His Val Phe Asn<br>985                    990                  995              1000 | 1776 |
| AGC GGC AAC GAG GTG TAC ATC GAC CGC ATC GAG TTC GTG CCC GCC GAG<br>Ser Gly Asn Glu Val Tyr Ile Asp Arg Ile Glu Phe Val Pro Ala Glu<br>                   1005                 1010                 1015 | 1824 |
| GTG ACC TTC GAG GCC GAG TAC GAC CTG GAG AGG GCT CAG AAG GCC GTG<br>Val Thr Phe Glu Ala Glu Tyr Asp Leu Glu Arg Ala Gln Lys Ala Val<br>           1020                 1025                 1030 | 1872 |
| AAC GAG CTG TTC ACC AGC AGC AAC CAG ATC GGC CTG AAG ACC GAC GTG<br>Asn Glu Leu Phe Thr Ser Ser Asn Gln Ile Gly Leu Lys Thr Asp Val<br>           1035                 1040                 1045 | 1920 |
| ACC GAC TAC CAC ATC GAT CAA GTA TCC AAT TTA GTT GAG TGT TTA TCT<br>Thr Asp Tyr His Ile Asp Gln Val Ser Asn Leu Val Glu Cys Leu Ser<br>           1050                 1055                 1060 | 1968 |
| GAT GAA TTT TGT CTG GAT GAA AAA AAA GAA TTG TCC GAG AAA GTC AAA<br>Asp Glu Phe Cys Leu Asp Glu Lys Lys Glu Leu Ser Glu Lys Val Lys<br>1065                 1070                 1075                 1080 | 2016 |
| CAT GCG AAG CGA CTT AGT GAT GAG CGG AAT TTA CTT CAA GAT CCA AAC<br>His Ala Lys Arg Leu Ser Asp Glu Arg Asn Leu Leu Gln Asp Pro Asn<br>                   1085                 1090                 1095 | 2064 |
| TTT AGA GGG ATC AAT AGA CAA CTA GAC CGT GGC TGG AGA GGA AGT ACG<br>Phe Arg Gly Ile Asn Arg Gln Leu Asp Arg Gly Trp Arg Gly Ser Thr<br>           1100                 1105                 1110 | 2112 |
| GAT ATT ACC ATC CAA GGA GGC GAT GAC GTA TTC AAA GAG AAT TAC GTT<br>Asp Ile Thr Ile Gln Gly Gly Asp Asp Val Phe Lys Glu Asn Tyr Val<br>                   1115                 1120                 1125 | 2160 |
| ACG CTA TTG GGT ACC TTT GAT GAG TGC TAT CCA ACG TAT TTA TAT CAA<br>Thr Leu Leu Gly Thr Phe Asp Glu Cys Tyr Pro Thr Tyr Leu Tyr Gln<br>           1130                 1135                 1140 | 2208 |
| AAA ATA GAT GAG TCG AAA TTA AAA GCC TAT ACC CGT TAC CAA TTA AGA<br>Lys Ile Asp Glu Ser Lys Leu Lys Ala Tyr Thr Arg Tyr Gln Leu Arg<br>1145                 1150                 1155                 1160 | 2256 |
| GGG TAT ATC GAA GAT AGT CAA GAC TTA GAA ATC TAT TTA ATT CGC TAC<br>Gly Tyr Ile Glu Asp Ser Gln Asp Leu Glu Ile Tyr Leu Ile Arg Tyr<br>                   1165                 1170                 1175 | 2304 |
| AAT GCC AAA CAC GAA ACA GTA AAT GTG CCA GGT ACG GGT TCC TTA TGG<br>Asn Ala Lys His Glu Thr Val Asn Val Pro Gly Thr Gly Ser Leu Trp<br>           1180                 1185                 1190 | 2352 |
| CCG CTT TCA GCC CCA AGT CCA ATC GGA AAA TGT GGG GAG CCG AAT CGA<br>Pro Leu Ser Ala Pro Ser Pro Ile Gly Lys Cys Gly Glu Pro Asn Arg<br>                   1195                 1200                 1205 | 2400 |
| TGC GCT CCG CAC CTG GAG TGG AAC CCG GAC CTA GAC TGC AGC TGC AGG<br>Cys Ala Pro His Leu Glu Trp Asn Pro Asp Leu Asp Cys Ser Cys Arg<br>           1210                 1215                 1220 | 2448 |
| GAC GGG GAG AAG TGC GCC CAT CAT TCC CAT CAT TTC TCC TTG GAC ATT<br>Asp Gly Glu Lys Cys Ala His His Ser His His Phe Ser Leu Asp Ile<br>1225                 1230                 1235                 1240 | 2496 |
| GAT GTT GGA TGT ACA GAC TTA AAT GAG GAC TTA GGT GTA TGG GTG ATA<br>Asp Val Gly Cys Thr Asp Leu Asn Glu Asp Leu Gly Val Trp Val Ile<br>                   1245                 1250                 1255 | 2544 |

-continued

| | |
|---|---|
| TTC AAG ATT AAG ACG CAA GAT GGC CAT GCA AGA CTA GGA AAT CTA GAA<br>Phe Lys Ile Lys Thr Gln Asp Gly His Ala Arg Leu Gly Asn Leu Glu<br>              1260                       1265                    1270 | 2592 |
| TTT CTC GAA GAG AAA CCA TTA GTA GGA GAA GCA CTA GCT CGT GTG AAA<br>Phe Leu Glu Glu Lys Pro Leu Val Gly Glu Ala Leu Ala Arg Val Lys<br>1275                       1280                       1285 | 2640 |
| AGA GCG GAG AAA AAA TGG AGA GAC AAA CGT GAA AAA TTG GAA TGG GAA<br>Arg Ala Glu Lys Lys Trp Arg Asp Lys Arg Glu Lys Leu Glu Trp Glu<br>        1290                       1295                    1300 | 2688 |
| ACA AAT ATT GTT TAT AAA GAG GCA AAA GAA TCT GTA GAT GCT TTA TTT<br>Thr Asn Ile Val Tyr Lys Glu Ala Lys Glu Ser Val Asp Ala Leu Phe<br>1305                     1310                     1315               1320 | 2736 |
| GTA AAC TCT CAA TAT GAT AGA TTA CAA GCG GAT ACC AAC ATC GCG ATG<br>Val Asn Ser Gln Tyr Asp Arg Leu Gln Ala Asp Thr Asn Ile Ala Met<br>              1325                     1330                  1335 | 2784 |
| ATT CAT GCG GCA GAT AAA CGC GTT CAT AGC ATT CGA GAA GCT TAT CTG<br>Ile His Ala Ala Asp Lys Arg Val His Ser Ile Arg Glu Ala Tyr Leu<br>        1340                     1345                    1350 | 2832 |
| CCT GAG CTG TCT GTG ATT CCG GGT GTC AAT GCG GCT ATT TTT GAA GAA<br>Pro Glu Leu Ser Val Ile Pro Gly Val Asn Ala Ala Ile Phe Glu Glu<br>1355                     1360                     1365 | 2880 |
| TTA GAA GGG CGT ATT TTC ACT GCA TTC TCC CTA TAT GAT GCG AGA AAT<br>Leu Glu Gly Arg Ile Phe Thr Ala Phe Ser Leu Tyr Asp Ala Arg Asn<br>              1370                     1375                  1380 | 2928 |
| GTC ATT AAA AAT GGT GAT TTT AAT AAT GGC TTA TCC TGC TGG AAC GTG<br>Val Ile Lys Asn Gly Asp Phe Asn Asn Gly Leu Ser Cys Trp Asn Val<br>1385                     1390                     1395               1400 | 2976 |
| AAA GGG CAT GTA GAT GTA GAA GAA CAA AAC AAC CAC CGT TCG GTC CTT<br>Lys Gly His Val Asp Val Glu Glu Gln Asn Asn His Arg Ser Val Leu<br>              1405                     1410                  1415 | 3024 |
| GTT GTT CCG GAA TGG GAA GCA GAA GTG TCA CAA GAA GTT CGT GTC TGT<br>Val Val Pro Glu Trp Glu Ala Glu Val Ser Gln Glu Val Arg Val Cys<br>        1420                     1425                    1430 | 3072 |
| CCG GGT CGT GGC TAT ATC CTT CGT GTC ACA GCG TAC AAG GAG GGA TAT<br>Pro Gly Arg Gly Tyr Ile Leu Arg Val Thr Ala Tyr Lys Glu Gly Tyr<br>1435                     1440                     1445 | 3120 |
| GGA GAA GGT TGC GTA ACC ATT CAT GAG ATC GAG AAC AAT ACA GAC GAA<br>Gly Glu Gly Cys Val Thr Ile His Glu Ile Glu Asn Asn Thr Asp Glu<br>        1450                     1455                    1460 | 3168 |
| CTG AAG TTT AGC AAC TGT GTA GAA GAG GAA GTA TAT CCA AAC AAC ACG<br>Leu Lys Phe Ser Asn Cys Val Glu Glu Glu Val Tyr Pro Asn Asn Thr<br>1465                     1470                     1475               1480 | 3216 |
| GTA ACG TGT AAT GAT TAT ACT GCG ACT CAA GAA GAA TAT GAG GGT ACG<br>Val Thr Cys Asn Asp Tyr Thr Ala Thr Gln Glu Glu Tyr Glu Gly Thr<br>              1485                     1490                  1495 | 3264 |
| TAC ACT TCT CGT AAT CGA GGA TAT GAC GGA GCC TAT GAA AGC AAT TCT<br>Tyr Thr Ser Arg Asn Arg Gly Tyr Asp Gly Ala Tyr Glu Ser Asn Ser<br>        1500                     1505                    1510 | 3312 |
| TCT GTA CCA GCT GAT TAT GCA TCA GCC TAT GAA GAA AAA GCA TAT ACA<br>Ser Val Pro Ala Asp Tyr Ala Ser Ala Tyr Glu Glu Lys Ala Tyr Thr<br>1515                     1520                     1525 | 3360 |
| GAT GGA CGA AGA GAC AAT CCT TGT GAA TCT AAC AGA GGA TAT GGG GAT<br>Asp Gly Arg Arg Asp Asn Pro Cys Glu Ser Asn Arg Gly Tyr Gly Asp<br>        1530                     1535                    1540 | 3408 |
| TAC ACA CCA CTA CCA GCT GGC TAT GTG ACA AAA GAA TTA GAG TAC TTC<br>Tyr Thr Pro Leu Pro Ala Gly Tyr Val Thr Lys Glu Leu Glu Tyr Phe<br>1545                     1550                     1555               1560 | 3456 |
| CCA GAA ACC GAT AAG GTA TGG ATT GAG ATC GGA GAA ACG GAA GGA ACA<br>Pro Glu Thr Asp Lys Val Trp Ile Glu Ile Gly Glu Thr Glu Gly Thr<br>              1565                     1570                  1575 | 3504 |

```
TTC ATC GTG GAC AGC GTG GAA TTA CTT CTT ATG GAG GAA TAA           3546
Phe Ile Val Asp Ser Val Glu Leu Leu Leu Met Glu Glu
            1580                    1585
```

(2) INFORMATION FOR SEQ ID NO:28:

(i) SEQUENCE CHARACTERISTICS:
        (A) LENGTH: 1181 amino acids
        (B) TYPE: amino acid
        (D) TOPOLOGY: linear (ii) MOLECULE TYPE: protein (xi) SEQUENCE DESCRIPTION: SEQ ID NO:28:

```
Met Asp Asn Asn Pro Asn Ile Asn Glu Cys Ile Pro Tyr Asn Cys Leu
 1               5                  10                  15

Ser Asn Pro Glu Val Glu Val Leu Gly Gly Glu Arg Ile Glu Thr Gly
                20                  25                  30

Tyr Thr Pro Ile Asp Ile Ser Leu Ser Leu Thr Gln Phe Leu Leu Ser
            35                  40                  45

Glu Phe Val Pro Gly Ala Gly Phe Val Leu Gly Leu Val Asp Ile Ile
        50                  55                  60

Trp Gly Ile Phe Gly Pro Ser Gln Trp Asp Ala Phe Leu Val Gln Ile
 65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
        195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Gly Ser Ile Arg Ser Pro His Leu Met Asp Ile Leu Asn Ser Ile Thr
    290                 295                 300

Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
```

```
              340                 345                 350
Gln Leu Gly Gln Gly Val Tyr Arg Thr Leu Ser Ser Thr Leu Tyr Arg
            355                 360                 365

Arg Pro Phe Asn Ile Gly Ile Asn Asn Gln Gln Leu Ser Val Leu Asp
370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
                420                 425                 430

Val Ser Met Phe Arg Ser Gly Phe Ser Asn Ser Val Ser Ile Ile
            435                 440                 445

Arg Ala Pro Met Phe Ser Trp Ile His Arg Ser Ala Glu Phe Asn Asn
450                 455                 460

Ile Ile Pro Ser Ser Gln Ile Thr Gln Ile Pro Leu Thr Lys Ser Thr
465                 470                 475                 480

Asn Leu Gly Ser Gly Thr Ser Val Val Lys Gly Pro Gly Phe Thr Gly
                485                 490                 495

Gly Asp Ile Leu Arg Arg Thr Ser Pro Gly Gln Ile Ser Thr Leu Arg
            500                 505                 510

Val Asn Ile Thr Ala Pro Leu Ser Gln Arg Tyr Arg Val Arg Ile Arg
            515                 520                 525

Tyr Ala Ser Thr Thr Asn Leu Gln Phe His Thr Ser Ile Asp Gly Arg
            530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
                565                 570                 575

Phe Ser Asn Gly Ser Ser Val Phe Thr Leu Ser Ala His Val Phe Asn
            580                 585                 590

Ser Gly Asn Glu Val Tyr Ile Asp Arg Ile Glu Phe Val Pro Ala Glu
            595                 600                 605

Val Thr Phe Glu Ala Glu Tyr Asp Leu Glu Arg Ala Gln Lys Ala Val
            610                 615                 620

Asn Glu Leu Phe Thr Ser Ser Asn Gln Ile Gly Leu Lys Thr Asp Val
625                 630                 635                 640

Thr Asp Tyr His Ile Asp Gln Val Ser Asn Leu Val Glu Cys Leu Ser
                645                 650                 655

Asp Glu Phe Cys Leu Asp Glu Lys Lys Glu Leu Ser Glu Lys Val Lys
                660                 665                 670

His Ala Lys Arg Leu Ser Asp Glu Arg Asn Leu Leu Gln Asp Pro Asn
            675                 680                 685

Phe Arg Gly Ile Asn Arg Gln Leu Asp Arg Gly Trp Arg Gly Ser Thr
690                 695                 700

Asp Ile Thr Ile Gln Gly Gly Asp Asp Val Phe Lys Glu Asn Tyr Val
705                 710                 715                 720

Thr Leu Leu Gly Thr Phe Asp Glu Cys Tyr Pro Thr Tyr Leu Tyr Gln
                725                 730                 735

Lys Ile Asp Glu Ser Lys Leu Lys Ala Tyr Thr Arg Tyr Gln Leu Arg
                740                 745                 750

Gly Tyr Ile Glu Asp Ser Gln Asp Leu Glu Ile Tyr Leu Ile Arg Tyr
            755                 760                 765
```

-continued

```
Asn Ala Lys His Glu Thr Val Asn Val Pro Gly Thr Gly Ser Leu Trp
770                 775                 780

Pro Leu Ser Ala Pro Ser Pro Ile Gly Lys Cys Gly Glu Pro Asn Arg
785                 790                 795                 800

Cys Ala Pro His Leu Glu Trp Asn Pro Asp Leu Asp Cys Ser Cys Arg
                805                 810                 815

Asp Gly Glu Lys Cys Ala His Ser His His Phe Ser Leu Asp Ile
            820                 825                 830

Asp Val Gly Cys Thr Asp Leu Asn Glu Asp Leu Gly Val Trp Val Ile
            835                 840                 845

Phe Lys Ile Lys Thr Gln Asp Gly His Ala Arg Leu Gly Asn Leu Glu
850                 855                 860

Phe Leu Glu Glu Lys Pro Leu Val Gly Glu Ala Leu Ala Arg Val Lys
865                 870                 875                 880

Arg Ala Glu Lys Lys Trp Arg Asp Lys Arg Glu Lys Leu Glu Trp Glu
                885                 890                 895

Thr Asn Ile Val Tyr Lys Glu Ala Lys Glu Ser Val Asp Ala Leu Phe
                900                 905                 910

Val Asn Ser Gln Tyr Asp Arg Leu Gln Ala Asp Thr Asn Ile Ala Met
            915                 920                 925

Ile His Ala Ala Asp Lys Arg Val His Ser Ile Arg Glu Ala Tyr Leu
930                 935                 940

Pro Glu Leu Ser Val Ile Pro Gly Val Asn Ala Ala Ile Phe Glu Glu
945                 950                 955                 960

Leu Glu Gly Arg Ile Phe Thr Ala Phe Ser Leu Tyr Asp Ala Arg Asn
                965                 970                 975

Val Ile Lys Asn Gly Asp Phe Asn Asn Gly Leu Ser Cys Trp Asn Val
            980                 985                 990

Lys Gly His Val Asp Val Glu Glu Gln Asn Asn His Arg Ser Val Leu
            995                 1000                1005

Val Val Pro Glu Trp Glu Ala Glu Val Ser Gln Glu Val Arg Val Cys
        1010                1015                1020

Pro Gly Arg Gly Tyr Ile Leu Arg Val Thr Ala Tyr Lys Glu Gly Tyr
1025                1030                1035                1040

Gly Glu Gly Cys Val Thr Ile His Glu Ile Glu Asn Asn Thr Asp Glu
                1045                1050                1055

Leu Lys Phe Ser Asn Cys Val Glu Glu Glu Val Tyr Pro Asn Asn Thr
            1060                1065                1070

Val Thr Cys Asn Asp Tyr Thr Ala Thr Gln Glu Glu Tyr Glu Gly Thr
            1075                1080                1085

Tyr Thr Ser Arg Asn Arg Gly Tyr Asp Gly Ala Tyr Glu Ser Asn Ser
1090                1095                1100

Ser Val Pro Ala Asp Tyr Ala Ser Ala Tyr Glu Glu Lys Ala Tyr Thr
1105                1110                1115                1120

Asp Gly Arg Arg Asp Asn Pro Cys Glu Ser Asn Arg Gly Tyr Gly Asp
                1125                1130                1135

Tyr Thr Pro Leu Pro Ala Gly Tyr Val Thr Lys Glu Leu Glu Tyr Phe
                1140                1145                1150

Pro Glu Thr Asp Lys Val Trp Ile Glu Ile Gly Glu Thr Glu Gly Thr
            1155                1160                1165

Phe Ile Val Asp Ser Val Glu Leu Leu Leu Met Glu Glu
1170                1175                1180

(2) INFORMATION FOR SEQ ID NO:29:
```

```
    (i) SEQUENCE CHARACTERISTICS:
        (A) LENGTH: 88 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer KE74A28"

(iii) HYPOTHETICAL: NO (xi) SEQUENCE DESCRIPTION: SEQ ID NO:29:

GCAGATCTGG ATCCATGCAC GCCGTGAAGG GCCCTTCTAG AAGGCCTATC GATAAAGAGC      60

TCCCCGGGGA TGGATTGCAC GCAGGTTC                                        88

(2) INFORMATION FOR SEQ ID NO:30:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer KE72A28"

(iii) HYPOTHETICAL: NO (xi) SEQUENCE DESCRIPTION: SEQ ID NO:30:

GCGTTAACAT GTCGACTCAG AAGAACTCGT CAAGAAGGCG                            40

(2) INFORMATION FOR SEQ ID NO:31:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer P1(a)"

(iii) HYPOTHETICAL: NO (xi) SEQUENCE DESCRIPTION: SEQ ID NO:31:

GTCGACAAGG ATCCAACAAT GG                                              22

(2) INFORMATION FOR SEQ ID NO:32:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer P1(b)"

(iii) HYPOTHETICAL: NO (xi) SEQUENCE DESCRIPTION: SEQ ID NO:32:

AATTGTCGAC AAGGATCCAA CAATGG                                          26

(2) INFORMATION FOR SEQ ID NO:33:

(i) SEQUENCE CHARACTERISTICS:
        (A) LENGTH: 23 base pairs
        (B) TYPE: nucleic acid
        (C) STRANDEDNESS: single
        (D) TOPOLOGY: linear
```

(ii) MOLECULE TYPE: other nucleic acid
            (A) DESCRIPTION: /desc = "primer P2(a)"

(iii) HYPOTHETICAL: NO (xi) SEQUENCE DESCRIPTION: SEQ ID NO:33:

ACACGCTGAC GTCGCGCAGC ACG                                                23

(2) INFORMATION FOR SEQ ID NO:34:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer P2(b)"

(iii) HYPOTHETICAL: NO (xi) SEQUENCE DESCRIPTION: SEQ ID NO:34:

AGCTACACGC TGACGTCGCG CAG                                                23

(2) INFORMATION FOR SEQ ID NO:35:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer A1"

(iii) HYPOTHETICAL: NO (xi) SEQUENCE DESCRIPTION: SEQ ID NO:35:

AATTGTCGAC                                                               10

(2) INFORMATION FOR SEQ ID NO:36:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer A2"

(iii) HYPOTHETICAL: NO (xi) SEQUENCE DESCRIPTION: SEQ ID NO:36:

GCGTGTAGCT                                                               10

(2) INFORMATION FOR SEQ ID NO:37:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer P3(a)"

(iii) HYPOTHETICAL: NO (xi) SEQUENCE DESCRIPTION: SEQ ID NO:37:

```
GCTGCGCGAC GTCAGCGTGT TCGG                                                    24

(2) INFORMATION FOR SEQ ID NO:38:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer P3(b)"

(iii) HYPOTHETICAL: NO (xi) SEQUENCE DESCRIPTION: SEQ ID NO:38:

AATTGCTGCG CGACGTCAGC GTG                                                     23

(2) INFORMATION FOR SEQ ID NO:39:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer P4(a)"

(iii) HYPOTHETICAL: NO (xi) SEQUENCE DESCRIPTION: SEQ ID NO:39:

GGCGTTGCCC ATGGTGCCGT ACAGG                                                   25

(2) INFORMATION FOR SEQ ID NO:40:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer P4(b)"

(iii) HYPOTHETICAL: NO (xi) SEQUENCE DESCRIPTION: SEQ ID NO:40:

AGCTGGCGTT GCCCATGGTG CCG                                                     23

(2) INFORMATION FOR SEQ ID NO:41:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer B1"

(iii) HYPOTHETICAL: NO (xi) SEQUENCE DESCRIPTION: SEQ ID NO:41:

AATTGCTGCG                                                                    10

(2) INFORMATION FOR SEQ ID NO:42:

(i) SEQUENCE CHARACTERISTICS:
        (A) LENGTH: 10 base pairs
        (B) TYPE: nucleic acid
```

```
        (C) STRANDEDNESS: single
        (D) TOPOLOGY: linear (ii) MOLECULE TYPE: other nucleic acid
        (A) DESCRIPTION: /desc = "primer B2"

(iii) HYPOTHETICAL: NO (xi) SEQUENCE DESCRIPTION: SEQ ID NO:42:

AACGCCAGCT                                                              10

(2) INFORMATION FOR SEQ ID NO:43:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer P5(a)"

(iii) HYPOTHETICAL: NO (xi) SEQUENCE DESCRIPTION: SEQ ID NO:43:

TTCCCCCTGT ACGGCACCAT GGGCAACGCC GC                                     32

(2) INFORMATION FOR SEQ ID NO:44:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer P5(b)"

(iii) HYPOTHETICAL: NO (xi) SEQUENCE DESCRIPTION: SEQ ID NO:44:

AATTGTACGG CACCATGGGC AAC                                               23

(2) INFORMATION FOR SEQ ID NO:45:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer P6(a)"

(iii) HYPOTHETICAL: NO (xi) SEQUENCE DESCRIPTION: SEQ ID NO:45:

GAAGCCGGGG CCCTTCACCA CGCTGG                                            26

(2) INFORMATION FOR SEQ ID NO:46:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer P6(b)"

(iii) HYPOTHETICAL: NO
```

(xi) SEQUENCE DESCRIPTION: SEQ ID NO:46:

AGCTGAAGCC GGGGCCCTTC ACC                                              23

(2) INFORMATION FOR SEQ ID NO:47:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer C1"

(iii) HYPOTHETICAL: NO (xi) SEQUENCE DESCRIPTION: SEQ ID NO:47:

AATTGTACGG                                                             10

(2) INFORMATION FOR SEQ ID NO:48:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer C2 - first half"

(iii) HYPOTHETICAL: NO (xi) SEQUENCE DESCRIPTION: SEQ ID NO:48:

TTCCCCTGTA CGG                                                         13

(2) INFORMATION FOR SEQ ID NO:49:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer C1 - second half"

(iii) HYPOTHETICAL: NO (xi) SEQUENCE DESCRIPTION: SEQ ID NO:49:

GGCTTCAGCT                                                             10

(2) INFORMATION FOR SEQ ID NO:50:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer PEPCivs#9 - forward"

(iii) HYPOTHETICAL: NO (xi) SEQUENCE DESCRIPTION: SEQ ID NO:50:

GTACAAAAAC CAGCAACTC                                                   19

(2) INFORMATION FOR SEQ ID NO:51:

(i) SEQUENCE CHARACTERISTICS:

(A) LENGTH: 19 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer PEPCivs#9 reverse"

(iii) HYPOTHETICAL: NO (xi) SEQUENCE DESCRIPTION: SEQ ID NO:51:

CTGCACAAAG TGGAGTAGT                                                        19

(2) INFORMATION FOR SEQ ID NO:52:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer P7(a)"

(iii) HYPOTHETICAL: NO (xi) SEQUENCE DESCRIPTION: SEQ ID NO:52:

TGGTGAAGGG CCCCGGCTTC ACCGG                                                 25

(2) INFORMATION FOR SEQ ID NO:53:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer P8(a)"

(iii) HYPOTHETICAL: NO (xi) SEQUENCE DESCRIPTION: SEQ ID NO:53:

ATCATCGATG AGCTCCTACA CCTGATCGAT GTGGTA                                     36

(2) INFORMATION FOR SEQ ID NO:54:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer for fourth quarter -
                 second half"

(iii) HYPOTHETICAL: NO (xi) SEQUENCE DESCRIPTION: SEQ ID NO:54:

ATCAGGAGCT CATCGATGAT                                                       20

(2) INFORMATION FOR SEQ ID NO:55:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer for third quarter - first half"

(iii) HYPOTHETICAL: NO (xi) SEQUENCE DESCRIPTION: SEQ ID NO:55:

TTCCCCCTGT A                                                                    11

(2) INFORMATION FOR SEQ ID NO:56:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "primer MK23A28"

(iii) HYPOTHETICAL: NO (xi) SEQUENCE DESCRIPTION: SEQ ID NO:56:

GGGGCTGCGG ATGCTGCCCT                                                           20

(2) INFORMATION FOR SEQ ID NO:57:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "primer MK25A28"

(iii) HYPOTHETICAL: NO (xi) SEQUENCE DESCRIPTION: SEQ ID NO:57:

GAGCTGACCC TGACCGTGCT                                                           20

(2) INFORMATION FOR SEQ ID NO:58:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "primer MK26A28"

(iii) HYPOTHETICAL: NO (xi) SEQUENCE DESCRIPTION: SEQ ID NO:58:

CACCTGATGG ACATCCTGAA                                                           20

(2) INFORMATION FOR SEQ ID NO:59:

(i) SEQUENCE CHARACTERISTICS:
       (A) LENGTH: 33 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "sequence in pCIB3073 prior
             to deletion"

(iii) HYPOTHETICAL: NO (xi) SEQUENCE DESCRIPTION: SEQ ID NO:59:

TATAAGGATC CCGGGGGCAA GATCTGAGAT ATG                                             33

(2) INFORMATION FOR SEQ ID NO:60:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer KE134A28"

(iii) HYPOTHETICAL: NO (xi) SEQUENCE DESCRIPTION: SEQ ID NO:60:

CGTGACCGAC TACCACATCG ATCAAGTATC CAATTTAGTT GAGT          44

(2) INFORMATION FOR SEQ ID NO:61:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer KE135A28"

(iii) HYPOTHETICAL: NO (xi) SEQUENCE DESCRIPTION: SEQ ID NO:61:

ACTCAACTAA ATTGGATACT TGATCGATGT GGTAGTCGGT CACG          44

(2) INFORMATION FOR SEQ ID NO:62:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer KE136A28"

(iii) HYPOTHETICAL: NO (xi) SEQUENCE DESCRIPTION: SEQ ID NO:62:

GCAGATCTGA GCTCTTAGGT ACCCAATAGC GTAACGT          37

(2) INFORMATION FOR SEQ ID NO:63:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer KE137A28"

(iii) HYPOTHETICAL: NO (xi) SEQUENCE DESCRIPTION: SEQ ID NO:63:

GCTGATTATG CATCAGCCTA T          21

(2) INFORMATION FOR SEQ ID NO:64:

(i) SEQUENCE CHARACTERISTICS:
        (A) LENGTH: 38 base pairs
        (B) TYPE: nucleic acid
        (C) STRANDEDNESS: single (D) TOPOLOGY: linear (ii) MOLECULE TYPE: other nucleic acid
        (A) DESCRIPTION: /desc = "primer KE138A28"

(iii) HYPOTHETICAL: NO (xi) SEQUENCE DESCRIPTION: SEQ ID NO:64:

GCAGATCTGA GCTCTTATTC CTCCATAAGA AGTAATTC                              38

(2) INFORMATION FOR SEQ ID NO:65:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer MK05A28"

(iii) HYPOTHETICAL: NO (xi) SEQUENCE DESCRIPTION: SEQ ID NO:65:

CAAAGGTACC CAATAGCGTA ACG                                             23

(2) INFORMATION FOR SEQ ID NO:66:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer MK35A28"

(iii) HYPOTHETICAL: NO (xi) SEQUENCE DESCRIPTION: SEQ ID NO:66:

AACGAGGTGT ACATCGACCG                                                 20

(2) INFORMATION FOR SEQ ID NO:67:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "forward primer for
            pCIB4434"

(iii) HYPOTHETICAL: NO (xi) SEQUENCE DESCRIPTION: SEQ ID NO:67:

GCACCGATAT CACCATCCAA GGAGGCGATG ACGTATTCAA AG                         42

(2) INFORMATION FOR SEQ ID NO:68:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "reverse primer for
            pCIB4434"

(iii) HYPOTHETICAL: NO (xi) SEQUENCE DESCRIPTION: SEQ ID NO:68:

AGCGCATCGA TTCGGCTCCC CGCACTTGCC GATTGGACTT GGGGCTGAAA G           51

(2) INFORMATION FOR SEQ ID NO:69:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer #1"

(iii) HYPOTHETICAL: NO (xi) SEQUENCE DESCRIPTION: SEQ ID NO:69:

ATTACGTTAC GCTATTGGGT ACCTTTGATG                                   30

(2) INFORMATION FOR SEQ ID NO:70:

(i) SEQUENCE CHARACTERISTICS:
            (A) LENGTH: 98 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer #2"

(iii) HYPOTHETICAL: NO (xi) SEQUENCE DESCRIPTION: SEQ ID NO:70:

TCCCCGTCCC TGCAGCTGCA GTCTAGGTCC GGGTTCCACT CCAGGTGCGG AGCGCATCGA  60

TTCGGCTCCC CGCACTTGCC GATTGGACTT GGGGCTGA                          98

(2) INFORMATION FOR SEQ ID NO:71:

(i) SEQUENCE CHARACTERISTICS:
            (A) LENGTH: 98 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer #3"

(iii) HYPOTHETICAL: NO (xi) SEQUENCE DESCRIPTION: SEQ ID NO:71:

CAAGTGCGGG GAGCCGAATC GATGCGCTCC GCACCTGGAG TGGAACCCGG ACCTAGACTG  60

CAGCTGCAGG GACGGGGAAA AATGTGCCCA TCATTCCC                          98

(2) INFORMATION FOR SEQ ID NO:72:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer #4"

(iii) HYPOTHETICAL: NO (xi) SEQUENCE DESCRIPTION: SEQ ID NO:72:

TGGTTTCTCT TCGAGAAATT CTAGATTTCC                                   30

(2) INFORMATION FOR SEQ ID NO:73:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer used to map
            transcriptional start site for TrpA gene"

(iii) HYPOTHETICAL: NO (xi) SEQUENCE DESCRIPTION: SEQ ID NO:73:

CCGTTCGTTC CTCCTTCGTC GAGG                                        24

(2) INFORMATION FOR SEQ ID NO:74:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: N-terminal (ix) FEATURE:
        (A) NAME/KEY: Peptide
        (B) LOCATION: 1..26
        (D) OTHER INFORMATION: /note= "N-terminal peptide from
            pollen specific protein"

(xi) SEQUENCE DESCRIPTION: SEQ ID NO:74:

Thr Thr Pro Leu Thr Phe Gln Val Gly Lys Gly Ser Lys Pro Gly His
1           5                10              15

Leu Ile Leu Thr Pro Asn Val Ala Thr Ile
          20              25

(2) INFORMATION FOR SEQ ID NO:75:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (ix) FEATURE:
        (A) NAME/KEY: Peptide
        (B) LOCATION: 1..20
        (D) OTHER INFORMATION: /note= "internal peptide of pollen
            specific protein"

(xi) SEQUENCE DESCRIPTION: SEQ ID NO:75:

Lys Pro Gly His Leu Ile Leu Thr Pro Asn Val Ala Thr Ile Ser Asp
1           5                10              15

Val Val Ile Lys
          20

(2) INFORMATION FOR SEQ ID NO:76:

(i) SEQUENCE CHARACTERISTICS:
              (A) LENGTH: 16 amino acids
              (B) TYPE: amino acid
              (C) STRANDEDNESS: single
              (D) TOPOLOGY: linear (ii) MOLECULE TYPE: peptide (iii) HYPOTHETICAL: NO (v) FRAGMENT TYPE: internal (ix) FEATURE:
              (A) NAME/KEY: Peptide
              (B) LOCATION: 1..16
              (D) OTHER INFORMATION: /note= "internal peptide from
                  pollen specific protein"

(xi) SEQUENCE DESCRIPTION: SEQ ID NO:76:

Ser Gly Gly Thr Arg Ile Ala Asp Asp Val Ile Pro Ala Asp Phe Lys
1               5                  10                  15

(2) INFORMATION FOR SEQ ID NO:77:

(i) SEQUENCE CHARACTERISTICS:
              (A) LENGTH: 12 amino acids
              (B) TYPE: amino acid
              (C) STRANDEDNESS: single
              (D) TOPOLOGY: linear (ii) MOLECULE TYPE: peptide (iii) HYPOTHETICAL: NO (v) FRAGMENT TYPE: internal (ix) FEATURE:
              (A) NAME/KEY: Peptide
              (B) LOCATION: 1..12
              (D) OTHER INFORMATION: /note= "internal peptide from
                  pollen specific protein"

(xi) SEQUENCE DESCRIPTION: SEQ ID NO:77:

Glu His Gly Gly Asp Asp Phe Ser Phe Thr Leu Lys
1               5                  10

(2) INFORMATION FOR SEQ ID NO:78:

(i) SEQUENCE CHARACTERISTICS:
              (A) LENGTH: 12 amino acids
              (B) TYPE: amino acid
              (C) STRANDEDNESS: single
              (D) TOPOLOGY: linear (ii) MOLECULE TYPE: peptide (iii) HYPOTHETICAL: NO (v) FRAGMENT TYPE: internal (ix) FEATURE:
              (A) NAME/KEY: Peptide
              (B) LOCATION: 1..12
              (D) OTHER INFORMATION: /note= "internal peptide from
                  pollen specific protein"

(xi) SEQUENCE DESCRIPTION: SEQ ID NO:78:

Glu Gly Pro Thr Gly Thr Trp Thr Leu Asp Thr Lys
1               5                  10

(2) INFORMATION FOR SEQ ID NO:79:

(i) SEQUENCE CHARACTERISTICS:

```
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide #51"

(iii) HYPOTHETICAL: NO (xi) SEQUENCE DESCRIPTION: SEQ ID NO:79:

AARTCRTCAB CACCRTGYTC                                                    20

(2) INFORMATION FOR SEQ ID NO:80:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide #58"

(iii) HYPOTHETICAL: NO (xi) SEQUENCE DESCRIPTION: SEQ ID NO:80:

CCYTTNCCCA CYTGRAA                                                       17

(2) INFORMATION FOR SEQ ID NO:81:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide PE51"

(iii) HYPOTHETICAL: NO (xi) SEQUENCE DESCRIPTION: SEQ ID NO:81:

TGGCCCATGG CTGCGGCGGG GAACGAGTGC GGC                                      33

(2) INFORMATION FOR SEQ ID NO:82:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer #42"

(iii) HYPOTHETICAL: NO (xi) SEQUENCE DESCRIPTION: SEQ ID NO:82:

AGCGGTCGAC CTGCAGGCAT GCGATCTGCA CCTCCCGCCG                               40

(2) INFORMATION FOR SEQ ID NO:83:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer #43"
```

(iii) HYPOTHETICAL: NO (xi) SEQUENCE DESCRIPTION: SEQ ID NO:83:

ATGGGCAAGG AGCTCGGG                                                         18

(2) INFORMATION FOR SEQ ID NO:84:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer #SK50"

(iii) HYPOTHETICAL: NO (xi) SEQUENCE DESCRIPTION: SEQ ID NO:84:

CCCTTCAAAA TCTAGAAACC T                                                     21

(2) INFORMATION FOR SEQ ID NO:85:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer #SK49"

(iii) HYPOTHETICAL: NO (xi) SEQUENCE DESCRIPTION: SEQ ID NO:85:

TAATGTCGAC GAACGGCGAG AGATGGA                                               27

(2) INFORMATION FOR SEQ ID NO:86:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer KE99A28"

(iii) HYPOTHETICAL: NO (xi) SEQUENCE DESCRIPTION: SEQ ID NO:86:

TGCGGTTACC GCCGATCACA TG                                                    22

(2) INFORMATION FOR SEQ ID NO:87:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer KE97A28"

(iii) HYPOTHETICAL: NO (xi) SEQUENCE DESCRIPTION: SEQ ID NO:87:

GCGGTACCGC GTCGACGCGG ATCCCGCGGC GGGAAGCTAA G                               41

(2) INFORMATION FOR SEQ ID NO:88:

(i) SEQUENCE CHARACTERISTICS:
    (A) LENGTH: 16 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "primer KE100A28"

(iii) HYPOTHETICAL: NO (xi) SEQUENCE DESCRIPTION: SEQ ID NO:88:

GTCGTCGACC GCAACA                                                  16

(2) INFORMATION FOR SEQ ID NO:89:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer KE98A28"

(iii) HYPOTHETICAL: NO (xi) SEQUENCE DESCRIPTION: SEQ ID NO:89:

GCGGTACCGC GTTAACGCGG ATCCTGTCCG ACACCGGAC                          39

(2) INFORMATION FOR SEQ ID NO:90:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer KE104A28"

(iii) HYPOTHETICAL: NO (xi) SEQUENCE DESCRIPTION: SEQ ID NO:90:

GATGTCGTCG ACCGCAACAC                                               20

(2) INFORMATION FOR SEQ ID NO:91:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer KE103A28"

(iii) HYPOTHETICAL: NO (xi) SEQUENCE DESCRIPTION: SEQ ID NO:91:

GCGGTACCGC GGATCCTGTC CGACACCGGA CGGCT                              35

(2) INFORMATION FOR SEQ ID NO:92:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid -continued

```
        (A) DESCRIPTION: /desc = "primer KE127"

(iii) HYPOTHETICAL: NO (xi) SEQUENCE DESCRIPTION: SEQ ID NO:92:

GCGGATCCGG CTGCGGCGGG GAACGA                                        26

(2) INFORMATION FOR SEQ ID NO:93:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer KE150A28"

(iii) HYPOTHETICAL: NO (xi) SEQUENCE DESCRIPTION: SEQ ID NO:93:

ATTCGCATGC ATGTTTCATT ATC                                           23

(2) INFORMATION FOR SEQ ID NO:94:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer KE151A28"

(iii) HYPOTHETICAL: NO (xi) SEQUENCE DESCRIPTION: SEQ ID NO:94:

GCTGGTACCA CGGATCCGTC GCTTCTGTGC AACAACC                            37
```

What is claimed is:

1. A nucleic acid molecule comprising a 1.8 kb promoter fragment isolated from the 5' flanking region upstream of the start site of the coding region of a plant tryptophan synthase alpha subunit (trpA) gene, wherein said promoter fragment is capable of directing pith-preferred expression of an associated coding sequence in a plant.

2. A nucleic acid molecule according to claim 1, wherein said plant trpA gene is a maize trpA gene.

3. A nucleic acid molecule according to claim 2, wherein said promoter fragment is isolated from the region upstream of nucleotide number 1839 of SEQ ID NO:18.

4. A nucleic acid molecule according to claim 2, wherein said promoter fragment comprises nucleotides 39–1838 of SEQ ID NO:18.

5. A chimeric DNA molecule comprising the nucleic acid molecule according to claim 1 operatively linked to a coding sequence of interest.

6. A chimeric DNA molecule comprising the nucleic acid molecule according to claim 2 operatively linked to a coding sequence of interest.

7. A chimeric DNA molecule according to claim 6, wherein the coding sequence of interest is the coding sequence of a maize trpA gene.

8. A chimeric DNA molecule according to claim 6, wherein the coding sequence of interest is the coding sequence of an insecticidal protein gene.

9. A chimeric DNA molecule according to claim 8, wherein the coding sequence of interest is the coding sequence of a *Bacillus thuringiensis* protein gene.

10. A plant transformation vector comprising the chimeric DNA molecule according to claim 5.

11. A plant transformation vector comprising the chimeric DNA molecule according to claim 6.

12. A plant transformation vector according to claim 11, which is plasmid pCIB4433 (NRRL B-18999).

13. A transgenic plant or plant part comprising the chimeric DNA molecule according to claim 5.

14. A transgenic plant or plant part comprising the chimeric DNA molecule according to claim 6.

15. A transgenic plant or plant part according to claim 14, which is maize.

* * * * *